US011098309B2

(12) United States Patent
Ott et al.

(10) Patent No.: US 11,098,309 B2
(45) Date of Patent: *Aug. 24, 2021

(54) COMPOSITIONS AND METHODS FOR REACTIVATING LATENT IMMUNODEFICIENCY VIRUS

(71) Applicant: The J. David Gladstone Institutes, a testamentary trust established under the Will of J. David Gladstone, San Francisco, CA (US)

(72) Inventors: Melanie Ott, Mill Valley, CA (US); Daniela Boehm, San Francisco, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,753

(22) Filed: May 24, 2019

(65) Prior Publication Data
US 2019/0338289 A1 Nov. 7, 2019

Related U.S. Application Data

(60) Division of application No. 15/488,212, filed on Apr. 14, 2017, now Pat. No. 10,351,853, which is a continuation-in-part of application No. PCT/US2015/055377, filed on Oct. 13, 2015.

(60) Provisional application No. 62/063,822, filed on Oct. 14, 2014.

(51) Int. Cl.
A61K 48/00 (2006.01)
C07H 21/04 (2006.01)
C12N 15/113 (2010.01)
A61K 38/15 (2006.01)
A61K 45/06 (2006.01)
A61K 31/19 (2006.01)
A61K 31/22 (2006.01)
A61K 31/365 (2006.01)
A61K 31/551 (2006.01)
A61K 31/713 (2006.01)
A61K 31/167 (2006.01)
A61K 31/222 (2006.01)

(52) U.S. Cl.
CPC ........ *C12N 15/1137* (2013.01); *A61K 31/167* (2013.01); *A61K 31/19* (2013.01); *A61K 31/22* (2013.01); *A61K 31/222* (2013.01); *A61K 31/365* (2013.01); *A61K 31/551* (2013.01); *A61K 31/713* (2013.01); *A61K 38/15* (2013.01); *A61K 45/06* (2013.01); *C12N 2310/14* (2013.01); *C12N 2310/531* (2013.01)

(58) Field of Classification Search
CPC .. A61K 45/06; A61K 2300/00; C12N 15/111; C12N 15/113; C12N 2310/14
See application file for complete search history.

(56) References Cited

U.S. PATENT DOCUMENTS

| | | |
|---|---|---|
| 3,687,808 A | 8/1972 | Merigan, Jr. et al. |
| 4,756,907 A | 7/1988 | Beck et al. |
| 5,034,506 A | 7/1991 | Summerton et al. |
| 5,334,711 A | 8/1994 | Sproat et al. |
| 5,489,677 A | 2/1996 | Sanghvi et al. |
| 5,539,082 A | 7/1996 | Nielsen et al. |
| 5,602,240 A | 2/1997 | De Mesmaeker et al. |
| 5,627,053 A | 5/1997 | Usman et al. |
| 5,714,331 A | 2/1998 | Buchardt et al. |
| 5,716,824 A | 2/1998 | Beigelman et al. |
| 5,719,262 A | 2/1998 | Buchardt et al. |
| 5,728,074 A | 3/1998 | Castellano et al. |
| 5,854,038 A | 12/1998 | Sullenger et al. |
| 6,086,909 A | 7/2000 | Harrison et al. |
| 6,096,010 A | 8/2000 | Walters et al. |
| 6,146,361 A | 11/2000 | DiBiasi et al. |
| 6,221,053 B1 | 4/2001 | Walters et al. |
| 6,248,095 B1 | 7/2001 | Giambattista et al. |
| 6,277,099 B1 | 8/2001 | Strowe et al. |
| 6,300,074 B1 | 10/2001 | Gold et al. |
| 6,476,079 B1 | 11/2002 | Jukarainen et al. |
| 7,256,286 B2 | 8/2007 | Wender et al. |
| 10,351,853 B2 | 7/2019 | Ott et al. |
| 2002/0012012 A1 | 1/2002 | Crain et al. |
| 2002/0086998 A1 | 7/2002 | Koch et al. |
| 2002/0094555 A1 | 7/2002 | Belotserkovskii et al. |
| 2002/0142980 A1 | 10/2002 | Thompson et al. |

(Continued)

FOREIGN PATENT DOCUMENTS

| | | |
|---|---|---|
| EP | 3206751 | 8/2017 |
| WO | WO 1991003162 | 3/1991 |

(Continued)

OTHER PUBLICATIONS

Bernhard et al. (FEBS Letters, 585,2011, 3549-3554).*
"European Application Serial No. 15851463.8, Communication Pursuant to Article 94(3) EPC dated Nov. 11, 2019", 4 pgs.
"U.S. Appl. No. 15/488,212, Preliminary Amendment filed Jul. 17, 2017", 7 pgs.
"U.S. Appl. No. 15/488,212, Restriction Requirement dated Apr. 26, 2018", 10 pgs.

(Continued)

Primary Examiner — Amy H Bowman
(74) Attorney, Agent, or Firm — Schwegman Lundberg & Woessner, P.A.

(57) ABSTRACT

The present disclosure provides compositions and methods for reactivating latent immunodeficiency virus and/or reducing transcription of HIV integrated into the genome of an HIV-infected cell. The present disclosure provides compositions and methods for treating an immunodeficiency virus infection.

9 Claims, 38 Drawing Sheets

Specification includes a Sequence Listing.

(56) References Cited

U.S. PATENT DOCUMENTS

| | | |
|---|---|---|
| 2002/0150936 A1 | 10/2002 | Beigelman et al. |
| 2003/0073640 A1 | 4/2003 | Beigelman et al. |
| 2004/0014959 A1 | 1/2004 | Sorensen et al. |
| 2004/0192626 A1 | 9/2004 | Mcswiggen et al. |
| 2004/0249178 A1 | 12/2004 | Vargeese et al. |
| 2005/0020525 A1 | 1/2005 | Mcswiggen et al. |
| 2005/0059817 A1 | 3/2005 | Beigelman et al. |
| 2005/0176018 A1 | 8/2005 | Thompson et al. |
| 2005/0233329 A1 | 10/2005 | Mcswiggen et al. |
| 2005/0234232 A1 | 10/2005 | Beigelman et al. |
| 2005/0239731 A1 | 10/2005 | Mcswiggen et al. |
| 2005/0282188 A1 | 12/2005 | Haeberli et al. |
| 2006/0117410 A1 | 6/2006 | Goff |
| 2009/0041809 A1 | 2/2009 | Emtage |
| 2009/0270492 A1 | 10/2009 | Wender |
| 2010/0216983 A1 | 8/2010 | Detlef et al. |
| 2012/0165514 A1 | 6/2012 | Sørensen et al. |
| 2014/0161785 A1 | 6/2014 | Liu et al. |
| 2018/0002699 A1 | 1/2018 | Ott et al. |

FOREIGN PATENT DOCUMENTS

| | | |
|---|---|---|
| WO | WO 1992007065 | 4/1992 |
| WO | WO 1993015187 | 8/1993 |
| WO | WO 1997026270 | 7/1997 |
| WO | WO 1998013526 | 4/1998 |
| WO | WO 1998039352 | 9/1998 |
| WO | WO 1999014226 | 3/1999 |
| WO | WO 2000066604 | 11/2000 |
| WO | WO 2005019453 | 3/2005 |
| WO | WO 2012051492 | 4/2012 |
| WO | 2013019710 | 2/2013 |
| WO | WO 2013050422 | 4/2013 |
| WO | WO 2013080400 | 6/2013 |
| WO | WO 2013165592 | 11/2013 |
| WO | 2016061131 | 4/2016 |

OTHER PUBLICATIONS

"U.S. Appl. No. 15/488,212, Response filed Jun. 19, 2018 to Restriction Requirement dated Apr. 26, 2018", 3 pgs.
"U.S. Appl. No. 15/488,212, Non Final Office Action dated Sep. 4, 2018", 13 pgs.
"U.S. Appl. No. 15/488,212, Response filed Dec. 20, 2018 to Non Final Office Action dated Sep. 4, 2018", 10 pgs.
"U.S. Appl. No. 15/488,212, Notice of Allowance dated Feb. 25, 2019", 9 pgs.
"U.S. Appl. No. 15/488,212, Notice of Allowance dated Mar. 26, 2019", 6 pgs.
"U.S. Appl. No. 15/488,212, 312 Amendment filed May 24, 2019", 5 pgs.
"U.S. Appl. No. 15/488,212, PTO Response to Rule 312 Communication dated Jun. 5, 2019", 2 pgs.
"U.S. Appl. No. 15/488,212, Notice of Allowability dated Jun. 7, 2019", 3 pgs.
"European Application Serial No. 15851463.8, Response to Communication pursuant to Rules 161(1) and 162 EPC filed Nov. 21, 2017", 11 pgs.
"European Application Serial No. 15851463.8, Extended European Search Report dated May 14, 2018", 6 pgs.
"European Application Serial No. 1585146.8, Response filed Dec. 4, 2018 to Extended European Search Report dated May 14, 2018", 11 pgs.
"International Application Serial No. PCT US2015 055377, International Search Report dated Feb. 4, 2016", 4 pgs.
"International Application Serial No. PCT US2015 055377, Written Opinion dated Feb. 4, 2016", 5 pgs.
"International Application Serial No. PCT US2015 055377, International Preliminary Report on Patentability dated Apr. 27, 2017", 7 pgs.
"European Application Serial No. 15851463.8, Response filed May 27, 2020 to Communication Pursuant to Article 94(3) EPC dated Nov. 11, 2019", 10 pgs.

U.S. Appl. No. 15/488,212 U.S. Pat. No. 10,351,853, filed Apr. 14, 2017, Compositions and Methods for Reactivating Latent Immunodeficiency Virus.
Abu-Farha, M., et al (2008) "The tale of two domains: proteomics and genomics analysis of SMYD2, a new histone methyltransferase"; *Mol Cell Proteomics 7*; pp. 560-572.
Abu-Farha, M., et al (2011) "Proteomic analyses of the SMYD family interactomes identify HSP90 as a novel target for SMYD2"; *Journal of molecular cell biology 3*; pp. 301-308.
Aguilera et al (2009) "Systemic in vivo distribution of activatable cell penetrating peptides is superior to that of cell penetrating peptides."; *Integr Biol (Camb)* (5-6); pp. 371-381.
Allshire, (2002) "RNAi and Heterochromatin—a Hushed-Up Affair"; *Science*, 297; pp. 1818-1819.
Archin, NM et al (2012) "Administration of vorinostat disrupts HIV-1 latency in patients on antiretroviral therapy"; *Nature 487*; pp. 482-485.
Archin, N.M., and Margolis, D.M. (2014) "Emerging strategies to deplete the HIV reservoir"; *Current opinion in infectious diseases 27*; pp. 29-35.
Aronin et al. (2006) "Target selectivity in mRNA silencing"; *Gene Ther.* 13(6); pp. 509-516.
Bagislar, S. et al (2016) "Smyd2 is a Myc-regulated gene critical for MLL-AF9 induced leukemogenesis"; *Oncotarget 7*; pp. 66398-66415.
Beck, D.B. et al (2012) "PR-Set7 and H4K20me1: at the crossroads of genome integrity, cell cycle, chromosome condensation, and transcription"; *Genes Dev 26*; pp. 325-337.
Beigelman et al (1995) "Chemical modification of hammerhead ribozymes. Catalytic activity and nuclease resistance"; *J. Biol. Chem.*, 270; pp. 25702-25708.
Boehm et al (2017) "SMYD2-Mediated Histone Methylation Contributes to HIV-1 Latency"; Cell Host & Microbe. 21(5); pp. 569-579.
Bonasio, R. et al. (2010) "MBT domain proteins in development and disease"; *Seminars in cell & developmental biology 21*; pp. 221-230.
Boudreau et al (2013) "siSPOTR: a tool for designing highly specific and potent siRNAs for human and mouse"; *Nucleic Acids Research* 41(1); e9; 12 pages.
Braasch Dwaine A. and Corey David R. (2002) "Novel antisense and peptide nucleic acid strategies for controlling gene expression"; *Biochemistry* 41(14); pp. 4503-4510.
Brown, M.A. et al (2006) "Identification and characterization of Smyd2: a split SET/MYND domain-containing histone H3 lysine 36-specific methyltransferase that interacts with the Sin3 histone deacetylase complex"; *Mol Cancer 5*;26.
Burgin et al. (1996) "Chemically modified hammerhead ribozymes with improved catalytic rates"; *Biochemistry 35*; pp. 14090-14097.
Burlina et al. (1997) "Chemical engineering of RNase resistant and catalytically active hammerhead ribozymes"; *Bioorg. Med. Chem.* 5; pp. 1999-2010.
Calpena, et al (2015) "Evolutionary History of the Smyd Gene Family in Metazoans: A Framework to Identify the Orthologs of Human Smyd Genes in *Drosophila* and Other Animal Species"; PLoS One 10(7); pp. 1-26.
Chan, J.K. et al (2013) "Calcium/calcineurin synergizes with prostratin to promote NF-kappaB dependent activation of latent HIV"; *PLoS One* 8(10), e77749; pp. 1-10.
Cho, H. S. et al.(2012) "RB1 methylation by SMYD2 enhances cell cycle progression through an increase of RB1 phosphorylation"; *Neoplasia 14*; pp. 476-486.
Colin et al. (2009) "Molecular control of HIV-1 postintegration latency: implications for the development of new therapeutic strategies"; *Retrovirology*, vol. 6, No. 111; pp. 1-29.
Cox, J., and Mann, M. (2008) "MaxQuant enables high peptide identification rates, individualized p.p.b.-range mass accuracies and proteome-wide protein quantification"; *Nature biotechnology 26*; pp. 1367-1372.
Crooke et al. (1996) "Pharmacokinetic properties of several novel oligonucleotide analogs in mice."; *J. Pharmacol. Exp. Ther* 277(2); pp. 923-937.
Deeks, S.G. (2012) "HIV: Shock and kill"; *Nature 487*; pp. 439-440.

(56) References Cited

OTHER PUBLICATIONS

Delmore, J.E. et al. (2011) "BET bromodomain inhibition as a therapeutic strategy to target c-Myc"; *Cell* 146(6); pp. 904-917.

Ding, et al (2013) "Involvement of histone methyltransferase GLP in HIV-1 latency through catalysis of H3K9 dimethylation"; *Virology.* 440(2); pp. 182-189.

Du, et al (2014) "SMYD proteins: key regulators in skeletal and cardiac muscle development and function"; The Anatomical Record 297:pp. 1650-1662.

Du Chene, I. et al. (2007) "Suv39H1 and HP1gamma are responsible for chromatin-mediated HIV-1 transcriptional silencing and post-integration latency"; *EMBO J* 26(2); pp. 424-435.

Easley, R., et al (2010) "Chromatin dynamics associated with HIV-1 Tat-activated transcription"; *Biochim Biophys Acta 1799*; pp. 275-285.

Fang, J., et al.(2002) "Purification and functional characterization of SET8, a nucleosomal histone H4-lysine 20-specific methyltransferase"; Current biology 12(13); pp. 1086-1099.

Ferguson, A.D., et al. (2011) "Structural basis of substrate methylation and inhibition of SMYD2"; *Structure* 19(9); pp. 1262-1273.

Filippakopoulos, P., et al. (2010) "Selective inhibition of BET bromodomains"; *Nature 468*, pp. 1067-1073.

Folks, T.M., et al. (1989) "Tumor necrosis factor alpha induces expression of human immunodeficiency virus in a chronically infected T-cell clone"; *Proceedings of the National Academy of Sciences of the United States of America 86*; pp. 2365-2368.

Francis, N.J., et al (2004) "Chromatin compaction by a polycomb group protein complex"; *Science 306*; pp. 1574-1577.

Friedman, J., et al (2011) "Epigenetic silencing of HIV-1 by the histone H3 lysine 27 methyltransferase enhancer of Zeste 2"; *J Virol* 85(17); pp. 9078-9089.

Grunweller et al. (2005) "RNA interference as a gene-specific approach for molecular medicine"; *Curr Med Chem.*12(26); pp. 3143-3161.

Hall et al. (2002) "Establishment and maintenance of a heterochromatin domain"; *Science*, 297; pp. 2232-2237.

Hamamoto, R., et al (2015) "Critical roles of non-histone protein lysine methylation in human tumorigenesis"; *Nature reviews. Cancer* 15(2); pp. 110-124.

Herold, J.M., et al. (2012). "Structure-activity relationships of methyl-lysine reader antagonists"; *Medchemcomm 3*; pp. 45-51.

Huang, J., et al (2006) "Repression of p53 activity by Smyd2-mediated methylation"; *Nature 444*; pp. 629-632.

Imai, K., et al (2010) "Involvement of histone H3 lysine 9 (H3K9) methyltransferase G9a in the maintenance of HIV-1 latency and its reactivation by BIX01294"; *J Biol Chem 285*, pp. 16538-16545.

Iyer et al (2007) "Batch RNAi selector: a standalone program to predict specific siRNA candidates in batches with enhanced sensitivity"; *Comput Methods Programs Biomed*, 85; pp. 203-209.

Jamieson, K., et al (2016) "Loss of HP1 causes depletion of H3K27me3 from facultative heterochromatin and gain of H3K27me2 at constitutive heterochromatin"; *Genome research 26*; pp. 97-107.

Jenuwein, Thomas (2002) "An RNA-Guided Pathway for the Epigenome"; *Science*, 297; pp. 2215-2218.

Jiang, Y., et al (2014) "Structural insights into estrogen receptor alpha methylation by histone methyltransferase SMYD2, a cellular event implicated in estrogen signaling regulation"; *Journal of molecular biology 426*; pp. 3413-3425.

Jordan, A., et al (2003) "HIV reproducibly establishes a latent infection after acute infection of T cells in vitro"; *EMBO J* 22(8); pp. 1868-1877.

Jordan, A., et al (2001) "The site of HIV-1 integration in the human genome determines basal transcriptional activity and response to Tat transactivation"; *EMBO J* 20(7); pp. 1726-1738.

Kabanov et al., (1990) "A new class of antivirals: antisense oligonucleotides combined with a hydrophobic substituent effectively inhibit influenza virus reproduction and synthesis of virus-specific proteins in MDCK cells"; *FEBS Lett. 259*; pp. 327-330.

Kaehlcke, K.,et al (2003) "Acetylation of Tat defines a cyclinT1-independent step in HIV transactivation"; *Mol Cell* 12(1); pp. 167-176.

Kalakonda, N., et al. (2008) "Histone H4 lysine 20 monomethylation promotes transcriptional repression by L3MBTL1"; *Oncogene 27*; pp. 4293-4304.

Kidder, et al (2017) "SMYD5 regulates H4K20me3-marked heterochromatin to safeguard ES cell self-renewal and prevent spurious differentiation"; Epigenetics & Chromatin 10:8; pp. 1-20.

Kundu, M., et al (1995) "Evidence that a cell cycle regulator, E2F1, down-regulates transcriptional activity of the human immunodeficiency virus type 1 promoter"; *J Virol* 69(11); pp. 6940-6946.

Kutsch, O. et al. (2002) "Direct and quantitative single-cell analysis of human immunodeficiency virus type 1 reactivation from latency"; *J Virol 76*; pp. 8776-8786.

Laird, G.M., et al. (2015) "Ex vivo analysis identifies effective HIV-1 latency-reversing drug combinations"; *The Journal of clinical investigation* 125(5); pp. 1901-1912.

Lalezari, et al. (2003) "Enfuvirtide, an HIV-1 fusion inhibitor, for drug-resistant HIV infection in North and South America"; *New England J. Med.*, 348(22); pp. 2175-2185.

Letsinger et al. (1989) "Cholesteryl-conjugated oligonucleotides: synthesis, properties, and activity as inhibitors of replication of human immunodeficiency virus in cell culture"; *Proc. Natl. Acad. Sci. USA 86*; pp. 6553-6556.

Maclean, B., et al (2010) "Skyline: an open source document editor for creating and analyzing targeted proteomics experiments"; *Bioinformatics 26*; pp. 966-968.

Martinez et al. (2002) "Single-stranded antisense siRNAs guide target RNA cleavage in RNAi"; *Cell* 110(5); pp. 563-574.

Mbonye, U. and Karn, J. (2014) "Transcriptional control of HIV latency: cellular signaling pathways, epigenetics, happenstance and the hope for a cure"; *Virology 454-455*; pp. 328-339.

Min, J., et al (2007) "L3MBTL1 recognition of mono- and dimethylated histones"; *Nat Struct Mol Biol 14*; pp. 1229-1230.

Murray, A.J., et al (2016) "The Latent Reservoir for HIV-1: How Immunologic Memory and Clonal Expansion Contribute to HIV-1 Persistence"; *J Immunol 197*; pp. 407-417.

Mysara et al. (2011) "MysiRNA-designer: a workflow for efficient siRNA design"; *PLoS*, 6(10):e25642; pp. 1-10.

Naito et al. (2004) "siDirect: highly effective, target-specific siRNA design software for mammalian RNA interference"; *Nucleic Acids Research 32*; W124-W129.

Naldini, L.,et al. (1996) in vivo gene delivery and stable transduction of nondividing cells by a lentiviral vector. Science 272, 263-267.

Nguyen et al. (2015) "LLY-507, a Cell-active, Potent, and Selective Inhibitor of Protein-lysine Methyltransferase SMYD2."; *J. Biol Chem. 290*; pp. 13641-13653.

Nicodeme, E., et al. (2010) "Suppression of inflammation by a synthetic histone mimic"; *Nature 468*; pp. 1119-1123.

Nishioka, K., et al. (2002) "PR-Set7 is a nucleosome-specific methyltransferase that modifies lysine 20 of histone H4 and is associated with silent chromatin"; *Mol Cell 9*; pp. 1201-1213.

Noguchi, et al. (2003) "PDX-1 protein containing its own antennapedia-like protein transduction domain can transduce pancreatic duct and islet cells"; Diabetes 52(7); pp. 1732-1737.

Oberhauser, et al. (1992) "Effective incorporation of 2'-O-methyl-oligoribonucleotides into liposomes and enhanced cell association through modification with thiocholesterol"; *Nucl. Acids Res.*20(3); pp. 533-538.

Oda, H., et al (2009) "Monomethylation of histone H4-lysine 20 is involved in chromosome structure and stability and is essential for mouse development"; *Mol Cell Biol* 29(8); pp. 2278-2295.

Olsen, J.B.,et al (2016) "Quantitative Profiling of the Activity of Protein Lysine Methyltransferase SMYD2 Using Silac-Based Proteomics. Molecular & cellular proteomics"; *Mol Cell Proteomics*. 15; pp. 892-905.

Ott, M., et al. (2010) "The Cellular lysine methyltransferase Set7/9-KMT7 binds HIV-1 TAR RNA, monomethylates the viral transactivator Tat, and enhances HIV transcription"; Cell Host Microbe 7, 234-244.

(56) References Cited

OTHER PUBLICATIONS

Pachaiyappan et al. (2004) "Design of small molecule epigenetic modulators"; *Bioorganic & Medicinal Chemistry Letters* vol. 24; pp. 21-32.
Pal-Bhadra et al. (2004) "Heterochromatic silencing and HP1 localization in *Drosophila* are dependent on the RNAi machinery"; *Science*, 303; pp. 669-672.
Patel, D.J., and Wang, Z. (2013). Readout of epigenetic modifications. Annual review of biochemistry 82, 81-118.
Pekaraik et al. (2005) "Design of shRNAs for RNAi—A lesson from pre-miRNA processing: possible clinical applications"; *Brain Res Bull*. 68(1-2); pp. 115-120; Epub Sep. 9, 2005.
Perrault et al. (1990) "Mixed deoxyribo-and ribo-oligonucleotides with catalytic activity"; *Nature* 344; pp. 565-568.
Pesavento, J. et al (2008) "Certain and progressive methylation of histone H4 at lysine 20 during the cell cycle"; *Mol Cell Biol* 28; pp. 468-486.
Piao, L., et al (2014) "The histone methyltransferase SMYD2 methylates PARP1 and promotes poly(ADP-ribosyl)ation activity in cancer cells"; *Neoplasia* 16(3); pp. 257-264.
Pushparaj et al. (2006) "Short interfering RNA (siRNA) as a novel therapeutic"; *Clin Exp Pharmacol Physiol*. 33(5-6); pp. 504-510.
Rasmussen, T.A., et al (2016) "Reversal of Latency as Part of a Cure for HIV-1"; *Trends in microbiology* 24; pp. 90-97.
Saddic, L.A., et al (2010) "Methylation of the retinoblastoma tumor suppressor by SMYD2"; . *J Biol Chem* 285; pp. 37733-37740.
Saison-Behmoaras et al. (1991) "Short modified antisense oligonucleotides directed against Ha-ras point mutation induce selective cleavage of the mRNA and inhibit T24 cells proliferation"; *EMBO J*. 10; pp. 1111-1118.
Schotta, G., et al (2004) "A silencing pathway to induce H3-K9 and H4-K20 trimethylation at constitutive heterochromatin"; *Genes Dev* 18; pp. 1251-1262.
Schotta, G., et al (2008) "A chromatin-wide transition to H4K20 monomethylation impairs genome integrity and programmed DNA rearrangements in the mouse"; *Genes Dev* 22; pp. 2048-2061.
Schroder, S., et al. (2013) "Acetylation of RNA polymerase II regulates growth-factor-induced gene transcription in mammalian cells"; *Mol Cell* 52; pp. 314-324.
Schwarz et al. (2002) "Evidence that siRNAs function as guides, not primers, in the *Drosophila* and human RNAi pathways"; *Molecular Cell*, 10, 537-568.
Shea et al., (1990) "Synthesis, hybridization properties and antiviral activity of lipid-oligodeoxynucleotide conjugates"; *Nucl. Acids Res*. 18(13); pp. 3777-3783.
Sheridan, P.L., et al (1997) "Histone acetyltransferases regulate HIV-1 enhancer activity in vitro"; *Genes Dev 11*; pp. 3327-3340.
Song, Y.,et al (2016) "Targeting histone methylation for cancer therapy: enzymes, inhibitors, biological activity and perspectives"; *Journal of hematology & oncology* 9; pp. 49-; 9:49,pp. 1-21.
Spina, C.A., et al. (2013) "An in-depth comparison of latent HIV-1 reactivation in multiple cell model systems and resting CD4+ T cells from aviremic patients"; *PLoS Pathog* 9, e1003834.
Stender, et al (2012) "Control of proinflammatory gene programs by regulated trimethylation and demethylation of histone H4K20"; Mol Cell 48(1); pp. 28-38.
Svinarchuk et al., (1993) "Inhibition of HIV proliferation in MT-4 cells by antisense oligonucleotide conjugated to lipophilic groups"; *Biochimie*, 75; pp. 49-54.
Tan, M., et al. (2011) "Identification of 67 histone marks and histone lysine crotonylation as a new type of histone modification"; *Cell 146*; pp. 1016-1028.
Throner, S.C., et al. (2015). "Discovery and synthesis of substrate competitive SMYD2 inhibitors"; Abstracts of Papers,. In 250th National Meeting of the American Chemical Society, (Boston, MA, Aug. 16-20, 2015; American Chemical Society: Washington, DC, 2015; MEDI 513).
Trojer, P., et al. (2011) "L3MBTL2 protein acts in concert with PcG protein-mediated monoubiquitination of H2A to establish a repressive chromatin structure"; *Mol Cell 42*; pp. 438-450.
Trojer, P., et al. (2007) "L3MBTL1, a histone-methylation-dependent chromatin lock"; *Cell 129*; pp. 915-928.
Van Lint, et al (1996) "Transcriptional activation and chromatin remodeling of the HIV-1 promoter in response to histone acetylation"; *EMBO J 15*; pp. 1112-1120.
Van Nuland, R., and Gozani, O. (2016) "Histone H4 Lysine 20 (H4K20) Methylation, Expanding the Signaling Potential of the Proteome One Methyl Moiety at a Time"; *Molecular & cellular proteomics : MCP 15*; pp. 55-764.
Verdel et al. (2004) "RNAi-mediated targeting of heterochromatin by the RITS complex"; *Science*, 303; pp. 672-676.
Verdin, E., et al (1993) "Chromatin disruption in the promoter of human immunodeficiency virus type 1 during transcriptional activation"; *EMBO J 12*; pp. 3249-3259.
Verma and Eckstein (1998) "Modified oligonucleotides: synthesis and strategy for users"; *Annu. Rev. Biochem.*, 67; pp. 99-134.
Volpe et al. (2002) "Regulation of heterochromatic silencing and histone H3 lysine-9 methylation by RNAi"; *Science 297*; pp. 1833-1837.
Wagner and Jung (2012) "New lysine methyltransferase drug targets in cancer"; *Nat. Biotechnol*. 30(7); pp. 622-623.
Wahlestedt et al. (2000) "Potent and nontoxic antisense oligonucleotides containing locked nucleic acids"; *Proc. Natl. Acad. Sci. U.S.A. 97*; pp. 5633-5638.
Wang, R., et al (2011) "The transcription factor Myc controls metabolic reprogramming upon T lymphocyte activation"; *Immunity 35*; pp. 871-882.
Wang et al. (2011) "Structure of Human SMYD2 Protein Reveals the Basis of p53 Tumor Suppressor Methylation" *J. Biol. Chem*. 286; pp. 38725-38737.
Wender et al. (2000) "The design, synthesis, and evaluation of molecules that enable or enhance cellular uptake: peptoid molecular transporters"; *Proc. Natl. Acad. Sci. USA 97*; pp. 13003-13008.
Williams, S.A., et al. (2006) "NF-kappaB p50 promotes HIV latency through HDAC recruitment and repression of transcriptional initiation"; *EMBO J 25*; pp. 139-149.
Wincott et al. (1995) "Synthesis, deprotection, analysis and purification of RNA and ribozymes"; *Nucleic Acids Res*. 23; pp. 2677-2684.
Wu, J., et al. (2011). "Biochemical characterization of human SET and MYND domain-containing protein 2 methyltransferase"; *Biochemistry 50*; pp. 6488-6497.
Xie et al. (2006) "Harnessing in vivo siRNA delivery for drug discovery and therapeutic development"; *Drug Discov Today* 11(1-2); pp. 67-73.
Xu et al. (2011) "Structure of human lysine methyltransferase Smyd2 reveals insights into the substrate divergence in Smyd proteins"; *J. Mol. Cell. Biol. 3*; pp. 293-300.
Zender et al. (2002) "VP22-mediated intercellular transport of p53 in hepatoma cells in vitro and in vivo"; *Cancer Gene Ther*. 9(6); pp. 489-496.
Zhang, X., et al. (2013) "Regulation of estrogen receptor alpha by histone methyltransferase SMYD2-mediated protein methylation"; *PNAS 110*; pp. 17284-17289.

\* cited by examiner

Amino Acid Sequence of human Smyd2

```
  1 mraegiggie rfcspgkgrg lralqpfqvg dlifscpaya yvitvnergn hceycftrke
 61 glskcgrckq afycnvecqk edwpmhklec spmvvfgenw npsetvrlta rilakqkihp
121 ertpseklia vkefeshldk idnekkdliq sdiaalhhfy skhlgfpdnd slvvlfaqvn
181 cngftiedee lshlgsaifp dvalmnhscc pnvivtykgt laevravqei kpgeevftsy
241 idilyptedr ndrlrdsyff tcecqecttk dkdkakveir klsdppkaea irdmvryarn
301 vieefrrakh ykspsellei celsqekmss vfedsnvyml hmmyqamgvc lymqdwegal
361 qyggkiikpy skhyplysin vasmwiklgr lymglehkaa gekalkkaia imevahgkdh
421 pyiseikqei esh (SEQ ID NO:1)
```

FIGURE 12

Nucleotide sequences of Smyd2 shRNAs, scramble control shRNA, and luciferase control shRNA

SMYD2 shRNAs
TRCN0000276155
Region:3UTR    Mean KnockDown Level: 0.92    Cell Line: A549
TRC Version: 2    Clone ID:NM_020197.2-1367s21c1
Sequence:CCGGACTTAGTTCAGAAACCTTAAACTCGAGTTTAAGGTTTCTGAACTAAGTTTTTTG

TRCN0000276082
Region:CDS    Mean KnockDown Level: 0.8    Cell Line: A549
TRC Version: 2    Clone ID:NM_020197.2-623s21c1
Sequence:CCGGCGATATTTCCTGATGTTGCATCTCGAGATGCAACATCAGGAAATATCGTTTTTG

TRCN0000276083
Region:CDS    Mean KnockDown Level: 0.95    Cell Line: A549
TRC Version: 2    Clone ID:NM_020197.2-421s21c1
Sequence:CCGGGCTGTGAAGGAGTTTGAATCACTCGAGTGATTCAAACTCCTTCACAGCTTTTTG

TRCN0000276085
Region:CDS    Mean KnockDown Level: 0.97    Cell Line: A549
TRC Version: 2    Clone ID:NM_020197.2-1281s21c1
Sequence:CCGGCGGCAAAGATCATCCATATATCTCGAGATATATGGATGATCTTTGCCGTTTTTG

TRCN0000130774
Region:CDS    Mean KnockDown Level: 0.93    Cell Line: A549
TRC Version: 1    Clone ID:NM_020197.1-1008s1c1
Sequence:CCGGGCTCTGTGTTTGAGGACAGTACTCGAGTACTGTCCTCAAACACAGAGCTTTTTG

TRCN0000130403
Region:CDS    Mean KnockDown Level: 0.93    Cell Line: A549
TRC Version: 1    Clone ID:NM_020197.1-410s1c1
Sequence:CCGGGCTGTGAAGGAGTTTGAATCACTCGAGTGATTCAAACTCCTTCACAGCTTTTTG

TRCN0000128349
Region:CDS    Mean KnockDown Level: 0.78    Cell Line: A549
TRC Version: 1    Clone ID:NM_020197.1-612s1c1
Sequence:CCGGCGATATTTCCTGATGTTGCATCTCGAGATGCAACATCAGGAAATATCGTTTTTG

Scramble Control shRNA

MISSION pLKO.1-puro, Non-Mammalian shRNA Control, TRC1/1.5 Non human or mouse shRNA
Sequence:CCGGCAACAAGATGAAGAGCACCAACTCGAGTTGGTGCTCTTCATCTTGTTGTTTTT

Luciferase Control shRNA

MISSION pLKO.1-puro Luciferase shRNA Control TRC1/1.5 shRNA targeting Luciferase
Sequence: CCGGCGCTGAGTACTTCGAAATGTCCTCGAGGACATTTCGAAGTACTCAGCGTTTTT

FIGURE 13

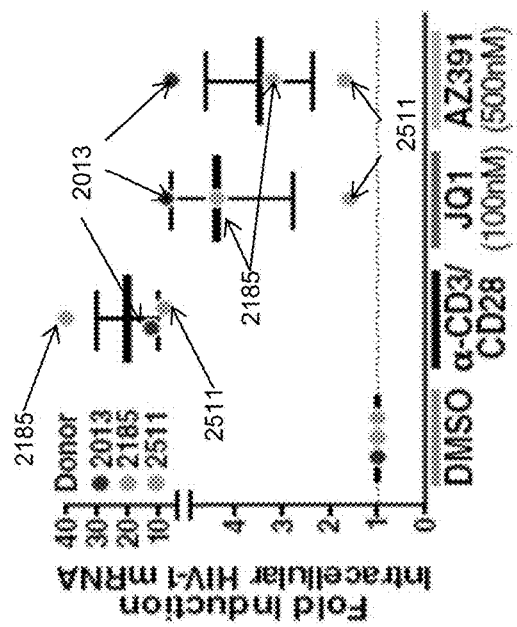
FIGURE 15E
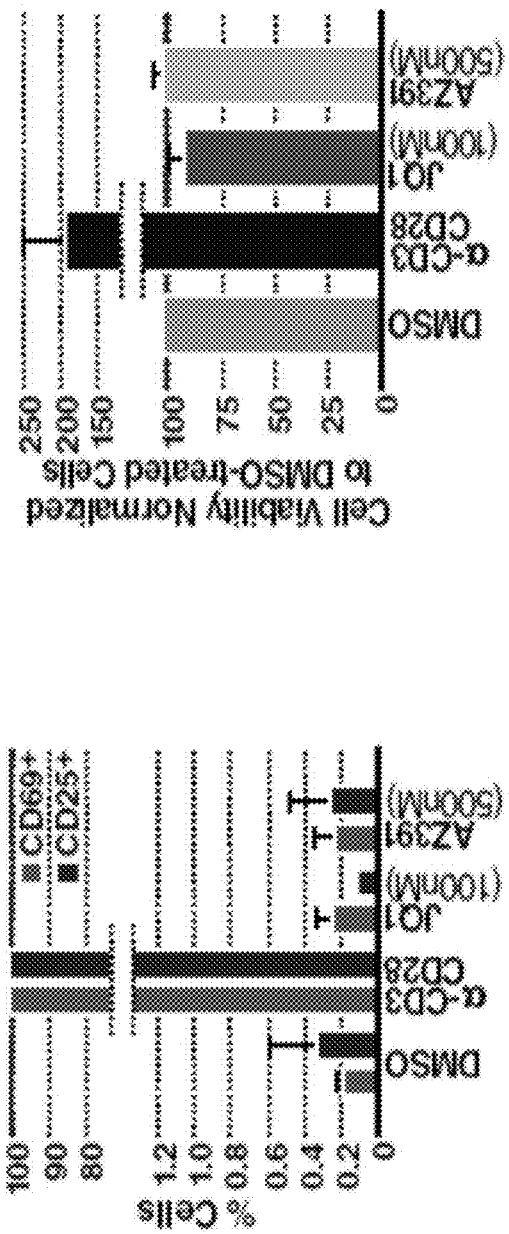
FIGURE 15G
FIGURE 15F

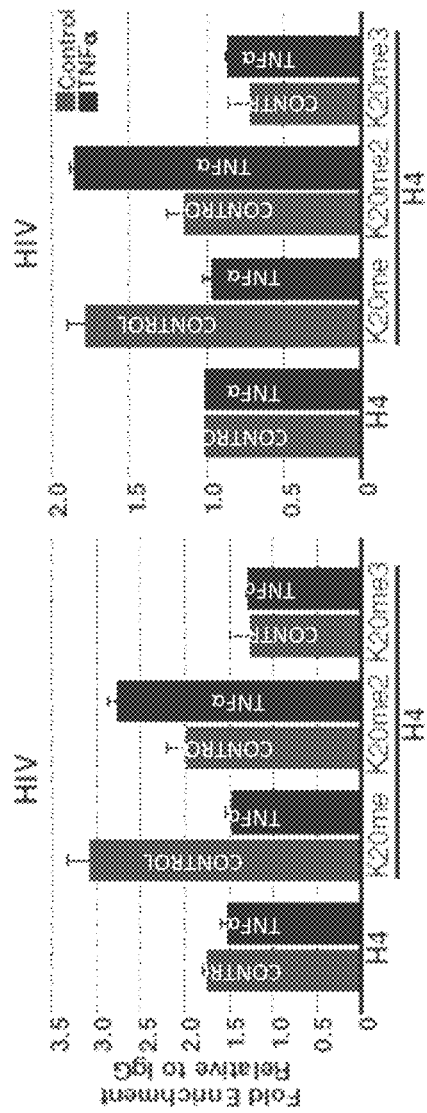
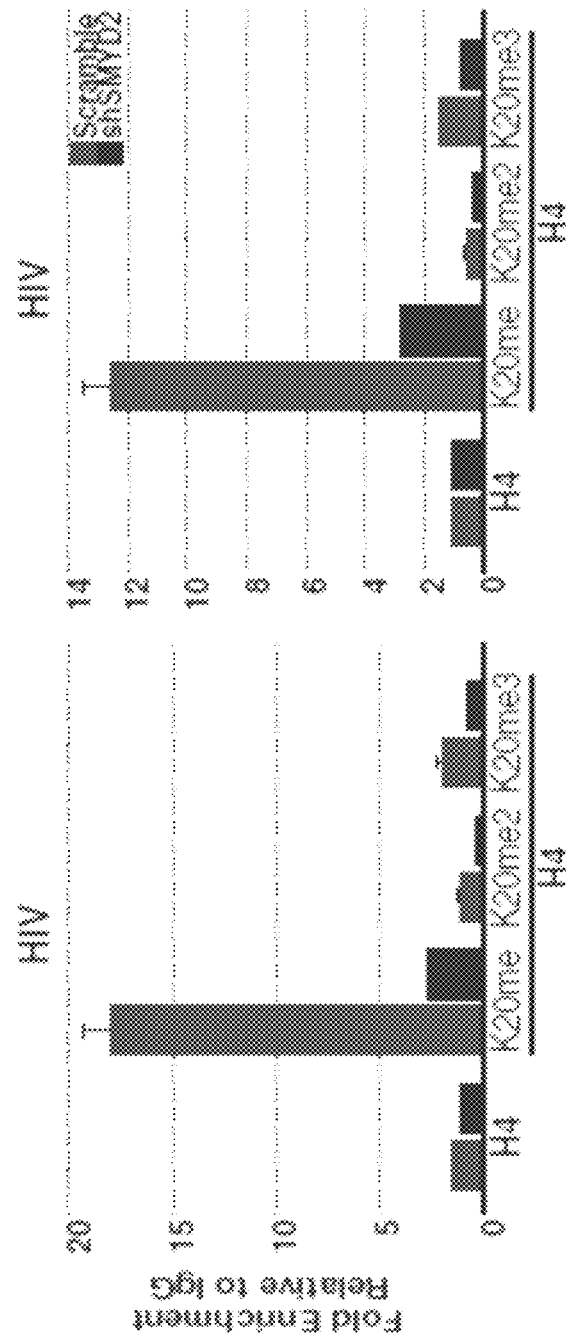
FIGURE 18A
FIGURE 18B

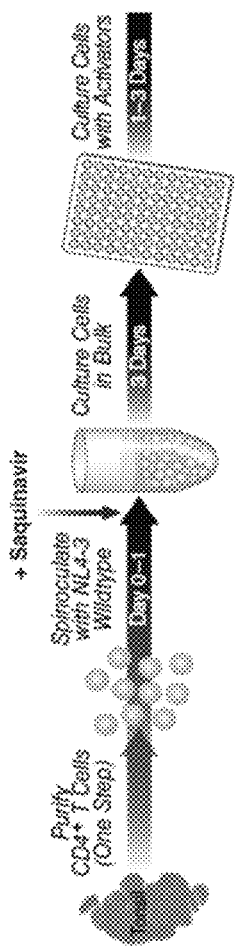
FIGURE 21A
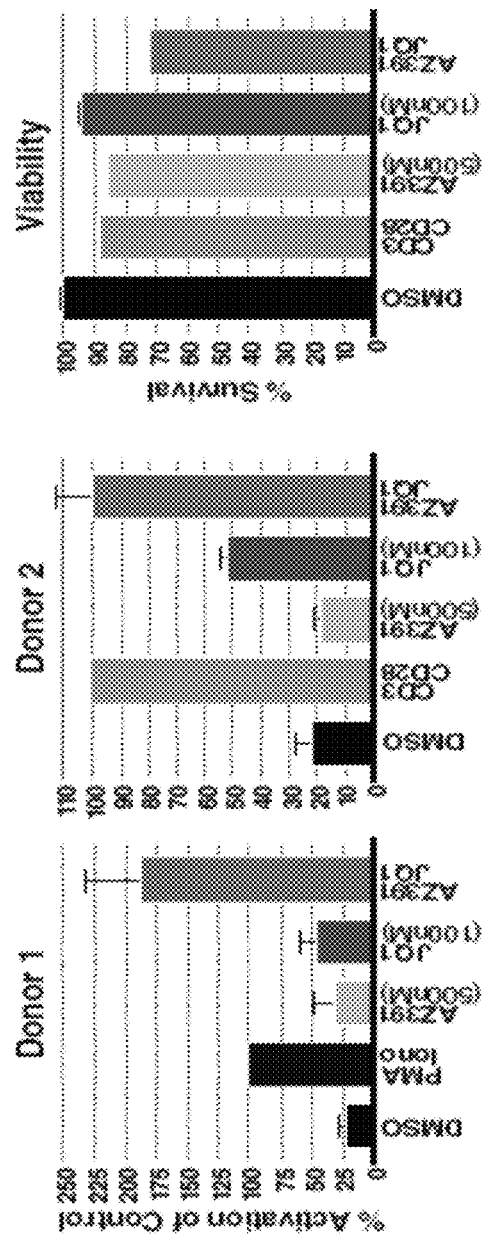
FIGURE 21B
FIGURE 21C

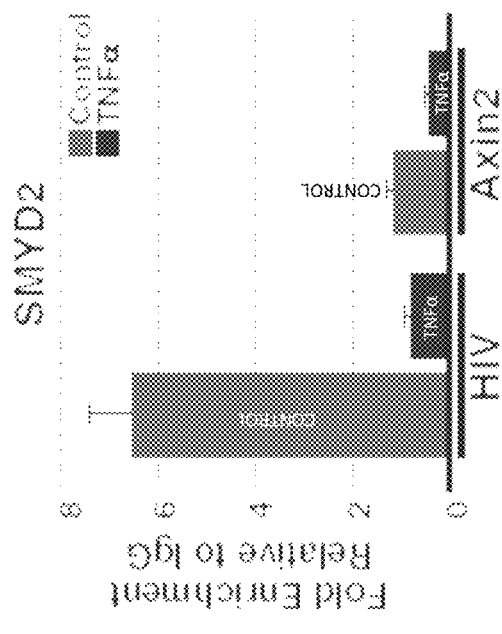
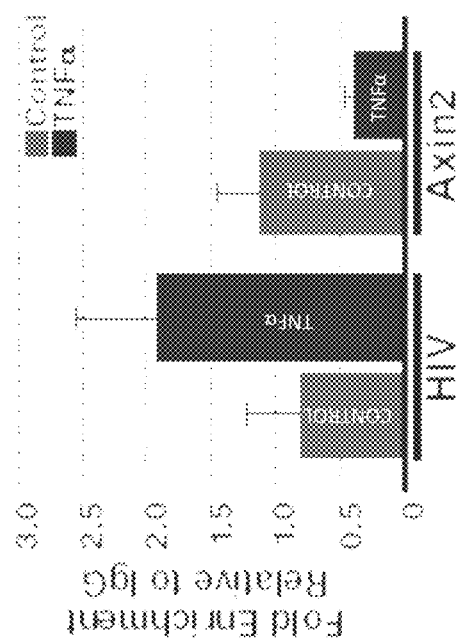
FIGURE 23A
FIGURE 23B

SEQUENCE LISTING

```
<160> NUMBER OF SEQ ID NOS: 145

<210> SEQ ID NO 1
<211> LENGTH: 433
<212> TYPE: PRT
<213> ORGANISM: Homo sapiens

<400> SEQUENCE: 1

Met Arg Ala Glu Gly Leu Gly Gly Leu Glu Arg Phe Cys Ser Pro Gly
1               5                   10                  15

Lys Gly Arg Gly Leu Arg Ala Leu Gln Pro Phe Gln Val Gly Asp Leu
            20                  25                  30

Leu Phe Ser Cys Pro Ala Tyr Ala Tyr Val Leu Thr Val Asn Glu Arg
        35                  40                  45

Gly Asn His Cys Glu Tyr Cys Phe Thr Arg Lys Glu Gly Leu Ser Lys
    50                  55                  60

Cys Gly Arg Cys Lys Gln Ala Phe Tyr Cys Asn Val Glu Cys Gln Lys
65                  70                  75                  80

Glu Asp Trp Pro Met His Lys Leu Glu Cys Ser Pro Met Val Val Phe
                85                  90                  95

Gly Glu Asn Trp Asn Pro Ser Glu Thr Val Arg Leu Thr Ala Arg Ile
            100                 105                 110

Leu Ala Lys Gln Lys Ile His Pro Glu Arg Thr Pro Ser Glu Lys Leu
        115                 120                 125

Leu Ala Val Lys Glu Phe Glu Ser His Leu Asp Lys Leu Asp Asn Glu
    130                 135                 140

Lys Lys Asp Leu Ile Gln Ser Asp Ile Ala Ala Leu His His Phe Tyr
145                 150                 155                 160

Ser Lys His Leu Gly Phe Pro Asp Asn Asp Ser Leu Val Val Leu Phe
                165                 170                 175

Ala Gln Val Asn Cys Asn Gly Phe Thr Ile Glu Asp Glu Glu Leu Ser
            180                 185                 190

His Leu Gly Ser Ala Ile Phe Pro Asp Val Ala Leu Met Asn His Ser
        195                 200                 205

Cys Cys Pro Asn Val Ile Val Thr Tyr Lys Gly Thr Leu Ala Glu Val
    210                 215                 220

Arg Ala Val Gln Glu Ile Lys Pro Gly Glu Glu Val Phe Thr Ser Tyr
225                 230                 235                 240

Ile Asp Leu Leu Tyr Pro Thr Glu Asp Arg Asn Asp Arg Leu Arg Asp
                245                 250                 255

Ser Tyr Phe Phe Thr Cys Glu Cys Gln Glu Cys Thr Thr Lys Asp Lys
            260                 265                 270

Asp Lys Ala Lys Val Glu Ile Arg Lys Leu Ser Asp Pro Pro Lys Ala
        275                 280                 285

Glu Ala Ile Arg Asp Met Val Arg Tyr Ala Arg Asn Val Ile Glu Glu
    290                 295                 300

Phe Arg Arg Ala Lys His Tyr Lys Ser Pro Ser Glu Leu Leu Glu Ile
305                 310                 315                 320
```

```
Cys Glu Leu Ser Gln Glu Lys Met Ser Ser Val Phe Glu Asp Ser Asn
            325                 330                 335

Val Tyr Met Leu His Met Met Tyr Gln Ala Met Gly Val Cys Leu Tyr
        340                 345                 350

Met Gln Asp Trp Glu Gly Ala Leu Gln Tyr Gly Gln Lys Ile Ile Lys
            355                 360                 365

Pro Tyr Ser Lys His Tyr Pro Leu Tyr Ser Leu Asn Val Ala Ser Met
        370                 375                 380

Trp Leu Lys Leu Gly Arg Leu Tyr Met Gly Leu Glu His Lys Ala Ala
385                 390                 395                 400

Gly Glu Lys Ala Leu Lys Lys Ala Ile Ala Ile Met Glu Val Ala His
            405                 410                 415

Gly Lys Asp His Pro Tyr Ile Ser Glu Ile Lys Gln Glu Ile Glu Ser
            420                 425                 430

His

<210> SEQ ID NO 2
<211> LENGTH: 58
<212> TYPE: DNA
<213> ORGANISM: Artificial sequence
<220> FEATURE:
<223> OTHER INFORMATION: synthetic nucleotide sequence

<400> SEQUENCE: 2
ccggacttag ttcagaaacc ttaaactcga gtttaaggtt tctgaactaa gtttttg      58

<210> SEQ ID NO 3
<211> LENGTH: 58
<212> TYPE: DNA
<213> ORGANISM: Artificial sequence
<220> FEATURE:
<223> OTHER INFORMATION: synthetic nucleotide sequence

<400> SEQUENCE: 3
ccggcgatat ttcctgatgt tgcatctcga gatgcaacat caggaaatat cgttttg      58

<210> SEQ ID NO 4
<211> LENGTH: 58
<212> TYPE: DNA
<213> ORGANISM: Artificial sequence
<220> FEATURE:
<223> OTHER INFORMATION: synthetic nucleotide sequence

<400> SEQUENCE: 4
ccgggctgtg aaggagtttg aatcactcga gtgattcaaa ctccttcaca gctttttg    58

<210> SEQ ID NO 5
<211> LENGTH: 58
<212> TYPE: DNA
<213> ORGANISM: Artificial sequence
<220> FEATURE:
<223> OTHER INFORMATION: synthetic nucleotide sequence

<400> SEQUENCE: 5
ccggcggcaa agatcatcca tatatctcga gatatatgga tgatctttgc cgttttg      58

<210> SEQ ID NO 6
<211> LENGTH: 59
<212> TYPE: DNA
<213> ORGANISM: Artificial sequence
<220> FEATURE:
<223> OTHER INFORMATION: synthetic nucleotide sequence
```

<400> SEQUENCE: 6
ccgggctctg tgtttgagga cagtactcga gtactgtcct caaacacaga gctttttg    59

<210> SEQ ID NO 7
<211> LENGTH: 59
<212> TYPE: DNA
<213> ORGANISM: Artificial sequence
<220> FEATURE:
<223> OTHER INFORMATION: synthetic nucleotide sequence

<400> SEQUENCE: 7
ccgggctgtg aaggagtttg aatcactcga gtgattcaaa ctccttcaca gctttttg    59

<210> SEQ ID NO 8
<211> LENGTH: 59
<212> TYPE: DNA
<213> ORGANISM: Artificial sequence
<220> FEATURE:
<223> OTHER INFORMATION: synthetic nucleotide sequence

<400> SEQUENCE: 8
ccggcgatat ttcctgatgt tgcatctcga gatgcaacat caggaaatat cgtttttg    59

<210> SEQ ID NO 9
<211> LENGTH: 57
<212> TYPE: DNA
<213> ORGANISM: Artificial sequence
<220> FEATURE:
<223> OTHER INFORMATION: synthetic nucleotide sequence

<400> SEQUENCE: 9
ccggcaacaa gatgaagagc accaactcga gttggtgctc ttcatcttgt tgttttt    57

<210> SEQ ID NO 10
<211> LENGTH: 57
<212> TYPE: DNA
<213> ORGANISM: Artificial sequence
<220> FEATURE:
<223> OTHER INFORMATION: synthetic nucleotide sequence

<400> SEQUENCE: 10
ccggcgctga gtacttcgaa atgtcctcga ggacatttcg aagtactcag cgttttt    57

<210> SEQ ID NO 11
<211> LENGTH: 11
<212> TYPE: PRT
<213> ORGANISM: Artificial sequence
<220> FEATURE:
<223> OTHER INFORMATION: synthetic peptide sequence

<400> SEQUENCE: 11

Tyr Gly Arg Lys Lys Arg Arg Gln Arg Arg Arg
1               5                   10

<210> SEQ ID NO 12
<211> LENGTH: 12
<212> TYPE: PRT
<213> ORGANISM: Artificial sequence
<220> FEATURE:
<223> OTHER INFORMATION: synthetic peptide sequence

<400> SEQUENCE: 12

Arg Arg Gln Arg Arg Thr Ser Lys Leu Met Lys Arg
1               5                   10

```
<210> SEQ ID NO 13
<211> LENGTH: 27
<212> TYPE: PRT
<213> ORGANISM: Artificial sequence
<220> FEATURE:
<223> OTHER INFORMATION: synthetic peptide sequence

<400> SEQUENCE: 13

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 14
<211> LENGTH: 33
<212> TYPE: PRT
<213> ORGANISM: Artificial sequence
<220> FEATURE:
<223> OTHER INFORMATION: synthetic peptide sequence

<400> SEQUENCE: 14

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 15
<211> LENGTH: 16
<212> TYPE: PRT
<213> ORGANISM: Artificial sequence
<220> FEATURE:
<223> OTHER INFORMATION: synthetic nucleotide sequence

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 9
<212> TYPE: PRT
<213> ORGANISM: Artificial sequence
<220> FEATURE:
<223> OTHER INFORMATION: synthetic nucleotide sequence

<400> SEQUENCE: 16

Arg Lys Lys Arg Arg Gln Arg Arg Arg
1               5

<210> SEQ ID NO 17
<211> LENGTH: 8
<212> TYPE: PRT
<213> ORGANISM: Artificial sequence
<220> FEATURE:
<223> OTHER INFORMATION: synthetic peptide sequence

<400> SEQUENCE: 17

Arg Lys Lys Arg Arg Gln Arg Arg
1               5

<210> SEQ ID NO 18
<211> LENGTH: 11
<212> TYPE: PRT
<213> ORGANISM: Artificial sequence
<220> FEATURE:
<223> OTHER INFORMATION: synthetic peptide sequence
```

```
<400> SEQUENCE: 18

Tyr Ala Arg Ala Ala Ala Arg Gln Ala Arg Ala
1               5                   10

<210> SEQ ID NO 19
<211> LENGTH: 11
<212> TYPE: PRT
<213> ORGANISM: Artificial sequence
<220> FEATURE:
<223> OTHER INFORMATION: synthetic peptide sequence

<400> SEQUENCE: 19

Thr His Arg Leu Pro Arg Arg Arg Arg Arg Arg
1               5                   10

<210> SEQ ID NO 20
<211> LENGTH: 11
<212> TYPE: PRT
<213> ORGANISM: Artificial sequence
<220> FEATURE:
<223> OTHER INFORMATION: synthetic peptide sequence

<400> SEQUENCE: 20

Gly Gly Arg Arg Ala Arg Arg Arg Arg Arg Arg
1               5                   10

<210> SEQ ID NO 21
<211> LENGTH: 36
<212> TYPE: PRT
<213> ORGANISM: Artificial sequence
<220> FEATURE:
<223> OTHER INFORMATION: synthetic peptide sequence

<400> SEQUENCE: 21

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 22
<211> LENGTH: 418
<212> TYPE: PRT
<213> ORGANISM: Homo sapiens

<400> SEQUENCE: 22

Met Ala Ala Ser Met Cys Asp Val Phe Ser Phe Cys Val Gly Val Ala
1               5                   10                  15

Gly Arg Ala Arg Val Ser Val Glu Val Arg Phe Val Ser Ser Ala Lys
            20                  25                  30

Gly Lys Gly Leu Phe Ala Thr Gln Leu Ile Arg Lys Gly Glu Thr Ile
        35                  40                  45

Phe Val Glu Arg Pro Leu Val Ala Ala Gln Phe Leu Trp Asn Ala Leu
    50                  55                  60

Tyr Arg Tyr Arg Ala Cys Asp His Cys Leu Arg Ala Leu Glu Lys Ala
65                  70                  75                  80

Glu Glu Asn Ala Gln Arg Leu Thr Gly Lys Pro Gly Gln Val Leu Pro
                85                  90                  95

His Pro Glu Leu Cys Thr Val Arg Lys Asp Leu His Gln Asn Cys Pro
            100                 105                 110
```

His Cys Gln Val Met Tyr Cys Ser Ala Glu Cys Arg Leu Ala Ala Thr
            115                 120                 125

Glu Gln Tyr His Gln Val Leu Cys Pro Gly Pro Ser Gln Asp Asp Pro
130                 135                 140

Leu His Pro Leu Asn Lys Leu Gln Glu Ala Trp Arg Ser Ile His Tyr
145                 150                 155                 160

Pro Pro Glu Thr Ala Ser Ile Met Leu Met Ala Arg Met Val Ala Thr
                165                 170                 175

Val Lys Gln Ala Lys Asp Lys Asp Arg Trp Ile Arg Leu Phe Ser Gln
            180                 185                 190

Phe Cys Asn Lys Thr Ala Asn Glu Glu Glu Ile Val His Lys Leu
            195                 200                 205

Leu Gly Asp Lys Phe Lys Gly Gln Leu Glu Leu Leu Arg Arg Leu Phe
            210                 215                 220

Thr Glu Ala Leu Tyr Glu Glu Ala Val Ser Gln Trp Phe Thr Pro Asp
225                 230                 235                 240

Gly Phe Arg Ser Leu Phe Ala Leu Val Gly Thr Asn Gly Gln Gly Ile
                245                 250                 255

Gly Thr Ser Ser Leu Ser Gln Trp Val His Ala Cys Asp Thr Leu Glu
            260                 265                 270

Leu Lys Pro Gln Asp Arg Glu Gln Leu Asp Ala Phe Ile Asp Gln Leu
            275                 280                 285

Tyr Lys Asp Ile Glu Ala Ala Thr Gly Glu Phe Leu Asn Cys Glu Gly
            290                 295                 300

Ser Gly Leu Phe Val Leu Gln Ser Cys Cys Asn His Ser Cys Val Pro
305                 310                 315                 320

Asn Ala Glu Thr Ser Phe Pro Glu Asn Asn Phe Leu Leu His Val Thr
                325                 330                 335

Ala Leu Glu Asp Ile Lys Pro Gly Glu Glu Ile Cys Ile Ser Tyr Leu
            340                 345                 350

Asp Cys Cys Gln Arg Glu Arg Ser Arg His Ser Arg His Lys Ile Leu
            355                 360                 365

Arg Glu Asn Tyr Leu Phe Val Cys Ser Cys Pro Lys Cys Leu Ala Glu
            370                 375                 380

Ala Asp Glu Pro Asn Val Thr Ser Glu Glu Glu Glu Glu Glu Glu
385                 390                 395                 400

Glu Glu Glu Gly Glu Pro Glu Asp Ala Glu Leu Gly Asp Glu Met Thr
                405                 410                 415

Asp Val

<210> SEQ ID NO 23
<211> LENGTH: 2969
<212> TYPE: PRT
<213> ORGANISM: Homo sapiens

<400> SEQUENCE: 23

Met Asp Pro Arg Asn Thr Ala Met Leu Gly Leu Gly Ser Asp Ser Glu
1               5                   10                  15

Gly Phe Ser Arg Lys Ser Pro Ser Ala Ile Ser Thr Gly Thr Leu Val
            20                  25                  30

Ser Lys Arg Glu Val Glu Leu Glu Lys Asn Thr Lys Glu Glu Glu Asp
        35                  40                  45

Leu Arg Lys Arg Asn Arg Glu Asn Ile Glu Ala Gly Lys Asp Asp
    50                  55                  60

```
Gly Leu Thr Asp Ala Gln Gln Gln Phe Ser Val Lys Glu Thr Asn Phe
 65                  70                  75                  80

Ser Glu Gly Asn Leu Lys Leu Lys Ile Gly Leu Gln Ala Lys Arg Thr
                 85                  90                  95

Lys Lys Pro Pro Lys Asn Leu Glu Asn Tyr Val Cys Arg Pro Ala Ile
            100                 105                 110

Lys Thr Thr Ile Lys His Pro Arg Lys Ala Leu Lys Ser Gly Lys Met
        115                 120                 125

Thr Asp Glu Lys Asn Glu His Cys Pro Ser Lys Arg Asp Pro Ser Lys
    130                 135                 140

Leu Tyr Lys Lys Ala Asp Asp Val Ala Ala Ile Glu Cys Gln Ser Glu
145                 150                 155                 160

Glu Val Ile Arg Leu His Ser Gln Gly Glu Asn Asn Pro Leu Ser Lys
                165                 170                 175

Lys Leu Ser Pro Val His Ser Glu Met Ala Asp Tyr Ile Asn Ala Thr
            180                 185                 190

Pro Ser Thr Leu Leu Gly Ser Arg Asp Pro Asp Leu Lys Asp Arg Ala
        195                 200                 205

Leu Leu Asn Gly Gly Thr Ser Val Thr Glu Lys Leu Ala Gln Leu Ile
210                 215                 220

Ala Thr Cys Pro Pro Ser Lys Ser Ser Lys Thr Lys Pro Lys Lys Leu
225                 230                 235                 240

Gly Thr Gly Thr Thr Ala Gly Leu Val Ser Lys Asp Leu Ile Arg Lys
                245                 250                 255

Ala Gly Val Gly Ser Val Ala Gly Ile Ile His Lys Asp Leu Ile Lys
            260                 265                 270

Lys Pro Thr Ile Ser Thr Ala Val Gly Leu Val Thr Lys Asp Pro Gly
        275                 280                 285

Lys Lys Pro Val Phe Asn Ala Ala Val Gly Leu Val Asn Lys Asp Ser
    290                 295                 300

Val Lys Lys Leu Gly Thr Gly Thr Thr Ala Val Phe Ile Asn Lys Asn
305                 310                 315                 320

Leu Gly Lys Lys Pro Gly Thr Ile Thr Thr Val Gly Leu Leu Ser Lys
                325                 330                 335

Asp Ser Gly Lys Lys Leu Gly Ile Gly Ile Val Pro Gly Leu Val His
            340                 345                 350

Lys Glu Ser Gly Lys Lys Leu Gly Leu Gly Thr Val Gly Leu Val
        355                 360                 365

Asn Lys Asp Leu Gly Lys Lys Leu Gly Ser Thr Val Gly Leu Val Ala
    370                 375                 380

Lys Asp Cys Ala Lys Lys Ile Val Ala Ser Ser Ala Met Gly Leu Val
385                 390                 395                 400

Asn Lys Asp Ile Gly Lys Lys Leu Met Ser Cys Pro Leu Ala Gly Leu
                405                 410                 415

Ile Ser Lys Asp Ala Ile Asn Leu Lys Ala Glu Ala Leu Leu Pro Thr
            420                 425                 430

Gln Glu Pro Leu Lys Ala Ser Cys Ser Thr Asn Ile Asn Asn Gln Glu
        435                 440                 445

Ser Gln Glu Leu Ser Glu Ser Leu Lys Asp Ser Ala Thr Ser Lys Thr
    450                 455                 460

Phe Glu Lys Asn Val Val Arg Gln Asn Lys Glu Ser Ile Leu Glu Lys
465                 470                 475                 480
```

```
Phe Ser Val Arg Lys Glu Ile Ile Asn Leu Glu Lys Glu Met Phe Asn
                485                 490                 495
Glu Gly Thr Cys Ile Gln Gln Asp Ser Phe Ser Ser Glu Lys Gly
            500                 505                 510
Ser Tyr Glu Thr Ser Lys His Glu Lys Gln Pro Val Tyr Cys Thr
        515                 520                 525
Ser Pro Asp Phe Lys Met Gly Gly Ala Ser Asp Val Ser Thr Ala Lys
    530                 535                 540
Ser Pro Phe Ser Ala Val Gly Glu Ser Asn Leu Pro Ser Pro Ser Pro
545                 550                 555                 560
Thr Val Ser Val Asn Pro Leu Thr Arg Ser Pro Glu Thr Ser Ser
                565                 570                 575
Gln Leu Ala Pro Asn Pro Leu Leu Leu Ser Ser Thr Thr Glu Leu Ile
                580                 585                 590
Glu Glu Ile Ser Glu Ser Val Gly Lys Asn Gln Phe Thr Ser Glu Ser
            595                 600                 605
Thr His Leu Asn Val Gly His Arg Ser Val Gly His Ser Ile Ser Ile
    610                 615                 620
Glu Cys Lys Gly Ile Asp Lys Glu Val Asn Asp Ser Lys Thr Thr His
625                 630                 635                 640
Ile Asp Ile Pro Arg Ile Ser Ser Ser Leu Gly Lys Lys Pro Ser Leu
                645                 650                 655
Thr Ser Glu Ser Ser Ile His Thr Ile Thr Pro Ser Val Val Asn Phe
                660                 665                 670
Thr Ser Leu Phe Ser Asn Lys Pro Phe Leu Lys Leu Gly Ala Val Ser
            675                 680                 685
Ala Ser Asp Lys His Cys Gln Val Ala Glu Ser Leu Ser Thr Ser Leu
    690                 695                 700
Gln Ser Lys Pro Leu Lys Lys Arg Lys Gly Arg Lys Pro Arg Trp Thr
705                 710                 715                 720
Lys Val Val Ala Arg Ser Thr Cys Arg Ser Pro Lys Gly Leu Glu Leu
                725                 730                 735
Glu Arg Ser Glu Leu Phe Lys Asn Val Ser Cys Ser Ser Leu Ser Asn
            740                 745                 750
Ser Asn Ser Glu Pro Ala Lys Phe Met Lys Asn Ile Gly Pro Pro Ser
        755                 760                 765
Phe Val Asp His Asp Phe Leu Lys Arg Arg Leu Pro Lys Leu Ser Lys
    770                 775                 780
Ser Thr Ala Pro Ser Leu Ala Leu Leu Ala Asp Ser Glu Lys Pro Ser
785                 790                 795                 800
His Lys Ser Phe Ala Thr His Lys Leu Ser Ser Ser Met Cys Val Ser
                805                 810                 815
Ser Asp Leu Leu Ser Asp Ile Tyr Lys Pro Lys Arg Gly Arg Pro Lys
            820                 825                 830
Ser Lys Glu Met Pro Gln Leu Glu Gly Pro Lys Arg Thr Leu Lys
        835                 840                 845
Ile Pro Ala Ser Lys Val Phe Ser Leu Gln Ser Lys Glu Glu Gln Glu
    850                 855                 860
Pro Pro Ile Leu Gln Pro Glu Ile Glu Ile Pro Ser Phe Lys Gln Gly
865                 870                 875                 880
Leu Ser Val Ser Pro Phe Pro Lys Lys Arg Gly Arg Pro Lys Arg Gln
                885                 890                 895
Met Arg Ser Pro Val Lys Met Lys Pro Pro Val Leu Ser Val Ala Pro
```

```
                900              905                910
Phe Val Ala Thr Glu Ser Pro Ser Lys Leu Glu Ser Glu Ser Asp Asn
             915                920                925
His Arg Ser Ser Ser Asp Phe Phe Glu Ser Glu Asp Gln Leu Gln Asp
         930                935                940
Pro Asp Asp Leu Asp Asp Ser His Arg Pro Ser Val Cys Ser Met Ser
945                950                955                960
Asp Leu Glu Met Glu Pro Asp Lys Lys Ile Thr Lys Arg Asn Asn Gly
                 965                970                975
Gln Leu Met Lys Thr Ile Ile Arg Lys Ile Asn Lys Met Lys Thr Leu
             980                985                990
Lys Arg Lys Lys Leu Leu Asn Gln Ile Leu Ser Ser Ser Val Glu Ser
         995                1000               1005
Ser Asn Lys Gly Lys Val Gln Ser Lys Leu His Asn Thr Val Ser
     1010               1015               1020
Ser Leu Ala Ala Thr Phe Gly Ser Lys Leu Gly Gln Gln Ile Asn
     1025               1030               1035
Val Ser Lys Lys Gly Thr Ile Tyr Ile Gly Lys Arg Arg Gly Arg
     1040               1045               1050
Lys Pro Lys Thr Val Leu Asn Gly Ile Leu Ser Gly Ser Pro Thr
     1055               1060               1065
Ser Leu Ala Val Leu Glu Gln Thr Ala Gln Gln Ala Ala Gly Ser
     1070               1075               1080
Ala Leu Gly Gln Ile Leu Pro Pro Leu Leu Pro Ser Ser Ala Ser
     1085               1090               1095
Ser Ser Glu Ile Leu Pro Ser Pro Ile Cys Ser Gln Ser Ser Gly
     1100               1105               1110
Thr Ser Gly Gly Gln Ser Pro Val Ser Ser Asp Ala Gly Phe Val
     1115               1120               1125
Glu Pro Ser Ser Val Pro Tyr Leu His Leu His Ser Arg Gln Gly
     1130               1135               1140
Ser Met Ile Gln Thr Leu Ala Met Lys Lys Ala Ser Lys Gly Arg
     1145               1150               1155
Arg Arg Leu Ser Pro Pro Thr Leu Leu Pro Asn Ser Pro Ser His
     1160               1165               1170
Leu Ser Glu Leu Thr Ser Leu Lys Glu Ala Thr Pro Ser Pro Ile
     1175               1180               1185
Ser Glu Ser His Ser Asp Glu Thr Ile Pro Ser Asp Ser Gly Ile
     1190               1195               1200
Gly Thr Asp Asn Asn Ser Thr Ser Asp Arg Ala Glu Lys Phe Cys
     1205               1210               1215
Gly Gln Lys Lys Arg Arg His Ser Phe Glu His Val Ser Leu Ile
     1220               1225               1230
Pro Pro Glu Thr Ser Thr Val Leu Ser Ser Leu Lys Glu Lys His
     1235               1240               1245
Lys His Lys Cys Lys Arg Arg Asn His Asp Tyr Leu Ser Tyr Asp
     1250               1255               1260
Lys Met Lys Arg Gln Lys Arg Lys Arg Lys Lys Tyr Pro Gln
     1265               1270               1275
Leu Arg Asn Arg Gln Asp Pro Asp Phe Ile Ala Glu Leu Glu Glu
     1280               1285               1290
Leu Ile Ser Arg Leu Ser Glu Ile Arg Ile Thr His Arg Ser His
     1295               1300               1305
```

```
His Phe Ile Pro Arg Asp Leu Leu Pro Thr Ile Phe Arg Ile Asn
1310                1315                1320

Phe Asn Ser Phe Tyr Thr His Pro Ser Phe Pro Leu Asp Pro Leu
1325                1330                1335

His Tyr Ile Arg Lys Pro Asp Leu Lys Lys Lys Arg Gly Arg Pro
1340                1345                1350

Pro Lys Met Arg Glu Ala Met Ala Glu Met Pro Phe Met His Ser
1355                1360                1365

Leu Ser Phe Pro Leu Ser Ser Thr Gly Phe Tyr Pro Ser Tyr Gly
1370                1375                1380

Met Pro Tyr Ser Pro Ser Pro Leu Thr Ala Ala Pro Ile Gly Leu
1385                1390                1395

Gly Tyr Tyr Gly Arg Tyr Pro Pro Thr Leu Tyr Pro Pro Pro Pro
1400                1405                1410

Ser Pro Ser Phe Thr Thr Pro Leu Pro Pro Ser Tyr Met His
1415                1420                1425

Ala Gly His Leu Leu Leu Asn Pro Ala Lys Tyr His Lys Lys Lys
1430                1435                1440

His Lys Leu Leu Arg Gln Glu Ala Phe Leu Thr Thr Ser Arg Thr
1445                1450                1455

Pro Leu Leu Ser Met Ser Thr Tyr Pro Ser Val Pro Pro Glu Met
1460                1465                1470

Ala Tyr Gly Trp Met Val Glu His Lys His Arg His Arg His Lys
1475                1480                1485

His Arg Glu His Arg Ser Ser Glu Gln Pro Gln Val Ser Met Asp
1490                1495                1500

Thr Gly Ser Ser Arg Ser Val Leu Glu Ser Leu Lys Arg Tyr Arg
1505                1510                1515

Phe Gly Lys Asp Ala Val Gly Glu Arg Tyr Lys His Lys Glu Lys
1520                1525                1530

His Arg Cys His Met Ser Cys Pro His Leu Ser Pro Ser Lys Ser
1535                1540                1545

Leu Ile Asn Arg Glu Glu Gln Trp Val His Arg Glu Pro Ser Glu
1550                1555                1560

Ser Ser Pro Leu Ala Leu Gly Leu Gln Thr Pro Leu Gln Ile Asp
1565                1570                1575

Cys Ser Glu Ser Ser Pro Ser Leu Ser Leu Gly Gly Phe Thr Pro
1580                1585                1590

Asn Ser Glu Pro Ala Ser Ser Asp Glu His Thr Asn Leu Phe Thr
1595                1600                1605

Ser Ala Ile Gly Ser Cys Arg Val Ser Asn Pro Asn Ser Ser Gly
1610                1615                1620

Arg Lys Lys Leu Thr Asp Ser Pro Gly Leu Phe Ser Ala Gln Asp
1625                1630                1635

Thr Ser Leu Asn Arg Leu His Arg Lys Glu Ser Leu Pro Ser Asn
1640                1645                1650

Glu Arg Ala Val Gln Thr Leu Ala Gly Ser Gln Pro Thr Ser Asp
1655                1660                1665

Lys Pro Ser Gln Arg Pro Ser Glu Ser Thr Asn Cys Ser Pro Thr
1670                1675                1680

Arg Lys Arg Ser Ser Ser Glu Ser Thr Ser Ser Thr Val Asn Gly
1685                1690                1695
```

Val Pro Ser Arg Ser Pro Arg Leu Val Ala Ser Gly Asp Asp Ser
    1700            1705                1710

Val Asp Ser Leu Leu Gln Arg Met Val Gln Asn Glu Asp Gln Glu
    1715            1720                1725

Pro Met Glu Lys Ser Ile Asp Ala Val Ile Ala Thr Ala Ser Ala
    1730            1735                1740

Pro Pro Ser Ser Ser Pro Gly Arg Ser His Ser Lys Asp Arg Thr
    1745            1750                1755

Leu Gly Lys Pro Asp Ser Leu Leu Val Pro Ala Val Thr Ser Asp
    1760            1765                1770

Ser Cys Asn Asn Ser Ile Ser Leu Leu Ser Glu Lys Leu Thr Ser
    1775            1780                1785

Ser Cys Ser Pro His His Ile Lys Arg Ser Val Val Glu Ala Met
    1790            1795                1800

Gln Arg Gln Ala Arg Lys Met Cys Asn Tyr Asp Lys Ile Leu Ala
    1805            1810                1815

Thr Lys Lys Asn Leu Asp His Val Asn Lys Ile Leu Lys Ala Lys
    1820            1825                1830

Lys Leu Gln Arg Gln Ala Arg Thr Gly Asn Asn Phe Val Lys Arg
    1835            1840                1845

Arg Pro Gly Arg Pro Arg Lys Cys Pro Leu Gln Ala Val Val Ser
    1850            1855                1860

Met Gln Ala Phe Gln Ala Ala Gln Phe Val Asn Pro Glu Leu Asn
    1865            1870                1875

Arg Asp Glu Glu Gly Ala Ala Leu His Leu Ser Pro Asp Thr Val
    1880            1885                1890

Thr Asp Val Ile Glu Ala Val Val Gln Ser Val Asn Leu Asn Pro
    1895            1900                1905

Glu His Lys Lys Gly Leu Lys Arg Lys Gly Trp Leu Leu Glu Glu
    1910            1915                1920

Gln Thr Arg Lys Lys Gln Lys Pro Leu Pro Glu Glu Glu Glu Gln
    1925            1930                1935

Glu Asn Asn Lys Ser Phe Asn Glu Ala Pro Val Glu Ile Pro Ser
    1940            1945                1950

Pro Ser Glu Thr Pro Ala Lys Pro Ser Glu Pro Glu Ser Thr Leu
    1955            1960                1965

Gln Pro Val Leu Ser Leu Ile Pro Arg Glu Lys Lys Pro Pro Arg
    1970            1975                1980

Pro Pro Lys Lys Lys Tyr Gln Lys Ala Gly Leu Tyr Ser Asp Val
    1985            1990                1995

Tyr Lys Thr Thr Asp Pro Lys Ser Arg Leu Ile Gln Leu Lys Lys
    2000            2005                2010

Glu Lys Leu Glu Tyr Thr Pro Gly Glu His Glu Tyr Gly Leu Phe
    2015            2020                2025

Pro Ala Pro Ile His Val Val Phe Phe Val Ser Gly Lys Tyr Leu
    2030            2035                2040

Arg Gln Lys Arg Ile Asp Phe Gln Leu Pro Tyr Asp Ile Leu Trp
    2045            2050                2055

Gln Trp Lys His Asn Gln Leu Tyr Lys Lys Pro Asp Val Pro Leu
    2060            2065                2070

Tyr Lys Lys Ile Arg Ser Asn Val Tyr Val Asp Val Lys Pro Leu
    2075            2080                2085

Ser Gly Tyr Glu Ala Thr Thr Cys Asn Cys Lys Lys Pro Asp Asp

```
                2090                2095               2100

Asp Thr Arg Lys Gly Cys Val Asp Asp Cys Leu Asn Arg Met Ile
    2105                2110               2115

Phe Ala Glu Cys Ser Pro Asn Thr Cys Pro Cys Gly Glu Gln Cys
    2120                2125               2130

Cys Asn Gln Arg Ile Gln Arg His Glu Trp Val Gln Cys Leu Glu
    2135                2140               2145

Arg Phe Arg Ala Glu Glu Lys Gly Trp Gly Ile Arg Thr Lys Glu
    2150                2155               2160

Pro Leu Lys Ala Gly Gln Phe Ile Ile Glu Tyr Leu Gly Glu Val
    2165                2170               2175

Val Ser Glu Gln Glu Phe Arg Asn Arg Met Ile Glu Gln Tyr His
    2180                2185               2190

Asn His Ser Asp His Tyr Cys Leu Asn Leu Asp Ser Gly Met Val
    2195                2200               2205

Ile Asp Ser Tyr Arg Met Gly Asn Glu Ala Arg Phe Ile Asn His
    2210                2215               2220

Ser Cys Asp Pro Asn Cys Glu Met Gln Lys Trp Ser Val Asn Gly
    2225                2230               2235

Val Tyr Arg Ile Gly Leu Tyr Ala Leu Lys Asp Met Pro Ala Gly
    2240                2245               2250

Thr Glu Leu Thr Tyr Asp Tyr Asn Phe His Ser Phe Asn Val Glu
    2255                2260               2265

Lys Gln Gln Leu Cys Lys Cys Gly Phe Glu Lys Cys Arg Gly Ile
    2270                2275               2280

Ile Gly Gly Lys Ser Gln Arg Val Asn Gly Leu Thr Ser Ser Lys
    2285                2290               2295

Asn Ser Gln Pro Met Ala Thr His Lys Lys Ser Gly Arg Ser Lys
    2300                2305               2310

Glu Lys Arg Lys Ser Lys His Lys Leu Lys Lys Arg Arg Gly His
    2315                2320               2325

Leu Ser Glu Glu Pro Ser Glu Asn Ile Asn Thr Pro Thr Arg Leu
    2330                2335               2340

Thr Pro Gln Leu Gln Met Lys Pro Met Ser Asn Arg Glu Arg Asn
    2345                2350               2355

Phe Val Leu Lys His His Val Phe Leu Val Arg Asn Trp Glu Lys
    2360                2365               2370

Ile Arg Gln Lys Gln Glu Glu Val Lys His Thr Ser Asp Asn Ile
    2375                2380               2385

His Ser Ala Ser Leu Tyr Thr Arg Trp Asn Gly Ile Cys Arg Asp
    2390                2395               2400

Asp Gly Asn Ile Lys Ser Asp Val Phe Met Thr Gln Phe Ser Ala
    2405                2410               2415

Leu Gln Thr Ala Arg Ser Val Arg Thr Arg Arg Leu Ala Ala Ala
    2420                2425               2430

Glu Glu Asn Ile Glu Val Ala Arg Ala Ala Arg Leu Ala Gln Ile
    2435                2440               2445

Phe Lys Glu Ile Cys Asp Gly Ile Ile Ser Tyr Lys Asp Ser Ser
    2450                2455               2460

Arg Gln Ala Leu Ala Ala Pro Leu Leu Asn Leu Pro Pro Lys Lys
    2465                2470               2475

Lys Asn Ala Asp Tyr Tyr Glu Lys Ile Ser Asp Pro Leu Asp Leu
    2480                2485               2490
```

```
Ile Thr Ile Glu Lys Gln Ile Leu Thr Gly Tyr Tyr Lys Thr Val
2495                2500                2505

Glu Ala Phe Asp Ala Asp Met Leu Lys Val Phe Arg Asn Ala Glu
2510                2515                2520

Lys Tyr Tyr Gly Arg Lys Ser Pro Val Gly Arg Asp Val Cys Arg
2525                2530                2535

Leu Arg Lys Ala Tyr Tyr Asn Ala Arg His Glu Ala Ser Ala Gln
2540                2545                2550

Ile Asp Glu Ile Val Gly Glu Thr Ala Ser Glu Ala Asp Ser Ser
2555                2560                2565

Glu Thr Ser Val Ser Glu Lys Glu Asn Gly His Glu Lys Asp Asp
2570                2575                2580

Asp Val Ile Arg Cys Ile Cys Gly Leu Tyr Lys Asp Glu Gly Leu
2585                2590                2595

Met Ile Gln Cys Asp Lys Cys Met Val Trp Gln His Cys Asp Cys
2600                2605                2610

Met Gly Val Asn Ser Asp Val Glu His Tyr Leu Cys Glu Gln Cys
2615                2620                2625

Asp Pro Arg Pro Val Asp Arg Glu Val Pro Met Ile Pro Arg Pro
2630                2635                2640

His Tyr Ala Gln Pro Gly Cys Val Tyr Phe Ile Cys Leu Leu Arg
2645                2650                2655

Asp Asp Leu Leu Leu Arg Gln Gly Asp Cys Val Tyr Leu Met Arg
2660                2665                2670

Asp Ser Arg Arg Thr Pro Asp Gly His Pro Val Arg Gln Ser Tyr
2675                2680                2685

Arg Leu Leu Ser His Ile Asn Arg Asp Lys Leu Asp Ile Phe Arg
2690                2695                2700

Ile Glu Lys Leu Trp Lys Asn Glu Lys Glu Arg Phe Ala Phe
2705                2710                2715

Gly His His Tyr Phe Arg Pro His Glu Thr His His Ser Pro Ser
2720                2725                2730

Arg Arg Phe Tyr His Asn Glu Leu Phe Arg Val Pro Leu Tyr Glu
2735                2740                2745

Ile Ile Pro Leu Glu Ala Val Val Gly Thr Cys Cys Val Leu Asp
2750                2755                2760

Leu Tyr Thr Tyr Cys Lys Gly Arg Pro Lys Gly Val Lys Glu Gln
2765                2770                2775

Asp Val Tyr Ile Cys Asp Tyr Arg Leu Asp Lys Ser Ala His Leu
2780                2785                2790

Phe Tyr Lys Ile His Arg Asn Arg Tyr Pro Val Cys Thr Lys Pro
2795                2800                2805

Tyr Ala Phe Asp His Phe Pro Lys Lys Leu Thr Pro Lys Lys Asp
2810                2815                2820

Phe Ser Pro His Tyr Val Pro Asp Asn Tyr Lys Arg Asn Gly Gly
2825                2830                2835

Arg Ser Ser Trp Lys Ser Glu Arg Ser Lys Pro Pro Leu Lys Asp
2840                2845                2850

Leu Gly Gln Glu Asp Asp Ala Leu Pro Leu Ile Glu Glu Val Leu
2855                2860                2865

Ala Ser Gln Glu Gln Ala Ala Asn Glu Ile Pro Ser Leu Glu Glu
2870                2875                2880
```

```
Pro Glu Arg Glu Gly Ala Thr Ala Asn Val Ser Glu Gly Glu Lys
    2885                2890                2895

Lys Thr Glu Glu Ser Ser Gln Glu Pro Gln Ser Thr Cys Thr Pro
    2900                2905                2910

Glu Glu Arg Arg His Asn Gln Arg Glu Arg Leu Asn Gln Ile Leu
    2915                2920                2925

Leu Asn Leu Leu Glu Lys Ile Pro Gly Lys Asn Ala Ile Asp Val
    2930                2935                2940

Thr Tyr Leu Leu Glu Glu Gly Ser Gly Arg Lys Leu Arg Arg Arg
    2945                2950                2955

Thr Leu Phe Ile Pro Glu Asn Ser Phe Arg Lys
    2960                2965

<210> SEQ ID NO 24
<211> LENGTH: 885
<212> TYPE: PRT
<213> ORGANISM: Homo sapiens

<400> SEQUENCE: 24

Met Lys Trp Leu Gly Glu Ser Lys Ile Met Val Val Asn Gly Arg Arg
1               5                   10                  15

Asn Gly Gly Lys Leu Ser Asn Asp His Gln Gln Asn Gln Ser Lys Leu
                20                  25                  30

Gln His Thr Gly Lys Asp Thr Leu Lys Ala Gly Lys Asn Ala Val Glu
            35                  40                  45

Arg Arg Ser Asn Arg Cys Asn Gly Asn Ser Gly Phe Glu Gly Gln Ser
        50                  55                  60

Arg Tyr Val Pro Ser Ser Gly Met Ser Ala Lys Glu Leu Cys Glu Asn
65                  70                  75                  80

Asp Asp Leu Ala Thr Ser Leu Val Leu Asp Pro Tyr Leu Gly Phe Gln
                85                  90                  95

Thr His Lys Met Asn Thr Ser Ala Phe Pro Ser Arg Ser Ser Arg His
            100                 105                 110

Phe Ser Lys Ser Asp Ser Phe Ser His Asn Asn Pro Val Arg Phe Arg
        115                 120                 125

Pro Ile Lys Gly Arg Gln Glu Glu Leu Lys Glu Val Ile Glu Arg Phe
    130                 135                 140

Lys Lys Asp Glu His Leu Glu Lys Ala Phe Lys Cys Leu Thr Ser Gly
145                 150                 155                 160

Glu Trp Ala Arg His Tyr Phe Leu Asn Lys Asn Lys Met Gln Glu Lys
                165                 170                 175

Leu Phe Lys Glu His Val Phe Ile Tyr Leu Arg Met Phe Ala Thr Asp
            180                 185                 190

Ser Gly Phe Glu Ile Leu Pro Cys Asn Arg Tyr Ser Ser Glu Gln Asn
        195                 200                 205

Gly Ala Lys Ile Val Ala Thr Lys Glu Trp Lys Arg Asn Asp Lys Ile
    210                 215                 220

Glu Leu Leu Val Gly Cys Ile Ala Glu Leu Ser Glu Ile Glu Glu Asn
225                 230                 235                 240

Met Leu Leu Arg His Gly Glu Asn Asp Phe Ser Val Met Tyr Ser Thr
                245                 250                 255

Arg Lys Asn Cys Ala Gln Leu Trp Leu Gly Pro Ala Ala Phe Ile Asn
            260                 265                 270

His Asp Cys Arg Pro Asn Cys Lys Phe Val Ser Thr Gly Arg Asp Thr
        275                 280                 285
```

```
Ala Cys Val Lys Ala Leu Arg Asp Ile Glu Pro Gly Glu Ile Ser
    290                 295                 300

Cys Tyr Tyr Gly Asp Gly Phe Phe Gly Glu Asn Asn Glu Phe Cys Glu
305                 310                 315                 320

Cys Tyr Thr Cys Glu Arg Arg Gly Thr Gly Ala Phe Lys Ser Arg Val
            325                 330                 335

Gly Leu Pro Ala Pro Ala Pro Val Ile Asn Ser Lys Tyr Gly Leu Arg
            340                 345                 350

Glu Thr Asp Lys Arg Leu Asn Arg Leu Lys Lys Leu Gly Asp Ser Ser
        355                 360                 365

Lys Asn Ser Asp Ser Gln Ser Val Ser Ser Asn Thr Asp Ala Asp Thr
    370                 375                 380

Thr Gln Glu Lys Asn Asn Ala Thr Ser Asn Arg Lys Ser Ser Val Gly
385                 390                 395                 400

Val Lys Lys Asn Ser Lys Ser Arg Thr Leu Thr Arg Gln Ser Met Ser
            405                 410                 415

Arg Ile Pro Ala Ser Ser Asn Ser Thr Ser Ser Lys Leu Thr His Ile
            420                 425                 430

Asn Asn Ser Arg Val Pro Lys Lys Leu Lys Pro Ala Lys Pro Leu
        435                 440                 445

Leu Ser Lys Ile Lys Leu Arg Asn His Cys Lys Arg Leu Glu Gln Lys
    450                 455                 460

Asn Ala Ser Arg Lys Leu Glu Met Gly Asn Leu Val Leu Lys Glu Pro
465                 470                 475                 480

Lys Val Val Leu Tyr Lys Asn Leu Pro Ile Lys Lys Asp Lys Glu Pro
            485                 490                 495

Glu Gly Pro Ala Gln Ala Ala Val Ala Ser Gly Cys Leu Thr Arg His
        500                 505                 510

Ala Ala Arg Glu His Arg Gln Asn Pro Val Arg Gly Ala His Ser Gln
    515                 520                 525

Gly Glu Ser Ser Pro Cys Thr Tyr Ile Thr Arg Arg Ser Val Arg Thr
530                 535                 540

Arg Thr Asn Leu Lys Glu Ala Ser Asp Ile Lys Leu Glu Pro Asn Thr
545                 550                 555                 560

Leu Asn Gly Tyr Lys Ser Ser Val Thr Glu Pro Cys Pro Asp Ser Gly
            565                 570                 575

Glu Gln Leu Gln Pro Ala Pro Val Leu Gln Glu Glu Leu Ala His
        580                 585                 590

Glu Thr Ala Gln Lys Gly Glu Ala Lys Cys His Lys Ser Asp Thr Gly
        595                 600                 605

Met Ser Lys Lys Lys Ser Arg Gln Gly Lys Leu Val Lys Gln Phe Ala
    610                 615                 620

Lys Ile Glu Glu Ser Thr Pro Val His Asp Ser Pro Gly Lys Asp Asp
625                 630                 635                 640

Ala Val Pro Asp Leu Met Gly Pro His Ser Asp Gln Gly Glu His Ser
            645                 650                 655

Gly Thr Val Gly Val Pro Val Ser Tyr Thr Asp Cys Ala Pro Ser Pro
            660                 665                 670

Val Gly Cys Ser Val Val Thr Ser Asp Ser Phe Lys Thr Lys Asp Ser
        675                 680                 685

Phe Arg Thr Ala Lys Ser Lys Lys Lys Arg Arg Ile Thr Arg Tyr Asp
    690                 695                 700
```

```
Ala Gln Leu Ile Leu Glu Asn Asn Ser Gly Ile Pro Lys Leu Thr Leu
705                 710                 715                 720

Arg Arg Arg His Asp Ser Ser Lys Thr Asn Asp Gln Glu Asn Asp
                725                 730                 735

Gly Met Asn Ser Ser Lys Ile Ser Ile Lys Leu Ser Lys Asp His Asp
                740                 745                 750

Asn Asp Asn Asn Leu Tyr Val Ala Lys Leu Asn Asn Gly Phe Asn Ser
                755                 760                 765

Gly Ser Gly Ser Ser Thr Lys Leu Lys Ile Gln Leu Lys Arg Asp
                770                 775                 780

Glu Glu Asn Arg Gly Ser Tyr Thr Gly Leu His Glu Asn Gly Val
785                 790                 795                 800

Cys Cys Ser Asp Pro Leu Ser Leu Leu Glu Ser Arg Met Glu Val Asp
                805                 810                 815

Asp Tyr Ser Gln Tyr Glu Glu Glu Ser Thr Asp Ser Ser Ser Ser
                820                 825                 830

Glu Gly Asp Glu Glu Asp Asp Tyr Asp Asp Phe Glu Asp Asp
                835                 840                 845

Phe Ile Pro Leu Pro Pro Ala Lys Arg Leu Arg Leu Ile Val Gly Lys
850                 855                 860

Asp Ser Ile Asp Ile Asp Ile Ser Ser Arg Arg Arg Glu Asp Gln Ser
865                 870                 875                 880

Leu Arg Leu Asn Ala
                885

<210> SEQ ID NO 25
<211> LENGTH: 393
<212> TYPE: PRT
<213> ORGANISM: Homo sapiens

<400> SEQUENCE: 25

Met Lys Trp Leu Gly Glu Ser Lys Ile Met Val Val Asn Gly Arg Arg
1               5                   10                  15

Asn Gly Gly Lys Leu Ser Asn Asp His Gln Gln Asn Gln Ser Lys Leu
                20                  25                  30

Gln His Thr Gly Lys Asp Thr Leu Lys Ala Gly Lys Asn Ala Val Glu
                35                  40                  45

Arg Arg Ser Asn Arg Cys Asn Gly Asn Ser Gly Phe Glu Gly Gln Ser
50                  55                  60

Arg Tyr Val Pro Ser Ser Gly Met Ser Ala Lys Glu Leu Cys Glu Asn
65                  70                  75                  80

Asp Asp Leu Ala Thr Ser Leu Val Leu Asp Pro Tyr Leu Gly Phe Gln
                85                  90                  95

Thr His Lys Met Asn Thr Ser Ala Phe Pro Ser Arg Ser Ser Arg His
                100                 105                 110

Phe Ser Lys Ser Asp Ser Phe Ser His Asn Asn Pro Val Arg Phe Arg
                115                 120                 125

Pro Ile Lys Gly Arg Gln Glu Glu Leu Lys Glu Val Ile Glu Arg Phe
130                 135                 140

Lys Lys Asp Glu His Leu Glu Lys Ala Phe Lys Cys Leu Thr Ser Gly
145                 150                 155                 160

Glu Trp Ala Arg His Tyr Phe Leu Asn Lys Asn Lys Met Gln Glu Lys
                165                 170                 175

Leu Phe Lys Glu His Val Phe Ile Tyr Leu Arg Met Phe Ala Thr Asp
                180                 185                 190
```

```
Ser Gly Phe Glu Ile Leu Pro Cys Asn Arg Tyr Ser Ser Glu Gln Asn
        195                 200                 205

Gly Ala Lys Ile Val Ala Thr Lys Glu Trp Lys Arg Asn Asp Lys Ile
    210                 215                 220

Glu Leu Val Gly Cys Ile Ala Glu Leu Ser Glu Ile Glu Asn
225                 230                 235                 240

Met Leu Leu Arg His Gly Glu Asn Asp Phe Ser Val Met Tyr Ser Thr
                245                 250                 255

Arg Lys Asn Cys Ala Gln Leu Trp Leu Gly Pro Ala Ala Phe Ile Asn
                260                 265                 270

His Asp Cys Arg Pro Asn Cys Lys Phe Val Ser Thr Gly Arg Asp Thr
                275                 280                 285

Ala Cys Val Lys Ala Leu Arg Asp Ile Glu Pro Gly Glu Glu Ile Ser
    290                 295                 300

Cys Tyr Tyr Gly Asp Gly Phe Phe Gly Glu Asn Asn Glu Phe Cys Glu
305                 310                 315                 320

Cys Tyr Thr Cys Glu Arg Arg Gly Thr Gly Ala Phe Lys Ser Arg Val
                325                 330                 335

Gly Leu Pro Ala Pro Ala Pro Val Ile Asn Ser Lys Tyr Gly Leu Arg
                340                 345                 350

Glu Thr Asp Lys Arg Leu Asn Arg Leu Lys Lys Leu Gly Asp Ser Ser
                355                 360                 365

Lys Asn Ser Asp Ser Gln Ser Val Ser Ser Asn Thr Asp Ala Asp Thr
                370                 375                 380

Thr Gln Glu Lys Asn Asn Ala Ser Lys
385                 390

<210> SEQ ID NO 26
<211> LENGTH: 278
<212> TYPE: PRT
<213> ORGANISM: Homo sapiens

<400> SEQUENCE: 26

Met Lys Trp Leu Gly Glu Ser Lys Ile Met Val Val Asn Gly Arg Arg
1               5                   10                  15

Asn Gly Gly Lys Leu Ser Asn Asp His Gln Gln Asn Gln Ser Lys Leu
                20                  25                  30

Gln His Thr Gly Lys Asp Thr Leu Lys Ala Gly Lys Asn Ala Val Glu
                35                  40                  45

Arg Arg Ser Asn Arg Cys Asn Gly Asn Ser Gly Phe Glu Gly Gln Ser
    50                  55                  60

Arg Tyr Val Pro Ser Ser Gly Met Ser Ala Lys Glu Leu Cys Glu Asn
65                  70                  75                  80

Asp Asp Leu Ala Thr Ser Leu Val Leu Asp Pro Tyr Leu Gly Phe Gln
                85                  90                  95

Thr His Lys Met Asn Thr Ser Ala Phe Pro Ser Arg Ser Arg His
                100                 105                 110

Phe Ser Lys Ser Asp Ser Phe Ser His Asn Asn Pro Val Arg Phe Arg
            115                 120                 125

Pro Ile Lys Gly Arg Gln Glu Glu Leu Lys Glu Val Ile Glu Arg Phe
            130                 135                 140

Lys Lys Asp Glu His Leu Glu Lys Ala Phe Lys Cys Leu Thr Ser Gly
145                 150                 155                 160

Glu Trp Ala Arg His Tyr Phe Leu Asn Lys Asn Lys Met Gln Glu Lys
```

```
                165                 170                 175
Leu Phe Lys Glu His Val Phe Ile Tyr Leu Arg Met Phe Ala Thr Asp
            180                 185                 190

Ser Gly Phe Glu Ile Leu Pro Cys Asn Arg Tyr Ser Ser Glu Gln Asn
        195                 200                 205

Gly Ala Lys Ile Val Ala Thr Lys Glu Trp Lys Arg Asn Asp Lys Ile
    210                 215                 220

Glu Leu Leu Val Gly Cys Ile Ala Glu Leu Ser Glu Ile Glu Asn
225                 230                 235                 240

Met Leu Leu Arg His Gly Glu Asn Asp Phe Ser Val Met Tyr Ser Thr
                245                 250                 255

Arg Lys Asn Cys Ala Gln Leu Trp Leu Gly Pro Ala Ala Phe Ile Asn
            260                 265                 270

His Asp Leu Ile Asn Ser
        275

<210> SEQ ID NO 27
<211> LENGTH: 412
<212> TYPE: PRT
<213> ORGANISM: Homo sapiens

<400> SEQUENCE: 27

Met Ala Glu Asn Leu Lys Gly Cys Ser Val Cys Cys Lys Ser Ser Trp
1               5                   10                  15

Asn Gln Leu Gln Asp Leu Cys Arg Leu Ala Lys Leu Ser Cys Pro Ala
            20                  25                  30

Leu Gly Ile Ser Lys Arg Asn Leu Tyr Asp Phe Glu Val Glu Tyr Leu
        35                  40                  45

Cys Asp Tyr Lys Lys Ile Arg Glu Gln Glu Tyr Tyr Leu Val Lys Trp
    50                  55                  60

Arg Gly Tyr Pro Asp Ser Glu Ser Thr Trp Glu Pro Arg Gln Asn Leu
65                  70                  75                  80

Lys Cys Val Arg Ile Leu Lys Gln Phe His Lys Asp Leu Glu Arg Glu
                85                  90                  95

Leu Leu Arg Arg His His Arg Ser Lys Thr Pro Arg His Leu Asp Pro
            100                 105                 110

Ser Leu Ala Asn Tyr Leu Val Gln Lys Ala Lys Gln Arg Arg Ala Leu
        115                 120                 125

Arg Arg Trp Glu Gln Glu Leu Asn Ala Lys Arg Ser His Leu Gly Arg
    130                 135                 140

Ile Thr Val Glu Asn Glu Val Asp Leu Asp Gly Pro Pro Arg Ala Phe
145                 150                 155                 160

Val Tyr Ile Asn Glu Tyr Arg Val Gly Glu Gly Ile Thr Leu Asn Gln
                165                 170                 175

Val Ala Val Gly Cys Glu Cys Gln Asp Cys Leu Trp Ala Pro Thr Gly
            180                 185                 190

Gly Cys Cys Pro Gly Ala Ser Leu His Lys Phe Ala Tyr Asn Asp Gln
        195                 200                 205

Gly Gln Val Arg Leu Arg Ala Gly Leu Pro Ile Tyr Glu Cys Asn Ser
    210                 215                 220

Arg Cys Arg Cys Gly Tyr Asp Cys Pro Asn Arg Val Val Gln Lys Gly
225                 230                 235                 240

Ile Arg Tyr Asp Leu Cys Ile Phe Arg Thr Asp Asp Gly Arg Gly Trp
                245                 250                 255
```

```
Gly Val Arg Thr Leu Glu Lys Ile Arg Lys Asn Ser Phe Val Met Glu
            260                 265                 270

Tyr Val Gly Glu Ile Ile Thr Ser Glu Glu Ala Glu Arg Arg Gly Gln
        275                 280                 285

Ile Tyr Asp Arg Gln Gly Ala Thr Tyr Leu Phe Asp Leu Asp Tyr Val
290                 295                 300

Glu Asp Val Tyr Thr Val Asp Ala Ala Tyr Tyr Gly Asn Ile Ser His
305                 310                 315                 320

Phe Val Asn His Ser Cys Asp Pro Asn Leu Gln Val Tyr Asn Val Phe
                325                 330                 335

Ile Asp Asn Leu Asp Glu Arg Leu Pro Arg Ile Ala Phe Phe Ala Thr
            340                 345                 350

Arg Thr Ile Arg Ala Gly Glu Glu Leu Thr Phe Asp Tyr Asn Met Gln
        355                 360                 365

Val Asp Pro Val Asp Met Glu Ser Thr Arg Met Asp Ser Asn Phe Gly
370                 375                 380

Leu Ala Gly Leu Pro Gly Ser Pro Lys Lys Arg Val Arg Ile Glu Cys
385                 390                 395                 400

Lys Cys Gly Thr Glu Ser Cys Arg Lys Tyr Leu Phe
                405                 410

<210> SEQ ID NO 28
<211> LENGTH: 423
<212> TYPE: PRT
<213> ORGANISM: Homo sapiens

<400> SEQUENCE: 28

Met Val Gly Met Ser Arg Leu Arg Asn Asp Arg Leu Ala Asp Pro Leu
1               5                   10                  15

Thr Gly Cys Ser Val Cys Cys Lys Ser Ser Trp Asn Gln Leu Gln Asp
            20                  25                  30

Leu Cys Arg Leu Ala Lys Leu Ser Cys Pro Ala Leu Gly Ile Ser Lys
        35                  40                  45

Arg Asn Leu Tyr Asp Phe Glu Val Glu Tyr Leu Cys Asp Tyr Lys Lys
50                  55                  60

Ile Arg Glu Gln Glu Tyr Tyr Leu Val Lys Trp Arg Gly Tyr Pro Asp
65                  70                  75                  80

Ser Glu Ser Thr Trp Glu Pro Arg Gln Asn Leu Lys Cys Val Arg Ile
                85                  90                  95

Leu Lys Gln Phe His Lys Asp Leu Glu Arg Glu Leu Leu Arg Arg His
            100                 105                 110

His Arg Ser Lys Thr Pro Arg His Leu Asp Pro Ser Leu Ala Asn Tyr
        115                 120                 125

Leu Val Gln Lys Ala Lys Gln Arg Arg Ala Leu Arg Arg Trp Glu Gln
130                 135                 140

Glu Leu Asn Ala Lys Arg Ser His Leu Gly Arg Ile Thr Val Glu Asn
145                 150                 155                 160

Glu Val Asp Leu Asp Gly Pro Pro Arg Ala Phe Val Tyr Ile Asn Glu
                165                 170                 175

Tyr Arg Val Gly Glu Gly Ile Thr Leu Asn Gln Val Ala Val Gly Cys
            180                 185                 190

Glu Cys Gln Asp Cys Leu Trp Ala Pro Thr Gly Gly Cys Cys Pro Gly
        195                 200                 205

Ala Ser Leu His Lys Phe Ala Tyr Asn Asp Gln Gly Gln Val Arg Leu
210                 215                 220
```

```
Arg Ala Gly Leu Pro Ile Tyr Glu Cys Asn Ser Arg Cys Arg Cys Gly
225                 230                 235                 240

Tyr Asp Cys Pro Asn Arg Val Val Gln Lys Gly Ile Arg Tyr Asp Leu
            245                 250                 255

Cys Ile Phe Arg Thr Asp Asp Gly Arg Gly Trp Gly Val Arg Thr Leu
        260                 265                 270

Glu Lys Ile Arg Lys Asn Ser Phe Val Met Glu Tyr Val Gly Glu Ile
        275                 280                 285

Ile Thr Ser Glu Glu Ala Glu Arg Arg Gly Gln Ile Tyr Asp Arg Gln
        290                 295                 300

Gly Ala Thr Tyr Leu Phe Asp Leu Asp Tyr Val Glu Asp Val Tyr Thr
305                 310                 315                 320

Val Asp Ala Ala Tyr Tyr Gly Asn Ile Ser His Phe Val Asn His Ser
                325                 330                 335

Cys Asp Pro Asn Leu Gln Val Tyr Asn Val Phe Ile Asp Asn Leu Asp
            340                 345                 350

Glu Arg Leu Pro Arg Ile Ala Phe Phe Ala Thr Arg Thr Ile Arg Ala
        355                 360                 365

Gly Glu Glu Leu Thr Phe Asp Tyr Asn Met Gln Val Asp Pro Val Asp
370                 375                 380

Met Glu Ser Thr Arg Met Asp Ser Asn Phe Gly Leu Ala Gly Leu Pro
385                 390                 395                 400

Gly Ser Pro Lys Lys Arg Val Arg Ile Glu Cys Lys Cys Gly Thr Glu
            405                 410                 415

Ser Cys Arg Lys Tyr Leu Phe
            420

<210> SEQ ID NO 29
<211> LENGTH: 15
<212> TYPE: PRT
<213> ORGANISM: Artificial sequence
<220> FEATURE:
<223> OTHER INFORMATION: synthetic peptide sequence

<400> SEQUENCE: 29

Arg His Arg Lys Val Leu Arg Asp Asn Ile Gln Gly Ile Thr Lys
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: synthetic peptide sequence
<220> FEATURE:
<221> NAME/KEY: Misc_feature
<222> LOCATION: (4)..(4)
<223> OTHER INFORMATION: methylation of lysine at position 4

<400> SEQUENCE: 30

Arg His Arg Lys Val Leu Arg Asp Asn Ile Gln Gly Ile Thr Lys
1               5                   10                  15

<210> SEQ ID NO 31
<211> LENGTH: 12
<212> TYPE: PRT
<213> ORGANISM: Artificial sequence
<220> FEATURE:
<223> OTHER INFORMATION: synthetic peptide sequence

<400> SEQUENCE: 31
```

Thr Val Thr Ala Met Asp Val Val Tyr Ala Leu Lys
1               5                   10

<210> SEQ ID NO 32
<211> LENGTH: 23
<212> TYPE: DNA
<213> ORGANISM: Artificial sequence
<220> FEATURE:
<223> OTHER INFORMATION: synthetic nucleotide sequence

<400> SEQUENCE: 32
cagatgctgc atataagcag ctg                                                23

<210> SEQ ID NO 33
<211> LENGTH: 31
<212> TYPE: DNA
<213> ORGANISM: Artificial sequence
<220> FEATURE:
<223> OTHER INFORMATION: synthetic nucleotide sequence

<400> SEQUENCE: 33
tttttttttt tttttttttt ttttgaagca c                                       31

<210> SEQ ID NO 34
<211> LENGTH: 20
<212> TYPE: DNA
<213> ORGANISM: Artificial sequence
<220> FEATURE:
<223> OTHER INFORMATION: synthetic nucleotide sequence
<220> FEATURE:
<221> NAME/KEY: Misc_feature
<222> LOCATION: (1)..(1)
<223> OTHER INFORMATION: FAM conjugated to 5" end at postion 1
<220> FEATURE:
<221> NAME/KEY: Misc_feature
<222> LOCATION: (20)..(20)
<223> OTHER INFORMATION: MGB conjugated to 3" end at postion 20

<400> SEQUENCE: 34
cctgtactgg gtctctctgg                                                    20

<210> SEQ ID NO 35
<211> LENGTH: 20
<212> TYPE: DNA
<213> ORGANISM: Artificial sequence
<220> FEATURE:
<223> OTHER INFORMATION: synthetic nucleotide sequence

<400> SEQUENCE: 35
agtgtgtgcc cgtctgttgt                                                    20

<210> SEQ ID NO 36
<211> LENGTH: 20
<212> TYPE: DNA
<213> ORGANISM: Artificial sequence
<220> FEATURE:
<223> OTHER INFORMATION: synthetic nucleotide sequence

<400> SEQUENCE: 36
ttcgctttca ggtccctgtt                                                    20

<210> SEQ ID NO 37
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 37
gccagagtca agccagtagt c                                               21

<210> SEQ ID NO 38
<211> LENGTH: 23
<212> TYPE: DNA
<213> ORGANISM: Artificial sequence
<220> FEATURE:
<223> OTHER INFORMATION: synthetic nucleotide sequence

<400> SEQUENCE: 38
tagcctaatg tggagtggat gtg                                             23

<210> SEQ ID NO 39
<211> LENGTH: 72
<212> TYPE: PRT
<213> ORGANISM: Artificial sequence
<220> FEATURE:
<223> OTHER INFORMATION: synthetic peptide sequence

<400> SEQUENCE: 39

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
            20                  25                  30

His Cys Gln Val Cys Phe Thr Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln
65                  70

<210> SEQ ID NO 40
<211> LENGTH: 21
<212> TYPE: PRT
<213> ORGANISM: Artificial sequence
<220> FEATURE:
<223> OTHER INFORMATION: synthetic peptide sequence

<400> SEQUENCE: 40

Met Ser Gly Arg Gly Lys Gly Gly Lys Gly Leu Gly Lys Gly Gly Ala
1               5                   10                  15

Lys Arg His Arg Lys
            20

<210> SEQ ID NO 41
<211> LENGTH: 10
<212> TYPE: PRT
<213> ORGANISM: Artificial sequence
<220> FEATURE:
<223> OTHER INFORMATION: synthetic peptide sequence

<400> SEQUENCE: 41

Gly Ala Lys Arg His Arg Lys Val Leu Arg
1               5                   10

<210> SEQ ID NO 42
<211> LENGTH: 3969
<212> TYPE: PRT
<213> ORGANISM: Homo sapiens

<400> SEQUENCE: 42

```
Met Ala His Ser Cys Arg Trp Arg Phe Pro Ala Arg Pro Gly Thr Thr
 1               5                  10                  15

Gly Gly Gly Gly Gly Gly Arg Gly Leu Gly Gly Ala Pro Arg
            20                  25                  30

Gln Arg Val Pro Ala Leu Leu Leu Pro Pro Gly Pro Pro Val Gly Gly
            35                  40                  45

Gly Gly Pro Gly Ala Pro Pro Ser Pro Pro Ala Val Ala Ala Ala
 50                  55                  60

Ala Ala Ala Gly Ser Ser Gly Ala Gly Val Pro Gly Gly Ala Ala Ala
 65                  70                  75                  80

Ala Ser Ala Ala Ser Ser Ser Ser Ala Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
            115                 120                 125

Phe Arg Ala Val Phe Gly Glu Ser Gly Gly Gly Gly Ser Gly Glu
 130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
            165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
            195                 200                 205

Lys Ile Lys Lys Lys Asp Ser Lys Ser Ile Glu Lys Lys Arg Gly Arg
210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
            245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Leu Lys Ser Lys Phe Lys Thr Gly
 275                 280                 285

Lys Leu Gln Ile Gly Arg Lys Gly Val Gln Ile Val Arg Arg Arg Gly
 290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
            325                 330                 335

Thr Pro Pro Leu Thr Lys Glu Asp Lys Thr Val Val Arg Gln Ser Pro
            340                 345                 350

Arg Arg Ile Lys Pro Val Arg Ile Ile Pro Ser Ser Lys Arg Thr Asp
 355                 360                 365

Ala Thr Ile Ala Lys Gln Leu Leu Gln Arg Ala Lys Lys Gly Ala Gln
 370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
            405                 410                 415

Ile Ser Ser Arg Ile Ile Lys Thr Pro Arg Arg Phe Ile Glu Asp Glu
```

```
              420                 425                 430
Asp Tyr Asp Pro Pro Ile Lys Ile Ala Arg Leu Glu Ser Thr Pro Asn
            435                 440                 445

Ser Arg Phe Ser Ala Pro Ser Cys Gly Ser Ser Glu Lys Ser Ser Ala
        450                 455                 460

Ala Ser Gln His Ser Ser Gln Met Ser Ser Asp Ser Ser Arg Ser Ser
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
            500                 505                 510

Leu Pro Ile Ser Gln Ser Pro Glu Asn Glu Ser Asn Asp Arg Arg Ser
        515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
    610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
    690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Ser Glu Leu Ser
        755                 760                 765

Pro Leu Thr Pro Pro Ser Ser Val Ser Ser Ser Leu Ser Ile Ser Val
    770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
            820                 825                 830

Thr Pro Leu Phe Pro Trp Phe Thr Pro Gly Ser Gln Thr Glu Arg Gly
        835                 840                 845
```

-continued

```
Arg Asn Lys Asp Lys Ala Pro Glu Glu Leu Ser Lys Asp Arg Asp Ala
    850                 855                 860
Asp Lys Ser Val Glu Lys Asp Lys Ser Arg Glu Arg Asp Arg Glu Arg
865                 870                 875                 880
Glu Lys Glu Asn Lys Arg Glu Ser Arg Lys Glu Lys Arg Lys Lys Gly
                885                 890                 895
Ser Glu Ile Gln Ser Ser Ser Ala Leu Tyr Pro Val Gly Arg Val Ser
                900                 905                 910
Lys Glu Lys Val Val Gly Glu Asp Val Ala Thr Ser Ser Ser Ala Lys
            915                 920                 925
Lys Ala Thr Gly Arg Lys Lys Ser Ser Ser His Asp Ser Gly Thr Asp
    930                 935                 940
Ile Thr Ser Val Thr Leu Gly Asp Thr Thr Ala Val Lys Thr Lys Ile
945                 950                 955                 960
Leu Ile Lys Lys Gly Arg Gly Asn Leu Glu Lys Thr Asn Leu Asp Leu
                965                 970                 975
Gly Pro Thr Ala Pro Ser Leu Glu Lys Glu Lys Thr Leu Cys Leu Ser
            980                 985                 990
Thr Pro Ser Ser Ser Thr Val Lys  His Ser Thr Ser Ser  Ile Gly Ser
        995                 1000                1005
Met Leu  Ala Gln Ala Asp Lys  Leu Pro Met Thr Asp  Lys Arg Val
    1010                1015                1020
Ala Ser  Leu Leu Lys Lys Ala  Lys Ala Gln Leu Cys  Lys Ile Glu
    1025                1030                1035
Lys Ser  Lys Ser Leu Lys Gln  Thr Asp Gln Pro Lys  Ala Gln Gly
    1040                1045                1050
Gln Glu  Ser Asp Ser Ser Glu  Thr Ser Val Arg Gly  Pro Arg Ile
    1055                1060                1065
Lys His  Val Cys Arg Arg Ala  Val Ala Leu Gly  Arg Lys Arg
    1070                1075                1080
Ala Val  Phe Pro Asp Asp Met  Pro Thr Leu Ser Ala  Leu Pro Trp
    1085                1090                1095
Glu Glu  Arg Glu Lys Ile Leu  Ser Ser Met Gly Asn  Asp Asp Lys
    1100                1105                1110
Ser Ser  Ile Ala Gly Ser Glu  Asp Ala Glu Pro Leu  Ala Pro Pro
    1115                1120                1125
Ile Lys  Pro Ile Lys Pro Val  Thr Arg Asn Lys Ala  Pro Gln Glu
    1130                1135                1140
Pro Pro  Val Lys Lys Gly Arg  Arg Ser Arg Arg Cys  Gly Gln Cys
    1145                1150                1155
Pro Gly  Cys Gln Val Pro Glu  Asp Cys Gly Val Cys  Thr Asn Cys
    1160                1165                1170
Leu Asp  Lys Pro Lys Phe Gly  Gly Arg Asn Ile Lys  Lys Gln Cys
    1175                1180                1185
Cys Lys  Met Arg Lys Cys Gln  Asn Leu Gln Trp Met  Pro Ser Lys
    1190                1195                1200
Ala Tyr  Leu Gln Lys Gln Ala  Lys Ala Val Lys Lys  Lys Glu Lys
    1205                1210                1215
Lys Ser  Lys Thr Ser Glu Lys  Lys Asp Ser Lys Glu  Ser Ser Val
    1220                1225                1230
Val Lys  Asn Val Val Asp Ser  Ser Gln Lys Pro Thr  Pro Ser Ala
    1235                1240                1245
```

```
Arg Glu Asp Pro Ala Pro Lys Lys Ser Ser Glu Pro Pro Pro
    1250                1255                1260

Arg Lys Pro Val Glu Glu Lys Ser Glu Glu Gly Asn Val Ser Ala
    1265                1270                1275

Pro Gly Pro Glu Ser Lys Gln Ala Thr Thr Pro Ala Ser Arg Lys
    1280                1285                1290

Ser Ser Lys Gln Val Ser Gln Pro Ala Leu Val Ile Pro Pro Gln
    1295                1300                1305

Pro Pro Thr Thr Gly Pro Pro Arg Lys Glu Val Pro Lys Thr Thr
    1310                1315                1320

Pro Ser Glu Pro Lys Lys Lys Gln Pro Pro Pro Glu Ser Gly
    1325                1330                1335

Pro Glu Gln Ser Lys Gln Lys Lys Val Ala Pro Arg Pro Ser Ile
    1340                1345                1350

Pro Val Lys Gln Lys Pro Lys Glu Lys Glu Lys Pro Pro Pro Val
    1355                1360                1365

Asn Lys Gln Glu Asn Ala Gly Thr Leu Asn Ile Leu Ser Thr Leu
    1370                1375                1380

Ser Asn Gly Asn Ser Ser Lys Gln Lys Ile Pro Ala Asp Gly Val
    1385                1390                1395

His Arg Ile Arg Val Asp Phe Lys Glu Asp Cys Glu Ala Glu Asn
    1400                1405                1410

Val Trp Glu Met Gly Gly Leu Gly Ile Leu Thr Ser Val Pro Ile
    1415                1420                1425

Thr Pro Arg Val Val Cys Phe Leu Cys Ala Ser Ser Gly His Val
    1430                1435                1440

Glu Phe Val Tyr Cys Gln Val Cys Cys Glu Pro Phe His Lys Phe
    1445                1450                1455

Cys Leu Glu Glu Asn Glu Arg Pro Leu Glu Asp Gln Leu Glu Asn
    1460                1465                1470

Trp Cys Cys Arg Arg Cys Lys Phe Cys His Val Cys Gly Arg Gln
    1475                1480                1485

His Gln Ala Thr Lys Gln Leu Leu Glu Cys Asn Lys Cys Arg Asn
    1490                1495                1500

Ser Tyr His Pro Glu Cys Leu Gly Pro Asn Tyr Pro Thr Lys Pro
    1505                1510                1515

Thr Lys Lys Lys Lys Val Trp Ile Cys Thr Lys Cys Val Arg Cys
    1520                1525                1530

Lys Ser Cys Gly Ser Thr Thr Pro Gly Lys Gly Trp Asp Ala Gln
    1535                1540                1545

Trp Ser His Asp Phe Ser Leu Cys His Asp Cys Ala Lys Leu Phe
    1550                1555                1560

Ala Lys Gly Asn Phe Cys Pro Leu Cys Asp Lys Cys Tyr Asp Asp
    1565                1570                1575

Asp Asp Tyr Glu Ser Lys Met Met Gln Cys Gly Lys Cys Asp Arg
    1580                1585                1590

Trp Val His Ser Lys Cys Glu Asn Leu Ser Asp Glu Met Tyr Glu
    1595                1600                1605

Ile Leu Ser Asn Leu Pro Glu Ser Val Ala Tyr Thr Cys Val Asn
    1610                1615                1620

Cys Thr Glu Arg His Pro Ala Glu Trp Arg Leu Ala Leu Glu Lys
    1625                1630                1635

Glu Leu Gln Ile Ser Leu Lys Gln Val Leu Thr Ala Leu Leu Asn
```

-continued

```
                1640                1645                1650

Ser Arg Thr Thr Ser His Leu Leu Arg Tyr Arg Gln Ala Ala Lys
    1655                1660                1665

Pro Pro Asp Leu Asn Pro Glu Thr Glu Glu Ser Ile Pro Ser Arg
    1670                1675                1680

Ser Ser Pro Glu Gly Pro Asp Pro Pro Val Leu Thr Glu Val Ser
    1685                1690                1695

Lys Gln Asp Gln Gln Pro Leu Asp Leu Glu Gly Val Lys Arg
    1700                1705                1710

Lys Met Asp Gln Gly Asn Tyr Thr Ser Val Leu Glu Phe Ser Asp
    1715                1720                1725

Asp Ile Val Lys Ile Ile Gln Ala Ala Ile Asn Ser Asp Gly Gly
    1730                1735                1740

Gln Pro Glu Ile Lys Lys Ala Asn Ser Met Val Lys Ser Phe Phe
    1745                1750                1755

Ile Arg Gln Met Glu Arg Val Phe Pro Trp Phe Ser Val Lys Lys
    1760                1765                1770

Ser Arg Phe Trp Glu Pro Asn Lys Val Ser Ser Asn Ser Gly Met
    1775                1780                1785

Leu Pro Asn Ala Val Leu Pro Pro Ser Leu Asp His Asn Tyr Ala
    1790                1795                1800

Gln Trp Gln Glu Arg Glu Glu Asn Ser His Thr Glu Gln Pro Pro
    1805                1810                1815

Leu Met Lys Lys Ile Ile Pro Ala Pro Lys Pro Lys Gly Pro Gly
    1820                1825                1830

Glu Pro Asp Ser Pro Thr Pro Leu His Pro Pro Thr Pro Pro Ile
    1835                1840                1845

Leu Ser Thr Asp Arg Ser Arg Glu Asp Ser Pro Glu Leu Asn Pro
    1850                1855                1860

Pro Pro Gly Ile Glu Asp Asn Arg Gln Cys Ala Leu Cys Leu Thr
    1865                1870                1875

Tyr Gly Asp Asp Ser Ala Asn Asp Ala Gly Arg Leu Leu Tyr Ile
    1880                1885                1890

Gly Gln Asn Glu Trp Thr His Val Asn Cys Ala Leu Trp Ser Ala
    1895                1900                1905

Glu Val Phe Glu Asp Asp Gly Ser Leu Lys Asn Val His Met
    1910                1915                1920

Ala Val Ile Arg Gly Lys Gln Leu Arg Cys Glu Phe Cys Gln Lys
    1925                1930                1935

Pro Gly Ala Thr Val Gly Cys Cys Leu Thr Ser Cys Thr Ser Asn
    1940                1945                1950

Tyr His Phe Met Cys Ser Arg Ala Lys Asn Cys Val Phe Leu Asp
    1955                1960                1965

Asp Lys Lys Val Tyr Cys Gln Arg His Arg Asp Leu Ile Lys Gly
    1970                1975                1980

Glu Val Val Pro Glu Asn Gly Phe Glu Val Phe Arg Arg Val Phe
    1985                1990                1995

Val Asp Phe Glu Gly Ile Ser Leu Arg Arg Lys Phe Leu Asn Gly
    2000                2005                2010

Leu Glu Pro Glu Asn Ile His Met Met Ile Gly Ser Met Thr Ile
    2015                2020                2025

Asp Cys Leu Gly Ile Leu Asn Asp Leu Ser Asp Cys Glu Asp Lys
    2030                2035                2040
```

Leu Phe Pro Ile Gly Tyr Gln Cys Ser Arg Val Tyr Trp Ser Thr
2045                2050                2055

Thr Asp Ala Arg Lys Arg Cys Val Tyr Thr Cys Lys Ile Val Glu
2060                2065                2070

Cys Arg Pro Pro Val Val Glu Pro Asp Ile Asn Ser Thr Val Glu
2075                2080                2085

His Asp Glu Asn Arg Thr Ile Ala His Ser Pro Thr Ser Phe Thr
2090                2095                2100

Glu Ser Ser Ser Lys Glu Ser Gln Asn Thr Ala Glu Ile Ile Ser
2105                2110                2115

Pro Pro Ser Pro Asp Arg Pro Pro His Ser Gln Thr Ser Gly Ser
2120                2125                2130

Cys Tyr Tyr His Val Ile Ser Lys Val Pro Arg Ile Arg Thr Pro
2135                2140                2145

Ser Tyr Ser Pro Thr Gln Arg Ser Pro Gly Cys Arg Pro Leu Pro
2150                2155                2160

Ser Ala Gly Ser Pro Thr Pro Thr Thr His Glu Ile Val Thr Val
2165                2170                2175

Gly Asp Pro Leu Leu Ser Ser Gly Leu Arg Ser Ile Gly Ser Arg
2180                2185                2190

Arg His Ser Thr Ser Ser Leu Ser Pro Gln Arg Ser Lys Leu Arg
2195                2200                2205

Ile Met Ser Pro Met Arg Thr Gly Asn Thr Tyr Ser Arg Asn Asn
2210                2215                2220

Val Ser Ser Val Ser Thr Thr Gly Thr Ala Thr Asp Leu Glu Ser
2225                2230                2235

Ser Ala Lys Val Val Asp His Val Leu Gly Pro Leu Asn Ser Ser
2240                2245                2250

Thr Ser Leu Gly Gln Asn Thr Ser Thr Ser Ser Asn Leu Gln Arg
2255                2260                2265

Thr Val Val Thr Val Gly Asn Lys Asn Ser His Leu Asp Gly Ser
2270                2275                2280

Ser Ser Ser Glu Met Lys Gln Ser Ser Ala Ser Asp Leu Val Ser
2285                2290                2295

Lys Ser Ser Ser Leu Lys Gly Glu Lys Thr Lys Val Leu Ser Ser
2300                2305                2310

Lys Ser Ser Glu Gly Ser Ala His Asn Val Ala Tyr Pro Gly Ile
2315                2320                2325

Pro Lys Leu Ala Pro Gln Val His Asn Thr Thr Ser Arg Glu Leu
2330                2335                2340

Asn Val Ser Lys Ile Gly Ser Phe Ala Glu Pro Ser Ser Val Ser
2345                2350                2355

Phe Ser Ser Lys Glu Ala Leu Ser Phe Pro His Leu His Leu Arg
2360                2365                2370

Gly Gln Arg Asn Asp Arg Asp Gln His Thr Asp Ser Thr Gln Ser
2375                2380                2385

Ala Asn Ser Ser Pro Asp Glu Asp Thr Glu Val Lys Thr Leu Lys
2390                2395                2400

Leu Ser Gly Met Ser Asn Arg Ser Ser Ile Ile Asn Glu His Met
2405                2410                2415

Gly Ser Ser Ser Arg Asp Arg Arg Gln Lys Gly Lys Lys Ser Cys
2420                2425                2430

```
Lys Glu Thr Phe Lys Glu Lys His Ser Ser Lys Ser Phe Leu Glu
2435                2440                2445

Pro Gly Gln Val Thr Gly Glu Glu Gly Asn Leu Lys Pro Glu
2450                2455                2460

Phe Met Asp Glu Val Leu Thr Pro Glu Tyr Met Gly Gln Arg Pro
2465                2470                2475

Cys Asn Asn Val Ser Ser Asp Lys Ile Gly Asp Lys Gly Leu Ser
2480                2485                2490

Met Pro Gly Val Pro Lys Ala Pro Pro Met Gln Val Glu Gly Ser
2495                2500                2505

Ala Lys Glu Leu Gln Ala Pro Arg Lys Arg Thr Val Lys Val Thr
2510                2515                2520

Leu Thr Pro Leu Lys Met Glu Asn Glu Ser Gln Ser Lys Asn Ala
2525                2530                2535

Leu Lys Glu Ser Ser Pro Ala Ser Pro Leu Gln Ile Glu Ser Thr
2540                2545                2550

Ser Pro Thr Glu Pro Ile Ser Ala Ser Glu Asn Pro Gly Asp Gly
2555                2560                2565

Pro Val Ala Gln Pro Ser Pro Asn Asn Thr Ser Cys Gln Asp Ser
2570                2575                2580

Gln Ser Asn Asn Tyr Gln Asn Leu Pro Val Gln Asp Arg Asn Leu
2585                2590                2595

Met Leu Pro Asp Gly Pro Lys Pro Gln Glu Asp Gly Ser Phe Lys
2600                2605                2610

Arg Arg Tyr Pro Arg Arg Ser Ala Arg Ala Arg Ser Asn Met Phe
2615                2620                2625

Phe Gly Leu Thr Pro Leu Tyr Gly Val Arg Ser Tyr Gly Glu Glu
2630                2635                2640

Asp Ile Pro Phe Tyr Ser Ser Ser Thr Gly Lys Lys Arg Gly Lys
2645                2650                2655

Arg Ser Ala Glu Gly Gln Val Asp Gly Ala Asp Asp Leu Ser Thr
2660                2665                2670

Ser Asp Glu Asp Asp Leu Tyr Tyr Tyr Asn Phe Thr Arg Thr Val
2675                2680                2685

Ile Ser Ser Gly Gly Glu Glu Arg Leu Ala Ser His Asn Leu Phe
2690                2695                2700

Arg Glu Glu Glu Gln Cys Asp Leu Pro Lys Ile Ser Gln Leu Asp
2705                2710                2715

Gly Val Asp Asp Gly Thr Glu Ser Asp Thr Ser Val Thr Ala Thr
2720                2725                2730

Thr Arg Lys Ser Ser Gln Ile Pro Lys Arg Asn Gly Lys Glu Asn
2735                2740                2745

Gly Thr Glu Asn Leu Lys Ile Asp Arg Pro Glu Asp Ala Gly Glu
2750                2755                2760

Lys Glu His Val Thr Lys Ser Ser Val Gly His Lys Asn Glu Pro
2765                2770                2775

Lys Met Asp Asn Cys His Ser Val Ser Arg Val Lys Thr Gln Gly
2780                2785                2790

Gln Asp Ser Leu Glu Ala Gln Leu Ser Ser Leu Glu Ser Ser Arg
2795                2800                2805

Arg Val His Thr Ser Thr Pro Ser Asp Lys Asn Leu Leu Asp Thr
2810                2815                2820

Tyr Asn Thr Glu Leu Leu Lys Ser Asp Ser Asp Asn Asn Asn Ser
```

```
            2825                2830                2835

Asp Asp Cys Gly Asn Ile Leu Pro Ser Asp Ile Met Asp Phe Val
    2840                2845                2850

Leu Lys Asn Thr Pro Ser Met Gln Ala Leu Gly Glu Ser Pro Glu
    2855                2860                2865

Ser Ser Ser Ser Glu Leu Leu Asn Leu Gly Glu Gly Leu Gly Leu
    2870                2875                2880

Asp Ser Asn Arg Glu Lys Asp Met Gly Leu Phe Glu Val Phe Ser
    2885                2890                2895

Gln Gln Leu Pro Thr Thr Glu Pro Val Asp Ser Ser Val Ser Ser
    2900                2905                2910

Ser Ile Ser Ala Glu Glu Gln Phe Glu Leu Pro Leu Glu Leu Pro
    2915                2920                2925

Ser Asp Leu Ser Val Leu Thr Thr Arg Ser Pro Thr Val Pro Ser
    2930                2935                2940

Gln Asn Pro Ser Arg Leu Ala Val Ile Ser Asp Ser Gly Glu Lys
    2945                2950                2955

Arg Val Thr Ile Thr Glu Lys Ser Val Ala Ser Glu Ser Asp
    2960                2965                2970

Pro Ala Leu Leu Ser Pro Gly Val Asp Pro Thr Pro Glu Gly His
    2975                2980                2985

Met Thr Pro Asp His Phe Ile Gln Gly His Met Asp Ala Asp His
    2990                2995                3000

Ile Ser Ser Pro Pro Cys Gly Ser Val Glu Gln Gly His Gly Asn
    3005                3010                3015

Asn Gln Asp Leu Thr Arg Asn Ser Ser Thr Pro Gly Leu Gln Val
    3020                3025                3030

Pro Val Ser Pro Thr Val Pro Ile Gln Asn Gln Lys Tyr Val Pro
    3035                3040                3045

Asn Ser Thr Asp Ser Pro Gly Pro Ser Gln Ile Ser Asn Ala Ala
    3050                3055                3060

Val Gln Thr Thr Pro Pro His Leu Lys Pro Ala Thr Glu Lys Leu
    3065                3070                3075

Ile Val Val Asn Gln Asn Met Gln Pro Leu Tyr Val Leu Gln Thr
    3080                3085                3090

Leu Pro Asn Gly Val Thr Gln Lys Ile Gln Leu Thr Ser Ser Val
    3095                3100                3105

Ser Ser Thr Pro Ser Val Met Glu Thr Asn Thr Ser Val Leu Gly
    3110                3115                3120

Pro Met Gly Gly Gly Leu Thr Leu Thr Thr Gly Leu Asn Pro Ser
    3125                3130                3135

Leu Pro Thr Ser Gln Ser Leu Phe Pro Ser Ala Ser Lys Gly Leu
    3140                3145                3150

Leu Pro Met Ser His His Gln His Leu His Ser Phe Pro Ala Ala
    3155                3160                3165

Thr Gln Ser Ser Phe Pro Pro Asn Ile Ser Asn Pro Pro Ser Gly
    3170                3175                3180

Leu Leu Ile Gly Val Gln Pro Pro Asp Pro Gln Leu Leu Val
    3185                3190                3195

Ser Glu Ser Ser Gln Arg Thr Asp Leu Ser Thr Thr Val Ala Thr
    3200                3205                3210

Pro Ser Ser Gly Leu Lys Lys Arg Pro Ile Ser Arg Leu Gln Thr
    3215                3220                3225
```

-continued

```
Arg Lys Asn Lys Lys Leu Ala Pro Ser Ser Thr Pro Ser Asn Ile
3230                3235                3240

Ala Pro Ser Asp Val Val Ser Asn Met Thr Leu Ile Asn Phe Thr
3245                3250                3255

Pro Ser Gln Leu Pro Asn His Pro Ser Leu Leu Asp Leu Gly Ser
3260                3265                3270

Leu Asn Thr Ser Ser His Arg Thr Val Pro Asn Ile Ile Lys Arg
3275                3280                3285

Ser Lys Ser Ser Ile Met Tyr Phe Glu Pro Ala Pro Leu Leu Pro
3290                3295                3300

Gln Ser Val Gly Gly Thr Ala Ala Thr Ala Ala Gly Thr Ser Thr
3305                3310                3315

Ile Ser Gln Asp Thr Ser His Leu Thr Ser Gly Ser Val Ser Gly
3320                3325                3330

Leu Ala Ser Ser Ser Ser Val Leu Asn Val Val Ser Met Gln Thr
3335                3340                3345

Thr Thr Thr Pro Thr Ser Ser Ala Ser Val Pro Gly His Val Thr
3350                3355                3360

Leu Thr Asn Pro Arg Leu Leu Gly Thr Pro Asp Ile Gly Ser Ile
3365                3370                3375

Ser Asn Leu Leu Ile Lys Ala Ser Gln Gln Ser Leu Gly Ile Gln
3380                3385                3390

Asp Gln Pro Val Ala Leu Pro Pro Ser Ser Gly Met Phe Pro Gln
3395                3400                3405

Leu Gly Thr Ser Gln Thr Pro Ser Thr Ala Ala Ile Thr Ala Ala
3410                3415                3420

Ser Ser Ile Cys Val Leu Pro Ser Thr Gln Thr Thr Gly Ile Thr
3425                3430                3435

Ala Ala Ser Pro Ser Gly Glu Ala Asp Glu His Tyr Gln Leu Gln
3440                3445                3450

His Val Asn Gln Leu Leu Ala Ser Lys Thr Gly Ile His Ser Ser
3455                3460                3465

Gln Arg Asp Leu Asp Ser Ala Ser Gly Pro Gln Val Ser Asn Phe
3470                3475                3480

Thr Gln Thr Val Asp Ala Pro Asn Ser Met Gly Leu Glu Gln Asn
3485                3490                3495

Lys Ala Leu Ser Ser Ala Val Gln Ala Ser Pro Thr Ser Pro Gly
3500                3505                3510

Gly Ser Pro Ser Ser Pro Ser Ser Gly Gln Arg Ser Ala Ser Pro
3515                3520                3525

Ser Val Pro Gly Pro Thr Lys Pro Lys Pro Lys Thr Lys Arg Phe
3530                3535                3540

Gln Leu Pro Leu Asp Lys Gly Asn Gly Lys Lys His Lys Val Ser
3545                3550                3555

His Leu Arg Thr Ser Ser Ser Glu Ala His Ile Pro Asp Gln Glu
3560                3565                3570

Thr Thr Ser Leu Thr Ser Gly Thr Gly Thr Pro Gly Ala Glu Ala
3575                3580                3585

Glu Gln Gln Asp Thr Ala Ser Val Glu Gln Ser Ser Gln Lys Glu
3590                3595                3600

Cys Gly Gln Pro Ala Gly Gln Val Ala Val Leu Pro Glu Val Gln
3605                3610                3615
```

| | | | | | | | | | | | |
|---|---|---|---|---|---|---|---|---|---|---|---|
|Val|Thr|Gln|Asn|Pro|Ala|Asn|Glu|Gln|Glu|Ser|Ala|Glu|Pro|Lys|
| |3620| | | |3625| | | |3630| | |

Val Thr Gln Asn Pro Ala Asn Glu Gln Glu Ser Ala Glu Pro Lys
      3620              3625              3630

Thr Val Glu Glu Glu Ser Asn Phe Ser Ser Pro Leu Met Leu
      3635              3640              3645

Trp Leu Gln Gln Glu Gln Lys Arg Lys Glu Ser Ile Thr Glu Lys
      3650              3655              3660

Lys Pro Lys Lys Gly Leu Val Phe Glu Ile Ser Ser Asp Asp Gly
      3665              3670              3675

Phe Gln Ile Cys Ala Glu Ser Ile Glu Asp Ala Trp Lys Ser Leu
      3680              3685              3690

Thr Asp Lys Val Gln Glu Ala Arg Ser Asn Ala Arg Leu Lys Gln
      3695              3700              3705

Leu Ser Phe Ala Gly Val Asn Gly Leu Arg Met Leu Gly Ile Leu
      3710              3715              3720

His Asp Ala Val Val Phe Leu Ile Glu Gln Leu Ser Gly Ala Lys
      3725              3730              3735

His Cys Arg Asn Tyr Lys Phe Arg Phe His Lys Pro Glu Glu Ala
      3740              3745              3750

Asn Glu Pro Pro Leu Asn Pro His Gly Ser Ala Arg Ala Glu Val
      3755              3760              3765

His Leu Arg Lys Ser Ala Phe Asp Met Phe Asn Phe Leu Ala Ser
      3770              3775              3780

Lys His Arg Gln Pro Pro Glu Tyr Asn Pro Asn Asp Glu Glu Glu
      3785              3790              3795

Glu Glu Val Gln Leu Lys Ser Ala Arg Arg Ala Thr Ser Met Asp
      3800              3805              3810

Leu Pro Met Pro Met Arg Phe Arg His Leu Lys Lys Thr Ser Lys
      3815              3820              3825

Glu Ala Val Gly Val Tyr Arg Ser Pro Ile His Gly Arg Gly Leu
      3830              3835              3840

Phe Cys Lys Arg Asn Ile Asp Ala Gly Glu Met Val Ile Glu Tyr
      3845              3850              3855

Ala Gly Asn Val Ile Arg Ser Ile Gln Thr Asp Lys Arg Glu Lys
      3860              3865              3870

Tyr Tyr Asp Ser Lys Gly Ile Gly Cys Tyr Met Phe Arg Ile Asp
      3875              3880              3885

Asp Ser Glu Val Val Asp Ala Thr Met His Gly Asn Ala Ala Arg
      3890              3895              3900

Phe Ile Asn His Ser Cys Glu Pro Asn Cys Tyr Ser Arg Val Ile
      3905              3910              3915

Asn Ile Asp Gly Gln Lys His Ile Val Ile Phe Ala Met Arg Lys
      3920              3925              3930

Ile Tyr Arg Gly Glu Glu Leu Thr Tyr Asp Tyr Lys Phe Pro Ile
      3935              3940              3945

Glu Asp Ala Ser Asn Lys Leu Pro Cys Asn Cys Gly Ala Lys Lys
      3950              3955              3960

Cys Arg Lys Phe Leu Asn
      3965

<210> SEQ ID NO 43
<211> LENGTH: 3931
<212> TYPE: PRT
<213> ORGANISM: Homo sapiens

<400> SEQUENCE: 43

-continued

```
Met Ala His Ser Cys Arg Trp Arg Phe Pro Ala Arg Pro Gly Thr Thr
1               5                   10                  15

Gly Gly Gly Gly Gly Gly Arg Arg Gly Leu Gly Gly Ala Pro Arg
            20                  25                  30

Gln Arg Val Pro Ala Leu Leu Leu Pro Pro Gly Pro Pro Val Gly Gly
        35                  40                  45

Gly Gly Pro Gly Ala Pro Pro Ser Pro Pro Ala Val Ala Ala Ala
    50                  55                  60

Ala Ala Ala Gly Ser Ser Gly Ala Gly Val Pro Gly Gly Ala Ala Ala
65              70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
            115                 120                 125

Phe Arg Ala Val Phe Gly Glu Ser Gly Gly Gly Gly Ser Gly Glu
        130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
        195                 200                 205

Lys Ile Lys Lys Lys Asp Ser Lys Ser Ile Glu Lys Lys Arg Gly Arg
210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
            245                 250                 255

Lys Arg Thr Pro Ser Ala Thr Phe Gln Gln Ala Thr Lys Ile Lys Lys
        260                 265                 270

Leu Arg Ala Gly Lys Leu Ser Pro Leu Lys Ser Lys Phe Lys Thr Gly
    275                 280                 285

Lys Leu Gln Ile Gly Arg Lys Gly Val Gln Ile Val Arg Arg Gly
        290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
            325                 330                 335

Thr Pro Pro Leu Thr Lys Glu Asp Lys Thr Val Val Arg Gln Ser Pro
            340                 345                 350

Arg Arg Ile Lys Pro Val Arg Ile Pro Ser Ser Lys Arg Thr Asp
        355                 360                 365

Ala Thr Ile Ala Lys Gln Leu Leu Gln Arg Ala Lys Lys Gly Ala Gln
    370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
            405                 410                 415
```

```
Ile Ser Ser Arg Ile Ile Lys Thr Pro Arg Arg Phe Ile Glu Asp Glu
            420                 425                 430

Asp Tyr Asp Pro Pro Ile Lys Ile Ala Arg Leu Glu Ser Thr Pro Asn
        435                 440                 445

Ser Arg Phe Ser Ala Pro Ser Cys Gly Ser Ser Glu Lys Ser Ser Ala
    450                 455                 460

Ala Ser Gln His Ser Ser Gln Met Ser Ser Asp Ser Ser Arg Ser Ser
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
            500                 505                 510

Leu Pro Ile Ser Gln Ser Pro Glu Asn Glu Ser Asn Asp Arg Arg Ser
        515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Gly Val Ser Asn Arg Lys Arg
                725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Glu Leu Ser
        755                 760                 765

Pro Leu Thr Pro Pro Ser Ser Val Ser Ser Ser Leu Ser Ile Ser Val
770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
            820                 825                 830

Thr Pro Leu Phe Pro Trp Phe Thr Pro Gly Ser Gln Thr Glu Arg Gly
```

-continued

```
            835                 840                 845
Arg Asn Lys Asp Lys Ala Pro Glu Glu Leu Ser Lys Asp Arg Asp Ala
            850                 855                 860
Asp Lys Ser Val Glu Lys Asp Lys Ser Arg Glu Arg Asp Arg Glu Arg
865                 870                 875                 880
Glu Lys Glu Asn Lys Arg Glu Ser Arg Lys Glu Lys Arg Lys Lys Gly
                    885                 890                 895
Ser Glu Ile Gln Ser Ser Ser Ala Leu Tyr Pro Val Gly Arg Val Ser
                    900                 905                 910
Lys Glu Lys Val Val Gly Glu Asp Val Ala Thr Ser Ser Ala Lys
            915                 920                 925
Lys Ala Thr Gly Arg Lys Lys Ser Ser Ser His Asp Ser Gly Thr Asp
            930                 935                 940
Ile Thr Ser Val Thr Leu Gly Asp Thr Thr Ala Val Lys Thr Lys Ile
945                 950                 955                 960
Leu Ile Lys Lys Gly Arg Gly Asn Leu Glu Lys Thr Asn Leu Asp Leu
                    965                 970                 975
Gly Pro Thr Ala Pro Ser Leu Glu Lys Glu Lys Thr Leu Cys Leu Ser
            980                 985                 990
Thr Pro Ser Ser Ser Thr Val Lys His Ser Thr Ser Ser Ile Gly Ser
            995                 1000                1005
Met Leu Ala Gln Ala Asp Lys Leu Pro Met Thr Asp Lys Arg Val
        1010                1015                1020
Ala Ser Leu Leu Lys Lys Ala Lys Ala Gln Leu Cys Lys Ile Glu
        1025                1030                1035
Lys Ser Lys Ser Leu Lys Gln Thr Asp Gln Pro Lys Ala Gln Gly
        1040                1045                1050
Gln Glu Ser Asp Ser Ser Glu Thr Ser Val Arg Gly Pro Arg Ile
        1055                1060                1065
Lys His Val Cys Arg Arg Ala Ala Val Ala Leu Gly Arg Lys Arg
        1070                1075                1080
Ala Val Phe Pro Asp Asp Met Pro Thr Leu Ser Ala Leu Pro Trp
        1085                1090                1095
Glu Glu Arg Glu Lys Ile Leu Ser Ser Met Gly Asn Asp Asp Lys
        1100                1105                1110
Ser Ser Ile Ala Gly Ser Glu Asp Ala Glu Pro Leu Ala Pro Pro
        1115                1120                1125
Ile Lys Pro Ile Lys Pro Val Thr Arg Asn Lys Ala Pro Gln Glu
        1130                1135                1140
Pro Pro Val Lys Lys Gly Arg Arg Ser Arg Arg Cys Gly Gln Cys
        1145                1150                1155
Pro Gly Cys Gln Val Pro Glu Asp Cys Gly Val Cys Thr Asn Cys
        1160                1165                1170
Leu Asp Lys Pro Lys Phe Gly Gly Arg Asn Ile Lys Lys Gln Cys
        1175                1180                1185
Cys Lys Met Arg Lys Cys Gln Asn Leu Gln Trp Met Pro Ser Lys
        1190                1195                1200
Ala Tyr Leu Gln Lys Gln Ala Lys Ala Val Lys Lys Lys Glu Lys
        1205                1210                1215
Lys Ser Lys Thr Ser Glu Lys Lys Asp Ser Lys Glu Ser Ser Val
        1220                1225                1230
Val Lys Asn Val Val Asp Ser Ser Gln Lys Pro Thr Pro Ser Ala
        1235                1240                1245
```

Arg Glu Asp Pro Ala Pro Lys Lys Ser Ser Glu Pro Pro Pro
    1250                1255            1260

Arg Lys Pro Val Glu Glu Lys Ser Glu Glu Gly Asn Val Ser Ala
    1265                1270            1275

Pro Gly Pro Glu Ser Lys Gln Ala Thr Thr Pro Ala Ser Arg Lys
    1280                1285            1290

Ser Ser Lys Gln Val Ser Gln Pro Ala Leu Val Ile Pro Pro Gln
    1295                1300            1305

Pro Pro Thr Thr Gly Pro Pro Arg Lys Glu Val Pro Lys Thr Thr
    1310                1315            1320

Pro Ser Glu Pro Lys Lys Gln Pro Pro Pro Glu Ser Gly
    1325                1330            1335

Pro Glu Gln Ser Lys Gln Lys Val Ala Pro Arg Pro Ser Ile
    1340                1345            1350

Pro Val Lys Gln Lys Pro Lys Glu Lys Glu Lys Pro Pro Pro Val
    1355                1360            1365

Asn Lys Gln Glu Asn Ala Gly Thr Leu Asn Ile Leu Ser Thr Leu
    1370                1375            1380

Ser Asn Gly Asn Ser Ser Lys Gln Lys Ile Pro Ala Asp Gly Val
    1385                1390            1395

His Arg Ile Arg Val Asp Phe Lys Phe Val Tyr Cys Gln Val Cys
    1400                1405            1410

Cys Glu Pro Phe His Lys Phe Cys Leu Glu Glu Asn Glu Arg Pro
    1415                1420            1425

Leu Glu Asp Gln Leu Glu Asn Trp Cys Cys Arg Arg Cys Lys Phe
    1430                1435            1440

Cys His Val Cys Gly Arg Gln His Gln Ala Thr Lys Gln Leu Leu
    1445                1450            1455

Glu Cys Asn Lys Cys Arg Asn Ser Tyr His Pro Glu Cys Leu Gly
    1460                1465            1470

Pro Asn Tyr Pro Thr Lys Pro Thr Lys Lys Lys Val Trp Ile
    1475                1480            1485

Cys Thr Lys Cys Val Arg Cys Lys Ser Cys Gly Ser Thr Thr Pro
    1490                1495            1500

Gly Lys Gly Trp Asp Ala Gln Trp Ser His Asp Phe Ser Leu Cys
    1505                1510            1515

His Asp Cys Ala Lys Leu Phe Ala Lys Gly Asn Phe Cys Pro Leu
    1520                1525            1530

Cys Asp Lys Cys Tyr Asp Asp Asp Tyr Glu Ser Lys Met Met
    1535                1540            1545

Gln Cys Gly Lys Cys Asp Arg Trp Val His Ser Lys Cys Glu Asn
    1550                1555            1560

Leu Ser Asp Glu Met Tyr Glu Ile Leu Ser Asn Leu Pro Glu Ser
    1565                1570            1575

Val Ala Tyr Thr Cys Val Asn Cys Thr Glu Arg His Pro Ala Glu
    1580                1585            1590

Trp Arg Leu Ala Leu Glu Lys Glu Leu Gln Ile Ser Leu Lys Gln
    1595                1600            1605

Val Leu Thr Ala Leu Leu Asn Ser Arg Thr Thr Ser His Leu Leu
    1610                1615            1620

Arg Tyr Arg Gln Ala Ala Lys Pro Pro Asp Leu Asn Pro Glu Thr
    1625                1630            1635

```
Glu Glu Ser Ile Pro Ser Arg Ser Ser Pro Glu Gly Pro Asp Pro
1640                1645                1650

Pro Val Leu Thr Glu Val Ser Lys Gln Asp Asp Gln Gln Pro Leu
1655                1660                1665

Asp Leu Glu Gly Val Lys Arg Lys Met Asp Gln Gly Asn Tyr Thr
1670                1675                1680

Ser Val Leu Glu Phe Ser Asp Asp Ile Val Lys Ile Ile Gln Ala
1685                1690                1695

Ala Ile Asn Ser Asp Gly Gly Gln Pro Glu Ile Lys Lys Ala Asn
1700                1705                1710

Ser Met Val Lys Ser Phe Phe Ile Arg Gln Met Glu Arg Val Phe
1715                1720                1725

Pro Trp Phe Ser Val Lys Lys Ser Arg Phe Trp Glu Pro Asn Lys
1730                1735                1740

Val Ser Ser Asn Ser Gly Met Leu Pro Asn Ala Val Leu Pro Pro
1745                1750                1755

Ser Leu Asp His Asn Tyr Ala Gln Trp Gln Glu Arg Glu Glu Asn
1760                1765                1770

Ser His Thr Glu Gln Pro Pro Leu Met Lys Lys Ile Ile Pro Ala
1775                1780                1785

Pro Lys Pro Lys Gly Pro Gly Glu Pro Asp Ser Pro Thr Pro Leu
1790                1795                1800

His Pro Pro Thr Pro Pro Ile Leu Ser Thr Asp Arg Ser Arg Glu
1805                1810                1815

Asp Ser Pro Glu Leu Asn Pro Pro Pro Gly Ile Glu Asp Asn Arg
1820                1825                1830

Gln Cys Ala Leu Cys Leu Thr Tyr Gly Asp Asp Ser Ala Asn Asp
1835                1840                1845

Ala Gly Arg Leu Leu Tyr Ile Gly Gln Asn Glu Trp Thr His Val
1850                1855                1860

Asn Cys Ala Leu Trp Ser Ala Glu Val Phe Glu Asp Asp Asp Gly
1865                1870                1875

Ser Leu Lys Asn Val His Met Ala Val Ile Arg Gly Lys Gln Leu
1880                1885                1890

Arg Cys Glu Phe Cys Gln Lys Pro Gly Ala Thr Val Gly Cys Cys
1895                1900                1905

Leu Thr Ser Cys Thr Ser Asn Tyr His Phe Met Cys Ser Arg Ala
1910                1915                1920

Lys Asn Cys Val Phe Leu Asp Asp Lys Lys Val Tyr Cys Gln Arg
1925                1930                1935

His Arg Asp Leu Ile Lys Gly Glu Val Val Pro Glu Asn Gly Phe
1940                1945                1950

Glu Val Phe Arg Arg Val Phe Val Asp Phe Glu Gly Ile Ser Leu
1955                1960                1965

Arg Arg Lys Phe Leu Asn Gly Leu Glu Pro Glu Asn Ile His Met
1970                1975                1980

Met Ile Gly Ser Met Thr Ile Asp Cys Leu Gly Ile Leu Asn Asp
1985                1990                1995

Leu Ser Asp Cys Glu Asp Lys Leu Phe Pro Ile Gly Tyr Gln Cys
2000                2005                2010

Ser Arg Val Tyr Trp Ser Thr Thr Asp Ala Arg Lys Arg Cys Val
2015                2020                2025

Tyr Thr Cys Lys Ile Val Glu Cys Arg Pro Pro Val Val Glu Pro
```

-continued

```
                2030                2035                2040
Asp Ile Asn Ser Thr Val Glu His Asp Glu Asn Arg Thr Ile Ala
        2045                2050                2055
His Ser Pro Thr Ser Phe Thr Glu Ser Ser Lys Glu Ser Gln
        2060                2065                2070
Asn Thr Ala Glu Ile Ile Ser Pro Pro Ser Pro Asp Arg Pro Pro
        2075                2080                2085
His Ser Gln Thr Ser Gly Ser Cys Tyr Tyr His Val Ile Ser Lys
        2090                2095                2100
Val Pro Arg Ile Arg Thr Pro Ser Tyr Ser Pro Thr Gln Arg Ser
        2105                2110                2115
Pro Gly Cys Arg Pro Leu Pro Ser Ala Gly Ser Pro Thr Pro Thr
        2120                2125                2130
Thr His Glu Ile Val Thr Val Gly Asp Pro Leu Leu Ser Ser Gly
        2135                2140                2145
Leu Arg Ser Ile Gly Ser Arg Arg His Ser Thr Ser Ser Leu Ser
        2150                2155                2160
Pro Gln Arg Ser Lys Leu Arg Ile Met Ser Pro Met Arg Thr Gly
        2165                2170                2175
Asn Thr Tyr Ser Arg Asn Asn Val Ser Ser Val Ser Thr Thr Gly
        2180                2185                2190
Thr Ala Thr Asp Leu Glu Ser Ser Ala Lys Val Val Asp His Val
        2195                2200                2205
Leu Gly Pro Leu Asn Ser Ser Thr Ser Leu Gly Gln Asn Thr Ser
        2210                2215                2220
Thr Ser Ser Asn Leu Gln Arg Thr Val Val Thr Val Gly Asn Lys
        2225                2230                2235
Asn Ser His Leu Asp Gly Ser Ser Ser Ser Glu Met Lys Gln Ser
        2240                2245                2250
Ser Ala Ser Asp Leu Val Ser Lys Ser Ser Ser Leu Lys Gly Glu
        2255                2260                2265
Lys Thr Lys Val Leu Ser Ser Lys Ser Ser Glu Gly Ser Ala His
        2270                2275                2280
Asn Val Ala Tyr Pro Gly Ile Pro Lys Leu Ala Pro Gln Val His
        2285                2290                2295
Asn Thr Thr Ser Arg Glu Leu Asn Val Ser Lys Ile Gly Ser Phe
        2300                2305                2310
Ala Glu Pro Ser Ser Val Ser Phe Ser Ser Lys Glu Ala Leu Ser
        2315                2320                2325
Phe Pro His Leu His Leu Arg Gly Gln Arg Asn Asp Arg Asp Gln
        2330                2335                2340
His Thr Asp Ser Thr Gln Ser Ala Asn Ser Ser Pro Asp Glu Asp
        2345                2350                2355
Thr Glu Val Lys Thr Leu Lys Leu Ser Gly Met Ser Asn Arg Ser
        2360                2365                2370
Ser Ile Ile Asn Glu His Met Gly Ser Ser Ser Arg Asp Arg Arg
        2375                2380                2385
Gln Lys Gly Lys Lys Ser Cys Lys Glu Thr Phe Lys Glu Lys His
        2390                2395                2400
Ser Ser Lys Ser Phe Leu Glu Pro Gly Gln Val Thr Thr Gly Glu
        2405                2410                2415
Glu Gly Asn Leu Lys Pro Glu Phe Met Asp Glu Val Leu Thr Pro
        2420                2425                2430
```

-continued

```
Glu Tyr Met Gly Gln Arg Pro Cys Asn Asn Val Ser Ser Asp Lys
    2435                2440                2445

Ile Gly Asp Lys Gly Leu Ser Met Pro Gly Val Pro Lys Ala Pro
    2450                2455                2460

Pro Met Gln Val Glu Gly Ser Ala Lys Glu Leu Gln Ala Pro Arg
    2465                2470                2475

Lys Arg Thr Val Lys Val Thr Leu Thr Pro Leu Lys Met Glu Asn
    2480                2485                2490

Glu Ser Gln Ser Lys Asn Ala Leu Lys Glu Ser Pro Ala Ser
    2495                2500                2505

Pro Leu Gln Ile Glu Ser Thr Ser Pro Thr Glu Pro Ile Ser Ala
    2510                2515                2520

Ser Glu Asn Pro Gly Asp Gly Pro Val Ala Gln Pro Ser Pro Asn
    2525                2530                2535

Asn Thr Ser Cys Gln Asp Ser Gln Ser Asn Asn Tyr Gln Asn Leu
    2540                2545                2550

Pro Val Gln Asp Arg Asn Leu Met Leu Pro Asp Gly Pro Lys Pro
    2555                2560                2565

Gln Glu Asp Gly Ser Phe Lys Arg Arg Tyr Pro Arg Arg Ser Ala
    2570                2575                2580

Arg Ala Arg Ser Asn Met Phe Phe Gly Leu Thr Pro Leu Tyr Gly
    2585                2590                2595

Val Arg Ser Tyr Gly Glu Glu Asp Ile Pro Phe Tyr Ser Ser Ser
    2600                2605                2610

Thr Gly Lys Lys Arg Gly Lys Arg Ser Ala Glu Gly Gln Val Asp
    2615                2620                2625

Gly Ala Asp Asp Leu Ser Thr Ser Asp Glu Asp Leu Tyr Tyr
    2630                2635                2640

Tyr Asn Phe Thr Arg Thr Val Ile Ser Ser Gly Gly Glu Glu Arg
    2645                2650                2655

Leu Ala Ser His Asn Leu Phe Arg Glu Glu Glu Gln Cys Asp Leu
    2660                2665                2670

Pro Lys Ile Ser Gln Leu Asp Gly Val Asp Asp Gly Thr Glu Ser
    2675                2680                2685

Asp Thr Ser Val Thr Ala Thr Thr Arg Lys Ser Ser Gln Ile Pro
    2690                2695                2700

Lys Arg Asn Gly Lys Glu Asn Gly Thr Glu Asn Leu Lys Ile Asp
    2705                2710                2715

Arg Pro Glu Asp Ala Gly Glu Lys Glu His Val Thr Lys Ser Ser
    2720                2725                2730

Val Gly His Lys Asn Glu Pro Lys Met Asp Asn Cys His Ser Val
    2735                2740                2745

Ser Arg Val Lys Thr Gln Gly Gln Asp Ser Leu Glu Ala Gln Leu
    2750                2755                2760

Ser Ser Leu Glu Ser Ser Arg Arg Val His Thr Ser Thr Pro Ser
    2765                2770                2775

Asp Lys Asn Leu Leu Asp Thr Tyr Asn Thr Glu Leu Leu Lys Ser
    2780                2785                2790

Asp Ser Asp Asn Asn Asn Ser Asp Asp Cys Gly Asn Ile Leu Pro
    2795                2800                2805

Ser Asp Ile Met Asp Phe Val Leu Lys Asn Thr Pro Ser Met Gln
    2810                2815                2820
```

```
Ala Leu Gly Glu Ser Pro Glu Ser Ser Ser Glu Leu Leu Asn
2825                2830                2835

Leu Gly Glu Gly Leu Gly Leu Asp Ser Asn Arg Glu Lys Asp Met
2840                2845                2850

Gly Leu Phe Glu Val Phe Ser Gln Gln Leu Pro Thr Thr Glu Pro
2855                2860                2865

Val Asp Ser Ser Val Ser Ser Ser Ile Ser Ala Glu Glu Gln Phe
2870                2875                2880

Glu Leu Pro Leu Glu Leu Pro Ser Asp Leu Ser Val Leu Thr Thr
2885                2890                2895

Arg Ser Pro Thr Val Pro Ser Gln Asn Pro Ser Arg Leu Ala Val
2900                2905                2910

Ile Ser Asp Ser Gly Glu Lys Arg Val Thr Ile Thr Glu Lys Ser
2915                2920                2925

Val Ala Ser Ser Glu Ser Asp Pro Ala Leu Leu Ser Pro Gly Val
2930                2935                2940

Asp Pro Thr Pro Glu Gly His Met Thr Pro Asp His Phe Ile Gln
2945                2950                2955

Gly His Met Asp Ala Asp His Ile Ser Ser Pro Pro Cys Gly Ser
2960                2965                2970

Val Glu Gln Gly His Gly Asn Asn Gln Asp Leu Thr Arg Asn Ser
2975                2980                2985

Ser Thr Pro Gly Leu Gln Val Pro Val Ser Pro Thr Val Pro Ile
2990                2995                3000

Gln Asn Gln Lys Tyr Val Pro Asn Ser Thr Asp Ser Pro Gly Pro
3005                3010                3015

Ser Gln Ile Ser Asn Ala Ala Val Gln Thr Thr Pro Pro His Leu
3020                3025                3030

Lys Pro Ala Thr Glu Lys Leu Ile Val Val Asn Gln Asn Met Gln
3035                3040                3045

Pro Leu Tyr Val Leu Gln Thr Leu Pro Asn Gly Val Thr Gln Lys
3050                3055                3060

Ile Gln Leu Thr Ser Ser Val Ser Ser Thr Pro Ser Val Met Glu
3065                3070                3075

Thr Asn Thr Ser Val Leu Gly Pro Met Gly Gly Gly Leu Thr Leu
3080                3085                3090

Thr Thr Gly Leu Asn Pro Ser Leu Pro Thr Ser Gln Ser Leu Phe
3095                3100                3105

Pro Ser Ala Ser Lys Gly Leu Leu Pro Met Ser His His Gln His
3110                3115                3120

Leu His Ser Phe Pro Ala Ala Thr Gln Ser Ser Phe Pro Pro Asn
3125                3130                3135

Ile Ser Asn Pro Pro Ser Gly Leu Leu Ile Gly Val Gln Pro Pro
3140                3145                3150

Pro Asp Pro Gln Leu Leu Val Ser Glu Ser Ser Gln Arg Thr Asp
3155                3160                3165

Leu Ser Thr Thr Val Ala Thr Pro Ser Ser Gly Leu Lys Lys Arg
3170                3175                3180

Pro Ile Ser Arg Leu Gln Thr Arg Lys Asn Lys Lys Leu Ala Pro
3185                3190                3195

Ser Ser Thr Pro Ser Asn Ile Ala Pro Ser Asp Val Val Ser Asn
3200                3205                3210

Met Thr Leu Ile Asn Phe Thr Pro Ser Gln Leu Pro Asn His Pro
```

-continued

|     | 3215 |     |     | 3220 |     |     |     | 3225 |     |
|-----|------|-----|-----|------|-----|-----|-----|------|-----|

Ser Leu Leu Asp Leu Gly Ser Leu Asn Thr Ser Ser His Arg Thr
               3230                    3235                    3240

Val Pro Asn Ile Ile Lys Arg Ser Lys Ser Ser Ile Met Tyr Phe
       3245                    3250                    3255

Glu Pro Ala Pro Leu Leu Pro Gln Ser Val Gly Gly Thr Ala Ala
       3260                    3265                    3270

Thr Ala Ala Gly Thr Ser Thr Ile Ser Gln Asp Thr Ser His Leu
       3275                    3280                    3285

Thr Ser Gly Ser Val Ser Gly Leu Ala Ser Ser Ser Val Leu
       3290                    3295                    3300

Asn Val Val Ser Met Gln Thr Thr Thr Pro Thr Ser Ser Ala
       3305                    3310                    3315

Ser Val Pro Gly His Val Thr Leu Thr Asn Pro Arg Leu Leu Gly
       3320                    3325                    3330

Thr Pro Asp Ile Gly Ser Ile Ser Asn Leu Leu Ile Lys Ala Ser
       3335                    3340                    3345

Gln Gln Ser Leu Gly Ile Gln Asp Gln Pro Val Ala Leu Pro Pro
       3350                    3355                    3360

Ser Ser Gly Met Phe Pro Gln Leu Gly Thr Ser Gln Thr Pro Ser
       3365                    3370                    3375

Thr Ala Ala Ile Thr Ala Ala Ser Ser Ile Cys Val Leu Pro Ser
       3380                    3385                    3390

Thr Gln Thr Thr Gly Ile Thr Ala Ala Ser Pro Ser Gly Glu Ala
       3395                    3400                    3405

Asp Glu His Tyr Gln Leu Gln His Val Asn Gln Leu Leu Ala Ser
       3410                    3415                    3420

Lys Thr Gly Ile His Ser Ser Gln Arg Asp Leu Asp Ser Ala Ser
       3425                    3430                    3435

Gly Pro Gln Val Ser Asn Phe Thr Gln Thr Val Asp Ala Pro Asn
       3440                    3445                    3450

Ser Met Gly Leu Glu Gln Asn Lys Ala Leu Ser Ser Ala Val Gln
       3455                    3460                    3465

Ala Ser Pro Thr Ser Pro Gly Gly Ser Pro Ser Ser Pro Ser Ser
       3470                    3475                    3480

Gly Gln Arg Ser Ala Ser Pro Ser Val Pro Gly Pro Thr Lys Pro
       3485                    3490                    3495

Lys Pro Lys Thr Lys Arg Phe Gln Leu Pro Leu Asp Lys Gly Asn
       3500                    3505                    3510

Gly Lys Lys His Lys Val Ser His Leu Arg Thr Ser Ser Ser Glu
       3515                    3520                    3525

Ala His Ile Pro Asp Gln Glu Thr Thr Ser Leu Thr Ser Gly Thr
       3530                    3535                    3540

Gly Thr Pro Gly Ala Glu Ala Glu Gln Gln Asp Thr Ala Ser Val
       3545                    3550                    3555

Glu Gln Ser Ser Gln Lys Glu Cys Gly Gln Pro Ala Gly Gln Val
       3560                    3565                    3570

Ala Val Leu Pro Glu Val Gln Val Thr Gln Asn Pro Ala Asn Glu
       3575                    3580                    3585

Gln Glu Ser Ala Glu Pro Lys Thr Val Glu Glu Glu Ser Asn
       3590                    3595                    3600

Phe Ser Ser Pro Leu Met Leu Trp Leu Gln Gln Glu Gln Lys Arg
       3605                    3610                    3615

-continued

Lys Glu Ser Ile Thr Glu Lys Lys Pro Lys Lys Gly Leu Val Phe
3620            3625            3630

Glu Ile Ser Ser Asp Asp Gly Phe Gln Ile Cys Ala Glu Ser Ile
3635            3640            3645

Glu Asp Ala Trp Lys Ser Leu Thr Asp Lys Val Gln Glu Ala Arg
3650            3655            3660

Ser Asn Ala Arg Leu Lys Gln Leu Ser Phe Ala Gly Val Asn Gly
3665            3670            3675

Leu Arg Met Leu Gly Ile Leu His Asp Ala Val Val Phe Leu Ile
3680            3685            3690

Glu Gln Leu Ser Gly Ala Lys His Cys Arg Asn Tyr Lys Phe Arg
3695            3700            3705

Phe His Lys Pro Glu Glu Ala Asn Glu Pro Pro Leu Asn Pro His
3710            3715            3720

Gly Ser Ala Arg Ala Glu Val His Leu Arg Lys Ser Ala Phe Asp
3725            3730            3735

Met Phe Asn Phe Leu Ala Ser Lys His Arg Gln Pro Pro Glu Tyr
3740            3745            3750

Asn Pro Asn Asp Glu Glu Glu Glu Val Gln Leu Lys Ser Ala
3755            3760            3765

Arg Arg Ala Thr Ser Met Asp Leu Pro Met Pro Met Arg Phe Arg
3770            3775            3780

His Leu Lys Lys Thr Ser Lys Glu Ala Val Gly Val Tyr Arg Ser
3785            3790            3795

Pro Ile His Gly Arg Gly Leu Phe Cys Lys Arg Asn Ile Asp Ala
3800            3805            3810

Gly Glu Met Val Ile Glu Tyr Ala Gly Asn Val Ile Arg Ser Ile
3815            3820            3825

Gln Thr Asp Lys Arg Glu Lys Tyr Tyr Asp Ser Lys Gly Ile Gly
3830            3835            3840

Cys Tyr Met Phe Arg Ile Asp Asp Ser Glu Val Val Asp Ala Thr
3845            3850            3855

Met His Gly Asn Ala Ala Arg Phe Ile Asn His Ser Cys Glu Pro
3860            3865            3870

Asn Cys Tyr Ser Arg Val Ile Asn Ile Asp Gly Gln Lys His Ile
3875            3880            3885

Val Ile Phe Ala Met Arg Lys Ile Tyr Arg Gly Glu Glu Leu Thr
3890            3895            3900

Tyr Asp Tyr Lys Phe Pro Ile Glu Asp Ala Ser Asn Lys Leu Pro
3905            3910            3915

Cys Asn Cys Gly Ala Lys Lys Cys Arg Lys Phe Leu Asn
3920            3925            3930

<210> SEQ ID NO 44
<211> LENGTH: 3972
<212> TYPE: PRT
<213> ORGANISM: Homo sapiens

<400> SEQUENCE: 44

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
                20                  25                  30

Gln Arg Val Pro Ala Leu Leu Leu Pro Pro Gly Pro Pro Val Gly Gly

```
              35                  40                  45
Gly Gly Pro Gly Ala Pro Pro Ser Pro Pro Ala Val Ala Ala Ala
 50                  55                  60
Ala Ala Ala Gly Ser Ser Gly Ala Gly Val Pro Gly Gly Ala Ala
 65                  70                  75                  80
Ala Ser Ala Ala Ser Ser Ser Ala Ser Ser Ser Ser Ser Ser Ser
                 85                  90                  95
Ser Ser Ala Ser Ser Gly Pro Ala Leu Leu Arg Val Gly Pro Gly Phe
             100                 105                 110
Asp Ala Ala Leu Gln Val Ser Ala Ala Ile Gly Thr Asn Leu Arg Arg
             115                 120                 125
Phe Arg Ala Val Phe Gly Glu Ser Gly Gly Gly Gly Ser Gly Glu
             130                 135                 140
Asp Glu Gln Phe Leu Gly Phe Gly Ser Asp Glu Val Arg Val Arg
 145                 150                 155                 160
Ser Pro Thr Arg Ser Pro Ser Val Lys Thr Ser Pro Arg Lys Pro Arg
                 165                 170                 175
Gly Arg Pro Arg Ser Gly Ser Asp Arg Asn Ser Ala Ile Leu Ser Asp
             180                 185                 190
Pro Ser Val Phe Ser Pro Leu Asn Lys Ser Glu Thr Lys Ser Gly Asp
             195                 200                 205
Lys Ile Lys Lys Lys Asp Ser Lys Ser Ile Glu Lys Lys Arg Gly Arg
 210                 215                 220
Pro Pro Thr Phe Pro Gly Val Lys Ile Lys Ile Thr His Gly Lys Asp
 225                 230                 235                 240
Ile Ser Glu Leu Pro Lys Gly Asn Lys Glu Asp Ser Leu Lys Lys Ile
                 245                 250                 255
Lys Arg Thr Pro Ser Ala Thr Phe Gln Gln Ala Thr Lys Ile Lys Lys
             260                 265                 270
Leu Arg Ala Gly Lys Leu Ser Pro Leu Lys Ser Lys Phe Lys Thr Gly
             275                 280                 285
Lys Leu Gln Ile Gly Arg Lys Gly Val Gln Ile Val Arg Arg Gly
 290                 295                 300
Arg Pro Pro Ser Thr Glu Arg Ile Lys Thr Pro Ser Gly Leu Leu Ile
 305                 310                 315                 320
Asn Ser Glu Leu Glu Lys Pro Gln Lys Val Arg Lys Asp Lys Glu Gly
                 325                 330                 335
Thr Pro Pro Leu Thr Lys Glu Asp Lys Thr Val Val Arg Gln Ser Pro
             340                 345                 350
Arg Arg Ile Lys Pro Val Arg Ile Ile Pro Ser Ser Lys Arg Thr Asp
             355                 360                 365
Ala Thr Ile Ala Lys Gln Leu Leu Gln Arg Ala Lys Lys Gly Ala Gln
             370                 375                 380
Lys Lys Ile Glu Lys Glu Ala Ala Gln Leu Gln Gly Arg Lys Val Lys
 385                 390                 395                 400
Thr Gln Val Lys Asn Ile Arg Gln Phe Ile Met Pro Val Val Ser Ala
                 405                 410                 415
Ile Ser Ser Arg Ile Ile Lys Thr Pro Arg Arg Phe Ile Glu Asp Glu
             420                 425                 430
Asp Tyr Asp Pro Pro Ile Lys Ile Ala Arg Leu Glu Ser Thr Pro Asn
             435                 440                 445
Ser Arg Phe Ser Ala Pro Ser Cys Gly Ser Ser Glu Lys Ser Ser Ala
 450                 455                 460
```

```
Ala Ser Gln His Ser Ser Gln Met Ser Ser Asp Ser Arg Ser Ser
465                 470                 475                 480

Ser Pro Ser Val Asp Thr Ser Thr Asp Ser Gln Ala Ser Glu Glu Ile
            485                 490                 495

Gln Val Leu Pro Glu Glu Arg Ser Asp Thr Pro Glu Val His Pro Pro
                500                 505                 510

Leu Pro Ile Ser Gln Ser Pro Glu Asn Glu Ser Asn Asp Arg Arg Ser
                515                 520                 525

Arg Arg Tyr Ser Val Ser Glu Arg Ser Phe Gly Ser Arg Thr Thr Lys
        530                 535                 540

Lys Leu Ser Thr Leu Gln Ser Ala Pro Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
                740                 745                 750

His Ser Met Arg Thr Arg Ser Gly Arg Leu Ser Ser Glu Leu Ser
            755                 760                 765

Pro Leu Thr Pro Pro Ser Ser Val Ser Ser Ser Leu Ser Ile Ser Val
        770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
            805                 810                 815

Arg Lys Gln Thr Ser Ala Pro Ala Glu Pro Phe Ser Ser Ser Ser Pro
                820                 825                 830

Thr Pro Leu Phe Pro Trp Phe Thr Pro Gly Ser Gln Thr Glu Arg Gly
            835                 840                 845

Arg Asn Lys Asp Lys Ala Pro Glu Glu Leu Ser Lys Asp Arg Asp Ala
        850                 855                 860

Asp Lys Ser Val Glu Lys Asp Lys Ser Arg Glu Arg Asp Arg Glu Arg
865                 870                 875                 880
```

```
Glu Lys Glu Asn Lys Arg Glu Ser Arg Lys Glu Arg Lys Lys Gly
            885                 890                 895

Ser Glu Ile Gln Ser Ser Ser Ala Leu Tyr Pro Val Gly Arg Val Ser
            900                 905                 910

Lys Glu Lys Val Val Gly Glu Asp Val Ala Thr Ser Ser Ala Lys
            915                 920                 925

Lys Ala Thr Gly Arg Lys Lys Ser Ser Ser His Asp Ser Gly Thr Asp
            930                 935                 940

Ile Thr Ser Val Thr Leu Gly Asp Thr Thr Ala Val Lys Thr Lys Ile
945                 950                 955                 960

Leu Ile Lys Lys Gly Arg Gly Asn Leu Glu Lys Thr Asn Leu Asp Leu
            965                 970                 975

Gly Pro Thr Ala Pro Ser Leu Glu Lys Glu Lys Thr Leu Cys Leu Ser
            980                 985                 990

Thr Pro Ser Ser Ser Thr Val Lys His Ser Thr Ser Ser Ile Gly Ser
            995                 1000                1005

Met Leu Ala Gln Ala Asp Lys Leu Pro Met Thr Asp Lys Arg Val
       1010                1015                1020

Ala Ser Leu Leu Lys Lys Ala Lys Ala Gln Leu Cys Lys Ile Glu
       1025                1030                1035

Lys Ser Lys Ser Leu Lys Gln Thr Asp Gln Pro Lys Ala Gln Gly
       1040                1045                1050

Gln Glu Ser Asp Ser Ser Glu Thr Ser Val Arg Gly Pro Arg Ile
       1055                1060                1065

Lys His Val Cys Arg Arg Ala Ala Val Ala Leu Gly Arg Lys Arg
       1070                1075                1080

Ala Val Phe Pro Asp Asp Met Pro Thr Leu Ser Ala Leu Pro Trp
       1085                1090                1095

Glu Glu Arg Glu Lys Ile Leu Ser Ser Met Gly Asn Asp Asp Lys
       1100                1105                1110

Ser Ser Ile Ala Gly Ser Glu Asp Ala Glu Pro Leu Ala Pro Pro
       1115                1120                1125

Ile Lys Pro Ile Lys Pro Val Thr Arg Asn Lys Ala Pro Gln Glu
       1130                1135                1140

Pro Pro Val Lys Lys Gly Arg Arg Ser Arg Arg Cys Gly Gln Cys
       1145                1150                1155

Pro Gly Cys Gln Val Pro Glu Asp Cys Gly Val Cys Thr Asn Cys
       1160                1165                1170

Leu Asp Lys Pro Lys Phe Gly Gly Arg Asn Ile Lys Lys Gln Cys
       1175                1180                1185

Cys Lys Met Arg Lys Cys Gln Asn Leu Gln Trp Met Pro Ser Lys
       1190                1195                1200

Ala Tyr Leu Gln Lys Gln Ala Lys Ala Val Lys Lys Lys Glu Lys
       1205                1210                1215

Lys Ser Lys Thr Ser Glu Lys Lys Asp Ser Lys Glu Ser Ser Val
       1220                1225                1230

Val Lys Asn Val Val Asp Ser Gln Lys Pro Thr Pro Ser Ala
       1235                1240                1245

Arg Glu Asp Pro Ala Pro Lys Lys Ser Ser Glu Pro Pro Pro
       1250                1255                1260

Arg Lys Pro Val Glu Glu Lys Ser Glu Glu Gly Asn Val Ser Ala
       1265                1270                1275

Pro Gly Pro Glu Ser Lys Gln Ala Thr Thr Pro Ala Ser Arg Lys
```

```
            1280                1285                1290
Ser Ser Lys Gln Val Ser Gln Pro Ala Leu Val Ile Pro Pro Gln
    1295                1300                1305

Pro Pro Thr Thr Gly Pro Pro Arg Lys Glu Val Pro Lys Thr Thr
    1310                1315                1320

Pro Ser Glu Pro Lys Lys Lys Gln Pro Pro Pro Glu Ser Gly
    1325                1330                1335

Pro Glu Gln Ser Lys Gln Lys Lys Val Ala Pro Arg Pro Ser Ile
    1340                1345                1350

Pro Val Lys Gln Lys Pro Lys Glu Lys Glu Lys Pro Pro Pro Val
    1355                1360                1365

Asn Lys Gln Glu Asn Ala Gly Thr Leu Asn Ile Leu Ser Thr Leu
    1370                1375                1380

Ser Asn Gly Asn Ser Ser Lys Gln Lys Ile Pro Ala Asp Gly Val
    1385                1390                1395

His Arg Ile Arg Val Asp Phe Lys Glu Asp Cys Glu Ala Glu Asn
    1400                1405                1410

Val Trp Glu Met Gly Gly Leu Gly Ile Leu Thr Ser Val Pro Ile
    1415                1420                1425

Thr Pro Arg Val Val Cys Phe Leu Cys Ala Ser Ser Gly His Val
    1430                1435                1440

Glu Phe Val Tyr Cys Gln Val Cys Cys Glu Pro Phe His Lys Phe
    1445                1450                1455

Cys Leu Glu Glu Asn Glu Arg Pro Leu Glu Asp Gln Leu Glu Asn
    1460                1465                1470

Trp Cys Cys Arg Arg Cys Lys Phe Cys His Val Cys Gly Arg Gln
    1475                1480                1485

His Gln Ala Thr Lys Gln Leu Leu Glu Cys Asn Lys Cys Arg Asn
    1490                1495                1500

Ser Tyr His Pro Glu Cys Leu Gly Pro Asn Tyr Pro Thr Lys Pro
    1505                1510                1515

Thr Lys Lys Lys Lys Val Trp Ile Cys Thr Lys Cys Val Arg Cys
    1520                1525                1530

Lys Ser Cys Gly Ser Thr Thr Pro Gly Lys Gly Trp Asp Ala Gln
    1535                1540                1545

Trp Ser His Asp Phe Ser Leu Cys His Asp Cys Ala Lys Leu Phe
    1550                1555                1560

Ala Lys Gly Asn Phe Cys Pro Leu Cys Asp Lys Cys Tyr Asp Asp
    1565                1570                1575

Asp Asp Tyr Glu Ser Lys Met Met Gln Cys Gly Lys Cys Asp Arg
    1580                1585                1590

Trp Val His Ser Lys Cys Glu Asn Leu Ser Gly Thr Glu Asp Glu
    1595                1600                1605

Met Tyr Glu Ile Leu Ser Asn Leu Pro Glu Ser Val Ala Tyr Thr
    1610                1615                1620

Cys Val Asn Cys Thr Glu Arg His Pro Ala Glu Trp Arg Leu Ala
    1625                1630                1635

Leu Glu Lys Glu Leu Gln Ile Ser Leu Lys Gln Val Leu Thr Ala
    1640                1645                1650

Leu Leu Asn Ser Arg Thr Thr Ser His Leu Leu Arg Tyr Arg Gln
    1655                1660                1665

Ala Ala Lys Pro Pro Asp Leu Asn Pro Glu Thr Glu Glu Ser Ile
    1670                1675                1680
```

Pro Ser Arg Ser Ser Pro Glu Gly Pro Asp Pro Val Leu Thr
    1685                1690            1695

Glu Val Ser Lys Gln Asp Gln Gln Pro Leu Asp Leu Glu Gly
    1700                1705            1710

Val Lys Arg Lys Met Asp Gln Gly Asn Tyr Thr Ser Val Leu Glu
    1715                1720            1725

Phe Ser Asp Asp Ile Val Lys Ile Ile Gln Ala Ala Ile Asn Ser
    1730                1735            1740

Asp Gly Gly Gln Pro Glu Ile Lys Lys Ala Asn Ser Met Val Lys
    1745                1750            1755

Ser Phe Phe Ile Arg Gln Met Glu Arg Val Phe Pro Trp Phe Ser
    1760                1765            1770

Val Lys Lys Ser Arg Phe Trp Glu Pro Asn Lys Val Ser Ser Asn
    1775                1780            1785

Ser Gly Met Leu Pro Asn Ala Val Leu Pro Pro Ser Leu Asp His
    1790                1795            1800

Asn Tyr Ala Gln Trp Gln Glu Arg Glu Glu Asn Ser His Thr Glu
    1805                1810            1815

Gln Pro Pro Leu Met Lys Lys Ile Ile Pro Ala Pro Lys Pro Lys
    1820                1825            1830

Gly Pro Gly Glu Pro Asp Ser Pro Thr Pro Leu His Pro Pro Thr
    1835                1840            1845

Pro Pro Ile Leu Ser Thr Asp Arg Ser Arg Glu Asp Ser Pro Glu
    1850                1855            1860

Leu Asn Pro Pro Gly Ile Glu Asp Asn Arg Gln Cys Ala Leu
    1865                1870            1875

Cys Leu Thr Tyr Gly Asp Asp Ser Ala Asn Asp Ala Gly Arg Leu
    1880                1885            1890

Leu Tyr Ile Gly Gln Asn Glu Trp Thr His Val Asn Cys Ala Leu
    1895                1900            1905

Trp Ser Ala Glu Val Phe Glu Asp Asp Asp Gly Ser Leu Lys Asn
    1910                1915            1920

Val His Met Ala Val Ile Arg Gly Lys Gln Leu Arg Cys Glu Phe
    1925                1930            1935

Cys Gln Lys Pro Gly Ala Thr Val Gly Cys Cys Leu Thr Ser Cys
    1940                1945            1950

Thr Ser Asn Tyr His Phe Met Cys Ser Arg Ala Lys Asn Cys Val
    1955                1960            1965

Phe Leu Asp Asp Lys Lys Val Tyr Cys Gln Arg His Arg Asp Leu
    1970                1975            1980

Ile Lys Gly Glu Val Val Pro Glu Asn Gly Phe Glu Val Phe Arg
    1985                1990            1995

Arg Val Phe Val Asp Phe Glu Gly Ile Ser Leu Arg Arg Lys Phe
    2000                2005            2010

Leu Asn Gly Leu Glu Pro Glu Asn Ile His Met Met Ile Gly Ser
    2015                2020            2025

Met Thr Ile Asp Cys Leu Gly Ile Leu Asn Asp Leu Ser Asp Cys
    2030                2035            2040

Glu Asp Lys Leu Phe Pro Ile Gly Tyr Gln Cys Ser Arg Val Tyr
    2045                2050            2055

Trp Ser Thr Thr Asp Ala Arg Lys Arg Cys Val Tyr Thr Cys Lys
    2060                2065            2070

-continued

```
Ile Val Glu Cys Arg Pro Val Val Glu Pro Asp Ile Asn Ser
2075             2080             2085

Thr Val Glu His Asp Glu Asn Arg Thr Ile Ala His Ser Pro Thr
2090             2095             2100

Ser Phe Thr Glu Ser Ser Ser Lys Glu Ser Gln Asn Thr Ala Glu
2105             2110             2115

Ile Ile Ser Pro Pro Ser Pro Asp Arg Pro Pro His Ser Gln Thr
2120             2125             2130

Ser Gly Ser Cys Tyr Tyr His Val Ile Ser Lys Val Pro Arg Ile
2135             2140             2145

Arg Thr Pro Ser Tyr Ser Pro Thr Gln Arg Ser Pro Gly Cys Arg
2150             2155             2160

Pro Leu Pro Ser Ala Gly Ser Pro Thr Pro Thr His Glu Ile
2165             2170             2175

Val Thr Val Gly Asp Pro Leu Leu Ser Ser Gly Leu Arg Ser Ile
2180             2185             2190

Gly Ser Arg Arg His Ser Thr Ser Ser Leu Ser Pro Gln Arg Ser
2195             2200             2205

Lys Leu Arg Ile Met Ser Pro Met Arg Thr Gly Asn Thr Tyr Ser
2210             2215             2220

Arg Asn Asn Val Ser Ser Val Ser Thr Thr Gly Thr Ala Thr Asp
2225             2230             2235

Leu Glu Ser Ser Ala Lys Val Val Asp His Val Leu Gly Pro Leu
2240             2245             2250

Asn Ser Ser Thr Ser Leu Gly Gln Asn Thr Ser Thr Ser Ser Asn
2255             2260             2265

Leu Gln Arg Thr Val Val Thr Val Gly Asn Lys Asn Ser His Leu
2270             2275             2280

Asp Gly Ser Ser Ser Ser Glu Met Lys Gln Ser Ser Ala Ser Asp
2285             2290             2295

Leu Val Ser Lys Ser Ser Ser Leu Lys Gly Glu Lys Thr Lys Val
2300             2305             2310

Leu Ser Ser Lys Ser Ser Glu Gly Ser Ala His Asn Val Ala Tyr
2315             2320             2325

Pro Gly Ile Pro Lys Leu Ala Pro Gln Val His Asn Thr Thr Ser
2330             2335             2340

Arg Glu Leu Asn Val Ser Lys Ile Gly Ser Phe Ala Glu Pro Ser
2345             2350             2355

Ser Val Ser Phe Ser Ser Lys Glu Ala Leu Ser Phe Pro His Leu
2360             2365             2370

His Leu Arg Gly Gln Arg Asn Asp Arg Asp Gln His Thr Asp Ser
2375             2380             2385

Thr Gln Ser Ala Asn Ser Ser Pro Asp Glu Asp Thr Glu Val Lys
2390             2395             2400

Thr Leu Lys Leu Ser Gly Met Ser Asn Arg Ser Ser Ile Ile Asn
2405             2410             2415

Glu His Met Gly Ser Ser Ser Arg Asp Arg Arg Gln Lys Gly Lys
2420             2425             2430

Lys Ser Cys Lys Glu Thr Phe Lys Glu Lys His Ser Ser Lys Ser
2435             2440             2445

Phe Leu Glu Pro Gly Gln Val Thr Thr Gly Glu Glu Gly Asn Leu
2450             2455             2460

Lys Pro Glu Phe Met Asp Glu Val Leu Thr Pro Glu Tyr Met Gly
```

```
                2465                2470                2475

Gln Arg Pro Cys Asn Asn Val Ser Ser Asp Lys Ile Gly Asp Lys
    2480                2485                2490

Gly Leu Ser Met Pro Gly Val Pro Lys Ala Pro Pro Met Gln Val
    2495                2500                2505

Glu Gly Ser Ala Lys Glu Leu Gln Ala Pro Arg Lys Arg Thr Val
    2510                2515                2520

Lys Val Thr Leu Thr Pro Leu Lys Met Glu Asn Glu Ser Gln Ser
    2525                2530                2535

Lys Asn Ala Leu Lys Glu Ser Ser Pro Ala Ser Pro Leu Gln Ile
    2540                2545                2550

Glu Ser Thr Ser Pro Thr Glu Pro Ile Ser Ala Ser Glu Asn Pro
    2555                2560                2565

Gly Asp Gly Pro Val Ala Gln Pro Ser Pro Asn Asn Thr Ser Cys
    2570                2575                2580

Gln Asp Ser Gln Ser Asn Asn Tyr Gln Asn Leu Pro Val Gln Asp
    2585                2590                2595

Arg Asn Leu Met Leu Pro Asp Gly Pro Lys Pro Gln Glu Asp Gly
    2600                2605                2610

Ser Phe Lys Arg Arg Tyr Pro Arg Arg Ser Ala Arg Ala Arg Ser
    2615                2620                2625

Asn Met Phe Phe Gly Leu Thr Pro Leu Tyr Gly Val Arg Ser Tyr
    2630                2635                2640

Gly Glu Glu Asp Ile Pro Phe Tyr Ser Ser Ser Thr Gly Lys Lys
    2645                2650                2655

Arg Gly Lys Arg Ser Ala Glu Gly Gln Val Asp Gly Ala Asp Asp
    2660                2665                2670

Leu Ser Thr Ser Asp Glu Asp Asp Leu Tyr Tyr Tyr Asn Phe Thr
    2675                2680                2685

Arg Thr Val Ile Ser Ser Gly Gly Glu Glu Arg Leu Ala Ser His
    2690                2695                2700

Asn Leu Phe Arg Glu Glu Glu Gln Cys Asp Leu Pro Lys Ile Ser
    2705                2710                2715

Gln Leu Asp Gly Val Asp Asp Gly Thr Glu Ser Asp Thr Ser Val
    2720                2725                2730

Thr Ala Thr Thr Arg Lys Ser Ser Gln Ile Pro Lys Arg Asn Gly
    2735                2740                2745

Lys Glu Asn Gly Thr Glu Asn Leu Lys Ile Asp Arg Pro Glu Asp
    2750                2755                2760

Ala Gly Glu Lys Glu His Val Thr Lys Ser Ser Val Gly His Lys
    2765                2770                2775

Asn Glu Pro Lys Met Asp Asn Cys His Ser Val Ser Arg Val Lys
    2780                2785                2790

Thr Gln Gly Gln Asp Ser Leu Glu Ala Gln Leu Ser Ser Leu Glu
    2795                2800                2805

Ser Ser Arg Arg Val His Thr Ser Thr Pro Ser Asp Lys Asn Leu
    2810                2815                2820

Leu Asp Thr Tyr Asn Thr Glu Leu Leu Lys Ser Asp Ser Asp Asn
    2825                2830                2835

Asn Asn Ser Asp Asp Cys Gly Asn Ile Leu Pro Ser Asp Ile Met
    2840                2845                2850

Asp Phe Val Leu Lys Asn Thr Pro Ser Met Gln Ala Leu Gly Glu
    2855                2860                2865
```

Ser Pro Glu Ser Ser Ser Glu Leu Asn Leu Gly Glu Gly
    2870              2875              2880

Leu Gly Leu Asp Ser Asn Arg Glu Lys Asp Met Gly Leu Phe Glu
    2885              2890              2895

Val Phe Ser Gln Gln Leu Pro Thr Thr Glu Pro Val Asp Ser Ser
    2900              2905              2910

Val Ser Ser Ser Ile Ser Ala Glu Glu Gln Phe Glu Leu Pro Leu
    2915              2920              2925

Glu Leu Pro Ser Asp Leu Ser Val Leu Thr Thr Arg Ser Pro Thr
    2930              2935              2940

Val Pro Ser Gln Asn Pro Ser Arg Leu Ala Val Ile Ser Asp Ser
    2945              2950              2955

Gly Glu Lys Arg Val Thr Ile Thr Glu Lys Ser Val Ala Ser Ser
    2960              2965              2970

Glu Ser Asp Pro Ala Leu Leu Ser Pro Gly Val Asp Pro Thr Pro
    2975              2980              2985

Glu Gly His Met Thr Pro Asp His Phe Ile Gln Gly His Met Asp
    2990              2995              3000

Ala Asp His Ile Ser Ser Pro Pro Cys Gly Ser Val Glu Gln Gly
    3005              3010              3015

His Gly Asn Asn Gln Asp Leu Thr Arg Asn Ser Ser Thr Pro Gly
    3020              3025              3030

Leu Gln Val Pro Val Ser Pro Thr Val Pro Ile Gln Asn Gln Lys
    3035              3040              3045

Tyr Val Pro Asn Ser Thr Asp Ser Pro Gly Pro Ser Gln Ile Ser
    3050              3055              3060

Asn Ala Ala Val Gln Thr Thr Pro Pro His Leu Lys Pro Ala Thr
    3065              3070              3075

Glu Lys Leu Ile Val Val Asn Gln Asn Met Gln Pro Leu Tyr Val
    3080              3085              3090

Leu Gln Thr Leu Pro Asn Gly Val Thr Gln Lys Ile Gln Leu Thr
    3095              3100              3105

Ser Ser Val Ser Ser Thr Pro Ser Val Met Glu Thr Asn Thr Ser
    3110              3115              3120

Val Leu Gly Pro Met Gly Gly Gly Leu Thr Leu Thr Thr Gly Leu
    3125              3130              3135

Asn Pro Ser Leu Pro Thr Ser Gln Ser Leu Phe Pro Ser Ala Ser
    3140              3145              3150

Lys Gly Leu Leu Pro Met Ser His His Gln His Leu His Ser Phe
    3155              3160              3165

Pro Ala Ala Thr Gln Ser Ser Phe Pro Pro Asn Ile Ser Asn Pro
    3170              3175              3180

Pro Ser Gly Leu Leu Ile Gly Val Gln Pro Pro Asp Pro Gln
    3185              3190              3195

Leu Leu Val Ser Glu Ser Ser Gln Arg Thr Asp Leu Ser Thr Thr
    3200              3205              3210

Val Ala Thr Pro Ser Ser Gly Leu Lys Lys Arg Pro Ile Ser Arg
    3215              3220              3225

Leu Gln Thr Arg Lys Asn Lys Lys Leu Ala Pro Ser Ser Thr Pro
    3230              3235              3240

Ser Asn Ile Ala Pro Ser Asp Val Val Ser Asn Met Thr Leu Ile
    3245              3250              3255

```
Asn Phe Thr Pro Ser Gln Leu Pro Asn His Pro Ser Leu Leu Asp
    3260                3265                3270

Leu Gly Ser Leu Asn Thr Ser Ser His Arg Thr Val Pro Asn Ile
    3275                3280                3285

Ile Lys Arg Ser Lys Ser Ser Ile Met Tyr Phe Glu Pro Ala Pro
    3290                3295                3300

Leu Leu Pro Gln Ser Val Gly Gly Thr Ala Ala Thr Ala Ala Gly
    3305                3310                3315

Thr Ser Thr Ile Ser Gln Asp Thr Ser His Leu Thr Ser Gly Ser
    3320                3325                3330

Val Ser Gly Leu Ala Ser Ser Ser Ser Val Leu Asn Val Val Ser
    3335                3340                3345

Met Gln Thr Thr Thr Thr Pro Thr Ser Ser Ala Ser Val Pro Gly
    3350                3355                3360

His Val Thr Leu Thr Asn Pro Arg Leu Leu Gly Thr Pro Asp Ile
    3365                3370                3375

Gly Ser Ile Ser Asn Leu Leu Ile Lys Ala Ser Gln Gln Ser Leu
    3380                3385                3390

Gly Ile Gln Asp Gln Pro Val Ala Leu Pro Pro Ser Ser Gly Met
    3395                3400                3405

Phe Pro Gln Leu Gly Thr Ser Gln Thr Pro Ser Thr Ala Ala Ile
    3410                3415                3420

Thr Ala Ala Ser Ser Ile Cys Val Leu Pro Ser Thr Gln Thr Thr
    3425                3430                3435

Gly Ile Thr Ala Ala Ser Pro Ser Gly Glu Ala Asp Glu His Tyr
    3440                3445                3450

Gln Leu Gln His Val Asn Gln Leu Leu Ala Ser Lys Thr Gly Ile
    3455                3460                3465

His Ser Ser Gln Arg Asp Leu Asp Ser Ala Ser Gly Pro Gln Val
    3470                3475                3480

Ser Asn Phe Thr Gln Thr Val Asp Ala Pro Asn Ser Met Gly Leu
    3485                3490                3495

Glu Gln Asn Lys Ala Leu Ser Ser Ala Val Gln Ala Ser Pro Thr
    3500                3505                3510

Ser Pro Gly Gly Ser Pro Ser Ser Pro Ser Ser Gly Gln Arg Ser
    3515                3520                3525

Ala Ser Pro Ser Val Pro Gly Pro Thr Lys Pro Lys Pro Lys Thr
    3530                3535                3540

Lys Arg Phe Gln Leu Pro Leu Asp Lys Gly Asn Gly Lys Lys His
    3545                3550                3555

Lys Val Ser His Leu Arg Thr Ser Ser Ser Glu Ala His Ile Pro
    3560                3565                3570

Asp Gln Glu Thr Thr Ser Leu Thr Ser Gly Thr Gly Thr Pro Gly
    3575                3580                3585

Ala Glu Ala Glu Gln Gln Asp Thr Ala Ser Val Glu Gln Ser Ser
    3590                3595                3600

Gln Lys Glu Cys Gly Gln Pro Ala Gly Gln Val Ala Val Leu Pro
    3605                3610                3615

Glu Val Gln Val Thr Gln Asn Pro Ala Asn Glu Gln Glu Ser Ala
    3620                3625                3630

Glu Pro Lys Thr Val Glu Glu Glu Ser Asn Phe Ser Ser Pro
    3635                3640                3645

Leu Met Leu Trp Leu Gln Gln Glu Gln Lys Arg Lys Glu Ser Ile
```

```
                3650                3655                3660
Thr Glu Lys Lys Pro Lys Gly Leu Val Phe Glu Ile Ser Ser
    3665                3670                3675
Asp Asp Gly Phe Gln Ile Cys Ala Glu Ser Ile Glu Asp Ala Trp
    3680                3685                3690
Lys Ser Leu Thr Asp Lys Val Gln Glu Ala Arg Ser Asn Ala Arg
    3695                3700                3705
Leu Lys Gln Leu Ser Phe Ala Gly Val Asn Gly Leu Arg Met Leu
    3710                3715                3720
Gly Ile Leu His Asp Ala Val Val Phe Leu Ile Glu Gln Leu Ser
    3725                3730                3735
Gly Ala Lys His Cys Arg Asn Tyr Lys Phe Arg Phe His Lys Pro
    3740                3745                3750
Glu Glu Ala Asn Glu Pro Pro Leu Asn Pro His Gly Ser Ala Arg
    3755                3760                3765
Ala Glu Val His Leu Arg Lys Ser Ala Phe Asp Met Phe Asn Phe
    3770                3775                3780
Leu Ala Ser Lys His Arg Gln Pro Pro Glu Tyr Asn Pro Asn Asp
    3785                3790                3795
Glu Glu Glu Glu Val Gln Leu Lys Ser Ala Arg Arg Ala Thr
    3800                3805                3810
Ser Met Asp Leu Pro Met Pro Met Arg Phe Arg His Leu Lys Lys
    3815                3820                3825
Thr Ser Lys Glu Ala Val Gly Val Tyr Arg Ser Pro Ile His Gly
    3830                3835                3840
Arg Gly Leu Phe Cys Lys Arg Asn Ile Asp Ala Gly Glu Met Val
    3845                3850                3855
Ile Glu Tyr Ala Gly Asn Val Ile Arg Ser Ile Gln Thr Asp Lys
    3860                3865                3870
Arg Glu Lys Tyr Tyr Asp Ser Lys Gly Ile Gly Cys Tyr Met Phe
    3875                3880                3885
Arg Ile Asp Asp Ser Glu Val Val Asp Ala Thr Met His Gly Asn
    3890                3895                3900
Ala Ala Arg Phe Ile Asn His Ser Cys Glu Pro Asn Cys Tyr Ser
    3905                3910                3915
Arg Val Ile Asn Ile Asp Gly Gln Lys His Ile Val Ile Phe Ala
    3920                3925                3930
Met Arg Lys Ile Tyr Arg Gly Glu Glu Leu Thr Tyr Asp Tyr Lys
    3935                3940                3945
Phe Pro Ile Glu Asp Ala Ser Asn Lys Leu Pro Cys Asn Cys Gly
    3950                3955                3960
Ala Lys Lys Cys Arg Lys Phe Leu Asn
    3965                3970

<210> SEQ ID NO 45
<211> LENGTH: 5537
<212> TYPE: PRT
<213> ORGANISM: Homo sapiens

<400> SEQUENCE: 45

Met Asp Ser Gln Lys Leu Ala Gly Glu Asp Lys Asp Ser Glu Pro Ala
1               5                   10                  15

Ala Asp Gly Pro Ala Ala Ser Glu Asp Pro Ser Ala Thr Glu Ser Asp
            20                  25                  30
```

-continued

```
Leu Pro Asn Pro His Val Gly Glu Val Ser Val Leu Ser Ser Gly Ser
             35                  40                  45

Pro Arg Leu Gln Glu Thr Pro Gln Asp Cys Ser Gly Gly Pro Val Arg
 50                  55                  60

Arg Cys Ala Leu Cys Asn Cys Gly Glu Pro Ser Leu His Gly Gln Arg
 65                  70                  75                  80

Glu Leu Arg Arg Phe Glu Leu Pro Phe Asp Trp Pro Arg Cys Pro Val
                 85                  90                  95

Val Ser Pro Gly Gly Ser Pro Gly Pro Asn Glu Ala Val Leu Pro Ser
            100                 105                 110

Glu Asp Leu Ser Gln Ile Gly Phe Pro Glu Gly Leu Thr Pro Ala His
            115                 120                 125

Leu Gly Glu Pro Gly Gly Ser Cys Trp Ala His His Trp Cys Ala Ala
    130                 135                 140

Trp Ser Ala Gly Val Trp Gly Gln Glu Gly Pro Glu Leu Cys Gly Val
145                 150                 155                 160

Asp Lys Ala Ile Phe Ser Gly Ile Ser Gln Arg Cys Ser His Cys Thr
                165                 170                 175

Arg Leu Gly Ala Ser Ile Pro Cys Arg Ser Pro Gly Cys Pro Arg Leu
            180                 185                 190

Tyr His Phe Pro Cys Ala Thr Ala Ser Gly Ser Phe Leu Ser Met Lys
            195                 200                 205

Thr Leu Gln Leu Leu Cys Pro Glu His Ser Glu Gly Ala Ala Tyr Leu
    210                 215                 220

Glu Glu Ala Arg Cys Ala Val Cys Glu Gly Pro Gly Glu Leu Cys Asp
225                 230                 235                 240

Leu Phe Phe Cys Thr Ser Cys Gly His His Tyr His Gly Ala Cys Leu
                245                 250                 255

Asp Thr Ala Leu Thr Ala Arg Lys Arg Ala Gly Trp Gln Cys Pro Glu
            260                 265                 270

Cys Lys Val Cys Gln Ala Cys Arg Lys Pro Gly Asn Asp Ser Lys Met
            275                 280                 285

Leu Val Cys Glu Thr Cys Asp Lys Gly Tyr His Thr Phe Cys Leu Lys
    290                 295                 300

Pro Pro Met Glu Glu Leu Pro Ala His Ser Trp Lys Cys Lys Ala Cys
305                 310                 315                 320

Arg Val Cys Arg Ala Cys Gly Ala Gly Ser Ala Glu Leu Asn Pro Asn
                325                 330                 335

Ser Glu Trp Phe Glu Asn Tyr Ser Leu Cys His Arg Cys His Lys Ala
            340                 345                 350

Gln Gly Gly Gln Thr Ile Arg Ser Val Ala Glu Gln His Thr Pro Val
            355                 360                 365

Cys Ser Arg Phe Ser Pro Pro Glu Pro Gly Asp Thr Pro Thr Asp Glu
    370                 375                 380

Pro Asp Ala Leu Tyr Val Ala Cys Gln Gly Gln Pro Lys Gly Gly His
385                 390                 395                 400

Val Thr Ser Met Gln Pro Lys Glu Pro Gly Pro Leu Gln Cys Glu Ala
                405                 410                 415

Lys Pro Leu Gly Lys Ala Gly Val Gln Leu Glu Pro Gln Leu Glu Ala
            420                 425                 430

Pro Leu Asn Glu Glu Met Pro Leu Leu Pro Pro Glu Glu Ser Pro
            435                 440                 445

Leu Ser Pro Pro Pro Glu Glu Ser Pro Thr Ser Pro Pro Glu Ala
```

```
                450                 455                 460
Ser Arg Leu Ser Pro Pro Glu Glu Leu Pro Ala Ser Pro Leu Pro
465                 470                 475                 480

Glu Ala Leu His Leu Ser Arg Pro Leu Glu Glu Ser Pro Leu Ser
                485                 490                 495

Pro Pro Glu Glu Ser Pro Leu Ser Pro Pro Glu Ser Ser Pro Phe
                500                 505                 510

Ser Pro Leu Glu Glu Ser Pro Leu Ser Pro Pro Glu Glu Ser Pro
                515                 520                 525

Ser Pro Ala Leu Glu Thr Pro Leu Ser Pro Pro Glu Ala Ser Pro
                530                 535                 540

Leu Ser Pro Pro Phe Glu Glu Ser Pro Leu Ser Pro Pro Glu Glu
545                 550                 555                 560

Leu Pro Thr Ser Pro Pro Glu Ala Ser Arg Leu Ser Pro Pro Pro
                565                 570                 575

Glu Glu Ser Pro Met Ser Pro Pro Glu Glu Ser Pro Met Ser Pro
                580                 585                 590

Pro Pro Glu Ala Ser Arg Leu Phe Pro Pro Phe Glu Glu Ser Pro Leu
                595                 600                 605

Ser Pro Pro Glu Glu Ser Pro Leu Ser Pro Pro Pro Glu Ala Ser
                610                 615                 620

Arg Leu Ser Pro Pro Glu Asp Ser Pro Met Ser Pro Pro Pro Glu
625                 630                 635                 640

Glu Ser Pro Met Ser Pro Pro Glu Val Ser Arg Leu Ser Pro Leu
                645                 650                 655

Pro Val Val Ser Arg Leu Ser Pro Pro Glu Glu Ser Pro Leu Ser
                660                 665                 670

Pro Pro Pro Glu Glu Ser Pro Thr Ser Pro Pro Glu Ala Ser Arg
                675                 680                 685

Leu Ser Pro Pro Glu Asp Ser Pro Thr Ser Pro Pro Pro Glu Asp
                690                 695                 700

Ser Pro Ala Ser Pro Pro Glu Asp Ser Leu Met Ser Leu Pro Leu
705                 710                 715                 720

Glu Glu Ser Pro Leu Leu Pro Leu Pro Glu Glu Pro Gln Leu Cys Pro
                725                 730                 735

Arg Ser Glu Gly Pro His Leu Ser Pro Arg Pro Glu Gly Pro His Leu
                740                 745                 750

Ser Pro Arg Pro Glu Glu Pro His Leu Ser Pro Gln Ala Glu Glu Pro
                755                 760                 765

His Leu Ser Pro Gln Pro Glu Glu Pro Cys Leu Cys Ala Val Pro Glu
770                 775                 780

Glu Pro His Leu Ser Pro Gln Ala Glu Gly His Leu Ser Pro Gln
785                 790                 795                 800

Pro Glu Glu Leu His Leu Ser Pro Gln Thr Glu Glu Pro His Leu Ser
                805                 810                 815

Pro Val Pro Glu Glu Pro Cys Leu Ser Pro Gln Pro Glu Glu Ser His
                820                 825                 830

Leu Ser Pro Gln Ser Glu Pro Cys Leu Ser Pro Arg Pro Glu Glu
                835                 840                 845

Ser His Leu Ser Pro Glu Leu Glu Lys Pro Pro Leu Ser Pro Arg Pro
850                 855                 860

Glu Lys Pro Pro Glu Pro Gly Gln Cys Pro Ala Pro Glu Glu Leu
865                 870                 875                 880
```

```
Pro Leu Phe Pro Pro Gly Glu Pro Ser Leu Ser Pro Leu Leu Gly
            885                 890                 895

Glu Pro Ala Leu Ser Glu Pro Gly Glu Pro Pro Leu Ser Pro Leu Pro
            900                 905                 910

Glu Glu Leu Pro Leu Ser Pro Ser Gly Glu Pro Ser Leu Ser Pro Gln
            915                 920                 925

Leu Met Pro Pro Asp Pro Leu Pro Pro Leu Ser Pro Ile Ile Thr
            930                 935                 940

Ala Ala Ala Pro Pro Ala Leu Ser Pro Leu Gly Glu Leu Glu Tyr Pro
945                 950                 955                 960

Phe Gly Ala Lys Gly Asp Ser Asp Pro Glu Ser Pro Leu Ala Ala Pro
            965                 970                 975

Ile Leu Glu Thr Pro Ile Ser Pro Pro Glu Ala Asn Cys Thr Asp
            980                 985                 990

Pro Glu Pro Val Pro Pro Met Ile Leu Pro Pro Ser Pro Gly Ser Pro
            995                 1000                1005

Val Gly Pro Ala Ser Pro Ile Leu Met Glu Pro Leu Pro Pro Gln
            1010                1015                1020

Cys Ser Pro Leu Leu Gln His Ser Leu Val Pro Gln Asn Ser Pro
            1025                1030                1035

Pro Ser Gln Cys Ser Pro Ala Leu Pro Leu Ser Val Pro Ser
            1040                1045                1050

Pro Leu Ser Pro Ile Gly Lys Val Val Gly Val Ser Asp Glu Ala
            1055                1060                1065

Glu Leu His Glu Met Glu Thr Glu Lys Val Ser Glu Pro Glu Cys
            1070                1075                1080

Pro Ala Leu Glu Pro Ser Ala Thr Ser Pro Leu Pro Ser Pro Met
            1085                1090                1095

Gly Asp Leu Ser Cys Pro Ala Pro Ser Pro Ala Pro Ala Leu Asp
            1100                1105                1110

Asp Phe Ser Gly Leu Gly Glu Asp Thr Ala Pro Leu Asp Gly Ile
            1115                1120                1125

Asp Ala Pro Gly Ser Gln Pro Glu Pro Gly Gln Thr Pro Gly Ser
            1130                1135                1140

Leu Ala Ser Glu Leu Lys Gly Ser Pro Val Leu Leu Asp Pro Glu
            1145                1150                1155

Glu Leu Ala Pro Val Thr Pro Met Glu Val Tyr Pro Glu Cys Lys
            1160                1165                1170

Gln Thr Ala Gly Gln Gly Ser Pro Cys Glu Glu Gln Glu Glu Pro
            1175                1180                1185

Arg Ala Pro Val Ala Pro Thr Pro Pro Thr Leu Ile Lys Ser Asp
            1190                1195                1200

Ile Val Asn Glu Ile Ser Asn Leu Ser Gln Gly Asp Ala Ser Ala
            1205                1210                1215

Ser Phe Pro Gly Ser Glu Pro Leu Leu Gly Ser Pro Asp Pro Glu
            1220                1225                1230

Gly Gly Gly Ser Leu Ser Met Glu Leu Gly Val Ser Thr Asp Val
            1235                1240                1245

Ser Pro Ala Arg Asp Glu Gly Ser Leu Arg Leu Cys Thr Asp Ser
            1250                1255                1260

Leu Pro Glu Thr Asp Asp Ser Leu Leu Cys Asp Ala Gly Thr Ala
            1265                1270                1275
```

-continued

Ile Ser Gly Gly Lys Ala Glu Gly Glu Lys Gly Arg Arg Arg Ser
    1280                1285                1290

Ser Pro Ala Arg Ser Arg Ile Lys Gln Gly Arg Ser Ser Ser Phe
    1295                1300                1305

Pro Gly Arg Arg Arg Pro Arg Gly Gly Ala His Gly Gly Arg Gly
    1310                1315                1320

Arg Gly Arg Ala Arg Leu Lys Ser Thr Ala Ser Ser Ile Glu Thr
    1325                1330                1335

Leu Val Val Ala Asp Ile Asp Ser Ser Pro Ser Lys Glu Glu Glu
    1340                1345                1350

Glu Glu Asp Asp Asp Thr Met Gln Asn Thr Val Val Leu Phe Ser
    1355                1360                1365

Asn Thr Asp Lys Phe Val Leu Met Gln Asp Met Cys Val Val Cys
    1370                1375                1380

Gly Ser Phe Gly Arg Gly Ala Glu Gly His Leu Leu Ala Cys Ser
    1385                1390                1395

Gln Cys Ser Gln Cys Tyr His Pro Tyr Cys Val Asn Ser Lys Ile
    1400                1405                1410

Thr Lys Val Met Leu Leu Lys Gly Trp Arg Cys Val Glu Cys Ile
    1415                1420                1425

Val Cys Glu Val Cys Gly Gln Ala Ser Asp Pro Ser Arg Leu Leu
    1430                1435                1440

Leu Cys Asp Asp Cys Asp Ile Ser Tyr His Thr Tyr Cys Leu Asp
    1445                1450                1455

Pro Pro Leu Leu Thr Val Pro Lys Gly Gly Trp Lys Cys Lys Trp
    1460                1465                1470

Cys Val Ser Cys Met Gln Cys Gly Ala Ala Ser Pro Gly Phe His
    1475                1480                1485

Cys Glu Trp Gln Asn Ser Tyr Thr His Cys Gly Pro Cys Ala Ser
    1490                1495                1500

Leu Val Thr Cys Pro Ile Cys His Ala Pro Tyr Val Glu Glu Asp
    1505                1510                1515

Leu Leu Ile Gln Cys Arg His Cys Glu Arg Trp Met His Ala Gly
    1520                1525                1530

Cys Glu Ser Leu Phe Thr Glu Asp Asp Val Glu Gln Ala Ala Asp
    1535                1540                1545

Glu Gly Phe Asp Cys Val Ser Cys Gln Pro Tyr Val Val Lys Pro
    1550                1555                1560

Val Ala Pro Val Ala Pro Glu Leu Val Pro Met Lys Val Lys
    1565                1570                1575

Glu Pro Glu Pro Gln Tyr Phe Arg Phe Glu Gly Val Trp Leu Thr
    1580                1585                1590

Glu Thr Gly Met Ala Leu Leu Arg Asn Leu Thr Met Ser Pro Leu
    1595                1600                1605

His Lys Arg Arg Gln Arg Arg Gly Arg Leu Gly Leu Pro Gly Glu
    1610                1615                1620

Ala Gly Leu Glu Gly Ser Glu Pro Ser Asp Ala Leu Gly Pro Asp
    1625                1630                1635

Asp Lys Lys Asp Gly Asp Leu Asp Thr Asp Glu Leu Leu Lys Gly
    1640                1645                1650

Glu Gly Gly Val Glu His Met Glu Cys Glu Ile Lys Leu Glu Gly
    1655                1660                1665

Pro Val Ser Pro Asp Val Glu Pro Gly Lys Glu Glu Thr Glu Glu

|  |  |  |  |  |  |  |  |  |  |
|---|---|---|---|---|---|---|---|---|---|
|  |  | 1670 |  |  | 1675 |  |  | 1680 |  |
| Ser | Lys 1685 | Lys | Arg | Lys 1690 | Arg | Lys | Pro | Tyr 1695 | Arg | Pro | Gly | Ile | Gly | Gly |

Ser Lys Lys Arg Lys Arg Lys Pro Tyr Arg Pro Gly Ile Gly Gly
    1685            1690            1695

Phe Met Val Arg Gln Arg Lys Ser His Thr Arg Thr Lys Lys Gly
    1700            1705            1710

Pro Ala Ala Gln Ala Glu Val Leu Ser Gly Asp Gly Gln Pro Asp
    1715            1720            1725

Glu Val Ile Pro Ala Asp Leu Pro Ala Glu Gly Ala Val Glu Gln
    1730            1735            1740

Ser Leu Ala Glu Gly Asp Glu Lys Lys Lys Gln Gln Arg Arg Gly
    1745            1750            1755

Arg Lys Lys Ser Lys Leu Glu Asp Met Phe Pro Ala Tyr Leu Gln
    1760            1765            1770

Glu Ala Phe Phe Gly Lys Glu Leu Leu Asp Leu Ser Arg Lys Ala
    1775            1780            1785

Leu Phe Ala Val Gly Val Gly Arg Pro Ser Phe Gly Leu Gly Thr
    1790            1795            1800

Pro Lys Ala Lys Gly Asp Gly Gly Ser Glu Arg Lys Glu Leu Pro
    1805            1810            1815

Thr Ser Gln Lys Gly Asp Asp Gly Pro Asp Ile Ala Asp Glu Glu
    1820            1825            1830

Ser Arg Gly Leu Glu Gly Lys Ala Asp Thr Pro Gly Pro Glu Asp
    1835            1840            1845

Gly Gly Val Lys Ala Ser Pro Val Pro Ser Asp Pro Glu Lys Pro
    1850            1855            1860

Gly Thr Pro Gly Glu Gly Met Leu Ser Ser Asp Leu Asp Arg Ile
    1865            1870            1875

Ser Thr Glu Glu Leu Pro Lys Met Glu Ser Lys Asp Leu Gln Gln
    1880            1885            1890

Leu Phe Lys Asp Val Leu Gly Ser Glu Arg Glu Gln His Leu Gly
    1895            1900            1905

Cys Gly Thr Pro Gly Leu Glu Gly Ser Arg Thr Pro Leu Gln Arg
    1910            1915            1920

Pro Phe Leu Gln Gly Gly Leu Pro Leu Gly Asn Leu Pro Ser Ser
    1925            1930            1935

Ser Pro Met Asp Ser Tyr Pro Gly Leu Cys Gln Ser Pro Phe Leu
    1940            1945            1950

Asp Ser Arg Glu Arg Gly Gly Phe Phe Ser Pro Glu Pro Gly Glu
    1955            1960            1965

Pro Asp Ser Pro Trp Thr Gly Ser Gly Gly Thr Thr Pro Ser Thr
    1970            1975            1980

Pro Thr Thr Pro Thr Thr Glu Gly Glu Gly Asp Gly Leu Ser Tyr
    1985            1990            1995

Asn Gln Arg Ser Leu Gln Arg Trp Glu Lys Asp Glu Glu Leu Gly
    2000            2005            2010

Gln Leu Ser Thr Ile Ser Pro Val Leu Tyr Ala Asn Ile Asn Phe
    2015            2020            2025

Pro Asn Leu Lys Gln Asp Tyr Pro Asp Trp Ser Ser Arg Cys Lys
    2030            2035            2040

Gln Ile Met Lys Leu Trp Arg Lys Val Pro Ala Ala Asp Lys Ala
    2045            2050            2055

Pro Tyr Leu Gln Lys Ala Lys Asp Asn Arg Ala Ala His Arg Ile
    2060            2065            2070

```
Asn Lys Val Gln Lys Gln Ala Glu Ser Gln Ile Asn Lys Gln Thr
    2075            2080                2085

Lys Val Gly Asp Ile Ala Arg Lys Thr Asp Arg Pro Ala Leu His
    2090            2095                2100

Leu Arg Ile Pro Pro Gln Pro Gly Ala Leu Gly Ser Pro Pro Pro
    2105            2110                2115

Ala Ala Ala Pro Thr Ile Phe Ile Gly Ser Pro Thr Thr Pro Ala
    2120            2125                2130

Gly Leu Ser Thr Ser Ala Asp Gly Phe Leu Lys Pro Pro Ala Gly
    2135            2140                2145

Ser Val Pro Gly Pro Asp Ser Pro Gly Glu Leu Phe Leu Lys Leu
    2150            2155                2160

Pro Pro Gln Val Pro Ala Gln Val Pro Ser Gln Asp Pro Phe Gly
    2165            2170                2175

Leu Ala Pro Ala Tyr Pro Leu Glu Pro Arg Phe Pro Thr Ala Pro
    2180            2185                2190

Pro Thr Tyr Pro Pro Tyr Pro Ser Pro Thr Gly Ala Pro Ala Gln
    2195            2200                2205

Pro Pro Met Leu Gly Ala Ser Ser Arg Pro Gly Ala Gly Gln Pro
    2210            2215                2220

Gly Glu Phe His Thr Thr Pro Pro Gly Thr Pro Arg His Gln Pro
    2225            2230                2235

Ser Thr Pro Asp Pro Phe Leu Lys Pro Arg Cys Pro Ser Leu Asp
    2240            2245                2250

Asn Leu Ala Val Pro Glu Ser Pro Gly Val Gly Gly Lys Ala
    2255            2260                2265

Ser Glu Pro Leu Leu Ser Pro Pro Phe Gly Glu Ser Arg Lys
    2270            2275                2280

Ala Leu Glu Val Lys Lys Glu Glu Leu Gly Ala Ser Ser Pro Ser
    2285            2290                2295

Tyr Gly Pro Pro Asn Leu Gly Phe Val Asp Ser Pro Ser Ser Gly
    2300            2305                2310

Thr His Leu Gly Gly Leu Glu Leu Lys Thr Pro Asp Val Phe Lys
    2315            2320                2325

Ala Pro Leu Thr Pro Arg Ala Ser Gln Val Glu Pro Gln Ser Pro
    2330            2335                2340

Gly Leu Gly Leu Arg Pro Gln Glu Pro Pro Ala Gln Ala Leu
    2345            2350                2355

Ala Pro Ser Pro Pro Ser His Pro Asp Ile Phe Arg Pro Gly Ser
    2360            2365                2370

Tyr Thr Asp Pro Tyr Ala Gln Pro Pro Leu Thr Pro Arg Pro Gln
    2375            2380                2385

Pro Pro Pro Pro Glu Ser Cys Cys Ala Leu Pro Pro Arg Ser Leu
    2390            2395                2400

Pro Ser Asp Pro Phe Ser Arg Val Pro Ala Ser Pro Gln Ser Gln
    2405            2410                2415

Ser Ser Ser Gln Ser Pro Leu Thr Pro Arg Pro Leu Ser Ala Glu
    2420            2425                2430

Ala Phe Cys Pro Ser Pro Val Thr Pro Arg Phe Gln Ser Pro Asp
    2435            2440                2445

Pro Tyr Ser Arg Pro Pro Ser Arg Pro Gln Ser Arg Asp Pro Phe
    2450            2455                2460
```

```
Ala Pro Leu His Lys Pro Pro Arg Pro Gln Pro Pro Glu Val Ala
2465                2470                2475

Phe Lys Ala Gly Ser Leu Ala His Thr Ser Leu Gly Ala Gly Gly
    2480                2485                2490

Phe Pro Ala Ala Leu Pro Ala Gly Pro Ala Gly Glu Leu His Ala
2495                2500                2505

Lys Val Pro Ser Gly Gln Pro Pro Asn Phe Val Arg Ser Pro Gly
    2510                2515                2520

Thr Gly Ala Phe Val Gly Thr Pro Ser Pro Met Arg Phe Thr Phe
2525                2530                2535

Pro Gln Ala Val Gly Glu Pro Ser Leu Lys Pro Pro Val Pro Gln
    2540                2545                2550

Pro Gly Leu Pro Pro Pro His Gly Ile Asn Ser His Phe Gly Pro
2555                2560                2565

Gly Pro Thr Leu Gly Lys Pro Gln Ser Thr Asn Tyr Thr Val Ala
    2570                2575                2580

Thr Gly Asn Phe His Pro Ser Gly Ser Pro Leu Gly Pro Ser Ser
2585                2590                2595

Gly Ser Thr Gly Glu Ser Tyr Gly Leu Ser Pro Leu Arg Pro Pro
    2600                2605                2610

Ser Val Leu Pro Pro Pro Ala Pro Asp Gly Ser Leu Pro Tyr Leu
2615                2620                2625

Ser His Gly Ala Ser Gln Arg Ser Gly Ile Thr Ser Pro Val Glu
    2630                2635                2640

Lys Arg Glu Asp Pro Gly Thr Gly Met Gly Ser Ser Leu Ala Thr
2645                2650                2655

Ala Glu Leu Pro Gly Thr Gln Asp Pro Gly Met Ser Gly Leu Ser
    2660                2665                2670

Gln Thr Glu Leu Glu Lys Gln Arg Gln Arg Gln Leu Arg Glu
2675                2680                2685

Leu Leu Ile Arg Gln Gln Ile Gln Arg Asn Thr Leu Arg Gln Glu
    2690                2695                2700

Lys Glu Thr Ala Ala Ala Ala Gly Ala Val Gly Pro Pro Gly
2705                2710                2715

Ser Trp Gly Ala Glu Pro Ser Ser Pro Ala Phe Glu Gln Leu Ser
    2720                2725                2730

Arg Gly Gln Thr Pro Phe Ala Gly Thr Gln Asp Lys Ser Ser Leu
2735                2740                2745

Val Gly Leu Pro Pro Ser Lys Leu Ser Gly Pro Ile Leu Gly Pro
    2750                2755                2760

Gly Ser Phe Pro Ser Asp Asp Arg Leu Ser Arg Pro Pro Pro Pro
2765                2770                2775

Ala Thr Pro Ser Ser Met Asp Val Asn Ser Arg Gln Leu Val Gly
    2780                2785                2790

Gly Ser Gln Ala Phe Tyr Gln Arg Ala Pro Tyr Pro Gly Ser Leu
2795                2800                2805

Pro Leu Gln Gln Gln Gln Gln Leu Trp Gln Gln Gln Gln Ala
    2810                2815                2820

Thr Ala Ala Thr Ser Met Arg Phe Ala Met Ser Ala Arg Phe Pro
2825                2830                2835

Ser Thr Pro Gly Pro Glu Leu Gly Arg Gln Ala Leu Gly Ser Pro
    2840                2845                2850

Leu Ala Gly Ile Ser Thr Arg Leu Pro Gly Pro Gly Glu Pro Val
```

```
                    2855                2860                2865

Pro  Gly  Pro  Ala  Gly  Pro  Ala  Gln  Phe  Ile  Glu  Leu  Arg  His  Asn
          2870                2875                2880

Val  Gln  Lys  Gly  Leu  Gly  Pro  Gly  Gly  Thr  Pro  Phe  Pro  Gly  Gln
          2885                2890                2895

Gly  Pro  Pro  Gln  Arg  Pro  Arg  Phe  Tyr  Pro  Val  Ser  Glu  Asp  Pro
          2900                2905                2910

His  Arg  Leu  Ala  Pro  Glu  Gly  Leu  Arg  Gly  Leu  Ala  Val  Ser  Gly
          2915                2920                2925

Leu  Pro  Pro  Gln  Lys  Pro  Ser  Ala  Pro  Pro  Ala  Pro  Glu  Leu  Asn
          2930                2935                2940

Asn  Ser  Leu  His  Pro  Thr  Pro  His  Thr  Lys  Gly  Pro  Thr  Leu  Pro
          2945                2950                2955

Thr  Gly  Leu  Glu  Leu  Val  Asn  Arg  Pro  Pro  Ser  Ser  Thr  Glu  Leu
          2960                2965                2970

Gly  Arg  Pro  Asn  Pro  Leu  Ala  Leu  Glu  Ala  Gly  Lys  Leu  Pro  Cys
          2975                2980                2985

Glu  Asp  Pro  Glu  Leu  Asp  Asp  Phe  Asp  Ala  His  Lys  Ala  Leu
          2990                2995                3000

Glu  Asp  Asp  Glu  Glu  Leu  Ala  His  Leu  Gly  Leu  Gly  Val  Asp  Val
          3005                3010                3015

Ala  Lys  Gly  Asp  Asp  Glu  Leu  Gly  Thr  Leu  Glu  Asn  Leu  Glu  Thr
          3020                3025                3030

Asn  Asp  Pro  His  Leu  Asp  Asp  Leu  Leu  Asn  Gly  Asp  Glu  Phe  Asp
          3035                3040                3045

Leu  Leu  Ala  Tyr  Thr  Asp  Pro  Glu  Leu  Asp  Thr  Gly  Asp  Lys  Lys
          3050                3055                3060

Asp  Ile  Phe  Asn  Glu  His  Leu  Arg  Leu  Val  Glu  Ser  Ala  Asn  Glu
          3065                3070                3075

Lys  Ala  Glu  Arg  Glu  Ala  Leu  Leu  Arg  Gly  Val  Glu  Pro  Gly  Pro
          3080                3085                3090

Leu  Gly  Pro  Glu  Glu  Arg  Pro  Pro  Ala  Ala  Asp  Ala  Ser  Glu
          3095                3100                3105

Pro  Arg  Leu  Ala  Ser  Val  Leu  Pro  Glu  Val  Lys  Pro  Lys  Val  Glu
          3110                3115                3120

Glu  Gly  Gly  Arg  His  Pro  Ser  Pro  Cys  Gln  Phe  Thr  Ile  Ala  Thr
          3125                3130                3135

Pro  Lys  Val  Glu  Pro  Ala  Pro  Ala  Ala  Asn  Ser  Leu  Gly  Leu  Gly
          3140                3145                3150

Leu  Lys  Pro  Gly  Gln  Ser  Met  Met  Gly  Ser  Arg  Asp  Thr  Arg  Met
          3155                3160                3165

Gly  Thr  Gly  Pro  Phe  Ser  Ser  Ser  Gly  His  Thr  Ala  Glu  Lys  Ala
          3170                3175                3180

Ser  Phe  Gly  Ala  Thr  Gly  Gly  Pro  Pro  Ala  His  Leu  Leu  Thr  Pro
          3185                3190                3195

Ser  Pro  Leu  Ser  Gly  Pro  Gly  Gly  Ser  Ser  Leu  Leu  Glu  Lys  Phe
          3200                3205                3210

Glu  Leu  Glu  Ser  Gly  Ala  Leu  Thr  Leu  Pro  Gly  Gly  Pro  Ala  Ala
          3215                3220                3225

Ser  Gly  Asp  Glu  Leu  Asp  Lys  Met  Glu  Ser  Ser  Leu  Val  Ala  Ser
          3230                3235                3240

Glu  Leu  Pro  Leu  Leu  Ile  Glu  Asp  Leu  Leu  Glu  His  Glu  Lys  Lys
          3245                3250                3255
```

```
Glu Leu Gln Lys Lys Gln Gln Leu Ser Ala Gln Leu Gln Pro Ala
    3260                3265                3270

Gln Gln Gln Gln Gln Gln Gln Gln His Ser Leu Leu Ser Ala
3275                3280                3285

Pro Gly Pro Ala Gln Ala Met Ser Leu Pro His Glu Gly Ser Ser
    3290                3295                3300

Pro Ser Leu Ala Gly Ser Gln Gln Gln Leu Ser Leu Gly Leu Ala
3305                3310                3315

Gly Ala Arg Gln Pro Gly Leu Pro Gln Pro Leu Met Pro Thr Gln
    3320                3325                3330

Pro Pro Ala His Ala Leu Gln Gln Arg Leu Ala Pro Ser Met Ala
3335                3340                3345

Met Val Ser Asn Gln Gly His Met Leu Ser Gly Gln His Gly Gly
    3350                3355                3360

Gln Ala Gly Leu Val Pro Gln Gln Ser Ser Gln Pro Val Leu Ser
3365                3370                3375

Gln Lys Pro Met Gly Thr Met Pro Pro Ser Met Cys Met Lys Pro
    3380                3385                3390

Gln Gln Leu Ala Met Gln Gln Leu Ala Asn Ser Phe Phe Pro
3395                3400                3405

Asp Thr Asp Leu Asp Lys Phe Ala Ala Glu Asp Ile Ile Asp Pro
    3410                3415                3420

Ile Ala Lys Ala Lys Met Val Ala Leu Lys Gly Ile Lys Lys Val
3425                3430                3435

Met Ala Gln Gly Ser Ile Gly Val Ala Pro Gly Met Asn Arg Gln
    3440                3445                3450

Gln Val Ser Leu Leu Ala Gln Arg Leu Ser Gly Gly Pro Ser Ser
3455                3460                3465

Asp Leu Gln Asn His Val Ala Ala Gly Ser Gly Gln Glu Arg Ser
    3470                3475                3480

Ala Gly Asp Pro Ser Gln Pro Arg Pro Asn Pro Pro Thr Phe Ala
3485                3490                3495

Gln Gly Val Ile Asn Glu Ala Asp Gln Arg Gln Tyr Glu Glu Trp
    3500                3505                3510

Leu Phe His Thr Gln Gln Leu Leu Gln Met Gln Leu Lys Val Leu
3515                3520                3525

Glu Glu Gln Ile Gly Val His Arg Lys Ser Arg Lys Ala Leu Cys
    3530                3535                3540

Ala Lys Gln Arg Thr Ala Lys Lys Ala Gly Arg Glu Phe Pro Glu
3545                3550                3555

Ala Asp Ala Glu Lys Leu Lys Leu Val Thr Glu Gln Gln Ser Lys
    3560                3565                3570

Ile Gln Lys Gln Leu Asp Gln Val Arg Lys Gln Gln Lys Glu His
3575                3580                3585

Thr Asn Leu Met Ala Glu Tyr Arg Asn Lys Gln Gln Gln Gln Gln
    3590                3595                3600

Gln Gln Gln Gln Gln Gln Gln Gln His Ser Ala Val Leu Ala
3605                3610                3615

Leu Ser Pro Ser Gln Ser Pro Arg Leu Leu Thr Lys Leu Pro Gly
    3620                3625                3630

Gln Leu Leu Pro Gly His Gly Leu Gln Pro Pro Gln Gly Pro Pro
3635                3640                3645
```

```
Gly Gly Gln Ala Gly Gly Leu Arg Leu Thr Pro Gly Gly Met Ala
3650                3655                3660

Leu Pro Gly Gln Pro Gly Gly Pro Phe Leu Asn Thr Ala Leu Ala
3665                3670                3675

Gln Gln Gln Gln Gln Gln His Ser Gly Gly Ala Gly Ser Leu Ala
3680                3685                3690

Gly Pro Ser Gly Gly Phe Phe Pro Gly Asn Leu Ala Leu Arg Ser
3695                3700                3705

Leu Gly Pro Asp Ser Arg Leu Leu Gln Glu Arg Gln Leu Gln Leu
3710                3715                3720

Gln Gln Gln Arg Met Gln Leu Ala Gln Lys Leu Gln Gln Gln Gln
3725                3730                3735

Gln Gln Gln Gln Gln Gln Gln His Leu Leu Gly Gln Val Ala Ile
3740                3745                3750

Gln Gln Gln Gln Gln Gln Gly Pro Gly Val Gln Thr Asn Gln Ala
3755                3760                3765

Leu Gly Pro Lys Pro Gln Gly Leu Met Pro Pro Ser Ser His Gln
3770                3775                3780

Gly Leu Leu Val Gln Gln Leu Ser Pro Gln Pro Gln Gly Pro
3785                3790                3795

Gln Gly Met Leu Gly Pro Ala Gln Val Ala Val Leu Gln Gln Gln
3800                3805                3810

His Pro Gly Ala Leu Gly Pro Gln Gly Pro His Arg Gln Val Leu
3815                3820                3825

Met Thr Gln Ser Arg Val Leu Ser Ser Pro Gln Leu Ala Gln Gln
3830                3835                3840

Gly Gln Gly Leu Met Gly His Arg Leu Val Thr Ala Gln Gln Gln
3845                3850                3855

Gln Gln Gln Gln Gln His Gln Gln Gly Ser Met Ala Gly Leu
3860                3865                3870

Ser His Leu Gln Gln Ser Leu Met Ser His Ser Gly Gln Pro Lys
3875                3880                3885

Leu Ser Ala Gln Pro Met Gly Ser Leu Gln Gln Leu Gln Gln Gln
3890                3895                3900

Gln Gln Leu Gln Gln Gln Gln Gln Leu Gln Gln Gln Gln Gln Gln
3905                3910                3915

Gln Leu Gln Gln Gln Gln Gln Leu Gln Gln Gln Gln Leu Gln Gln
3920                3925                3930

Gln Gln Gln Gln Gln Gln Leu Gln Gln Gln Gln Gln Gln Gln Leu
3935                3940                3945

Gln Gln Gln Gln Gln Gln Leu Gln Gln Gln Gln Gln Gln Gln Gln
3950                3955                3960

Gln Gln Phe Gln Gln Gln Gln Gln Gln Gln Met Gly Leu Leu
3965                3970                3975

Asn Gln Ser Arg Thr Leu Leu Ser Pro Gln Gln Gln Gln Gln Gln
3980                3985                3990

Gln Val Ala Leu Gly Pro Gly Met Pro Ala Lys Pro Leu Gln His
3995                4000                4005

Phe Ser Ser Pro Gly Ala Leu Gly Pro Thr Leu Leu Leu Thr Gly
4010                4015                4020

Lys Glu Gln Asn Thr Val Asp Pro Ala Val Ser Ser Glu Ala Thr
4025                4030                4035

Glu Gly Pro Ser Thr His Gln Gly Gly Pro Leu Ala Ile Gly Thr
```

```
                4040               4045                4050
Thr Pro Glu Ser Met Ala Thr Glu Pro Gly Glu Val Lys Pro Ser
    4055                4060                4065

Leu Ser Gly Asp Ser Gln Leu Leu Val Gln Pro Gln Pro Gln
    4070                4075                4080

Pro Gln Pro Ser Ser Leu Gln Leu Gln Pro Pro Leu Arg Leu Pro
    4085                4090                4095

Gly Gln Gln Gln Gln Val Ser Leu Leu His Thr Ala Gly Gly
    4100                4105                4110

Gly Ser His Gly Gln Leu Gly Ser Gly Ser Ser Glu Ala Ser
    4115                4120                4125

Ser Val Pro His Leu Leu Ala Gln Pro Ser Val Ser Leu Gly Asp
    4130                4135                4140

Gln Pro Gly Ser Met Thr Gln Asn Leu Leu Gly Pro Gln Gln Pro
    4145                4150                4155

Met Leu Glu Arg Pro Met Gln Asn Asn Thr Gly Pro Gln Pro Pro
    4160                4165                4170

Lys Pro Gly Pro Val Leu Gln Ser Gly Gln Gly Leu Pro Gly Val
    4175                4180                4185

Gly Ile Met Pro Thr Val Gly Gln Leu Arg Ala Gln Leu Gln Gly
    4190                4195                4200

Val Leu Ala Lys Asn Pro Gln Leu Arg His Leu Ser Pro Gln Gln
    4205                4210                4215

Gln Gln Gln Leu Gln Ala Leu Leu Met Gln Arg Gln Leu Gln Gln
    4220                4225                4230

Ser Gln Ala Val Arg Gln Thr Pro Pro Tyr Gln Glu Pro Gly Thr
    4235                4240                4245

Gln Thr Ser Pro Leu Gln Gly Leu Leu Gly Cys Gln Pro Gln Leu
    4250                4255                4260

Gly Gly Phe Pro Gly Pro Gln Thr Gly Pro Leu Gln Glu Leu Gly
    4265                4270                4275

Ala Gly Pro Arg Pro Gln Gly Pro Pro Arg Leu Pro Ala Pro Pro
    4280                4285                4290

Gly Ala Leu Ser Thr Gly Pro Val Leu Gly Pro Val His Pro Thr
    4295                4300                4305

Pro Pro Pro Ser Ser Pro Gln Glu Pro Lys Arg Pro Ser Gln Leu
    4310                4315                4320

Pro Ser Pro Ser Ser Gln Leu Pro Thr Glu Ala Gln Leu Pro Pro
    4325                4330                4335

Thr His Pro Gly Thr Pro Lys Pro Gln Gly Pro Thr Leu Glu Pro
    4340                4345                4350

Pro Pro Gly Arg Val Ser Pro Ala Ala Ala Gln Leu Ala Asp Thr
    4355                4360                4365

Leu Phe Ser Lys Gly Leu Gly Pro Trp Asp Pro Asp Asn Leu
    4370                4375                4380

Ala Glu Thr Gln Lys Pro Glu Gln Ser Ser Leu Val Pro Gly His
    4385                4390                4395

Leu Asp Gln Val Asn Gly Gln Val Val Pro Glu Ala Ser Gln Leu
    4400                4405                4410

Ser Ile Lys Gln Glu Pro Arg Glu Glu Pro Cys Ala Leu Gly Ala
    4415                4420                4425

Gln Ser Val Lys Arg Glu Ala Asn Gly Glu Pro Ile Gly Ala Pro
    4430                4435                4440
```

```
Gly Thr Ser Asn His Leu Leu Leu Ala Gly Pro Arg Ser Glu Ala
4445                4450                4455

Gly His Leu Leu Leu Gln Lys Leu Leu Arg Ala Lys Asn Val Gln
4460                4465                4470

Leu Ser Thr Gly Arg Gly Ser Glu Gly Leu Arg Ala Glu Ile Asn
4475                4480                4485

Gly His Ile Asp Ser Lys Leu Ala Gly Leu Glu Gln Lys Leu Gln
4490                4495                4500

Gly Thr Pro Ser Asn Lys Glu Asp Ala Ala Arg Lys Pro Leu
4505                4510                4515

Thr Pro Lys Pro Lys Arg Val Gln Lys Ala Ser Asp Arg Leu Val
4520                4525                4530

Ser Ser Arg Lys Lys Leu Arg Lys Glu Asp Gly Val Arg Ala Ser
4535                4540                4545

Glu Ala Leu Leu Lys Gln Leu Lys Gln Glu Leu Ser Leu Leu Pro
4550                4555                4560

Leu Thr Glu Pro Ala Ile Thr Ala Asn Phe Ser Leu Phe Ala Pro
4565                4570                4575

Phe Gly Ser Gly Cys Pro Val Asn Gly Gln Ser Gln Leu Arg Gly
4580                4585                4590

Ala Phe Gly Ser Gly Ala Leu Pro Thr Gly Pro Asp Tyr Tyr Ser
4595                4600                4605

Gln Leu Leu Thr Lys Asn Asn Leu Ser Asn Pro Thr Pro Pro
4610                4615                4620

Ser Ser Leu Pro Pro Thr Pro Pro Pro Ser Val Gln Gln Lys Met
4625                4630                4635

Val Asn Gly Val Thr Pro Ser Glu Glu Leu Gly Glu His Pro Lys
4640                4645                4650

Asp Ala Ala Ser Ala Arg Asp Ser Glu Arg Ala Leu Arg Asp Thr
4655                4660                4665

Ser Glu Val Lys Ser Leu Asp Leu Leu Ala Ala Leu Pro Thr Pro
4670                4675                4680

Pro His Asn Gln Thr Glu Asp Val Arg Met Glu Ser Asp Glu Asp
4685                4690                4695

Ser Asp Ser Pro Asp Ser Ile Val Pro Ala Ser Ser Pro Glu Ser
4700                4705                4710

Ile Leu Gly Glu Glu Ala Pro Arg Phe Pro His Leu Gly Ser Gly
4715                4720                4725

Arg Trp Glu Gln Glu Asp Arg Ala Leu Ser Pro Val Ile Pro Leu
4730                4735                4740

Ile Pro Arg Ala Ser Ile Pro Val Phe Pro Asp Thr Lys Pro Tyr
4745                4750                4755

Gly Ala Leu Gly Leu Glu Val Pro Gly Lys Leu Pro Val Thr Thr
4760                4765                4770

Trp Glu Lys Gly Lys Gly Ser Glu Val Ser Val Met Leu Thr Val
4775                4780                4785

Ser Ala Ala Ala Lys Asn Leu Asn Gly Val Met Val Ala Val
4790                4795                4800

Ala Glu Leu Leu Ser Met Lys Ile Pro Asn Ser Tyr Glu Val Leu
4805                4810                4815

Phe Pro Glu Ser Pro Ala Arg Ala Gly Thr Glu Pro Lys Lys Gly
4820                4825                4830
```

```
Glu Ala Glu Gly Pro Gly Gly Lys Glu Lys Gly Leu Glu Gly Lys
4835                4840                    4845

Ser Pro Asp Thr Gly Pro Asp Trp Leu Lys Gln Phe Asp Ala Val
4850                4855                    4860

Leu Pro Gly Tyr Thr Leu Lys Ser Gln Leu Asp Ile Leu Ser Leu
4865                4870                    4875

Leu Lys Gln Glu Ser Pro Ala Pro Glu Pro Pro Thr Gln His Ser
4880                4885                    4890

Tyr Thr Tyr Asn Val Ser Asn Leu Asp Val Arg Gln Leu Ser Ala
4895                4900                    4905

Pro Pro Pro Glu Glu Pro Ser Pro Pro Pro Ser Pro Leu Ala Pro
4910                4915                    4920

Ser Pro Ala Ser Pro Pro Thr Glu Pro Leu Val Glu Leu Pro Thr
4925                4930                    4935

Glu Pro Leu Ala Glu Pro Pro Val Pro Ser Pro Leu Pro Leu Ala
4940                4945                    4950

Ser Ser Pro Glu Ser Ala Arg Pro Lys Pro Arg Ala Arg Pro Pro
4955                4960                    4965

Glu Glu Gly Glu Asp Ser Arg Pro Pro Arg Leu Lys Lys Trp Lys
4970                4975                    4980

Gly Val Arg Trp Lys Arg Leu Arg Leu Leu Leu Thr Ile Gln Lys
4985                4990                    4995

Gly Ser Gly Arg Gln Glu Asp Glu Arg Glu Val Ala Glu Phe Met
5000                5005                    5010

Glu Gln Leu Gly Thr Ala Leu Arg Pro Asp Lys Val Pro Arg Asp
5015                5020                    5025

Met Arg Arg Cys Cys Phe Cys His Glu Glu Gly Asp Gly Ala Thr
5030                5035                    5040

Asp Gly Pro Ala Arg Leu Leu Asn Leu Asp Leu Asp Leu Trp Val
5045                5050                    5055

His Leu Asn Cys Ala Leu Trp Ser Thr Glu Val Tyr Glu Thr Gln
5060                5065                    5070

Gly Gly Ala Leu Met Asn Val Glu Val Ala Leu His Arg Gly Leu
5075                5080                    5085

Leu Thr Lys Cys Ser Leu Cys Gln Arg Thr Gly Ala Thr Ser Ser
5090                5095                    5100

Cys Asn Arg Met Arg Cys Pro Asn Val Tyr His Phe Ala Cys Ala
5105                5110                    5115

Ile Arg Ala Lys Cys Met Phe Phe Lys Asp Lys Thr Met Leu Cys
5120                5125                    5130

Pro Met His Lys Ile Lys Gly Pro Cys Glu Gln Glu Leu Ser Ser
5135                5140                    5145

Phe Ala Val Phe Arg Arg Val Tyr Ile Glu Arg Asp Glu Val Lys
5150                5155                    5160

Gln Ile Ala Ser Ile Ile Gln Arg Gly Glu Arg Leu His Met Phe
5165                5170                    5175

Arg Val Gly Gly Leu Val Phe His Ala Ile Gly Gln Leu Leu Pro
5180                5185                    5190

His Gln Met Ala Asp Phe His Ser Ala Thr Ala Leu Tyr Pro Val
5195                5200                    5205

Gly Tyr Glu Ala Thr Arg Ile Tyr Trp Ser Leu Arg Thr Asn Asn
5210                5215                    5220

Arg Arg Cys Cys Tyr Arg Cys Ser Ile Gly Glu Asn Asn Gly Arg
```

```
                 5225                5230                5235

Pro Glu Phe Val Ile Lys Val Ile Glu Gln Gly Leu Glu Asp Leu
        5240                5245                5250

Val Phe Thr Asp Ala Ser Pro Gln Ala Val Trp Asn Arg Ile Ile
        5255                5260                5265

Glu Pro Val Ala Ala Met Arg Lys Glu Ala Asp Met Leu Arg Leu
        5270                5275                5280

Phe Pro Glu Tyr Leu Lys Gly Glu Glu Leu Phe Gly Leu Thr Val
        5285                5290                5295

His Ala Val Leu Arg Ile Ala Glu Ser Leu Pro Gly Val Glu Ser
        5300                5305                5310

Cys Gln Asn Tyr Leu Phe Arg Tyr Gly Arg His Pro Leu Met Glu
        5315                5320                5325

Leu Pro Leu Met Ile Asn Pro Thr Gly Cys Ala Arg Ser Glu Pro
        5330                5335                5340

Lys Ile Leu Thr His Tyr Lys Arg Pro His Thr Leu Asn Ser Thr
        5345                5350                5355

Ser Met Ser Lys Ala Tyr Gln Ser Thr Phe Thr Gly Glu Thr Asn
        5360                5365                5370

Thr Pro Tyr Ser Lys Gln Phe Val His Ser Lys Ser Ser Gln Tyr
        5375                5380                5385

Arg Arg Leu Arg Thr Glu Trp Lys Asn Asn Val Tyr Leu Ala Arg
        5390                5395                5400

Ser Arg Ile Gln Gly Leu Gly Leu Tyr Ala Ala Lys Asp Leu Glu
        5405                5410                5415

Lys His Thr Met Val Ile Glu Tyr Ile Gly Thr Ile Ile Arg Asn
        5420                5425                5430

Glu Val Ala Asn Arg Arg Glu Lys Ile Tyr Glu Glu Gln Asn Arg
        5435                5440                5445

Gly Ile Tyr Met Phe Arg Ile Asn Asn Glu His Val Ile Asp Ala
        5450                5455                5460

Thr Leu Thr Gly Gly Pro Ala Arg Tyr Ile Asn His Ser Cys Ala
        5465                5470                5475

Pro Asn Cys Val Ala Glu Val Val Thr Phe Asp Lys Glu Asp Lys
        5480                5485                5490

Ile Ile Ile Ile Ser Ser Arg Arg Ile Pro Lys Gly Glu Glu Leu
        5495                5500                5505

Thr Tyr Asp Tyr Gln Phe Asp Phe Glu Asp Asp Gln His Lys Ile
        5510                5515                5520

Pro Cys His Cys Gly Ala Trp Asn Cys Arg Lys Trp Met Asn
        5525                5530                5535

<210> SEQ ID NO 46
<211> LENGTH: 5540
<212> TYPE: PRT
<213> ORGANISM: Homo sapiens

<400> SEQUENCE: 46

Met Asp Ser Gln Lys Leu Ala Gly Glu Asp Lys Asp Ser Pro Ala
1               5                   10                  15

Ala Asp Gly Pro Ala Ala Ser Glu Asp Pro Ser Ala Thr Glu Ser Asp
                20                  25                  30

Leu Pro Asn Pro His Val Gly Val Ser Val Leu Ser Ser Gly Ser
                35                  40                  45
```

```
Pro Arg Leu Gln Glu Thr Pro Gln Asp Cys Ser Gly Gly Pro Val Arg
    50                  55                  60
Arg Cys Ala Leu Cys Asn Cys Gly Glu Pro Ser Leu His Gly Gln Arg
65                  70                  75                  80
Glu Leu Arg Arg Phe Glu Leu Pro Phe Asp Trp Pro Arg Cys Pro Val
                85                  90                  95
Val Ser Pro Gly Gly Ser Pro Gly Pro Asn Glu Ala Val Leu Pro Ser
            100                 105                 110
Glu Asp Leu Ser Gln Ile Gly Phe Pro Glu Gly Leu Thr Pro Ala His
        115                 120                 125
Leu Gly Glu Pro Gly Gly Ser Cys Trp Ala His His Trp Cys Ala Ala
    130                 135                 140
Trp Ser Ala Gly Val Trp Gly Gln Glu Gly Pro Glu Leu Cys Gly Val
145                 150                 155                 160
Asp Lys Ala Ile Phe Ser Gly Ile Ser Gln Arg Cys Ser His Cys Thr
                165                 170                 175
Arg Leu Gly Ala Ser Ile Pro Cys Arg Ser Pro Gly Cys Pro Arg Leu
            180                 185                 190
Tyr His Phe Pro Cys Ala Thr Ala Ser Gly Ser Phe Leu Ser Met Lys
        195                 200                 205
Thr Leu Gln Leu Leu Cys Pro Glu His Ser Glu Gly Ala Ala Tyr Leu
    210                 215                 220
Glu Glu Ala Arg Cys Ala Val Cys Glu Gly Pro Gly Glu Leu Cys Asp
225                 230                 235                 240
Leu Phe Phe Cys Thr Ser Cys Gly His His Tyr His Gly Ala Cys Leu
                245                 250                 255
Asp Thr Ala Leu Thr Ala Arg Lys Arg Ala Gly Trp Gln Cys Pro Glu
            260                 265                 270
Cys Lys Val Cys Gln Ala Cys Arg Lys Pro Gly Asn Asp Ser Lys Met
        275                 280                 285
Leu Val Cys Glu Thr Cys Asp Lys Gly Tyr His Thr Phe Cys Leu Lys
    290                 295                 300
Pro Pro Met Glu Glu Leu Pro Ala His Ser Trp Lys Cys Lys Ala Cys
305                 310                 315                 320
Arg Val Cys Arg Ala Cys Gly Ala Gly Ser Ala Glu Leu Asn Pro Asn
                325                 330                 335
Ser Glu Trp Phe Glu Asn Tyr Ser Leu Cys His Arg Cys His Lys Ala
            340                 345                 350
Gln Gly Gly Gln Thr Ile Arg Ser Val Ala Glu Gln His Thr Pro Val
        355                 360                 365
Cys Ser Arg Phe Ser Pro Pro Glu Pro Gly Asp Thr Pro Thr Asp Glu
    370                 375                 380
Pro Asp Ala Leu Tyr Val Ala Cys Gln Gly Gln Pro Lys Gly Gly His
385                 390                 395                 400
Val Thr Ser Met Gln Pro Lys Glu Pro Gly Pro Leu Gln Cys Glu Ala
                405                 410                 415
Lys Pro Leu Gly Lys Ala Gly Val Gln Leu Glu Pro Gln Leu Glu Ala
            420                 425                 430
Pro Leu Asn Glu Glu Met Pro Leu Leu Pro Pro Glu Ser Pro
        435                 440                 445
Leu Ser Pro Pro Glu Glu Ser Pro Thr Ser Pro Pro Glu Ala
    450                 455                 460
Ser Arg Leu Ser Pro Pro Pro Glu Glu Leu Pro Ala Ser Pro Leu Pro
```

-continued

```
              465                 470                 475                 480
        Glu Ala Leu His Leu Ser Arg Pro Leu Glu Glu Ser Pro Leu Ser Pro
                        485                 490                 495
        Pro Pro Glu Glu Ser Pro Leu Ser Pro Pro Glu Ser Ser Pro Phe
                    500                 505                 510
        Ser Pro Leu Glu Glu Ser Pro Leu Ser Pro Pro Glu Glu Ser Pro Pro
                    515                 520                 525
        Ser Pro Ala Leu Glu Thr Pro Leu Ser Pro Pro Glu Ala Ser Pro
                    530                 535                 540
        Leu Ser Pro Pro Phe Glu Glu Ser Pro Leu Ser Pro Pro Glu Glu
        545                 550                 555                 560
        Leu Pro Thr Ser Pro Pro Glu Ala Ser Arg Leu Ser Pro Pro Pro
                        565                 570                 575
        Glu Glu Ser Pro Met Ser Pro Pro Glu Glu Ser Pro Met Ser Pro
                    580                 585                 590
        Pro Pro Glu Ala Ser Arg Leu Phe Pro Pro Phe Glu Glu Ser Pro Leu
                    595                 600                 605
        Ser Pro Pro Glu Glu Ser Pro Leu Ser Pro Pro Glu Ala Ser
                    610                 615                 620
        Arg Leu Ser Pro Pro Glu Asp Ser Pro Met Ser Pro Pro Glu
        625                 630                 635                 640
        Glu Ser Pro Met Ser Pro Pro Glu Val Ser Arg Leu Ser Pro Leu
                        645                 650                 655
        Pro Val Val Ser Arg Leu Ser Pro Pro Glu Glu Ser Pro Leu Ser
                    660                 665                 670
        Pro Pro Pro Glu Glu Ser Pro Thr Ser Pro Pro Glu Ala Ser Arg
                    675                 680                 685
        Leu Ser Pro Pro Glu Asp Ser Pro Thr Ser Pro Pro Glu Asp
                    690                 695                 700
        Ser Pro Ala Ser Pro Pro Glu Asp Ser Leu Met Ser Leu Pro Leu
        705                 710                 715                 720
        Glu Glu Ser Pro Leu Leu Pro Leu Pro Glu Glu Pro Gln Leu Cys Pro
                        725                 730                 735
        Arg Ser Glu Gly Pro His Leu Ser Pro Arg Pro Glu Glu Pro His Leu
                    740                 745                 750
        Ser Pro Arg Pro Glu Glu Pro His Leu Ser Pro Gln Ala Glu Glu Pro
                    755                 760                 765
        His Leu Ser Pro Gln Pro Glu Glu Pro Cys Leu Cys Ala Val Pro Glu
                    770                 775                 780
        Glu Pro His Leu Ser Pro Gln Ala Glu Gly Pro His Leu Ser Pro Gln
        785                 790                 795                 800
        Pro Glu Glu Leu His Leu Ser Pro Gln Thr Glu Glu Pro His Leu Ser
                        805                 810                 815
        Pro Val Pro Glu Glu Pro Cys Leu Ser Pro Gln Pro Glu Glu Ser His
                    820                 825                 830
        Leu Ser Pro Gln Ser Glu Glu Pro Cys Leu Ser Pro Arg Pro Glu Glu
                    835                 840                 845
        Ser His Leu Ser Pro Glu Leu Glu Lys Pro Pro Leu Ser Pro Arg Pro
                    850                 855                 860
        Glu Lys Pro Pro Glu Glu Pro Gly Gln Cys Pro Ala Pro Glu Glu Leu
        865                 870                 875                 880
        Pro Leu Phe Pro Pro Pro Gly Glu Pro Ser Leu Ser Pro Leu Leu Gly
                        885                 890                 895
```

```
Glu Pro Ala Leu Ser Glu Pro Gly Glu Pro Leu Ser Pro Leu Pro
            900                 905                 910

Glu Glu Leu Pro Leu Ser Pro Ser Gly Glu Pro Ser Leu Ser Pro Gln
            915                 920                 925

Leu Met Pro Pro Asp Pro Leu Pro Pro Leu Ser Pro Ile Ile Thr
            930                 935                 940

Ala Ala Ala Pro Pro Ala Leu Ser Pro Leu Gly Glu Leu Glu Tyr Pro
945                 950                 955                 960

Phe Gly Ala Lys Gly Asp Ser Asp Pro Glu Ser Pro Leu Ala Ala Pro
            965                 970                 975

Ile Leu Glu Thr Pro Ile Ser Pro Pro Glu Ala Asn Cys Thr Asp
            980                 985                 990

Pro Glu Pro Val Pro Pro Met Ile Leu Pro Pro Ser Pro Gly Ser Pro
            995                 1000                1005

Val Gly Pro Ala Ser Pro Ile Leu Met Glu Pro Leu Pro Pro Gln
            1010                1015                1020

Cys Ser Pro Leu Leu Gln His Ser Leu Val Pro Gln Asn Ser Pro
            1025                1030                1035

Pro Ser Gln Cys Ser Pro Pro Ala Leu Pro Leu Ser Val Pro Ser
            1040                1045                1050

Pro Leu Ser Pro Ile Gly Lys Val Val Gly Val Ser Asp Glu Ala
            1055                1060                1065

Glu Leu His Glu Met Glu Thr Glu Lys Val Ser Glu Pro Glu Cys
            1070                1075                1080

Pro Ala Leu Glu Pro Ser Ala Thr Ser Pro Leu Pro Ser Pro Met
            1085                1090                1095

Gly Asp Leu Ser Cys Pro Ala Pro Ser Pro Ala Pro Ala Leu Asp
            1100                1105                1110

Asp Phe Ser Gly Leu Gly Glu Asp Thr Ala Pro Leu Asp Gly Ile
            1115                1120                1125

Asp Ala Pro Gly Ser Gln Pro Glu Pro Gly Gln Thr Pro Gly Ser
            1130                1135                1140

Leu Ala Ser Glu Leu Lys Gly Ser Pro Val Leu Leu Asp Pro Glu
            1145                1150                1155

Glu Leu Ala Pro Val Thr Pro Met Glu Val Tyr Pro Glu Cys Lys
            1160                1165                1170

Gln Thr Ala Gly Gln Gly Ser Pro Cys Glu Gln Glu Glu Pro
            1175                1180                1185

Arg Ala Pro Val Ala Pro Thr Pro Pro Thr Leu Ile Lys Ser Asp
            1190                1195                1200

Ile Val Asn Glu Ile Ser Asn Leu Ser Gln Gly Asp Ala Ser Ala
            1205                1210                1215

Ser Phe Pro Gly Ser Glu Pro Leu Leu Gly Ser Pro Asp Pro Glu
            1220                1225                1230

Gly Gly Gly Ser Leu Ser Met Glu Leu Gly Val Ser Thr Asp Val
            1235                1240                1245

Ser Pro Ala Arg Asp Glu Gly Ser Leu Arg Leu Cys Thr Asp Ser
            1250                1255                1260

Leu Pro Glu Thr Asp Asp Ser Leu Leu Cys Asp Ala Gly Thr Ala
            1265                1270                1275

Ile Ser Gly Gly Lys Ala Glu Gly Glu Lys Gly Arg Arg Ser
            1280                1285                1290
```

```
Ser Pro Ala Arg Ser Arg Ile Lys Gln Gly Arg Ser Ser Ser Phe
    1295                1300                1305

Pro Gly Arg Arg Arg Pro Arg Gly Gly Ala His Gly Gly Arg Gly
    1310                1315                1320

Arg Gly Arg Ala Arg Leu Lys Ser Thr Ala Ser Ser Ile Glu Thr
    1325                1330                1335

Leu Val Val Ala Asp Ile Asp Ser Ser Pro Ser Lys Glu Glu Glu
    1340                1345                1350

Glu Glu Asp Asp Asp Thr Met Gln Asn Thr Val Val Leu Phe Ser
    1355                1360                1365

Asn Thr Asp Lys Phe Val Leu Met Gln Asp Met Cys Val Val Cys
    1370                1375                1380

Gly Ser Phe Gly Arg Gly Ala Glu Gly His Leu Leu Ala Cys Ser
    1385                1390                1395

Gln Cys Ser Gln Cys Tyr His Pro Tyr Cys Val Asn Ser Lys Ile
    1400                1405                1410

Thr Lys Val Met Leu Leu Lys Gly Trp Arg Cys Val Glu Cys Ile
    1415                1420                1425

Val Cys Glu Val Cys Gly Gln Ala Ser Asp Pro Ser Arg Leu Leu
    1430                1435                1440

Leu Cys Asp Asp Cys Asp Ile Ser Tyr His Thr Tyr Cys Leu Asp
    1445                1450                1455

Pro Pro Leu Leu Thr Val Pro Lys Gly Gly Trp Lys Cys Lys Trp
    1460                1465                1470

Cys Val Ser Cys Met Gln Cys Gly Ala Ala Ser Pro Gly Phe His
    1475                1480                1485

Cys Glu Trp Gln Asn Ser Tyr Thr His Cys Gly Pro Cys Ala Ser
    1490                1495                1500

Leu Val Thr Cys Pro Ile Cys His Ala Pro Tyr Val Glu Glu Asp
    1505                1510                1515

Leu Leu Ile Gln Cys Arg His Cys Glu Arg Trp Met His Ala Gly
    1520                1525                1530

Cys Glu Ser Leu Phe Thr Glu Asp Asp Val Glu Gln Ala Ala Asp
    1535                1540                1545

Glu Gly Phe Asp Cys Val Ser Cys Gln Pro Tyr Val Val Lys Pro
    1550                1555                1560

Val Ala Pro Val Ala Pro Glu Leu Val Pro Met Lys Val Lys
    1565                1570                1575

Glu Pro Glu Pro Gln Tyr Phe Arg Phe Glu Gly Val Trp Leu Thr
    1580                1585                1590

Glu Thr Gly Met Ala Leu Leu Arg Asn Leu Thr Met Ser Pro Leu
    1595                1600                1605

His Lys Arg Arg Gln Arg Arg Gly Arg Leu Gly Leu Pro Gly Glu
    1610                1615                1620

Ala Gly Leu Glu Gly Ser Glu Pro Ser Asp Ala Leu Gly Pro Asp
    1625                1630                1635

Asp Lys Lys Asp Gly Asp Leu Asp Thr Asp Glu Leu Leu Lys Gly
    1640                1645                1650

Glu Gly Gly Val Glu His Met Glu Cys Glu Ile Lys Leu Glu Gly
    1655                1660                1665

Pro Val Ser Pro Asp Val Glu Pro Gly Lys Glu Glu Thr Glu Glu
    1670                1675                1680

Ser Lys Lys Arg Lys Arg Lys Pro Tyr Arg Pro Gly Ile Gly Gly
```

```
            1685                1690                1695

Phe Met Val Arg Gln Arg Lys Ser His Thr Arg Thr Lys Lys Gly
        1700                1705                1710

Pro Ala Ala Gln Ala Glu Val Leu Ser Gly Asp Gly Gln Pro Asp
        1715                1720                1725

Glu Gly Glu Thr Val Ile Pro Ala Asp Leu Pro Ala Glu Gly Ala
        1730                1735                1740

Val Glu Gln Ser Leu Ala Glu Gly Asp Glu Lys Lys Lys Gln Gln
        1745                1750                1755

Arg Arg Gly Arg Lys Lys Ser Lys Leu Glu Asp Met Phe Pro Ala
        1760                1765                1770

Tyr Leu Gln Glu Ala Phe Phe Gly Lys Glu Leu Leu Asp Leu Ser
        1775                1780                1785

Arg Lys Ala Leu Phe Ala Val Gly Val Gly Arg Pro Ser Phe Gly
        1790                1795                1800

Leu Gly Thr Pro Lys Ala Lys Gly Asp Gly Gly Ser Glu Arg Lys
        1805                1810                1815

Glu Leu Pro Thr Ser Gln Lys Gly Asp Asp Gly Pro Asp Ile Ala
        1820                1825                1830

Asp Glu Glu Ser Arg Gly Leu Glu Gly Lys Ala Asp Thr Pro Gly
        1835                1840                1845

Pro Glu Asp Gly Gly Val Lys Ala Ser Pro Val Pro Ser Asp Pro
        1850                1855                1860

Glu Lys Pro Gly Thr Pro Gly Glu Gly Met Leu Ser Ser Asp Leu
        1865                1870                1875

Asp Arg Ile Ser Thr Glu Glu Leu Pro Lys Met Glu Ser Lys Asp
        1880                1885                1890

Leu Gln Gln Leu Phe Lys Asp Val Leu Gly Ser Glu Arg Glu Gln
        1895                1900                1905

His Leu Gly Cys Gly Thr Pro Gly Leu Glu Gly Ser Arg Thr Pro
        1910                1915                1920

Leu Gln Arg Pro Phe Leu Gln Gly Gly Leu Pro Leu Gly Asn Leu
        1925                1930                1935

Pro Ser Ser Ser Pro Met Asp Ser Tyr Pro Gly Leu Cys Gln Ser
        1940                1945                1950

Pro Phe Leu Asp Ser Arg Glu Arg Gly Phe Phe Ser Pro Glu
        1955                1960                1965

Pro Gly Glu Pro Asp Ser Pro Trp Thr Gly Ser Gly Gly Thr Thr
        1970                1975                1980

Pro Ser Thr Pro Thr Thr Pro Thr Thr Glu Gly Glu Gly Asp Gly
        1985                1990                1995

Leu Ser Tyr Asn Gln Arg Ser Leu Gln Arg Trp Glu Lys Asp Glu
        2000                2005                2010

Glu Leu Gly Gln Leu Ser Thr Ile Ser Pro Val Leu Tyr Ala Asn
        2015                2020                2025

Ile Asn Phe Pro Asn Leu Lys Gln Asp Tyr Pro Asp Trp Ser Ser
        2030                2035                2040

Arg Cys Lys Gln Ile Met Lys Leu Trp Arg Lys Val Pro Ala Ala
        2045                2050                2055

Asp Lys Ala Pro Tyr Leu Gln Lys Ala Lys Asp Asn Arg Ala Ala
        2060                2065                2070

His Arg Ile Asn Lys Val Gln Lys Gln Ala Glu Ser Gln Ile Asn
        2075                2080                2085
```

```
Lys Gln Thr Lys Val Gly Asp Ile Ala Arg Lys Thr Asp Arg Pro
    2090            2095                2100

Ala Leu His Leu Arg Ile Pro Pro Gln Pro Gly Ala Leu Gly Ser
    2105            2110                2115

Pro Pro Pro Ala Ala Ala Pro Thr Ile Phe Ile Gly Ser Pro Thr
    2120            2125                2130

Thr Pro Ala Gly Leu Ser Thr Ser Ala Asp Gly Phe Leu Lys Pro
    2135            2140                2145

Pro Ala Gly Ser Val Pro Gly Pro Asp Ser Pro Gly Glu Leu Phe
    2150            2155                2160

Leu Lys Leu Pro Pro Gln Val Pro Ala Gln Val Pro Ser Gln Asp
    2165            2170                2175

Pro Phe Gly Leu Ala Pro Ala Tyr Pro Leu Glu Pro Arg Phe Pro
    2180            2185                2190

Thr Ala Pro Pro Thr Tyr Pro Pro Tyr Pro Ser Pro Thr Gly Ala
    2195            2200                2205

Pro Ala Gln Pro Pro Met Leu Gly Ala Ser Ser Arg Pro Gly Ala
    2210            2215                2220

Gly Gln Pro Gly Glu Phe His Thr Thr Pro Pro Gly Thr Pro Arg
    2225            2230                2235

His Gln Pro Ser Thr Pro Asp Pro Phe Leu Lys Pro Arg Cys Pro
    2240            2245                2250

Ser Leu Asp Asn Leu Ala Val Pro Glu Ser Pro Gly Val Gly Gly
    2255            2260                2265

Gly Lys Ala Ser Glu Pro Leu Leu Ser Pro Pro Pro Phe Gly Glu
    2270            2275                2280

Ser Arg Lys Ala Leu Glu Val Lys Lys Glu Glu Leu Gly Ala Ser
    2285            2290                2295

Ser Pro Ser Tyr Gly Pro Pro Asn Leu Gly Phe Val Asp Ser Pro
    2300            2305                2310

Ser Ser Gly Thr His Leu Gly Gly Leu Glu Leu Lys Thr Pro Asp
    2315            2320                2325

Val Phe Lys Ala Pro Leu Thr Pro Arg Ala Ser Gln Val Glu Pro
    2330            2335                2340

Gln Ser Pro Gly Leu Gly Leu Arg Pro Gln Glu Pro Pro Pro Ala
    2345            2350                2355

Gln Ala Leu Ala Pro Ser Pro Pro Ser His Pro Asp Ile Phe Arg
    2360            2365                2370

Pro Gly Ser Tyr Thr Asp Pro Tyr Ala Gln Pro Pro Leu Thr Pro
    2375            2380                2385

Arg Pro Gln Pro Pro Pro Glu Ser Cys Cys Ala Leu Pro Pro
    2390            2395                2400

Arg Ser Leu Pro Ser Asp Pro Phe Ser Arg Val Pro Ala Ser Pro
    2405            2410                2415

Gln Ser Gln Ser Ser Ser Gln Ser Pro Leu Thr Pro Arg Pro Leu
    2420            2425                2430

Ser Ala Glu Ala Phe Cys Pro Ser Pro Val Thr Pro Arg Phe Gln
    2435            2440                2445

Ser Pro Asp Pro Tyr Ser Arg Pro Pro Ser Arg Pro Gln Ser Arg
    2450            2455                2460

Asp Pro Phe Ala Pro Leu His Lys Pro Pro Arg Pro Gln Pro Pro
    2465            2470                2475
```

```
Glu Val Ala Phe Lys Ala Gly Ser Leu Ala His Thr Ser Leu Gly
    2480              2485              2490

Ala Gly Gly Phe Pro Ala Ala Leu Pro Ala Gly Pro Ala Gly Glu
    2495              2500              2505

Leu His Ala Lys Val Pro Ser Gly Gln Pro Pro Asn Phe Val Arg
    2510              2515              2520

Ser Pro Gly Thr Gly Ala Phe Val Gly Thr Pro Pro Met Arg
    2525              2530              2535

Phe Thr Phe Pro Gln Ala Val Gly Glu Pro Ser Leu Lys Pro Pro
    2540              2545              2550

Val Pro Gln Pro Gly Leu Pro Pro Pro His Gly Ile Asn Ser His
    2555              2560              2565

Phe Gly Pro Gly Pro Thr Leu Gly Lys Pro Gln Ser Thr Asn Tyr
    2570              2575              2580

Thr Val Ala Thr Gly Asn Phe His Pro Ser Gly Ser Pro Leu Gly
    2585              2590              2595

Pro Ser Ser Gly Ser Thr Gly Glu Ser Tyr Gly Leu Ser Pro Leu
    2600              2605              2610

Arg Pro Pro Ser Val Leu Pro Pro Ala Pro Asp Gly Ser Leu
    2615              2620              2625

Pro Tyr Leu Ser His Gly Ala Ser Gln Arg Ser Gly Ile Thr Ser
    2630              2635              2640

Pro Val Glu Lys Arg Glu Asp Pro Gly Thr Gly Met Gly Ser Ser
    2645              2650              2655

Leu Ala Thr Ala Glu Leu Pro Gly Thr Gln Asp Pro Gly Met Ser
    2660              2665              2670

Gly Leu Ser Gln Thr Glu Leu Glu Lys Gln Arg Gln Arg Gln Arg
    2675              2680              2685

Leu Arg Glu Leu Leu Ile Arg Gln Gln Ile Gln Arg Asn Thr Leu
    2690              2695              2700

Arg Gln Glu Lys Glu Thr Ala Ala Ala Ala Gly Ala Val Gly
    2705              2710              2715

Pro Pro Gly Ser Trp Gly Ala Glu Pro Ser Ser Pro Ala Phe Glu
    2720              2725              2730

Gln Leu Ser Arg Gly Gln Thr Pro Phe Ala Gly Thr Gln Asp Lys
    2735              2740              2745

Ser Ser Leu Val Gly Leu Pro Pro Ser Lys Leu Ser Gly Pro Ile
    2750              2755              2760

Leu Gly Pro Gly Ser Phe Pro Ser Asp Asp Arg Leu Ser Arg Pro
    2765              2770              2775

Pro Pro Pro Ala Thr Pro Ser Ser Met Asp Val Asn Ser Arg Gln
    2780              2785              2790

Leu Val Gly Gly Ser Gln Ala Phe Tyr Gln Arg Ala Pro Tyr Pro
    2795              2800              2805

Gly Ser Leu Pro Leu Gln Gln Gln Gln Gln Leu Trp Gln Gln
    2810              2815              2820

Gln Gln Ala Thr Ala Ala Thr Ser Met Arg Phe Ala Met Ser Ala
    2825              2830              2835

Arg Phe Pro Ser Thr Pro Gly Pro Glu Leu Gly Arg Gln Ala Leu
    2840              2845              2850

Gly Ser Pro Leu Ala Gly Ile Ser Thr Arg Leu Pro Gly Pro Gly
    2855              2860              2865

Glu Pro Val Pro Gly Pro Ala Gly Pro Ala Gln Phe Ile Glu Leu
```

```
              2870                2875                2880

Arg His Asn Val Gln Lys Gly Leu Gly Pro Gly Gly Thr Pro Phe
         2885                2890                2895

Pro Gly Gln Gly Pro Pro Gln Arg Pro Arg Phe Tyr Pro Val Ser
         2900                2905                2910

Glu Asp Pro His Arg Leu Ala Pro Glu Gly Leu Arg Gly Leu Ala
         2915                2920                2925

Val Ser Gly Leu Pro Pro Gln Lys Pro Ser Ala Pro Pro Ala Pro
         2930                2935                2940

Glu Leu Asn Asn Ser Leu His Pro Thr Pro His Thr Lys Gly Pro
         2945                2950                2955

Thr Leu Pro Thr Gly Leu Glu Leu Val Asn Arg Pro Pro Ser Ser
         2960                2965                2970

Thr Glu Leu Gly Arg Pro Asn Pro Leu Ala Leu Glu Ala Gly Lys
         2975                2980                2985

Leu Pro Cys Glu Asp Pro Glu Leu Asp Asp Phe Asp Ala His
         2990                2995                3000

Lys Ala Leu Glu Asp Asp Glu Leu Ala His Leu Gly Leu Gly
         3005                3010                3015

Val Asp Val Ala Lys Gly Asp Asp Glu Leu Gly Thr Leu Glu Asn
         3020                3025                3030

Leu Glu Thr Asn Asp Pro His Leu Asp Asp Leu Leu Asn Gly Asp
         3035                3040                3045

Glu Phe Asp Leu Leu Ala Tyr Thr Asp Pro Glu Leu Asp Thr Gly
         3050                3055                3060

Asp Lys Lys Asp Ile Phe Asn Glu His Leu Arg Leu Val Glu Ser
         3065                3070                3075

Ala Asn Glu Lys Ala Glu Arg Glu Ala Leu Leu Arg Gly Val Glu
         3080                3085                3090

Pro Gly Pro Leu Gly Pro Glu Glu Arg Pro Pro Ala Ala Asp
         3095                3100                3105

Ala Ser Glu Pro Arg Leu Ala Ser Val Leu Pro Glu Val Lys Pro
         3110                3115                3120

Lys Val Glu Glu Gly Gly Arg His Pro Ser Pro Cys Gln Phe Thr
         3125                3130                3135

Ile Ala Thr Pro Lys Val Glu Pro Ala Pro Ala Ala Asn Ser Leu
         3140                3145                3150

Gly Leu Gly Leu Lys Pro Gly Gln Ser Met Met Gly Ser Arg Asp
         3155                3160                3165

Thr Arg Met Gly Thr Gly Pro Phe Ser Ser Ser Gly His Thr Ala
         3170                3175                3180

Glu Lys Ala Ser Phe Gly Ala Thr Gly Gly Pro Pro Ala His Leu
         3185                3190                3195

Leu Thr Pro Ser Pro Leu Ser Gly Pro Gly Gly Ser Ser Leu Leu
         3200                3205                3210

Glu Lys Phe Glu Leu Glu Ser Gly Ala Leu Thr Leu Pro Gly Gly
         3215                3220                3225

Pro Ala Ala Ser Gly Asp Glu Leu Asp Lys Met Glu Ser Ser Leu
         3230                3235                3240

Val Ala Ser Glu Leu Pro Leu Leu Ile Glu Asp Leu Leu Glu His
         3245                3250                3255

Glu Lys Lys Glu Leu Gln Lys Lys Gln Gln Leu Ser Ala Gln Leu
         3260                3265                3270
```

```
Gln Pro Ala Gln Gln Gln Gln Gln Gln Gln His Ser Leu
    3275                3280            3285

Leu Ser Ala Pro Gly Pro Ala Gln Ala Met Ser Leu Pro His Glu
    3290            3295            3300

Gly Ser Ser Pro Ser Leu Ala Gly Ser Gln Gln Gln Leu Ser Leu
    3305            3310            3315

Gly Leu Ala Gly Ala Arg Gln Pro Gly Leu Pro Gln Pro Leu Met
    3320            3325            3330

Pro Thr Gln Pro Pro Ala His Ala Leu Gln Gln Arg Leu Ala Pro
    3335            3340            3345

Ser Met Ala Met Val Ser Asn Gln Gly His Met Leu Ser Gly Gln
    3350            3355            3360

His Gly Gly Gln Ala Gly Leu Val Pro Gln Gln Ser Ser Gln Pro
    3365            3370            3375

Val Leu Ser Gln Lys Pro Met Gly Thr Met Pro Pro Ser Met Cys
    3380            3385            3390

Met Lys Pro Gln Gln Leu Ala Met Gln Gln Leu Ala Asn Ser
    3395            3400            3405

Phe Phe Pro Asp Thr Asp Leu Asp Lys Phe Ala Ala Glu Asp Ile
    3410            3415            3420

Ile Asp Pro Ile Ala Lys Ala Lys Met Val Ala Leu Lys Gly Ile
    3425            3430            3435

Lys Lys Val Met Ala Gln Gly Ser Ile Gly Val Ala Pro Gly Met
    3440            3445            3450

Asn Arg Gln Gln Val Ser Leu Leu Ala Gln Arg Leu Ser Gly Gly
    3455            3460            3465

Pro Ser Ser Asp Leu Gln Asn His Val Ala Ala Gly Ser Gly Gln
    3470            3475            3480

Glu Arg Ser Ala Gly Asp Pro Ser Gln Pro Arg Pro Asn Pro Pro
    3485            3490            3495

Thr Phe Ala Gln Gly Val Ile Asn Glu Ala Asp Gln Arg Gln Tyr
    3500            3505            3510

Glu Glu Trp Leu Phe His Thr Gln Gln Leu Leu Gln Met Gln Leu
    3515            3520            3525

Lys Val Leu Glu Glu Gln Ile Gly Val His Arg Lys Ser Arg Lys
    3530            3535            3540

Ala Leu Cys Ala Lys Gln Arg Thr Ala Lys Lys Ala Gly Arg Glu
    3545            3550            3555

Phe Pro Glu Ala Asp Ala Glu Lys Leu Lys Leu Val Thr Glu Gln
    3560            3565            3570

Gln Ser Lys Ile Gln Lys Gln Leu Asp Gln Val Arg Lys Gln Gln
    3575            3580            3585

Lys Glu His Thr Asn Leu Met Ala Glu Tyr Arg Asn Lys Gln Gln
    3590            3595            3600

Gln Gln Gln Gln Gln Gln Gln Gln Gln Gln Gln Gln His Ser Ala
    3605            3610            3615

Val Leu Ala Leu Ser Pro Ser Gln Ser Pro Arg Leu Leu Thr Lys
    3620            3625            3630

Leu Pro Gly Gln Leu Leu Pro Gly His Gly Leu Gln Pro Pro Gln
    3635            3640            3645

Gly Pro Pro Gly Gly Gln Ala Gly Gly Leu Arg Leu Thr Pro Gly
    3650            3655            3660
```

```
Gly Met Ala Leu Pro Gly Gln Pro Gly Gly Pro Phe Leu Asn Thr
3665                3670                3675

Ala Leu Ala Gln Gln Gln Gln Gln Gln His Ser Gly Gly Ala Gly
    3680                3685                3690

Ser Leu Ala Gly Pro Ser Gly Gly Phe Phe Pro Gly Asn Leu Ala
    3695                3700                3705

Leu Arg Ser Leu Gly Pro Asp Ser Arg Leu Leu Gln Glu Arg Gln
    3710                3715                3720

Leu Gln Leu Gln Gln Gln Arg Met Gln Leu Ala Gln Lys Leu Gln
    3725                3730                3735

Gln Gln Gln Gln Gln Gln Gln Gln Gln His Leu Leu Gly Gln
    3740                3745                3750

Val Ala Ile Gln Gln Gln Gln Gln Gly Pro Gly Val Gln Thr
    3755                3760                3765

Asn Gln Ala Leu Gly Pro Lys Pro Gln Gly Leu Met Pro Pro Ser
    3770                3775                3780

Ser His Gln Gly Leu Leu Val Gln Gln Leu Ser Pro Gln Pro Pro
    3785                3790                3795

Gln Gly Pro Gln Gly Met Leu Gly Pro Ala Gln Val Ala Val Leu
    3800                3805                3810

Gln Gln Gln His Pro Gly Ala Leu Gly Pro Gln Gly Pro His Arg
    3815                3820                3825

Gln Val Leu Met Thr Gln Ser Arg Val Leu Ser Ser Pro Gln Leu
    3830                3835                3840

Ala Gln Gln Gly Gln Gly Leu Met Gly His Arg Leu Val Thr Ala
    3845                3850                3855

Gln Gln Gln Gln Gln Gln Gln His Gln Gln Gln Gly Ser Met
    3860                3865                3870

Ala Gly Leu Ser His Leu Gln Gln Ser Leu Met Ser His Ser Gly
    3875                3880                3885

Gln Pro Lys Leu Ser Ala Gln Pro Met Gly Ser Leu Gln Gln Leu
    3890                3895                3900

Gln Gln Gln Gln Gln Leu Gln Gln Gln Gln Leu Gln Gln Gln
    3905                3910                3915

Gln Gln Gln Gln Leu Gln Gln Gln Gln Leu Gln Gln Gln
    3920                3925                3930

Leu Gln Gln Gln Gln Gln Gln Gln Leu Gln Gln Gln Gln Gln
    3935                3940                3945

Gln Gln Leu Gln Gln Gln Gln Gln Leu Gln Gln Gln Gln Gln
    3950                3955                3960

Gln Gln Gln Gln Gln Phe Gln Gln Gln Gln Gln Gln Gln Met
    3965                3970                3975

Gly Leu Leu Asn Gln Ser Arg Thr Leu Leu Ser Pro Gln Gln Gln
    3980                3985                3990

Gln Gln Gln Gln Val Ala Leu Gly Pro Gly Met Pro Ala Lys Pro
    3995                4000                4005

Leu Gln His Phe Ser Ser Pro Gly Ala Leu Gly Pro Thr Leu Leu
    4010                4015                4020

Leu Thr Gly Lys Glu Gln Asn Thr Val Asp Pro Ala Val Ser Ser
    4025                4030                4035

Glu Ala Thr Glu Gly Pro Ser Thr His Gln Gly Gly Pro Leu Ala
    4040                4045                4050

Ile Gly Thr Thr Pro Glu Ser Met Ala Thr Glu Pro Gly Glu Val
```

```
                4055                4060                4065
Lys Pro Ser Leu Ser Gly Asp Ser Gln Leu Leu Val Gln Pro
    4070                4075                4080
Gln Pro Gln Pro Gln Pro Ser Ser Leu Gln Leu Gln Pro Pro Leu
    4085                4090                4095
Arg Leu Pro Gly Gln Gln Gln Gln Gln Val Ser Leu Leu His Thr
    4100                4105                4110
Ala Gly Gly Gly Ser His Gly Gln Leu Gly Ser Gly Ser Ser Ser
    4115                4120                4125
Glu Ala Ser Ser Val Pro His Leu Leu Ala Gln Pro Ser Val Ser
    4130                4135                4140
Leu Gly Asp Gln Pro Gly Ser Met Thr Gln Asn Leu Leu Gly Pro
    4145                4150                4155
Gln Gln Pro Met Leu Glu Arg Pro Met Gln Asn Asn Thr Gly Pro
    4160                4165                4170
Gln Pro Pro Lys Pro Gly Pro Val Leu Gln Ser Gly Gln Gly Leu
    4175                4180                4185
Pro Gly Val Gly Ile Met Pro Thr Val Gly Gln Leu Arg Ala Gln
    4190                4195                4200
Leu Gln Gly Val Leu Ala Lys Asn Pro Gln Leu Arg His Leu Ser
    4205                4210                4215
Pro Gln Gln Gln Gln Leu Gln Ala Leu Leu Met Gln Arg Gln
    4220                4225                4230
Leu Gln Gln Ser Gln Ala Val Arg Gln Thr Pro Pro Tyr Gln Glu
    4235                4240                4245
Pro Gly Thr Gln Thr Ser Pro Leu Gln Gly Leu Leu Gly Cys Gln
    4250                4255                4260
Pro Gln Leu Gly Gly Phe Pro Gly Pro Gln Thr Gly Pro Leu Gln
    4265                4270                4275
Glu Leu Gly Ala Gly Pro Arg Pro Gln Gly Pro Pro Arg Leu Pro
    4280                4285                4290
Ala Pro Pro Gly Ala Leu Ser Thr Gly Pro Val Leu Gly Pro Val
    4295                4300                4305
His Pro Thr Pro Pro Pro Ser Ser Pro Gln Glu Pro Lys Arg Pro
    4310                4315                4320
Ser Gln Leu Pro Ser Pro Ser Ser Gln Leu Pro Thr Glu Ala Gln
    4325                4330                4335
Leu Pro Pro Thr His Pro Gly Thr Pro Lys Pro Gln Gly Pro Thr
    4340                4345                4350
Leu Glu Pro Pro Pro Gly Arg Val Ser Pro Ala Ala Ala Gln Leu
    4355                4360                4365
Ala Asp Thr Leu Phe Ser Lys Gly Leu Gly Pro Trp Asp Pro Pro
    4370                4375                4380
Asp Asn Leu Ala Glu Thr Gln Lys Pro Glu Gln Ser Ser Leu Val
    4385                4390                4395
Pro Gly His Leu Asp Gln Val Asn Gly Gln Val Val Pro Glu Ala
    4400                4405                4410
Ser Gln Leu Ser Ile Lys Gln Glu Pro Arg Glu Glu Pro Cys Ala
    4415                4420                4425
Leu Gly Ala Gln Ser Val Lys Arg Glu Ala Asn Gly Glu Pro Ile
    4430                4435                4440
Gly Ala Pro Gly Thr Ser Asn His Leu Leu Leu Ala Gly Pro Arg
    4445                4450                4455
```

```
Ser Glu Ala Gly His Leu Leu Leu Gln Lys Leu Leu Arg Ala Lys
    4460            4465                4470

Asn Val Gln Leu Ser Thr Gly Arg Gly Ser Glu Gly Leu Arg Ala
    4475            4480                4485

Glu Ile Asn Gly His Ile Asp Ser Lys Leu Ala Gly Leu Glu Gln
    4490            4495                4500

Lys Leu Gln Gly Thr Pro Ser Asn Lys Glu Asp Ala Ala Ala Arg
    4505            4510                4515

Lys Pro Leu Thr Pro Lys Pro Lys Arg Val Gln Lys Ala Ser Asp
    4520            4525                4530

Arg Leu Val Ser Ser Arg Lys Lys Leu Arg Lys Glu Asp Gly Val
    4535            4540                4545

Arg Ala Ser Glu Ala Leu Leu Lys Gln Leu Lys Gln Glu Leu Ser
    4550            4555                4560

Leu Leu Pro Leu Thr Glu Pro Ala Ile Thr Ala Asn Phe Ser Leu
    4565            4570                4575

Phe Ala Pro Phe Gly Ser Gly Cys Pro Val Asn Gly Gln Ser Gln
    4580            4585                4590

Leu Arg Gly Ala Phe Gly Ser Gly Ala Leu Pro Thr Gly Pro Asp
    4595            4600                4605

Tyr Tyr Ser Gln Leu Leu Thr Lys Asn Asn Leu Ser Asn Pro Pro
    4610            4615                4620

Thr Pro Pro Ser Ser Leu Pro Pro Thr Pro Pro Pro Ser Val Gln
    4625            4630                4635

Gln Lys Met Val Asn Gly Val Thr Pro Ser Glu Glu Leu Gly Glu
    4640            4645                4650

His Pro Lys Asp Ala Ala Ser Ala Arg Asp Ser Glu Arg Ala Leu
    4655            4660                4665

Arg Asp Thr Ser Glu Val Lys Ser Leu Asp Leu Leu Ala Ala Leu
    4670            4675                4680

Pro Thr Pro Pro His Asn Gln Thr Glu Asp Val Arg Met Glu Ser
    4685            4690                4695

Asp Glu Asp Ser Asp Ser Pro Asp Ser Ile Val Pro Ala Ser Ser
    4700            4705                4710

Pro Glu Ser Ile Leu Gly Glu Glu Ala Pro Arg Phe Pro His Leu
    4715            4720                4725

Gly Ser Gly Arg Trp Glu Gln Glu Asp Arg Ala Leu Ser Pro Val
    4730            4735                4740

Ile Pro Leu Ile Pro Arg Ala Ser Ile Pro Val Phe Pro Asp Thr
    4745            4750                4755

Lys Pro Tyr Gly Ala Leu Gly Leu Glu Val Pro Gly Lys Leu Pro
    4760            4765                4770

Val Thr Thr Trp Glu Lys Gly Lys Gly Ser Glu Val Ser Val Met
    4775            4780                4785

Leu Thr Val Ser Ala Ala Ala Lys Asn Leu Asn Gly Val Met
    4790            4795                4800

Val Ala Val Ala Glu Leu Leu Ser Met Lys Ile Pro Asn Ser Tyr
    4805            4810                4815

Glu Val Leu Phe Pro Glu Ser Pro Ala Arg Ala Gly Thr Glu Pro
    4820            4825                4830

Lys Lys Gly Glu Ala Glu Gly Pro Gly Gly Lys Glu Lys Gly Leu
    4835            4840                4845
```

```
Glu Gly Lys Ser Pro Asp Thr Gly Pro Asp Trp Leu Lys Gln Phe
4850             4855             4860

Asp Ala Val Leu Pro Gly Tyr Thr Leu Lys Ser Gln Leu Asp Ile
4865             4870             4875

Leu Ser Leu Leu Lys Gln Glu Ser Pro Ala Pro Glu Pro Pro Thr
4880             4885             4890

Gln His Ser Tyr Thr Tyr Asn Val Ser Asn Leu Asp Val Arg Gln
4895             4900             4905

Leu Ser Ala Pro Pro Glu Glu Pro Ser Pro Pro Ser Pro
4910             4915             4920

Leu Ala Pro Ser Pro Ala Ser Pro Pro Thr Glu Pro Leu Val Glu
4925             4930             4935

Leu Pro Thr Glu Pro Leu Ala Glu Pro Pro Val Pro Ser Pro Leu
4940             4945             4950

Pro Leu Ala Ser Ser Pro Glu Ser Ala Arg Pro Lys Pro Arg Ala
4955             4960             4965

Arg Pro Pro Glu Glu Gly Glu Asp Ser Arg Pro Arg Leu Lys
4970             4975             4980

Lys Trp Lys Gly Val Arg Trp Lys Arg Leu Arg Leu Leu Leu Thr
4985             4990             4995

Ile Gln Lys Gly Ser Gly Arg Gln Glu Asp Glu Arg Glu Val Ala
5000             5005             5010

Glu Phe Met Glu Gln Leu Gly Thr Ala Leu Arg Pro Asp Lys Val
5015             5020             5025

Pro Arg Asp Met Arg Arg Cys Cys Phe Cys His Glu Glu Gly Asp
5030             5035             5040

Gly Ala Thr Asp Gly Pro Ala Arg Leu Leu Asn Leu Asp Leu Asp
5045             5050             5055

Leu Trp Val His Leu Asn Cys Ala Leu Trp Ser Thr Glu Val Tyr
5060             5065             5070

Glu Thr Gln Gly Gly Ala Leu Met Asn Val Glu Val Ala Leu His
5075             5080             5085

Arg Gly Leu Leu Thr Lys Cys Ser Leu Cys Gln Arg Thr Gly Ala
5090             5095             5100

Thr Ser Ser Cys Asn Arg Met Arg Cys Pro Asn Val Tyr His Phe
5105             5110             5115

Ala Cys Ala Ile Arg Ala Lys Cys Met Phe Phe Lys Asp Lys Thr
5120             5125             5130

Met Leu Cys Pro Met His Lys Ile Lys Gly Pro Cys Glu Gln Glu
5135             5140             5145

Leu Ser Ser Phe Ala Val Phe Arg Arg Val Tyr Ile Glu Arg Asp
5150             5155             5160

Glu Val Lys Gln Ile Ala Ser Ile Ile Gln Arg Gly Glu Arg Leu
5165             5170             5175

His Met Phe Arg Val Gly Gly Leu Val Phe His Ala Ile Gly Gln
5180             5185             5190

Leu Leu Pro His Gln Met Ala Asp Phe His Ser Ala Thr Ala Leu
5195             5200             5205

Tyr Pro Val Gly Tyr Glu Ala Thr Arg Ile Tyr Trp Ser Leu Arg
5210             5215             5220

Thr Asn Asn Arg Arg Cys Cys Tyr Arg Cys Ser Ile Gly Glu Asn
5225             5230             5235

Asn Gly Arg Pro Glu Phe Val Ile Lys Val Ile Glu Gln Gly Leu
```

```
                5240                5245                5250

Glu Asp Leu Val Phe Thr Asp Ala Ser Pro Gln Ala Val Trp Asn
            5255                5260                5265

Arg Ile Ile Glu Pro Val Ala Ala Met Arg Lys Glu Ala Asp Met
        5270                5275                5280

Leu Arg Leu Phe Pro Glu Tyr Leu Lys Gly Glu Glu Leu Phe Gly
    5285                5290                5295

Leu Thr Val His Ala Val Leu Arg Ile Ala Glu Ser Leu Pro Gly
5300                5305                5310

Val Glu Ser Cys Gln Asn Tyr Leu Phe Arg Tyr Gly Arg His Pro
5315                5320                5325

Leu Met Glu Leu Pro Leu Met Ile Asn Pro Thr Gly Cys Ala Arg
5330                5335                5340

Ser Glu Pro Lys Ile Leu Thr His Tyr Lys Arg Pro His Thr Leu
5345                5350                5355

Asn Ser Thr Ser Met Ser Lys Ala Tyr Gln Ser Thr Phe Thr Gly
5360                5365                5370

Glu Thr Asn Thr Pro Tyr Ser Lys Gln Phe Val His Ser Lys Ser
5375                5380                5385

Ser Gln Tyr Arg Arg Leu Arg Thr Glu Trp Lys Asn Asn Val Tyr
5390                5395                5400

Leu Ala Arg Ser Arg Ile Gln Gly Leu Gly Leu Tyr Ala Ala Lys
5405                5410                5415

Asp Leu Glu Lys His Thr Met Val Ile Glu Tyr Ile Gly Thr Ile
5420                5425                5430

Ile Arg Asn Glu Val Ala Asn Arg Arg Glu Lys Ile Tyr Glu Glu
5435                5440                5445

Gln Asn Arg Gly Ile Tyr Met Phe Arg Ile Asn Asn Glu His Val
5450                5455                5460

Ile Asp Ala Thr Leu Thr Gly Gly Pro Ala Arg Tyr Ile Asn His
5465                5470                5475

Ser Cys Ala Pro Asn Cys Val Ala Glu Val Val Thr Phe Asp Lys
5480                5485                5490

Glu Asp Lys Ile Ile Ile Ile Ser Ser Arg Arg Ile Pro Lys Gly
5495                5500                5505

Glu Glu Leu Thr Tyr Asp Tyr Gln Phe Asp Phe Glu Asp Asp Gln
5510                5515                5520

His Lys Ile Pro Cys His Cys Gly Ala Trp Asn Cys Arg Lys Trp
5525                5530                5535

Met Asn
5540

<210> SEQ ID NO 47
<211> LENGTH: 4911
<212> TYPE: PRT
<213> ORGANISM: Homo sapiens

<400> SEQUENCE: 47

Met Ser Ser Glu Glu Asp Lys Ser Val Glu Gln Pro Gln Pro Pro
1               5                   10                  15

Pro Pro Pro Glu Glu Pro Gly Ala Pro Ala Pro Ser Pro Ala Ala Ala
                20                  25                  30

Asp Lys Arg Pro Arg Gly Arg Pro Arg Lys Asp Gly Ala Ser Pro Phe
            35                  40                  45
```

```
Gln Arg Ala Arg Lys Lys Pro Arg Ser Arg Gly Lys Thr Ala Val Glu
 50                  55                  60

Asp Glu Asp Ser Met Asp Gly Leu Glu Thr Thr Glu Thr Glu Thr Ile
 65                  70                  75                  80

Val Glu Thr Glu Ile Lys Glu Gln Ser Ala Glu Asp Ala Glu Ala
                 85                  90                  95

Glu Val Asp Asn Ser Lys Gln Leu Ile Pro Thr Leu Gln Arg Ser Val
                100                 105                 110

Ser Glu Glu Ser Ala Asn Ser Leu Val Ser Val Gly Val Glu Ala Lys
                115                 120                 125

Ile Ser Glu Gln Leu Cys Ala Phe Cys Tyr Cys Gly Glu Lys Ser Ser
130                 135                 140

Leu Gly Gln Gly Asp Leu Lys Gln Phe Arg Ile Thr Pro Gly Phe Ile
145                 150                 155                 160

Leu Pro Trp Arg Asn Gln Pro Ser Asn Lys Lys Asp Ile Asp Asp Asn
                165                 170                 175

Ser Asn Gly Thr Tyr Glu Lys Met Gln Asn Ser Ala Pro Arg Lys Gln
                180                 185                 190

Arg Gly Gln Arg Lys Glu Arg Ser Pro Gln Gln Asn Ile Val Ser Cys
                195                 200                 205

Val Ser Val Ser Thr Gln Thr Ala Ser Asp Asp Gln Ala Gly Lys Leu
210                 215                 220

Trp Asp Glu Leu Ser Leu Val Gly Leu Pro Asp Ala Ile Asp Ile Gln
225                 230                 235                 240

Ala Leu Phe Asp Ser Thr Gly Thr Cys Trp Ala His His Arg Cys Val
                245                 250                 255

Glu Trp Ser Leu Gly Val Cys Gln Met Glu Glu Pro Leu Leu Val Asn
                260                 265                 270

Val Asp Lys Ala Val Val Ser Gly Ser Thr Glu Arg Cys Ala Phe Cys
                275                 280                 285

Lys His Leu Gly Ala Thr Ile Lys Cys Cys Glu Lys Cys Thr Gln
                290                 295                 300

Met Tyr His Tyr Pro Cys Ala Ala Gly Ala Gly Thr Phe Gln Asp Phe
305                 310                 315                 320

Ser His Ile Phe Leu Leu Cys Pro Glu His Ile Asp Gln Ala Pro Glu
                325                 330                 335

Arg Ser Lys Glu Asp Ala Asn Cys Ala Val Cys Asp Ser Pro Gly Asp
                340                 345                 350

Leu Leu Asp Gln Phe Phe Cys Thr Thr Cys Gly Gln His Tyr His Gly
                355                 360                 365

Met Cys Leu Asp Ile Ala Val Thr Pro Leu Lys Arg Ala Gly Trp Gln
370                 375                 380

Cys Pro Glu Cys Lys Val Cys Gln Asn Cys Lys Gln Ser Gly Glu Asp
385                 390                 395                 400

Ser Lys Met Leu Val Cys Asp Thr Cys Asp Lys Gly Tyr His Thr Phe
                405                 410                 415

Cys Leu Gln Pro Val Met Lys Ser Val Pro Thr Asn Gly Trp Lys Cys
                420                 425                 430

Lys Asn Cys Arg Ile Cys Ile Glu Cys Gly Thr Arg Ser Ser Ser Gln
                435                 440                 445

Trp His His Asn Cys Leu Ile Cys Asp Asn Cys Tyr Gln Gln Gln Asp
450                 455                 460

Asn Leu Cys Pro Phe Cys Gly Lys Cys Tyr His Pro Glu Leu Gln Lys
```

-continued

```
            465                 470                 475                 480
        Asp Met Leu His Cys Asn Met Cys Lys Arg Trp Val His Leu Glu Cys
                        485                 490                 495

Asp Lys Pro Thr Asp His Glu Leu Asp Thr Gln Leu Lys Glu Glu Tyr
                        500                 505                 510

Ile Cys Met Tyr Cys Lys His Leu Gly Ala Glu Met Asp Arg Leu Gln
                        515                 520                 525

Pro Gly Glu Glu Val Glu Ile Ala Glu Leu Thr Thr Asp Tyr Asn Asn
                        530                 535                 540

Glu Met Glu Val Glu Gly Pro Glu Asp Gln Met Val Phe Ser Glu Gln
        545                 550                 555                 560

Ala Ala Asn Lys Asp Val Asn Gly Gln Glu Ser Thr Pro Gly Ile Val
                        565                 570                 575

Pro Asp Ala Val Gln Val His Thr Glu Glu Gln Lys Ser His Pro
                        580                 585                 590

Ser Glu Ser Leu Asp Thr Asp Ser Leu Leu Ile Ala Val Ser Ser Gln
                        595                 600                 605

His Thr Val Asn Thr Glu Leu Glu Lys Gln Ile Ser Asn Glu Val Asp
                        610                 615                 620

Ser Glu Asp Leu Lys Met Ser Ser Glu Val Lys His Ile Cys Gly Glu
        625                 630                 635                 640

Asp Gln Ile Glu Asp Lys Met Glu Val Thr Glu Asn Ile Glu Val Val
                        645                 650                 655

Thr His Gln Ile Thr Val Gln Gln Glu Gln Leu Gln Leu Leu Glu Glu
                        660                 665                 670

Pro Glu Thr Val Val Ser Arg Glu Glu Ser Arg Pro Pro Lys Leu Val
                        675                 680                 685

Met Glu Ser Val Thr Leu Pro Leu Glu Thr Leu Val Ser Pro His Glu
                        690                 695                 700

Glu Ser Ile Ser Leu Cys Pro Glu Glu Gln Leu Val Ile Glu Arg Leu
        705                 710                 715                 720

Gln Gly Glu Lys Glu Gln Lys Glu Asn Ser Glu Leu Ser Thr Gly Leu
                        725                 730                 735

Met Asp Ser Glu Met Thr Pro Thr Ile Glu Gly Cys Val Lys Asp Val
                        740                 745                 750

Ser Tyr Gln Gly Gly Lys Ser Ile Lys Leu Ser Ser Glu Thr Glu Ser
                        755                 760                 765

Ser Phe Ser Ser Ala Asp Ile Ser Lys Ala Asp Val Ser Ser Ser
                        770                 775                 780

Pro Thr Pro Ser Ser Asp Leu Pro Ser His Asp Met Leu His Asn Tyr
        785                 790                 795                 800

Pro Ser Ala Leu Ser Ser Ala Gly Asn Ile Met Pro Thr Thr Tyr
                        805                 810                 815

Ile Ser Val Thr Pro Lys Ile Gly Met Gly Lys Pro Ala Ile Thr Lys
                        820                 825                 830

Arg Lys Phe Ser Pro Gly Arg Pro Arg Ser Lys Gln Gly Ala Trp Ser
                        835                 840                 845

Thr His Asn Thr Val Ser Pro Pro Ser Trp Ser Pro Asp Ile Ser Glu
                        850                 855                 860

Gly Arg Glu Ile Phe Lys Pro Arg Gln Leu Pro Gly Ser Ala Ile Trp
        865                 870                 875                 880

Ser Ile Lys Val Gly Arg Gly Ser Gly Phe Pro Gly Lys Arg Arg Pro
                        885                 890                 895
```

```
Arg Gly Ala Gly Leu Ser Gly Arg Gly Arg Gly Arg Ser Lys Leu
            900                 905                 910
Lys Ser Gly Ile Gly Ala Val Val Leu Pro Gly Val Ser Thr Ala Asp
            915                 920                 925
Ile Ser Ser Asn Lys Asp Asp Glu Glu Asn Ser Met His Asn Thr Val
        930                 935                 940
Val Leu Phe Ser Ser Ser Asp Lys Phe Thr Leu Asn Gln Asp Met Cys
945                 950                 955                 960
Val Val Cys Gly Ser Phe Gly Gln Gly Ala Glu Gly Arg Leu Leu Ala
                965                 970                 975
Cys Ser Gln Cys Gly Gln Cys Tyr His Pro Tyr Cys Val Ser Ile Lys
            980                 985                 990
Ile Thr Lys Val Val Leu Ser Lys Gly Trp Arg Cys Leu Glu Cys Thr
            995                 1000                1005
Val Cys Glu Ala Cys Gly Lys Ala Thr Asp Pro Gly Arg Leu Leu
        1010                1015                1020
Leu Cys Asp Asp Cys Asp Ile Ser Tyr His Thr Tyr Cys Leu Asp
        1025                1030                1035
Pro Pro Leu Gln Thr Val Pro Lys Gly Gly Trp Lys Cys Lys Trp
        1040                1045                1050
Cys Val Trp Cys Arg His Cys Gly Ala Thr Ser Ala Gly Leu Arg
        1055                1060                1065
Cys Glu Trp Gln Asn Asn Tyr Thr Gln Cys Ala Pro Cys Ala Ser
        1070                1075                1080
Leu Ser Ser Cys Pro Val Cys Tyr Arg Asn Tyr Arg Glu Glu Asp
        1085                1090                1095
Leu Ile Leu Gln Cys Arg Gln Cys Asp Arg Trp Met His Ala Val
        1100                1105                1110
Cys Gln Asn Leu Asn Thr Glu Glu Val Glu Asn Val Ala Asp
        1115                1120                1125
Ile Gly Phe Asp Cys Ser Met Cys Arg Pro Tyr Met Pro Ala Ser
        1130                1135                1140
Asn Val Pro Ser Ser Asp Cys Cys Glu Ser Ser Leu Val Ala Gln
        1145                1150                1155
Ile Val Thr Lys Val Lys Glu Leu Asp Pro Pro Lys Thr Tyr Thr
        1160                1165                1170
Gln Asp Gly Val Cys Leu Thr Glu Ser Gly Met Thr Gln Leu Gln
        1175                1180                1185
Ser Leu Thr Val Thr Val Pro Arg Arg Lys Arg Ser Lys Pro Lys
        1190                1195                1200
Leu Lys Leu Lys Ile Ile Asn Gln Asn Ser Val Ala Val Leu Gln
        1205                1210                1215
Thr Pro Pro Asp Ile Gln Ser Glu His Ser Arg Asp Gly Glu Met
        1220                1225                1230
Asp Asp Ser Arg Glu Gly Glu Leu Met Asp Cys Asp Gly Lys Ser
        1235                1240                1245
Glu Ser Ser Pro Glu Arg Glu Ala Val Asp Asp Glu Thr Lys Gly
        1250                1255                1260
Val Glu Gly Thr Asp Gly Val Lys Lys Arg Lys Arg Lys Pro Tyr
        1265                1270                1275
Arg Pro Gly Ile Gly Gly Phe Met Val Arg Gln Arg Ser Arg Thr
        1280                1285                1290
```

```
Gly Gln Gly Lys Thr Lys Arg Ser Val Ile Arg Lys Asp Ser Ser
    1295                1300                1305

Gly Ser Ile Ser Glu Gln Leu Pro Cys Arg Asp Asp Gly Trp Ser
    1310                1315                1320

Glu Gln Leu Pro Asp Thr Leu Val Asp Glu Ser Val Ser Val Thr
    1325                1330                1335

Glu Ser Thr Glu Lys Ile Lys Lys Arg Tyr Arg Lys Arg Lys Asn
    1340                1345                1350

Lys Leu Glu Glu Thr Phe Pro Ala Tyr Leu Gln Glu Ala Phe Phe
    1355                1360                1365

Gly Lys Asp Leu Leu Asp Thr Ser Arg Gln Ser Lys Ile Ser Leu
    1370                1375                1380

Asp Asn Leu Ser Glu Asp Gly Ala Gln Leu Leu Tyr Lys Thr Asn
    1385                1390                1395

Met Asn Thr Gly Phe Leu Asp Pro Ser Leu Asp Pro Leu Leu Ser
    1400                1405                1410

Ser Ser Ser Ala Pro Thr Lys Ser Gly Thr His Gly Pro Ala Asp
    1415                1420                1425

Asp Pro Leu Ala Asp Ile Ser Glu Val Leu Asn Thr Asp Asp Asp
    1430                1435                1440

Ile Leu Gly Ile Ile Ser Asp Asp Leu Ala Lys Ser Val Asp His
    1445                1450                1455

Ser Asp Ile Gly Pro Val Thr Asp Asp Pro Ser Ser Leu Pro Gln
    1460                1465                1470

Pro Asn Val Asn Gln Ser Ser Arg Pro Leu Ser Glu Glu Gln Leu
    1475                1480                1485

Asp Gly Ile Leu Ser Pro Glu Leu Asp Lys Met Val Thr Asp Gly
    1490                1495                1500

Ala Ile Leu Gly Lys Leu Tyr Lys Ile Pro Glu Leu Gly Gly Lys
    1505                1510                1515

Asp Val Glu Asp Leu Phe Thr Ala Val Leu Ser Pro Ala Asn Thr
    1520                1525                1530

Gln Pro Thr Pro Leu Pro Gln Pro Pro Pro Thr Gln Leu Leu
    1535                1540                1545

Pro Ile His Asn Gln Asp Ala Phe Ser Arg Met Pro Leu Met Asn
    1550                1555                1560

Gly Leu Ile Gly Ser Ser Pro His Leu Pro His Asn Ser Leu Pro
    1565                1570                1575

Pro Gly Ser Gly Leu Gly Thr Phe Ser Ala Ile Ala Gln Ser Ser
    1580                1585                1590

Tyr Pro Asp Ala Arg Asp Lys Asn Ser Ala Phe Asn Pro Met Ala
    1595                1600                1605

Ser Asp Pro Asn Asn Ser Trp Thr Ser Ser Ala Pro Thr Val Glu
    1610                1615                1620

Gly Glu Asn Asp Thr Met Ser Asn Ala Gln Arg Ser Thr Leu Lys
    1625                1630                1635

Trp Glu Lys Glu Glu Ala Leu Gly Glu Met Ala Thr Val Ala Pro
    1640                1645                1650

Val Leu Tyr Thr Asn Ile Asn Phe Pro Asn Leu Lys Glu Glu Phe
    1655                1660                1665

Pro Asp Trp Thr Thr Arg Val Lys Gln Ile Ala Lys Leu Trp Arg
    1670                1675                1680

Lys Ala Ser Ser Gln Glu Arg Ala Pro Tyr Val Gln Lys Ala Arg
```

```
               1685                1690                1695

Asp Asn Arg Ala Ala Leu Arg Ile Asn Lys Val Gln Met Ser Asn
    1700                1705                1710

Asp Ser Met Lys Arg Gln Gln Gln Asp Ser Ile Asp Pro Ser
    1715                1720                1725

Ser Arg Ile Asp Ser Glu Leu Phe Lys Asp Pro Leu Lys Gln Arg
    1730                1735                1740

Glu Ser Glu His Glu Gln Glu Trp Lys Phe Arg Gln Gln Met Arg
    1745                1750                1755

Gln Lys Ser Lys Gln Gln Ala Lys Ile Glu Ala Thr Gln Lys Leu
    1760                1765                1770

Glu Gln Val Lys Asn Glu Gln Gln Gln Gln Gln Gln Gln Gln Phe
    1775                1780                1785

Gly Ser Gln His Leu Leu Val Gln Ser Gly Ser Asp Thr Pro Ser
    1790                1795                1800

Ser Gly Ile Gln Ser Pro Leu Thr Pro Gln Pro Gly Asn Gly Asn
    1805                1810                1815

Met Ser Pro Ala Gln Ser Phe His Lys Glu Leu Phe Thr Lys Gln
    1820                1825                1830

Pro Pro Ser Thr Pro Thr Ser Thr Ser Ser Asp Asp Val Phe Val
    1835                1840                1845

Lys Pro Gln Ala Pro Pro Pro Pro Ala Pro Ser Arg Ile Pro
    1850                1855                1860

Ile Gln Asp Ser Leu Ser Gln Ala Gln Thr Ser Gln Pro Pro Ser
    1865                1870                1875

Pro Gln Val Phe Ser Pro Gly Ser Ser Asn Ser Arg Pro Pro Ser
    1880                1885                1890

Pro Met Asp Pro Tyr Ala Lys Met Val Gly Thr Pro Arg Pro Pro
    1895                1900                1905

Pro Val Gly His Ser Phe Ser Arg Arg Asn Ser Ala Ala Pro Val
    1910                1915                1920

Glu Asn Cys Thr Pro Leu Ser Ser Val Ser Arg Pro Leu Gln Met
    1925                1930                1935

Asn Glu Thr Thr Ala Asn Arg Pro Ser Pro Val Arg Asp Leu Cys
    1940                1945                1950

Ser Ser Ser Thr Thr Asn Asn Asp Pro Tyr Ala Lys Pro Pro Asp
    1955                1960                1965

Thr Pro Arg Pro Val Met Thr Asp Gln Phe Pro Lys Ser Leu Gly
    1970                1975                1980

Leu Ser Arg Ser Pro Val Val Ser Glu Gln Thr Ala Lys Gly Pro
    1985                1990                1995

Ile Ala Ala Gly Thr Ser Asp His Phe Thr Lys Pro Ser Pro Arg
    2000                2005                2010

Ala Asp Val Phe Gln Arg Gln Arg Ile Pro Asp Ser Tyr Ala Arg
    2015                2020                2025

Pro Leu Leu Thr Pro Ala Pro Leu Asp Ser Gly Pro Gly Pro Phe
    2030                2035                2040

Lys Thr Pro Met Gln Pro Pro Ser Ser Gln Asp Pro Tyr Gly
    2045                2050                2055

Ser Val Ser Gln Ala Ser Arg Arg Leu Ser Val Asp Pro Tyr Glu
    2060                2065                2070

Arg Pro Ala Leu Thr Pro Arg Pro Ile Asp Asn Phe Ser His Asn
    2075                2080                2085
```

```
Gln Ser Asn Asp Pro Tyr Ser Gln Pro Pro Leu Thr Pro His Pro
    2090            2095            2100

Ala Val Asn Glu Ser Phe Ala His Pro Ser Arg Ala Phe Ser Gln
    2105            2110            2115

Pro Gly Thr Ile Ser Arg Pro Thr Ser Gln Asp Pro Tyr Ser Gln
    2120            2125            2130

Pro Pro Gly Thr Pro Arg Pro Val Val Asp Ser Tyr Ser Gln Ser
    2135            2140            2145

Ser Gly Thr Ala Arg Ser Asn Thr Asp Pro Tyr Ser Gln Pro Pro
    2150            2155            2160

Gly Thr Pro Arg Pro Thr Thr Val Asp Pro Tyr Ser Gln Gln Pro
    2165            2170            2175

Gln Thr Pro Arg Pro Ser Thr Gln Thr Asp Leu Phe Val Thr Pro
    2180            2185            2190

Val Thr Asn Gln Arg His Ser Asp Pro Tyr Ala His Pro Pro Gly
    2195            2200            2205

Thr Pro Arg Pro Gly Ile Ser Val Pro Tyr Ser Gln Pro Pro Ala
    2210            2215            2220

Thr Pro Arg Pro Arg Ile Ser Glu Gly Phe Thr Arg Ser Ser Met
    2225            2230            2235

Thr Arg Pro Val Leu Met Pro Asn Gln Asp Pro Phe Leu Gln Ala
    2240            2245            2250

Ala Gln Asn Arg Gly Pro Ala Leu Pro Gly Pro Leu Val Arg Pro
    2255            2260            2265

Pro Asp Thr Cys Ser Gln Thr Pro Arg Pro Pro Gly Pro Gly Leu
    2270            2275            2280

Ser Asp Thr Phe Ser Arg Val Ser Pro Ser Ala Ala Arg Asp Pro
    2285            2290            2295

Tyr Asp Gln Ser Pro Met Thr Pro Arg Ser Gln Ser Asp Ser Phe
    2300            2305            2310

Gly Thr Ser Gln Thr Ala His Asp Val Ala Asp Gln Pro Arg Pro
    2315            2320            2325

Gly Ser Glu Gly Ser Phe Cys Ala Ser Ser Asn Ser Pro Met His
    2330            2335            2340

Ser Gln Gly Gln Gln Phe Ser Gly Val Ser Gln Leu Pro Gly Pro
    2345            2350            2355

Val Pro Thr Ser Gly Val Thr Asp Thr Gln Asn Thr Val Asn Met
    2360            2365            2370

Ala Gln Ala Asp Thr Glu Lys Leu Arg Gln Arg Gln Lys Leu Arg
    2375            2380            2385

Glu Ile Ile Leu Gln Gln Gln Gln Lys Lys Ile Ala Gly Arg
    2390            2395            2400

Gln Glu Lys Gly Ser Gln Asp Ser Pro Ala Val Pro His Pro Gly
    2405            2410            2415

Pro Leu Gln His Trp Gln Pro Glu Asn Val Asn Gln Ala Phe Thr
    2420            2425            2430

Arg Pro Pro Pro Pro Tyr Pro Gly Asn Ile Arg Ser Pro Val Ala
    2435            2440            2445

Pro Pro Leu Gly Pro Arg Tyr Ala Val Phe Pro Lys Asp Gln Arg
    2450            2455            2460

Gly Pro Tyr Pro Pro Asp Val Ala Ser Met Gly Met Arg Pro His
    2465            2470            2475
```

```
Gly Phe Arg Phe Gly Phe Pro Gly Gly Ser His Gly Thr Met Pro
    2480            2485                2490

Ser Gln Glu Arg Phe Leu Val Pro Pro Gln Gln Ile Gln Gly Ser
    2495            2500                2505

Gly Val Ser Pro Gln Leu Arg Arg Ser Val Ser Val Asp Met Pro
    2510            2515                2520

Arg Pro Leu Asn Asn Ser Gln Met Asn Asn Pro Val Gly Leu Pro
    2525            2530                2535

Gln His Phe Ser Pro Gln Ser Leu Pro Val Gln Gln His Asn Ile
    2540            2545                2550

Leu Gly Gln Ala Tyr Ile Glu Leu Arg His Arg Ala Pro Asp Gly
    2555            2560                2565

Arg Gln Arg Leu Pro Phe Ser Ala Pro Pro Gly Ser Val Val Glu
    2570            2575                2580

Ala Ser Ser Asn Leu Arg His Gly Asn Phe Ile Pro Arg Pro Asp
    2585            2590                2595

Phe Pro Gly Pro Arg His Thr Asp Pro Met Arg Arg Pro Pro Gln
    2600            2605                2610

Gly Leu Pro Asn Gln Leu Pro Val His Pro Asp Leu Glu Gln Val
    2615            2620                2625

Pro Pro Ser Gln Gln Glu Gln Gly His Ser Val His Ser Ser Ser
    2630            2635                2640

Met Val Met Arg Thr Leu Asn His Pro Leu Gly Gly Glu Phe Ser
    2645            2650                2655

Glu Ala Pro Leu Ser Thr Ser Val Pro Ser Glu Thr Thr Ser Asp
    2660            2665                2670

Asn Leu Gln Ile Thr Thr Gln Pro Ser Asp Gly Leu Glu Glu Lys
    2675            2680                2685

Leu Asp Ser Asp Asp Pro Ser Val Lys Glu Leu Asp Val Lys Asp
    2690            2695                2700

Leu Glu Gly Val Glu Val Lys Asp Leu Asp Asp Glu Asp Leu Glu
    2705            2710                2715

Asn Leu Asn Leu Asp Thr Glu Asp Gly Lys Val Val Glu Leu Asp
    2720            2725                2730

Thr Leu Asp Asn Leu Glu Thr Asn Asp Pro Asn Leu Asp Asp Leu
    2735            2740                2745

Leu Arg Ser Gly Glu Phe Asp Ile Ile Ala Tyr Thr Asp Pro Glu
    2750            2755                2760

Leu Asp Met Gly Asp Lys Lys Ser Met Phe Asn Glu Glu Leu Asp
    2765            2770                2775

Leu Pro Ile Asp Asp Lys Leu Asp Asn Gln Cys Val Ser Val Glu
    2780            2785                2790

Pro Lys Lys Lys Glu Gln Glu Asn Lys Thr Leu Val Leu Ser Asp
    2795            2800                2805

Lys His Ser Pro Gln Lys Lys Ser Thr Val Thr Asn Glu Val Lys
    2810            2815                2820

Thr Glu Val Leu Ser Pro Asn Ser Lys Val Glu Ser Lys Cys Glu
    2825            2830                2835

Thr Glu Lys Asn Asp Glu Asn Lys Asp Asn Val Asp Thr Pro Cys
    2840            2845                2850

Ser Gln Ala Ser Ala His Ser Asp Leu Asn Asp Gly Glu Lys Thr
    2855            2860                2865

Ser Leu His Pro Cys Asp Pro Asp Leu Phe Glu Lys Arg Thr Asn
```

-continued

```
                2870                2875                2880

Arg Glu Thr Ala Pro Ser Ala Asn Val Ile Gln Ala Ser Thr
            2885                2890                2895

Gln Leu Pro Ala Gln Asp Val Ile Asn Ser Cys Gly Ile Thr Gly
            2900                2905                2910

Ser Thr Pro Val Leu Ser Ser Leu Leu Ala Asn Glu Lys Ser Asp
            2915                2920                2925

Asn Ser Asp Ile Arg Pro Ser Gly Ser Pro Pro Pro Thr Leu
            2930                2935                2940

Pro Ala Ser Pro Ser Asn His Val Ser Ser Leu Pro Pro Phe Ile
            2945                2950                2955

Ala Pro Pro Gly Arg Val Leu Asp Asn Ala Met Asn Ser Asn Val
            2960                2965                2970

Thr Val Val Ser Arg Val Asn His Val Phe Ser Gln Gly Val Gln
            2975                2980                2985

Val Asn Pro Gly Leu Ile Pro Gly Gln Ser Thr Val Asn His Ser
            2990                2995                3000

Leu Gly Thr Gly Lys Pro Ala Thr Gln Thr Gly Pro Gln Thr Ser
            3005                3010                3015

Gln Ser Gly Thr Ser Ser Met Ser Gly Pro Gln Gln Leu Met Ile
            3020                3025                3030

Pro Gln Thr Leu Ala Gln Gln Asn Arg Glu Arg Pro Leu Leu Leu
            3035                3040                3045

Glu Glu Gln Pro Leu Leu Leu Gln Asp Leu Leu Asp Gln Glu Arg
            3050                3055                3060

Gln Glu Gln Gln Gln Gln Arg Gln Met Gln Ala Met Ile Arg Gln
            3065                3070                3075

Arg Ser Glu Pro Phe Phe Pro Asn Ile Asp Phe Asp Ala Ile Thr
            3080                3085                3090

Asp Pro Ile Met Lys Ala Lys Met Val Ala Leu Lys Gly Ile Asn
            3095                3100                3105

Lys Val Met Ala Gln Asn Asn Leu Gly Met Pro Pro Met Val Met
            3110                3115                3120

Ser Arg Phe Pro Phe Met Gly Gln Val Val Thr Gly Thr Gln Asn
            3125                3130                3135

Ser Glu Gly Gln Asn Leu Gly Pro Gln Ala Ile Pro Gln Asp Gly
            3140                3145                3150

Ser Ile Thr His Gln Ile Ser Arg Pro Asn Pro Asn Phe Gly
            3155                3160                3165

Pro Gly Phe Val Asn Asp Ser Gln Arg Lys Gln Tyr Glu Glu Trp
            3170                3175                3180

Leu Gln Glu Thr Gln Gln Leu Leu Gln Met Gln Gln Lys Tyr Leu
            3185                3190                3195

Glu Glu Gln Ile Gly Ala His Arg Lys Ser Lys Lys Ala Leu Ser
            3200                3205                3210

Ala Lys Gln Arg Thr Ala Lys Lys Ala Gly Arg Glu Phe Pro Glu
            3215                3220                3225

Glu Asp Ala Glu Gln Leu Lys His Val Thr Glu Gln Gln Ser Met
            3230                3235                3240

Val Gln Lys Gln Leu Glu Gln Ile Arg Lys Gln Gln Lys Glu His
            3245                3250                3255

Ala Glu Leu Ile Glu Asp Tyr Arg Ile Lys Gln Gln Gln Gln Cys
            3260                3265                3270
```

```
Ala Met Ala Pro Pro Thr Met Met Pro Ser Val Gln Pro Gln Pro
    3275                3280                3285

Pro Leu Ile Pro Gly Ala Thr Pro Pro Thr Met Ser Gln Pro Thr
    3290                3295                3300

Phe Pro Met Val Pro Gln Gln Leu Gln His Gln Gln His Thr Thr
    3305                3310                3315

Val Ile Ser Gly His Thr Ser Pro Val Arg Met Pro Ser Leu Pro
    3320                3325                3330

Gly Trp Gln Pro Asn Ser Ala Pro Ala His Leu Pro Leu Asn Pro
    3335                3340                3345

Pro Arg Ile Gln Pro Pro Ile Ala Gln Leu Pro Ile Lys Thr Cys
    3350                3355                3360

Thr Pro Ala Pro Gly Thr Val Ser Asn Ala Asn Pro Gln Ser Gly
    3365                3370                3375

Pro Pro Pro Arg Val Glu Phe Asp Asp Asn Asn Pro Phe Ser Glu
    3380                3385                3390

Ser Phe Gln Glu Arg Glu Arg Lys Glu Arg Leu Arg Glu Gln Gln
    3395                3400                3405

Glu Arg Gln Arg Ile Gln Leu Met Gln Glu Val Asp Arg Gln Arg
    3410                3415                3420

Ala Leu Gln Gln Arg Met Glu Met Glu Gln His Gly Met Val Gly
    3425                3430                3435

Ser Glu Ile Ser Ser Ser Arg Thr Ser Val Ser Gln Ile Pro Phe
    3440                3445                3450

Tyr Ser Ser Asp Leu Pro Cys Asp Phe Met Gln Pro Leu Gly Pro
    3455                3460                3465

Leu Gln Gln Ser Pro Gln His Gln Gln Gln Met Gly Gln Val Leu
    3470                3475                3480

Gln Gln Gln Asn Ile Gln Gln Gly Ser Ile Asn Ser Pro Ser Thr
    3485                3490                3495

Gln Thr Phe Met Gln Thr Asn Glu Arg Arg Gln Val Gly Pro Pro
    3500                3505                3510

Ser Phe Val Pro Asp Ser Pro Ser Ile Pro Val Gly Ser Pro Asn
    3515                3520                3525

Phe Ser Ser Val Lys Gln Gly His Gly Asn Leu Ser Gly Thr Ser
    3530                3535                3540

Phe Gln Gln Ser Pro Val Arg Pro Ser Phe Thr Pro Ala Leu Pro
    3545                3550                3555

Ala Ala Pro Pro Val Ala Asn Ser Ser Leu Pro Cys Gly Gln Asp
    3560                3565                3570

Ser Thr Ile Thr His Gly Ser Tyr Pro Gly Ser Thr Gln Ser
    3575                3580                3585

Leu Ile Gln Leu Tyr Ser Asp Ile Ile Pro Glu Glu Lys Gly Lys
    3590                3595                3600

Lys Lys Arg Thr Arg Lys Lys Arg Asp Asp Asp Ala Glu Ser
    3605                3610                3615

Thr Lys Ala Pro Ser Thr Pro His Ser Asp Ile Thr Ala Pro Pro
    3620                3625                3630

Thr Pro Gly Ile Ser Glu Thr Thr Ser Thr Pro Ala Val Ser Thr
    3635                3640                3645

Pro Ser Glu Leu Pro Gln Gln Ala Asp Gln Glu Ser Val Glu Pro
    3650                3655                3660
```

```
Val Gly Pro Ser Thr Pro Asn Met Ala Ala Gly Gln Leu Cys Thr
    3665            3670                3675

Glu Leu Glu Asn Lys Leu Pro Asn Ser Asp Phe Ser Gln Ala Thr
    3680            3685                3690

Pro Asn Gln Gln Thr Tyr Ala Asn Ser Glu Val Asp Lys Leu Ser
    3695            3700                3705

Met Glu Thr Pro Ala Lys Thr Glu Glu Ile Lys Leu Glu Lys Ala
    3710            3715                3720

Glu Thr Glu Ser Cys Pro Gly Gln Glu Glu Pro Lys Leu Glu Glu
    3725            3730                3735

Gln Asn Gly Ser Lys Val Glu Gly Asn Ala Val Ala Cys Pro Val
    3740            3745                3750

Ser Ser Ala Gln Ser Pro Pro His Ser Ala Gly Ala Pro Ala Ala
    3755            3760                3765

Lys Gly Asp Ser Gly Asn Glu Leu Leu Lys His Leu Leu Lys Asn
    3770            3775                3780

Lys Lys Ser Ser Ser Leu Leu Asn Gln Lys Pro Glu Gly Ser Ile
    3785            3790                3795

Cys Ser Glu Asp Asp Cys Thr Lys Asp Asn Lys Leu Val Glu Lys
    3800            3805                3810

Gln Asn Pro Ala Glu Gly Leu Gln Thr Leu Gly Ala Gln Met Gln
    3815            3820                3825

Gly Gly Phe Gly Cys Gly Asn Gln Leu Pro Lys Thr Asp Gly Gly
    3830            3835                3840

Ser Glu Thr Lys Lys Gln Arg Ser Lys Arg Thr Gln Arg Thr Gly
    3845            3850                3855

Glu Lys Ala Ala Pro Arg Ser Lys Lys Arg Lys Lys Asp Glu Glu
    3860            3865                3870

Glu Lys Gln Ala Met Tyr Ser Ser Thr Asp Thr Phe Thr His Leu
    3875            3880                3885

Lys Gln Gln Asn Asn Leu Ser Asn Pro Pro Thr Pro Pro Ala Ser
    3890            3895                3900

Leu Pro Pro Thr Pro Pro Met Ala Cys Gln Lys Met Ala Asn
    3905            3910                3915

Gly Phe Ala Thr Thr Glu Glu Leu Ala Gly Lys Ala Gly Val Leu
    3920            3925                3930

Val Ser His Glu Val Thr Lys Thr Leu Gly Pro Lys Pro Phe Gln
    3935            3940                3945

Leu Pro Phe Arg Pro Gln Asp Asp Leu Leu Ala Arg Ala Leu Ala
    3950            3955                3960

Gln Gly Pro Lys Thr Val Asp Val Pro Ala Ser Leu Pro Thr Pro
    3965            3970                3975

Pro His Asn Asn Gln Glu Glu Leu Arg Ile Gln Asp His Cys Gly
    3980            3985                3990

Asp Arg Asp Thr Pro Asp Ser Phe Val Pro Ser Ser Ser Pro Glu
    3995            4000                4005

Ser Val Val Gly Val Glu Val Ser Arg Tyr Pro Asp Leu Ser Leu
    4010            4015                4020

Val Lys Glu Glu Pro Pro Glu Pro Val Pro Ser Pro Ile Ile Pro
    4025            4030                4035

Ile Leu Pro Ser Thr Ala Gly Lys Ser Ser Glu Ser Arg Arg Asn
    4040            4045                4050

Asp Ile Lys Thr Glu Pro Gly Thr Leu Tyr Phe Ala Ser Pro Phe
```

```
          4055                4060                4065
Gly Pro Ser Pro Asn Gly Pro Arg Ser Gly Leu Ile Ser Val Ala
          4070                4075                4080
Ile Thr Leu His Pro Thr Ala Ala Glu Asn Ile Ser Ser Val Val
          4085                4090                4095
Ala Ala Phe Ser Asp Leu Leu His Val Arg Ile Pro Asn Ser Tyr
          4100                4105                4110
Glu Val Ser Ser Ala Pro Asp Val Pro Ser Met Gly Leu Val Ser
          4115                4120                4125
Ser His Arg Ile Asn Pro Gly Leu Glu Tyr Arg Gln His Leu Leu
          4130                4135                4140
Leu Arg Gly Pro Pro Pro Gly Ser Ala Asn Pro Pro Arg Leu Val
          4145                4150                4155
Ser Ser Tyr Arg Leu Lys Gln Pro Asn Val Pro Phe Pro Pro Thr
          4160                4165                4170
Ser Asn Gly Leu Ser Gly Tyr Lys Asp Ser Ser His Gly Ile Ala
          4175                4180                4185
Glu Ser Ala Ala Leu Arg Pro Gln Trp Cys Cys His Cys Lys Val
          4190                4195                4200
Val Ile Leu Gly Ser Gly Val Arg Lys Ser Phe Lys Asp Leu Thr
          4205                4210                4215
Leu Leu Asn Lys Asp Ser Arg Glu Ser Thr Lys Arg Val Glu Lys
          4220                4225                4230
Asp Ile Val Phe Cys Ser Asn Asn Cys Phe Ile Leu Tyr Ser Ser
          4235                4240                4245
Thr Ala Gln Ala Lys Asn Ser Glu Asn Lys Glu Ser Ile Pro Ser
          4250                4255                4260
Leu Pro Gln Ser Pro Met Arg Glu Thr Pro Ser Lys Ala Phe His
          4265                4270                4275
Gln Tyr Ser Asn Asn Ile Ser Thr Leu Asp Val His Cys Leu Pro
          4280                4285                4290
Gln Leu Pro Glu Lys Ala Ser Pro Pro Ala Ser Pro Pro Ile Ala
          4295                4300                4305
Phe Pro Pro Ala Phe Glu Ala Ala Gln Val Glu Ala Lys Pro Asp
          4310                4315                4320
Glu Leu Lys Val Thr Val Lys Leu Lys Pro Arg Leu Arg Ala Val
          4325                4330                4335
His Gly Gly Phe Glu Asp Cys Arg Pro Leu Asn Lys Lys Trp Arg
          4340                4345                4350
Gly Met Lys Trp Lys Lys Trp Ser Ile His Ile Val Ile Pro Lys
          4355                4360                4365
Gly Thr Phe Lys Pro Pro Cys Glu Asp Glu Ile Asp Glu Phe Leu
          4370                4375                4380
Lys Lys Leu Gly Thr Ser Leu Lys Pro Asp Pro Val Pro Lys Asp
          4385                4390                4395
Tyr Arg Lys Cys Cys Phe Cys His Glu Glu Gly Asp Gly Leu Thr
          4400                4405                4410
Asp Gly Pro Ala Arg Leu Leu Asn Leu Asp Leu Asp Leu Trp Val
          4415                4420                4425
His Leu Asn Cys Ala Leu Trp Ser Thr Glu Val Tyr Glu Thr Gln
          4430                4435                4440
Ala Gly Ala Leu Ile Asn Val Glu Leu Ala Leu Arg Arg Gly Leu
          4445                4450                4455
```

-continued

```
Gln Met Lys Cys Val Phe Cys His Lys Thr Gly Ala Thr Ser Gly
    4460            4465                4470

Cys His Arg Phe Arg Cys Thr Asn Ile Tyr His Phe Thr Cys Ala
    4475            4480                4485

Ile Lys Ala Gln Cys Met Phe Phe Lys Asp Lys Thr Met Leu Cys
    4490            4495                4500

Pro Met His Lys Pro Lys Gly Ile His Glu Gln Glu Leu Ser Tyr
    4505            4510                4515

Phe Ala Val Phe Arg Arg Val Tyr Val Gln Arg Asp Glu Val Arg
    4520            4525                4530

Gln Ile Ala Ser Ile Val Gln Arg Gly Glu Arg Asp His Thr Phe
    4535            4540                4545

Arg Val Gly Ser Leu Ile Phe His Thr Ile Gly Gln Leu Leu Pro
    4550            4555                4560

Gln Gln Met Gln Ala Phe His Ser Pro Lys Ala Leu Phe Pro Val
    4565            4570                4575

Gly Tyr Glu Ala Ser Arg Leu Tyr Trp Ser Thr Arg Tyr Ala Asn
    4580            4585                4590

Arg Arg Cys Arg Tyr Leu Cys Ser Ile Glu Glu Lys Asp Gly Arg
    4595            4600                4605

Pro Val Phe Val Ile Arg Ile Val Glu Gln Gly His Glu Asp Leu
    4610            4615                4620

Val Leu Ser Asp Ile Ser Pro Lys Gly Val Trp Asp Lys Ile Leu
    4625            4630                4635

Glu Pro Val Ala Cys Val Arg Lys Lys Ser Glu Met Leu Gln Leu
    4640            4645                4650

Phe Pro Ala Tyr Leu Lys Gly Glu Asp Leu Phe Gly Leu Thr Val
    4655            4660                4665

Ser Ala Val Ala Arg Ile Ala Glu Ser Leu Pro Gly Val Glu Ala
    4670            4675                4680

Cys Glu Asn Tyr Thr Phe Arg Tyr Gly Arg Asn Pro Leu Met Glu
    4685            4690                4695

Leu Pro Leu Ala Val Asn Pro Thr Gly Cys Ala Arg Ser Glu Pro
    4700            4705                4710

Lys Met Ser Ala His Val Lys Arg Phe Val Leu Arg Pro His Thr
    4715            4720                4725

Leu Asn Ser Thr Ser Thr Ser Lys Ser Phe Gln Ser Thr Val Thr
    4730            4735                4740

Gly Glu Leu Asn Ala Pro Tyr Ser Lys Gln Phe Val His Ser Lys
    4745            4750                4755

Ser Ser Gln Tyr Arg Lys Met Lys Thr Glu Trp Lys Ser Asn Val
    4760            4765                4770

Tyr Leu Ala Arg Ser Arg Ile Gln Gly Leu Gly Leu Tyr Ala Ala
    4775            4780                4785

Arg Asp Ile Glu Lys His Thr Met Val Ile Glu Tyr Ile Gly Thr
    4790            4795                4800

Ile Ile Arg Asn Glu Val Ala Asn Arg Lys Glu Lys Leu Tyr Glu
    4805            4810                4815

Ser Gln Asn Arg Gly Val Tyr Met Phe Arg Met Asp Asn Asp His
    4820            4825                4830

Val Ile Asp Ala Thr Leu Thr Gly Gly Pro Ala Arg Tyr Ile Asn
    4835            4840                4845
```

His Ser Cys Ala Pro Asn Cys Val Ala Glu Val Val Thr Phe Glu
    4850            4855                4860

Arg Gly His Lys Ile Ile Ile Ser Ser Ser Arg Arg Ile Gln Lys
    4865            4870                4875

Gly Glu Glu Leu Cys Tyr Asp Tyr Lys Phe Asp Phe Glu Asp Asp
    4880            4885                4890

Gln His Lys Ile Pro Cys His Cys Gly Ala Val Asn Cys Arg Lys
    4895            4900                4905

Trp Met Asn
    4910

<210> SEQ ID NO 48
<211> LENGTH: 4025
<212> TYPE: PRT
<213> ORGANISM: Homo sapiens

<400> SEQUENCE: 48

Met His Asn Thr Val Val Leu Phe Ser Ser Asp Lys Phe Thr Leu
1               5                   10                  15

Asn Gln Asp Met Cys Val Val Cys Gly Ser Phe Gly Gln Gly Ala Glu
                20                  25                  30

Gly Arg Leu Leu Ala Cys Ser Gln Cys Gly Gln Cys Tyr His Pro Tyr
                35                  40                  45

Cys Val Ser Ile Lys Ile Thr Lys Val Val Leu Ser Lys Gly Trp Arg
50                  55                  60

Cys Leu Glu Cys Thr Val Cys Glu Ala Cys Gly Lys Ala Thr Asp Pro
65                  70                  75                  80

Gly Arg Leu Leu Leu Cys Asp Asp Cys Asp Ile Ser Tyr His Thr Tyr
                85                  90                  95

Cys Leu Asp Pro Pro Leu Gln Thr Val Pro Lys Gly Gly Trp Lys Cys
                100                 105                 110

Lys Trp Cys Val Trp Cys Arg His Cys Gly Ala Thr Ser Ala Gly Leu
                115                 120                 125

Arg Cys Glu Trp Gln Asn Asn Tyr Thr Gln Cys Ala Pro Cys Ala Ser
    130                 135                 140

Leu Ser Ser Cys Pro Val Cys Tyr Arg Asn Tyr Arg Glu Glu Asp Leu
145                 150                 155                 160

Ile Leu Gln Cys Arg Gln Cys Asp Arg Trp Met His Ala Val Cys Gln
                165                 170                 175

Asn Leu Asn Thr Glu Glu Glu Val Glu Asn Val Ala Asp Ile Gly Phe
                180                 185                 190

Asp Cys Ser Met Cys Arg Pro Tyr Met Pro Ala Ser Asn Val Pro Ser
                195                 200                 205

Ser Asp Cys Cys Glu Ser Ser Leu Val Ala Gln Ile Val Thr Lys Val
    210                 215                 220

Lys Glu Leu Asp Pro Pro Lys Thr Tyr Thr Gln Asp Gly Val Cys Leu
225                 230                 235                 240

Thr Glu Ser Gly Met Thr Gln Leu Gln Ser Leu Thr Val Thr Val Pro
                245                 250                 255

Arg Arg Lys Arg Ser Lys Pro Lys Leu Lys Leu Lys Ile Ile Asn Gln
                260                 265                 270

Asn Ser Val Ala Val Leu Gln Thr Pro Pro Asp Ile Gln Ser Glu His
                275                 280                 285

Ser Arg Asp Gly Glu Met Asp Asp Ser Arg Glu Gly Glu Leu Met Asp
    290                 295                 300

```
Cys Asp Gly Lys Ser Glu Ser Ser Pro Glu Arg Glu Ala Val Asp Asp
305                 310                 315                 320

Glu Thr Lys Gly Val Glu Gly Thr Asp Gly Val Lys Arg Lys Arg
            325                 330                 335

Lys Pro Tyr Arg Pro Gly Ile Gly Gly Phe Met Val Arg Gln Arg Ser
            340                 345                 350

Arg Thr Gly Gln Gly Lys Thr Lys Arg Ser Val Ile Arg Lys Asp Ser
                355                 360                 365

Ser Gly Ser Ile Ser Glu Gln Leu Pro Cys Arg Asp Asp Gly Trp Ser
            370                 375                 380

Glu Gln Leu Pro Asp Thr Leu Val Asp Glu Ser Val Ser Val Thr Glu
385                 390                 395                 400

Ser Thr Glu Lys Ile Lys Lys Arg Tyr Arg Lys Arg Lys Asn Lys Leu
                405                 410                 415

Glu Glu Thr Phe Pro Ala Tyr Leu Gln Glu Ala Phe Phe Gly Lys Asp
                420                 425                 430

Leu Leu Asp Thr Ser Arg Gln Ser Lys Ile Ser Leu Asp Asn Leu Ser
            435                 440                 445

Glu Asp Gly Ala Gln Leu Leu Tyr Lys Thr Asn Met Asn Thr Gly Phe
450                 455                 460

Leu Asp Pro Ser Leu Asp Pro Leu Leu Ser Ser Ser Ala Pro Thr
465                 470                 475                 480

Lys Ser Gly Thr His Gly Pro Ala Asp Asp Pro Leu Ala Asp Ile Ser
            485                 490                 495

Glu Val Leu Asn Thr Asp Asp Ile Leu Gly Ile Ser Asp Asp
                500                 505                 510

Leu Ala Lys Ser Val Asp His Ser Asp Ile Gly Pro Val Thr Asp Asp
            515                 520                 525

Pro Ser Ser Leu Pro Gln Pro Asn Val Asn Gln Ser Ser Arg Pro Leu
            530                 535                 540

Ser Glu Glu Gln Leu Asp Gly Ile Leu Ser Pro Glu Leu Asp Lys Met
545                 550                 555                 560

Val Thr Asp Gly Ala Ile Leu Gly Lys Leu Tyr Lys Ile Pro Glu Leu
                565                 570                 575

Gly Gly Lys Asp Val Glu Asp Leu Phe Thr Ala Val Leu Ser Pro Ala
            580                 585                 590

Asn Thr Gln Pro Thr Pro Leu Pro Gln Pro Pro Pro Thr Gln Leu
            595                 600                 605

Leu Pro Ile His Asn Gln Asp Ala Phe Ser Arg Met Pro Leu Met Asn
            610                 615                 620

Gly Leu Ile Gly Ser Ser Pro His Leu Pro His Asn Ser Leu Pro Pro
625                 630                 635                 640

Gly Ser Gly Leu Gly Thr Phe Ser Ala Ile Ala Gln Ser Ser Tyr Pro
                645                 650                 655

Asp Ala Arg Asp Lys Asn Ser Ala Phe Asn Pro Met Ala Ser Asp Pro
            660                 665                 670

Asn Asn Ser Trp Thr Ser Ser Ala Pro Thr Val Glu Gly Glu Asn Asp
            675                 680                 685

Thr Met Ser Asn Ala Gln Arg Ser Thr Leu Lys Trp Glu Lys Glu Glu
            690                 695                 700

Ala Leu Gly Glu Met Ala Thr Val Ala Pro Val Leu Tyr Thr Asn Ile
705                 710                 715                 720
```

-continued

Asn Phe Pro Asn Leu Lys Glu Glu Phe Pro Asp Trp Thr Thr Arg Val
                725                 730                 735

Lys Gln Ile Ala Lys Leu Trp Arg Lys Ala Ser Ser Gln Glu Arg Ala
                740                 745                 750

Pro Tyr Val Gln Lys Ala Arg Asp Asn Arg Ala Ala Leu Arg Ile Asn
                755                 760                 765

Lys Val Gln Met Ser Asn Asp Ser Met Lys Arg Gln Gln Gln Gln Asp
                770                 775                 780

Ser Ile Asp Pro Ser Ser Arg Ile Asp Ser Glu Leu Phe Lys Asp Pro
785                 790                 795                 800

Leu Lys Gln Arg Glu Ser Glu His Glu Gln Glu Trp Lys Phe Arg Gln
                805                 810                 815

Gln Met Arg Gln Lys Ser Lys Gln Gln Ala Lys Ile Glu Ala Thr Gln
                820                 825                 830

Lys Leu Glu Gln Val Lys Asn Glu Gln Gln Gln Gln Gln Gln Gln Gln
                835                 840                 845

Phe Gly Ser Gln His Leu Leu Val Gln Ser Gly Ser Asp Thr Pro Ser
                850                 855                 860

Ser Gly Ile Gln Ser Pro Leu Thr Pro Gln Pro Gly Asn Gly Asn Met
865                 870                 875                 880

Ser Pro Ala Gln Ser Phe His Lys Glu Leu Phe Thr Lys Gln Pro Pro
                885                 890                 895

Ser Thr Pro Thr Ser Thr Ser Ser Asp Asp Val Phe Val Lys Pro Gln
                900                 905                 910

Ala Pro Pro Pro Pro Ala Pro Ser Arg Ile Pro Ile Gln Asp Ser
                915                 920                 925

Leu Ser Gln Ala Gln Thr Ser Gln Pro Pro Ser Pro Gln Val Phe Ser
                930                 935                 940

Pro Gly Ser Ser Asn Ser Arg Pro Pro Ser Pro Met Asp Pro Tyr Ala
945                 950                 955                 960

Lys Met Val Gly Thr Pro Arg Pro Pro Pro Val Gly His Ser Phe Ser
                965                 970                 975

Arg Arg Asn Ser Ala Ala Pro Val Glu Asn Cys Thr Pro Leu Ser Ser
                980                 985                 990

Val Ser Arg Pro Leu Gln Met Asn Glu Thr Thr Ala Asn Arg Pro Ser
                995                1000                1005

Pro Val Arg Asp Leu Cys Ser Ser Ser Thr Thr Asn Asn Asp Pro
                1010                1015                1020

Tyr Ala Lys Pro Pro Asp Thr Pro Arg Pro Val Met Thr Asp Gln
                1025                1030                1035

Phe Pro Lys Ser Leu Gly Leu Ser Arg Ser Pro Val Val Ser Glu
                1040                1045                1050

Gln Thr Ala Lys Gly Pro Ile Ala Ala Gly Thr Ser Asp His Phe
                1055                1060                1065

Thr Lys Pro Ser Pro Arg Ala Asp Val Phe Gln Arg Gln Arg Ile
                1070                1075                1080

Pro Asp Ser Tyr Ala Arg Pro Leu Leu Thr Pro Ala Pro Leu Asp
                1085                1090                1095

Ser Gly Pro Gly Pro Phe Lys Thr Pro Met Gln Pro Pro Pro Ser
                1100                1105                1110

Ser Gln Asp Pro Tyr Gly Ser Val Ser Gln Ala Ser Arg Arg Leu
                1115                1120                1125

Ser Val Asp Pro Tyr Glu Arg Pro Ala Leu Thr Pro Arg Pro Ile

```
                1130              1135              1140

Asp Asn Phe Ser His Asn Gln Ser Asn Asp Pro Tyr Ser Gln Pro
        1145              1150              1155

Pro Leu Thr Pro His Pro Ala Val Asn Glu Ser Phe Ala His Pro
        1160              1165              1170

Ser Arg Ala Phe Ser Gln Pro Gly Thr Ile Ser Arg Pro Thr Ser
        1175              1180              1185

Gln Asp Pro Tyr Ser Gln Pro Pro Gly Thr Pro Arg Pro Val Val
        1190              1195              1200

Asp Ser Tyr Ser Gln Ser Ser Gly Thr Ala Arg Ser Asn Thr Asp
        1205              1210              1215

Pro Tyr Ser Gln Pro Pro Gly Thr Pro Arg Pro Thr Thr Val Asp
        1220              1225              1230

Pro Tyr Ser Gln Gln Pro Gln Thr Pro Arg Pro Ser Thr Gln Thr
        1235              1240              1245

Asp Leu Phe Val Thr Pro Val Thr Asn Gln Arg His Ser Asp Pro
        1250              1255              1260

Tyr Ala His Pro Pro Gly Thr Pro Arg Pro Gly Ile Ser Val Pro
        1265              1270              1275

Tyr Ser Gln Pro Pro Ala Thr Pro Arg Pro Arg Ile Ser Glu Gly
        1280              1285              1290

Phe Thr Arg Ser Ser Met Thr Arg Pro Val Leu Met Pro Asn Gln
        1295              1300              1305

Asp Pro Phe Leu Gln Ala Ala Gln Asn Arg Gly Pro Ala Leu Pro
        1310              1315              1320

Gly Pro Leu Val Arg Pro Pro Asp Thr Cys Ser Gln Thr Pro Arg
        1325              1330              1335

Pro Pro Gly Pro Gly Leu Ser Asp Thr Phe Ser Arg Val Ser Pro
        1340              1345              1350

Ser Ala Ala Arg Asp Pro Tyr Asp Gln Ser Pro Met Thr Pro Arg
        1355              1360              1365

Ser Gln Ser Asp Ser Phe Gly Thr Ser Gln Thr Ala His Asp Val
        1370              1375              1380

Ala Asp Gln Pro Arg Pro Gly Ser Glu Gly Ser Phe Cys Ala Ser
        1385              1390              1395

Ser Asn Ser Pro Met His Ser Gln Gly Gln Gln Phe Ser Gly Val
        1400              1405              1410

Ser Gln Leu Pro Gly Pro Val Pro Thr Ser Gly Val Thr Asp Thr
        1415              1420              1425

Gln Asn Thr Val Asn Met Ala Gln Ala Asp Thr Glu Lys Leu Arg
        1430              1435              1440

Gln Arg Gln Lys Leu Arg Glu Ile Ile Leu Gln Gln Gln Gln Gln
        1445              1450              1455

Lys Lys Ile Ala Gly Arg Gln Glu Lys Gly Ser Gln Asp Ser Pro
        1460              1465              1470

Ala Val Pro His Pro Gly Pro Leu Gln His Trp Gln Pro Glu Asn
        1475              1480              1485

Val Asn Gln Ala Phe Thr Arg Pro Pro Pro Tyr Pro Gly Asn
        1490              1495              1500

Ile Arg Ser Pro Val Ala Pro Pro Leu Gly Pro Arg Tyr Ala Val
        1505              1510              1515

Phe Pro Lys Asp Gln Arg Gly Pro Tyr Pro Pro Asp Val Ala Ser
        1520              1525              1530
```

```
Met Gly Met Arg Pro His Gly Phe Arg Phe Gly Phe Pro Gly Gly
1535                1540                1545

Ser His Gly Thr Met Pro Ser Gln Glu Arg Phe Leu Val Pro Pro
1550                1555                1560

Gln Gln Ile Gln Gly Ser Gly Val Ser Pro Gln Leu Arg Arg Ser
1565                1570                1575

Val Ser Val Asp Met Pro Arg Pro Leu Asn Asn Ser Gln Met Asn
1580                1585                1590

Asn Pro Val Gly Leu Pro Gln His Phe Ser Pro Gln Ser Leu Pro
1595                1600                1605

Val Gln Gln His Asn Ile Leu Gly Gln Ala Tyr Ile Glu Leu Arg
1610                1615                1620

His Arg Ala Pro Asp Gly Arg Gln Arg Leu Pro Phe Ser Ala Pro
1625                1630                1635

Pro Gly Ser Val Val Glu Ala Ser Ser Asn Leu Arg His Gly Asn
1640                1645                1650

Phe Ile Pro Arg Pro Asp Phe Pro Gly Pro Arg His Thr Asp Pro
1655                1660                1665

Met Arg Arg Pro Pro Gln Gly Leu Pro Asn Gln Leu Pro Val His
1670                1675                1680

Pro Asp Leu Glu Gln Val Pro Pro Ser Gln Gln Glu Gln Gly His
1685                1690                1695

Ser Val His Ser Ser Ser Met Val Met Arg Thr Leu Asn His Pro
1700                1705                1710

Leu Gly Gly Glu Phe Ser Glu Ala Pro Leu Ser Thr Ser Val Pro
1715                1720                1725

Ser Glu Thr Thr Ser Asp Asn Leu Gln Ile Thr Thr Gln Pro Ser
1730                1735                1740

Asp Gly Leu Glu Glu Lys Leu Asp Ser Asp Pro Ser Val Lys
1745                1750                1755

Glu Leu Asp Val Lys Asp Leu Glu Gly Val Glu Val Lys Asp Leu
1760                1765                1770

Asp Asp Glu Asp Leu Glu Asn Leu Asn Leu Asp Thr Glu Asp Gly
1775                1780                1785

Lys Val Val Glu Leu Asp Thr Leu Asp Asn Leu Glu Thr Asn Asp
1790                1795                1800

Pro Asn Leu Asp Asp Leu Leu Arg Ser Gly Glu Phe Asp Ile Ile
1805                1810                1815

Ala Tyr Thr Asp Pro Glu Leu Asp Met Gly Asp Lys Lys Ser Met
1820                1825                1830

Phe Asn Glu Glu Leu Asp Leu Pro Ile Asp Asp Lys Leu Asp Asn
1835                1840                1845

Gln Cys Val Ser Val Glu Pro Lys Lys Lys Glu Gln Glu Asn Lys
1850                1855                1860

Thr Leu Val Leu Ser Asp Lys His Ser Pro Gln Lys Lys Ser Thr
1865                1870                1875

Val Thr Asn Glu Val Lys Thr Glu Val Leu Ser Pro Asn Ser Lys
1880                1885                1890

Val Glu Ser Lys Cys Glu Thr Glu Lys Asn Asp Glu Asn Lys Asp
1895                1900                1905

Asn Val Asp Thr Pro Cys Ser Gln Ala Ser Ala His Ser Asp Leu
1910                1915                1920
```

```
Asn Asp Gly Glu Lys Thr Ser Leu His Pro Cys Asp Pro Asp Leu
1925                    1930                1935

Phe Glu Lys Arg Thr Asn Arg Glu Thr Ala Gly Pro Ser Ala Asn
1940                    1945                1950

Val Ile Gln Ala Ser Thr Gln Leu Pro Ala Gln Asp Val Ile Asn
1955                    1960                1965

Ser Cys Gly Ile Thr Gly Ser Thr Pro Val Leu Ser Ser Leu Leu
1970                    1975                1980

Ala Asn Glu Lys Ser Asp Asn Ser Asp Ile Arg Pro Ser Gly Ser
1985                    1990                1995

Pro Pro Pro Pro Thr Leu Pro Ala Ser Pro Ser Asn His Val Ser
2000                    2005                2010

Ser Leu Pro Pro Phe Ile Ala Pro Pro Gly Arg Val Leu Asp Asn
2015                    2020                2025

Ala Met Asn Ser Asn Val Thr Val Val Ser Arg Val Asn His Val
2030                    2035                2040

Phe Ser Gln Gly Val Gln Val Asn Pro Gly Leu Ile Pro Gly Gln
2045                    2050                2055

Ser Thr Val Asn His Ser Leu Gly Thr Gly Lys Pro Ala Thr Gln
2060                    2065                2070

Thr Gly Pro Gln Thr Ser Gln Ser Gly Thr Ser Ser Met Ser Gly
2075                    2080                2085

Pro Gln Gln Leu Met Ile Pro Gln Thr Leu Ala Gln Gln Asn Arg
2090                    2095                2100

Glu Arg Pro Leu Leu Leu Glu Glu Gln Pro Leu Leu Leu Gln Asp
2105                    2110                2115

Leu Leu Asp Gln Glu Arg Gln Glu Gln Gln Gln Arg Gln Met
2120                    2125                2130

Gln Ala Met Ile Arg Gln Arg Ser Glu Pro Phe Phe Pro Asn Ile
2135                    2140                2145

Asp Phe Asp Ala Ile Thr Asp Pro Ile Met Lys Ala Lys Met Val
2150                    2155                2160

Ala Leu Lys Gly Ile Asn Lys Val Met Ala Gln Asn Asn Leu Gly
2165                    2170                2175

Met Pro Pro Met Val Met Ser Arg Phe Pro Phe Met Gly Gln Val
2180                    2185                2190

Val Thr Gly Thr Gln Asn Ser Glu Gly Gln Asn Leu Gly Pro Gln
2195                    2200                2205

Ala Ile Pro Gln Asp Gly Ser Ile Thr His Gln Ile Ser Arg Pro
2210                    2215                2220

Asn Pro Pro Asn Phe Gly Pro Gly Phe Val Asn Asp Ser Gln Arg
2225                    2230                2235

Lys Gln Tyr Glu Glu Trp Leu Gln Glu Thr Gln Gln Leu Leu Gln
2240                    2245                2250

Met Gln Gln Lys Tyr Leu Glu Glu Gln Ile Gly Ala His Arg Lys
2255                    2260                2265

Ser Lys Lys Ala Leu Ser Ala Lys Gln Arg Thr Ala Lys Lys Ala
2270                    2275                2280

Gly Arg Glu Phe Pro Glu Glu Asp Ala Glu Gln Leu Lys His Val
2285                    2290                2295

Thr Glu Gln Gln Ser Met Val Gln Lys Gln Leu Glu Gln Ile Arg
2300                    2305                2310

Lys Gln Gln Lys Glu His Ala Glu Leu Ile Glu Asp Tyr Arg Ile
```

|      |      |      |      |      |      |      |      |      |      |      |      |
|------|------|------|------|------|------|------|------|------|------|------|------|
|      |      | 2315 |      |      |      | 2320 |      |      |      | 2325 |      |
| Lys  | Gln  | Gln  | Gln  | Cys  | Ala  | Met  | Ala  | Pro  | Pro  | Thr  | Met  | Met Pro
|      |      | 2330 |      |      |      | 2335 |      |      |      | 2340 |      |
| Ser  | Val  | Gln  | Pro  | Gln  | Pro  | Pro  | Leu  | Ile  | Pro  | Gly  | Ala  | Thr Pro Pro
|      |      | 2345 |      |      |      | 2350 |      |      |      | 2355 |      |
| Thr  | Met  | Ser  | Gln  | Pro  | Thr  | Phe  | Pro  | Met  | Val  | Pro  | Gln  | Gln Leu Gln
|      |      | 2360 |      |      |      | 2365 |      |      |      | 2370 |      |
| His  | Gln  | Gln  | His  | Thr  | Thr  | Val  | Ile  | Ser  | Gly  | His  | Thr  | Ser Pro Val
|      |      | 2375 |      |      |      | 2380 |      |      |      | 2385 |      |
| Arg  | Met  | Pro  | Ser  | Leu  | Pro  | Gly  | Trp  | Gln  | Pro  | Asn  | Ser  | Ala Pro Ala
|      |      | 2390 |      |      |      | 2395 |      |      |      | 2400 |      |
| His  | Leu  | Pro  | Leu  | Asn  | Pro  | Pro  | Arg  | Ile  | Gln  | Pro  | Pro  | Ile Ala Gln
|      |      | 2405 |      |      |      | 2410 |      |      |      | 2415 |      |
| Leu  | Pro  | Ile  | Lys  | Thr  | Cys  | Thr  | Pro  | Ala  | Pro  | Gly  | Thr  | Val Ser Asn
|      |      | 2420 |      |      |      | 2425 |      |      |      | 2430 |      |
| Ala  | Asn  | Pro  | Gln  | Ser  | Gly  | Pro  | Pro  | Pro  | Arg  | Val  | Glu  | Phe Asp Asp
|      |      | 2435 |      |      |      | 2440 |      |      |      | 2445 |      |
| Asn  | Asn  | Pro  | Phe  | Ser  | Glu  | Ser  | Phe  | Gln  | Glu  | Arg  | Glu  | Arg Lys Glu
|      |      | 2450 |      |      |      | 2455 |      |      |      | 2460 |      |
| Arg  | Leu  | Arg  | Glu  | Gln  | Gln  | Glu  | Arg  | Gln  | Arg  | Ile  | Gln  | Leu Met Gln
|      |      | 2465 |      |      |      | 2470 |      |      |      | 2475 |      |
| Glu  | Val  | Asp  | Arg  | Gln  | Arg  | Ala  | Leu  | Gln  | Gln  | Arg  | Met  | Glu Met Glu
|      |      | 2480 |      |      |      | 2485 |      |      |      | 2490 |      |
| Gln  | His  | Gly  | Met  | Val  | Gly  | Ser  | Glu  | Ile  | Ser  | Ser  | Ser  | Arg Thr Ser
|      |      | 2495 |      |      |      | 2500 |      |      |      | 2505 |      |
| Val  | Ser  | Gln  | Ile  | Pro  | Phe  | Tyr  | Ser  | Ser  | Asp  | Leu  | Pro  | Cys Asp Phe
|      |      | 2510 |      |      |      | 2515 |      |      |      | 2520 |      |
| Met  | Gln  | Pro  | Leu  | Gly  | Pro  | Leu  | Gln  | Gln  | Ser  | Pro  | Gln  | His Gln Gln
|      |      | 2525 |      |      |      | 2530 |      |      |      | 2535 |      |
| Gln  | Met  | Gly  | Gln  | Val  | Leu  | Gln  | Gln  | Gln  | Asn  | Ile  | Gln  | Gln Gly Ser
|      |      | 2540 |      |      |      | 2545 |      |      |      | 2550 |      |
| Ile  | Asn  | Ser  | Pro  | Ser  | Thr  | Gln  | Thr  | Phe  | Met  | Gln  | Thr  | Asn Glu Arg
|      |      | 2555 |      |      |      | 2560 |      |      |      | 2565 |      |
| Arg  | Gln  | Val  | Gly  | Pro  | Pro  | Ser  | Phe  | Val  | Pro  | Asp  | Ser  | Pro Ser Ile
|      |      | 2570 |      |      |      | 2575 |      |      |      | 2580 |      |
| Pro  | Val  | Gly  | Ser  | Pro  | Asn  | Phe  | Ser  | Ser  | Val  | Lys  | Gln  | Gly His Gly
|      |      | 2585 |      |      |      | 2590 |      |      |      | 2595 |      |
| Asn  | Leu  | Ser  | Gly  | Thr  | Ser  | Phe  | Gln  | Gln  | Ser  | Pro  | Val  | Arg Pro Ser
|      |      | 2600 |      |      |      | 2605 |      |      |      | 2610 |      |
| Phe  | Thr  | Pro  | Ala  | Leu  | Pro  | Ala  | Ala  | Pro  | Pro  | Val  | Ala  | Asn Ser Ser
|      |      | 2615 |      |      |      | 2620 |      |      |      | 2625 |      |
| Leu  | Pro  | Cys  | Gly  | Gln  | Asp  | Ser  | Thr  | Ile  | Thr  | His  | Gly  | His Ser Tyr
|      |      | 2630 |      |      |      | 2635 |      |      |      | 2640 |      |
| Pro  | Gly  | Ser  | Thr  | Gln  | Ser  | Leu  | Ile  | Gln  | Leu  | Tyr  | Ser  | Asp Ile Ile
|      |      | 2645 |      |      |      | 2650 |      |      |      | 2655 |      |
| Pro  | Glu  | Glu  | Lys  | Gly  | Lys  | Lys  | Lys  | Arg  | Thr  | Arg  | Lys  | Lys Lys Arg
|      |      | 2660 |      |      |      | 2665 |      |      |      | 2670 |      |
| Asp  | Asp  | Asp  | Ala  | Glu  | Ser  | Thr  | Lys  | Ala  | Pro  | Ser  | Thr  | Pro His Ser
|      |      | 2675 |      |      |      | 2680 |      |      |      | 2685 |      |
| Asp  | Ile  | Thr  | Ala  | Pro  | Pro  | Thr  | Pro  | Gly  | Ile  | Ser  | Glu  | Thr Thr Ser
|      |      | 2690 |      |      |      | 2695 |      |      |      | 2700 |      |
| Thr  | Pro  | Ala  | Val  | Ser  | Thr  | Pro  | Ser  | Glu  | Leu  | Pro  | Gln  | Gln Ala Asp
|      |      | 2705 |      |      |      | 2710 |      |      |      | 2715 |      |

```
Gln Glu Ser Val Glu Pro Val Gly Pro Ser Thr Pro Asn Met Ala
    2720            2725            2730

Ala Gly Gln Leu Cys Thr Glu Leu Glu Asn Lys Leu Pro Asn Ser
    2735            2740            2745

Asp Phe Ser Gln Ala Thr Pro Asn Gln Gln Thr Tyr Ala Asn Ser
    2750            2755            2760

Glu Val Asp Lys Leu Ser Met Glu Thr Pro Ala Lys Thr Glu Glu
    2765            2770            2775

Ile Lys Leu Glu Lys Ala Glu Thr Glu Ser Cys Pro Gly Gln Glu
    2780            2785            2790

Glu Pro Lys Leu Glu Glu Gln Asn Gly Ser Lys Val Glu Gly Asn
    2795            2800            2805

Ala Val Ala Cys Pro Val Ser Ser Ala Gln Ser Pro Pro His Ser
    2810            2815            2820

Ala Gly Ala Pro Ala Ala Lys Gly Asp Ser Gly Asn Glu Leu Leu
    2825            2830            2835

Lys His Leu Leu Lys Asn Lys Lys Ser Ser Ser Leu Leu Asn Gln
    2840            2845            2850

Lys Pro Glu Gly Ser Ile Cys Ser Glu Asp Asp Cys Thr Lys Asp
    2855            2860            2865

Asn Lys Leu Val Glu Lys Gln Asn Pro Ala Glu Gly Leu Gln Thr
    2870            2875            2880

Leu Gly Ala Gln Met Gln Gly Gly Phe Gly Cys Gly Asn Gln Leu
    2885            2890            2895

Pro Lys Thr Asp Gly Gly Ser Glu Thr Lys Lys Gln Arg Ser Lys
    2900            2905            2910

Arg Thr Gln Arg Thr Gly Glu Lys Ala Ala Pro Arg Ser Lys Lys
    2915            2920            2925

Arg Lys Lys Asp Glu Glu Glu Lys Gln Ala Met Tyr Ser Ser Thr
    2930            2935            2940

Asp Thr Phe Thr His Leu Lys Gln Val Arg Gln Leu Ser Leu Leu
    2945            2950            2955

Pro Leu Met Glu Pro Ile Ile Gly Val Asn Phe Ala His Phe Leu
    2960            2965            2970

Pro Tyr Gly Ser Gly Gln Phe Asn Ser Gly Asn Arg Leu Leu Gly
    2975            2980            2985

Thr Phe Gly Ser Ala Thr Leu Glu Gly Val Ser Asp Tyr Tyr Ser
    2990            2995            3000

Gln Leu Ile Tyr Lys Gln Asn Asn Leu Ser Asn Pro Pro Thr Pro
    3005            3010            3015

Pro Ala Ser Leu Pro Pro Thr Pro Pro Pro Met Ala Cys Gln Lys
    3020            3025            3030

Met Ala Asn Gly Phe Ala Thr Thr Glu Glu Leu Ala Gly Lys Ala
    3035            3040            3045

Gly Val Leu Val Ser His Glu Val Thr Lys Thr Leu Gly Pro Lys
    3050            3055            3060

Pro Phe Gln Leu Pro Phe Arg Pro Gln Asp Asp Leu Leu Ala Arg
    3065            3070            3075

Ala Leu Ala Gln Gly Pro Lys Thr Val Asp Val Pro Ala Ser Leu
    3080            3085            3090

Pro Thr Pro Pro His Asn Asn Gln Glu Glu Leu Arg Ile Gln Asp
    3095            3100            3105
```

```
His Cys Gly Asp Arg Asp Thr Pro Asp Ser Phe Val Pro Ser Ser
3110                3115                3120

Ser Pro Glu Ser Val Val Gly Val Glu Val Ser Arg Tyr Pro Asp
3125                3130                3135

Leu Ser Leu Val Lys Glu Glu Pro Pro Glu Pro Val Pro Ser Pro
3140                3145                3150

Ile Ile Pro Ile Leu Pro Ser Thr Ala Gly Lys Ser Ser Glu Ser
3155                3160                3165

Arg Arg Asn Asp Ile Lys Thr Glu Pro Gly Thr Leu Tyr Phe Ala
3170                3175                3180

Ser Pro Phe Gly Pro Ser Pro Asn Gly Pro Arg Ser Gly Leu Ile
3185                3190                3195

Ser Val Ala Ile Thr Leu His Pro Thr Ala Ala Glu Asn Ile Ser
3200                3205                3210

Ser Val Val Ala Ala Phe Ser Asp Leu Leu His Val Arg Ile Pro
3215                3220                3225

Asn Ser Tyr Glu Val Ser Ser Ala Pro Asp Val Pro Ser Met Gly
3230                3235                3240

Leu Val Ser Ser His Arg Ile Asn Pro Gly Leu Glu Tyr Arg Gln
3245                3250                3255

His Leu Leu Leu Arg Gly Pro Pro Pro Gly Ser Ala Asn Pro Pro
3260                3265                3270

Arg Leu Val Ser Ser Tyr Arg Leu Lys Gln Pro Asn Val Pro Phe
3275                3280                3285

Pro Pro Thr Ser Asn Gly Leu Ser Gly Tyr Lys Asp Ser Ser His
3290                3295                3300

Gly Ile Ala Glu Ser Ala Ala Leu Arg Pro Gln Trp Cys Cys His
3305                3310                3315

Cys Lys Val Val Ile Leu Gly Ser Gly Val Arg Lys Ser Phe Lys
3320                3325                3330

Asp Leu Thr Leu Leu Asn Lys Asp Ser Arg Glu Ser Thr Lys Arg
3335                3340                3345

Val Glu Lys Asp Ile Val Phe Cys Ser Asn Asn Cys Phe Ile Leu
3350                3355                3360

Tyr Ser Ser Thr Ala Gln Ala Lys Asn Ser Glu Asn Lys Glu Ser
3365                3370                3375

Ile Pro Ser Leu Pro Gln Ser Pro Met Arg Glu Thr Pro Ser Lys
3380                3385                3390

Ala Phe His Gln Tyr Ser Asn Asn Ile Ser Thr Leu Asp Val His
3395                3400                3405

Cys Leu Pro Gln Leu Pro Glu Lys Ala Ser Pro Ala Ser Pro
3410                3415                3420

Pro Ile Ala Phe Pro Pro Ala Phe Glu Ala Ala Gln Val Glu Ala
3425                3430                3435

Lys Pro Asp Glu Leu Lys Val Thr Val Lys Leu Lys Pro Arg Leu
3440                3445                3450

Arg Ala Val His Gly Gly Phe Glu Asp Cys Arg Pro Leu Asn Lys
3455                3460                3465

Lys Trp Arg Gly Met Lys Trp Lys Lys Trp Ser Ile His Ile Val
3470                3475                3480

Ile Pro Lys Gly Thr Phe Lys Pro Pro Cys Glu Asp Glu Ile Asp
3485                3490                3495

Glu Phe Leu Lys Lys Leu Gly Thr Ser Leu Lys Pro Asp Pro Val
```

```
                3500                3505                3510
Pro Lys Asp Tyr Arg Lys Cys Cys Phe Cys His Glu Glu Gly Asp
    3515                3520                3525

Gly Leu Thr Asp Gly Pro Ala Arg Leu Leu Asn Leu Asp Leu Asp
    3530                3535                3540

Leu Trp Val His Leu Asn Cys Ala Leu Trp Ser Thr Glu Val Tyr
    3545                3550                3555

Glu Thr Gln Ala Gly Ala Leu Ile Asn Val Glu Leu Ala Leu Arg
    3560                3565                3570

Arg Gly Leu Gln Met Lys Cys Val Phe Cys His Lys Thr Gly Ala
    3575                3580                3585

Thr Ser Gly Cys His Arg Phe Arg Cys Thr Asn Ile Tyr His Phe
    3590                3595                3600

Thr Cys Ala Ile Lys Ala Gln Cys Met Phe Phe Lys Asp Lys Thr
    3605                3610                3615

Met Leu Cys Pro Met His Lys Pro Lys Gly Ile His Glu Gln Glu
    3620                3625                3630

Leu Ser Tyr Phe Ala Val Phe Arg Arg Val Tyr Val Gln Arg Asp
    3635                3640                3645

Glu Val Arg Gln Ile Ala Ser Ile Val Gln Arg Gly Glu Arg Asp
    3650                3655                3660

His Thr Phe Arg Val Gly Ser Leu Ile Phe His Thr Ile Gly Gln
    3665                3670                3675

Leu Leu Pro Gln Gln Met Gln Ala Phe His Ser Pro Lys Ala Leu
    3680                3685                3690

Phe Pro Val Gly Tyr Glu Ala Ser Arg Leu Tyr Trp Ser Thr Arg
    3695                3700                3705

Tyr Ala Asn Arg Arg Cys Arg Tyr Leu Cys Ser Ile Glu Glu Lys
    3710                3715                3720

Asp Gly Arg Pro Val Phe Val Ile Arg Ile Val Glu Gln Gly His
    3725                3730                3735

Glu Asp Leu Val Leu Ser Asp Ile Ser Pro Lys Gly Val Trp Asp
    3740                3745                3750

Lys Ile Leu Glu Pro Val Ala Cys Val Arg Lys Lys Ser Glu Met
    3755                3760                3765

Leu Gln Leu Phe Pro Ala Tyr Leu Lys Gly Glu Asp Leu Phe Gly
    3770                3775                3780

Leu Thr Val Ser Ala Val Ala Arg Ile Ala Glu Ser Leu Pro Gly
    3785                3790                3795

Val Glu Ala Cys Glu Asn Tyr Thr Phe Arg Tyr Gly Arg Asn Pro
    3800                3805                3810

Leu Met Glu Leu Pro Leu Ala Val Asn Pro Thr Gly Cys Ala Arg
    3815                3820                3825

Ser Glu Pro Lys Met Ser Ala His Val Lys Arg Pro His Thr Leu
    3830                3835                3840

Asn Ser Thr Ser Thr Ser Lys Ser Phe Gln Ser Thr Val Thr Gly
    3845                3850                3855

Glu Leu Asn Ala Pro Tyr Ser Lys Gln Phe Val His Ser Lys Ser
    3860                3865                3870

Ser Gln Tyr Arg Lys Met Lys Thr Glu Trp Lys Ser Asn Val Tyr
    3875                3880                3885

Leu Ala Arg Ser Arg Ile Gln Gly Leu Gly Leu Tyr Ala Ala Arg
    3890                3895                3900
```

-continued

```
Asp Ile Glu Lys His Thr Met Val Ile Glu Tyr Ile Gly Thr Ile
    3905                3910                3915

Ile Arg Asn Glu Val Ala Asn Arg Lys Glu Lys Leu Tyr Glu Ser
    3920                3925                3930

Gln Asn Arg Gly Val Tyr Met Phe Arg Met Asp Asn Asp His Val
    3935                3940                3945

Ile Asp Ala Thr Leu Thr Gly Gly Pro Ala Arg Tyr Ile Asn His
    3950                3955                3960

Ser Cys Ala Pro Asn Cys Val Ala Glu Val Val Thr Phe Glu Arg
    3965                3970                3975

Gly His Lys Ile Ile Ile Ser Ser Ser Arg Arg Ile Gln Lys Gly
    3980                3985                3990

Glu Glu Leu Cys Tyr Asp Tyr Lys Phe Asp Phe Glu Asp Asp Gln
    3995                4000                4005

His Lys Ile Pro Cys His Cys Gly Ala Val Asn Cys Arg Lys Trp
    4010                4015                4020

Met Asn
    4025
```

<210> SEQ ID NO 49
<211> LENGTH: 4968
<212> TYPE: PRT
<213> ORGANISM: Homo sapiens

<400> SEQUENCE: 49

```
Met Ser Ser Glu Glu Asp Lys Ser Val Glu Gln Pro Gln Pro Pro
1               5                   10                  15

Pro Pro Pro Glu Glu Pro Gly Ala Pro Ala Pro Ser Pro Ala Ala Ala
                20                  25                  30

Asp Lys Arg Pro Arg Gly Arg Pro Arg Lys Asp Gly Ala Ser Pro Phe
            35                  40                  45

Gln Arg Ala Arg Lys Lys Pro Arg Ser Arg Gly Lys Thr Ala Val Glu
        50                  55                  60

Asp Glu Asp Ser Met Asp Gly Leu Glu Thr Thr Glu Thr Glu Thr Ile
65                  70                  75                  80

Val Glu Thr Glu Ile Lys Glu Gln Ser Ala Glu Glu Asp Ala Glu Ala
                85                  90                  95

Glu Val Asp Asn Ser Lys Gln Leu Ile Pro Thr Leu Gln Arg Ser Val
                100                 105                 110

Ser Glu Glu Ser Ala Asn Ser Leu Val Ser Val Gly Val Glu Ala Lys
            115                 120                 125

Ile Ser Glu Gln Leu Cys Ala Phe Cys Tyr Cys Gly Glu Lys Ser Ser
        130                 135                 140

Leu Gly Gln Gly Asp Leu Lys Gln Phe Arg Ile Thr Pro Gly Phe Ile
145                 150                 155                 160

Leu Pro Trp Arg Asn Gln Pro Ser Asn Lys Lys Asp Ile Asp Asp Asn
                165                 170                 175

Ser Asn Gly Thr Tyr Glu Lys Met Gln Asn Ser Ala Pro Arg Lys Gln
                180                 185                 190

Arg Gly Gln Arg Lys Glu Arg Ser Pro Gln Gln Asn Ile Val Ser Cys
            195                 200                 205

Val Ser Val Ser Thr Gln Thr Ala Ser Asp Asp Gln Ala Gly Lys Leu
        210                 215                 220

Trp Asp Glu Leu Ser Leu Val Gly Leu Pro Asp Ala Ile Asp Ile Gln
```

```
                225                 230                 235                 240
        Ala Leu Phe Asp Ser Thr Gly Thr Cys Trp Ala His His Arg Cys Val
                        245                 250                 255

Glu Trp Ser Leu Gly Val Cys Gln Met Glu Glu Pro Leu Leu Val Asn
                        260                 265                 270

Val Asp Lys Ala Val Val Ser Gly Ser Thr Glu Arg Cys Ala Phe Cys
                        275                 280                 285

Lys His Leu Gly Ala Thr Ile Lys Cys Cys Glu Lys Cys Thr Gln
                        290                 295                 300

Met Tyr His Tyr Pro Cys Ala Ala Gly Ala Gly Thr Phe Gln Asp Phe
        305                 310                 315                 320

Ser His Ile Phe Leu Leu Cys Pro Glu His Ile Asp Gln Ala Pro Glu
                        325                 330                 335

Arg Ser Lys Glu Asp Ala Asn Cys Ala Val Cys Asp Ser Pro Gly Asp
                        340                 345                 350

Leu Leu Asp Gln Phe Phe Cys Thr Thr Cys Gly Gln His Tyr His Gly
                        355                 360                 365

Met Cys Leu Asp Ile Ala Val Thr Pro Leu Lys Arg Ala Gly Trp Gln
        370                 375                 380

Cys Pro Glu Cys Lys Val Cys Gln Asn Cys Lys Gln Ser Gly Glu Asp
        385                 390                 395                 400

Ser Lys Met Leu Val Cys Asp Thr Cys Asp Lys Gly Tyr His Thr Phe
                        405                 410                 415

Cys Leu Gln Pro Val Met Lys Ser Val Pro Thr Asn Gly Trp Lys Cys
                        420                 425                 430

Lys Asn Cys Arg Ile Cys Ile Glu Cys Gly Thr Arg Ser Ser Ser Gln
                        435                 440                 445

Trp His His Asn Cys Leu Ile Cys Asp Asn Cys Tyr Gln Gln Gln Asp
                        450                 455                 460

Asn Leu Cys Pro Phe Cys Gly Lys Cys Tyr His Pro Glu Leu Gln Lys
        465                 470                 475                 480

Asp Met Leu His Cys Asn Met Cys Lys Arg Trp Val His Leu Glu Cys
                        485                 490                 495

Asp Lys Pro Thr Asp His Glu Leu Asp Thr Gln Leu Lys Glu Glu Tyr
                        500                 505                 510

Ile Cys Met Tyr Cys Lys His Leu Gly Ala Glu Met Asp Arg Leu Gln
                        515                 520                 525

Pro Gly Glu Glu Val Glu Ile Ala Glu Leu Thr Thr Asp Tyr Asn Asn
                        530                 535                 540

Glu Met Glu Val Glu Gly Pro Glu Asp Gln Met Val Phe Ser Glu Gln
        545                 550                 555                 560

Ala Ala Asn Lys Asp Val Asn Gly Gln Glu Ser Thr Pro Gly Ile Val
                        565                 570                 575

Pro Asp Ala Val Gln Val His Thr Glu Glu Gln Gln Lys Ser His Pro
                        580                 585                 590

Ser Glu Ser Leu Asp Thr Asp Ser Leu Leu Ile Ala Val Ser Ser Gln
                        595                 600                 605

His Thr Val Asn Thr Glu Leu Glu Lys Gln Ile Ser Asn Glu Val Asp
                        610                 615                 620

Ser Glu Asp Leu Lys Met Ser Ser Glu Val Lys His Ile Cys Gly Glu
        625                 630                 635                 640

Asp Gln Ile Glu Asp Lys Met Glu Val Thr Glu Asn Ile Glu Val Val
                        645                 650                 655
```

-continued

```
Thr His Gln Ile Thr Val Gln Gln Glu Gln Leu Gln Leu Leu Glu Glu
            660             665             670
Pro Glu Thr Val Val Ser Arg Glu Ser Arg Pro Pro Lys Leu Val
            675             680             685
Met Glu Ser Val Thr Leu Pro Leu Glu Thr Leu Val Ser Pro His Glu
    690             695             700
Glu Ser Ile Ser Leu Cys Pro Glu Glu Gln Leu Val Ile Glu Arg Leu
705             710             715             720
Gln Gly Glu Lys Glu Gln Lys Glu Asn Ser Glu Leu Ser Thr Gly Leu
            725             730             735
Met Asp Ser Glu Met Thr Pro Thr Ile Glu Gly Cys Val Lys Asp Val
            740             745             750
Ser Tyr Gln Gly Gly Lys Ser Ile Lys Leu Ser Ser Glu Thr Glu Ser
            755             760             765
Ser Phe Ser Ser Ser Ala Asp Ile Ser Lys Ala Asp Val Ser Ser Ser
            770             775             780
Pro Thr Pro Ser Ser Asp Leu Pro Ser His Asp Met Leu His Asn Tyr
785             790             795             800
Pro Ser Ala Leu Ser Ser Ser Ala Gly Asn Ile Met Pro Thr Thr Tyr
            805             810             815
Ile Ser Val Thr Pro Lys Ile Gly Met Gly Lys Pro Ala Ile Thr Lys
            820             825             830
Arg Lys Phe Ser Pro Gly Arg Pro Arg Ser Lys Gln Gly Ala Trp Ser
            835             840             845
Thr His Asn Thr Val Ser Pro Pro Ser Trp Ser Pro Asp Ile Ser Glu
            850             855             860
Gly Arg Glu Ile Phe Lys Pro Arg Gln Leu Pro Gly Ser Ala Ile Trp
865             870             875             880
Ser Ile Lys Val Gly Arg Gly Ser Gly Phe Pro Gly Lys Arg Arg Pro
            885             890             895
Arg Gly Ala Gly Leu Ser Gly Arg Gly Gly Arg Gly Arg Ser Lys Leu
            900             905             910
Lys Ser Gly Ile Gly Ala Val Val Leu Pro Gly Val Ser Thr Ala Asp
            915             920             925
Ile Ser Ser Asn Lys Asp Asp Glu Glu Asn Ser Met His Asn Thr Val
            930             935             940
Val Leu Phe Ser Ser Ser Asp Lys Phe Thr Leu Asn Gln Asp Met Cys
945             950             955             960
Val Val Cys Gly Ser Phe Gly Gln Gly Ala Glu Gly Arg Leu Leu Ala
            965             970             975
Cys Ser Gln Cys Gly Gln Cys Tyr His Pro Tyr Cys Val Ser Ile Lys
            980             985             990
Ile Thr Lys Val Val Leu Ser Lys Gly Trp Arg Cys Leu Glu Cys Thr
            995             1000            1005
Val Cys Glu Ala Cys Gly Lys Ala Thr Asp Pro Gly Arg Leu Leu
            1010            1015            1020
Leu Cys Asp Asp Cys Asp Ile Ser Tyr His Thr Tyr Cys Leu Asp
            1025            1030            1035
Pro Pro Leu Gln Thr Val Pro Lys Gly Gly Trp Lys Cys Lys Trp
            1040            1045            1050
Cys Val Trp Cys Arg His Cys Gly Ala Thr Ser Ala Gly Leu Arg
            1055            1060            1065
```

| | | | | | | | | | | | |
|---|---|---|---|---|---|---|---|---|---|---|---|
|Cys|Glu|Trp|Gln|Asn|Asn|Tyr|Thr|Gln|Cys|Ala|Pro|Cys|Ala|Ser|
|1070| | | | |1075| | | |1080| | |

Cys Glu Trp Gln Asn Asn Tyr Thr Gln Cys Ala Pro Cys Ala Ser
    1070              1075              1080

Leu Ser Ser Cys Pro Val Cys Tyr Arg Asn Tyr Arg Glu Glu Asp
    1085              1090              1095

Leu Ile Leu Gln Cys Arg Gln Cys Asp Arg Trp Met His Ala Val
    1100              1105              1110

Cys Gln Asn Leu Asn Thr Glu Glu Val Glu Asn Val Ala Asp
    1115              1120              1125

Ile Gly Phe Asp Cys Ser Met Cys Arg Pro Tyr Met Pro Ala Ser
    1130              1135              1140

Asn Val Pro Ser Ser Asp Cys Cys Glu Ser Ser Leu Val Ala Gln
    1145              1150              1155

Ile Val Thr Lys Val Lys Glu Leu Asp Pro Pro Lys Thr Tyr Thr
    1160              1165              1170

Gln Asp Gly Val Cys Leu Thr Glu Ser Gly Met Thr Gln Leu Gln
    1175              1180              1185

Ser Leu Thr Val Thr Val Pro Arg Arg Lys Arg Ser Lys Pro Lys
    1190              1195              1200

Leu Lys Leu Lys Ile Ile Asn Gln Asn Ser Val Ala Val Leu Gln
    1205              1210              1215

Thr Pro Pro Asp Ile Gln Ser Glu His Ser Arg Asp Gly Glu Met
    1220              1225              1230

Asp Asp Ser Arg Glu Gly Glu Leu Met Asp Cys Asp Gly Lys Ser
    1235              1240              1245

Glu Ser Ser Pro Glu Arg Glu Ala Val Asp Asp Glu Thr Lys Gly
    1250              1255              1260

Val Glu Gly Thr Asp Gly Val Lys Lys Arg Lys Lys Pro Tyr
    1265              1270              1275

Arg Pro Gly Ile Gly Gly Phe Met Val Arg Gln Arg Ser Arg Thr
    1280              1285              1290

Gly Gln Gly Lys Thr Lys Arg Ser Val Ile Arg Lys Asp Ser Ser
    1295              1300              1305

Gly Ser Ile Ser Glu Gln Leu Pro Cys Arg Asp Asp Gly Trp Ser
    1310              1315              1320

Glu Gln Leu Pro Asp Thr Leu Val Asp Glu Ser Val Ser Val Thr
    1325              1330              1335

Glu Ser Thr Glu Lys Ile Lys Lys Arg Tyr Arg Lys Arg Lys Asn
    1340              1345              1350

Lys Leu Glu Glu Thr Phe Pro Ala Tyr Leu Gln Glu Ala Phe Phe
    1355              1360              1365

Gly Lys Asp Leu Leu Asp Thr Ser Arg Gln Ser Lys Ile Ser Leu
    1370              1375              1380

Asp Asn Leu Ser Glu Asp Gly Ala Gln Leu Leu Tyr Lys Thr Asn
    1385              1390              1395

Met Asn Thr Gly Phe Leu Asp Pro Ser Leu Asp Pro Leu Leu Ser
    1400              1405              1410

Ser Ser Ser Ala Pro Thr Lys Ser Gly Thr His Gly Pro Ala Asp
    1415              1420              1425

Asp Pro Leu Ala Asp Ile Ser Glu Val Leu Asn Thr Asp Asp Asp
    1430              1435              1440

Ile Leu Gly Ile Ile Ser Asp Leu Ala Lys Ser Val Asp His
    1445              1450              1455

Ser Asp Ile Gly Pro Val Thr Asp Asp Pro Ser Ser Leu Pro Gln

```
          1460                1465                1470

Pro Asn Val Asn Gln Ser Ser Arg Pro Leu Ser Glu Glu Gln Leu
    1475                1480                1485

Asp Gly Ile Leu Ser Pro Glu Leu Asp Lys Met Val Thr Asp Gly
    1490                1495                1500

Ala Ile Leu Gly Lys Leu Tyr Lys Ile Pro Glu Leu Gly Gly Lys
    1505                1510                1515

Asp Val Glu Asp Leu Phe Thr Ala Val Leu Ser Pro Ala Asn Thr
    1520                1525                1530

Gln Pro Thr Pro Leu Pro Gln Pro Pro Pro Thr Gln Leu Leu
    1535                1540                1545

Pro Ile His Asn Gln Asp Ala Phe Ser Arg Met Pro Leu Met Asn
    1550                1555                1560

Gly Leu Ile Gly Ser Ser Pro His Leu Pro His Asn Ser Leu Pro
    1565                1570                1575

Pro Gly Ser Gly Leu Gly Thr Phe Ser Ala Ile Ala Gln Ser Ser
    1580                1585                1590

Tyr Pro Asp Ala Arg Asp Lys Asn Ser Ala Phe Asn Pro Met Ala
    1595                1600                1605

Ser Asp Pro Asn Asn Ser Trp Thr Ser Ser Ala Pro Thr Val Glu
    1610                1615                1620

Gly Glu Asn Asp Thr Met Ser Asn Ala Gln Arg Ser Thr Leu Lys
    1625                1630                1635

Trp Glu Lys Glu Glu Ala Leu Gly Glu Met Ala Thr Val Ala Pro
    1640                1645                1650

Val Leu Tyr Thr Asn Ile Asn Phe Pro Asn Leu Lys Glu Glu Phe
    1655                1660                1665

Pro Asp Trp Thr Thr Arg Val Lys Gln Ile Ala Lys Leu Trp Arg
    1670                1675                1680

Lys Ala Ser Ser Gln Glu Arg Ala Pro Tyr Val Gln Lys Ala Arg
    1685                1690                1695

Asp Asn Arg Ala Ala Leu Arg Ile Asn Lys Val Gln Met Ser Asn
    1700                1705                1710

Asp Ser Met Lys Arg Gln Gln Gln Gln Asp Ser Ile Asp Pro Ser
    1715                1720                1725

Ser Arg Ile Asp Ser Glu Leu Phe Lys Asp Pro Leu Lys Gln Arg
    1730                1735                1740

Glu Ser Glu His Glu Gln Glu Trp Lys Phe Arg Gln Gln Met Arg
    1745                1750                1755

Gln Lys Ser Lys Gln Gln Ala Lys Ile Glu Ala Thr Gln Lys Leu
    1760                1765                1770

Glu Gln Val Lys Asn Glu Gln Gln Gln Gln Gln Gln Gln Gln Phe
    1775                1780                1785

Gly Ser Gln His Leu Leu Val Gln Ser Gly Ser Asp Thr Pro Ser
    1790                1795                1800

Ser Gly Ile Gln Ser Pro Leu Thr Pro Gln Pro Gly Asn Gly Asn
    1805                1810                1815

Met Ser Pro Ala Gln Ser Phe His Lys Glu Leu Phe Thr Lys Gln
    1820                1825                1830

Pro Pro Ser Thr Pro Thr Ser Thr Ser Ser Asp Asp Val Phe Val
    1835                1840                1845

Lys Pro Gln Ala Pro Pro Pro Pro Pro Ala Pro Ser Arg Ile Pro
    1850                1855                1860
```

```
Ile Gln Asp Ser Leu Ser Gln Ala Gln Thr Ser Gln Pro Pro Ser
1865                1870                1875

Pro Gln Val Phe Ser Pro Gly Ser Ser Asn Ser Arg Pro Pro Ser
1880                1885                1890

Pro Met Asp Pro Tyr Ala Lys Met Val Gly Thr Pro Arg Pro Pro
1895                1900                1905

Pro Val Gly His Ser Phe Ser Arg Arg Asn Ser Ala Ala Pro Val
1910                1915                1920

Glu Asn Cys Thr Pro Leu Ser Ser Val Ser Arg Pro Leu Gln Met
1925                1930                1935

Asn Glu Thr Thr Ala Asn Arg Pro Ser Pro Val Arg Asp Leu Cys
1940                1945                1950

Ser Ser Ser Thr Thr Asn Asn Asp Pro Tyr Ala Lys Pro Pro Asp
1955                1960                1965

Thr Pro Arg Pro Val Met Thr Asp Gln Phe Pro Lys Ser Leu Gly
1970                1975                1980

Leu Ser Arg Ser Pro Val Val Ser Glu Gln Thr Ala Lys Gly Pro
1985                1990                1995

Ile Ala Ala Gly Thr Ser Asp His Phe Thr Lys Pro Ser Pro Arg
2000                2005                2010

Ala Asp Val Phe Gln Arg Gln Arg Ile Pro Asp Ser Tyr Ala Arg
2015                2020                2025

Pro Leu Leu Thr Pro Ala Pro Leu Asp Ser Gly Pro Gly Pro Phe
2030                2035                2040

Lys Thr Pro Met Gln Pro Pro Pro Ser Ser Gln Asp Pro Tyr Gly
2045                2050                2055

Ser Val Ser Gln Ala Ser Arg Arg Leu Ser Val Asp Pro Tyr Glu
2060                2065                2070

Arg Pro Ala Leu Thr Pro Arg Pro Ile Asp Asn Phe Ser His Asn
2075                2080                2085

Gln Ser Asn Asp Pro Tyr Ser Gln Pro Pro Leu Thr Pro His Pro
2090                2095                2100

Ala Val Asn Glu Ser Phe Ala His Pro Ser Arg Ala Phe Ser Gln
2105                2110                2115

Pro Gly Thr Ile Ser Arg Pro Thr Ser Gln Asp Pro Tyr Ser Gln
2120                2125                2130

Pro Pro Gly Thr Pro Arg Pro Val Val Asp Ser Tyr Ser Gln Ser
2135                2140                2145

Ser Gly Thr Ala Arg Ser Asn Thr Asp Pro Tyr Ser Gln Pro Pro
2150                2155                2160

Gly Thr Pro Arg Pro Thr Thr Val Asp Pro Tyr Ser Gln Gln Pro
2165                2170                2175

Gln Thr Pro Arg Pro Ser Thr Gln Thr Asp Leu Phe Val Thr Pro
2180                2185                2190

Val Thr Asn Gln Arg His Ser Asp Pro Tyr Ala His Pro Pro Gly
2195                2200                2205

Thr Pro Arg Pro Gly Ile Ser Val Pro Tyr Ser Gln Pro Pro Ala
2210                2215                2220

Thr Pro Arg Pro Arg Ile Ser Glu Gly Phe Thr Arg Ser Ser Met
2225                2230                2235

Thr Arg Pro Val Leu Met Pro Asn Gln Asp Pro Phe Leu Gln Ala
2240                2245                2250
```

```
Ala Gln Asn Arg Gly Pro Ala Leu Pro Gly Pro Leu Val Arg Pro
2255                2260                2265

Pro Asp Thr Cys Ser Gln Thr Pro Arg Pro Pro Gly Pro Gly Leu
2270                2275                2280

Ser Asp Thr Phe Ser Arg Val Ser Pro Ser Ala Ala Arg Asp Pro
2285                2290                2295

Tyr Asp Gln Ser Pro Met Thr Pro Arg Ser Gln Ser Asp Ser Phe
2300                2305                2310

Gly Thr Ser Gln Thr Ala His Asp Val Ala Asp Gln Pro Arg Pro
2315                2320                2325

Gly Ser Glu Gly Ser Phe Cys Ala Ser Ser Asn Ser Pro Met His
2330                2335                2340

Ser Gln Gly Gln Gln Phe Ser Gly Val Ser Gln Leu Pro Gly Pro
2345                2350                2355

Val Pro Thr Ser Gly Val Thr Asp Thr Gln Asn Thr Val Asn Met
2360                2365                2370

Ala Gln Ala Asp Thr Glu Lys Leu Arg Gln Arg Gln Lys Leu Arg
2375                2380                2385

Glu Ile Ile Leu Gln Gln Gln Gln Lys Lys Ile Ala Gly Arg
2390                2395                2400

Gln Glu Lys Gly Ser Gln Asp Ser Pro Ala Val Pro His Pro Gly
2405                2410                2415

Pro Leu Gln His Trp Gln Pro Glu Asn Val Asn Gln Ala Phe Thr
2420                2425                2430

Arg Pro Pro Pro Pro Tyr Pro Gly Asn Ile Arg Ser Pro Val Ala
2435                2440                2445

Pro Pro Leu Gly Pro Arg Tyr Ala Val Phe Pro Lys Asp Gln Arg
2450                2455                2460

Gly Pro Tyr Pro Pro Asp Val Ala Ser Met Gly Met Arg Pro His
2465                2470                2475

Gly Phe Arg Phe Gly Phe Pro Gly Gly Ser His Gly Thr Met Pro
2480                2485                2490

Ser Gln Glu Arg Phe Leu Val Pro Pro Gln Gln Ile Gln Gly Ser
2495                2500                2505

Gly Val Ser Pro Gln Leu Arg Arg Ser Val Ser Val Asp Met Pro
2510                2515                2520

Arg Pro Leu Asn Asn Ser Gln Met Asn Asn Pro Val Gly Leu Pro
2525                2530                2535

Gln His Phe Ser Pro Gln Ser Leu Pro Val Gln Gln His Asn Ile
2540                2545                2550

Leu Gly Gln Ala Tyr Ile Glu Leu Arg His Arg Ala Pro Asp Gly
2555                2560                2565

Arg Gln Arg Leu Pro Phe Ser Ala Pro Pro Gly Ser Val Val Glu
2570                2575                2580

Ala Ser Ser Asn Leu Arg His Gly Asn Phe Ile Pro Arg Pro Asp
2585                2590                2595

Phe Pro Gly Pro Arg His Thr Asp Pro Met Arg Arg Pro Pro Gln
2600                2605                2610

Gly Leu Pro Asn Gln Leu Pro Val His Pro Asp Leu Glu Gln Val
2615                2620                2625

Pro Pro Ser Gln Gln Glu Gln Gly His Ser Val His Ser Ser Ser
2630                2635                2640

Met Val Met Arg Thr Leu Asn His Pro Leu Gly Gly Glu Phe Ser
```

2645                2650                 2655

Glu Ala Pro Leu Ser Thr Ser  Val Pro Ser Glu Thr  Thr Ser Asp
    2660            2665                 2670

Asn Leu Gln Ile Thr Thr Gln  Pro Ser Asp Gly Leu  Glu Glu Lys
    2675            2680                 2685

Leu Asp Ser Asp Asp Pro Ser  Val Lys Glu Leu Asp  Val Lys Asp
    2690            2695                 2700

Leu Glu Gly Val Glu Val Lys  Asp Leu Asp Asp Glu  Asp Leu Glu
    2705            2710                 2715

Asn Leu Asn Leu Asp Thr Glu  Asp Gly Lys Val Val  Glu Leu Asp
    2720            2725                 2730

Thr Leu Asp Asn Leu Glu Thr  Asn Asp Pro Asn Leu  Asp Asp Leu
    2735            2740                 2745

Leu Arg Ser Gly Glu Phe Asp  Ile Ile Ala Tyr Thr  Asp Pro Glu
    2750            2755                 2760

Leu Asp Met Gly Asp Lys Lys  Ser Met Phe Asn Glu  Glu Leu Asp
    2765            2770                 2775

Leu Pro Ile Asp Asp Lys Leu  Asp Asn Gln Cys Val  Ser Val Glu
    2780            2785                 2790

Pro Lys Lys Lys Glu Gln Glu  Asn Lys Thr Leu Val  Leu Ser Asp
    2795            2800                 2805

Lys His Ser Pro Gln Lys Lys  Ser Thr Val Thr Asn  Glu Val Lys
    2810            2815                 2820

Thr Glu Val Leu Ser Pro Asn  Ser Lys Val Glu Ser  Lys Cys Glu
    2825            2830                 2835

Thr Glu Lys Asn Asp Glu Asn  Lys Asp Asn Val Asp  Thr Pro Cys
    2840            2845                 2850

Ser Gln Ala Ser Ala His Ser  Asp Leu Asn Asp Gly  Glu Lys Thr
    2855            2860                 2865

Ser Leu His Pro Cys Asp Pro  Asp Leu Phe Glu Lys  Arg Thr Asn
    2870            2875                 2880

Arg Glu Thr Ala Gly Pro Ser  Ala Asn Val Ile Gln  Ala Ser Thr
    2885            2890                 2895

Gln Leu Pro Ala Gln Asp Val  Ile Asn Ser Cys Gly  Ile Thr Gly
    2900            2905                 2910

Ser Thr Pro Val Leu Ser Ser  Leu Leu Ala Asn Glu  Lys Ser Asp
    2915            2920                 2925

Asn Ser Asp Ile Arg Pro Ser  Gly Ser Pro Pro Pro  Pro Thr Leu
    2930            2935                 2940

Pro Ala Ser Pro Ser Asn His  Val Ser Ser Leu Pro  Pro Phe Ile
    2945            2950                 2955

Ala Pro Pro Gly Arg Val Leu  Asp Asn Ala Met Asn  Ser Asn Val
    2960            2965                 2970

Thr Val Val Ser Arg Val Asn  His Val Phe Ser Gln  Gly Val Gln
    2975            2980                 2985

Val Asn Pro Gly Leu Ile Pro  Gly Gln Ser Thr Val  Asn His Ser
    2990            2995                 3000

Leu Gly Thr Gly Lys Pro Ala  Thr Gln Thr Gly Pro  Gln Thr Ser
    3005            3010                 3015

Gln Ser Gly Thr Ser Ser Met  Ser Gly Pro Gln Gln  Leu Met Ile
    3020            3025                 3030

Pro Gln Thr Leu Ala Gln Gln  Asn Arg Glu Arg Pro  Leu Leu Leu
    3035            3040                 3045

```
Glu Glu Gln Pro Leu Leu Leu Gln Asp Leu Leu Asp Gln Glu Arg
    3050                3055                3060

Gln Glu Gln Gln Gln Gln Arg Gln Met Gln Ala Met Ile Arg Gln
    3065                3070                3075

Arg Ser Glu Pro Phe Phe Pro Asn Ile Asp Phe Asp Ala Ile Thr
    3080                3085                3090

Asp Pro Ile Met Lys Ala Lys Met Val Ala Leu Lys Gly Ile Asn
    3095                3100                3105

Lys Val Met Ala Gln Asn Asn Leu Gly Met Pro Pro Met Val Met
    3110                3115                3120

Ser Arg Phe Pro Phe Met Gly Gln Val Val Thr Gly Thr Gln Asn
    3125                3130                3135

Ser Glu Gly Gln Asn Leu Gly Pro Gln Ala Ile Pro Gln Asp Gly
    3140                3145                3150

Ser Ile Thr His Gln Ile Ser Arg Pro Asn Pro Pro Asn Phe Gly
    3155                3160                3165

Pro Gly Phe Val Asn Asp Ser Gln Arg Lys Gln Tyr Glu Glu Trp
    3170                3175                3180

Leu Gln Glu Thr Gln Gln Leu Leu Gln Met Gln Gln Lys Tyr Leu
    3185                3190                3195

Glu Glu Gln Ile Gly Ala His Arg Lys Ser Lys Lys Ala Leu Ser
    3200                3205                3210

Ala Lys Gln Arg Thr Ala Lys Lys Ala Gly Arg Glu Phe Pro Glu
    3215                3220                3225

Glu Asp Ala Glu Gln Leu Lys His Val Thr Glu Gln Gln Ser Met
    3230                3235                3240

Val Gln Lys Gln Leu Glu Gln Ile Arg Lys Gln Gln Lys Glu His
    3245                3250                3255

Ala Glu Leu Ile Glu Asp Tyr Arg Ile Lys Gln Gln Gln Gln Cys
    3260                3265                3270

Ala Met Ala Pro Pro Thr Met Met Pro Ser Val Gln Pro Gln Pro
    3275                3280                3285

Pro Leu Ile Pro Gly Ala Thr Pro Pro Thr Met Ser Gln Pro Thr
    3290                3295                3300

Phe Pro Met Val Pro Gln Gln Leu Gln His Gln Gln His Thr Thr
    3305                3310                3315

Val Ile Ser Gly His Thr Ser Pro Val Arg Met Pro Ser Leu Pro
    3320                3325                3330

Gly Trp Gln Pro Asn Ser Ala Pro Ala His Leu Pro Leu Asn Pro
    3335                3340                3345

Pro Arg Ile Gln Pro Pro Ile Ala Gln Leu Pro Ile Lys Thr Cys
    3350                3355                3360

Thr Pro Ala Pro Gly Thr Val Ser Asn Ala Asn Pro Gln Ser Gly
    3365                3370                3375

Pro Pro Pro Arg Val Glu Phe Asp Asp Asn Asn Pro Phe Ser Glu
    3380                3385                3390

Ser Phe Gln Glu Arg Glu Arg Lys Glu Arg Leu Arg Glu Gln Gln
    3395                3400                3405

Glu Arg Gln Arg Ile Gln Leu Met Gln Glu Val Asp Arg Gln Arg
    3410                3415                3420

Ala Leu Gln Gln Arg Met Glu Met Glu Gln His Gly Met Val Gly
    3425                3430                3435
```

```
Ser Glu Ile Ser Ser Ser Arg Thr Ser Val Ser Gln Ile Pro Phe
3440                3445                3450

Tyr Ser Ser Asp Leu Pro Cys Asp Phe Met Gln Pro Leu Gly Pro
    3455                3460                3465

Leu Gln Gln Ser Pro Gln His Gln Gln Gln Met Gly Gln Val Leu
3470                3475                3480

Gln Gln Gln Asn Ile Gln Gln Gly Ser Ile Asn Ser Pro Ser Thr
3485                3490                3495

Gln Thr Phe Met Gln Thr Asn Glu Arg Arg Gln Val Gly Pro Pro
3500                3505                3510

Ser Phe Val Pro Asp Ser Pro Ser Ile Pro Val Gly Ser Pro Asn
3515                3520                3525

Phe Ser Ser Val Lys Gln Gly His Gly Asn Leu Ser Gly Thr Ser
3530                3535                3540

Phe Gln Gln Ser Pro Val Arg Pro Ser Phe Thr Pro Ala Leu Pro
3545                3550                3555

Ala Ala Pro Pro Val Ala Asn Ser Ser Leu Pro Cys Gly Gln Asp
3560                3565                3570

Ser Thr Ile Thr His Gly His Ser Tyr Pro Gly Ser Thr Gln Ser
3575                3580                3585

Leu Ile Gln Leu Tyr Ser Asp Ile Ile Pro Glu Glu Lys Gly Lys
3590                3595                3600

Lys Lys Arg Thr Arg Lys Lys Arg Asp Asp Asp Ala Glu Ser
3605                3610                3615

Thr Lys Ala Pro Ser Thr Pro His Ser Asp Ile Thr Ala Pro Pro
3620                3625                3630

Thr Pro Gly Ile Ser Glu Thr Ser Thr Pro Ala Val Ser Thr
3635                3640                3645

Pro Ser Glu Leu Pro Gln Gln Ala Asp Gln Glu Ser Val Glu Pro
3650                3655                3660

Val Gly Pro Ser Thr Pro Asn Met Ala Ala Gly Gln Leu Cys Thr
3665                3670                3675

Glu Leu Glu Asn Lys Leu Pro Asn Ser Asp Phe Ser Gln Ala Thr
3680                3685                3690

Pro Asn Gln Gln Thr Tyr Ala Asn Ser Glu Val Asp Lys Leu Ser
3695                3700                3705

Met Glu Thr Pro Ala Lys Thr Glu Glu Ile Lys Leu Glu Lys Ala
3710                3715                3720

Glu Thr Glu Ser Cys Pro Gly Gln Glu Glu Pro Lys Leu Glu Glu
3725                3730                3735

Gln Asn Gly Ser Lys Val Glu Gly Asn Ala Val Ala Cys Pro Val
3740                3745                3750

Ser Ser Ala Gln Ser Pro Pro His Ser Ala Gly Ala Pro Ala Ala
3755                3760                3765

Lys Gly Asp Ser Gly Asn Glu Leu Leu Lys His Leu Leu Lys Asn
3770                3775                3780

Lys Lys Ser Ser Ser Leu Leu Asn Gln Lys Pro Glu Gly Ser Ile
3785                3790                3795

Cys Ser Glu Asp Asp Cys Thr Lys Asp Asn Lys Leu Val Glu Lys
3800                3805                3810

Gln Asn Pro Ala Glu Gly Leu Gln Thr Leu Gly Ala Gln Met Gln
3815                3820                3825

Gly Gly Phe Gly Cys Gly Asn Gln Leu Pro Lys Thr Asp Gly Gly
```

```
            3830                3835                3840

Ser Glu Thr Lys Lys Gln Arg Ser Lys Arg Thr Gln Arg Thr Gly
            3845                3850                3855

Glu Lys Ala Ala Pro Arg Ser Lys Lys Arg Lys Lys Asp Glu Glu
            3860                3865                3870

Glu Lys Gln Ala Met Tyr Ser Ser Thr Asp Thr Phe Thr His Leu
            3875                3880                3885

Lys Gln Val Arg Gln Leu Ser Leu Leu Pro Leu Met Glu Pro Ile
            3890                3895                3900

Ile Gly Val Asn Phe Ala His Phe Leu Pro Tyr Gly Ser Gly Gln
            3905                3910                3915

Phe Asn Ser Gly Asn Arg Leu Leu Gly Thr Phe Gly Ser Ala Thr
            3920                3925                3930

Leu Glu Gly Val Ser Asp Tyr Tyr Ser Gln Leu Ile Tyr Lys Gln
            3935                3940                3945

Asn Asn Leu Ser Asn Pro Pro Thr Pro Pro Ala Ser Leu Pro Pro
            3950                3955                3960

Thr Pro Pro Pro Met Ala Cys Gln Lys Met Ala Asn Gly Phe Ala
            3965                3970                3975

Thr Thr Glu Glu Leu Ala Gly Lys Ala Gly Val Leu Val Ser His
            3980                3985                3990

Glu Val Thr Lys Thr Leu Gly Pro Lys Pro Phe Gln Leu Pro Phe
            3995                4000                4005

Arg Pro Gln Asp Asp Leu Leu Ala Arg Ala Leu Ala Gln Gly Pro
            4010                4015                4020

Lys Thr Val Asp Val Pro Ala Ser Leu Pro Thr Pro Pro His Asn
            4025                4030                4035

Asn Gln Glu Glu Leu Arg Ile Gln Asp His Cys Gly Asp Arg Asp
            4040                4045                4050

Thr Pro Asp Ser Phe Val Pro Ser Ser Ser Pro Glu Ser Val Val
            4055                4060                4065

Gly Val Glu Val Ser Arg Tyr Pro Asp Leu Ser Leu Val Lys Glu
            4070                4075                4080

Glu Pro Pro Glu Pro Val Pro Ser Pro Ile Ile Pro Ile Leu Pro
            4085                4090                4095

Ser Thr Ala Gly Lys Ser Ser Glu Ser Arg Arg Asn Asp Ile Lys
            4100                4105                4110

Thr Glu Pro Gly Thr Leu Tyr Phe Ala Ser Pro Phe Gly Pro Ser
            4115                4120                4125

Pro Asn Gly Pro Arg Ser Gly Leu Ile Ser Val Ala Ile Thr Leu
            4130                4135                4140

His Pro Thr Ala Ala Glu Asn Ile Ser Ser Val Val Ala Ala Phe
            4145                4150                4155

Ser Asp Leu Leu His Val Arg Ile Pro Asn Ser Tyr Glu Val Ser
            4160                4165                4170

Ser Ala Pro Asp Val Pro Ser Met Gly Leu Val Ser Ser His Arg
            4175                4180                4185

Ile Asn Pro Gly Leu Glu Tyr Arg Gln His Leu Leu Leu Arg Gly
            4190                4195                4200

Pro Pro Pro Gly Ser Ala Asn Pro Pro Arg Leu Val Ser Ser Tyr
            4205                4210                4215

Arg Leu Lys Gln Pro Asn Val Pro Phe Pro Pro Thr Ser Asn Gly
            4220                4225                4230
```

```
Leu Ser Gly Tyr Lys Asp Ser Ser His Gly Ile Ala Glu Ser Ala
    4235            4240                4245
Ala Leu Arg Pro Gln Trp Cys Cys His Cys Lys Val Val Ile Leu
    4250            4255                4260
Gly Ser Gly Val Arg Lys Ser Phe Lys Asp Leu Thr Leu Leu Asn
    4265            4270                4275
Lys Asp Ser Arg Glu Ser Thr Lys Arg Val Glu Lys Asp Ile Val
    4280            4285                4290
Phe Cys Ser Asn Asn Cys Phe Ile Leu Tyr Ser Ser Thr Ala Gln
    4295            4300                4305
Ala Lys Asn Ser Glu Asn Lys Glu Ser Ile Pro Ser Leu Pro Gln
    4310            4315                4320
Ser Pro Met Arg Glu Thr Pro Ser Lys Ala Phe His Gln Tyr Ser
    4325            4330                4335
Asn Asn Ile Ser Thr Leu Asp Val His Cys Leu Pro Gln Leu Pro
    4340            4345                4350
Glu Lys Ala Ser Pro Pro Ala Ser Pro Pro Ile Ala Phe Pro Pro
    4355            4360                4365
Ala Phe Glu Ala Ala Gln Val Glu Ala Lys Pro Asp Glu Leu Lys
    4370            4375                4380
Val Thr Val Lys Leu Lys Pro Arg Leu Arg Ala Val His Gly Gly
    4385            4390                4395
Phe Glu Asp Cys Arg Pro Leu Asn Lys Lys Trp Arg Gly Met Lys
    4400            4405                4410
Trp Lys Lys Trp Ser Ile His Ile Val Ile Pro Lys Gly Thr Phe
    4415            4420                4425
Lys Pro Pro Cys Glu Asp Glu Ile Asp Glu Phe Leu Lys Lys Leu
    4430            4435                4440
Gly Thr Ser Leu Lys Pro Asp Pro Val Pro Lys Asp Tyr Arg Lys
    4445            4450                4455
Cys Cys Phe Cys His Glu Glu Gly Asp Gly Leu Thr Asp Gly Pro
    4460            4465                4470
Ala Arg Leu Leu Asn Leu Asp Leu Asp Leu Trp Val His Leu Asn
    4475            4480                4485
Cys Ala Leu Trp Ser Thr Glu Val Tyr Glu Thr Gln Ala Gly Ala
    4490            4495                4500
Leu Ile Asn Val Glu Leu Ala Leu Arg Arg Gly Leu Gln Met Lys
    4505            4510                4515
Cys Val Phe Cys His Lys Thr Gly Ala Thr Ser Gly Cys His Arg
    4520            4525                4530
Phe Arg Cys Thr Asn Ile Tyr His Phe Thr Cys Ala Ile Lys Ala
    4535            4540                4545
Gln Cys Met Phe Phe Lys Asp Lys Thr Met Leu Cys Pro Met His
    4550            4555                4560
Lys Pro Lys Gly Ile His Glu Gln Glu Leu Ser Tyr Phe Ala Val
    4565            4570                4575
Phe Arg Arg Val Tyr Val Gln Arg Asp Glu Val Arg Gln Ile Ala
    4580            4585                4590
Ser Ile Val Gln Arg Gly Glu Arg Asp His Thr Phe Arg Val Gly
    4595            4600                4605
Ser Leu Ile Phe His Thr Ile Gly Gln Leu Leu Pro Gln Gln Met
    4610            4615                4620
```

-continued

| | | | | | | | | | | | | | | |
|---|---|---|---|---|---|---|---|---|---|---|---|---|---|---|
|Gln|Ala|Phe|His|Ser|Pro|Lys|Ala|Leu|Phe|Pro|Val|Gly|Tyr|Glu|
| |4625| | | |4630| | | |4635| | | | | |

Gln Ala Phe His Ser Pro Lys Ala Leu Phe Pro Val Gly Tyr Glu
    4625            4630            4635

Ala Ser Arg Leu Tyr Trp Ser Thr Arg Tyr Ala Asn Arg Arg Cys
    4640            4645            4650

Arg Tyr Leu Cys Ser Ile Glu Glu Lys Asp Gly Arg Pro Val Phe
    4655            4660            4665

Val Ile Arg Ile Val Glu Gln Gly His Glu Asp Leu Val Leu Ser
    4670            4675            4680

Asp Ile Ser Pro Lys Gly Val Trp Asp Lys Ile Leu Glu Pro Val
    4685            4690            4695

Ala Cys Val Arg Lys Lys Ser Glu Met Leu Gln Leu Phe Pro Ala
    4700            4705            4710

Tyr Leu Lys Gly Glu Asp Leu Phe Gly Leu Thr Val Ser Ala Val
    4715            4720            4725

Ala Arg Ile Ala Glu Ser Leu Pro Gly Val Glu Ala Cys Glu Asn
    4730            4735            4740

Tyr Thr Phe Arg Tyr Gly Arg Asn Pro Leu Met Glu Leu Pro Leu
    4745            4750            4755

Ala Val Asn Pro Thr Gly Cys Ala Arg Ser Glu Pro Lys Met Ser
    4760            4765            4770

Ala His Val Lys Arg Phe Val Leu Arg Pro His Thr Leu Asn Ser
    4775            4780            4785

Thr Ser Thr Ser Lys Ser Phe Gln Ser Thr Val Thr Gly Glu Leu
    4790            4795            4800

Asn Ala Pro Tyr Ser Lys Gln Phe Val His Ser Lys Ser Ser Gln
    4805            4810            4815

Tyr Arg Lys Met Lys Thr Glu Trp Lys Ser Asn Val Tyr Leu Ala
    4820            4825            4830

Arg Ser Arg Ile Gln Gly Leu Gly Leu Tyr Ala Arg Asp Ile
    4835            4840            4845

Glu Lys His Thr Met Val Ile Glu Tyr Ile Gly Thr Ile Ile Arg
    4850            4855            4860

Asn Glu Val Ala Asn Arg Lys Glu Lys Leu Tyr Glu Ser Gln Asn
    4865            4870            4875

Arg Gly Val Tyr Met Phe Arg Met Asp Asn Asp His Val Ile Asp
    4880            4885            4890

Ala Thr Leu Thr Gly Gly Pro Ala Arg Tyr Ile Asn His Ser Cys
    4895            4900            4905

Ala Pro Asn Cys Val Ala Glu Val Val Thr Phe Glu Arg Gly His
    4910            4915            4920

Lys Ile Ile Ile Ser Ser Ser Arg Arg Ile Gln Lys Gly Glu Glu
    4925            4930            4935

Leu Cys Tyr Asp Tyr Lys Phe Asp Phe Glu Asp Asp Gln His Lys
    4940            4945            4950

Ile Pro Cys His Cys Gly Ala Val Asn Cys Arg Lys Trp Met Asn
    4955            4960            4965

<210> SEQ ID NO 50
<211> LENGTH: 2715
<212> TYPE: PRT
<213> ORGANISM: Homo sapiens

<400> SEQUENCE: 50

Met Ala Ala Ala Ala Gly Gly Gly Ser Cys Pro Gly Pro Gly Ser Ala
1               5                   10                  15

```
Arg Gly Arg Phe Pro Gly Arg Pro Arg Gly Ala Gly Gly Gly Gly
            20                  25                  30

Arg Gly Gly Arg Gly Asn Gly Ala Glu Arg Val Arg Val Ala Leu Arg
        35                  40                  45

Arg Gly Gly Gly Ala Thr Gly Pro Gly Gly Ala Glu Pro Gly Glu Asp
50                      55                  60

Thr Ala Leu Leu Arg Leu Leu Gly Leu Arg Arg Gly Leu Arg Arg Leu
65                  70                  75                  80

Arg Arg Leu Trp Ala Gly Pro Arg Val Gln Arg Gly Arg Gly Arg Gly
                85                  90                  95

Arg Gly Arg Gly Trp Gly Pro Ser Arg Gly Cys Val Pro Glu Glu
        100                 105                 110

Ser Ser Asp Gly Glu Ser Asp Glu Glu Phe Gln Gly Phe His Ser
        115                 120                 125

Asp Glu Asp Val Ala Pro Ser Ser Leu Arg Ser Ala Leu Arg Ser Gln
130                 135                 140

Arg Gly Arg Ala Pro Arg Gly Arg Gly Arg Lys His Lys Thr Thr Pro
145                 150                 155                 160

Leu Pro Pro Pro Arg Leu Ala Asp Val Ala Pro Thr Pro Pro Lys Thr
                165                 170                 175

Pro Ala Arg Lys Arg Gly Glu Glu Gly Thr Glu Arg Met Val Gln Ala
            180                 185                 190

Leu Thr Glu Leu Leu Arg Arg Ala Gln Ala Pro Gln Ala Pro Arg Ser
        195                 200                 205

Arg Ala Cys Glu Pro Ser Thr Pro Arg Arg Ser Arg Gly Arg Pro Pro
210                 215                 220

Gly Arg Pro Ala Gly Pro Cys Arg Arg Lys Gln Gln Ala Val Val Val
225                 230                 235                 240

Ala Glu Ala Ala Val Thr Ile Pro Lys Pro Glu Pro Pro Pro Val
                245                 250                 255

Val Pro Val Lys His Gln Thr Gly Ser Trp Lys Cys Lys Glu Gly Pro
            260                 265                 270

Gly Pro Gly Pro Gly Thr Pro Arg Arg Gly Gly Gln Ser Ser Arg Gly
        275                 280                 285

Gly Arg Gly Gly Arg Gly Arg Gly Arg Gly Gly Leu Pro Phe Val
290                 295                 300

Ile Lys Phe Val Ser Arg Ala Lys Lys Val Lys Met Gly Gln Leu Ser
305                 310                 315                 320

Leu Gly Leu Glu Ser Gly Gln Gly Gln Gly Gln His Glu Glu Ser Trp
                325                 330                 335

Gln Asp Val Pro Gln Arg Arg Val Gly Ser Gly Gln Gly Gly Ser Pro
            340                 345                 350

Cys Trp Lys Lys Gln Glu Gln Lys Leu Asp Asp Glu Glu Glu Lys
        355                 360                 365

Lys Glu Glu Glu Lys Asp Lys Glu Gly Glu Glu Lys Glu Glu Arg
        370                 375                 380

Ala Val Ala Glu Glu Met Met Pro Ala Ala Glu Lys Glu Glu Ala Lys
385                 390                 395                 400

Leu Pro Pro Pro Pro Leu Thr Pro Pro Ala Pro Ser Pro Pro Pro
                405                 410                 415

Leu Pro Pro Pro Ser Thr Ser Pro Pro Pro Leu Cys Pro Pro Pro
                420                 425                 430
```

```
Pro Pro Pro Val Ser Pro Pro Leu Pro Ser Pro Pro Pro Pro
        435             440             445

Ala Gln Glu Glu Gln Glu Glu Ser Pro Pro Val Val Pro Ala Thr
450             455             460

Cys Ser Arg Lys Arg Gly Arg Pro Pro Leu Thr Pro Ser Gln Arg Ala
465             470             475             480

Glu Arg Glu Ala Ala Arg Ala Gly Pro Glu Gly Thr Ser Pro Thr
            485             490             495

Pro Thr Pro Ser Thr Ala Thr Gly Gly Pro Pro Glu Asp Ser Pro Thr
        500             505             510

Val Ala Pro Lys Ser Thr Thr Phe Leu Lys Asn Ile Arg Gln Phe Ile
        515             520             525

Met Pro Val Val Ser Ala Arg Ser Ser Arg Val Ile Lys Thr Pro Arg
    530             535             540

Arg Phe Met Asp Glu Asp Pro Pro Lys Pro Pro Lys Val Glu Val Ser
545             550             555             560

Pro Val Leu Arg Pro Ile Thr Thr Ser Pro Val Pro Gln Glu
            565             570             575

Pro Ala Pro Val Pro Ser Pro Pro Arg Ala Pro Thr Pro Pro Ser Thr
            580             585             590

Pro Val Pro Leu Pro Glu Lys Arg Arg Ser Ile Leu Arg Glu Pro Thr
        595             600             605

Phe Arg Trp Thr Ser Leu Thr Arg Glu Leu Pro Pro Pro Pro Ala
    610             615             620

Pro Pro Pro Pro Pro Ala Pro Ser Pro Pro Ala Pro Ala Thr Ser
625             630             635             640

Ser Arg Arg Pro Leu Leu Leu Arg Ala Pro Gln Phe Thr Pro Ser Glu
            645             650             655

Ala His Leu Lys Ile Tyr Glu Ser Val Leu Thr Pro Pro Leu Gly
            660             665             670

Ala Pro Glu Ala Pro Glu Pro Glu Pro Pro Ala Asp Asp Ser Pro
            675             680             685

Ala Glu Pro Glu Pro Arg Ala Val Gly Arg Thr Asn His Leu Ser Leu
    690             695             700

Pro Arg Phe Ala Pro Val Val Thr Thr Pro Val Lys Ala Glu Val Ser
705             710             715             720

Pro His Gly Ala Pro Ala Leu Ser Asn Gly Pro Gln Thr Gln Ala Gln
            725             730             735

Leu Leu Gln Pro Leu Gln Ala Leu Gln Thr Gln Leu Leu Pro Gln Ala
        740             745             750

Leu Pro Pro Pro Gln Pro Gln Leu Gln Pro Pro Ser Pro Gln Gln
        755             760             765

Met Pro Pro Leu Glu Lys Ala Arg Ile Ala Gly Val Gly Ser Leu Pro
    770             775             780

Leu Ser Gly Val Glu Glu Lys Met Phe Ser Leu Leu Lys Arg Ala Lys
785             790             795             800

Val Gln Leu Phe Lys Ile Asp Gln Gln Gln Gln Lys Val Ala Ala
            805             810             815

Ser Met Pro Leu Ser Pro Gly Gly Gln Met Glu Val Ala Gly Ala
            820             825             830

Val Lys Gln Ile Ser Asp Arg Gly Pro Val Arg Ser Glu Asp Glu Ser
        835             840             845

Val Glu Ala Lys Arg Glu Arg Pro Ser Gly Pro Glu Ser Pro Val Gln
```

-continued

```
               850                 855                 860
Gly Pro Arg Ile Lys His Val Cys Arg His Ala Ala Val Ala Leu Gly
865                 870                 875                 880

Gln Ala Arg Ala Met Val Pro Glu Asp Val Pro Arg Leu Ser Ala Leu
                885                 890                 895

Pro Leu Arg Asp Arg Gln Asp Leu Ala Thr Glu Asp Thr Ser Ser Ala
                900                 905                 910

Ser Glu Thr Glu Ser Val Pro Ser Arg Ser Arg Arg Gly Lys Val Glu
                915                 920                 925

Ala Ala Gly Pro Gly Gly Glu Ser Glu Pro Thr Gly Ser Gly Gly Thr
                930                 935                 940

Leu Ala His Thr Pro Arg Arg Ser Leu Pro Ser His His Gly Lys Lys
945                 950                 955                 960

Met Arg Met Ala Arg Cys Gly His Cys Arg Gly Cys Leu Arg Val Gln
                965                 970                 975

Asp Cys Gly Ser Cys Val Asn Cys Leu Asp Lys Pro Lys Phe Gly Gly
                980                 985                 990

Pro Asn Thr Lys Lys Gln Cys Cys  Val Tyr Arg Lys Cys  Asp Lys Ile
                995                 1000                1005

Glu Ala  Arg Lys Met Glu Arg  Leu Ala Lys Lys Gly  Arg Thr Ile
    1010                1015                1020

Val Lys  Thr Leu Leu Pro Trp  Asp Ser Asp Glu Ser  Pro Glu Ala
    1025                1030                1035

Ser Pro  Gly Pro Pro Gly Pro  Arg Arg Gly Ala Gly  Ala Gly Gly
    1040                1045                1050

Pro Arg  Glu Glu Val Val Ala  His Pro Gly Pro Glu  Glu Gln Asp
    1055                1060                1065

Ser Leu  Leu Gln Arg Lys Ser  Ala Arg Arg Cys Val  Lys Gln Arg
    1070                1075                1080

Pro Ser  Tyr Asp Ile Phe Glu  Asp Ser Asp Asp Ser  Glu Pro Gly
    1085                1090                1095

Gly Pro  Pro Ala Pro Arg Arg  Arg Thr Pro Arg Glu  Asn Glu Leu
    1100                1105                1110

Pro Leu  Pro Glu Pro Glu Glu  Gln Ser Arg Pro Arg  Lys Pro Thr
    1115                1120                1125

Leu Gln  Pro Val Leu Gln Leu  Lys Ala Arg Arg Arg  Leu Asp Lys
    1130                1135                1140

Asp Ala  Leu Ala Pro Gly Pro  Phe Ala Ser Phe Pro  Asn Gly Trp
    1145                1150                1155

Thr Gly  Lys Gln Lys Ser Pro  Asp Gly Val His Arg  Val Arg Val
    1160                1165                1170

Asp Phe  Lys Glu Asp Cys Asp  Leu Glu Asn Val Trp  Leu Met Gly
    1175                1180                1185

Gly Leu  Ser Val Leu Thr Ser  Val Pro Gly Gly Pro  Pro Met Val
    1190                1195                1200

Cys Leu  Leu Cys Ala Ser Lys  Gly Leu His Glu Leu  Val Phe Cys
    1205                1210                1215

Gln Val  Cys Cys Asp Pro Phe  His Pro Phe Cys Leu  Glu Glu Ala
    1220                1225                1230

Glu Arg  Pro Leu Pro Gln His  His Asp Thr Trp Cys  Cys Arg Arg
    1235                1240                1245

Cys Lys  Phe Cys His Val Cys  Gly Arg Lys Gly Arg  Gly Ser Lys
    1250                1255                1260
```

-continued

```
His Leu Leu Glu Cys Glu Arg Cys Arg His Ala Tyr His Pro Ala
    1265            1270            1275

Cys Leu Gly Pro Ser Tyr Pro Thr Arg Ala Thr Arg Lys Arg Arg
    1280            1285            1290

His Trp Ile Cys Ser Ala Cys Val Arg Cys Lys Ser Cys Gly Ala
    1295            1300            1305

Thr Pro Gly Lys Asn Trp Asp Val Glu Trp Ser Gly Asp Tyr Ser
    1310            1315            1320

Leu Cys Pro Arg Cys Thr Gln Leu Tyr Glu Lys Gly Asn Tyr Cys
    1325            1330            1335

Pro Ile Cys Thr Arg Cys Tyr Glu Asp Asn Asp Tyr Glu Ser Lys
    1340            1345            1350

Met Met Gln Cys Ala Gln Cys Asp His Trp Val His Ala Lys Cys
    1355            1360            1365

Glu Gly Leu Ser Asp Glu Asp Tyr Glu Ile Leu Ser Gly Leu Pro
    1370            1375            1380

Asp Ser Val Leu Tyr Thr Cys Gly Pro Cys Ala Gly Ala Ala Gln
    1385            1390            1395

Pro Arg Trp Arg Glu Ala Leu Ser Gly Ala Leu Gln Gly Gly Leu
    1400            1405            1410

Arg Gln Val Leu Gln Gly Leu Leu Ser Ser Lys Val Val Gly Pro
    1415            1420            1425

Leu Leu Leu Cys Thr Gln Cys Gly Pro Asp Gly Lys Gln Leu His
    1430            1435            1440

Pro Gly Pro Cys Gly Leu Gln Ala Val Ser Gln Arg Phe Glu Asp
    1445            1450            1455

Gly His Tyr Lys Ser Val His Ser Phe Met Glu Asp Met Val Gly
    1460            1465            1470

Ile Leu Met Arg His Ser Glu Glu Gly Glu Thr Pro Asp Arg Arg
    1475            1480            1485

Ala Gly Gly Gln Met Lys Gly Leu Leu Leu Lys Leu Leu Glu Ser
    1490            1495            1500

Ala Phe Gly Trp Phe Asp Ala His Asp Pro Lys Tyr Trp Arg Arg
    1505            1510            1515

Ser Thr Arg Leu Pro Asn Gly Val Leu Pro Asn Ala Val Leu Pro
    1520            1525            1530

Pro Ser Leu Asp His Val Tyr Ala Gln Trp Arg Gln Gln Glu Pro
    1535            1540            1545

Glu Thr Pro Glu Ser Gly Gln Pro Pro Gly Asp Pro Ser Ala Ala
    1550            1555            1560

Phe Gln Gly Lys Asp Pro Ala Ala Phe Ser His Leu Glu Asp Pro
    1565            1570            1575

Arg Gln Cys Ala Leu Cys Leu Lys Tyr Gly Asp Ala Asp Ser Lys
    1580            1585            1590

Glu Ala Gly Arg Leu Leu Tyr Ile Gly Gln Asn Glu Trp Thr His
    1595            1600            1605

Val Asn Cys Ala Ile Trp Ser Ala Glu Val Phe Glu Glu Asn Asp
    1610            1615            1620

Gly Ser Leu Lys Asn Val His Ala Ala Val Ala Arg Gly Arg Gln
    1625            1630            1635

Met Arg Cys Glu Leu Cys Leu Lys Pro Gly Ala Thr Val Gly Cys
    1640            1645            1650
```

-continued

```
Cys Leu Ser Ser Cys Leu Ser Asn Phe His Phe Met Cys Ala Arg
1655                1660                1665

Ala Ser Tyr Cys Ile Phe Gln Asp Asp Lys Lys Val Phe Cys Gln
1670                1675                1680

Lys His Thr Asp Leu Leu Asp Gly Lys Glu Ile Val Asn Pro Asp
1685                1690                1695

Gly Phe Asp Val Leu Arg Arg Val Tyr Val Asp Phe Glu Gly Ile
1700                1705                1710

Asn Phe Lys Arg Lys Phe Leu Thr Gly Leu Glu Pro Asp Ala Ile
1715                1720                1725

Asn Val Leu Ile Gly Ser Ile Arg Ile Asp Ser Leu Gly Thr Leu
1730                1735                1740

Ser Asp Leu Ser Asp Cys Glu Gly Arg Leu Phe Pro Ile Gly Tyr
1745                1750                1755

Gln Cys Ser Arg Leu Tyr Trp Ser Thr Val Asp Ala Arg Arg Arg
1760                1765                1770

Cys Trp Tyr Arg Cys Arg Ile Leu Glu Tyr Arg Pro Trp Gly Pro
1775                1780                1785

Arg Glu Glu Pro Ala His Leu Glu Ala Ala Glu Asn Gln Thr
1790                1795                1800

Ile Val His Ser Pro Ala Pro Ser Ser Glu Pro Pro Gly Gly Glu
1805                1810                1815

Asp Pro Pro Leu Asp Thr Asp Val Leu Val Pro Gly Ala Pro Glu
1820                1825                1830

Arg His Ser Pro Ile Gln Asn Leu Asp Pro Pro Leu Arg Pro Asp
1835                1840                1845

Ser Gly Ser Ala Pro Pro Pro Ala Pro Arg Ser Phe Ser Gly Ala
1850                1855                1860

Arg Ile Lys Val Pro Asn Tyr Ser Pro Ser Arg Arg Pro Leu Gly
1865                1870                1875

Gly Val Ser Phe Gly Pro Leu Pro Ser Pro Gly Ser Pro Ser Ser
1880                1885                1890

Leu Thr His His Ile Pro Thr Val Gly Asp Pro Asp Phe Pro Ala
1895                1900                1905

Pro Pro Arg Arg Ser Arg Arg Pro Ser Pro Leu Ala Pro Arg Pro
1910                1915                1920

Pro Pro Ser Arg Trp Ala Ser Pro Pro Leu Lys Thr Ser Pro Gln
1925                1930                1935

Leu Arg Val Pro Pro Pro Thr Ser Val Val Thr Ala Leu Thr Pro
1940                1945                1950

Thr Ser Gly Glu Leu Ala Pro Pro Gly Pro Ala Pro Ser Pro Pro
1955                1960                1965

Pro Pro Glu Asp Leu Gly Pro Asp Phe Glu Asp Met Glu Val Val
1970                1975                1980

Ser Gly Leu Ser Ala Ala Asp Leu Asp Phe Ala Ala Ser Leu Leu
1985                1990                1995

Gly Thr Glu Pro Phe Gln Glu Glu Ile Val Ala Ala Gly Ala Met
2000                2005                2010

Gly Ser Ser His Gly Gly Pro Gly Asp Ser Ser Glu Glu Ser
2015                2020                2025

Ser Pro Thr Ser Arg Tyr Ile His Phe Pro Val Thr Val Val Ser
2030                2035                2040

Ala Pro Gly Leu Ala Pro Ser Ala Thr Pro Gly Ala Pro Arg Ile
```

-continued

```
            2045                2050                2055
Glu Gln Leu Asp Gly Val Asp Asp Gly Thr Asp Ser Glu Ala Glu
            2060                2065                2070
Ala Val Gln Gln Pro Arg Gly Gln Gly Thr Pro Ser Gly Pro
            2075                2080                2085
Gly Val Val Arg Ala Gly Val Leu Gly Ala Ala Gly Asp Arg Ala
            2090                2095                2100
Arg Pro Pro Glu Asp Leu Pro Ser Glu Ile Val Asp Phe Val Leu
            2105                2110                2115
Lys Asn Leu Gly Gly Pro Gly Asp Gly Gly Ala Gly Pro Arg Glu
            2120                2125                2130
Glu Ser Leu Pro Pro Ala Pro Pro Leu Ala Asn Gly Ser Gln Pro
            2135                2140                2145
Ser Gln Gly Leu Thr Ala Ser Pro Ala Asp Pro Thr Arg Thr Phe
            2150                2155                2160
Ala Trp Leu Pro Gly Ala Pro Gly Val Arg Val Leu Ser Leu Gly
            2165                2170                2175
Pro Ala Pro Glu Pro Pro Lys Pro Ala Thr Ser Lys Ile Ile Leu
            2180                2185                2190
Val Asn Lys Leu Gly Gln Val Phe Val Lys Met Ala Gly Glu Gly
            2195                2200                2205
Glu Pro Val Pro Pro Val Lys Gln Pro Pro Leu Pro Pro Thr
            2210                2215                2220
Ile Ser Pro Thr Ala Pro Thr Ser Trp Thr Leu Pro Pro Gly Pro
            2225                2230                2235
Leu Leu Gly Val Leu Pro Val Val Gly Val Val Arg Pro Ala Pro
            2240                2245                2250
Pro Pro Pro Pro Pro Pro Leu Thr Leu Val Leu Ser Ser Gly Pro
            2255                2260                2265
Ala Ser Pro Pro Arg Gln Ala Ile Arg Val Lys Arg Val Ser Thr
            2270                2275                2280
Phe Ser Gly Arg Ser Pro Pro Ala Pro Pro Tyr Lys Ala Pro
            2285                2290                2295
Arg Leu Asp Glu Asp Gly Glu Ala Ser Glu Asp Thr Pro Gln Val
            2300                2305                2310
Pro Gly Leu Gly Ser Gly Gly Phe Ser Arg Val Arg Met Lys Thr
            2315                2320                2325
Pro Thr Val Arg Gly Val Leu Asp Leu Asp Arg Pro Gly Glu Pro
            2330                2335                2340
Ala Gly Glu Glu Ser Pro Gly Pro Leu Gln Glu Arg Ser Pro Leu
            2345                2350                2355
Leu Pro Leu Pro Glu Asp Gly Pro Pro Gln Val Pro Asp Gly Pro
            2360                2365                2370
Pro Asp Leu Leu Leu Glu Ser Gln Trp His His Tyr Ser Gly Glu
            2375                2380                2385
Ala Ser Ser Ser Glu Glu Pro Pro Ser Pro Asp Asp Lys Glu
            2390                2395                2400
Asn Gln Ala Pro Lys Arg Thr Gly Pro His Leu Arg Phe Glu Ile
            2405                2410                2415
Ser Ser Glu Asp Gly Phe Ser Val Glu Ala Glu Ser Leu Glu Gly
            2420                2425                2430
Ala Trp Arg Thr Leu Ile Glu Lys Val Gln Glu Ala Arg Gly His
            2435                2440                2445
```

```
Ala Arg Leu Arg His Leu Ser Phe Ser Gly Met Ser Gly Ala Arg
    2450                2455                2460

Leu Leu Gly Ile His His Asp Ala Val Ile Phe Leu Ala Glu Gln
    2465                2470                2475

Leu Pro Gly Ala Gln Arg Cys Gln His Tyr Lys Phe Arg Tyr His
    2480                2485                2490

Gln Gln Gly Glu Gly Gln Glu Glu Pro Pro Leu Asn Pro His Gly
    2495                2500                2505

Ala Ala Arg Ala Glu Val Tyr Leu Arg Lys Cys Thr Phe Asp Met
    2510                2515                2520

Phe Asn Phe Leu Ala Ser Gln His Arg Val Leu Pro Glu Gly Ala
    2525                2530                2535

Thr Cys Asp Glu Glu Glu Asp Glu Val Gln Leu Arg Ser Thr Arg
    2540                2545                2550

Arg Ala Thr Ser Leu Glu Leu Pro Met Ala Met Arg Phe Arg His
    2555                2560                2565

Leu Lys Lys Thr Ser Lys Glu Ala Val Gly Val Tyr Arg Ser Ala
    2570                2575                2580

Ile His Gly Arg Gly Leu Phe Cys Lys Arg Asn Ile Asp Ala Gly
    2585                2590                2595

Glu Met Val Ile Glu Tyr Ser Gly Ile Val Ile Arg Ser Val Leu
    2600                2605                2610

Thr Asp Lys Arg Glu Lys Phe Tyr Asp Gly Lys Gly Ile Gly Cys
    2615                2620                2625

Tyr Met Phe Arg Met Asp Asp Phe Asp Val Val Asp Ala Thr Met
    2630                2635                2640

His Gly Asn Ala Ala Arg Phe Ile Asn His Ser Cys Glu Pro Asn
    2645                2650                2655

Cys Phe Ser Arg Val Ile His Val Glu Gly Gln Lys His Ile Val
    2660                2665                2670

Ile Phe Ala Leu Arg Arg Ile Leu Arg Gly Glu Glu Leu Thr Tyr
    2675                2680                2685

Asp Tyr Lys Phe Pro Ile Glu Asp Ala Ser Asn Lys Leu Pro Cys
    2690                2695                2700

Asn Cys Gly Ala Lys Arg Cys Arg Arg Phe Leu Asn
    2705                2710                2715

<210> SEQ ID NO 51
<211> LENGTH: 582
<212> TYPE: PRT
<213> ORGANISM: Homo sapiens

<400> SEQUENCE: 51

Met Ala Ala Ala Gly Gly Ser Cys Pro Gly Pro Gly Ser Ala
1               5                   10                  15

Arg Gly Arg Phe Pro Gly Arg Pro Arg Gly Ala Gly Gly Gly Gly
                20                  25                  30

Arg Gly Gly Arg Gly Asn Gly Ala Glu Arg Val Arg Val Ala Leu Arg
        35                  40                  45

Arg Gly Gly Gly Ala Thr Gly Pro Gly Gly Ala Glu Pro Gly Glu Asp
    50                  55                  60

Thr Ala Leu Leu Arg Leu Leu Gly Leu Arg Arg Gly Leu Arg Arg Leu
65                  70                  75                  80

Arg Arg Leu Trp Ala Gly Pro Arg Val Gln Arg Gly Arg Gly Arg Gly
```

```
                    85                  90                  95
Arg Gly Arg Gly Trp Gly Pro Ser Arg Gly Cys Val Pro Glu Glu Glu
            100                 105                 110

Ser Ser Asp Gly Glu Ser Asp Glu Glu Glu Phe Gln Gly Phe His Ser
            115                 120                 125

Asp Glu Asp Val Ala Pro Ser Ser Leu Arg Ser Ala Leu Arg Ser Gln
        130                 135                 140

Arg Gly Arg Ala Pro Arg Gly Arg Gly Arg Lys His Lys Thr Thr Pro
145                 150                 155                 160

Leu Pro Pro Pro Arg Leu Ala Asp Val Ala Pro Thr Pro Pro Lys Thr
                165                 170                 175

Pro Ala Arg Lys Arg Gly Glu Glu Gly Thr Glu Arg Met Val Gln Ala
            180                 185                 190

Leu Thr Glu Leu Leu Arg Arg Ala Gln Ala Pro Gln Ala Pro Arg Ser
            195                 200                 205

Arg Ala Cys Glu Pro Ser Thr Pro Arg Arg Ser Arg Gly Arg Pro Pro
        210                 215                 220

Gly Arg Pro Ala Gly Pro Cys Arg Arg Lys Gln Gln Ala Val Val Val
225                 230                 235                 240

Ala Glu Ala Ala Val Thr Ile Pro Lys Pro Glu Pro Pro Pro Pro Val
                245                 250                 255

Val Pro Val Lys His Gln Thr Gly Ser Trp Lys Cys Lys Glu Gly Pro
            260                 265                 270

Gly Pro Gly Pro Gly Thr Pro Arg Arg Gly Gly Gln Ser Ser Arg Gly
        275                 280                 285

Gly Arg Gly Gly Arg Gly Arg Gly Gly Gly Leu Pro Phe Val
        290                 295                 300

Ile Lys Phe Val Ser Arg Ala Lys Lys Val Lys Met Gly Gln Leu Ser
305                 310                 315                 320

Leu Gly Leu Glu Ser Gly Gln Gly Gln Gly His Glu Glu Ser Trp
                325                 330                 335

Gln Asp Val Pro Gln Arg Arg Val Gly Ser Gly Gln Gly Ser Pro
            340                 345                 350

Cys Trp Lys Lys Gln Glu Gln Lys Leu Asp Asp Glu Glu Glu Lys
        355                 360                 365

Lys Glu Glu Glu Lys Asp Lys Glu Gly Glu Lys Glu Glu Arg
        370                 375                 380

Ala Val Ala Glu Glu Met Met Pro Ala Ala Glu Lys Glu Glu Ala Lys
385                 390                 395                 400

Leu Pro Pro Pro Leu Thr Pro Pro Ala Pro Ser Pro Pro Pro Pro
                405                 410                 415

Leu Pro Pro Pro Ser Thr Ser Pro Pro Pro Leu Cys Pro Pro Pro
            420                 425                 430

Pro Pro Pro Val Ser Pro Pro Leu Pro Ser Pro Pro Pro Pro
        435                 440                 445

Ala Gln Glu Glu Gln Glu Ser Pro Pro Val Val Pro Ala Thr
            450                 455                 460

Cys Ser Arg Lys Arg Gly Arg Pro Pro Leu Thr Pro Ser Gln Arg Ala
465                 470                 475                 480

Glu Arg Glu Ala Ala Arg Ala Gly Pro Glu Gly Thr Ser Pro Thr
                485                 490                 495

Pro Thr Pro Ser Thr Ala Thr Gly Gly Pro Pro Glu Asp Ser Pro Thr
            500                 505                 510
```

```
Val Ala Pro Lys Ser Thr Thr Phe Leu Lys Asn Ile Arg Gln Phe Ile
            515                 520                 525

Met Pro Val Pro Leu Ser Gln Ser Leu Leu Pro Met Thr Leu Gln
        530                 535                 540

Leu Ser Leu Ser Leu Gly Gln Trp Ala Ala Pro Thr Thr Ser Ala Cys
545                 550                 555                 560

Leu Asp Ser Pro Leu Trp Ser Pro Leu Leu Arg Pro Arg Cys Pro
                565                 570                 575

Leu Thr Gly Leu Gln Leu
                580

<210> SEQ ID NO 52
<211> LENGTH: 1858
<212> TYPE: PRT
<213> ORGANISM: Homo sapiens

<400> SEQUENCE: 52

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
        35                  40                  45

Ser Ser His His Ser His Ser Tyr Ile Gly Leu Pro Tyr Ala Asp His
    50                  55                  60

Asn Tyr Gly Ala Arg Pro Pro Pro Thr Pro Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
        115                 120                 125

Asp Gly Tyr Met Ile Cys Cys Asp Lys Cys Ser Val Trp Gln His Ile
    130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
        195                 200                 205

Thr Pro Thr Ser Ile Thr Leu Thr Ala Ser Arg Val Ser Lys Val Asn
    210                 215                 220

Asp Lys Arg Arg Lys Lys Ser Gly Glu Lys Gln His Ile Ser Lys
225                 230                 235                 240

Cys Lys Lys Ala Phe Arg Glu Gly Ser Arg Lys Ser Ser Arg Val Lys
                245                 250                 255

Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
        275                 280                 285

Asn Asn Gln Tyr Ser Glu Gly Val Gln Arg Glu Ala Gln Arg Ile Ala
```

-continued

```
            290                 295                 300
Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
                340                 345                 350

Ala Leu Ile Ile Glu Tyr Arg Gly Lys Phe Met Leu Arg Glu Gln Phe
            355                 360                 365

Glu Ala Asn Gly Tyr Phe Phe Lys Arg Pro Tyr Pro Phe Val Leu Phe
            370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
                420                 425                 430

Ile His Ser Ile Pro Lys Gly Thr Glu Ile Thr Ile Ala Phe Asp Phe
            435                 440                 445

Asp Tyr Gly Asn Cys Lys Tyr Lys Val Asp Cys Ala Cys Leu Lys Glu
            450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
            515                 520                 525

Lys Leu Ser Pro Leu Arg Leu Ser Val Ser Asn Asn Gln Glu Pro Asp
            530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Arg Glu Gln Ala Leu Glu Arg Ile Ser Thr Ala
            595                 600                 605

Lys Thr Glu Val Lys Thr Glu Cys Lys Asp Thr Gln Ile Val Ser Asp
610                 615                 620

Ala Glu Val Ile Gln Glu Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Pro Asp Ile Glu Val Thr Ser
            675                 680                 685

Gln Gln Asn Asp Ile Glu Asn Thr Val Leu Thr Ile Glu Pro Glu Thr
            690                 695                 700

Glu Thr Ala Leu Ala Glu Ile Ile Thr Glu Thr Glu Val Pro Ala Leu
705                 710                 715                 720
```

-continued

```
Asn Lys Cys Pro Thr Lys Tyr Pro Lys Thr Lys Lys His Leu Val Asn
            725                 730                 735

Glu Trp Leu Ser Glu Lys Asn Glu Lys Thr Gly Lys Pro Ser Asp Gly
            740                 745                 750

Leu Ser Glu Arg Pro Leu Arg Ile Thr Thr Asp Pro Glu Val Leu Ala
            755                 760                 765

Thr Gln Leu Asn Ser Leu Pro Gly Leu Thr Tyr Ser Pro His Val Tyr
770                 775                 780

Ser Thr Pro Lys His Tyr Ile Arg Phe Thr Ser Pro Phe Leu Ser Glu
785                 790                 795                 800

Lys Arg Arg Lys Glu Pro Thr Glu Asn Ile Ser Gly Ser Cys Lys
            805                 810                 815

Lys Arg Trp Leu Lys Gln Ala Leu Glu Glu Asn Ser Ala Ile Leu
            820                 825                 830

His Arg Phe Asn Ser Pro Cys Gln Glu Arg Ser Arg Ser Pro Ala Val
            835                 840                 845

Asn Gly Glu Asn Lys Ser Pro Leu Leu Leu Asn Asp Ser Cys Ser Leu
            850                 855                 860

Pro Asp Leu Thr Thr Pro Leu Lys Lys Arg Arg Phe Tyr Gln Leu Leu
865                 870                 875                 880

Asp Ser Val Tyr Ser Glu Thr Ser Thr Pro Thr Pro Ser Pro Tyr Ala
            885                 890                 895

Thr Pro Thr His Thr Asp Ile Thr Pro Met Asp Pro Ser Phe Ala Thr
            900                 905                 910

Pro Pro Arg Ile Lys Ser Asp Asp Glu Thr Cys Arg Asn Gly Tyr Lys
            915                 920                 925

Pro Ile Tyr Ser Pro Val Thr Pro Val Thr Pro Gly Thr Pro Gly Asn
            930                 935                 940

Thr Met His Phe Glu Asn Ile Ser Ser Pro Glu Ser Ser Pro Glu Ile
945                 950                 955                 960

Lys Arg Arg Thr Tyr Ser Gln Glu Gly Tyr Asp Arg Ser Ser Thr Met
            965                 970                 975

Leu Thr Leu Gly Pro Phe Arg Asn Ser Asn Leu Thr Glu Leu Gly Leu
            980                 985                 990

Gln Glu Ile Lys Thr Ile Gly Tyr  Thr Ser Pro Arg Ser  Arg Thr Glu
            995                 1000                1005

Val Asn Arg Gln Cys Pro Gly  Glu Lys Glu Pro Val  Ser Asp Leu
1010                1015                 1020

Gln Leu Gly Leu Asp Ala Val  Glu Pro Thr Ala Leu  His Lys Thr
            1025                1030                 1035

Leu Glu Thr Pro Ala His Asp  Arg Ala Glu Pro Asn  Ser Gln Leu
            1040                1045                 1050

Asp Ser Thr His Ser Gly Arg  Gly Thr Met Tyr Ser  Ser Trp Val
            1055                1060                 1065

Lys Ser Pro Asp Arg Thr Gly  Val Asn Phe Ser Val  Asn Ser Asn
            1070                1075                 1080

Leu Arg Asp Leu Thr Pro Ser  His Gln Leu Glu Val  Gly Gly Gly
            1085                1090                 1095

Phe Arg Ile Ser Glu Ser Lys  Cys Leu Met Gln Asp  Asp Thr Arg
            1100                1105                 1110

Gly Met Phe Met Glu Thr Thr  Val Phe Cys Thr Ser  Glu Asp Gly
            1115                1120                 1125
```

-continued

Leu Val Ser Gly Phe Gly Arg Thr Val Asn Asp Asn Leu Ile Asp
1130                1135                1140

Gly Asn Cys Thr Pro Gln Asn Pro Pro Gln Lys Lys Lys Val Ser
1145                1150                1155

Leu Leu Glu Tyr Arg Lys Arg Gln Arg Glu Ala Arg Lys Ser Gly
1160                1165                1170

Ser Lys Thr Glu Asn Phe Pro Leu Ile Ser Val Ser Pro His Ala
1175                1180                1185

Ser Gly Ser Leu Ser Asn Asn Gly Asp Gly Cys Ala Ser Ser Asn
1190                1195                1200

Asp Asn Gly Glu Gln Val Asp His Thr Ala Ser Leu Pro Leu Pro
1205                1210                1215

Thr Pro Ala Thr Val Tyr Asn Ala Thr Ser Glu Glu Thr Ser Asn
1220                1225                1230

Asn Cys Pro Val Lys Asp Ala Thr Ala Ser Glu Lys Asn Glu Pro
1235                1240                1245

Glu Val Gln Trp Thr Ala Ser Thr Ser Val Glu Gln Val Arg Glu
1250                1255                1260

Arg Ser Tyr Gln Arg Ala Leu Leu Leu Ser Asp His Arg Lys Asp
1265                1270                1275

Lys Asp Ser Gly Gly Glu Ser Pro Cys Val Ser Cys Ser Pro Ser
1280                1285                1290

His Val Gln Ser Ser Pro Ser Ser His Ser Asn His Ile Pro Gln
1295                1300                1305

Leu Gln Ala Lys Gly Pro Val Pro Ser Phe Ser Glu Leu Met Glu
1310                1315                1320

Asp Pro Asp Pro Glu Asn Pro Glu Pro Thr Thr Asn Glu Cys
1325                1330                1335

Pro Ser Pro Asp Thr Ser Gln Asn Thr Cys Lys Ser Pro Pro Lys
1340                1345                1350

Met Ser Lys Pro Gly Ser Pro Gly Ser Val Ile Pro Ala Gln Ala
1355                1360                1365

His Gly Lys Ile Phe Thr Lys Pro Asp Pro Gln Trp Asp Ser Thr
1370                1375                1380

Val Ser Ala Ser Glu Ala Glu Asn Gly Val His Leu Lys Thr Glu
1385                1390                1395

Leu Gln Gln Lys Gln Leu Ser Asn Asn Asn Gln Ala Leu Ser Lys
1400                1405                1410

Asn His Pro Pro Gln Thr His Val Arg Asn Ser Ser Glu Gln Leu
1415                1420                1425

Ser Gln Lys Leu Pro Ser Val Pro Thr Lys Leu His Cys Pro Pro
1430                1435                1440

Ser Pro His Leu Glu Asn Pro Pro Lys Ser Ser Thr Pro His Thr
1445                1450                1455

Pro Val Gln His Gly Tyr Leu Ser Pro Lys Pro Pro Ser Gln Gln
1460                1465                1470

Leu Gly Ser Pro Tyr Arg Pro His His Ser Gln Ser Pro Gln Val
1475                1480                1485

Gly Thr Pro Gln Arg Glu Pro Gln Arg Asn Phe Tyr Pro Ala Ala
1490                1495                1500

Gln Asn Leu Pro Ala Asn Thr Gln Gln Ala Thr Ser Gly Thr Leu
1505                1510                1515

Phe Thr Gln Thr Pro Ser Gly Gln Ser Ser Ala Thr Tyr Ser Gln

```
                    1520                1525                1530

Phe Asn Gln Gln Ser Leu Asn Ser Thr Ala Pro Pro Pro Pro Pro
            1535                1540                1545

Pro Pro Pro Pro Ser Ser Ser Tyr Tyr Gln Asn Gln Gln Pro Ser
            1550                1555                1560

Ala Asn Phe Gln Asn Tyr Asn Gln Leu Lys Gly Ser Leu Ser Gln
            1565                1570                1575

Gln Thr Val Phe Thr Ser Gly Pro Asn Gln Ala Leu Pro Gly Thr
            1580                1585                1590

Thr Ser Gln Gln Thr Val Pro Gly His His Val Thr Pro Gly His
            1595                1600                1605

Phe Leu Pro Ser Gln Asn Pro Thr Ile His His Gln Thr Ala Ala
            1610                1615                1620

Ala Val Val Pro Pro Pro Pro Pro Pro Ala Pro Gly Pro
            1625                1630                1635

His Leu Val Gln Gln Pro Asn Ser His Gln Gln His Ser Val Ala
            1640                1645                1650

His Val Val Gly Pro Val His Ala Val Thr Pro Gly Ser His Ile
            1655                1660                1665

His Ser Gln Thr Ala Gly His His Leu Pro Pro Pro Pro Pro
            1670                1675                1680

Pro Gly Pro Ala Pro His His His Pro Pro Pro His Pro Ser Thr
            1685                1690                1695

Gly Leu Gln Gly Leu Gln Ala Gln His Gln His Val Val Asn Ser
            1700                1705                1710

Ala Pro Pro Pro Pro Pro Pro Pro Pro Ser Ser Val Leu Ala
            1715                1720                1725

Ser Gly His His Thr Thr Ser Ala Gln Ala Leu His His Pro Pro
            1730                1735                1740

His Gln Gly Pro Pro Leu Phe Pro Ser Ser Ala His Pro Thr Val
            1745                1750                1755

Pro Pro Tyr Pro Ser Gln Ala Thr His His Thr Thr Leu Gly Pro
            1760                1765                1770

Gly Pro Gln His Gln Pro Ser Gly Thr Gly Pro His Cys Pro Leu
            1775                1780                1785

Pro Val Thr Gly Pro His Leu Gln Pro Gln Gly Pro Asn Ser Ile
            1790                1795                1800

Pro Thr Pro Thr Ala Ser Gly Phe Cys Pro His Pro Gly Ser Val
            1805                1810                1815

Ala Leu Pro His Gly Val Gln Gly Pro Gln Gln Ala Ser Pro Val
            1820                1825                1830

Pro Gly Gln Ile Pro Ile His Arg Ala Gln Val Pro Pro Thr Phe
            1835                1840                1845

Gln Asn Asn Tyr His Gly Ser Gly Trp His
            1850                1855

<210> SEQ ID NO 53
<211> LENGTH: 1778
<212> TYPE: PRT
<213> ORGANISM: Homo sapiens

<400> SEQUENCE: 53

Met Ser Ile Val Ile Pro Leu Gly Val Asp Thr Ala Glu Thr Ser Tyr
1               5                   10                  15
```

```
Leu Glu Met Ala Ala Gly Ser Glu Pro Ser Val Glu Ala Ser Pro
         20                  25                  30

Val Val Val Glu Lys Ser Asn Ser Tyr Pro His Gln Leu Tyr Thr Ser
             35                  40                  45

Ser Ser His His Ser His Ser Tyr Ile Gly Leu Pro Tyr Ala Asp His
        50                  55                  60

Asn Tyr Gly Ala Arg Pro Pro Thr Pro Pro Ala Ser Pro Pro Pro
65                  70                  75                  80

Ser Val Leu Ile Ser Lys Asn Glu Val Gly Ile Phe Thr Thr Pro Asn
                 85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
            115                 120                 125

Asp Gly Tyr Met Ile Cys Cys Asp Lys Cys Ser Val Trp Gln His Ile
130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
            195                 200                 205

Thr Pro Thr Ser Ile Thr Leu Thr Ala Ser Arg Val Ser Lys Val Asn
210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Arg Val Lys
                245                 250                 255

Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
            275                 280                 285

Asn Asn Gln Tyr Ser Glu Gly Val Gln Arg Glu Ala Gln Arg Ile Ala
290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
            340                 345                 350

Ala Leu Ile Ile Glu Tyr Arg Gly Lys Phe Met Leu Arg Glu Gln Phe
            355                 360                 365

Glu Ala Asn Gly Tyr Phe Phe Lys Arg Pro Tyr Pro Phe Val Leu Phe
            370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
            420                 425                 430

Ile His Ser Ile Pro Lys Gly Thr Glu Ile Thr Ile Ala Phe Asp Phe
```

```
                435                 440                 445
Asp Tyr Gly Asn Cys Lys Tyr Lys Val Asp Cys Ala Cys Leu Lys Glu
450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Met Thr Arg
                485                 490                 495

Glu Glu Arg Lys Met Glu Ala Ile Leu Gln Ala Phe Ala Arg Leu Glu
                500                 505                 510

Lys Arg Glu Lys Arg Arg Glu Gln Ala Leu Glu Arg Ile Ser Thr Ala
                515                 520                 525

Lys Thr Glu Val Lys Thr Glu Cys Lys Asp Thr Gln Ile Val Ser Asp
530                 535                 540

Ala Glu Val Ile Gln Gln Ala Lys Glu Glu Asn Ala Ser Lys Pro
545                 550                 555                 560

Thr Pro Ala Lys Val Asn Arg Thr Lys Gln Arg Lys Ser Phe Ser Arg
                565                 570                 575

Ser Arg Thr His Ile Gly Gln Gln Arg Arg Arg His Arg Thr Val Ser
                580                 585                 590

Met Cys Ser Asp Ile Gln Pro Ser Pro Asp Ile Glu Val Thr Ser
                595                 600                 605

Gln Gln Asn Asp Ile Glu Asn Thr Val Leu Thr Ile Glu Pro Glu Thr
610                 615                 620

Glu Thr Ala Leu Ala Glu Ile Ile Thr Glu Thr Glu Val Pro Ala Leu
625                 630                 635                 640

Asn Lys Cys Pro Thr Lys Tyr Pro Lys Thr Lys Lys His Leu Val Asn
                645                 650                 655

Glu Trp Leu Ser Glu Lys Asn Glu Lys Thr Gly Lys Pro Ser Asp Gly
                660                 665                 670

Leu Ser Glu Arg Pro Leu Arg Ile Thr Thr Asp Pro Glu Val Leu Ala
                675                 680                 685

Thr Gln Leu Asn Ser Leu Pro Gly Leu Thr Tyr Ser Pro His Val Tyr
690                 695                 700

Ser Thr Pro Lys His Tyr Ile Arg Phe Thr Ser Pro Phe Leu Ser Glu
705                 710                 715                 720

Lys Arg Arg Arg Lys Glu Pro Thr Glu Asn Ile Ser Gly Ser Cys Lys
                725                 730                 735

Lys Arg Trp Leu Lys Gln Ala Leu Glu Glu Asn Ser Ala Ile Leu
                740                 745                 750

His Arg Phe Asn Ser Pro Cys Gln Glu Arg Ser Arg Ser Pro Ala Val
                755                 760                 765

Asn Gly Glu Asn Lys Ser Pro Leu Leu Leu Asn Asp Ser Cys Ser Leu
                770                 775                 780

Pro Asp Leu Thr Thr Pro Leu Lys Lys Arg Arg Phe Tyr Gln Leu Leu
785                 790                 795                 800

Asp Ser Val Tyr Ser Glu Thr Ser Pro Thr Ser Pro Tyr Ala
                805                 810                 815

Thr Pro Thr His Thr Asp Ile Pro Met Asp Pro Ser Phe Ala Thr
                820                 825                 830

Pro Pro Arg Ile Lys Ser Asp Asp Glu Thr Cys Arg Asn Gly Tyr Lys
                835                 840                 845

Pro Ile Tyr Ser Pro Val Thr Pro Val Thr Pro Gly Thr Pro Gly Asn
850                 855                 860
```

```
Thr Met His Phe Glu Asn Ile Ser Ser Pro Glu Ser Pro Glu Ile
865                 870                 875                 880

Lys Arg Arg Thr Tyr Ser Gln Glu Gly Tyr Asp Arg Ser Ser Thr Met
                885                 890                 895

Leu Thr Leu Gly Pro Phe Arg Asn Ser Asn Leu Thr Glu Leu Gly Leu
            900                 905                 910

Gln Glu Ile Lys Thr Ile Gly Tyr Thr Ser Pro Arg Ser Arg Thr Glu
        915                 920                 925

Val Asn Arg Gln Cys Pro Gly Glu Lys Glu Pro Val Ser Asp Leu Gln
    930                 935                 940

Leu Gly Leu Asp Ala Val Glu Pro Thr Ala Leu His Lys Thr Leu Glu
945                 950                 955                 960

Thr Pro Ala His Asp Arg Ala Glu Pro Asn Ser Gln Leu Asp Ser Thr
                965                 970                 975

His Ser Gly Arg Gly Thr Met Tyr Ser Ser Trp Val Lys Ser Pro Asp
            980                 985                 990

Arg Thr Gly Val Asn Phe Ser Val  Asn Ser Asn Leu Arg  Asp Leu Thr
        995                 1000                 1005

Pro Ser  His Gln Leu Glu Val  Gly Gly Gly Phe Arg  Ile Ser Glu
    1010                 1015                 1020

Ser Lys  Cys Leu Met Gln Asp  Asp Thr Arg Gly Met  Phe Met Glu
    1025                 1030                 1035

Thr Thr  Val Phe Cys Thr Ser  Glu Asp Gly Leu Val  Ser Gly Phe
    1040                 1045                 1050

Gly Arg  Thr Val Asn Asp Asn  Leu Ile Asp Gly Asn  Cys Thr Pro
    1055                 1060                 1065

Gln Asn  Pro Pro Gln Lys Lys  Lys Val Ser Leu Leu  Glu Tyr Arg
    1070                 1075                 1080

Lys Arg  Gln Arg Glu Ala Arg  Lys Ser Gly Ser Lys  Thr Glu Asn
    1085                 1090                 1095

Phe Pro  Leu Ile Ser Val Ser  Pro His Ala Ser Gly  Ser Leu Ser
    1100                 1105                 1110

Asn Asn  Gly Asp Gly Cys Ala  Ser Ser Asn Asp Asn  Gly Glu Gln
    1115                 1120                 1125

Val Asp  His Thr Ala Ser Leu  Pro Leu Pro Thr Pro  Ala Thr Val
    1130                 1135                 1140

Tyr Asn  Ala Thr Ser Glu Glu  Thr Ser Asn Asn Cys  Pro Val Lys
    1145                 1150                 1155

Asp Ala  Thr Ala Ser Glu Lys  Asn Glu Pro Glu Val  Gln Trp Thr
    1160                 1165                 1170

Ala Ser  Thr Ser Val Glu Gln  Val Arg Glu Arg Ser  Tyr Gln Arg
    1175                 1180                 1185

Ala Leu  Leu Leu Ser Asp His  Arg Lys Asp Lys Asp  Ser Gly Gly
    1190                 1195                 1200

Glu Ser  Pro Cys Val Ser Cys  Ser Pro Ser His Val  Gln Ser Ser
    1205                 1210                 1215

Pro Ser  Ser His Ser Asn His  Ile Pro Gln Leu Gln  Ala Lys Gly
    1220                 1225                 1230

Pro Val  Pro Ser Phe Ser Glu  Leu Met Glu Asp Pro  Asp Pro Glu
    1235                 1240                 1245

Asn Pro  Glu Pro Thr Thr Thr  Asn Glu Cys Pro Ser  Pro Asp Thr
    1250                 1255                 1260
```

```
Ser Gln Asn Thr Cys Lys Ser Pro Pro Lys Met Ser Lys Pro Gly
1265                1270                1275

Ser Pro Gly Ser Val Ile Pro Ala Gln Ala His Gly Lys Ile Phe
1280                1285                1290

Thr Lys Pro Asp Pro Gln Trp Asp Ser Thr Val Ser Ala Ser Glu
1295                1300                1305

Ala Glu Asn Gly Val His Leu Lys Thr Glu Leu Gln Gln Lys Gln
1310                1315                1320

Leu Ser Asn Asn Asn Gln Ala Leu Ser Lys Asn His Pro Pro Gln
1325                1330                1335

Thr His Val Arg Asn Ser Ser Glu Gln Leu Ser Gln Lys Leu Pro
1340                1345                1350

Ser Val Pro Thr Lys Leu His Cys Pro Pro Ser Pro His Leu Glu
1355                1360                1365

Asn Pro Pro Lys Ser Ser Thr Pro His Thr Pro Val Gln His Gly
1370                1375                1380

Tyr Leu Ser Pro Lys Pro Pro Ser Gln Gln Leu Gly Ser Pro Tyr
1385                1390                1395

Arg Pro His His Ser Gln Ser Pro Gln Val Gly Thr Pro Gln Arg
1400                1405                1410

Glu Pro Gln Arg Asn Phe Tyr Pro Ala Ala Gln Asn Leu Pro Ala
1415                1420                1425

Asn Thr Gln Gln Ala Thr Ser Gly Thr Leu Phe Thr Gln Thr Pro
1430                1435                1440

Ser Gly Gln Ser Ser Ala Thr Tyr Ser Gln Phe Asn Gln Gln Ser
1445                1450                1455

Leu Asn Ser Thr Ala Pro Pro Pro Pro Pro Pro Pro Pro Pro Ser
1460                1465                1470

Ser Ser Tyr Tyr Gln Asn Gln Gln Pro Ser Ala Asn Phe Gln Asn
1475                1480                1485

Tyr Asn Gln Leu Lys Gly Ser Leu Ser Gln Gln Thr Val Phe Thr
1490                1495                1500

Ser Gly Pro Asn Gln Ala Leu Pro Gly Thr Thr Ser Gln Gln Thr
1505                1510                1515

Val Pro Gly His His Val Thr Pro Gly His Phe Leu Pro Ser Gln
1520                1525                1530

Asn Pro Thr Ile His His Gln Thr Ala Ala Ala Val Val Pro Pro
1535                1540                1545

Pro Pro Pro Pro Pro Ala Pro Gly Pro His Leu Val Gln Gln
1550                1555                1560

Pro Asn Ser His Gln Gln His Ser Val Ala His Val Val Gly Pro
1565                1570                1575

Val His Ala Val Thr Pro Gly Ser His Ile His Ser Gln Thr Ala
1580                1585                1590

Gly His His Leu Pro Pro Pro Pro Pro Pro Gly Pro Ala Pro
1595                1600                1605

His His His Pro Pro Pro His Pro Ser Thr Gly Leu Gln Gly Leu
1610                1615                1620

Gln Ala Gln His Gln His Val Val Asn Ser Ala Pro Pro Pro Pro
1625                1630                1635

Pro Pro Pro Pro Pro Ser Ser Val Leu Ala Ser Gly His His Thr
1640                1645                1650

Thr Ser Ala Gln Ala Leu His His Pro Pro His Gln Gly Pro Pro
```

```
                    1655                1660                1665

Leu Phe Pro Ser Ser Ala His Pro Thr Val Pro Pro Tyr Pro Ser
        1670                1675                1680

Gln Ala Thr His His Thr Thr Leu Gly Pro Gly Pro Gln His Gln
        1685                1690                1695

Pro Ser Gly Thr Gly Pro His Cys Pro Leu Pro Val Thr Gly Pro
        1700                1705                1710

His Leu Gln Pro Gln Gly Pro Asn Ser Ile Pro Thr Pro Thr Ala
        1715                1720                1725

Ser Gly Phe Cys Pro His Pro Gly Ser Val Ala Leu Pro His Gly
        1730                1735                1740

Val Gln Gly Pro Gln Gln Ala Ser Pro Val Pro Gly Gln Ile Pro
        1745                1750                1755

Ile His Arg Ala Gln Val Pro Pro Thr Phe Gln Asn Asn Tyr His
        1760                1765                1770

Gly Ser Gly Trp His
        1775

<210> SEQ ID NO 54
<211> LENGTH: 609
<212> TYPE: PRT
<213> ORGANISM: Homo sapiens

<400> SEQUENCE: 54

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
        35                  40                  45

Ser Ser His His Ser His Ser Tyr Ile Gly Leu Pro Tyr Ala Asp His
    50                  55                  60

Asn Tyr Gly Ala Arg Pro Pro Pro Thr Pro Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
        115                 120                 125

Asp Gly Tyr Met Ile Cys Cys Asp Lys Cys Ser Val Trp Gln His Ile
    130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
        195                 200                 205

Thr Pro Thr Ser Ile Thr Leu Thr Ala Ser Arg Val Ser Lys Val Asn
    210                 215                 220

Asp Lys Arg Arg Lys Lys Ser Gly Glu Lys Glu Gln His Ile Ser Lys
225                 230                 235                 240
```

```
Cys Lys Lys Ala Phe Arg Glu Gly Ser Arg Lys Ser Arg Val Lys
                245                 250                 255

Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
        275                 280                 285

Asn Asn Gln Tyr Ser Glu Gly Val Gln Arg Glu Ala Gln Arg Ile Ala
    290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
            340                 345                 350

Ala Leu Ile Ile Glu Tyr Arg Gly Lys Phe Met Leu Arg Glu Gln Phe
        355                 360                 365

Glu Ala Asn Gly Tyr Phe Phe Lys Arg Pro Tyr Pro Phe Val Leu Phe
    370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
            420                 425                 430

Ile His Ser Ile Pro Lys Gly Thr Glu Ile Thr Ile Ala Phe Asp Phe
        435                 440                 445

Asp Tyr Gly Asn Cys Lys Tyr Lys Val Asp Cys Ala Cys Leu Lys Glu
    450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
        515                 520                 525

Lys Leu Ser Pro Leu Arg Leu Ser Val Ser Asn Asn Gln Glu Pro Asp
    530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Val Ser
                565                 570                 575

Trp Glu Ala Ser Ser Leu Gly Leu Val Thr Ala Ala Leu His Met Val
            580                 585                 590

Ile Val Ala Ala Phe Thr Trp Ala Phe Thr Leu Phe Phe Glu Val Ser
        595                 600                 605

Glu

<210> SEQ ID NO 55
<211> LENGTH: 865
<212> TYPE: PRT
<213> ORGANISM: Homo sapiens

<400> SEQUENCE: 55
```

-continued

```
Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
            35                  40                  45

Ser Ser His His Ser His Ser Tyr Ile Gly Leu Pro Tyr Ala Asp His
        50                  55                  60

Asn Tyr Gly Ala Arg Pro Pro Thr Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
                100                 105                 110

Ser Tyr Gly Thr Asp Val Thr Arg Cys Ile Cys Gly Phe Thr His Asp
                115                 120                 125

Asp Gly Tyr Met Ile Cys Cys Asp Lys Cys Ser Val Trp Gln His Ile
                130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
                180                 185                 190

Glu Ser Gly Asp Glu Val Pro Val Glu Leu Tyr Thr Ala Phe Gln His
                195                 200                 205

Thr Pro Thr Ser Ile Thr Leu Thr Ala Ser Arg Val Ser Lys Val Asn
                210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Ser Arg Val Lys
                245                 250                 255

Gly Ser Ala Pro Glu Ile Asp Pro Ser Ser Asp Gly Ser Asn Phe Gly
                260                 265                 270

Trp Glu Thr Lys Ile Lys Ala Trp Met Asp Arg Tyr Glu Glu Ala Asn
                275                 280                 285

Asn Asn Gln Tyr Ser Glu Gly Val Gln Arg Glu Ala Gln Arg Ile Ala
                290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
                340                 345                 350

Ala Leu Ile Ile Glu Tyr Arg Gly Lys Phe Met Leu Arg Glu Gln Phe
                355                 360                 365

Glu Ala Asn Gly Tyr Phe Phe Lys Arg Pro Tyr Pro Phe Val Leu Phe
                370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
```

```
            420                 425                 430
Ile His Ser Ile Pro Lys Gly Thr Glu Ile Thr Ile Ala Phe Asp Phe
            435                 440                 445

Asp Tyr Gly Asn Cys Lys Tyr Lys Val Asp Cys Ala Cys Leu Lys Glu
    450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
        515                 520                 525

Lys Leu Ser Pro Leu Arg Leu Ser Val Ser Asn Asn Gln Glu Pro Asp
    530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Glu Gln Ala Leu Glu Arg Ile Ser Thr Ala
        595                 600                 605

Lys Thr Glu Val Lys Thr Glu Cys Lys Asp Thr Gln Ile Val Ser Asp
    610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Ser Pro Asp Ile Glu Val Thr Ser
        675                 680                 685

Gln Gln Asn Asp Ile Glu Asn Thr Val Leu Thr Ile Glu Pro Glu Thr
690                 695                 700

Glu Thr Ala Leu Ala Glu Ile Ile Thr Glu Thr Glu Val Pro Ala Leu
705                 710                 715                 720

Asn Lys Cys Pro Thr Lys Tyr Pro Lys Thr Lys Lys His Leu Val Asn
                725                 730                 735

Glu Trp Leu Ser Glu Lys Asn Glu Lys Thr Gly Lys Pro Ser Asp Gly
            740                 745                 750

Leu Ser Glu Arg Pro Leu Arg Ile Thr Thr Asp Pro Glu Val Leu Ala
        755                 760                 765

Thr Gln Leu Asn Ser Leu Pro Gly Leu Thr Tyr Ser Pro His Val Tyr
    770                 775                 780

Ser Thr Pro Lys His Tyr Ile Arg Phe Thr Ser Pro Phe Leu Ser Glu
785                 790                 795                 800

Lys Arg Arg Lys Glu Pro Thr Glu Asn Ile Ser Gly Ser Cys Lys
                805                 810                 815

Lys Arg Trp Leu Lys Gln Ala Leu Glu Glu Asn Ser Ala Ile Leu
            820                 825                 830

His Arg Phe Asn Ser Pro Cys Gln Glu Arg Ser Arg Ser Pro Ala Val
        835                 840                 845
```

```
Asn Glu Tyr Phe Phe Pro Arg Lys Phe Ser Arg Asn Lys Glu Thr His
            850                 855                 860
Leu
865

<210> SEQ ID NO 56
<211> LENGTH: 1653
<212> TYPE: PRT
<213> ORGANISM: Homo sapiens

<400> SEQUENCE: 56

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
            35                  40                  45

Ser Ser His His Ser His Ser Tyr Ile Gly Leu Pro Tyr Ala Asp His
        50                  55                  60

Asn Tyr Gly Ala Arg Pro Pro Thr Pro Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
            115                 120                 125

Asp Gly Tyr Met Ile Cys Cys Asp Lys Cys Ser Val Trp Gln His Ile
        130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
            195                 200                 205

Thr Pro Thr Ser Ile Thr Leu Thr Ala Ser Arg Val Ser Lys Val Asn
        210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Ser Arg Val Lys
                245                 250                 255

Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
            275                 280                 285

Asn Asn Gln Tyr Ser Glu Gly Val Gln Arg Glu Ala Gln Arg Ile Ala
        290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
```

-continued

```
            340                 345                 350
Ala Leu Ile Ile Glu Tyr Arg Gly Lys Phe Met Leu Arg Glu Gln Phe
            355                 360                 365

Glu Ala Asn Gly Tyr Phe Phe Lys Arg Pro Tyr Pro Phe Val Leu Phe
        370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
            420                 425                 430

Ile His Ser Ile Pro Lys Gly Thr Glu Ile Thr Ile Ala Phe Asp Phe
            435                 440                 445

Asp Tyr Gly Asn Cys Lys Tyr Lys Val Asp Cys Ala Cys Leu Lys Glu
        450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
            515                 520                 525

Lys Leu Ser Pro Leu Arg Leu Ser Val Ser Asn Asn Gln Glu Pro Asp
        530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Arg Glu Gln Ala Leu Glu Arg Ile Ser Thr Ala
            595                 600                 605

Lys Thr Glu Val Lys Thr Glu Cys Lys Asp Thr Gln Ile Val Ser Asp
        610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Pro Asp Ile Glu Val Thr Ser
            675                 680                 685

Gln Gln Asn Asp Ile Glu Asn Thr Val Leu Thr Ile Glu Pro Glu Thr
        690                 695                 700

Glu Thr Ala Leu Ala Glu Ile Ile Thr Glu Thr Val Pro Ala Leu
705                 710                 715                 720

Asn Lys Cys Pro Thr Lys Tyr Pro Lys Thr Lys Lys His Leu Val Asn
                725                 730                 735

Glu Trp Leu Ser Glu Lys Asn Glu Lys Thr Gly Lys Pro Ser Asp Gly
            740                 745                 750

Leu Ser Glu Arg Pro Leu Arg Ile Thr Thr Asp Pro Glu Val Leu Ala
            755                 760                 765
```

```
Thr Gln Leu Asn Ser Leu Pro Gly Leu Thr Tyr Ser Pro His Val Tyr
    770             775             780

Ser Thr Pro Lys His Tyr Ile Arg Phe Thr Ser Pro Phe Leu Ser Glu
785             790             795             800

Lys Arg Arg Arg Lys Glu Pro Thr Glu Asn Ile Ser Gly Ser Cys Lys
                805             810             815

Lys Arg Trp Leu Lys Gln Ala Leu Glu Glu Asn Ser Ala Ile Leu
            820             825             830

His Arg Phe Asn Ser Pro Cys Gln Glu Arg Ser Arg Ser Pro Ala Val
            835             840             845

Asn Gly Glu Asn Lys Ser Pro Leu Leu Leu Asn Asp Ser Cys Ser Leu
    850             855             860

Pro Asp Leu Thr Thr Pro Leu Lys Lys Arg Arg Phe Tyr Gln Leu Leu
865             870             875             880

Asp Ser Val Tyr Ser Glu Thr Ser Thr Pro Thr Pro Ser Pro Tyr Ala
            885             890             895

Thr Pro Thr His Thr Asp Ile Thr Pro Met Asp Pro Ser Phe Ala Thr
            900             905             910

Pro Pro Arg Ile Lys Ser Asp Asp Glu Thr Cys Arg Asn Gly Tyr Lys
            915             920             925

Pro Ile Tyr Ser Pro Val Thr Pro Val Thr Pro Gly Thr Pro Gly Asn
    930             935             940

Thr Met His Phe Glu Asn Ile Ser Ser Pro Glu Ser Ser Pro Glu Ile
945             950             955             960

Lys Arg Arg Thr Tyr Ser Gln Glu Gly Tyr Asp Arg Ser Ser Thr Met
            965             970             975

Leu Thr Leu Gly Pro Phe Arg Asn Ser Asn Leu Thr Glu Leu Gly Leu
            980             985             990

Gln Glu Ile Lys Thr Ile Gly Tyr  Thr Ser Pro Arg Ser  Arg Thr Glu
    995             1000            1005

Val Asn Arg Gln Cys Pro Gly  Glu Lys Glu Pro Val  Ser Asp Leu
    1010            1015            1020

Gln Leu  Gly Leu Asp Ala Val  Glu Pro Thr Ala Leu  His Lys Thr
    1025            1030            1035

Leu Glu  Thr Pro Ala His Asp  Arg Ala Glu Pro Asn  Ser Gln Leu
    1040            1045            1050

Asp Ser  Thr His Ser Gly Arg  Gly Thr Met Tyr Ser  Ser Trp Val
    1055            1060            1065

Lys Ser  Pro Asp Arg Thr Gly  Val Asn Phe Ser Val  Asn Ser Asn
    1070            1075            1080

Leu Arg  Asp Leu Thr Pro Ser  His Gln Leu Glu Val  Gly Gly Gly
    1085            1090            1095

Phe Arg  Ile Ser Glu Ser Lys  Cys Leu Met Gln Asp  Asp Thr Arg
    1100            1105            1110

Gly Met  Phe Met Glu Thr Thr  Val Phe Cys Thr Ser  Glu Asp Gly
    1115            1120            1125

Leu Val  Ser Gly Phe Gly Arg  Thr Val Asn Asp Asn  Leu Ile Asp
    1130            1135            1140

Gly Asn  Cys Thr Pro Gln Asn  Pro Pro Gln Lys Lys  Lys Val Ser
    1145            1150            1155

Leu Leu  Glu Tyr Arg Lys Arg  Gln Arg Glu Ala Arg  Lys Ser Gly
    1160            1165            1170
```

```
Ser Lys Thr Glu Asn Phe Pro Leu Ile Ser Val Ser Pro His Ala
1175                1180                1185

Ser Gly Ser Leu Ser Asn Asn Gly Asp Gly Cys Ala Ser Ser Asn
1190                1195                1200

Asp Asn Gly Glu Gln Val Asp His Thr Ala Ser Leu Pro Leu Pro
1205                1210                1215

Thr Pro Ala Thr Val Tyr Asn Ala Thr Ser Glu Glu Thr Ser Asn
1220                1225                1230

Asn Cys Pro Val Lys Asp Ala Thr Ala Ser Glu Lys Asn Glu Pro
1235                1240                1245

Glu Val Gln Trp Thr Ala Ser Thr Ser Val Glu Gln Val Arg Glu
1250                1255                1260

Arg Ser Tyr Gln Arg Ala Leu Leu Leu Ser Asp His Arg Lys Asp
1265                1270                1275

Lys Asp Ser Gly Gly Glu Ser Pro Cys Val Ser Cys Ser Pro Ser
1280                1285                1290

His Val Gln Ser Ser Pro Ser Ser His Ser Asn His Ile Pro Gln
1295                1300                1305

Leu Gln Ala Lys Gly Pro Val Pro Ser Phe Ser Glu Leu Met Glu
1310                1315                1320

Asp Pro Asp Pro Glu Asn Pro Glu Pro Thr Thr Thr Asn Glu Cys
1325                1330                1335

Pro Ser Pro Asp Thr Ser Gln Asn Thr Cys Lys Ser Pro Pro Lys
1340                1345                1350

Met Ser Lys Pro Gly Ser Pro Gly Ser Val Ile Pro Ala Gln Ala
1355                1360                1365

His Gly Lys Ile Phe Thr Lys Pro Asp Pro Gln Trp Asp Ser Thr
1370                1375                1380

Val Ser Ala Ser Glu Ala Glu Asn Gly Val His Leu Lys Thr Glu
1385                1390                1395

Leu Gln Gln Lys Gln Leu Ser Asn Asn Asn Gln Ala Leu Ser Lys
1400                1405                1410

Asn His Pro Pro Gln Thr His Val Arg Asn Ser Ser Glu Gln Leu
1415                1420                1425

Ser Gln Lys Leu Pro Ser Val Pro Thr Lys Leu His Cys Pro Pro
1430                1435                1440

Ser Pro His Leu Glu Asn Pro Pro Lys Ser Ser Thr Pro His Thr
1445                1450                1455

Pro Val Gln His Gly Tyr Leu Ser Pro Lys Pro Pro Ser Gln Gln
1460                1465                1470

Leu Gly Ser Pro Tyr Arg Pro His His Ser Gln Ser Pro Gln Val
1475                1480                1485

Gly Thr Pro Gln Arg Glu Pro Gln Arg Asn Phe Tyr Pro Ala Ala
1490                1495                1500

Gln Asn Leu Pro Val Phe Trp Leu Leu Gly Ile Ile Pro His Gln
1505                1510                1515

Leu Lys Pro Tyr Thr Thr His Leu Ile Lys Asp Leu His Phe Phe
1520                1525                1530

Leu Arg Val Leu Ile Gln Leu Tyr His Arg Ile Pro His Lys Leu
1535                1540                1545

His Ile Ile Pro Leu Trp Asp Arg Asp Pro Ser Thr Ser Leu Leu
1550                1555                1560

Glu Gln Gly His Ile Val His Tyr Leu Ser Gln Val Leu Ile Ser
```

```
                    1565                1570                1575

Ser Pro Lys Asp Gln Thr Val Phe Gln His Leu Leu Leu Gln Gly
            1580                1585                1590

Ser Val Leu Ile Leu Ala Leu Trp Pro Cys His Met Gly Phe Lys
            1595                1600                1605

Asp Leu Ser Arg His Leu Gln Cys Leu Asp Arg Phe Gln Phe Thr
            1610                1615                1620

Glu His Arg Cys His Gln His Phe Lys Thr Ile Thr Met Gly Gln
            1625                1630                1635

Gly Gly Ile Lys Met Asp Ser Lys Asn Ile Phe Leu Asn Val Leu
            1640                1645                1650

<210> SEQ ID NO 57
<211> LENGTH: 1621
<212> TYPE: PRT
<213> ORGANISM: Homo sapiens

<400> SEQUENCE: 57

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
            35                  40                  45

Ser Ser His His Ser His Ser Tyr Ile Gly Leu Pro Tyr Ala Asp His
            50                  55                  60

Asn Tyr Gly Ala Arg Pro Pro Thr Pro Ala Ser Pro Pro Pro
65                  70                  75                  80

Ser Val Leu Ile Ser Lys Asn Glu Val Gly Ile Phe Thr Thr Pro Asn
            85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
            115                 120                 125

Asp Gly Tyr Met Ile Cys Cys Asp Lys Cys Ser Val Trp Gln His Ile
            130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
            165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
            195                 200                 205

Thr Pro Thr Ser Ile Thr Leu Thr Ala Ser Arg Val Ser Lys Val Asn
            210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Ser Arg Val Lys
            245                 250                 255

Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
            275                 280                 285
```

```
Asn Asn Gln Tyr Ser Glu Gly Val Gln Arg Glu Ala Gln Arg Ile Ala
    290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
            340                 345                 350

Ala Leu Ile Ile Glu Tyr Arg Gly Lys Phe Met Leu Arg Glu Gln Phe
                355                 360                 365

Glu Ala Asn Gly Tyr Phe Phe Lys Arg Pro Tyr Pro Phe Val Leu Phe
370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
            420                 425                 430

Ile His Ser Ile Pro Lys Gly Thr Glu Ile Thr Ile Ala Phe Asp Phe
                435                 440                 445

Asp Tyr Gly Asn Cys Lys Tyr Lys Val Asp Cys Ala Cys Leu Lys Glu
450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
                515                 520                 525

Lys Leu Ser Pro Leu Arg Leu Ser Val Ser Asn Gln Glu Pro Asp
530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Arg Glu Gln Ala Leu Glu Arg Ile Ser Thr Ala
                595                 600                 605

Lys Thr Glu Val Lys Thr Glu Cys Lys Asp Thr Gln Ile Val Ser Asp
610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Pro Asp Ile Glu Val Thr Ser
                675                 680                 685

Gln Gln Asn Asp Ile Glu Asn Thr Val Leu Thr Ile Glu Pro Glu Thr
690                 695                 700

Glu Thr Ala Leu Ala Glu Ile Ile Thr Glu Thr Glu Val Pro Ala Leu
```

```
                705                 710                 715                 720
        Asn Lys Cys Pro Thr Lys Tyr Pro Lys Thr Lys His Leu Val Asn
                        725                 730                 735

Glu Trp Leu Ser Glu Lys Asn Glu Lys Thr Gly Lys Pro Ser Asp Gly
                        740                 745                 750

Leu Ser Glu Arg Pro Leu Arg Ile Thr Thr Asp Pro Glu Val Leu Ala
                        755                 760                 765

Thr Gln Leu Asn Ser Leu Pro Gly Leu Thr Tyr Ser Pro His Val Tyr
                        770                 775                 780

Ser Thr Pro Lys His Tyr Ile Arg Phe Thr Ser Pro Phe Leu Ser Glu
        785                 790                 795                 800

Lys Arg Arg Arg Lys Glu Pro Thr Glu Asn Ile Ser Gly Ser Cys Lys
                        805                 810                 815

Lys Arg Trp Leu Lys Gln Ala Leu Glu Glu Asn Ser Ala Ile Leu
                        820                 825                 830

His Arg Phe Asn Ser Pro Cys Gln Glu Arg Ser Arg Ser Pro Ala Val
                        835                 840                 845

Asn Gly Glu Asn Lys Ser Pro Leu Leu Leu Asn Asp Ser Cys Ser Leu
        850                 855                 860

Pro Asp Leu Thr Thr Pro Leu Lys Lys Arg Arg Phe Tyr Gln Leu Leu
        865                 870                 875                 880

Asp Ser Val Tyr Ser Glu Thr Ser Thr Pro Thr Pro Ser Pro Tyr Ala
                        885                 890                 895

Thr Pro Thr His Thr Asp Ile Thr Pro Met Asp Pro Ser Phe Ala Thr
                        900                 905                 910

Pro Pro Arg Ile Lys Ser Asp Asp Glu Thr Cys Arg Asn Gly Tyr Lys
                        915                 920                 925

Pro Ile Tyr Ser Pro Val Thr Pro Val Thr Pro Gly Thr Pro Gly Asn
                        930                 935                 940

Thr Met His Phe Glu Asn Ile Ser Ser Pro Glu Ser Ser Pro Glu Ile
        945                 950                 955                 960

Lys Arg Arg Thr Tyr Ser Gln Glu Gly Tyr Asp Arg Ser Ser Thr Met
                        965                 970                 975

Leu Thr Leu Gly Pro Phe Arg Asn Ser Asn Leu Thr Glu Leu Gly Leu
                        980                 985                 990

Gln Glu Ile Lys Thr Ile Gly Tyr  Thr Ser Pro Arg Ser  Arg Thr Glu
                        995                 1000                1005

Val Asn Arg Gln Cys Pro Gly  Glu Lys Glu Pro Val  Ser Asp Leu
            1010                1015                1020

Gln Leu Gly Leu Asp Ala Val  Glu Pro Thr Ala Leu  His Lys Thr
            1025                1030                1035

Leu Glu Thr Pro Ala His Asp  Arg Ala Glu Pro Asn  Ser Gln Leu
            1040                1045                1050

Asp Ser Thr His Ser Gly Arg  Gly Thr Met Tyr Ser  Ser Trp Val
            1055                1060                1065

Lys Ser Pro Asp Arg Thr Gly  Val Asn Phe Ser Val  Asn Ser Asn
            1070                1075                1080

Leu Arg Asp Leu Thr Pro Ser  His Gln Leu Glu Val  Gly Gly Gly
            1085                1090                1095

Phe Arg Ile Ser Glu Ser Lys  Cys Leu Met Gln Asp  Asp Thr Arg
            1100                1105                1110

Gly Met Phe Met Glu Thr Thr  Val Phe Cys Thr Ser  Glu Asp Gly
            1115                1120                1125
```

-continued

```
Leu Val Ser Gly Phe Gly Arg Thr Val Asn Asp Asn Leu Ile Asp
    1130                1135                1140

Gly Asn Cys Thr Pro Gln Asn Pro Pro Gln Lys Lys Lys Val Ser
    1145                1150                1155

Leu Leu Glu Tyr Arg Lys Arg Gln Arg Glu Ala Arg Lys Ser Gly
    1160                1165                1170

Ser Lys Thr Glu Asn Phe Pro Leu Ile Ser Val Ser Pro His Ala
    1175                1180                1185

Ser Gly Ser Leu Ser Asn Asn Gly Asp Gly Cys Ala Ser Ser Asn
    1190                1195                1200

Asp Asn Gly Glu Gln Val Asp His Thr Ala Ser Leu Pro Leu Pro
    1205                1210                1215

Thr Pro Ala Thr Val Tyr Asn Ala Thr Ser Glu Glu Thr Ser Asn
    1220                1225                1230

Asn Cys Pro Val Lys Asp Ala Thr Ala Ser Glu Lys Asn Glu Pro
    1235                1240                1245

Glu Val Gln Trp Thr Ala Ser Thr Ser Val Glu Gln Val Arg Glu
    1250                1255                1260

Arg Ser Tyr Gln Arg Ala Leu Leu Leu Ser Asp His Arg Lys Asp
    1265                1270                1275

Lys Asp Ser Gly Gly Glu Ser Pro Cys Val Ser Cys Ser Pro Ser
    1280                1285                1290

His Val Gln Ser Ser Pro Ser Ser His Ser Asn His Ile Pro Gln
    1295                1300                1305

Leu Gln Ala Lys Gly Pro Val Pro Ser Phe Ser Glu Leu Met Glu
    1310                1315                1320

Asp Pro Asp Pro Glu Asn Pro Glu Pro Thr Thr Thr Asn Glu Cys
    1325                1330                1335

Pro Ser Pro Asp Thr Ser Gln Asn Thr Cys Lys Ser Pro Pro Lys
    1340                1345                1350

Met Ser Lys Pro Gly Ser Pro Gly Ser Val Ile Pro Ala Gln Ala
    1355                1360                1365

His Gly Lys Ile Phe Thr Lys Pro Asp Pro Gln Trp Asp Ser Thr
    1370                1375                1380

Val Ser Ala Ser Glu Ala Glu Asn Gly Val His Leu Lys Thr Glu
    1385                1390                1395

Leu Gln Gln Lys Gln Leu Ser Asn Asn Asn Gln Ala Leu Ser Lys
    1400                1405                1410

Asn His Pro Pro Gln Thr His Val Arg Asn Ser Ser Glu Gln Leu
    1415                1420                1425

Ser Gln Lys Leu Pro Ser Val Pro Thr Lys Leu His Cys Pro Ser
    1430                1435                1440

Ser Pro Ser Thr Thr Pro Ser Ile His Arg Thr Pro Arg Ser Thr
    1445                1450                1455

Ser Thr Thr Pro Ala Cys Cys Lys Phe Ser Thr Pro Thr Thr Pro
    1460                1465                1470

Ser Ala Ala Thr Phe Gln Cys Phe Gly Phe Trp Ala Ser Tyr His
    1475                1480                1485

Ile Ser Ser Ser Leu Thr Pro Pro Thr Ser Ser Arg Thr Ser Thr
    1490                1495                1500

Phe Ser Phe Glu Cys Ser Ser Asn Cys Thr Thr Val Ser Leu Thr
    1505                1510                1515
```

```
Ser Tyr Thr Ser Tyr His Phe Gly Thr Gly Thr Pro Ala Pro Ala
    1520                1525                1530

Phe Trp Asn Arg Ala Thr Leu Ser Ile Thr Cys His Arg Ser Ser
    1535                1540                1545

Ser Pro Ala Pro Arg Thr Lys Gln Tyr Ser Asn Thr Tyr Cys Phe
    1550                1555                1560

Arg Val Leu Ser Ser Ser Trp Leu Cys Gly Pro Ala Thr Trp Gly
    1565                1570                1575

Ser Arg Thr Ser Ala Gly Ile Ser Ser Ala Trp Thr Asp Ser Asn
    1580                1585                1590

Ser Gln Ser Thr Gly Ala Thr Asn Ile Ser Lys Gln Leu Pro Trp
    1595                1600                1605

Val Arg Val Ala Leu Lys Trp Thr Pro Lys Thr Phe Phe
    1610                1615                1620

<210> SEQ ID NO 58
<211> LENGTH: 1816
<212> TYPE: PRT
<213> ORGANISM: Homo sapiens

<400> SEQUENCE: 58

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Gly Ala Ser Pro
                20                  25                  30

Val Val Val Glu Lys Ser Asn Ser Tyr Pro His Gln Leu Tyr Thr Ser
            35                  40                  45

Ser Ser His His Ser His Ser Tyr Ile Gly Leu Pro Tyr Ala Asp His
        50                  55                  60

Asn Tyr Gly Ala Arg Pro Pro Pro Thr Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
                100                 105                 110

Ser Tyr Gly Thr Asp Val Thr Arg Cys Ile Cys Gly Phe Thr His Asp
            115                 120                 125

Asp Gly Tyr Met Ile Cys Cys Asp Lys Cys Ser Val Trp Gln His Ile
        130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
        195                 200                 205

Thr Pro Thr Ser Ile Thr Leu Thr Ala Ser Arg Val Ser Lys Val Asn
    210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Ser Arg Val Lys
                245                 250                 255

Gly Ser Ala Pro Glu Ile Asp Pro Ser Ser Asp Gly Ser Asn Phe Gly
            260                 265                 270
```

```
Trp Glu Thr Lys Ile Lys Ala Trp Met Asp Arg Tyr Glu Glu Ala Asn
            275                 280                 285

Asn Asn Gln Tyr Ser Glu Gly Val Gln Arg Glu Ala Gln Arg Ile Ala
    290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
            340                 345                 350

Ala Leu Ile Ile Glu Tyr Arg Gly Lys Phe Met Leu Arg Glu Gln Phe
            355                 360                 365

Glu Ala Asn Gly Tyr Phe Phe Lys Arg Pro Tyr Pro Phe Val Leu Phe
    370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
            420                 425                 430

Ile His Ser Ile Pro Lys Gly Thr Glu Ile Thr Ile Ala Phe Asp Phe
            435                 440                 445

Asp Tyr Gly Asn Cys Lys Tyr Lys Val Asp Cys Ala Cys Leu Lys Glu
    450                 455                 460

Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Lys Gly Lys Lys Asp Lys
                485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
            515                 520                 525

Lys Leu Ser Pro Leu Arg Leu Ser Val Ser Asn Asn Gln Glu Pro Asp
530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Arg Glu Gln Ala Leu Glu Arg Ile Ser Thr Ala
            595                 600                 605

Lys Thr Glu Val Lys Thr Glu Cys Lys Asp Thr Gln Ile Val Ser Asp
    610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg Arg His Arg Thr Val Ser
            660                 665                 670

Met Cys Ser Asp Ile Gln Pro Ser Ser Pro Asp Ile Glu Val Thr Ser
            675                 680                 685
```

```
Gln Gln Asn Asp Ile Glu Asn Thr Val Leu Thr Ile Glu Pro Glu Thr
690                 695                 700

Glu Thr Ala Leu Ala Glu Ile Ile Thr Glu Thr Glu Val Pro Ala Leu
705                 710                 715                 720

Asn Lys Cys Pro Thr Lys Tyr Pro Lys Thr Lys Lys His Leu Val Asn
            725                 730                 735

Glu Trp Leu Ser Glu Lys Asn Glu Lys Thr Gly Lys Pro Ser Asp Gly
            740                 745                 750

Leu Ser Glu Arg Pro Leu Arg Ile Thr Thr Asp Pro Glu Val Leu Ala
            755                 760                 765

Thr Gln Leu Asn Ser Leu Pro Gly Leu Thr Tyr Ser Pro His Val Tyr
770                 775                 780

Ser Thr Pro Lys His Tyr Ile Arg Phe Thr Ser Pro Phe Leu Ser Glu
785                 790                 795                 800

Lys Arg Arg Arg Lys Glu Pro Thr Glu Asn Ile Ser Gly Ser Cys Lys
                805                 810                 815

Lys Arg Trp Leu Lys Gln Ala Leu Glu Glu Asn Ser Ala Ile Leu
            820                 825                 830

His Arg Phe Asn Ser Pro Cys Gln Glu Arg Ser Arg Ser Pro Ala Val
835                 840                 845

Asn Gly Glu Asn Lys Ser Pro Leu Leu Leu Asn Asp Ser Cys Ser Leu
850                 855                 860

Pro Asp Leu Thr Thr Pro Leu Lys Lys Arg Arg Phe Tyr Gln Leu Leu
865                 870                 875                 880

Asp Ser Val Tyr Ser Glu Thr Ser Thr Pro Thr Pro Ser Pro Tyr Ala
            885                 890                 895

Thr Pro Thr His Thr Asp Ile Thr Pro Met Asp Pro Ser Phe Ala Thr
                900                 905                 910

Pro Pro Arg Ile Lys Ser Asp Asp Glu Thr Cys Arg Asn Gly Tyr Lys
            915                 920                 925

Pro Ile Tyr Ser Pro Val Thr Pro Val Thr Pro Gly Thr Pro Gly Asn
            930                 935                 940

Thr Met His Phe Glu Asn Ile Ser Ser Pro Glu Ser Ser Pro Glu Ile
945                 950                 955                 960

Lys Arg Arg Thr Tyr Ser Gln Glu Gly Tyr Asp Arg Ser Ser Thr Met
            965                 970                 975

Leu Thr Leu Gly Pro Phe Arg Asn Ser Asn Leu Thr Glu Leu Gly Leu
            980                 985                 990

Gln Glu Ile Lys Thr Ile Gly Tyr Thr Ser Pro Arg Ser Arg Thr Glu
            995                 1000                1005

Val Asn Arg Gln Cys Pro Gly Glu Lys Glu Pro Val Ser Asp Leu
    1010                1015                1020

Gln Leu Gly Leu Asp Ala Val Glu Pro Thr Ala Leu His Lys Thr
    1025                1030                1035

Leu Glu Thr Pro Ala His Asp Arg Ala Glu Pro Asn Ser Gln Leu
    1040                1045                1050

Asp Ser Thr His Ser Gly Arg Gly Thr Met Tyr Ser Ser Trp Val
    1055                1060                1065

Lys Ser Pro Asp Arg Thr Gly Val Asn Phe Ser Val Asn Ser Asn
    1070                1075                1080

Leu Arg Asp Leu Thr Pro Ser His Gln Leu Glu Val Gly Gly Gly
    1085                1090                1095

Phe Arg Ile Ser Glu Ser Lys Cys Leu Met Gln Asp Asp Thr Arg
```

-continued

```
            1100                1105                1110
Gly Met Phe Met Glu Thr Thr Val Phe Cys Thr Ser Glu Asp Gly
        1115                1120                1125
Leu Val Ser Gly Phe Gly Arg Thr Val Asn Asp Asn Leu Ile Asp
        1130                1135                1140
Gly Asn Cys Thr Pro Gln Asn Pro Pro Gln Lys Lys Lys Val Ser
        1145                1150                1155
Leu Leu Glu Tyr Arg Lys Arg Gln Arg Glu Ala Arg Lys Ser Gly
        1160                1165                1170
Ser Lys Thr Glu Asn Phe Pro Leu Ile Ser Val Ser Pro His Ala
        1175                1180                1185
Ser Gly Ser Leu Ser Asn Asn Gly Asp Gly Cys Ala Ser Ser Asn
        1190                1195                1200
Asp Asn Gly Glu Gln Val Asp His Thr Ala Ser Leu Pro Leu Pro
        1205                1210                1215
Thr Pro Ala Thr Val Tyr Asn Ala Thr Ser Glu Glu Thr Ser Asn
        1220                1225                1230
Asn Cys Pro Val Lys Asp Ala Thr Ala Ser Glu Lys Asn Glu Pro
        1235                1240                1245
Glu Val Gln Trp Thr Ala Ser Thr Ser Val Glu Gln Val Arg Glu
        1250                1255                1260
Arg Ser Tyr Gln Arg Ala Leu Leu Leu Ser Asp His Arg Lys Asp
        1265                1270                1275
Lys Asp Ser Asp Pro Asp Pro Glu Asn Pro Glu Pro Thr Thr Thr
        1280                1285                1290
Asn Glu Cys Pro Ser Pro Asp Thr Ser Gln Asn Thr Cys Lys Ser
        1295                1300                1305
Pro Pro Lys Met Ser Lys Pro Gly Ser Pro Gly Ser Val Ile Pro
        1310                1315                1320
Ala Gln Ala His Gly Lys Ile Phe Thr Lys Pro Asp Pro Gln Trp
        1325                1330                1335
Asp Ser Thr Val Ser Ala Ser Glu Ala Glu Asn Gly Val His Leu
        1340                1345                1350
Lys Thr Glu Leu Gln Gln Lys Gln Leu Ser Asn Asn Asn Gln Ala
        1355                1360                1365
Leu Ser Lys Asn His Pro Pro Gln Thr His Val Arg Asn Ser Ser
        1370                1375                1380
Glu Gln Leu Ser Gln Lys Leu Pro Ser Val Pro Thr Lys Leu His
        1385                1390                1395
Cys Pro Pro Ser Pro His Leu Glu Asn Pro Pro Lys Ser Ser Thr
        1400                1405                1410
Pro His Thr Pro Val Gln His Gly Tyr Leu Ser Pro Lys Pro Pro
        1415                1420                1425
Ser Gln Gln Leu Gly Ser Pro Tyr Arg Pro His His Ser Gln Ser
        1430                1435                1440
Pro Gln Val Gly Thr Pro Gln Arg Glu Pro Gln Arg Asn Phe Tyr
        1445                1450                1455
Pro Ala Ala Gln Asn Leu Pro Ala Asn Thr Gln Gln Ala Thr Ser
        1460                1465                1470
Gly Thr Leu Phe Thr Gln Thr Pro Ser Gly Gln Ser Ser Ala Thr
        1475                1480                1485
Tyr Ser Gln Phe Asn Gln Gln Ser Leu Asn Ser Thr Ala Pro Pro
        1490                1495                1500
```

Pro Pro Pro Pro Pro Pro Ser Ser Ser Tyr Tyr Gln Asn Gln
            1505                1510                1515

Gln Pro Ser Ala Asn Phe Gln Asn Tyr Asn Gln Leu Lys Gly Ser
    1520                1525                1530

Leu Ser Gln Gln Thr Val Phe Thr Ser Gly Pro Asn Gln Ala Leu
1535                1540                1545

Pro Gly Thr Thr Ser Gln Gln Thr Val Pro Gly His His Val Thr
    1550                1555                1560

Pro Gly His Phe Leu Pro Ser Gln Asn Pro Thr Ile His His Gln
    1565                1570                1575

Thr Ala Ala Ala Val Val Pro Pro Pro Pro Pro Pro Pro Pro Ala
    1580                1585                1590

Pro Gly Pro His Leu Val Gln Gln Pro Asn Ser His Gln Gln His
    1595                1600                1605

Ser Val Ala His Val Val Gly Pro Val His Ala Val Thr Pro Gly
    1610                1615                1620

Ser His Ile His Ser Gln Thr Ala Gly His His Leu Pro Pro Pro
    1625                1630                1635

Pro Pro Pro Pro Gly Pro Ala Pro His His His Pro Pro Pro His
    1640                1645                1650

Pro Ser Thr Gly Leu Gln Gly Leu Gln Ala Gln His Gln His Val
    1655                1660                1665

Val Asn Ser Ala Pro Pro Pro Pro Pro Pro Pro Ser Ser
    1670                1675                1680

Val Leu Ala Ser Gly His His Thr Thr Ser Ala Gln Ala Leu His
    1685                1690                1695

His Pro Pro His Gln Gly Pro Pro Leu Phe Pro Ser Ser Ala His
    1700                1705                1710

Pro Thr Val Pro Pro Tyr Pro Ser Gln Ala Thr His His Thr Thr
    1715                1720                1725

Leu Gly Pro Gly Pro Gln His Gln Pro Ser Gly Thr Gly Pro His
    1730                1735                1740

Cys Pro Leu Pro Val Thr Gly Pro His Leu Gln Pro Gln Gly Pro
    1745                1750                1755

Asn Ser Ile Pro Thr Pro Ala Ser Gly Phe Cys Pro His Pro
    1760                1765                1770

Gly Ser Val Ala Leu Pro His Gly Val Gln Gly Pro Gln Gln Ala
    1775                1780                1785

Ser Pro Val Pro Gly Gln Ile Pro Ile His Arg Ala Gln Val Pro
    1790                1795                1800

Pro Thr Phe Gln Asn Asn Tyr His Gly Ser Gly Trp His
    1805                1810                1815

<210> SEQ ID NO 59
<211> LENGTH: 1168
<212> TYPE: PRT
<213> ORGANISM: Homo sapiens

<400> SEQUENCE: 59

Met Ser Ile Val Ile Pro Leu Gly Val Asp Thr Ala Glu Thr Ser Tyr
1               5                   10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser

```
                35                  40                  45
Ser Ser His His Ser His Ser Tyr Ile Gly Leu Pro Tyr Ala Asp His
            50                  55                  60
Asn Tyr Gly Ala Arg Pro Pro Thr Pro Ala Ser Pro Pro Pro
65                  70                  75                  80
Ser Val Leu Ile Ser Lys Asn Glu Val Gly Ile Phe Thr Thr Pro Asn
                85                  90                  95
Phe Asp Glu Thr Ser Ser Ala Thr Thr Ile Ser Thr Ser Glu Asp Gly
                100                 105                 110
Ser Tyr Gly Thr Asp Val Thr Arg Cys Ile Cys Gly Phe Thr His Asp
                115                 120                 125
Asp Gly Tyr Met Ile Cys Cys Asp Lys Cys Ser Val Trp Gln His Ile
            130                 135                 140
Asp Cys Met Gly Ile Asp Arg Gln His Ile Pro Asp Thr Tyr Leu Cys
145                 150                 155                 160
Glu Arg Cys Gln Pro Arg Asn Leu Asp Lys Glu Arg Ala Val Leu Leu
                165                 170                 175
Gln Arg Arg Lys Arg Glu Asn Met Ser Asp Gly Asp Thr Ser Ala Thr
            180                 185                 190
Glu Ser Gly Asp Glu Val Pro Val Glu Leu Tyr Thr Ala Phe Gln His
            195                 200                 205
Thr Pro Thr Ser Ile Thr Leu Thr Ala Ser Arg Val Ser Lys Val Asn
210                 215                 220
Asp Lys Arg Arg Lys Lys Ser Gly Glu Lys Glu Gln His Ile Ser Lys
225                 230                 235                 240
Cys Lys Lys Ala Phe Arg Glu Gly Ser Arg Lys Ser Arg Val Lys
                245                 250                 255
Gly Ser Ala Pro Glu Ile Asp Pro Ser Ser Asp Gly Ser Asn Phe Gly
                260                 265                 270
Trp Glu Thr Lys Ile Lys Ala Trp Met Asp Arg Tyr Glu Glu Ala Asn
            275                 280                 285
Asn Asn Gln Tyr Ser Glu Gly Val Gln Arg Glu Ala Gln Arg Ile Ala
290                 295                 300
Leu Arg Leu Gly Asn Gly Asn Asp Lys Lys Glu Met Asn Lys Ser Asp
305                 310                 315                 320
Leu Asn Thr Asn Asn Leu Leu Phe Lys Pro Pro Val Glu Ser His Ile
                325                 330                 335
Gln Lys Asn Lys Lys Ile Leu Lys Ser Ala Lys Asp Leu Pro Pro Asp
            340                 345                 350
Ala Leu Ile Ile Glu Tyr Arg Gly Lys Phe Met Leu Arg Glu Gln Phe
            355                 360                 365
Glu Ala Asn Gly Tyr Phe Phe Lys Arg Pro Tyr Pro Phe Val Leu Phe
            370                 375                 380
Tyr Ser Lys Phe His Gly Leu Glu Met Cys Val Asp Ala Arg Thr Phe
385                 390                 395                 400
Gly Asn Glu Ala Arg Phe Ile Arg Arg Ser Cys Thr Pro Asn Ala Glu
                405                 410                 415
Val Arg His Glu Ile Gln Asp Gly Thr Ile His Leu Tyr Ile Tyr Ser
                420                 425                 430
Ile His Ser Ile Pro Lys Gly Thr Glu Ile Thr Ile Ala Phe Asp Phe
            435                 440                 445
Asp Tyr Gly Asn Cys Lys Tyr Lys Val Asp Cys Ala Cys Leu Lys Glu
            450                 455                 460
```

-continued

```
Asn Pro Glu Cys Pro Val Leu Lys Arg Ser Ser Glu Ser Met Glu Asn
465                 470                 475                 480

Ile Asn Ser Gly Tyr Glu Thr Arg Arg Lys Gly Lys Lys Asp Lys
            485                 490                 495

Asp Ile Ser Lys Glu Lys Asp Thr Gln Asn Gln Asn Ile Thr Leu Asp
            500                 505                 510

Cys Glu Gly Thr Thr Asn Lys Met Lys Ser Pro Glu Thr Lys Gln Arg
            515                 520                 525

Lys Leu Ser Pro Leu Arg Leu Ser Val Ser Asn Asn Gln Glu Pro Asp
530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
                580                 585                 590

Lys Arg Glu Lys Arg Arg Glu Gln Ala Leu Glu Arg Ile Ser Thr Ala
            595                 600                 605

Lys Thr Glu Val Lys Thr Glu Cys Lys Asp Thr Gln Ile Val Ser Asp
610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Ser Pro Asp Ile Glu Val Thr Ser
            675                 680                 685

Gln Gln Asn Asp Ile Glu Asn Thr Val Leu Thr Ile Glu Pro Glu Thr
            690                 695                 700

Glu Thr Ala Leu Ala Glu Ile Ile Thr Glu Thr Glu Val Pro Ala Leu
705                 710                 715                 720

Asn Lys Cys Pro Thr Lys Tyr Pro Lys Thr Lys Lys His Leu Val Asn
                725                 730                 735

Glu Trp Leu Ser Glu Lys Asn Glu Lys Thr Gly Lys Pro Ser Asp Gly
                740                 745                 750

Leu Ser Glu Arg Pro Leu Arg Ile Thr Thr Asp Pro Glu Val Leu Ala
            755                 760                 765

Thr Gln Leu Asn Ser Leu Pro Gly Leu Thr Tyr Ser Pro His Val Tyr
770                 775                 780

Ser Thr Pro Lys His Tyr Ile Arg Phe Thr Ser Pro Phe Leu Ser Glu
785                 790                 795                 800

Lys Arg Arg Arg Lys Glu Pro Thr Glu Asn Ile Ser Gly Ser Cys Lys
                805                 810                 815

Lys Arg Trp Leu Lys Gln Ala Leu Glu Glu Asn Ser Ala Ile Leu
            820                 825                 830

His Arg Phe Asn Ser Pro Cys Gln Glu Arg Ser Arg Ser Pro Ala Val
            835                 840                 845

Asn Gly Glu Asn Lys Ser Pro Leu Leu Leu Asn Asp Ser Cys Ser Leu
850                 855                 860

Pro Asp Leu Thr Thr Pro Leu Lys Lys Arg Arg Phe Tyr Gln Leu Leu
865                 870                 875                 880
```

Asp Ser Val Tyr Ser Glu Thr Ser Thr Pro Thr Ser Pro Tyr Ala
            885                 890                 895

Thr Pro Thr His Thr Asp Ile Thr Pro Met Asp Pro Ser Phe Ala Thr
        900                 905                 910

Pro Pro Arg Ile Lys Ser Asp Asp Glu Thr Cys Arg Asn Gly Tyr Lys
    915                 920                 925

Pro Ile Tyr Ser Pro Val Thr Pro Val Thr Pro Gly Thr Pro Gly Asn
930                 935                 940

Thr Met His Phe Glu Asn Ile Ser Ser Pro Glu Ser Ser Pro Glu Ile
945                 950                 955                 960

Lys Arg Arg Thr Tyr Ser Gln Glu Gly Tyr Asp Arg Ser Ser Thr Met
            965                 970                 975

Leu Thr Leu Gly Pro Phe Arg Asn Ser Asn Leu Thr Glu Leu Gly Leu
        980                 985                 990

Gln Glu Ile Lys Thr Ile Gly Tyr Thr Ser Pro Arg Ser Arg Thr Glu
    995                 1000                1005

Val Asn Arg Gln Cys Pro Gly Glu Lys Glu Pro Val Ser Asp Leu
    1010                1015                1020

Gln Leu Gly Leu Asp Ala Val Glu Pro Thr Ala Leu His Lys Thr
    1025                1030                1035

Leu Glu Thr Pro Ala His Asp Arg Ala Glu Pro Asn Ser Gln Leu
    1040                1045                1050

Asp Ser Thr His Ser Gly Arg Gly Thr Met Tyr Ser Ser Trp Val
    1055                1060                1065

Lys Ser Pro Asp Arg Thr Gly Val Asn Phe Ser Val Asn Ser Asn
    1070                1075                1080

Leu Arg Asp Leu Thr Pro Ser His Gln Leu Glu Val Gly Gly Gly
    1085                1090                1095

Phe Arg Ile Ser Glu Ser Lys Cys Leu Met Gln Asp Asp Thr Arg
    1100                1105                1110

Gly Met Phe Met Glu Thr Thr Val Phe Cys Thr Ser Glu Asp Gly
    1115                1120                1125

Leu Val Ser Gly Phe Gly Arg Thr Val Asn Asp Asn Leu Ile Asp
    1130                1135                1140

Gly Asn Cys Thr Pro Gln Asn Pro Pro Gln Lys Lys Lys Ser Pro
    1145                1150                1155

Val Gly Asn Phe Val Gly Ser Asn Val Val
    1160                1165

<210> SEQ ID NO 60
<211> LENGTH: 366
<212> TYPE: PRT
<213> ORGANISM: Homo sapiens

<400> SEQUENCE: 60

Met Asp Ser Asp Asp Glu Met Val Glu Ala Val Glu Gly His Leu
1               5                   10                  15

Asp Asp Asp Gly Leu Pro His Gly Phe Cys Thr Val Thr Tyr Ser Ser
                20                  25                  30

Thr Asp Arg Phe Glu Gly Asn Phe Val His Gly Glu Lys Asn Gly Arg
        35                  40                  45

Gly Lys Phe Phe Phe Asp Gly Ser Thr Leu Glu Gly Tyr Tyr Val
    50                  55                  60

Asp Asp Ala Leu Gln Gly Gln Gly Val Tyr Thr Tyr Glu Asp Gly Gly
65                  70                  75                  80

```
Val Leu Gln Gly Thr Tyr Val Asp Gly Glu Leu Asn Gly Pro Ala Gln
                 85                  90                  95

Glu Tyr Asp Thr Asp Gly Arg Leu Ile Phe Lys Gly Gln Tyr Lys Asp
            100                 105                 110

Asn Ile Arg His Gly Val Cys Trp Ile Tyr Tyr Pro Asp Gly Gly Ser
        115                 120                 125

Leu Val Gly Glu Val Asn Glu Asp Gly Glu Met Thr Gly Glu Lys Ile
    130                 135                 140

Ala Tyr Val Tyr Pro Asp Glu Arg Thr Ala Leu Tyr Gly Lys Phe Ile
145                 150                 155                 160

Asp Gly Glu Met Ile Glu Gly Lys Leu Ala Thr Leu Met Ser Thr Glu
                165                 170                 175

Glu Gly Arg Pro His Phe Glu Leu Met Pro Gly Asn Ser Val Tyr His
            180                 185                 190

Phe Asp Lys Ser Thr Ser Ser Cys Ile Ser Thr Asn Ala Leu Leu Pro
        195                 200                 205

Asp Pro Tyr Glu Ser Glu Arg Val Tyr Val Ala Glu Ser Leu Ile Ser
    210                 215                 220

Ser Ala Gly Glu Gly Leu Phe Ser Lys Val Ala Val Gly Pro Asn Thr
225                 230                 235                 240

Val Met Ser Phe Tyr Asn Gly Val Arg Ile Thr His Gln Glu Val Asp
                245                 250                 255

Ser Arg Asp Trp Ala Leu Asn Gly Asn Thr Leu Ser Leu Asp Glu Glu
            260                 265                 270

Thr Val Ile Asp Val Pro Glu Pro Tyr Asn His Val Ser Lys Tyr Cys
        275                 280                 285

Ala Ser Leu Gly His Lys Ala Asn His Ser Phe Thr Pro Asn Cys Ile
    290                 295                 300

Tyr Asp Met Phe Val His Pro Arg Phe Gly Pro Ile Lys Cys Ile Arg
305                 310                 315                 320

Thr Leu Arg Ala Val Glu Ala Asp Glu Glu Leu Thr Val Ala Tyr Gly
                325                 330                 335

Tyr Asp His Ser Pro Pro Gly Lys Ser Gly Pro Glu Ala Pro Glu Trp
            340                 345                 350

Tyr Gln Val Glu Leu Lys Ala Phe Gln Ala Thr Gln Gln Lys
        355                 360                 365

<210> SEQ ID NO 61
<211> LENGTH: 393
<212> TYPE: PRT
<213> ORGANISM: Homo sapiens

<400> SEQUENCE: 61

Met Gly Glu Gly Gly Ala Ala Ala Ala Leu Val Ala Ala Ala Ala Ala
1               5                   10                  15

Ala Ala Ala Ala Ala Ala Val Val Ala Gly Gln Arg Arg Arg Arg Arg
            20                  25                  30

Leu Gly Arg Arg Ala Arg Cys His Gly Pro Gly Arg Ala Ala Gly Gly
        35                  40                  45

Lys Met Ser Lys Pro Cys Ala Val Glu Ala Ala Ala Ala Ala Val Ala
    50                  55                  60

Ala Thr Ala Pro Gly Pro Glu Met Val Glu Arg Arg Gly Pro Gly Arg
65                  70                  75                  80

Pro Arg Thr Asp Gly Glu Asn Val Phe Thr Gly Gln Ser Lys Ile Tyr
```

```
                    85                  90                  95

Ser Tyr Met Ser Pro Asn Lys Cys Ser Gly Met Arg Phe Pro Leu Gln
                100                 105                 110

Glu Glu Asn Ser Val Thr His His Glu Val Lys Cys Gln Gly Lys Pro
            115                 120                 125

Leu Ala Gly Ile Tyr Arg Lys Arg Glu Lys Arg Asn Ala Gly Asn
        130                 135                 140

Ala Val Arg Ser Ala Met Lys Ser Glu Glu Gln Lys Ile Lys Asp Ala
145                 150                 155                 160

Arg Lys Gly Pro Leu Val Pro Phe Pro Asn Gln Lys Ser Glu Ala Ala
                165                 170                 175

Glu Pro Pro Lys Thr Pro Pro Ser Ser Cys Asp Ser Thr Asn Ala Ala
            180                 185                 190

Ile Ala Lys Gln Ala Leu Lys Lys Pro Ile Lys Gly Lys Gln Ala Pro
        195                 200                 205

Arg Lys Lys Ala Gln Gly Lys Thr Gln Gln Asn Arg Lys Leu Thr Asp
210                 215                 220

Phe Tyr Pro Val Arg Arg Ser Ser Arg Lys Ser Lys Ala Glu Leu Gln
225                 230                 235                 240

Ser Glu Glu Arg Lys Arg Ile Asp Glu Leu Ile Glu Ser Gly Lys Glu
                245                 250                 255

Glu Gly Met Lys Ile Asp Leu Ile Asp Gly Lys Gly Arg Gly Val Ile
            260                 265                 270

Ala Thr Lys Gln Phe Ser Arg Gly Asp Phe Val Val Glu Tyr His Gly
        275                 280                 285

Asp Leu Ile Glu Ile Thr Asp Ala Lys Lys Arg Glu Ala Leu Tyr Ala
    290                 295                 300

Gln Asp Pro Ser Thr Gly Cys Tyr Met Tyr Tyr Phe Gln Tyr Leu Ser
305                 310                 315                 320

Lys Thr Tyr Cys Val Asp Ala Thr Arg Glu Thr Asn Arg Leu Gly Arg
                325                 330                 335

Leu Ile Asn His Ser Lys Cys Gly Asn Cys Gln Thr Lys Leu His Asp
            340                 345                 350

Ile Asp Gly Val Pro His Leu Ile Leu Ile Ala Ser Arg Asp Ile Ala
        355                 360                 365

Ala Gly Glu Glu Leu Leu Tyr Asp Tyr Gly Asp Arg Ser Lys Ala Ser
    370                 375                 380

Ile Glu Ala His Pro Trp Leu Lys His
385                 390

<210> SEQ ID NO 62
<211> LENGTH: 352
<212> TYPE: PRT
<213> ORGANISM: Homo sapiens

<400> SEQUENCE: 62

Met Ala Arg Gly Arg Lys Met Ser Lys Pro Arg Ala Val Glu Ala Ala
1               5                   10                  15

Ala Ala Ala Ala Ala Val Ala Thr Ala Pro Gly Pro Glu Met Val
            20                  25                  30

Glu Arg Arg Gly Pro Gly Arg Pro Arg Thr Asp Gly Glu Asn Val Phe
        35                  40                  45

Thr Gly Gln Ser Lys Ile Tyr Ser Tyr Met Ser Pro Asn Lys Cys Ser
    50                  55                  60
```

```
Gly Met Arg Phe Pro Leu Gln Glu Glu Asn Ser Val Thr His His Glu
65                  70                  75                  80

Val Lys Cys Gln Gly Lys Pro Leu Ala Gly Ile Tyr Arg Lys Arg Glu
                85                  90                  95

Glu Lys Arg Asn Ala Gly Asn Ala Val Arg Ser Ala Met Lys Ser Glu
            100                 105                 110

Glu Gln Lys Ile Lys Asp Ala Arg Lys Gly Pro Leu Val Pro Phe Pro
        115                 120                 125

Asn Gln Lys Ser Glu Ala Ala Glu Pro Pro Lys Thr Pro Pro Ser Ser
130                 135                 140

Cys Asp Ser Thr Asn Ala Ala Ile Ala Lys Gln Ala Leu Lys Lys Pro
145                 150                 155                 160

Ile Lys Gly Lys Gln Ala Pro Arg Lys Lys Ala Gln Gly Lys Thr Gln
                165                 170                 175

Gln Asn Arg Lys Leu Thr Asp Phe Tyr Pro Val Arg Arg Ser Ser Arg
            180                 185                 190

Lys Ser Lys Ala Glu Leu Gln Ser Glu Glu Arg Lys Arg Ile Asp Glu
        195                 200                 205

Leu Ile Glu Ser Gly Lys Glu Glu Gly Met Lys Ile Asp Leu Ile Asp
210                 215                 220

Gly Lys Gly Arg Gly Val Ile Ala Thr Lys Gln Phe Ser Arg Gly Asp
225                 230                 235                 240

Phe Val Val Glu Tyr His Gly Asp Leu Ile Glu Ile Thr Asp Ala Lys
                245                 250                 255

Lys Arg Glu Ala Leu Tyr Ala Gln Asp Pro Ser Thr Gly Cys Tyr Met
            260                 265                 270

Tyr Tyr Phe Gln Tyr Leu Ser Lys Thr Tyr Cys Val Asp Ala Thr Arg
        275                 280                 285

Glu Thr Asn Arg Leu Gly Arg Leu Ile Asn His Ser Lys Cys Gly Asn
290                 295                 300

Cys Gln Thr Lys Leu His Asp Ile Asp Gly Val Pro His Leu Ile Leu
305                 310                 315                 320

Ile Ala Ser Arg Asp Ile Ala Ala Gly Glu Glu Leu Leu Tyr Asp Tyr
                325                 330                 335

Gly Asp Arg Ser Lys Ala Ser Ile Glu Ala His Pro Trp Leu Lys His
            340                 345                 350

<210> SEQ ID NO 63
<211> LENGTH: 719
<212> TYPE: PRT
<213> ORGANISM: Homo sapiens

<400> SEQUENCE: 63

Met Gly Glu Lys Asn Gly Asp Ala Lys Thr Phe Trp Met Glu Leu Glu
1               5                   10                  15

Asp Asp Gly Lys Val Asp Phe Ile Phe Glu Gln Val Gln Asn Val Leu
                20                  25                  30

Gln Ser Leu Lys Gln Lys Ile Lys Asp Gly Ser Ala Thr Asn Lys Glu
            35                  40                  45

Tyr Ile Gln Ala Met Ile Leu Val Asn Glu Ala Thr Ile Ile Asn Ser
        50                  55                  60

Ser Thr Ser Ile Lys Gly Ala Ser Gln Lys Glu Val Asn Ala Gln Ser
65                  70                  75                  80

Ser Asp Pro Met Pro Val Thr Gln Lys Glu Gln Glu Asn Lys Ser Asn
                85                  90                  95
```

-continued

```
Ala Phe Pro Ser Thr Ser Cys Glu Asn Ser Phe Pro Glu Asp Cys Thr
                100                 105                 110

Phe Leu Thr Thr Glu Asn Lys Glu Ile Leu Ser Leu Glu Asp Lys Val
            115                 120                 125

Val Asp Phe Arg Glu Lys Asp Ser Ser Ser Asn Leu Ser Tyr Gln Ser
130                 135                 140

His Asp Cys Ser Gly Ala Cys Leu Met Lys Met Pro Leu Asn Leu Lys
145                 150                 155                 160

Gly Glu Asn Pro Leu Gln Leu Pro Ile Lys Cys His Phe Gln Arg Arg
                165                 170                 175

His Ala Lys Thr Asn Ser His Ser Ser Ala Leu His Val Ser Tyr Lys
            180                 185                 190

Thr Pro Cys Gly Arg Ser Leu Arg Asn Val Glu Glu Val Phe Arg Tyr
        195                 200                 205

Leu Leu Glu Thr Glu Cys Asn Phe Leu Phe Thr Asp Asn Phe Ser Phe
210                 215                 220

Asn Thr Tyr Val Gln Leu Ala Arg Asn Tyr Pro Lys Gln Lys Glu Val
225                 230                 235                 240

Val Ser Asp Val Asp Ile Ser Asn Gly Val Glu Ser Val Pro Ile Ser
                245                 250                 255

Phe Cys Asn Glu Ile Asp Ser Arg Lys Leu Pro Gln Phe Lys Tyr Arg
            260                 265                 270

Lys Thr Val Trp Pro Arg Ala Tyr Asn Leu Thr Asn Phe Ser Ser Met
        275                 280                 285

Phe Thr Asp Ser Cys Asp Cys Ser Glu Gly Cys Ile Asp Ile Thr Lys
        290                 295                 300

Cys Ala Cys Leu Gln Leu Thr Ala Arg Asn Ala Lys Thr Ser Pro Leu
305                 310                 315                 320

Ser Ser Asp Lys Ile Thr Thr Gly Tyr Lys Tyr Lys Arg Leu Gln Arg
                325                 330                 335

Gln Ile Pro Thr Gly Ile Tyr Glu Cys Ser Leu Leu Cys Lys Cys Asn
            340                 345                 350

Arg Gln Leu Cys Gln Asn Arg Val Val Gln His Gly Pro Gln Val Arg
        355                 360                 365

Leu Gln Val Phe Lys Thr Glu Gln Lys Gly Trp Gly Val Arg Cys Leu
    370                 375                 380

Asp Asp Ile Asp Arg Gly Thr Phe Val Cys Ile Tyr Ser Gly Arg Leu
385                 390                 395                 400

Leu Ser Arg Ala Asn Thr Glu Lys Ser Tyr Gly Ile Asp Glu Asn Gly
                405                 410                 415

Arg Asp Glu Asn Thr Met Lys Asn Ile Phe Ser Lys Arg Lys Leu
            420                 425                 430

Glu Val Ala Cys Ser Asp Cys Glu Val Glu Val Leu Pro Leu Gly Leu
        435                 440                 445

Glu Thr His Pro Arg Thr Ala Lys Thr Glu Lys Cys Pro Pro Lys Phe
    450                 455                 460

Ser Asn Asn Pro Lys Glu Leu Thr Val Glu Thr Lys Tyr Asp Asn Ile
465                 470                 475                 480

Ser Arg Ile Gln Tyr His Ser Val Ile Arg Asp Pro Glu Ser Lys Thr
                485                 490                 495

Ala Ile Phe Gln His Asn Gly Lys Lys Met Glu Phe Val Ser Ser Glu
            500                 505                 510
```

```
Ser Val Thr Pro Glu Asp Asn Asp Gly Phe Lys Pro Arg Glu His
        515                 520                 525

Leu Asn Ser Lys Thr Lys Gly Ala Gln Lys Asp Ser Ser Asn His
        530                 535                 540

Val Asp Glu Phe Glu Asp Asn Leu Leu Ile Glu Ser Asp Val Ile Asp
545                 550                 555                 560

Ile Thr Lys Tyr Arg Glu Glu Thr Pro Pro Arg Ser Arg Cys Asn Gln
                565                 570                 575

Ala Thr Thr Leu Asp Asn Gln Asn Ile Lys Lys Ala Ile Glu Val Gln
                580                 585                 590

Ile Gln Lys Pro Gln Glu Gly Arg Ser Thr Ala Cys Gln Arg Gln Gln
        595                 600                 605

Val Phe Cys Asp Glu Glu Leu Leu Ser Glu Thr Lys Asn Thr Ser Ser
        610                 615                 620

Asp Ser Leu Thr Lys Phe Asn Lys Gly Asn Val Phe Leu Leu Asp Ala
625                 630                 635                 640

Thr Lys Glu Gly Asn Val Gly Arg Phe Leu Asn His Ser Cys Cys Pro
                645                 650                 655

Asn Leu Leu Val Gln Asn Val Phe Val Glu Thr His Asn Arg Asn Phe
        660                 665                 670

Pro Leu Val Ala Phe Phe Thr Asn Arg Tyr Val Lys Ala Arg Thr Glu
        675                 680                 685

Leu Thr Trp Asp Tyr Gly Tyr Glu Ala Gly Thr Val Pro Glu Lys Glu
        690                 695                 700

Ile Phe Cys Gln Cys Gly Val Asn Lys Cys Arg Lys Lys Ile Leu
705                 710                 715

<210> SEQ ID NO 64
<211> LENGTH: 707
<212> TYPE: PRT
<213> ORGANISM: Homo sapiens

<400> SEQUENCE: 64

Met Gly Glu Lys Asn Gly Asp Ala Lys Thr Phe Trp Met Glu Leu Glu
1               5                   10                  15

Asp Asp Gly Lys Val Asp Phe Ile Phe Glu Gln Val Gln Asn Val Leu
                20                  25                  30

Gln Ser Leu Lys Gln Lys Ile Lys Asp Gly Ser Ala Thr Asn Lys Glu
        35                  40                  45

Tyr Ile Gln Ala Met Ile Leu Val Asn Glu Ala Thr Ile Ile Asn Ser
    50                  55                  60

Ser Thr Ser Ile Lys Asp Pro Met Pro Val Thr Gln Lys Glu Gln Glu
65              70                  75                  80

Asn Lys Ser Asn Ala Phe Pro Ser Thr Ser Cys Glu Asn Ser Phe Pro
                85                  90                  95

Glu Asp Cys Thr Phe Leu Thr Thr Glu Asn Lys Glu Ile Leu Ser Leu
            100                 105                 110

Glu Asp Lys Val Val Asp Phe Arg Glu Lys Asp Ser Ser Ser Asn Leu
        115                 120                 125

Ser Tyr Gln Ser His Asp Cys Ser Gly Ala Cys Leu Met Lys Met Pro
    130                 135                 140

Leu Asn Leu Lys Gly Glu Asn Pro Leu Gln Leu Pro Ile Lys Cys His
145                 150                 155                 160

Phe Gln Arg Arg His Ala Lys Thr Asn Ser His Ser Ser Ala Leu His
                165                 170                 175
```

```
Val Ser Tyr Lys Thr Pro Cys Gly Arg Ser Leu Arg Asn Val Glu Glu
            180                 185                 190

Val Phe Arg Tyr Leu Leu Glu Thr Glu Cys Asn Phe Leu Phe Thr Asp
        195                 200                 205

Asn Phe Ser Phe Asn Thr Tyr Val Gln Leu Ala Arg Asn Tyr Pro Lys
    210                 215                 220

Gln Lys Glu Val Val Ser Asp Val Asp Ile Ser Asn Gly Val Glu Ser
225                 230                 235                 240

Val Pro Ile Ser Phe Cys Asn Glu Ile Asp Ser Arg Lys Leu Pro Gln
                245                 250                 255

Phe Lys Tyr Arg Lys Thr Val Trp Pro Arg Ala Tyr Asn Leu Thr Asn
            260                 265                 270

Phe Ser Ser Met Phe Thr Asp Ser Cys Asp Cys Ser Glu Gly Cys Ile
        275                 280                 285

Asp Ile Thr Lys Cys Ala Cys Leu Gln Leu Thr Ala Arg Asn Ala Lys
    290                 295                 300

Thr Ser Pro Leu Ser Ser Asp Lys Ile Thr Thr Gly Tyr Lys Tyr Lys
305                 310                 315                 320

Arg Leu Gln Arg Gln Ile Pro Thr Gly Ile Tyr Glu Cys Ser Leu Leu
                325                 330                 335

Cys Lys Cys Asn Arg Gln Leu Cys Gln Asn Arg Val Val Gln His Gly
            340                 345                 350

Pro Gln Val Arg Leu Gln Val Phe Lys Thr Glu Gln Lys Gly Trp Gly
        355                 360                 365

Val Arg Cys Leu Asp Asp Ile Asp Arg Gly Thr Phe Val Cys Ile Tyr
    370                 375                 380

Ser Gly Arg Leu Leu Ser Arg Ala Asn Thr Glu Lys Ser Tyr Gly Ile
385                 390                 395                 400

Asp Glu Asn Gly Arg Asp Glu Asn Thr Met Lys Asn Ile Phe Ser Lys
                405                 410                 415

Lys Arg Lys Leu Glu Val Ala Cys Ser Asp Cys Glu Val Glu Val Leu
            420                 425                 430

Pro Leu Gly Leu Glu Thr His Pro Arg Thr Ala Lys Thr Glu Lys Cys
        435                 440                 445

Pro Pro Lys Phe Ser Asn Asn Pro Lys Glu Leu Thr Val Glu Thr Lys
    450                 455                 460

Tyr Asp Asn Ile Ser Arg Ile Gln Tyr His Ser Val Ile Arg Asp Pro
465                 470                 475                 480

Glu Ser Lys Thr Ala Ile Phe Gln His Asn Gly Lys Lys Met Glu Phe
                485                 490                 495

Val Ser Ser Glu Ser Val Thr Pro Glu Asp Asn Asp Gly Phe Lys Pro
            500                 505                 510

Pro Arg Glu His Leu Asn Ser Lys Thr Lys Gly Ala Gln Lys Asp Ser
        515                 520                 525

Ser Ser Asn His Val Asp Glu Phe Glu Asp Asn Leu Leu Ile Glu Ser
    530                 535                 540

Asp Val Ile Asp Ile Thr Lys Tyr Arg Glu Glu Thr Pro Pro Arg Ser
545                 550                 555                 560

Arg Cys Asn Gln Ala Thr Thr Leu Asp Asn Gln Asn Ile Lys Lys Ala
                565                 570                 575

Ile Glu Val Gln Ile Gln Lys Pro Gln Glu Gly Arg Ser Thr Ala Cys
            580                 585                 590
```

```
Gln Arg Gln Gln Val Phe Cys Asp Glu Leu Leu Ser Glu Thr Lys
            595                 600                 605

Asn Thr Ser Ser Asp Ser Leu Thr Lys Phe Asn Lys Gly Asn Val Phe
610                 615                 620

Leu Leu Asp Ala Thr Lys Glu Gly Asn Val Gly Arg Phe Leu Asn His
625                 630                 635                 640

Ser Cys Cys Pro Asn Leu Leu Val Gln Asn Val Phe Val Glu Thr His
                645                 650                 655

Asn Arg Asn Phe Pro Leu Val Ala Phe Phe Thr Asn Arg Tyr Val Lys
            660                 665                 670

Ala Arg Thr Glu Leu Thr Trp Asp Tyr Gly Tyr Glu Ala Gly Thr Val
        675                 680                 685

Pro Glu Lys Glu Ile Phe Cys Gln Cys Gly Val Asn Lys Cys Arg Lys
    690                 695                 700

Lys Ile Leu
705

<210> SEQ ID NO 65
<211> LENGTH: 718
<212> TYPE: PRT
<213> ORGANISM: Homo sapiens

<400> SEQUENCE: 65

Met Gly Glu Lys Asn Gly Asp Ala Lys Thr Phe Trp Met Glu Leu Glu
1               5                   10                  15

Asp Asp Gly Lys Val Asp Phe Ile Phe Glu Gln Val Gln Asn Val Leu
            20                  25                  30

Gln Ser Leu Lys Gln Lys Ile Lys Asp Gly Ser Ala Thr Asn Lys Glu
        35                  40                  45

Tyr Ile Gln Ala Met Ile Leu Val Asn Glu Ala Thr Ile Ile Asn Ser
    50                  55                  60

Ser Thr Ser Ile Lys Gly Ala Ser Gln Lys Glu Val Asn Ala Gln Ser
65                  70                  75                  80

Ser Asp Pro Met Pro Val Thr Gln Lys Glu Gln Glu Asn Lys Ser Asn
                85                  90                  95

Ala Phe Pro Ser Thr Ser Cys Glu Asn Ser Phe Pro Glu Asp Cys Thr
            100                 105                 110

Phe Leu Thr Thr Glu Asn Lys Glu Ile Leu Ser Leu Glu Asp Lys Val
        115                 120                 125

Val Asp Phe Arg Glu Lys Asp Ser Ser Ser Asn Leu Ser Tyr Gln Ser
    130                 135                 140

His Asp Cys Ser Gly Ala Cys Leu Met Lys Met Pro Leu Asn Leu Lys
145                 150                 155                 160

Gly Glu Asn Pro Leu Gln Leu Pro Ile Lys Cys His Phe Gln Arg Arg
                165                 170                 175

His Ala Lys Thr Asn Ser His Ser Ser Ala Leu His Val Ser Tyr Lys
            180                 185                 190

Thr Pro Cys Gly Arg Ser Leu Arg Asn Val Glu Glu Val Phe Arg Tyr
        195                 200                 205

Leu Leu Glu Thr Glu Cys Asn Phe Leu Phe Thr Asp Asn Phe Ser Phe
    210                 215                 220

Asn Thr Tyr Val Gln Leu Ala Arg Asn Tyr Pro Lys Gln Lys Glu Val
225                 230                 235                 240

Val Ser Asp Val Asp Ile Ser Asn Gly Val Glu Ser Val Pro Ile Ser
                245                 250                 255
```

```
Phe Cys Asn Glu Ile Asp Ser Arg Lys Leu Pro Gln Phe Lys Tyr Arg
            260                 265                 270

Lys Thr Val Trp Pro Arg Ala Tyr Asn Leu Thr Asn Phe Ser Ser Met
        275                 280                 285

Phe Thr Asp Ser Cys Asp Cys Ser Glu Gly Cys Ile Asp Ile Thr Lys
    290                 295                 300

Cys Ala Cys Leu Gln Leu Thr Ala Arg Asn Ala Lys Thr Ser Pro Leu
305                 310                 315                 320

Ser Ser Asp Lys Ile Thr Thr Gly Tyr Lys Tyr Lys Arg Leu Gln Arg
                325                 330                 335

Gln Ile Pro Thr Gly Ile Tyr Glu Cys Ser Leu Leu Cys Lys Cys Asn
            340                 345                 350

Arg Gln Leu Cys Gln Asn Arg Val Val Gln His Gly Pro Gln Val Arg
        355                 360                 365

Leu Gln Val Phe Lys Thr Glu Gln Lys Gly Trp Gly Val Arg Cys Leu
    370                 375                 380

Asp Asp Ile Asp Arg Gly Thr Phe Val Cys Ile Tyr Ser Gly Arg Leu
385                 390                 395                 400

Leu Ser Arg Ala Asn Thr Glu Lys Ser Tyr Gly Ile Asp Glu Asn Gly
                405                 410                 415

Arg Asp Glu Asn Thr Met Lys Asn Ile Phe Ser Lys Arg Lys Leu
            420                 425                 430

Glu Val Ala Cys Ser Asp Cys Glu Val Glu Val Leu Pro Leu Gly Leu
        435                 440                 445

Glu Thr His Pro Arg Thr Ala Lys Thr Glu Lys Cys Pro Pro Lys Phe
    450                 455                 460

Ser Asn Asn Pro Lys Glu Leu Thr Val Glu Thr Lys Tyr Asp Asn Ile
465                 470                 475                 480

Ser Arg Ile Gln Tyr His Ser Val Ile Arg Asp Pro Glu Ser Lys Thr
                485                 490                 495

Ala Ile Phe Gln His Asn Gly Lys Lys Met Glu Phe Val Ser Ser Glu
            500                 505                 510

Ser Val Thr Pro Glu Asp Asn Asp Gly Phe Pro Pro Arg Glu His Leu
        515                 520                 525

Asn Ser Lys Thr Lys Gly Ala Gln Lys Asp Ser Ser Ser Asn His Val
    530                 535                 540

Asp Glu Phe Glu Asp Asn Leu Leu Ile Glu Ser Asp Val Ile Asp Ile
545                 550                 555                 560

Thr Lys Tyr Arg Glu Glu Thr Pro Pro Arg Ser Arg Cys Asn Gln Ala
                565                 570                 575

Thr Thr Leu Asp Asn Gln Asn Ile Lys Lys Ala Ile Glu Val Gln Ile
            580                 585                 590

Gln Lys Pro Gln Glu Gly Arg Ser Thr Ala Cys Gln Arg Gln Gln Val
        595                 600                 605

Phe Cys Asp Glu Glu Leu Leu Ser Glu Thr Lys Asn Thr Ser Ser Asp
    610                 615                 620

Ser Leu Thr Lys Phe Asn Lys Gly Asn Val Phe Leu Leu Asp Ala Thr
625                 630                 635                 640

Lys Glu Gly Asn Val Gly Arg Phe Leu Asn His Ser Cys Cys Pro Asn
                645                 650                 655

Leu Leu Val Gln Asn Val Phe Val Glu Thr His Asn Arg Asn Phe Pro
            660                 665                 670
```

-continued

```
Leu Val Ala Phe Phe Thr Asn Arg Tyr Val Lys Ala Arg Thr Glu Leu
            675                 680                 685

Thr Trp Asp Tyr Gly Tyr Glu Ala Gly Thr Val Pro Glu Lys Glu Ile
690                 695                 700

Phe Cys Gln Cys Gly Val Asn Lys Cys Arg Lys Lys Ile Leu
705                 710                 715

<210> SEQ ID NO 66
<211> LENGTH: 684
<212> TYPE: PRT
<213> ORGANISM: Homo sapiens

<400> SEQUENCE: 66

Met Phe Ala Glu Ala Ala Lys Thr Thr Arg Pro Cys Gly Met Ala Glu
1               5                   10                  15

Phe Lys Glu Lys Pro Glu Ala Pro Thr Glu Gln Leu Asp Val Ala Cys
                20                  25                  30

Gly Gln Glu Asn Leu Pro Val Gly Ala Trp Pro Pro Gly Ala Ala Pro
            35                  40                  45

Ala Pro Phe Gln Tyr Thr Pro Asp His Val Val Gly Pro Gly Ala Asp
        50                  55                  60

Ile Asp Pro Thr Gln Ile Thr Phe Pro Gly Cys Ile Cys Val Lys Thr
65                  70                  75                  80

Pro Cys Leu Pro Gly Thr Cys Ser Cys Leu Arg His Gly Glu Asn Tyr
                85                  90                  95

Asp Asp Asn Ser Cys Leu Arg Asp Ile Gly Ser Gly Gly Lys Tyr Ala
                100                 105                 110

Glu Pro Val Phe Glu Cys Asn Val Leu Cys Arg Cys Ser Asp His Cys
            115                 120                 125

Arg Asn Arg Val Val Gln Lys Gly Leu Gln Phe His Phe Gln Val Phe
        130                 135                 140

Lys Thr His Lys Lys Gly Trp Gly Leu Arg Thr Leu Glu Phe Ile Pro
145                 150                 155                 160

Lys Gly Arg Phe Val Cys Glu Tyr Ala Gly Glu Val Leu Gly Phe Ser
                165                 170                 175

Glu Val Gln Arg Arg Ile His Leu Gln Thr Lys Ser Asp Ser Asn Tyr
            180                 185                 190

Ile Ile Ala Ile Arg Glu His Val Tyr Asn Gly Gln Val Met Glu Thr
        195                 200                 205

Phe Val Asp Pro Thr Tyr Ile Gly Asn Ile Gly Arg Phe Leu Asn His
    210                 215                 220

Ser Cys Glu Pro Asn Leu Leu Met Ile Pro Val Arg Ile Asp Ser Met
225                 230                 235                 240

Val Pro Lys Leu Ala Leu Phe Ala Ala Lys Asp Ile Val Pro Glu Glu
                245                 250                 255

Glu Leu Ser Tyr Asp Tyr Ser Gly Arg Tyr Leu Asn Leu Thr Val Ser
            260                 265                 270

Glu Asp Lys Glu Arg Leu Asp His Gly Lys Leu Arg Lys Pro Cys Tyr
        275                 280                 285

Cys Gly Ala Lys Ser Cys Thr Ala Phe Leu Pro Phe Asp Ser Ser Leu
    290                 295                 300

Tyr Cys Pro Val Glu Lys Ser Asn Ile Ser Cys Gly Asn Glu Lys Glu
305                 310                 315                 320

Pro Ser Met Cys Gly Ser Ala Pro Ser Val Phe Pro Ser Cys Lys Arg
                325                 330                 335
```

```
Leu Thr Leu Glu Thr Met Lys Met Met Leu Asp Lys Lys Gln Ile Arg
            340                 345                 350

Ala Ile Phe Leu Phe Glu Phe Lys Met Gly Arg Lys Ala Ala Glu Thr
            355                 360                 365

Thr Arg Asn Ile Asn Asn Ala Phe Gly Pro Gly Thr Ala Asn Glu Arg
        370                 375                 380

Thr Val Gln Trp Trp Phe Lys Lys Phe Cys Lys Gly Asp Glu Ser Leu
385                 390                 395                 400

Glu Asp Glu Glu Arg Ser Gly Arg Pro Ser Glu Val Asp Asn Asp Gln
                405                 410                 415

Leu Arg Ala Ile Ile Glu Ala Asp Pro Leu Thr Thr Thr Arg Glu Val
            420                 425                 430

Ala Glu Glu Leu Asn Val Asn His Ser Thr Val Val Arg His Leu Lys
            435                 440                 445

Gln Ile Gly Lys Val Lys Lys Leu Asp Lys Trp Val Pro His Glu Leu
        450                 455                 460

Thr Glu Asn Gln Lys Asn Arg Arg Phe Glu Val Ser Ser Ser Leu Ile
465                 470                 475                 480

Leu Arg Asn His Asn Glu Pro Phe Leu Asp Arg Ile Val Thr Cys Asp
                485                 490                 495

Glu Lys Trp Ile Leu Tyr Asp Asn Arg Arg Arg Ser Ala Gln Trp Leu
            500                 505                 510

Asp Gln Glu Glu Ala Pro Lys His Phe Pro Lys Pro Ile Leu His Pro
        515                 520                 525

Lys Lys Val Met Val Thr Ile Trp Trp Ser Ala Ala Gly Leu Ile His
530                 535                 540

Tyr Ser Phe Leu Asn Pro Gly Glu Thr Ile Thr Ser Glu Lys Tyr Ala
545                 550                 555                 560

Gln Glu Ile Asp Glu Met Asn Gln Lys Leu Gln Arg Leu Gln Leu Ala
                565                 570                 575

Leu Val Asn Arg Lys Gly Pro Ile Leu Leu His Asp Asn Ala Arg Pro
            580                 585                 590

His Val Ala Gln Pro Thr Leu Gln Lys Leu Asn Glu Leu Gly Tyr Glu
        595                 600                 605

Val Leu Pro His Pro Pro Tyr Ser Pro Asp Leu Leu Pro Thr Asn Tyr
610                 615                 620

His Val Phe Lys His Leu Asn Asn Phe Leu Gln Gly Lys Arg Phe His
625                 630                 635                 640

Asn Gln Gln Asp Ala Glu Asn Ala Phe Gln Glu Phe Val Glu Ser Gln
                645                 650                 655

Ser Thr Asp Phe Tyr Ala Thr Gly Ile Asn Gln Leu Ile Ser Arg Trp
            660                 665                 670

Gln Lys Cys Val Asp Cys Asn Gly Ser Tyr Phe Asp
        675                 680

<210> SEQ ID NO 67
<211> LENGTH: 365
<212> TYPE: PRT
<213> ORGANISM: Homo sapiens

<400> SEQUENCE: 67

Met Phe Ala Glu Ala Ala Lys Thr Thr Arg Pro Cys Gly Met Ala Glu
1               5                   10                  15

Phe Lys Glu Lys Pro Glu Ala Pro Thr Glu Gln Leu Asp Val Ala Cys
```

```
                    20                  25                  30
Gly Gln Glu Asn Leu Pro Val Gly Ala Trp Pro Pro Gly Ala Ala Pro
                35                  40                  45

Ala Pro Phe Gln Tyr Thr Pro Asp His Val Val Gly Pro Gly Ala Asp
         50                  55                  60

Ile Asp Pro Thr Gln Ile Thr Phe Pro Gly Cys Ile Cys Val Lys Thr
 65                  70                  75                  80

Pro Cys Leu Pro Gly Thr Cys Ser Cys Leu Arg His Gly Glu Asn Tyr
                 85                  90                  95

Asp Asp Asn Ser Cys Leu Arg Asp Ile Gly Ser Gly Gly Lys Tyr Ala
            100                 105                 110

Glu Pro Val Phe Glu Cys Asn Val Leu Cys Arg Cys Ser Asp His Cys
        115                 120                 125

Arg Asn Arg Val Val Gln Lys Gly Leu Gln Phe His Phe Gln Val Phe
    130                 135                 140

Lys Thr His Lys Lys Gly Trp Gly Leu Arg Thr Leu Glu Phe Ile Pro
145                 150                 155                 160

Lys Gly Arg Phe Val Cys Glu Tyr Ala Gly Glu Val Leu Gly Phe Ser
                165                 170                 175

Glu Val Gln Arg Arg Ile His Leu Gln Thr Lys Ser Asp Ser Asn Tyr
            180                 185                 190

Ile Ile Ala Ile Arg Glu His Val Tyr Asn Gly Gln Val Met Glu Thr
        195                 200                 205

Phe Val Asp Pro Thr Tyr Ile Gly Asn Ile Gly Arg Phe Leu Asn His
    210                 215                 220

Ser Cys Glu Pro Asn Leu Leu Met Ile Pro Val Arg Ile Asp Ser Met
225                 230                 235                 240

Val Pro Lys Leu Ala Leu Phe Ala Ala Lys Asp Ile Val Pro Glu Glu
                245                 250                 255

Glu Leu Ser Tyr Asp Tyr Ser Gly Arg Tyr Leu Asn Leu Thr Val Ser
            260                 265                 270

Glu Asp Lys Glu Arg Leu Asp His Gly Lys Leu Arg Lys Pro Cys Tyr
        275                 280                 285

Cys Gly Ala Lys Ser Cys Thr Ala Phe Leu Pro Phe Asp Ser Ser Leu
    290                 295                 300

Tyr Cys Pro Val Glu Lys Ser Asn Ile Ser Cys Gly Asn Glu Lys Glu
305                 310                 315                 320

Pro Ser Met Cys Gly Ser Ala Pro Ser Val Phe Pro Ser Cys Lys Arg
                325                 330                 335

Leu Thr Leu Glu Val Ser Leu Phe Ser Asp Lys Gln Leu Ala Pro Pro
            340                 345                 350

Tyr Ser Gly Arg Gln Trp Leu Ala Ser Phe Thr Ser Ala
        355                 360                 365

<210> SEQ ID NO 68
<211> LENGTH: 545
<212> TYPE: PRT
<213> ORGANISM: Homo sapiens

<400> SEQUENCE: 68

Met Phe Ala Glu Ala Ala Lys Thr Thr Arg Pro Cys Gly Met Ala Glu
  1               5                  10                  15

Phe Lys Glu Lys Pro Gly Ala Pro Thr Glu Gln Leu Asp Val Ala Cys
                 20                  25                  30
```

```
Gly Gln Glu Asn Leu Pro Val Gly Ala Trp Pro Pro Gly Ala Ala Pro
            35                  40                  45
Ala Pro Phe Gln Tyr Thr Pro Asp His Val Val Gly Pro Gly Ala Asp
 50                  55                  60
Ile Asp Pro Thr Gln Ile Thr Phe Pro Gly Cys Ile Cys Val Lys Thr
 65                  70                  75                  80
Pro Cys Leu Pro Gly Thr Cys Ser Cys Leu Arg His Gly Glu Asn Tyr
                 85                  90                  95
Asp Asp Asn Ser Cys Leu Arg Asp Ile Gly Ser Gly Lys Tyr Ala
            100                 105                 110
Glu Pro Val Phe Glu Cys Asn Val Leu Cys Arg Cys Ser Asp His Cys
            115                 120                 125
Arg Asn Arg Val Val Gln Lys Gly Leu Gln Phe His Phe Gln Val Phe
130                 135                 140
Lys Thr His Lys Lys Gly Trp Gly Leu Arg Thr Leu Glu Phe Ile Pro
145                 150                 155                 160
Lys Gly Ser Ser Leu Tyr Cys Pro Val Glu Lys Ser Asn Ile Ser Cys
                165                 170                 175
Gly Asn Glu Lys Glu Pro Ser Met Cys Gly Ser Ala Pro Ser Val Phe
            180                 185                 190
Pro Ser Cys Lys Arg Leu Thr Leu Glu Thr Met Lys Met Met Leu Asp
            195                 200                 205
Lys Lys Gln Ile Arg Ala Ile Phe Leu Phe Glu Phe Lys Met Gly Arg
            210                 215                 220
Lys Ala Ala Glu Thr Thr Arg Asn Ile Asn Asn Ala Phe Gly Pro Gly
225                 230                 235                 240
Thr Ala Asn Glu Arg Thr Val Gln Trp Trp Phe Lys Lys Phe Cys Lys
                245                 250                 255
Gly Asp Glu Ser Leu Glu Asp Glu Arg Ser Gly Arg Pro Ser Glu
            260                 265                 270
Val Asp Asn Asp Gln Leu Arg Ala Ile Ile Glu Ala Asp Pro Leu Thr
            275                 280                 285
Thr Thr Arg Glu Val Ala Glu Glu Leu Asn Val Asn His Ser Thr Val
290                 295                 300
Val Arg His Leu Lys Gln Ile Gly Lys Val Lys Lys Leu Asp Lys Trp
305                 310                 315                 320
Val Pro His Glu Leu Thr Glu Asn Gln Lys Asn Arg Arg Phe Glu Val
                325                 330                 335
Ser Ser Ser Leu Ile Leu Arg Asn His Asn Glu Pro Phe Leu Asp Arg
            340                 345                 350
Ile Val Thr Cys Asp Glu Lys Trp Ile Leu Tyr Asp Asn Arg Arg Arg
            355                 360                 365
Ser Ala Gln Trp Leu Asp Gln Glu Glu Ala Pro Lys His Phe Pro Lys
            370                 375                 380
Pro Ile Leu His Pro Lys Lys Val Met Val Thr Ile Trp Trp Ser Ala
385                 390                 395                 400
Ala Gly Leu Ile His Tyr Ser Phe Leu Asn Pro Gly Glu Thr Ile Thr
                405                 410                 415
Ser Glu Lys Tyr Ala Gln Glu Ile Asp Glu Met Asn Gln Lys Leu Gln
            420                 425                 430
Arg Leu Gln Leu Ala Leu Val Asn Arg Lys Gly Pro Ile Leu Leu His
            435                 440                 445
Asp Asn Ala Arg Pro His Val Ala Gln Pro Thr Leu Gln Lys Leu Asn
```

```
              450             455             460
Glu Leu Gly Tyr Glu Val Leu Pro His Pro Tyr Ser Pro Asp Leu
465                 470                 475                 480

Leu Pro Thr Asn Tyr His Val Phe Lys His Leu Asn Asn Phe Leu Gln
                485                 490                 495

Gly Lys Arg Phe His Asn Gln Gln Asp Ala Glu Asn Ala Phe Gln Glu
                500                 505                 510

Phe Val Glu Ser Gln Ser Thr Asp Phe Tyr Ala Thr Gly Ile Asn Gln
                515                 520                 525

Leu Ile Ser Arg Trp Gln Lys Cys Val Asp Cys Asn Gly Ser Tyr Phe
            530                 535                 540

Asp
545

<210> SEQ ID NO 69
<211> LENGTH: 428
<212> TYPE: PRT
<213> ORGANISM: Homo sapiens

<400> SEQUENCE: 69

Met Glu Pro Leu Lys Val Glu Lys Phe Ala Thr Ala Lys Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
            260                 265                 270
```

```
Ala Asp Met Leu Thr Gly Asp Glu Gln Val Trp Lys Glu Val Gln Glu
            275                 280                 285

Ser Leu Lys Lys Ile Glu Glu Leu Lys Ala His Trp Lys Trp Glu Gln
290                 295                 300

Val Leu Ala Met Cys Gln Ala Ile Ile Ser Ser Asn Ser Glu Arg Leu
305                 310                 315                 320

Pro Asp Ile Asn Ile Tyr Gln Leu Lys Val Leu Asp Cys Ala Met Asp
                325                 330                 335

Ala Cys Ile Asn Leu Gly Leu Leu Glu Ala Leu Phe Tyr Gly Thr
            340                 345                 350

Arg Thr Met Glu Pro Tyr Arg Ile Phe Phe Pro Gly Ser His Pro Val
            355                 360                 365

Arg Gly Val Gln Val Met Lys Val Gly Lys Leu Gln Leu His Gln Gly
370                 375                 380

Met Phe Pro Gln Ala Met Lys Asn Leu Arg Leu Ala Phe Asp Ile Met
385                 390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425

<210> SEQ ID NO 70
<211> LENGTH: 258
<212> TYPE: PRT
<213> ORGANISM: Homo sapiens

<400> SEQUENCE: 70

Met Glu Glu Glu Glu Lys Val Ile Cys Asn Ser Phe Thr Ile Cys
1               5                   10                  15

Asn Ala Glu Met Gln Glu Val Gly Val Gly Leu Tyr Pro Ser Ile Ser
                20                  25                  30

Leu Leu Asn His Ser Cys Asp Pro Asn Cys Ser Ile Val Phe Asn Gly
            35                  40                  45

Pro His Leu Leu Leu Arg Ala Val Arg Asp Ile Glu Val Gly Glu Glu
50                  55                  60

Leu Thr Ile Cys Tyr Leu Asp Met Leu Met Thr Ser Glu Glu Arg Arg
65                  70                  75                  80

Lys Gln Leu Arg Asp Gln Tyr Cys Phe Glu Cys Asp Cys Phe Arg Cys
                85                  90                  95

Gln Thr Gln Asp Lys Asp Ala Asp Met Leu Thr Gly Asp Glu Gln Val
            100                 105                 110

Trp Lys Glu Val Gln Glu Ser Leu Lys Lys Ile Glu Glu Leu Lys Ala
        115                 120                 125

His Trp Lys Trp Glu Gln Val Leu Ala Met Cys Gln Ala Ile Ile Ser
    130                 135                 140

Ser Asn Ser Glu Arg Leu Pro Asp Ile Asn Ile Tyr Gln Leu Lys Val
145                 150                 155                 160

Leu Asp Cys Ala Met Asp Ala Cys Ile Asn Leu Gly Leu Leu Glu Glu
                165                 170                 175

Ala Leu Phe Tyr Gly Thr Arg Thr Met Glu Pro Tyr Arg Ile Phe Phe
            180                 185                 190

Pro Gly Ser His Pro Val Arg Gly Val Gln Val Met Lys Val Gly Lys
        195                 200                 205

Leu Gln Leu His Gln Gly Met Phe Pro Gln Ala Met Lys Asn Leu Arg
    210                 215                 220
```

```
Leu Ala Phe Asp Ile Met Arg Val Thr His Gly Arg Glu His Ser Leu
225                 230                 235                 240

Ile Glu Asp Leu Ile Leu Leu Glu Glu Cys Asp Ala Asn Ile Arg
            245                 250                 255

Ala Ser

<210> SEQ ID NO 71
<211> LENGTH: 369
<212> TYPE: PRT
<213> ORGANISM: Homo sapiens

<400> SEQUENCE: 71

Met Arg Cys Ser Gln Cys Arg Val Ala Lys Tyr Cys Ser Ala Lys Cys
1               5                   10                  15

Gln Lys Lys Ala Trp Pro Asp His Lys Arg Glu Cys Lys Cys Leu Lys
            20                  25                  30

Ser Cys Lys Pro Arg Tyr Pro Pro Asp Ser Val Arg Leu Leu Gly Arg
        35                  40                  45

Val Val Phe Lys Leu Met Asp Gly Ala Pro Ser Glu Ser Glu Lys Leu
    50                  55                  60

Tyr Ser Phe Tyr Asp Leu Glu Ser Asn Ile Asn Lys Leu Thr Glu Asp
65                  70                  75                  80

Lys Lys Glu Gly Leu Arg Gln Leu Val Met Thr Phe Gln His Phe Met
                85                  90                  95

Arg Glu Glu Ile Gln Asp Ala Ser Gln Leu Pro Pro Ala Phe Asp Leu
            100                 105                 110

Phe Glu Ala Phe Ala Lys Val Ile Cys Asn Ser Phe Thr Ile Cys Asn
        115                 120                 125

Ala Glu Met Gln Glu Val Gly Val Gly Leu Tyr Pro Ser Ile Ser Leu
    130                 135                 140

Leu Asn His Ser Cys Asp Pro Asn Cys Ser Ile Val Phe Asn Gly Pro
145                 150                 155                 160

His Leu Leu Arg Ala Val Arg Asp Ile Glu Val Gly Glu Glu Leu
                165                 170                 175

Thr Ile Cys Tyr Leu Asp Met Leu Met Thr Ser Glu Glu Arg Arg Lys
            180                 185                 190

Gln Leu Arg Asp Gln Tyr Cys Phe Glu Cys Asp Cys Phe Arg Cys Gln
        195                 200                 205

Thr Gln Asp Lys Asp Ala Asp Met Leu Thr Gly Asp Glu Gln Val Trp
    210                 215                 220

Lys Glu Val Gln Glu Ser Leu Lys Lys Ile Glu Glu Leu Lys Ala His
225                 230                 235                 240

Trp Lys Trp Glu Gln Val Leu Ala Met Cys Gln Ala Ile Ile Ser Ser
                245                 250                 255

Asn Ser Glu Arg Leu Pro Asp Ile Asn Ile Tyr Gln Leu Lys Val Leu
            260                 265                 270

Asp Cys Ala Met Asp Ala Cys Ile Asn Leu Gly Leu Leu Glu Glu Ala
        275                 280                 285

Leu Phe Tyr Gly Thr Arg Thr Met Glu Pro Tyr Arg Ile Phe Phe Pro
    290                 295                 300

Gly Ser His Pro Val Arg Gly Val Gln Val Met Lys Val Gly Lys Leu
305                 310                 315                 320

Gln Leu His Gln Gly Met Phe Pro Gln Ala Met Lys Asn Leu Arg Leu
                325                 330                 335
```

-continued

```
Ala Phe Asp Ile Met Arg Val Thr His Gly Arg Glu His Ser Leu Ile
                340                 345                 350

Glu Asp Leu Ile Leu Leu Glu Glu Cys Asp Ala Asn Ile Arg Ala
        355                 360                 365

Ser

<210> SEQ ID NO 72
<211> LENGTH: 462
<212> TYPE: PRT
<213> ORGANISM: Homo sapiens

<400> SEQUENCE: 72

Met Gly Pro Asp Arg Val Thr Ala Arg Glu Leu Cys Glu Asn Asp Asp
1               5                   10                  15

Leu Ala Thr Ser Leu Val Leu Asp Pro Tyr Leu Gly Phe Arg Thr His
            20                  25                  30

Lys Met Asn Val Ser Pro Val Pro Pro Leu Arg Arg Gln Gln His Leu
        35                  40                  45

Arg Ser Ala Leu Glu Thr Phe Leu Arg Gln Arg Asp Leu Glu Ala Ala
    50                  55                  60

Tyr Arg Ala Leu Thr Leu Gly Gly Trp Thr Ala Arg Tyr Phe Gln Ser
65                  70                  75                  80

Arg Gly Pro Arg Gln Glu Ala Ala Leu Lys Thr His Val Tyr Arg Tyr
                85                  90                  95

Leu Arg Ala Phe Leu Pro Glu Ser Gly Phe Thr Ile Leu Pro Cys Thr
            100                 105                 110

Arg Tyr Ser Met Glu Thr Asn Gly Ala Lys Ile Val Ser Thr Arg Ala
        115                 120                 125

Trp Lys Lys Asn Glu Lys Leu Glu Leu Leu Val Gly Cys Ile Ala Glu
    130                 135                 140

Leu Arg Glu Ala Asp Glu Gly Leu Leu Arg Ala Gly Glu Asn Asp Phe
145                 150                 155                 160

Ser Ile Met Tyr Ser Thr Arg Lys Arg Ser Ala Gln Leu Trp Leu Gly
                165                 170                 175

Pro Ala Ala Phe Ile Asn His Asp Cys Lys Pro Asn Cys Lys Phe Val
            180                 185                 190

Pro Ala Asp Gly Asn Ala Ala Cys Val Lys Val Leu Arg Asp Ile Glu
        195                 200                 205

Pro Gly Asp Glu Val Thr Cys Phe Tyr Gly Glu Gly Phe Phe Gly Glu
    210                 215                 220

Lys Asn Glu His Cys Glu Cys His Thr Cys Glu Arg Lys Gly Glu Gly
225                 230                 235                 240

Ala Phe Arg Thr Arg Pro Arg Glu Pro Ala Leu Pro Pro Arg Pro Leu
                245                 250                 255

Asp Lys Tyr Gln Leu Arg Glu Thr Lys Arg Arg Leu Gln Gln Gly Leu
            260                 265                 270

Asp Ser Gly Ser Arg Gln Gly Leu Leu Gly Pro Arg Ala Cys Val His
        275                 280                 285

Pro Ser Pro Leu Arg Arg Asp Pro Phe Cys Ala Ala Cys Gln Pro Leu
    290                 295                 300

Arg Leu Pro Ala Cys Ser Ala Arg Pro Asp Thr Ser Pro Leu Trp Leu
305                 310                 315                 320

Gln Trp Leu Pro Gln Pro Gln Pro Arg Val Arg Pro Arg Lys Arg Arg
                325                 330                 335
```

```
Arg Pro Arg Pro Arg Ala Pro Val Leu Ser Thr His His Ala Ala
            340                 345                 350

Arg Val Ser Leu His Arg Trp Gly Gly Cys Gly Pro His Cys Arg Leu
        355                 360                 365

Arg Gly Glu Ala Leu Val Ala Leu Gly Gln Pro Pro His Ala Arg Trp
    370                 375                 380

Ala Pro Gln Gln Asp Trp His Trp Ala Arg Arg Tyr Gly Leu Pro Tyr
385                 390                 395                 400

Val Val Arg Val Asp Leu Arg Arg Leu Ala Pro Ala Pro Ala Thr
                405                 410                 415

Pro Ala Pro Ala Gly Thr Pro Gly Pro Ile Leu Ile Pro Lys Gln Ala
                420                 425                 430

Leu Ala Phe Ala Pro Phe Ser Pro Pro Lys Arg Leu Arg Leu Val Val
            435                 440                 445

Ser His Gly Ser Ile Asp Leu Asp Val Gly Gly Glu Glu Leu
    450                 455                 460

<210> SEQ ID NO 73
<211> LENGTH: 97
<212> TYPE: PRT
<213> ORGANISM: Homo sapiens

<400> SEQUENCE: 73

Met Gly Pro Asp Arg Val Thr Ala Arg Glu Leu Cys Glu Asn Asp Asp
1               5                   10                  15

Leu Ala Thr Ser Leu Val Leu Asp Pro Tyr Leu Gly Phe Arg Thr His
            20                  25                  30

Lys Met Asn Val Arg Ser Ile Ala Thr Ser Val Pro Ser Cys Arg Lys
        35                  40                  45

Val Ala Leu Pro Ser Cys Pro Ala Arg Ala Thr Pro Trp Arg Pro Thr
    50                  55                  60

Gly Pro Arg Ser Cys Pro Leu Val Leu Gly Lys Arg Met Arg Ser Trp
65                  70                  75                  80

Ser Cys Trp Trp Ala Ala Leu Gln Ser Cys Gly Arg Gln Met Arg Gly
            85                  90                  95

Cys

<210> SEQ ID NO 74
<211> LENGTH: 59
<212> TYPE: DNA
<213> ORGANISM: Artificial sequence
<220> FEATURE:
<223> OTHER INFORMATION: synthetic nucleotide sequence

<400> SEQUENCE: 74
ccgggctatg gaattacaa cccatctcga gatgggttgt aattcccata gcttttttg      59

<210> SEQ ID NO 75
<211> LENGTH: 59
<212> TYPE: DNA
<213> ORGANISM: Artificial sequence
<220> FEATURE:
<223> OTHER INFORMATION: synthetic nucleotide sequence

<400> SEQUENCE: 75
ccggctgtga cactctggag ttgaactcga gttcaactcc agagtgtcac agtttttg      59

<210> SEQ ID NO 76
```

```
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 76
gctatgggaa ttacaaccca t                                              21

<210> SEQ ID NO 77
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 77
ctgtgacact ctggagttga a                                              21

<210> SEQ ID NO 78
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 78
gagtcgattg atccaattaa a                                              21

<210> SEQ ID NO 79
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 79
cgtctacgaa aggcctatta c                                              21

<210> SEQ ID NO 80
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 80
tcgccaacac gagtgttata t                                              21

<210> SEQ ID NO 81
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 81
cacgttgaac aagtgcattt a                                              21

<210> SEQ ID NO 82
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 82
```

```
cacattggag agaggcgatt t                                              21

<210> SEQ ID NO 83
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 83
gcccgcaaga agaagctaaa c                                              21

<210> SEQ ID NO 84
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 84
cgagtcaata acgccagcta t                                              21

<210> SEQ ID NO 85
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 85
cctcggttct gagtcgtata a                                              21

<210> SEQ ID NO 86
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 86
cacacattcc tgaccagaga t                                              21

<210> SEQ ID NO 87
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 87
cctcttcgac ttagacaaca a                                              21

<210> SEQ ID NO 88
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 88
agacgtgcaa gcaggtcttt c                                              21

<210> SEQ ID NO 89
<211> LENGTH: 21
<212> TYPE: DNA
```

```
<213> ORGANISM: Artificial sequence
<220> FEATURE:
<223> OTHER INFORMATION: synthetic nucleotide sequence

<400> SEQUENCE: 89
ctatctggca gtgcgagaat g                                             21

<210> SEQ ID NO 90
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 90
gctaggttaa ttgggaccaa a                                             21

<210> SEQ ID NO 91
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 91
ccaacacaag tcatcccatt a                                             21

<210> SEQ ID NO 92
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 92
gcactgttaa acattccact t                                             21

<210> SEQ ID NO 93
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 93
cgcctaaagc agctctcatt t                                             21

<210> SEQ ID NO 94
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 94
catctacatg ttccgaataa a                                             21

<210> SEQ ID NO 95
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 95
cgtagaagag gacctactaa t                                             21
```

<210> SEQ ID NO 96
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 96
cccacctgaa tcatcacctt t                                    21

<210> SEQ ID NO 97
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 97
cctcgcctca agaaatggaa a                                    21

<210> SEQ ID NO 98
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 98
gaggcgattc aacacaccat t                                    21

<210> SEQ ID NO 99
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 99
ccctgttaga atgcccagtt t                                    21

<210> SEQ ID NO 100
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 100
accctcatgt tcagggtgga t                                    21

<210> SEQ ID NO 101
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 101
ccagcactat aagttccgtt a                                    21

<210> SEQ ID NO 102
<211> LENGTH: 21
<212> TYPE: DNA
<213> ORGANISM: Artificial sequence
<220> FEATURE:

<223> OTHER INFORMATION: synthetic nucleotide sequence

<400> SEQUENCE: 102
gctgatttga tgctgtatga t    21

<210> SEQ ID NO 103
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 103
gctgttccct tccagattta a    21

<210> SEQ ID NO 104
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 104
gtgctaattt cacggtataa a    21

<210> SEQ ID NO 105
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 105
ccgagacgtc tcaggttaat c    21

<210> SEQ ID NO 106
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 106
cctctctttg aatcttccat t    21

<210> SEQ ID NO 107
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 107
cggaaagcca agttcacctt t    21

<210> SEQ ID NO 108
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 108
ggagattacc tatgactata a    21

```
<210> SEQ ID NO 109
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 109
acatgcggga gaagcgttat g                                              21

<210> SEQ ID NO 110
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 110
cctgaagaat gatgagataa t                                              21

<210> SEQ ID NO 111
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 111
gccctatgac tctcttggtt a                                              21

<210> SEQ ID NO 112
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 112
agcgtgtatt ccactcataa t                                              21

<210> SEQ ID NO 113
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 113
agacttgttg agcccattaa a                                              21

<210> SEQ ID NO 114
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 114
gacctatgcc acagacttaa a                                              21

<210> SEQ ID NO 115
<211> LENGTH: 21
<212> TYPE: DNA
<213> ORGANISM: Artificial sequence
<220> FEATURE:
<223> OTHER INFORMATION: synthetic nucleotide sequence
```

```
<400> SEQUENCE: 115
gtggacatac ggtagtaata a                                          21

<210> SEQ ID NO 116
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 116
gccagggtat tattatagaa t                                          21

<210> SEQ ID NO 117
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 117
cttatgaatc agaaagggtt t                                          21

<210> SEQ ID NO 118
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 118
gtttcctgaa actgggttaa t                                          21

<210> SEQ ID NO 119
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 119
gaatcgcaaa cttacggatt t                                          21

<210> SEQ ID NO 120
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 120
cagtgactaa ttgtgagtct t                                          21

<210> SEQ ID NO 121
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 121
cgtgacttca tagaggagta t                                          21

<210> SEQ ID NO 122
<211> LENGTH: 21
```

-continued

```
<212> TYPE: DNA
<213> ORGANISM: Artificial sequence
<220> FEATURE:
<223> OTHER INFORMATION: synthetic nucleotide sequence

<400> SEQUENCE: 122
gctgaaatta aagccatgca a                                      21

<210> SEQ ID NO 123
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 123
cctgtttgtg aaattagctt a                                      21

<210> SEQ ID NO 124
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 124
caagtgttca agacgcataa a                                      21

<210> SEQ ID NO 125
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 125
gaaaggctag atcatgggaa a                                      21

<210> SEQ ID NO 126
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 126
cgcacatctt cggagtgatt a                                      21

<210> SEQ ID NO 127
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 127
gcaatcatga ggcagtgaaa t                                      21

<210> SEQ ID NO 128
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 128
```
gctgtgaagg agtttgaatc a                                              21

<210> SEQ ID NO 129
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 129
gctgtgaagg agtttgaatc a                                              21

<210> SEQ ID NO 130
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 130
gctctgtgtt tgaggacagt a                                              21

<210> SEQ ID NO 131
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 131
agcctgattg aagatttgat t                                              21

<210> SEQ ID NO 132
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 132
cagcctgatt gaagatttga t                                              21

<210> SEQ ID NO 133
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 133
ccagaagatg aaatcctgtt t                                              21

<210> SEQ ID NO 134
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 134
gcttatgcgt agatccttta a                                              21

<210> SEQ ID NO 135
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 135
cgttgggatt catggcctat t                                              21

<210> SEQ ID NO 136
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 136
gcaggtgtac aacgtcttca t                                              21

<210> SEQ ID NO 137
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 137
gcacagattg cttctttcaa a                                              21

<210> SEQ ID NO 138
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 138
gcccaccttc agacttctat t                                              21

<210> SEQ ID NO 139
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 139
catctaagct aactcatata a                                              21

<210> SEQ ID NO 140
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 140
ttggttcttg atccctattt a                                              21

<210> SEQ ID NO 141
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 141
tgacccttga ctccagcata g                                              21

```
<210> SEQ ID NO 142
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 142
gtgtccactc gtgcttggaa a                                           21

<210> SEQ ID NO 143
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 143
gaatgacttc agcatcatgt a                                           21

<210> SEQ ID NO 144
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 144
gtgtgacctc atctttctca t                                           21

<210> SEQ ID NO 145
<211> LENGTH: 21
<212> TYPE: DNA
<213> ORGANISM: Artificial sequence
<220> FEATURE:
<223> OTHER INFORMATION: synthetic nucleotide sequence

<400> SEQUENCE: 145
atcggataaa gatccacttt g                                           21
```

COMPOSITIONS AND METHODS FOR REACTIVATING LATENT IMMUNODEFICIENCY VIRUS

CROSS-REFERENCE

This application is a Divisional of U.S. application Ser. No. 15/488,212 filed Apr. 14, 2017, now U.S. Pat. No. 10,351,853, which is a Continuation-In-Part of International Application No. PCT/US2015/055377, filed Oct. 13, 2015, which application claims the benefit of U.S. Provisional Application No. 62/063,822, filed Oct. 14, 2014, which applications are incorporated herein by reference in their entirety.

INTRODUCTION

Combination antiretroviral therapy can control HIV-1 replication and delay disease progression. However, despite the complete suppression of detectable viremia in many patients, viremia reemerges rapidly after interruption of treatment, consistent with the existence of a latent viral reservoir. This reservoir is thought to consist mainly of latently infected resting memory CD4+ T cells. Due to the long half-life of this reservoir (44 months), it has been estimated that its total eradication with current treatment would require over 60 years.

Latently infected cells contain replication-competent integrated HIV-1 genomes that are blocked at the transcriptional level, resulting in the absence of viral protein expression. HIV depends on both cellular and viral factors for efficient transcription of its genome, and the activity of the HIV promoter is tightly linked to the level of activation of its host cell.

LITERATURE

Ferguson et al. (2011) *Structure* 19:1262; Xu et al. (2011) *J. Mol. Cell. Biol.* 3:293; Wang et al. (2011) *J. Biol. Chem.* 286:38725; Wagner and Jung (2012) *Nat. Biotechnol.* 30:622; Nguyen et al. (2015) *J. Biol Chem.* 290: 13641; Abu-Farha, M., Lambert, J. P., Al-Madhoun, A. S., Elisma, F., Skerjanc, I. S., and Figeys, D. (2008). The tale of two domains: proteomics and genomics analysis of SMYD2, a new histone methyltransferase. Mol Cell Proteomics 7, 560-572; Abu-Farha, M., Lanouette, S., Elisma, F., Tremblay, V., Butson, J., Figeys, D., and Couture, J. F. (2011). Proteomic analyses of the SMYD family interactomes identify HSP90 as a novel target for SMYD2. Journal of molecular cell biology 3, 301-308; Archin, N. M., Liberty, A. L., Kashuba, A. D., Choudhary, S. K., Kuruc, J. D., Crooks, A. M., Parker, D. C., Anderson, E. M., Kearney, M. F., Strain, M. C., et al. (2012). Administration of vorinostat disrupts HIV-1 latency in patients on antiretroviral therapy. Nature 487, 482-485; Archin, N. M., and Margolis, D. M. (2014). Emerging strategies to deplete the HIV reservoir. Current opinion in infectious diseases 27, 29-35; Bagislar, S., Sabo, A., Kress, T. R., Doni, M., Nicoli, P., Campaner, S., and Amati, B. (2016). Smyd2 is a Myc-regulated gene critical for MLL-AF9 induced leukemogenesis. Oncotarget 7, 66398-66415; Beck, D. B., Oda, H., Shen, S. S., and Reinberg, D. (2012). PR-Set7 and H4K20me1: at the crossroads of genome integrity, cell cycle, chromosome condensation, and transcription. Genes Dev 26, 325-337; Bonasio, R., Lecona, E., and Reinberg, D. (2010). MBT domain proteins in development and disease. Seminars in cell & developmental biology 21, 221-230; Brown, M. A., Sims, R. J., 3rd, Gottlieb, P. D., and Tucker, P. W. (2006). Identification and characterization of Smyd2: a split SET/MYND domain-containing histone H3 lysine 36-specific methyltransferase that interacts with the Sin3 histone deacetylase complex. Mol Cancer 5, 26; Chan, J. K., Bhattacharyya, D., Lassen, K. G., Ruelas, D., and Greene, W. C. (2013). Calcium/calcineurin synergizes with prostratin to promote NF-kappaB dependent activation of latent HIV. PLoS One 8, e77749; Cho, H. S., Hayami, S., Toyokawa, G., Maejima, K., Yamane, Y., Suzuki, T., Dohmae, N., Kogure, M., Kang, D., Neal, D. E., et al. (2012). RB1 methylation by SMYD2 enhances cell cycle progression through an increase of RB1 phosphorylation. Neoplasia 14, 476-486; Cowen, S. D. (2013). Targeting the Substrate Binding Site of Methyl Transferases; Structure Based Design of SMYD2 Inhibitors. In EpiCongress 2013, Boston, Mass., Jul. 23-24, 2013; Deeks, S. G. (2012). HIV: Shock and kill. Nature 487, 439-440; Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET bromodomain inhibition as a therapeutic strategy to target c-Myc. Cell 146, 904-917; du Chene, I., Basyuk, E., Lin, Y. L., Triboulet, R., Knezevich, A., Chable-Bessia, C., Mettling, C., Baillat, V., Reynes, J., Corbeau, P., et al. (2007). Suv39H1 and HP1-gamma are responsible for chromatin-mediated HIV-1 transcriptional silencing and post-integration latency. EMBO J 26, 424-435; Easley, R., Van Duyne, R., Coley, W., Guendel, I., Dadgar, S., Kehn-Hall, K., and Kashanchi, F. (2010). Chromatin dynamics associated with HIV-1 Tat-activated transcription. Biochim Biophys Acta 1799, 275-285; Fang, J., Feng, Q., Ketel, C. S., Wang, H., Cao, R., Xia, L., Erdjument-Bromage, H., Tempst, P., Simon, J. A., and Zhang, Y. (2002). Purification and functional characterization of SETS, a nucleosomal histone H4-lysine 20-specific methyltransferase. Current biology: CB 12, 1086-1099; Ferguson, A. D., Larsen, N. A., Howard, T., Pollard, H., Green, I., Grande, C., Cheung, T., Garcia-Arenas, R., Cowen, S., Wu, J., et al. (2011). Structural basis of substrate methylation and inhibition of SMYD2. Structure 19, 1262-1273; Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073; Folks, T. M., Clouse, K. A., Justement, J., Rabson, A., Duh, E., Kehrl, J. H., and Fauci, A. S. (1989). Tumor necrosis factor alpha induces expression of human immunodeficiency virus in a chronically infected T-cell clone. Proceedings of the National Academy of Sciences of the United States of America 86, 2365-2368; Francis, N. J., Kingston, R. E., and Woodcock, C. L. (2004). Chromatin compaction by a polycomb group protein complex. Science 306, 1574-1577; Friedman, J., Cho, W. K., Chu, C. K., Keedy, K. S., Archin, N. M., Margolis, D. M., and Karn, J. (2011). Epigenetic silencing of HIV-1 by the histone H3 lysine 27 methyltransferase enhancer of Zeste 2. J Virol 85, 9078-9089; Hamamoto, R., Saloura, V., and Nakamura, Y. (2015). Critical roles of non-histone protein lysine methylation in human tumorigenesis. Nature reviews. Cancer 15, 110-124; Herold, J. M., James, L. I., Korboukh, V. K., Gao, C., Coil, K. E., Bua, D. J., Norris, J. L., Kireev, D. B., Brown, P. J., Jin, J., et al. (2012). Structure-activity relationships of methyl-lysine reader antagonists. Medchemcomm 3, 45-51; Huang, J., Perez-Burgos, L., Placek, B. J., Sengupta, R., Richter, M., Dorsey, J. A., Kubicek, S., Opravil, S., Jenuwein, T., and Berger, S. L. (2006). Repression of p53 activity by Smyd2-mediated methylation. Nature 444, 629-632; Imai, K., Togami, H., and Okamoto, T. (2010). Involvement of histone H3 lysine 9 (H3K9) methyltransferase G9a in the maintenance of HIV-1 latency and its reactivation by BIX01294. J Biol Chem 285, 16538-16545; Jamieson, K., Wiles, E. T., McNaught, K. J., Sidoli, S., Leggett, N., Shao, Y., Garcia, B. A., and Selker, E. U. (2016). Loss of HP1 causes depletion of H3K27me3 from facultative heterochromatin and gain of H3K27me2 at constitutive heterochromatin. Genome research 26, 97-107; Jiang, Y., Trescott, L., Holcomb, J., Zhang, X., Brunzelle, J., Sirinupong, N., Shi, X., and Yang, Z. (2014). Structural insights into estrogen receptor alpha methylation by histone methyltransferase SMYD2, a cellular event implicated in estrogen signaling regulation. Journal of molecular biology 426, 3413-3425; Jordan, A., Bisgrove, D., and Verdin, E. (2003). HIV reproducibly establishes a latent infection after acute infection of T cells in vitro. EMBO J 22, 1868-1877; Jordan, A., Defechereux, P., and Verdin, E. (2001). The site of HIV-1 integration in the human genome determines basal transcriptional activity and response to Tat transactivation. EMBO J 20, 1726-1738; Kaehlcke, K., Don, A., Hetzer-Egger, C., Kiermer, V., Henklein, P., Schnoelzer, M., Loret, E., Cole, P. A., Verdin, E., and Ott, M. (2003). Acetylation of Tat defines a cyclinT1-independent step in HIV transactivation. Mol Cell 12, 167-176; Kalakonda, N., Fischle, W., Boccuni, P., Gurvich, N., Hoya-Arias, R., Zhao, X., Miyata, Y., Macgrogan, D., Zhang, J., Sims, J. K., et al. (2008). Histone H4 lysine 20 monomethylation promotes transcriptional repression by L3MBTL1. Oncogene 27, 4293-4304; Kundu, M., Srinivasan, A., Pomerantz, R. J., and Khalili, K. (1995). Evidence that a cell cycle regulator, E2F1, down-regulates transcriptional activity of the human immunodeficiency virus type 1 promoter. J Virol 69, 6940-6946; Kutsch, O., Benveniste, E. N., Shaw, G. M., and Levy, D. N. (2002). Direct and quantitative single-cell analysis of human immunodeficiency virus type 1 reactivation from latency. J Virol 76, 8776-8786; Laird, G. M., Bullen, C. K., Rosenbloom, D. I., Martin, A. R., Hill, A. L., Durand, C. M., Siliciano, J. D., and Siliciano, R. F. (2015). Ex vivo analysis identifies effective HIV-1 latency-reversing drug combinations. The Journal of clinical investigation 125, 1901-1912; Mbonye, U., and Karn, J. (2014). Transcriptional control of HIV latency: cellular signaling pathways, epigenetics, happenstance and the hope for a cure. Virology 454-455, 328-339; Min, J., Allali-Hassani, A., Nady, N., Qi, C., Ouyang, H., Liu, Y., MacKenzie, F., Vedadi, M., and Arrowsmith, C. H. (2007). L3MBTL1 recognition of mono- and dimethylated histones. Nat Struct Mol Biol 14, 1229-1230; Murray, A. J., Kwon, K. J., Farber, D. L., and Siliciano, R. F. (2016). The Latent Reservoir for HIV-1: How Immunologic Memory and Clonal Expansion Contribute to HIV-1 Persistence. J Immunol 197, 407-417; Naldini, L., Blomer, U., Gallay, P., Ory, D., Mulligan, R., Gage, F. H., Verma, I. M., and Trono, D. (1996). In vivo gene delivery and stable transduction of nondividing cells by a lentiviral vector. Science 272, 263-267; Nicodeme, E., Jeffrey, K. L., Schaefer, U., Beinke, S., Dewell, S., Chung, C. W., Chandwani, R., Marazzi, I., Wilson, P., Coste, H., et al. (2010). Suppression of inflammation by a synthetic histone mimic. Nature 468, 1119-1123; Nishioka, K., Rice, J. C., Sarma, K., Erdjument-Bromage, H., Werner, J., Wang, Y., Chuikov, S., Valenzuela, P., Tempst, P., Steward, R., et al. (2002). PR-Set7 is a nucleosome-specific methyltransferase that modifies lysine 20 of histone H4 and is associated with silent chromatin. Mol Cell 9, 1201-1213; Oda, H., Okamoto, I., Murphy, N., Chu, J., Price, S. M., Shen, M. M., Torres-Padilla, M. E., Heard, E., and Reinberg, D. (2009). Monomethylation of histone H4-lysine 20 is involved in chromosome structure and stability and is essential for mouse development. Mol Cell Biol 29, 2278-2295; Olsen, J. B., Cao, X. J., Han, B., Chen, L. H., Horvath, A., Richardson, T. I., Campbell, R. M., Garcia, B. A., and Nguyen, H. (2016). Quantitative Profiling of the Activity of Protein Lysine Methyltransferase SMYD2 Using SILAC-Based Proteomics. Molecular & cellular proteomics: MCP 15, 892-905; Ott, M., Geyer, M., and Zhou, Q. (2011). The control of HIV transcription: keeping RNA polymerase II on track. Cell Host Microbe 10, 426-435; Pagans, S., Kauder, S. E., Kaehlcke, K., Sakane, N., Schroeder, S., Dormeyer, W., Trievel, R. C., Verdin, E., Schnolzer, M., and Ott, M. (2010). The Cellular lysine methyltransferase Set7/9-KMT7 binds HIV-1 TAR RNA, monomethylates the viral transactivator Tat, and enhances HIV transcription. Cell Host Microbe 7, 234-244; Patel, D. J., and Wang, Z. (2013). Readout of epigenetic modifications. Annual review of biochemistry 82, 81-118; Pesavento, J. J., Yang, H., Kelleher, N. L., and Mizzen, C. A. (2008). Certain and progressive methylation of histone H4 at lysine 20 during the cell cycle. Mol Cell Biol 28, 468-486; Piao, L., Kang, D., Suzuki, T., Masuda, A., Dohmae, N., Nakamura, Y., and Hamamoto, R. (2014). The histone methyltransferase SMYD2 methylates PARP1 and promotes poly(ADP-ribosyl)ation activity in cancer cells. Neoplasia 16, 257-264, 264 e252; Rasmussen, T. A., Tolstrup, M., and Sogaard, O. S. (2016). Reversal of Latency as Part of a Cure for HIV-1. Trends in microbiology 24, 90-97; Saddic, L. A., West, L. E., Aslanian, A., Yates, J. R., 3rd, Rubin, S. M., Gozani, O., and Sage, J. (2010). Methylation of the retinoblastoma tumor suppressor by SMYD2. J Biol Chem 285, 37733-37740; Schotta, G., Lachner, M., Sarma, K., Ebert, A., Sengupta, R., Reuter, G., Reinberg, D., and Jenuwein, T. (2004). A silencing pathway to induce H3-K9 and H4-K20 trimethylation at constitutive heterochromatin. Genes Dev 18, 1251-1262; Schotta, G., Sengupta, R., Kubicek, S., Malin, S., Kauer, M., Callen, E., Celeste, A., Pagani, M., Opravil, S., De La Rosa-Velazquez, I. A., et al. (2008). A chromatin-wide transition to H4K20 monomethylation impairs genome integrity and programmed DNA rearrangements in the mouse. Genes Dev 22, 2048-2061; Schroder, S., Herker, E., Itzen, F., He, D., Thomas, S., Gilchrist, D. A., Kaehlcke, K., Cho, S., Pollard, K. S., Capra, J. A., et al. (2013). Acetylation of RNA polymerase II regulates growth-factor-induced gene transcription in mammalian cells. Mol Cell 52, 314-324; Sheridan, P. L., Mayall, T. P., Verdin, E., and Jones, K. A. (1997). Histone acetyltransferases regulate HIV-1 enhancer activity in vitro. Genes Dev 11, 3327-3340; Song, Y., Wu, F., and Wu, J. (2016). Targeting histone methylation for cancer therapy: enzymes, inhibitors, biological activity and perspectives. Journal of hematology & oncology 9, 49; Spina, C. A., Anderson, J., Archin, N. M., Bosque, A., Chan, J., Famiglietti, M., Greene, W. C., Kashuba, A., Lewin, S. R., Margolis, D. M., et al. (2013). An in-depth comparison of latent HIV-1 reactivation in multiple cell model systems and resting CD4+ T cells from aviremic patients. PLoS Pathog 9, e1003834; Tan, M., Luo, H., Lee, S., Jin, F., Yang, J. S., Montellier, E., Buchou, T., Cheng, Z., Rousseaux, S., Rajagopal, N., et al. (2011). Identification of 67 histone marks and histone lysine crotonylation as a new type of histone modification. Cell 146, 1016-1028; Throner, S. C., S.; Russell, D. J.; Dakin, L.; Chen, H.; Larsen, N. A.; Godin, R. E.; Zheng, X.; Molina, A.; Wu, J.; Cheung, T.; Howard, T.; Garcia-Arenas, R.; Keen, N.; Ferguson, A. D. (2015). Abstracts of Papers. In 250th National Meeting of the American Chemical Society, (Boston, Mass., Aug. 16-20, 2015; American Chemical Society: Washington, D C, 2015; MEDI 513); Trojer, P., Cao, A. R., Gao, Z., Li, Y., Zhang, J., Xu, X., Li, G., Losson, R., Erdjument-Bromage, H., Tempst, P., et al. (2011). L3MBTL2 protein acts in concert with PcG protein-mediated monoubiquitination of H2A to establish a repressive chromatin structure. Mol Cell 42, 438-450; Trojer, P., Li, G., Sims, R. J., 3rd, Vaquero, A., Kalakonda, N., Boccuni, P., Lee, D., Erdjument-Bromage, H., Tempst, P., Nimer, S. D., et al. (2007). L3MBTL1, a histone-methylation-dependent chromatin lock. Cell 129, 915-928; Van Lint, C., Emiliani, S., Ott, M., and Verdin, E. (1996). Transcriptional activation and chromatin remodeling of the HIV-1 promoter in response to histone acetylation. EMBO J 15, 1112-1120; van Nuland, R., and Gozani, O. (2016). Histone H4 Lysine 20 (H4K20) Methylation, Expanding the Signaling Potential of the Proteome One Methyl Moiety at a Time. Molecular & cellular proteomics: MCP 15, 755-764; Verdin, E., Paras, P., Jr., and Van Lint, C. (1993). Chromatin disruption in the promoter of human immunodeficiency virus type 1 during transcriptional activation. EMBO J 12, 3249-3259; Wang, R., Dillon, C. P., Shi, L. Z., Milasta, S., Carter, R., Finkelstein, D., McCormick, L. L., Fitzgerald, P., Chi, H., Munger, J., et al. (2011). The transcription factor Myc controls metabolic reprogramming upon T lymphocyte activation. Immunity 35, 871-882; Williams, S. A., Chen, L. F., Kwon, H., Ruiz-Jarabo, C. M., Verdin, E., and Greene, W. C. (2006). NF-kappaB p50 promotes HIV latency through HDAC recruitment and repression of transcriptional initiation. EMBO J 25, 139-149; Wu, J., Cheung, T., Grande, C., Ferguson, A. D., Zhu, X., Theriault, K., Code, E., Birr, C., Keen, N., and Chen, H. (2011). Biochemical characterization of human SET and MYND domain-containing protein 2 methyltransferase. Biochemistry 50, 6488-6497. Zhang, X., Tanaka, K., Yan, J., Li, J., Peng, D., Jiang, Y., Yang, Z., Barton, M. C., Wen, H., and Shi, X. (2013). Regulation of estrogen receptor alpha by histone methyltransferase SMYD2-mediated protein methylation. Proceedings of the National Academy of Sciences of the United States of America 110, 17284-17289; Cox, J., and Mann, M. (2008). MaxQuant enables high peptide identification rates, individualized p.p.b.-range mass accuracies and proteome-wide protein quantification. Nature biotechnology 26, 1367-1372; MacLean, B., Tomazela, D. M., Shulman, N., Chambers, M., Finney, G. L., Frewen, B., Kern, R., Tabb, D. L., Liebler, D. C., and MacCoss, M. J. (2010). Skyline: an open source document editor for creating and analyzing targeted proteomics experiments. Bioinformatics 26, 966-968.

SUMMARY

The present disclosure provides compositions and methods for reactivating latent immunodeficiency virus and/or reducing transcription of HIV integrated into the genome of an HIV-infected cell. The present disclosure provides compositions and methods for treating an immunodeficiency virus infection.

The present disclosure provides a method of reactivating latent human immunodeficiency virus (HIV) integrated into the genome of a cell infected with HIV, the method comprising contacting the cell with a Smyd2 inhibitor (and/or an ASH1L inhibitor, and/or an SUV420H1 inhibitor, and/or an SUV39H1 inhibitor) that reactivates latent HIV integrated into the genome of the cell. In some cases, the SMYD2 is a polypeptide comprises an amino acid sequence having at least 95%, at least 98%, at least 99%, or 100%, amino acid sequence identity to the amino acid sequence set forth in SEQ ID NO:1. In some cases, the method comprises administering at least a second agent that reactivates latent HIV. In some cases, the at least a second agent is a histone deacetylase (HDAC) inhibitor, a protein kinase C (PKC) activator, or a bromodomain inhibitor. In some cases, the HDAC inhibitor is suberoylanilidehydroxamic (SAHA), romidepsin, or sodium butyrate. In some cases, the PKC activator is prostratin, bryostatin, a chemical analog of prostratin, or a chemical analog of bryostatin. In some cases, the bromodomain inhibitor is JQ1.

The present disclosure provides a method of reducing the number of cells containing a latent human immunodeficiency virus in an individual, the method comprising administering to the individual an effective amount of a SMYD2 inhibitor (and/or an ASH1L inhibitor, and/or an SUV420H1 inhibitor, and/or an SUV39H1 inhibitor) that reactivates latent HIV integrated into the genome of one or more cells in the individual. In some cases, said administering is effective to reduce the number of cells containing a latent human immunodeficiency virus in the individual by at least 20%. In some cases, the method comprises administering two or more agents that reactivates latent HIV integrated into the genome. In some cases, the method comprises administering a SMYD2 inhibitor (and/or an ASH1L inhibitor, and/or an SUV420H1 inhibitor, and/or an SUV39H1 inhibitor), and an anti-viral agent (e.g., an anti-viral agent that inhibits an immunodeficiency virus function; e.g., an anti-viral agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity).

The present disclosure provides a method of treating a human immunodeficiency virus (HIV) infection in an individual, the method comprising: administering to an individual an effective amount of a first active agent, wherein the first active agent is a SMYD2 inhibitor (and/or an ASH1L inhibitor, and/or an SUV420H1 inhibitor, and/or an SUV39H1 inhibitor) that reactivates latent HIV integrated into the genome of a cell in the individual; and administering to the individual an effective amount of a second active agent, wherein the second active agent inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. In some cases, one or both of said administering steps is by a vaginal route of administration, by a rectal route of administration, by an oral route of administration, or by an intravenous route of administration. In some cases, the method comprises administering at least a second agent that reactivates latent HIV. In some cases, the at least a second agent is an HDAC inhibitor, a PKC activator, or a bromodomain inhibitor. In some cases, the HDAC inhibitor is SAHA, romidepsin, or sodium butyrate. In some cases, the PKC activator is prostratin, bryostatin, a chemical analog of prostratin, or a chemical analog of bryostatin. In some cases, the bromodomain inhibitor is JQ1.

The present disclosure provides a drug delivery device comprising: a) a first container comprising a SMYD2 inhibitor (and/or an ASH1L inhibitor, and/or an SUV420H1 inhibitor, and/or an SUV39H1 inhibitor) that reactivates latent immunodeficiency virus transcription; and b) a second container comprising an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. The first and second containers can be syringes, vials, or ampules.

In some embodiments of a method of the present disclosure, or a device of the present disclosure, the SMYD2 inhibitor (and/or an ASH1L inhibitor, and/or an SUV420H1 inhibitor, and/or an SUV39H1 inhibitor) is a small molecule SMYD2 inhibitor (and/or a small molecule ASH1L inhibitor, and/or a small molecule SUV420H1 inhibitor, and/or a small molecule SUV39H1 inhibitor). In some embodiments of a method of the present disclosure, or a device of the present disclosure, the SMYD2 inhibitor (and/or an ASH1L inhibitor, and/or an SUV420H1 inhibitor, and/or an SUV39H1 inhibitor) is an siNA, or a nucleic acid encoding an siNA. In some embodiments of a method of the present disclosure, or a device of the present disclosure, the SMYD2 inhibitor is an siNA comprising a SMYD2 shRNA nucleotide sequence set forth in FIG. 13. In some embodiments of a method of the present disclosure, or a device of the present disclosure, the SMYD2 inhibitor is a nucleic acid comprising a nucleotide sequence encoding an siNA comprising a SMYD2 shRNA nucleotide sequence set forth in FIG. 13. In some embodiments of a method of the present disclosure, or a device of the present disclosure, the SMYD2 inhibitor is an expression vector comprising a nucleotide sequence encoding an siNA comprising a SMYD2 shRNA nucleotide sequence set forth in FIG. 13.

The present disclosure provides a method of identifying an agent for reactivating latent human immunodeficiency virus (HIV) integrated into the genome of a cell infected with HIV, the method comprising contacting a cell having a latent human immunodeficiency virus (HIV) integrated into the genome of the cell with a SMYD2 inhibitor (and/or an ASH1L inhibitor, and/or an SUV420H1 inhibitor, and/or an SUV39H1 inhibitor), and determining whether the SMYD2 inhibitor (and/or an ASH1L inhibitor, and/or an SUV420H1 inhibitor, and/or an SUV39H1 inhibitor) reactivates latent HIV integrated into the genome of the cell. In some cases, the SMYD2 is a polypeptide comprises an amino acid sequence having at least 95%, at least 98%, at least 99%, or 100%, amino acid sequence identity to the amino acid sequence set forth in SEQ ID NO:1. In some cases, the method comprises administering at least a second agent that reactivates latent HIV. In some cases, the at least a second agent is a histone deacetylase (HDAC) inhibitor, a protein kinase C (PKC) activator, or a bromodomain inhibitor. In some cases, the HDAC inhibitor is suberoylanilidehydroxamic (SAHA), romidepsin, or sodium butyrate. In some cases, the PKC activator is prostratin, bryostatin, a chemical analog of prostratin, or a chemical analog of bryostatin. In some cases, the bromodomain inhibitor is JQ1.

The present disclosure provides a method of identifying a candidate agent for reducing the number of cells containing a latent human immunodeficiency virus in an individual, the method comprising contacting one or more cells having a latent human immunodeficiency virus (HIV) integrated into the genome of the cells with a SMYD2 inhibitor (and/or an ASH1L inhibitor, and/or an SUV420H1 inhibitor, and/or an SUV39H1 inhibitor), and identifying whether the SMYD2 inhibitor (and/or an ASH1L inhibitor, and/or an SUV420H1 inhibitor, and/or an SUV39H1 inhibitor) reactivates latent HIV integrated into the genome of the one or more cells, wherein a SMYD2 inhibitor (and/or an ASH1L inhibitor, and/or an SUV420H1 inhibitor, and/or an SUV39H1 inhibitor) that reactivates latent HIV integrated into the genome of the one or more cells is a candidate agent for reducing the number of cells containing a latent human immunodeficiency virus in the individual. In some cases, the method comprises contacting the one or more cells with a SMYD2 inhibitor (and/or an ASH1L inhibitor, and/or an SUV420H1 inhibitor, and/or an SUV39H1 inhibitor), and an anti-viral agent (e.g., an anti-viral agent that inhibits an immunodeficiency virus function; e.g., an anti-viral agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity).

The present disclosure provides a method of identifying a candidate agent for treating a human immunodeficiency virus (HIV) infection in an individual, the method comprising: contacting one or more cells having a latent human immunodeficiency virus (HIV) integrated into the genome of the cells with a first active agent, wherein the first active agent is a SMYD2 inhibitor (and/or an ASH1L inhibitor, and/or an SUV420H1 inhibitor, and/or an SUV39H1 inhibitor) that reactivates latent HIV integrated into the genome of a cell in the individual; and contacting the one or more cells with a second active agent, wherein the second active agent inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity. In some cases, the method comprises contacting the one or more cells with at least a second agent that reactivates latent HIV. In some cases, the at least a second agent is an HDAC inhibitor, a PKC activator, or a bromodomain inhibitor. In some cases, the HDAC inhibitor is SAHA, romidepsin, or sodium butyrate. In some cases, the PKC activator is prostratin, bryostatin, a chemical analog of prostratin, or a chemical analog of bryostatin. In some cases, the bromodomain inhibitor is JQ1.

BRIEF DESCRIPTION OF THE DRAWINGS

FIG. 12 provides an amino add sequence of human SMYD2 (SEQ ID NO: 1).

FIG. 13 provides nucleotide sequences of SMYD2 shRNAs, scramble control shRNA, and luciferase control shRNA (from top to bottom SEQ ID NOs: 2-10).

FIGS. 15A-G depict the structural formulae for AZ505, AZ506, and AZ391, and the reactivation of latent HIV-1 with SMYD2 inhibitor X2 (AZ391) in CD4⁺ T cells from HIV-1 infected individuals. (A) Structures of each compound are shown. (B) Intracellular HIV-1 mRNA levels in CD4⁺ T cells, obtained from an infected individual (#1036) and treated ex vivo with AZ391, JQ1 or a combination of both, in indicated concentrations, presented as fold induction relative to DMSO control. Activation with αCD3/αCD28-Dynabeads was performed as control. (C) Flow cytometry of T-cell activation markers CD69 and CD25 in the same experiment. For each treatment group, CD69⁺ (left) and CD25⁺ (right). Shown as percentage of positive cells relative to αCD3/αCD28-treated cells (D) Cell viability as measured by CellTiter-Blue® Cell Viability assay (Promega) and Zombie Violet Fixable Viability kit (BioLegend) and presented as percentage of DMSO control treated cells. Data points indicate average of three technical replicates of donor #1036. (E-G) Same experiments as in b-d but performed with CD4⁺ T cells obtained from three additional individuals (2013, 2185, 2511) with a single concentration of AZ391 (500 nM). In f and g, average of the three biological replicates (±SD) is show. For (F), for each treatment group, CD69⁺ (left) and CD25⁺ (right).

FIGS. 18A and 18B depict ChIP data showing that methylation of histone 4 at lysine 20 depends on SMYD2. (A) ChIP experiments performed with antibodies against H4, H4K20me, H4K20me2, and H4K20me3 at the HIV LTR, followed by qPCR using primers specific for HIV-1 LTR Nuc1 or AXIN2. H4K20me1 was highly present at the uninduced HIV-LTR (left) but reduced in response to TNFα (right). H4K20me2 increased after treatment with TNFα, while histone H4 remained unchanged. Left panel shows results relative to IgG control, and right panel shows results relative to histone H4. (B) ChIP experiments of histone H4 and the H4K20 methyl marks performed in SMYD2 knockdown (right) or scrambled control cells (left). H4K20me1 is present at the uninduced HIV-LTR in the scrambled control cells (left), and decreased sevenfold upon SMYD2 knockdown (right). Left panel shows results relative to IgG control and right panel shows results relative to histone H4.

FIGS. 21A-E provide data showing that SMYD2 inhibitor X2 in combination with JQ1 reactivates latent HIV-1 in ex vivo infected human lymphocyte aggregate cultures (HLAC) from tonsils spin-infected with high concentrations of an HIV-luciferase reporter virus. (A) Scheme of the primary HLAC latency model. (B) A combination of PMA/

Ionomycin or αCD3/αCD28 was used to induce maximal reactivation. Results are expressed as percentage of reactivation relative to values obtained in control-induced cells in each donor. In two donors, addition of AZ391, JQ1 or a combination of both, were tested in addition to PMA/Ionomycin or αCD3/αCD28. Data represent average (±SD) of three technical replicates per donor. (C) Cell viability was measured with CellTiter-Blue Cell Viability Assay (Promega). Percent survival of one representative donor (#2) is shown. Data represent the average (±SD) of three technical replicates of donor #2. (D-E) Flow cytometry of T-cell activation marker CD25 and CD69 in human CD4+ T-cells isolated from blood and incubated with AZ391 (1 µM) and/or JQ1 (500 nM), or PMA (10 ng/ml) and Ionomycin (500 nM). Shown are the percentages of positive cells relative to total CD3+CD4+ T cells (D) or median fluorescence intensity (MFI) (E). Data points indicate four biological replicates (1-way ANOVA with Dunnett's multiple comparison test p<0.01, n=4).

FIGS. 22A-D provide data showing the viability, cytotoxicity and apoptosis of cells treated with SMYD2 inhibitor X2. ApoTox-Glo™ Triplex Assays (Promega) were performed in AZ391-treated A2 J-Lat cells (A), A72 J-Lat cells (B), and primary CD4+ T cells from 2 independent blood donors (C) and (D). AZ391 treatment did not reduce viability nor increase cytotoxicity and caspase-3/7 activity at concentrations lower than 5 µM. All measurements were repeated at least three times and an average of one experiment of three technical replicates (±SD) is shown.

FIGS. 23A and 23B depict ChIP data showing the dissociation of SMYD2 and association of RELA to the HIV-LTR in response to TNFα stimulation. (A) ChIP experiments of SMYD2 in A2 J-Lat cells, either non-stimulated (control) or in response to TNFα stimulation at the HIV LTR nuc-1 region (left) or at the AXIN2 gene (right). SMYD2 is present at the HIV-LTR under non-stimulated conditions (control) and was displaced in response to TNFα stimulation at the HIV LTR. All ChIPs and qPCRs were repeated at least three times, and representative results of three technical replicates are shown. (B) ChIP experiments of RELA in A2 J-Lat cells, either non-stimulated (control) or in response to TNFα stimulation at the HIV LTR nuc-1 region (left) or at the AXIN2 gene (right). RELA is recruited to the HIV promoter after treatment with TNFα. No association of SMYD2 or RELA with AXIN2 was observed. All ChIPs and qPCRs were repeated at least three times, and representative results of three technical replicates are shown.

Figure 24C:
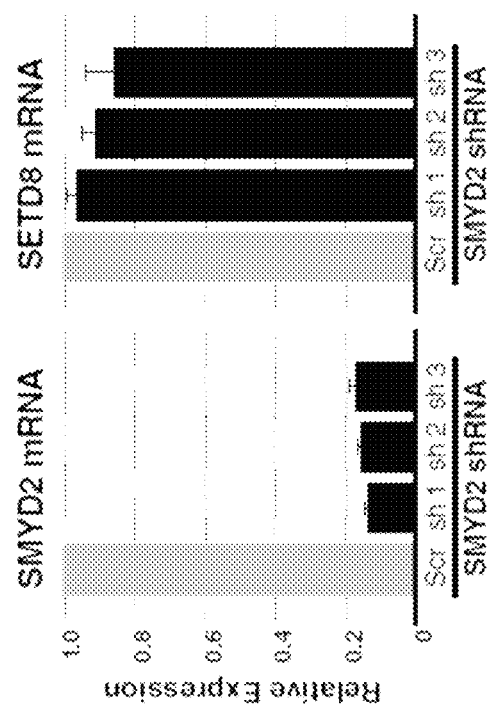
Figure 24A:
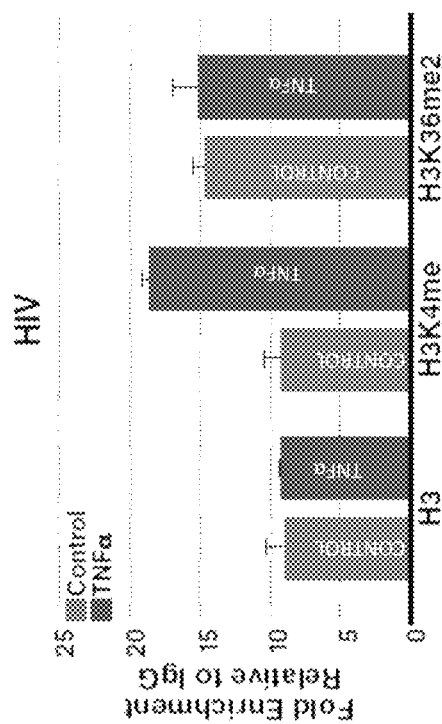
Figure 24B:
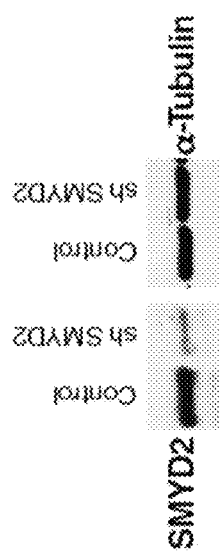

FIGS. 24A-C depict ChIP data showing that H3K4me but not H3K36me2 is enhanced at the HIV-LTR in response to TNF α treatment and that knockdown of SMYD2 does not change the expression level of monomethyltransferase SETD8. (A) ChIP experiments of histone 3 lysine 4 (H3K4me1) and histone 3 lysine 36 (H3K36me2) in A2 J-Lat cell lines, either non-stimulated (control) or in response to TNFα stimulation at the HIV LTR nuc-1 region (left) or at the AXIN2 gene (right). H3K36me2 remained unchanged in control and activated cells, while H3K4me1 was enriched~twofold in response to TNFα. Results are shown relative to IgG control. All ChIPs and qPCRs were repeated at least three times, and representative results of three technical replicates are shown. (B) SMYD2 knockdown was confirmed by western blotting in A72 J-Lat cells. (C) RNA was isolated from A72 J-Lat cells and mRNA levels were analyzed by RT-qPCR and normalized to RPL13A RNA. SMYD2 knockdown did not change expression level of SETD8.

FIGS. 25A-E provide graphs showing that L3MBTL1 knockdown or inhibition with UNC926 reactivates latent HIV-1. (AB) J-Lat cell line A72 was treated with L3MBTL1 inhibitor UNC926 ($K_d$=3.9 µM) at increasing concentrations (10 nM-100 µM) without or combined with 0.1 ng/ml TNFα for 18 h and analyzed by flow cytometry. Activation is observed only at 100 µM given the low affinity of UNC926 (A). No effect on viability as measured by forward-side scatter analysis is observed even at high drug concentrations (B). Data represent average (±SD) of three independent experiments. (C) Percentage of GFP+ A72 J-Lat cells after shRNA-mediated L3MBTL1 knockdown. Data represent average (±SD) of three independent experiments. (D) Cell viability was monitored by forward-side scatter analysis. (E) shRNA knockdown was confirmed using qPCR and did not exceed ~40% knockdown.

FIGS. 26A-D depict data showing that SMYD5 is an activator of basal HIV-1 transcription. Successful knockdown of SMYD5 suppressed reactivation of viral latency. (A) SMYD5 mRNA levels in J-Lat 5A8 cells using two lentiviral shRNAs. (B) Cells were activated with CD3/CD28 antibodies for 18 h and GFP+ cells analyzed by FACS. For each treatment group, from left to right: Scramble, shSMYD5#1(SEQ ID NO:74), shSMYD5#2(SEQ ID NO:75), or (C) Cell viability (% survival) monitored by forward and side scatter analysis. For each treatment group, from left to right: Scramble, shSMYD5#1, shSMYD5#2. (D) Primers specific for SMYD5, p65 and the viral LTR region were used to analyze basal RNA production by RT-qPCR. Ct values were normalized to RPL13A RNA. Average (±SD) of three experiments is shown each time.

Figure 27:
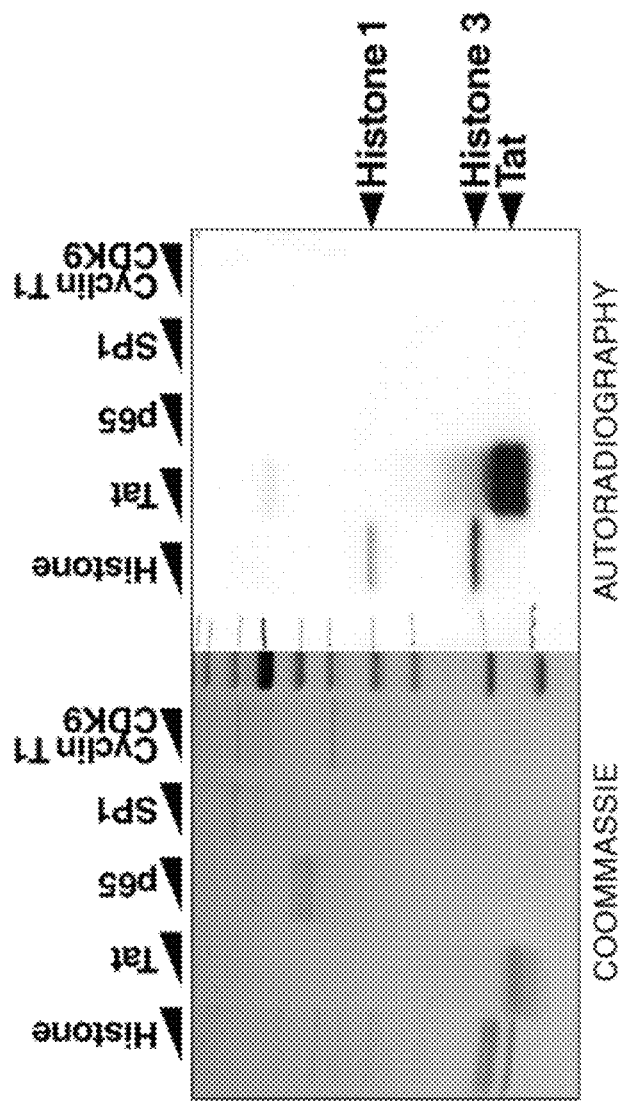

FIG. 27 provides results showing that SMYD5 methylates histones H1 and H3 and Tat in vitro. SDS-PAGE (left) and autoradiography (right).

Figure 28A:
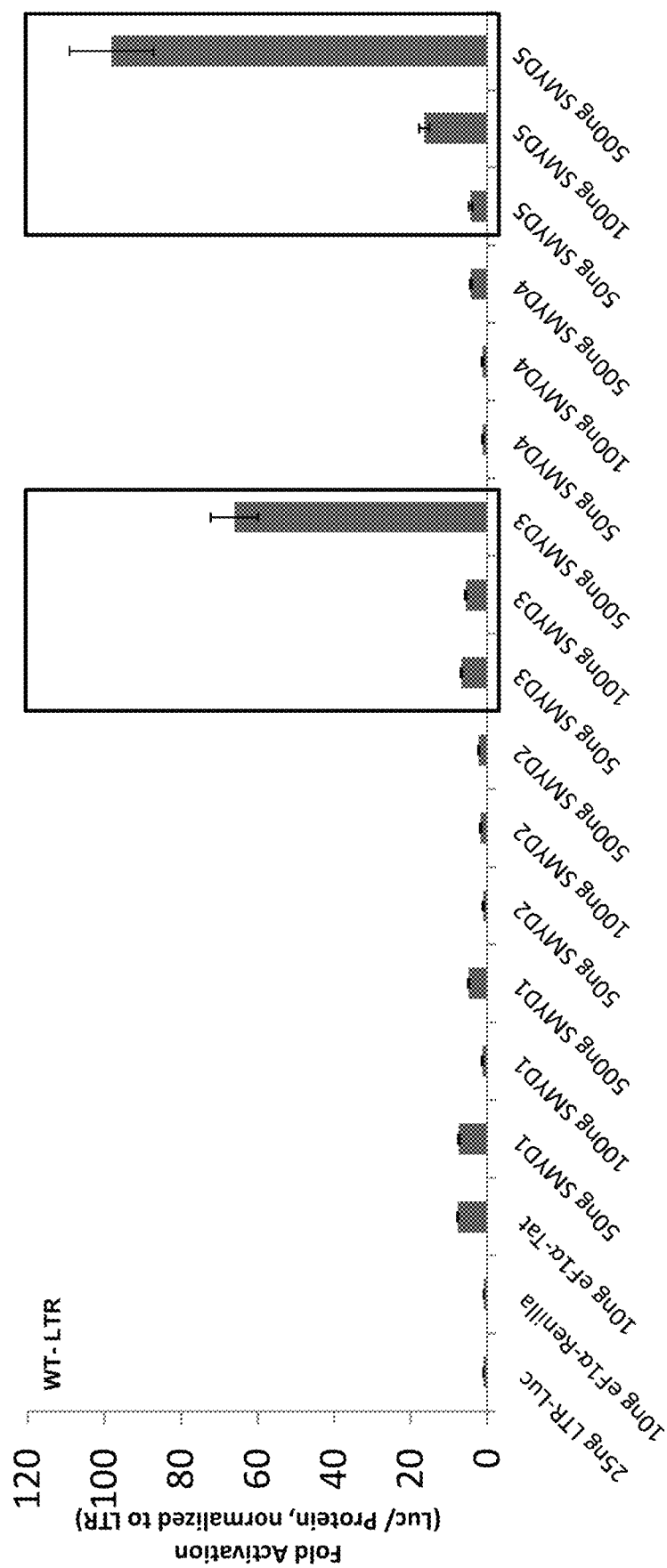
Figure 28B:
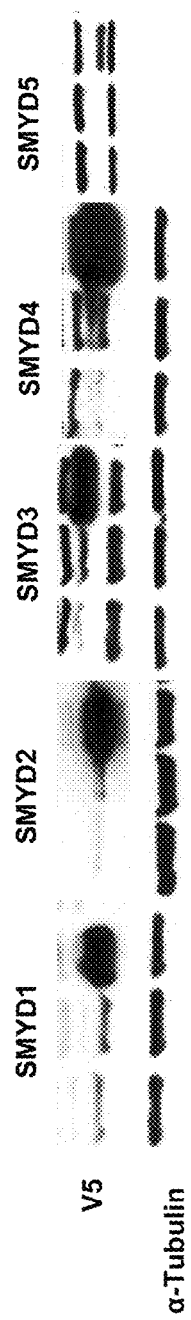

FIGS. 28A and 28B depict data showing that SMYD5 activates HIV transcription. (A) HeLa cells were transfected with an HIV-LTR-luciferase construct and expression vectors for Tat and SMYD5. (B) Overexpression of SMYD1, SMYD2, SMYD3 AND SMYD5 were confirmed by western blotting in HeLa cells.

DEFINITIONS

As used herein, "Smyd2" or "SMYD2" (also known as SET and MYND domain containing—2 histone methyltransferase; lysine N-methyltransferase 3C; HKSM-B; KMT3C; SET and MYND domain-containing protein 2; ZMYND14; N-lysine methyltransferase SMYD2; Zinc Finger, MYND domain containing) refers to a polypeptide comprising an amino acid sequence having at least about 80%, at least about 85%, at least about 90%, at least about 95%, at least about 98%, at least about 99%, or 100%, amino acid sequence identity over a contiguous stretch of from 350 amino acids to 400 amino acids, or from 400 amino acids to 433 amino acids, of the amino acid sequence depicted in FIG. 12 (SEQ ID NO:1). Structural information relating to SMYD2 is found in, e.g., Wang et al. (2011) *J. Biol. Chem.* 286:38725.

As used herein, "SMYD5" (also known as SET and MYND domain-containing protein 5) refers to a polypeptide comprising an amino acid sequence having at least about 80%, at least about 85%, at least about 90%, at least about 95%, at least about 98%, at least about 99%, or 100%, amino acid sequence identity over a contiguous stretch of from 350 amino acids to 400 amino acids, or from 400 amino acids to 418 amino acids, of the amino acid sequence of SEQ ID NO:22. Structure and function information relating to SMYD5 is found in, e.g., Spellmon et al. (2015) *Int. J. Mol. Sciences.* 16:1406.

As used herein, "ASH1L" (also known as Histone-lysine N-methyltransferase ASH1L; ASH1-like protein; Absent small and homeotic disks protein 1 homolog; Lysine N-methyltransferase 2H) refers to a polypeptide comprising an amino acid sequence having at least about 80%, at least about 85%, at least about 90%, at least about 95%, at least about 98%, at least about 99%, or 100%, amino acid sequence identity over a contiguous stretch of from 2375 amino acids to 2740 amino acids, or from 2740 amino acids to 2969 amino acids, of the amino acid sequence of SEQ ID NO: 23. Structural information relating to ASH1L is found in, e.g. An et al. (2011) *J. Biol. Chem.* 286: 8369.

As used herein, "SUV420H1" (also known as Histone-lysine N-methyltransferase KMT5B; lysine N-methyltransferase 5B; Lysine-specific methyltransferase 5B; Suppressor of variegation 4-20 homolog 1) refers to a polypeptide comprising an amino acid sequence having at least about 80%, at least about 85%, at least about 90%, at least about 95%, at least about 98%, at least about 99%, or 100%, amino acid sequence identity to the amino acid sequence of SEQ ID NO:24, SEQ ID NO:25 or SEQ ID NO:26.

As used herein, "SUV39H1" (also known as Histone-lysine N-methyltransferase SUV39H1; Histone H3-K9 methyltransferase 1; H3-K9-HMTase 1; Lysine N-methyltransferase 1A; Position-effect variegation 3-9 homolog; Suppressor of variegation 3-9 homolog 1; Su(var)3-9 homolog 1) refers to a polypeptide comprising an amino acid sequence having at least about 80%, at least about 85%, at least about 90%, at least about 95%, at least about 98%, at least about 99%, or 100%, amino acid sequence identity to the amino acid sequence of SEQ ID NO:27 or SEQ ID NO:28. Structural information relating to SUV39H1 is found in, e.g. Wang et al. (2012) *PLoS One* 7(12): e52977.

The term "immunodeficiency virus" includes human immunodeficiency virus (HIV), feline immunodeficiency virus, and simian immunodeficiency virus. The term "human immunodeficiency virus" as used herein, refers to human immunodeficiency virus-1 (HIV-1); human immunodeficiency virus-2 (HIV-2); and any of a variety of HIV subtypes and quasispecies.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'- methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Smyd2 inhibitor" or "SMYD2 inhibitor" includes a plurality of such inhibitor and reference to "the SMYD2 polypeptide" includes reference to one or more SMYD2 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of reactivating latent HIV integrated into the genome of an HIV-infected cell and/or reducing transcription of HIV integrated into the genome of an HIV-infected cell. In some embodiments, the methods involve contacting an HIV-infected cell in which HIV is latent with an agent that inhibits methyltransferase activity of a SMYD2 polypeptide, an ASH1L polypeptide, a SUV420H1 polypeptide or a SUV39H1 polypeptide and/or selectively reduces the level of a SMYD2 polypeptide, an ASH1L polypeptide, a SUV420H1 polypeptide or a SUV39H1 polypeptide, respectively, in the cell.

The present disclosure provides methods for reducing the reservoir of latent immunodeficiency virus in an individual, where the methods involve contacting an HIV-infected cell in which HIV is latent with an agent that inhibits methyltransferase activity of a SMYD2 polypeptide, an ASH1L polypeptide, a SUV420H1 polypeptide or a SUV39H1 polypeptide and/or selectively reduces the level of a SMYD2 polypeptide, an ASH1L polypeptide, a SUV420H1 polypeptide or a SUV39H1 polypeptide in the cell. The present disclosure provides methods of treating an immunodeficiency virus infection in an individual, the methods generally involving co-administering to the individual an agent that reactivates latent HIV and an anti-HIV agent.

An agent that inhibits methyltransferase activity of a SMYD2 polypeptide and/or that reduces the level of a SMYD2 polypeptide in a cell, and that activates latent HIV is referred to herein as a "Smyd2 inhibitor" or a "SMYD2 inhibitor". An agent that inhibits methyltransferase activity of an ASH1L polypeptide and/or that reduces the level of an ASH1L polypeptide in a cell, and that activates latent HIV is referred to herein as an "ASH1L inhibitor." An agent that inhibits methyltransferase activity of a SUV420H1 polypeptide and/or that reduces the level of a SUV420H1 polypeptide in a cell, and that activates latent HIV is referred to herein as a "SUV420H1 inhibitor." An agent that inhibits methyltransferase activity of a SUV39H1 polypeptide and/or that reduces the level of a SUV39H1 polypeptide in a cell, and that activates latent HIV is referred to herein as a "SUV39H1 inhibitor." In some cases, a SMYD2 inhibitor suitable for use in a method of the present disclosure inhibits an enzymatic activity of SMYD2. In some cases, an ASH1L inhibitor for use in a method of the present disclosure inhibits an enzymatic activity of ASH1L. In some cases, a SUV420H1 inhibitor for use in a method of the present disclosure inhibits an enzymatic activity of SUV420H1. In some cases, a SUV39H1 inhibitor for use in a method of the present disclosure inhibits an enzymatic activity of SUV39H1. In some cases, a SMYD2 inhibitor suitable for use in a method of the present disclosure reduces the level of a SMYD2 polypeptide in a cell. In some cases, an ASH1L inhibitor suitable for use in a method of the present disclosure reduces the level of an ASH1L polypeptide in a cell. In some cases, a SUV420H1 inhibitor suitable for use in a method of the present disclosure reduces the level of a SUV420H1 polypeptide in a cell. In some cases, a SUV39H1 inhibitor suitable for use in a method of the present disclosure reduces the level of a SUV39H1 polypeptide in a cell. Regardless of the mechanism, an inhibitor suitable for use in a method of the present disclosure, e.g., a SMYD2 inhibitor, an ASH1L inhibitor, a SUV420H1 inhibitor or a SUV39H1 inhibitor, activates latent HIV in a cell harboring latent HIV.

In some cases, a suitable active agent for use in a method of the present disclosure for activating latent HIV is an agent that inhibits SMYD2 enzymatic activity, ASH1L enzymatic activity, SUV420H1 enzymatic activity or SUV39H1 enzymatic activity by at least 10%, at least 20%, at least 30%, at least 40%, at least 50%, at least 60%, at least 70%, at least 80%, or at least 90%, compared to the enzymatic activity of the SMYD2 polypeptide, the ASH1L polypeptide, SUV420H1 polypeptide or SUV39H1 polypeptide, respectively, in the absence of the active agent. SMYD2, ASH1L, SUV420H1 or SUV39H1 enzymatic activities can be measured using any known assay for methyltransferase activity.

In some cases, a suitable active agent for use in a method of the present disclosure for activating latent HIV is an agent that reduces the level of SMYD2 polypeptide, ASH1L polypeptide, SUV420H1 polypeptide or SUV39H1 polypeptide in a cell by at least 10%, at least 20%, at least 30%, at least 40%, at least 50%, at least 60%, at least 70%, at least 80%, or at least 90%, compared to the level of the SMYD2 polypeptide, the ASH1L polypeptide, the SUV420H1 polypeptide or the SUV39H1 polypeptide in the cell in the absence of the agent.

An effective amount of an active agent that inhibits methyltransferase activity of a SMYD2 polypeptide, an ASH1L polypeptide, a SUV420H1 polypeptide or a SUV39H1 polypeptide and/or reduces the level of a SMYD2 polypeptide, an ASH1L polypeptide, a SUV420H1 polypeptide or a SUV39H1 polypeptide in a cell is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182(6):1636-1642.

In some cases, an effective amount of a SMYD2 inhibitor, an ASH1L inhibitor, an SUV420H1 inhibitor or an SUV39H1 inhibitor is an amount that is effective to reduce the number of cells, in a cell population, present in an individual and containing a latent human immunodeficiency virus, by at least 20%, at least 30%, at least 40%, at least 50%, at least 60%, at least 70%, at least 80%, or at least 90%. The cell population can be a population of HIV-infected cells in an individual.

In some cases, a method for reducing the reservoir of latent immunodeficiency virus in an individual involves activating basal HIV-1 transcription in order to reactivate latent HIV integrated into the genome of an HIV-infected cell. The methods generally involve contacting an HIV-infected cell in which HIV is latent with an agent that induces methyltransferase activity of a SMYD5 polypeptide, and/or increases the level of a SMYD5 polypeptide in the cell. The present disclosure provides methods for reducing the reservoir of latent immunodeficiency virus in an individual, where the methods involve contacting an HIV-infected cell in which HIV is latent with an agent that induces methyltransferase activity of a SMYD5 polypeptide and/or increases the level of a SMYD5 polypeptide in the cell. The present disclosure provides methods of treating an immunodeficiency virus infection in an individual, the methods generally involving co-administering to the individual an agent that reactivates latent HIV and an anti-HIV agent.

An agent that induces methyltransferase activity of a SMYD5 polypeptide and/or that increases the level of a SMYD5 polypeptide in a cell, and that activates basal HIV-1 transcription is referred to herein as a "Smyd5 activator." In some cases, a SMYD5 activator suitable for use in a method of the present disclosure induces an enzymatic activity of SMYD5. In some cases, a SMYD5 activator suitable for use in a method of the present disclosure increases the level of a SMYD5 polypeptide in a cell. Regardless of the mechanism, an activator suitable for use in a method of the present disclosure activates basal HIV-1 transcription in a cell harboring latent HIV.

In some cases, a suitable active agent for use in a method of the present disclosure for activating latent HIV is an agent that induces SMYD5 enzymatic activity, by at least 10%, at least 20%, at least 30%, at least 40%, at least 50%, at least 60%, at least 70%, at least 80%, or at least 90%, compared to the enzymatic activity of the SMYD5 polypeptide in the absence of the active agent. Smyd5 enzymatic activity can be measured using any known assay for methyltransferase activity.

In some cases, a suitable active agent for use in a method of the present disclosure for activating basal HIV-1 transcription is an agent that increases the level of SMYD5 polypeptide in a cell by at least 10%, at least 20%, at least 30%, at least 40%, at least 50%, at least 60%, at least 70%, at least 80%, or at least 90%, compared to the level of the SMYD5 polypeptide in the cell in the absence of the agent.

An effective amount of an active agent that induces methyltransferase activity of a SMYD5 polypeptide and/or increases the level of a SMYD5 polypeptide in a cell is an amount that activates basal HIV-1 transcription and reduces the reservoir of latent HIV in an individual by at least about 20%, at least about 30%, at least about 40%, at least about 50%, at least about 60%, at least about 70%, at least about 80%, or at least about 90%.

As described above for SMYD5, an active agent that induces methyltransferase activity and/or that increases the level of one or more of the following lysine methyl transferases: MLL (comprising the amino acid sequence of any of SEQ ID NOs: 42, 43, and 44), MLL2 (comprising the amino acid sequence of SEQ ID NO: 45 or 46), MLL3 (comprising the amino acid sequence of any of SEQ ID NOs: 47, 48 and 49), MLL4 (comprising the amino acid sequence of SEQ ID NO: 50 or 51), MLL5 (comprising the amino acid sequence of any of SEQ ID NOs: 52, 53, 54, 55, 56, 57, 58, and 59), SETD7/9 (comprising the amino acid sequence of SEQ ID NO: 60), SETD8 (comprising the amino acid sequence of SEQ ID NO: 61 or 62), SETDB2 (comprising the amino acid sequence of any of SEQ ID NOs: 63, 64, and 65), SETMAR (comprising the amino acid sequence of any of SEQ ID NOs: 66, 67, and 68), SMYD3 (comprising the amino acid sequence of any of SEQ ID NOs: 69, 70, and 71), and SUV420H2 (comprising the amino acid sequence of SEQ ID NO: 72 or 73), may be used in the methods described herein to reactivate latent HIV integrated into the genome of an HIV-infected cell.

SMYD5 is identified herein as an activator of HIV transcription. Accordingly, inhibitors of SMYD5, e.g., siNA or small molecule inhibitors, may find use in therapies designed to block transcription of the integrated HIV provirus. This transcriptional "shut-off" may reduce the pool of the latently infected cells by diminishing reservoir replenishment, which may accelerate the eradication of the latent reservoir. See, e.g., G. Mousseau and S. Valente, *Biology*, 2012, 1:668-697.

An agent that inhibits methyltransferase activity of a SMYD5 polypeptide and/or that reduces the level of a SMYD5 polypeptide in a cell is referred to herein as a "SMYD5 inhibitor." In some cases, a SMYD5 inhibitor suitable for use in a method of the present disclosure inhibits an enzymatic activity of SMYD5. In some cases, a SMYD5 inhibitor suitable for use in a method of the present disclosure reduces the level of a SMYD5 polypeptide in a cell.

In some cases, a suitable active agent for use in a method of the present disclosure is an agent that inhibits SMYD5 enzymatic, activity, by at least 10%, at least 20%, at least 30%, at least 40%, at least 50%, at least 60%, at least 70%, at least 80%, or at least 90%, compared to the enzymatic activity of the SMYD5 polypeptide in the absence of the active agent. SMYD5 enzymatic activity can be measured using any known assay for methyltransferase activity.

In some cases, a suitable active agent for use in a method of the present disclosure is an agent that reduces the level of SMYD5 polypeptide in a cell by at least 10%, at least 20%, at least 30%, at least 40%, at least 50%, at least 60%, at least 70%, at least 80%, or at least 90%, compared to the level of the SMYD5 polypeptide in the cell in the absence of the agent.

An effective amount of an active agent that inhibits methyltransferase activity of a SMYD5 polypeptide and/or reduces the level of a SMYD5 polypeptide in a cell is an amount that inhibits basal HIV-1 transcription and reduces the reservoir of latent HIV in an individual by at least about 20%, at least about 30%, at least about 40%, at least about 50%, at least about 60%, at least about 70%, at least about 80%, or at least about 90%.

As described above for SMYD5, an active agent (e.g., siNA or small molecule inhibitors) that inhibits one or more of the following lysine methyl transferases): MLL (comprising the amino acid sequence of any of SEQ ID NOs: 42, 43, and 44), MLL2 (comprising the amino acid sequence of SEQ ID NO: 45 or 46), MLL3 (comprising the amino acid sequence of any of SEQ ID NOs: 47, 48 and 49), MLL4 (comprising the amino acid sequence of SEQ ID NO: 50 or 51), MLL5 (comprising the amino acid sequence of any of SEQ ID NOs: 52, 53, 54, 55, 56, 57, 58, and 59), SETD7/9 (comprising the amino acid sequence of SEQ ID NO: 60), SETD8 (comprising the amino acid sequence of SEQ ID NO: 61 or 62), SETDB2 (comprising the amino acid sequence of any of SEQ ID NOs: 63, 64, and 65), SETMAR (comprising the amino acid sequence of any of SEQ ID NOs: 66, 67, and 68), SMYD3 (comprising the amino acid sequence of any of SEQ ID NOs: 69, 70, and 71), and SUV420H2 (comprising the amino acid sequence of SEQ ID NO: 72 or 73), may be used in the methods described herein to block transcription of the integrated HIV provirus.

In some embodiments, the present disclosure provides a screening assay designed to screen for activators or inhibitors of one or more of the lysine methyl transferases described herein. For example, methyl transferase activity can be measured, using any suitable assay, in the presence or absence of a candidate agent, e.g., a small molecule, to determine whether the candidate agent is an activator or inhibitor of the lysine methyl transferase.

Active Agents

Suitable active agents include agents that inhibit methyltransferase activity of a SMYD2 polypeptide and/or reduce the level of a SMYD2 polypeptide in a cell. Suitable active agents include SMYD2 inhibitors that reactivate latent immunodeficiency virus (e.g., HIV) in a cell.

Suitable active agents also include agents that inhibit methyltransferase activity of an ASH1L polypeptide, a SUV420H1 polypeptide and/or a SUV39H1 polypeptide and/or reduce the level of an ASH1L polypeptide, an SUV420H1 polypeptide and/or an SUV39H1 polypeptide in a cell. Suitable active agents include ASH1L inhibitors, SUV420H1 inhibitors and SUV39H1 inhibitors that reactivate latent immunodeficiency virus (e.g. HIV) in a cell.

Suitable active agents also include agents that reduce methytransferase activity of a SMYD5 polypeptide and/or reduce the level of a SMYD5 polypeptide in a cell. Suitable active agents include SMYD5 inhibitors that reduce basal-HIV transcription in a cell.

Small Molecule Inhibitors

In some cases, the active agent is a small molecule inhibitor of methyltransferase activity of a SMYD2 polypeptide, an ASH1L polypeptide, an SUV420H1 polypeptide and/or an SUV39H1 polypeptide. In some cases, the active agent is a small molecule inhibitor of methyltransferase activity of a SMYD2 polypeptide, where the active agent is a selective SMYD2 inhibitor. In some cases, the activate agent is a small molecule inhibitor of methyltransferase activity of an ASH1L polypeptide, where the active agent is a selective ASH1L inhibitor. In some cases, the activate agent is a small molecule inhibitor of methyltransferase activity of an SUV420H1 polypeptide, where the active agent is a selective SUV420H1 inhibitor. In some cases, the activate agent is a small molecule inhibitor of methyltransferase activity of an SUV39H1 polypeptide, where the active agent is a selective SUV39H1 inhibitor. A selective SMYD2 inhibitor does not substantially inhibit a SMYD1 polypeptide, a SMYD3 polypeptide, a SMYD4 polypeptide, or a SMYD5 polypeptide, or any other methyltransferase. A selective ASH1L inhibitor does not substantially inhibit other SET domain-containing histone lysine methyltransferase or any other methyltransferase. A selective SUV420H1 inhibitor does not substantially inhibit other SET domain-containing histone lysine methyltransferase or any other methyltransferase. A selective SUV39H1 does not substantially inhibit other SET domain-containing histone lysine methyltransferase or any other methyltransferase.

In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 0.001 µM to about 100 µM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 0.001 µM to about 10 µM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 0.001 µM to about 1 µM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 0.001 µM to about 0.002 µM, from about 0.002 µM to about 0.003 µM, from about 0.003 µM to about 0.005 µM, from about 0.005 µM to about 0.010 µM, from about 0.010 µM to about 0.015 µM, from about 0.015 µM to about 0.02 µM, from about 0.02 µM to about 0.05 µM, from about 0.05 µM to about 0.1 µM, from about 0.1 µM to about 0.5 µM, or from about 0.5 µM to about 1.0 µM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 1.0 µM to about 5 µM, from about 5 µM to about 10 µM, from about 10 µM to about 25 µM, from about 25 µM to about 50 µM, from about 50 µM to about 75 µM, or from about 75 µM to about 100 µM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 100 µM to about 1 nM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 1 nM to about 50 nM. In some cases, the active agent is a small molecule inhibitor of methyltransferase activity of a SMYD2 polypeptide, an ASH1L polypeptide, an SUV420H1 polypeptide and/or an SUV39H1 polypeptide; and the active agent has an $IC_{50}$ of from about 50 nM to about 100 nM.

An example of a suitable active agent is AZ505 or a pharmaceutically acceptable derivative, e.g., salt thereof. AZ505 (N-cyclohexyl-3-(3,4-dichlorophenethyl)amino)-N-(2-((2-(5-hydroxy-3-oxo-3,4-dihydro-2H-benzo[b][1,4]oxazin-8-yl)ethyl)amino)ethyl)propanamide bis(2,2,2-trifluoroacetate)) is a selective SMYD2 inhibitor. Ferguson et al. (2011) *Structure* 19:1262. AZ505 has the following structure:

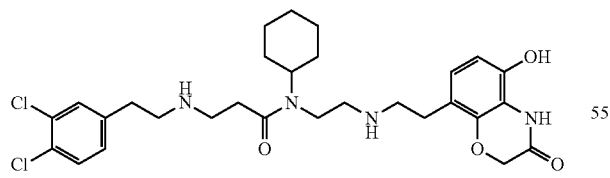

In some cases, it may be desirable to administer AZ505 in combination with a cell-permeability enhancer and/or administer an AZ505 derivative which has increased cell-permeability relative to AZ505. In some cases, it may be desirable to administer AZ505 as a conjugate with a PTD or CPP as described herein.

An example of a suitable active agent is LLY-507 or a pharmaceutically acceptable derivative, e.g., salt thereof. LLY-507 is a potent inhibitor of SMYD2 with in vitro $IC_{50}$ less than 15 nm, and approximately 100-fold selectivity over other methyltransferases and other non-epigenetic targets. LLY-507 has the following structure:

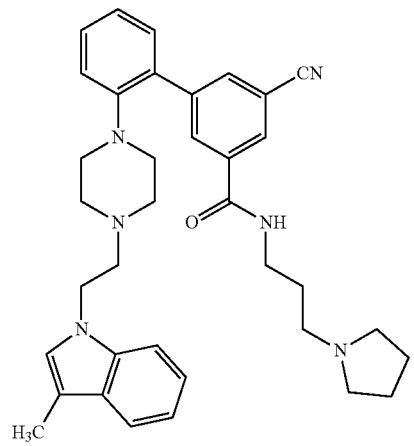 [SMILES: Cc1cn(CCN2CCN(c3ccccc3-c3cc(C#N)cc(C(=O)NCCCN4CCCC4)c3)CC2)c2ccccc12]

Another example of a suitable active agent is AZ506, also referred herein as "X1", or a pharmaceutically acceptable derivative, e.g., salt thereof. AZ506 is a potent and selective bi-arylpiperazine, cell-permeable substrate competitive SMYD2 inhibitor with $IC_{50}$ 0.017 µM. AZ506 has the following structure:

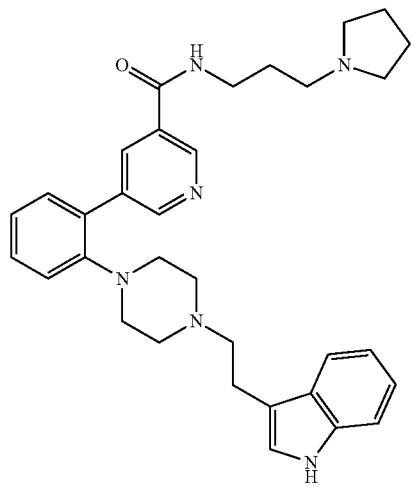 [SMILES: O=C(NCCCN1CCCC1)c1cncc(-c2ccccc2N2CCN(CCc3c[nH]c4ccccc34)CC2)c1]

An example of a suitable active agent is AZ391, also referred herein as "X2", or a pharmaceutically acceptable derivative, e.g., salt thereof. AZ391 is a potent and selective bi-arylpiperazine substrate competitive SMYD2 inhibitor with IC$_{50}$ 0.062 µM. AZ391 has the following structure:

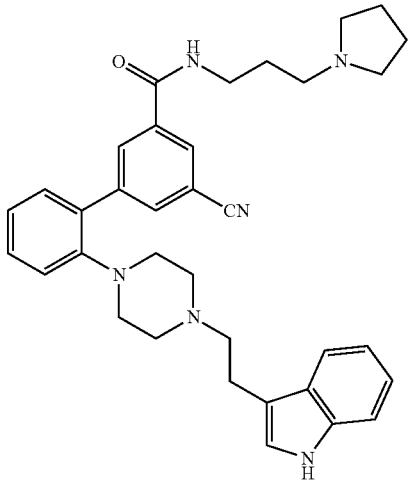 [SMILES: N#Cc1cc(C(=O)NCCCN2CCCC2)cc(-c2ccccc2N2CCN(CCc3c[nH]c4ccccc34)CC2)c1]

Combinations of two or more SMYD2 inhibitors can also be used in a method of the present disclosure.

An example of a suitable active agent is A-196 also known as Cyclopentyl-(6,7-dichloro-4-pyridin-4-yl-phthalazin-1-yl)-amine, or a pharmaceutically acceptable derivative, e.g., salt thereof. A-196 is a potent and selective inhibitor of SUV420H1 that inhibits the methylation of H4K20me. A-196 has the following structure:

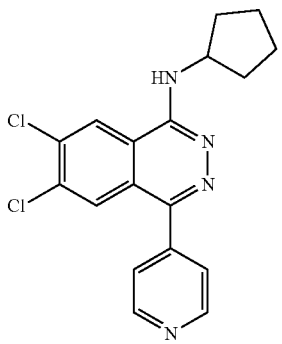 [SMILES: Clc1cc2c(NC3CCCC3)nnc(-c3ccncc3)c2cc1Cl]

An example of a suitable active agent is BIX-01294 also known as diazepin-quinazolin-amine derivative, or a pharmaceutically acceptable derivative, e.g., salt thereof. BIX-01294 is a SUV39H1 inhibitor that selectively impairs the generation of H3K9me2. BIX-01294 has the following structure:

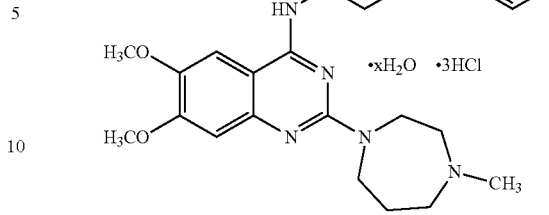

An example of a suitable active agent is UNC0638 also known as 2-Cyclohexyl-N-(1-isopropylpiperidin-4-yl)-6-methoxy-7-(3-(pyrrolidin-1-yl)propoxy) quinazolin-4-amine, or a pharmaceutically acceptable derivative, e.g., salt thereof. UNC0638 is a selective inhibitor of SUV39H1. UNC0638 has the following structure:

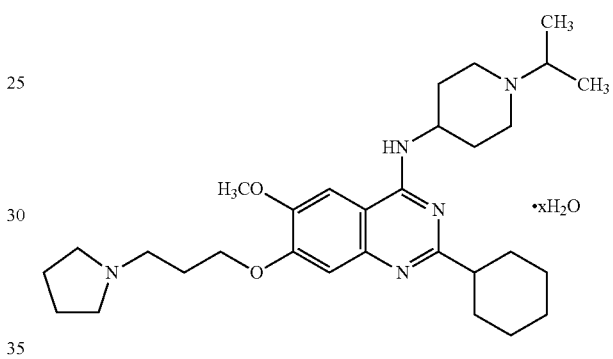

Combinations of two or more SUV39H1 inhibitors can also be used in a method of the present disclosure.

Small Molecule Inhibitors of SMYD5

In some cases, the active agent is a small molecule inhibitor of methyltransferase activity of a SMYD5 polypeptide. In some cases, the active agent is a small molecule inhibitor of methyltransferase activity of a SMYD5 polypeptide, where the active agent is a selective SMYD5 inhibitor. A selective SMYD5 inhibitor does not substantially inhibit a SMYD1 polypeptide, a SMYD2 polypeptide, a SMYD3 polypeptide, or a SMYD4 polypeptide, or any other methyltransferase.

Inhibitors, e.g., siNA or small molecule inhibitors, may also be of interest in connection with the targeting of one or more of the additional HIV transcription activators identified in the shRNA screen described herein. For example, small molecule inhibitors of one or more of the following lysine methyl transferases: MLL (comprising the amino acid sequence of any of SEQ ID NOs: 42, 43, and 44), MLL2 (comprising the amino acid sequence of SEQ ID NO: 45 or 46), MLL3 (comprising the amino acid sequence of any of SEQ ID NOs: 47, 48 and 49), MLL4 (comprising the amino acid sequence of SEQ ID NO: 50 or 51), MLL5 (comprising the amino acid sequence of any of SEQ ID NOs: 52, 53, 54, 55, 56, 57, 58, and 59), SETD7/9 (comprising the amino acid sequence of SEQ ID NO: 60), SETD8 (comprising the amino acid sequence of SEQ ID NO: 61 or 62), SETDB2 (comprising the amino acid sequence of any of SEQ ID NOs: 63, 64, and 65), SETMAR (comprising the amino acid sequence of any of SEQ ID NOs: 66, 67, and 68), SMYD3 (comprising the amino acid sequence of any of SEQ ID NOs: 69, 70, and 71), and SUV420H2 (comprising the amino acid sequence of SEQ ID NO: 72 or 73) may be used in the methods and compositions described herein. In some embodiments, such inhibitors will be selective inhibitors. Such inhibitors may be used alone or in combination with one or more inhibitors as described herein, e.g., one or more small molecule inhibitors as described herein, and/or in a combination therapy as described herein.

Nucleic Acid Inhibitors

In some cases, an active agent is a short interfering nucleic acid (siNA). The terms "short interfering nucleic acid," "siNA," "short interfering RNA," "siRNA," "shRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. As used herein, siNA includes short hairpin RNA (shRNA), short interfering RNA (siRNA), and the like.

A nucleic acid encoding an siNA is also contemplated for use in a method of the present disclosure, where the nucleic acid comprises a nucleotide sequence encoding the siNA. A nucleic acid encoding an siNA that reduces the level of SMYD2 polypeptide in a cell can comprise a promoter operably linked to the nucleotide sequence encoding the siNA. The nucleic acid can be present in a recombinant expression vector, e.g., a recombinant viral vector (e.g., a lentivirus-based vector; an adeno-associated virus-based vector; and the like). Suitable promoters include those that are functional in a mammalian cell, e.g., a $CD4^+$ T cell. A suitable promoter includes, e.g., a CD4 promoter.

Non-limiting examples of suitable siNA sequences include the SMYD2 shRNA sequences depicted in FIG. 13.

In some embodiments, siNA is produced by methods not requiring the production of dsRNA, e.g., chemical synthesis or de novo synthesis or direct synthesis. Chemically synthesized siRNA may be synthesized on a custom basis or may be synthesized on a non-custom or stock or pre-designed basis. Custom designed siRNA are routinely available from various manufactures (e.g., Ambion®, a division of Life Technologies®, Grand Island, N.Y.; Thermo Scientific®, a division of Fisher Scientific®, Pittsburgh, Pa.; Sigma-Aldrich®, St. Louis, Mo.; Qiagen®, Hilden, Germany; etc.) which provide access to various tools for the design of siRNA. Tools for the design of siNA allow for the selection of one or more siRNA nucleotide sequences based on computational programs that apply algorithms on longer input nucleotide sequences to identify candidate siNA sequences likely to be effective in producing an RNAi effect. Such algorithms can be fully automated or semi-automated, e.g., allowing for user input to guide sRNA selection. Programs applying algorithms for siNA sequence selection are available remotely on the World Wide Web, e.g., at the websites of manufacturers of chemically synthesized siNA or at the websites of independent, e.g. open source, developers or at the websites of academic institutions. Programs applying algorithms for siRNA sequence selection may also be obtained, e.g., downloaded or received on compact disk as software. Such programs are well known in the art, see e.g., Naito et al. (2004) *Nucleic Acids Research*, 32:W124-W129; Boudreau et al. (2013) *Nucleic Acids Research*, 41:e9; Mysara et al. (2011) *PLoS*, 6:e25642; and Iyer et al. (2007) *Comput Methods Programs Biomed*, 85:203-9, which are incorporated herein by reference.

Publicly available tools to facilitate design of siNAs are available in the art. See, e.g., DEQOR: Design and Quality Control of RNAi (available on the internet at http://deqor(dot)mpi-cbg(dot)de/deqor_new/input(dot)html). See also, Henschel et al. *Nucleic Acids Res.* 2004 Jul. 1; 32 (Web Server issue):W113-20. DEQOR is a web-based program which uses a scoring system based on state-of-the-art parameters for siNA design to evaluate the inhibitory potency of siNAs. DEQOR, therefore, can help to predict (i) regions in a gene that show high silencing capacity based on the base pair composition and (ii) siNAs with high silencing potential for chemical synthesis. In addition, each siNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Design of RNAi molecules, when given a target gene, is routine in the art. See also US 2005/0282188 (which is incorporated herein by reference) as well as references cited therein. See, e.g., Pushparaj et al. *Clin Exp Pharmacol Physiol.* 2006 May-June; 33(5-6):504-10; Lutzelberger et al. *Handb Exp Pharmacol.* 2006; (173):243-59; Aronin et al. *Gene Ther.* 2006 March; 13(6):509-16; Xie et al. *Drug Discov Today.* 2006 January; 11(1-2):67-73; Grunweller et al. *Curr Med Chem.* 2005; 12(26):3143-61; and Pekaraik et al. *Brain Res Bull.* 2005 Dec. 15; 68(1-2):115-20. Epub 2005 Sep. 9.

Methods for design and production of siNAs to a desired target are known in the art, and their application to SMYD2 for the purposes disclosed herein will be readily apparent to the ordinarily skilled artisan, as are methods of production of siNAs having modifications (e.g., chemical modifications) to provide for, e.g., enhanced stability, bioavailability, and other properties to enhance use as therapeutics. In addition, methods for formulation and delivery of siNAs (e.g., siRNAs; shRNAs) to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell*, 110, 563-574 and Schwarz et al., 2002, *Molecular Cell*, 10, 537-568), or 5',3'-diphosphate.

In certain embodiments, the siNA molecule contains separate sense and antisense sequences or regions, wherein the sense and antisense regions are covalently linked by nucleotide or non-nucleotide linker molecules as is known in the art, or are alternately non-covalently linked by ionic interactions, hydrogen bonding, van der Waals interactions, hydrophobic interactions, and/or stacking interactions. In certain embodiments, the siNA molecules comprise a nucleotide sequence that is complementary to a nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompass chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules suitable for use in a method of the present disclosure optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In some embodiments, an siNA is an siRNA. In some embodiments, an siNA is a shRNA. In some embodiments, a DNA comprising a nucleotide sequence encoding an siRNA is used. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene (e.g., SMYD2) at the post-transcriptional level or the pre-transcriptional level. In a non-limiting example, epigenetic regulation of gene expression by siNA molecules suitable for use in a method of the present disclosure can result from siNA mediated modification of chromatin structure or methylation pattern to alter gene expression (see, for example, Verdel et al., 2004, *Science*, 303, 672-676; Pal-Bhadra et al., 2004, *Science*, 303, 669-672; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237).

siNA (e.g., siRNA; shRNA; etc.) molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178).

siNA (e.g., siRNA, shRNA, etc.) molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant an siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300, 074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which is hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules (e.g., siRNA, shRNA, etc.) having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the siNA molecules described herein can be attached to biologically active molecules via linkers that are biodegradable, such as biodegradable nucleic acid linker molecules.

Nucleic Acid Modifications

In some embodiments, a SMYD2 inhibitor (e.g., a dsRNA, a siNA, etc.) has one or more modifications, e.g., a base modification, a backbone modification, etc., to provide the nucleic acid with an enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'-O-methyl modified nucleotides, 2' Fluoro modified nucleotides, locked nucleic acid (LNA) modified nucleotides, peptide nucleic acid (PNA) modified nucleotides, nucleotides with phosphorothioate (PS) linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases the melting temperature (Tm) of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siNAs to improve stability in serum or other biological fluids.

Locked nucleic acid (LNA) bases have a modification to the ribose backbone that locks the base in the C3'-endo position, which favors RNA A-type helix duplex geometry. This modification significantly increases Tm and is also very nuclease resistant. Multiple LNA insertions can be placed in an oligonucleotide ("oligo") at any position except the 3'-end. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject siNA (e.g., siNA, shRNA, etc.) has one or more nucleotides that are 2'-O-Methyl modified nucleotides. In some embodiments, a subject siNA (e.g., a dsRNA, a siNA, a shRNA, etc.) has one or more 2' Fluoro modified nucleotides. In some embodiments, a subject nucleic acid (e.g., a dsRNA, a siNA, a shRNA, etc.) has one or more LNA bases. In some embodiments, a subject nucleic acid (e.g., a dsRNA, a siNA, a shRNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, an shRNA, etc.) has a 5' cap (e.g., a 7-methylguanylate cap (m7G)). In some embodiments, a subject nucleic acid (e.g., a dsRNA, a siNA, a shRNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be basic (the nucleobase is missing or has a hydroxyl group in place thereof). Various salts (such as, for example, potassium or sodium), mixed salts and free acid forms are also included.

In some embodiments, a subject siNA comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject siNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general, the incorporation of CeNA monomers into a DNA chain increases the stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. Patent Publication Nos. 20120165514, 20100216983, 20090041809, 20060117410, 20040014959, 20020094555, and 20020086998.

Modified Sugar Moieties

A subject siNA can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O—dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2$ $CH_2$ $CH_2NH_2$), allyl (—$CH_2$—CH=$CH_2$), —O-allyl $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject siNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methyl cytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject siNA involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject siNA.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the 3' terminus of an exogenous polynucleotide (e.g., a siNA). In some embodiments, a PTD is covalently linked to the 5' terminus of an exogenous polynucleotide (e.g., a siNA). Exemplary PTDs include but are not limited to a minimal undecapeptide protein transduction domain (corresponding to residues 47-57 of HIV-1 TAT comprising YGRKKRRQRRR (SEQ ID NO:11)); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); a Drosophila Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:12); Transportan GWTLNSAGYLLGKINLKA-LAALAKKIL (SEQ ID NO:13); KALAWEAKLAKA-LAKALAKHLAKALAKALKCEA (SEQ ID NO:14); and RQIKIWFQNRRMKWKK (SEQ ID NO:15). Exemplary PTDs include but are not limited to, YGRKKRRQRRR (SEQ ID NO:11), RKKRRQRRR (SEQ ID NO:16); an arginine homopolymer of from 3 arginine residues to 50 arginine residues; Exemplary PTD domain amino acid sequences include, but are not limited to, any of the following: YGRKKRRQRRR (SEQ ID NO:11); RKKRRQRR (SEQ ID NO:17); YARAAARQARA (SEQ ID NO:18); THRLPRRRRRR (SEQ ID NO:19); and GGRRARRRRRR (SEQ ID NO:20). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Combination Therapy

The present disclosure provides combination therapy for treating an immunodeficiency virus infection in an individual.

Combination Therapy—Two or More Agents that Reactivate Latent HIV

In some embodiments, a method of the present disclosure of treating an immunodeficiency virus infection in an individual in need thereof involves administering to the individual an effective amount of two or more agents that activate immunodeficiency virus transcription. In some cases, the two or more agents act synergistically to reactivate latent immunodeficiency virus.

In some cases, a method of the present disclosure of treating an immunodeficiency virus infection in an individual in need thereof involves: a) administering to the individual an effective amount of a SMYD2 inhibitor, an ASH1L inhibitor, an SUV420H1 inhibitor and/or a SUV39H1 inhibitor that activates immunodeficiency virus transcription; and b) administering to the individual an effective amount of a second agent that activates latent immunodeficiency virus transcription.

Suitable second agents that activate latent immunodeficiency virus transcription include, e.g., a bromodomain inhibitor; a protein kinase C (PKC) activator, such as prostratin, bryostatin, a chemical analog of prostratin, a chemical analog of bryostatin, and the like; a histone deacetylase (HDAC) inhibitor such as suberoylanilidehydroxamic (SAHA), romidepsin, sodium butyrate, and the like.

Bromodomain inhibitors suitable for use include, e.g., JQ1, which has the following structure:

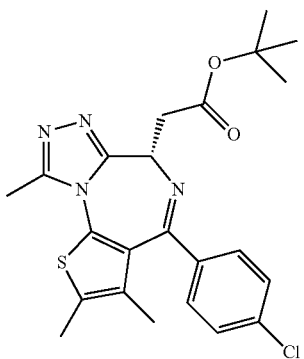 [SMILES: Cc1sc2c(c1C)C(c1ccc(Cl)cc1)=N[C@@H](CC(=O)OC(C)(C)C)c1nnc(C)n1-2]

Suitable bromodomain inhibitors include compounds of formula I:

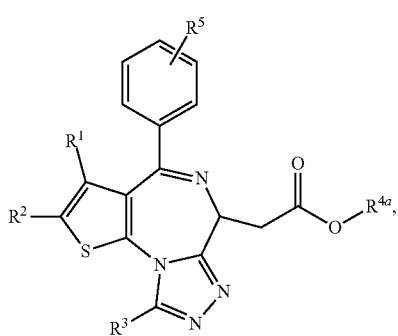

(I)

wherein

R1 is selected from hydrogen, alkyl, substituted alkyl, alkenyl, substituted alkenyl, alkynyl, substituted alkynyl, alkoxy, substituted alkoxy, and acyl;

R2 is selected from hydrogen, alkyl, substituted alkyl, alkenyl, substituted alkenyl, alkynyl, substituted alkynyl, alkoxy, substituted alkoxy, and acyl;

R3 is selected from hydrogen, alkyl, substituted alkyl, alkenyl, substituted alkenyl, alkynyl, substituted alkynyl, alkoxy, substituted alkoxy, and acyl;

R4a is selected from hydrogen, C1-C3 alkyl, C5-C10 alkyl, and substituted alkyl;

R5 is selected from hydrogen, alkyl, substituted alkyl, alkenyl, substituted alkenyl, alkynyl, substituted alkynyl, hydroxy, alkoxy, substituted alkoxy, acyloxy, thiol, acyl, amino, substituted amino, aminoacyl, acylamino, azido, carboxyl, carboxylalkyl, cyano, halogen, and nitro;

and salts or solvates or stereoisomers thereof.

In formula I, $R^1$ is selected from hydrogen, alkyl, substituted alkyl, alkenyl, substituted alkenyl, alkynyl, substituted alkynyl, alkoxy, substituted alkoxy, and acyl. In certain instances, $R^1$ is hydrogen. In certain instances, $R^1$ is alkyl or substituted alkyl. In certain instances, $R^1$ is alkyl, such as $C_1$-$C_6$ alkyl, including $C_1$-$C_3$ alkyl. In certain instances, $R^1$ is methyl, ethyl, n-propyl, or isopropyl. In certain instances, $R^1$ is methyl. In certain instances, $R^1$ is alkenyl or substituted alkenyl. In certain instances, $R^1$ is selected from alkynyl or substituted alkynyl. In certain instances, $R^1$ is alkoxy or substituted alkoxy. In certain instances, $R^1$ is acyl.

In formula I, $R^2$ is selected from hydrogen, alkyl, substituted alkyl, alkenyl, substituted alkenyl, alkynyl, substituted alkynyl, alkoxy, substituted alkoxy, and acyl. In certain instances, $R^2$ is hydrogen. In certain instances, $R^2$ is alkyl or substituted alkyl. In certain instances, $R^2$ is alkyl, such as $C_1$-$C_6$ alkyl, including $C_1$-$C_3$ alkyl. In certain instances, $R^2$ is methyl, ethyl, n-propyl, or isopropyl. In certain instances, $R^2$ is methyl. In certain instances, $R^2$ is alkenyl or substituted alkenyl. In certain instances, $R^2$ is selected from alkynyl or substituted alkynyl. In certain instances, $R^2$ is alkoxy or substituted alkoxy. In certain instances, $R^2$ is acyl.

In formula I, $R^3$ is selected from hydrogen, alkyl, substituted alkyl, alkenyl, substituted alkenyl, alkynyl, substituted alkynyl, alkoxy, substituted alkoxy, and acyl. In certain instances, $R^3$ is hydrogen. In certain instances, $R^3$ is alkyl or substituted alkyl. In certain instances, $R^3$ is alkyl, such as $C_1$-$C_6$ alkyl, including $C_1$-$C_3$ alkyl. In certain instances, $R^3$ is methyl, ethyl, n-propyl, or isopropyl. In certain instances, $R^3$ is methyl. In certain instances, $R^3$ is alkenyl or substituted alkenyl. In certain instances, $R^3$ is selected from alkynyl or substituted alkynyl. In certain instances, $R^3$ is alkoxy or substituted alkoxy. In certain instances, $R^3$ is acyl.

In formula I, $R^{4a}$ is selected from hydrogen, $C_1$-$C_3$ alkyl, $C_5$-$C_{10}$ alkyl, and substituted alkyl. In certain instances, $R^{4a}$ is hydrogen. In certain instances, $R^{4a}$ is $C_1$-$C_3$ alkyl. In certain instances, $R^{4a}$ is $C_5$-$C_{10}$ alkyl. In certain instances, $R^{4a}$ is substituted alkyl. In certain instances, $R^{4a}$ is methyl, ethyl, n-propyl, or isopropyl. In certain instances, $R^{4a}$ is methyl.

In formula I, $R^5$ is selected from hydrogen, alkyl, substituted alkyl, alkenyl, substituted alkenyl, alkynyl, substituted alkynyl, hydroxy, alkoxy, substituted alkoxy, acyloxy, thiol, acyl, amino, substituted amino, aminoacyl, acylamino, azido, carboxyl, carboxylalkyl, cyano, halogen, and nitro.

In certain instances, $R^5$ is hydrogen. In certain instances, $R^5$ is alkyl or substituted alkyl. In certain instances, $R^5$ is alkenyl or substituted alkenyl. In certain instances, $R^5$ is alkynyl or substituted alkynyl. In certain instances, $R^5$ is hydroxy, alkoxy, substituted alkoxy, or acyloxy. In certain instances, $R^5$ is thiol. In certain instances, $R^5$ is acyl. In certain instances, $R^5$ is amino, substituted amino, aminoacyl, acylamino, or azido. In certain instances, $R^5$ is carboxyl or carboxylalkyl. In certain instances, $R^5$ is cyano. In certain instances, $R^5$ is nitro. In certain instances, $R^5$ is halogen. In certain instances, $R^5$ is fluoro. In certain instances, $R^5$ is chloro. In certain instances, $R^5$ is bromo.

In certain instances, formula I is the following formula:

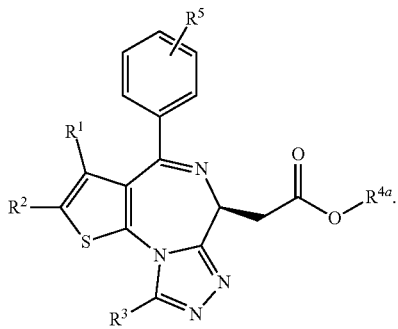

A particular compound of interest, and salts or solvates or stereoisomers thereof, includes:

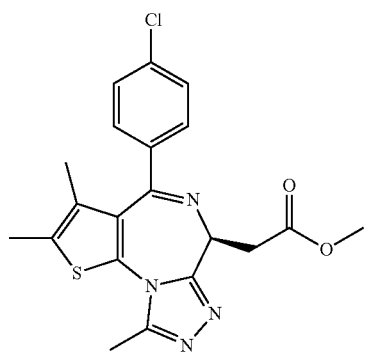

(Methyl 2-((6S)-4-(4-chlorophenyl)-2,3,9-trimethyl-6H-thieno[3,2-f][1,2,4]triazolo[4,3-a][1,4]diazepin-6-yl)acetate).

Suitable HDAC inhibitors include hydroxamic acids (e.g., vorinostat (suberoylanilide hydroxamic acid, SAHA, Archin et al., AIDS Res Hum Retroviruses, 25(2): 207-12, 2009; Contreras et al. J Blol Chem, 284:6782-9, 2009), belinostat (PXD101), LAQ824; and panobinostat (LBH589); and benzamides (e.g., entinostat (MS-275), CI994; and mocetinostat (MGCD0103). Suitable HDAC inhibitors include butyric acid (including sodium butyrate and other salt forms), Valproic acid (including Mg valproate and other salt forms), suberoylanilide hydroxamic acid (SAHA), Vorinostat, Romidepsin (trade name Istodax), Panobinostat (LBH589), Belinostat (PXD101), Mocetinostat (MGCD0103), PCI-24781, Entinostat (MS-275), SB939, Resminostat (4SC-201); Givinostat (ITF2357), CUDC-101, AR-42, CHR-2845, CHR-3996, 4SC-202, sulforaphane, BML-210, M344, CI-994; CI-994 (Tacedinaline); BML-210; M344; MGCD0103 (Mocetinostat); and Tubastatin A. Additional suitable HDAC inhibitors are described in U.S. Pat. No. 7,399,787.

Suitable bryostatins include bryostatin-1; a bryostatin analog as described in U.S. Pat. No. 6,624,189; bryostatin-2; a bryostatin analog as described in U.S. Pat. No. 7,256,286; a bryostatin analog described in U.S. Patent Publication No. 20090270492; a bryostatin analog described in WO 2013/165592; etc.

In some embodiments, a method of the present disclosure of treating an immunodeficiency virus infection in an individual in need thereof involves: a) administering to the individual an effective amount of two or more agents that activate immunodeficiency virus transcription; and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, the co-administration of compounds results in synergism, and the combination is therefore a synergistic combination. As used herein, a "synergistic combination" or a "synergistic amount" of (i) a SMYD2 inhibitor that activates immunodeficiency virus transcription; and (ii) a second agent that activates immunodeficiency virus transcription is an amount that is more effective in activating immunodeficiency virus transcription when co-administered than the incremental increase that could be predicted or expected from a merely additive combination of (i) and (ii) when each is administered at the same dosage alone (not co-administered).

In some cases, a method of the present disclosure of treating an immunodeficiency virus infection in an individual in need thereof involves: a) administering to the individual an effective amount of AZ505; and b) administering to the individual an effective amount of JQ1. In some cases, a method of the present disclosure of treating an immunodeficiency virus infection in an individual in need thereof involves: a) administering to the individual an effective amount of AZ505; and b) administering to the individual an effective amount of SAHA. In some cases, a method of the present disclosure of treating an immunodeficiency virus infection in an individual in need thereof involves: a) administering to the individual an effective amount of AZ505; and b) administering to the individual an effective amount of bryostatin or a bryostatin analog. In some cases, a method of the present disclosure of treating an immunodeficiency virus infection in an individual in need thereof involves: a) administering to the individual an effective amount of AZ505; and b) administering to the individual an effective amount of an HDAC inhibitor. In some cases, a method of the present disclosure of treating an immunodeficiency virus infection in an individual in need thereof involves: a) administering to the individual an effective amount of AZ505; and b) administering to the individual an effective amount of prostratin or a prostratin analog.

In some cases, a method of the present disclosure of treating an immunodeficiency virus infection in an individual in need thereof involves: a) administering to the individual an effective amount of AZ506 and/or AZ391 (or another suitable methyltransferase inhibitor as described herein), or a pharmaceutically acceptable derivative, e.g., salt thereof; and b) administering to the individual an effective amount of JQ1. In some cases, a method of the present disclosure of treating an immunodeficiency virus infection in an individual in need thereof involves: a) administering to the individual an effective amount of AZ506 and/or AZ391 (or another suitable methyltransferase inhibitor as described herein), or a pharmaceutically acceptable derivative, e.g., salt thereof; and b) administering to the individual an effective amount of SAHA. In some cases, a method of the present disclosure of treating an immunodeficiency virus infection in an individual in need thereof involves: a) administering to the individual an effective amount of AZ506 and/or AZ391 (or another suitable methyltransferase inhibitor as described herein), or a pharmaceutically acceptable derivative, e.g., salt thereof; and b) administering to the individual an effective amount of bryostatin or a bryostatin analog. In some cases, a method of the present disclosure of treating an immunodeficiency virus infection in an individual in need thereof involves: a) administering to the individual an effective amount of AZ506 and/or AZ391 (or another suitable methyltransferase inhibitor as described herein), or a pharmaceutically acceptable derivative, e.g., salt thereof; and b) administering to the individual an effective amount of an HDAC inhibitor. In some cases, a method of the present disclosure of treating an immunodeficiency virus infection in an individual in need thereof involves: a) administering to the individual an effective amount of AZ506 and/or AZ391 (or another suitable methyltransferase inhibitor as described herein), or a pharmaceutically acceptable derivative, e.g., salt thereof; and b) administering to the individual an effective amount of prostratin or a prostratin analog.

Combination Therapy—SMYD2 Inhibitor (and/or ASH1L Inhibitor and/or SUV420H1 Inhibitor and/or SUV39H1 Inhibitor)+Anti-Viral Agent In some embodiments, a method of the present disclosure of treating an immunodeficiency virus infection in an individual in need thereof involves: a) administering to the individual an effective amount of a SMYD2 inhibitor (and/or ASH1L inhibitor and/or SUV420H1 inhibitor and/or SUV39H1 inhibitor) that activates immunodeficiency virus transcription; and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a method of the present disclosure of treating an immunodeficiency virus infection in an individual in need thereof involves: a) administering to the individual an effective amount of an agent that inhibits SMYD2 enzymatic activity (and/or ASH1L enzymatic activity and/or SUV420H1 enzymatic activity and/or SUV39H1 enzymatic activity) and/or reduces the level of SMYD2 polypeptide (and/or ASH1L polypeptide and/or SUV420H1 polypeptide and/or SUV39H1 polypeptide) in a cell, and that activates immunodeficiency virus transcription; and b) administering to the individual an effective amount of an agent that inhibits an immunodeficiency virus function. The immunodeficiency virus function can be selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a compound that is a SMYD2 inhibitor (and/or an ASH1L inhibitor, and/or an SUV420H1 inhibitor, and/or an SUV39H1 inhibitor) (e.g., an agent that inhibits SMYD2 enzymatic activity and/or reduces the level of SMYD2 polypeptide in a cell) and that activates immunodeficiency virus transcription is administered in combination therapy (i.e., co-administered) with: 1) one or more nucleoside reverse transcriptase inhibitors (e.g., Combivir, Epivir, Hivid, Retrovir, Videx, Zerit, Ziagen, etc.); 2) one or more non-nucleoside reverse transcriptase inhibitors (e.g., Rescriptor, Sustiva, Viramune, etc.); 3) one or more protease inhibitors (e.g., Agenerase, Crixivan, Fortovase, Invirase, Kaletra, Norvir, Viracept, etc.); 4) an anti-HIV agent such as a protease inhibitor and a nucleoside reverse transcriptase inhibitor; 5) an anti-HIV agent such as a protease inhibitor, a nucleoside reverse transcriptase inhibitor, and a non-nucleoside reverse transcriptase inhibitor; 6) an anti-HIV agent such as a protease inhibitor and a non-nucleoside reverse transcriptase inhibitor, and/or 7) an anti-viral (e.g., HIV) agent such as a protein kinase C (PKC) activator (e.g., prostratin). Other combinations of an effective amount of a SMYD2 inhibitor with one or more anti-HIV agents, such as one or more of a protease inhibitor, a nucleoside reverse transcriptase inhibitor, a non-nucleoside reverse transcriptase inhibitor, and a protein kinase C (PKC) activator are contemplated.

A PKC activator (e.g., prostratin ((1aR,1bS,4aR,7aS,7bR, 8R,9aS)-4a,7b-dihydroxy-3-(hydroxymethyl)-1,1,6,8-tetramethyl-5-oxo-1,1a,1b,4,4a, 5,7a,7b, 8,9-decahydro-9aH-cyclopropa[3,4]benzo[1,2-e]azulen-9a-yl)) can be administered in a separate formulation from a SMYD2 inhibitor. A PKC activator can be co-formulated with a SMYD2 inhibitor, and the co-formulation administered to an individual.

In some embodiments, the co-administration of compounds results in synergism, and the combination is therefore a synergistic combination. As used herein, a "synergistic combination" or a "synergistic amount" of (i) a SMYD2 inhibitor that activates immunodeficiency virus transcription and (ii) an anti-viral agent (e.g., a nucleoside reverse transcriptase inhibitor, a non-nucleoside reverse transcriptase inhibitor, a protease inhibitor, an anti-HIV agent, a protein kinase C (PKC) activator, etc.) is an amount that is more effective in reducing immunodeficiency virus load when co-administered than the incremental increase that could be predicted or expected from a merely additive combination of (i) and (ii) when each is administered at the same dosage alone (not co-administered). As used herein, a "synergistic combination" or a "synergistic amount" of (i) a SMYD2 inhibitor that activates immunodeficiency virus transcription and (ii) a second agent that activates latent immunodeficiency virus transcription, is an amount that is more effective in reactivating latent immunodeficiency virus transcription when co-administered than the incremental increase that could be predicted or expected from a merely additive combination of (i) and (ii) when each is administered at the same dosage alone (not co-administered).

Any of a variety of methods can be used to determine whether a treatment method is effective. For example, methods of determining whether the methods of the present disclosure are effective in reducing immunodeficiency virus (e.g., HIV) viral load, and/or treating an immunodeficiency virus (e.g., HIV) infection, are any known test for indicia of immunodeficiency virus (e.g., HIV) infection, including, but not limited to, measuring viral load, e.g., by measuring the amount of immunodeficiency virus (e.g., HIV) in a biological sample, e.g., using a polymerase chain reaction (PCR) with primers specific for an immunodeficiency virus (e.g., HIV) polynucleotide sequence; detecting and/or measuring a polypeptide encoded by an immunodeficiency virus (e.g., HIV), e.g., p24, gp120, reverse transcriptase, using, e.g., an immunological assay such as an enzyme-linked immunosorbent assay (ELISA) with an antibody specific for the polypeptide; and measuring the $CD4^+$ T cell count in the individual.

Formulations, Dosages, and Routes of Administration

In general, an active agent (e.g., a SMYD2 inhibitor) is prepared in a pharmaceutically acceptable composition(s) for delivery to a host. In the context of reducing immunodeficiency virus transcription, the terms "active agent," "drug," "agent," "therapeutic agent," and the like are used interchangeably herein to refer to an agent that is a SMYD2 inhibitor (and/or an ASH1L inhibitor, and/or an SUV420H1 inhibitor, and/or an SUV39H1 inhibitor) and that activates latent immunodeficiency virus transcription.

Pharmaceutically acceptable carriers suitable for use with active agents (and optionally one or more additional therapeutic agents) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

An active agent is administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes an active agent as described above, and optionally one or more additional therapeutic agent.

In a subject method, an active agent may be administered to the host using any convenient means capable of resulting in the desired degree of reduction of immunodeficiency virus transcription. Thus, an active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with a method of the present disclosure. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered in an injectable formulation. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration comprises an active agent formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration comprises an active agent formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent is one which provides up to about 1 mg to about 1000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, or from about 500 mg to about 1000 mg of an active agent can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the number of viral particles per unit blood. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys), that are susceptible to immunodeficiency virus (e.g., HIV) infection. In many embodiments, the hosts will be humans.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating an immunodeficiency virus (e.g., an HIV) infection. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present invention provides a delivery system comprising an active agent (a SMYD2 inhibitor; optionally also one or more additional therapeutic agents). In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a delivery system of the present disclosure comprises an injection device. Exemplary, non-limiting drug delivery devices include injections devices, such as pen injectors, and needle/syringe devices. In some embodiments, the invention provides an injection delivery device that is pre-loaded with a formulation comprising an effective amount of a SMYD2 inhibitor. For example, a subject delivery device comprises an injection device pre-loaded with a single dose of a SMYD2 inhibitor. A injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096, 010, 6,146,361, 6,248,095, 6,277,099, and 6,221,053; and the like. The medication delivery pen can be disposable, or reusable and refillable.

The present invention provides a delivery system for vaginal or rectal delivery of an active agent to the vagina or rectum of an individual. The delivery system comprises a device for insertion into the vagina or rectum. In some embodiments, the delivery system comprises an applicator for delivery of a formulation into the vagina or rectum; and a container that contains a formulation comprising an active agent. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909. If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. The active agent is incorporated into a silicone matrix which is coated onto a cylindrical drug-free polyurethane sponge, as described in the literature.

Pessaries, tablets, and suppositories are other examples of drug delivery systems which can be used, e.g., in carrying out a method of the present disclosure. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10-100 µm and can be prepared from starch, gelatin, albumin, collagen, or dextran.

Another system is a container comprising a subject formulation (e.g., a tube) that is adapted for use with an applicator. The active agent is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

Combination Therapy

In some embodiments, a SMYD2 inhibitor (and/or an ASH1L inhibitor, and/or an SUV420H1 inhibitor, and/or an SUV39H1 inhibitor) is administered in combination therapy with one or more additional therapeutic agents. Suitable additional therapeutic agents include agents that inhibit one or more functions of an immunodeficiency virus; agents that treat or ameliorate a symptom of an immunodeficiency virus infection; agents that treat an infection that occurs secondary to an immunodeficiency virus infection; and the like. As noted above, suitable additional therapeutic agents include agents (other than a SMYD2 inhibitor) that reactivate latent immunodeficiency virus.

Therapeutic agents include, e.g., beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™ 3TC), protease inhibitors, saquinavir (Invirase™, Fortovase™), ritonavir (Norvir™) nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

In some embodiments, a SMYD2 inhibitor (and/or an ASH1L inhibitor, and/or an SUV420H1 inhibitor, and/or an SUV39H1 inhibitor) is administered in combination therapy with two or more anti-HIV agents. For example, a SMYD2 inhibitor (and/or an ASH1L inhibitor, and/or an SUV420H1 inhibitor, and/or an SUV39H1 inhibitor) can be administered in combination therapy with one, two, or three nucleoside reverse transcriptase inhibitors (e.g., Combivir, Epivir, Hivid, Retrovir, Videx, Zerit, Ziagen, etc.). A SMYD2 inhibitor (and/or an ASH1L inhibitor, and/or an SUV420H1 inhibitor, and/or an SUV39H1 inhibitor) can be administered in combination therapy with one or two non-nucleoside reverse transcriptase inhibitors (e.g., Rescriptor, Sustiva, Viramune, etc.). A SMYD2 inhibitor (and/or an ASH1L inhibitor, and/or an SUV420H1 inhibitor, and/or an SUV39H1 inhibitor) can be administered in combination therapy with one or two protease inhibitors (e.g., Agenerase, Crixivan, Fortovase, Invirase, Kaletra, Norvir, Viracept, etc.). A SMYD2 inhibitor (and/or an ASH1L inhibitor, and/or an SUV420H1 inhibitor, and/or an SUV39H1 inhibitor) can be administered in combination therapy with a protease inhibitor and a nucleoside reverse transcriptase inhibitor. A SMYD2 inhibitor (and/or an ASH1L inhibitor, and/or an SUV420H1 inhibitor, and/or an SUV39H1 inhibitor) can be administered in combination therapy with a protease inhibitor, a nucleoside reverse transcriptase inhibitor, and a non-nucleoside reverse transcriptase inhibitor. A SMYD2 inhibitor (and/or an ASH1L inhibitor, and/or an SUV420H1 inhibitor, and/or an SUV39H1 inhibitor) can be administered in combination therapy with a protease inhibitor and a non-nucleoside reverse transcriptase inhibitor. Other combinations of a SMYD2 inhibitor (and/or an ASH1L inhibitor, and/or an SUV420H1 inhibitor, and/or an SUV39H1 inhibitor) with one or more of a protease inhibitor, a nucleoside reverse transcriptase inhibitor, and a non-nucleoside reverse transcriptase inhibitor are contemplated.

In some embodiments, a treatment method of the present disclosure involves administering: a) a SMYD2 inhibitor (and/or an ASH1L inhibitor, and/or an SUV420H1 inhibitor, and/or an SUV39H1 inhibitor); and b) an agent that inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

In some embodiments, a subject treatment method involves administering: a) a SMYD2 inhibitor (and/or an ASH1L inhibitor, and/or an SUV420H1 inhibitor, and/or an SUV39H1 inhibitor); and b) an HIV inhibitor, where suitable HIV inhibitors include, but are not limited to, one or more nucleoside/nucleotide reverse transcriptase inhibitors (NRTIs), non-nucleoside reverse transcriptase inhibitors (NNRTIs), protease inhibitors (PIs), fusion inhibitors, integrase inhibitors, chemokine receptor (e.g., CXCR4, CCR5) inhibitors, and hydroxyurea.

Nucleoside reverse transcriptase inhibitors include, but are not limited to, abacavir (ABC; ZIAGEN™), didanosine (dideoxyinosine (ddI); VIDEX™) lamivudine (3TC; EPIVIR™), stavudine (d4T; ZERIT™, ZERIT XR™), zalcitabine (dideoxycytidine (ddC); HIVID™), zidovudine (ZDV, formerly known as azidothymidine (AZT); RETROVIR™), abacavir, zidovudine, and lamivudine (TRIZIVIR™), zidovudine and lamivudine (COMBIVIR™), and emtricitabine (EMTRIVA™). Nucleotide reverse transcriptase inhibitors include tenofovir disoproxil fumarate (VIREAD™). Non-nucleoside reverse transcriptase inhibitors for HIV include, but are not limited to, nevirapine (VIRAIVIUNE™), delavirdine mesylate (RESCRIPTOR™), and efavirenz (SUSTIVA™).

Protease inhibitors (PIs) for treating HIV infection include amprenavir (AGENERASE™), saquinavir mesylate (FORTOVASE™, INVIRASE™), ritonavir (NORVIR™), indinavir sulfate (CRIXIVAN™), nelfmavir mesylate (VIRACEPT™), lopinavir and ritonavir (KALETRA™), atazanavir (REYATAZ™), and fosamprenavir (LEXIVA™).

Fusion inhibitors prevent fusion between the virus and the cell from occurring, and therefore, prevent HIV infection and multiplication. Fusion inhibitors include, but are not limited to, enfuvirtide (FUZEON™), Lalezari et al., New England J. Med., 348:2175-2185 (2003); and maraviroc (SELZENTRY™, Pfizer).

An integrase inhibitor blocks the action of integrase, preventing HIV-1 genetic material from integrating into the host DNA, and thereby stopping viral replication. Integrase inhibitors include, but are not limited to, raltegravir (ISENTRESS™, Merck); and elvitegravir (GS 9137, Gilead Sciences).

Maturation inhibitors include, e.g., bevirimat (3β-(3-carboxy-3-methyl-butanoyloxy) lup-20(29)-en-28-oic acid); and Vivecon (MPC9055).

In some embodiments, a subject treatment method involves administering: a) a SMYD2 inhibitor (and/or an ASH1L inhibitor, and/or an SUV420H1 inhibitor, and/or an SUV39H1 inhibitor); and b) one or more of: (1) an HIV protease inhibitor selected from amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) an HIV non-nucleoside inhibitor of reverse transcriptase selected from capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirene), efavirenz, BILR 355 BS, VRX 840773, UK-453061, and RDEA806; (3) an HIV nucleoside inhibitor of reverse transcriptase selected from zidovudine, emtricitabine, didanosine, stavudine, zalcitabine, lamivudine, abacavir, amdoxovir, elvucitabine, alovudine, MIV-210, racivir, D-d4FC, emtricitabine, phosphazide, fozivudine tidoxil, apricitibine (AVX754), amdoxovir, KP-1461, and fosalvudine tidoxil (formerly HDP 99.0003); (4) an HIV nucleotide inhibitor of reverse transcriptase selected from tenofovir and adefovir; (5) an HIV integrase inhibitor selected from curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-538158, GSK364735C, BMS-707035, MK-2048, and BA 011; (6) a gp41 inhibitor selected from enfuvirtide, sifuvirtide, FB006M, and TRI-1144; (7) a CXCR4 inhibitor, such as AMD-070; (8) an entry inhibitor, such as SP01A; (9) a gp120 inhibitor, such as BMS-488043 and/or BlockAide/CR; (10) a G6PD and NADH-oxidase inhibitor, such as immunitin; (11) a CCR5 inhibitors selected from the group consisting of aplaviroc, vicriviroc, maraviroc, PRO-140, INCB15050, PF-232798 (Pfizer), and CCR5 mAb004; (12) another drug for treating HIV selected from BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS119, ALG 889, and PA-1050040 (PA-040); (13) any combinations or mixtures of the above.

As further examples, in some embodiments, a subject treatment method involves administering: a) a SMYD2 inhibitor (and/or an ASH1L inhibitor, and/or an SUV420H1 inhibitor, and/or an SUV39H1 inhibitor); and b) one or more of: i) amprenavir (Agenerase; (3S)-oxolan-3-yl N—R2S, 3R)-3-hydroxy-4-[N-(2-methylpropyl)(4-aminobenzene)sulfonamido]-1-phenylbutan-2-yl]carbamate) in an amount of 600 mg or 1200 mg twice daily; ii) tipranavir (Aptivus; N-{3-[(1R)-1-[(2R)-6-hydroxy-4-oxo-2-(2-phenylethyl)-2-propyl-3,4-dihydro-2H-pyran-5-yl]propyl]phenyl}-5-(trifluoromethyl)pyridine-2-sulfonamide) in an amount of 500 mg twice daily; iii) idinavir (Crixivan; (2S)-1-[(2S,4R)-4-benzyl-2-hydroxy-4-{[(1S,2R)-2-hydroxy-2,3-dihydro-1H-inden-1-yl]carbamoyl}butyl]-N-tert-butyl-4-(pyridin-3-yl-methyl)piperazine-2-carboxamide) in an amount of 800 mg three times daily; iv) saquinavir (Invirase; 2S)—N-[(2S,3R)-4-[(3S)-3-(tert-butylcarbamoyl)-decahydroisoquinolin-2-yl]-3-hydroxy-1-phenylbutan-2-yl]-2-(quinolin-2-ylformamido)butanediamide) in an amount of 1,000 mg twice daily; v) lopinavir and ritonavir (Kaleta; where lopinavir is 2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide; and ritonavir is 1,3-thiazol-5-ylmethyl N-[(2S,3S,5S)-3-hydroxy-5-[(2S)-3-methyl-2-{[methyl({[2-(propan-2-yl)-1,3-thiazol-4-yl]methyl}) carbamoyl]amino}butanamido]-1,6-diphenylhexan-2-yl] carbamate) in an amount of 133 mg twice daily; vi) fosamprenavir (Lexiva; {[(2R,3S)-1-[N-(2-methylpropyl)(4-aminobenzene)sulfonamido]-3-({[(3S)-oxolan-3-yloxy] carbonyl}amino)-4-phenylbutan-2-yl]oxy}phosphonic acid)

in an amount of 700 mg or 1400 mg twice daily); vii) ritonavir (Norvir) in an amount of 600 mg twice daily; viii) nelfinavir (Viracept; (3S,4aS,8aS)—N-tert-butyl-2-[(2R,3R)-2-hydroxy-3-[(3-hydroxy-2-methylphenyl)formamido]-4-(phenylsulfanyl)butyl]-decahydroisoquinoline-3-carboxamide) in an amount of 750 mg three times daily or in an amount of 1250 mg twice daily; ix) Fuzeon (Acetyl-YTSLIHSLIEESQNQ QEKNEQELLELDKWASLWNWF-amide (SEQ ID NO:21)) in an amount of 90 mg twice daily; x) Combivir in an amount of 150 mg lamivudine (3TC; 2',3'-dideoxy-3'-thiacytidine) and 300 mg zidovudine (AZT; azidothymidine) twice daily; xi) emtricitabine (Emtriva; 4-amino-5-fluoro-1-[(2R,5S)-2-(hydroxymethyl)-1,3-oxathiolan-5-yl]-1,2-dihydropyrimidin-2-one) in an amount of 200 mg once daily; xii) Epzicom in an amount of 600 mg abacavir (ABV; {(1S,4R)-4-[2-amino-6-(cyclopropylamino)-9H-purin-9-yl]cyclopent-2-en-1-yl}methanol) and 300 mg 3TC once daily; xiii) zidovudine (Retrovir; AZT or azidothymidine) in an amount of 200 mg three times daily; xiv) Trizivir in an amount of 150 mg 3TC and 300 mg ABV and 300 mg AZT twice daily; xv) Truvada in an amount of 200 mg emtricitabine and 300 mg tenofovir (({[(2R)-1-(6-amino-9H-purin-9-yl)propan-2-yl]oxy}methyl)phosphonic acid) once daily; xvi) didanosine (Videx; 2',3'-dideoxyinosine) in an amount of 400 mg once daily; xvii) tenofovir (Viread) in an amount of 300 mg once daily; xviii) abacavir (Ziagen) in an amount of 300 mg twice daily; xix) atazanavir (Reyataz; methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate) in an amount of 300 mg once daily or 400 mg once daily; xx) lamivudine (Epivir) in an amount of 150 mg twice daily; xxi) stavudine (Zerit; 2'-3'-didehydro-2'-3'-dideoxythymidine) in an amount of 40 mg twice daily; xxii) delavirdine (Rescriptor; N-[2-({4-[3-(propan-2-ylamino)pyridin-2-yl]piperazin-1-yl}carbonyl)-1H-indol-5-yl]methanesulfonamide) in an amount of 400 mg three times daily; xxiii) efavirenz (Sustiva; (4S)-6-chloro-4-(2-cyclopropylethynyl)-4-(trifluoromethyl)-2,4-dihydro-1H-3,1-benzoxazin-2-one) in an amount of 600 mg once daily); xxiv) nevirapine (Viramune; 11-cyclopropyl-4-methyl-5,11-dihydro-6H-dipyrido[3,2-b:2',3'-e][1,4]diazepin-6-one) in an amount of 200 mg twice daily); xxv) bevirimat; and xxvi) Vivecon.

In some embodiments, a subject treatment method involves administering: a) a SMYD2 inhibitor (and/or an ASH1L inhibitor, and/or an SUV420H1 inhibitor, and/or an SUV39H1 inhibitor); and b) a PKC activator. An example of a suitable PKC activator is prostratin ((1aR,1bS,4aR,7aS,7bR,8R,9aS)-4,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-yl). The PKC activator can be administered in a separate formulation from a SMYD2 inhibitor. A PKC activator can be co-formulated with a SMYD2 inhibitor, and the co-formulation administered to an individual. The present disclosure provides a kit comprising a PKC activator in a first container; and a SMYD2 inhibitor in a second container.

Subjects Suitable for Treatment

The methods of the present disclosure are suitable for treating individuals who have an immunodeficiency virus infection, e.g., who have been diagnosed as having an immunodeficiency virus infection.

The methods of the present disclosure are suitable for treating individuals who have an HIV infection (e.g., who have been diagnosed as having an HIV infection), and individuals who are at risk of contracting an HIV infection. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals. Individuals suitable for treatment include individuals infected with, or at risk of becoming infected with, HIV-1 and/or HIV-2 and/or HIV-3, or any variant thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: SMYD2 Inhibitors Activate Latent HIV

Materials and Methods

HEK293T and Jurkat cells were obtained from the American Type Culture Collection. J-Lat (clones A2 and A72) cell lines were cultured as described in Jordan et al., EMBO J. 2003 Apr. 15:22(8):1868-77. HEK293T cells were cultured in DMEM supplemented with 10% fetal bovine serum (FBS), 1% L-glutamine and 1% penicillin-streptomycin (Life Technologies). Tumor necrosis factor-alpha (TNFα) (Sigma-Aldrich) was used at concentrations of 0.5 or 1 ng/ml. Human αCD3/αCD28 beads (Life Technologies) were used at a concentration of 1 bead/cell ratio.

ShRNA-Mediated Knockdown Experiments and Flow Cytometry Analysis

ShRNA-expressing lentiviral vectors were purchased from Open Biosystems. The plasmids TRCN0000276155, TRCN0000276082, TRCN0000276083, TRCN0000276085, TRCN0000130774, TRCN0000130403, and TRCN0000128349 were used to deplete SMYD2. The pLKO.1 vector containing scramble shRNA was used as control. Pseudotyped viral stocks were produced in $2 \times 10^6$ HEK293T cells by the calcium phosphate method by co-transfection of 10 μg of shRNA-expressing lentiviral vectors, together with 6.5 μg of the lentiviral packaging construct pCMVdelta R8.91 and 3.5 μg of VSV-G glycoprotein-expressing vector, and titered for p24 content. J-Lat A72 cells (containing a long terminal repeat (LTR)-green fluorescent protein (GFP) (LTR-GFP) construct) were spin-infected with virus (1 ng of p24 per $10^6$ cells) containing shRNAs against SMYD2 or nontargeting control shRNAs; infected cells were selected with puromycin (2 μg/ml; Sigma). After 4 days of selection, cells were treated with the indicated concentration of drugs. The percentage of GFP+ cells was determined after 18 h using a MACSQuant VYB fluorescence activated cell sorting (FACS) analyzer (Miltenyi Biotech GmbH). Cell viability was monitored by forward and side scatter analysis. Analysis was conducted on 3×20,000 live cells per condition, and all experiments were independently repeated at least three times. Data were analyzed using FlowJo 9.4 (Tree Star). Nucleotide sequences of SMYD2 shRNAs, scramble control shRNA, and luciferase control shRNA are provided in FIG. 13.

In Vitro Methylation Assays

For protein reactions, 2 μg of histones (isolated from HEK293T cells), and synthetic Tat protein were incubated overnight at 30° C. with recombinant SMYD2 (Sigma) in a buffer containing 50 mM TrisHCl pH 9, 0.01% Tween 20, 2 mM dithiothreitol (DTT) and 1.1 μCi of $^3$H-labeled SAM (Perkin Elmer). Peptide reactions contained 2 μg of each peptide and recombinant SMYD2. Reaction mixtures were fractionated on 15% sodium dodecyl sulfate-polyacrylamide gel electrophoresis (SDS-PAGE) for proteins or on 10-20% Tris-Tricine gradient gels for peptides (BioRad). After coomassie staining, gels were treated with Amplify (GE Healthcare) for 30 min, dried and exposed to hyperfilm (GE Healthcare) overnight.

Use of Polyclonal Anti-meARM Antibodies

The anti-meARM (α-meARM) antibodies were generated in rabbits immunized with chemically synthesized K51-monomethylated ARM. For western blotting of synthetic Tat proteins, biotinylated synthetic Tat was incubated in the presence or absence of SMYD2 enzyme and nonradioactive SAM.

Primary T-Cell Model of HIV Latency ("Greene Model")

Peripheral blood mononuclear cells (PBMC) were isolated by Ficoll-Hypaque density gradient centrifugation of buffy coats from HIV-seronegative donors (Blood Centers of the Pacific). PBMCs were immediately processed to isolate CD4$^+$ T cells. Total CD4$^+$ T cells were isolated by negative selection, according to manufacturer's protocol, with the EasySep CD4$^+$ T-cell Enrichment Kit (Stem Cell Technologies). Isolated CD4$^+$ T cells were cultured in RPMI as described above at a concentration of 1×10$^6$ cells/ml for 24 h before HIV infection.

CD4$^+$ T cells were counted, collected as pellets by centrifugation at 1500 rpm for 5 min at room temperature, and resuspended in the appropriate volume of concentrated viral NL4-3-Luc supernatant. Typically, 50-200 ng of p24Gag per 4×10$^5$ CD4$^+$ T cells were used. Spinoculations with NL4-3-Luc virus were performed in 96-well V-bottom plates with up to 5×10$^5$ CD4$^+$ T cells per well. All spinoculations were performed in volumes of 200 μl or less. Cells and virus were centrifuged at 2000 rpm for 1.5-2 h at room temperature. After spinoculation, cells were pooled and cultured at a concentration of 1×10$^6$ cells/ml in RPMI 1640 containing 10% FBS and supplemented with 5 μM saquinavir for 3 days to prevent residual spreading infection. Saquinavir was purchased from Sigma.

For reactivation of latent HIV-1 provirus, cells were counted and collected as pellets by centrifugation at 1500 rpm for 10 min. Cells were then plated in 96-well U-bottom plates at concentrations of 1×106/200 μl in the presence of the indicated activator. Unless otherwise indicated, cells were cultured either in medium alone or stimulated with, 5 μg/ml phytohemagglutinin (PHA) (Sigma), 10 ng/ml TNF-α, or anti-CD3+anti-CD28 beads at a ratio of 1:1. Cells were harvested 48 hr after stimulation, washed one time with phosphate buffered saline (PBS), and lysed in 60 μl of Cell Lysis Buffer (Promega) After 15 min of lysis, the luciferase activity in cell extracts was quantified with a BD Monolight Luminometer after mixing 20 μl of lysate with 100 μl of substrate (Luciferase Assay System-Promega). Relative light units were normalized to protein content determined by BCA assay (Pierce). Cell survival rates were measured by flow cytometry immediately before lysis.

Results

Knockdown of SMYD2 Reactivates HIV-LTR

Figure 1:
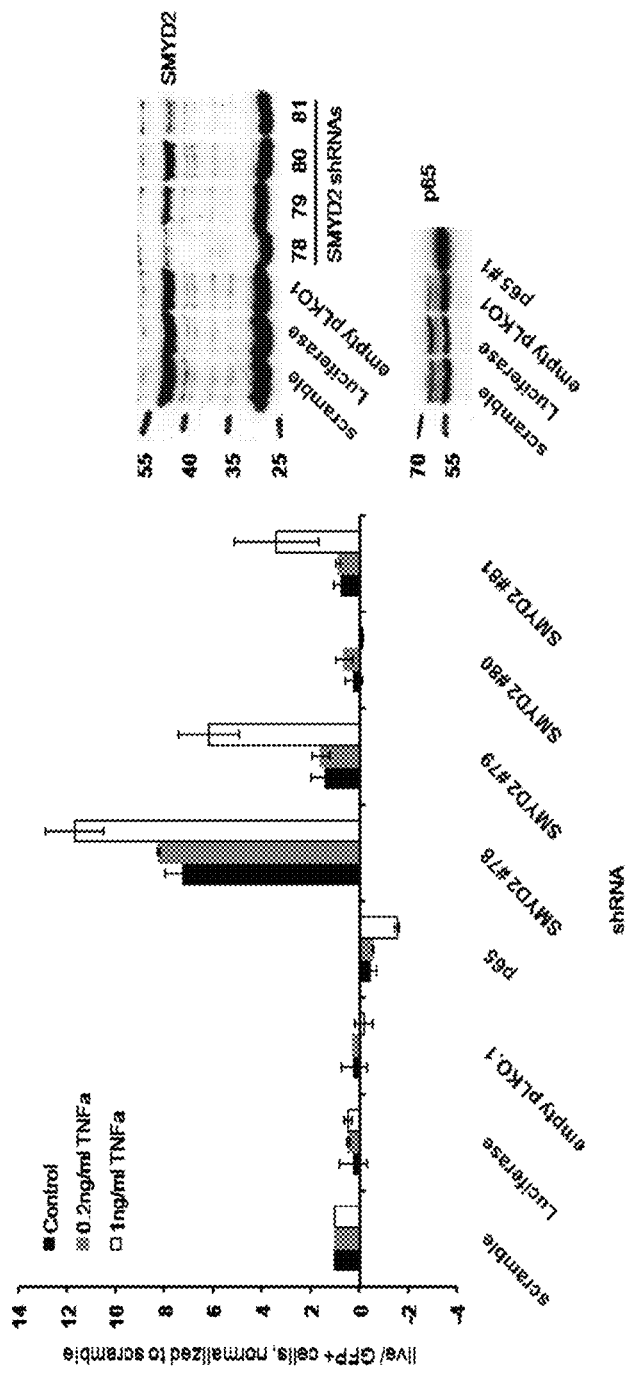
FIG. 1 depicts the effect of shRNA-mediated knockdown of SMYD2 on HIV transcription in A2 J-Lat cells. Confirmation of SMYD2 knockdown is shown in the western blot (right).
Figure 2:
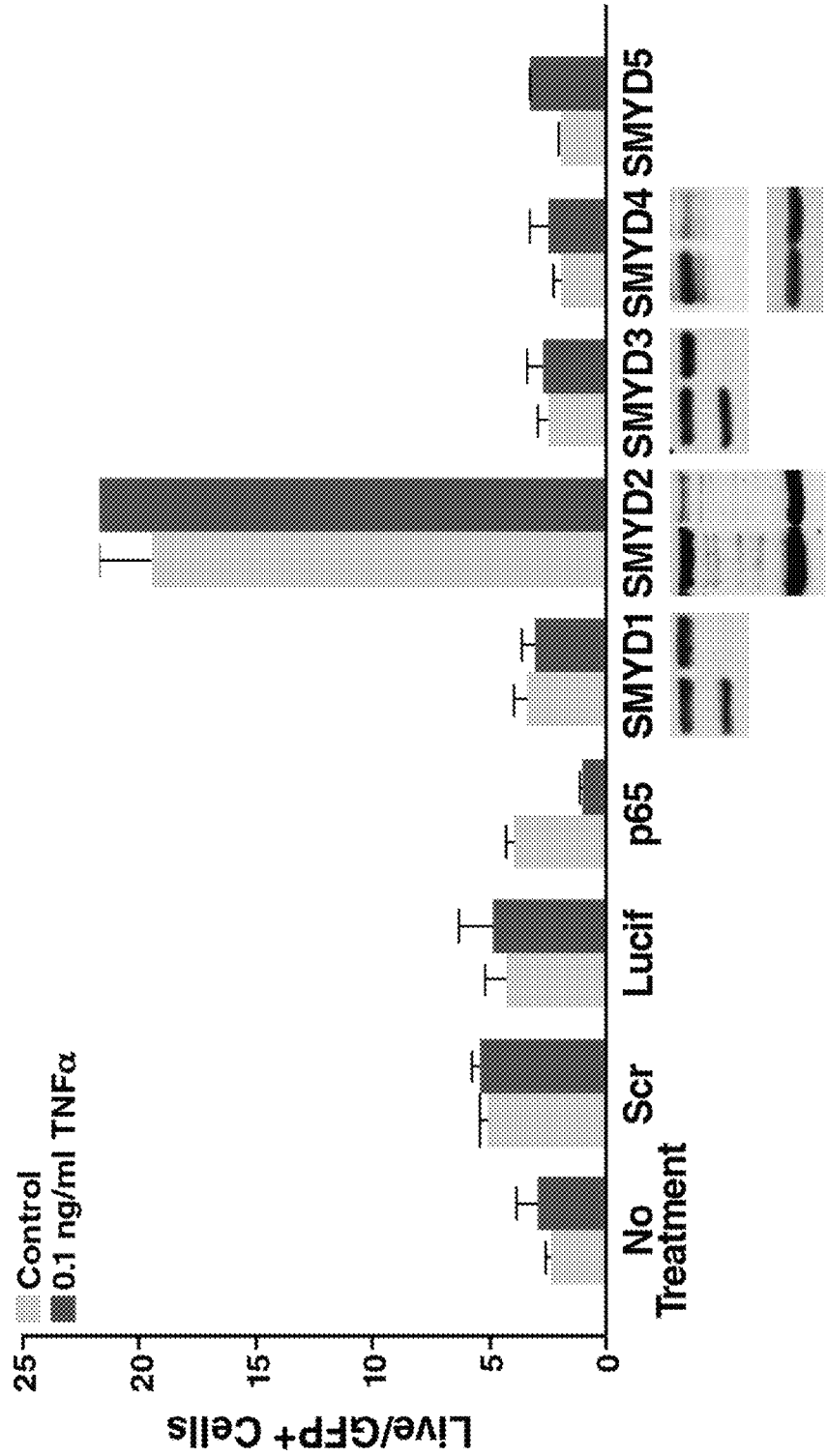
FIG. 2 depicts data showing that SMYD2, but not SMYD1, SMYD3, SMYD4, or SMYD5, is a repressor of latent HIV.

To test the functional relevance of SMYD2 in HIV latency, lentiviral shRNA knockdown studies of endogenous SMYD2 proteins were performed in a J-Lat cell line harboring a latent lentiviral construct expressing Tat with GFP from the HIV LTR (clone A2; LTR-Tat-IRES-GFP). As shown in FIG. 1, knockdown of SMYD2 resulted in a robust activation of the HIV LTR, and this effect was enhanced in response to JQ1 and TNFα. However, this effect was not specific for Tat: the same effect was observed in A72 cells, containing a latent LTR-GFP construct lacking Tat. Here, an up to 20-fold increase in GFP$^+$ cells resulted from SMYD2 knockdown alone. As shown in FIG. 2, this effect was specific to SMYD2 as knockdown of related proteins SMYD1, 3, 4, and 5 did not reactivate HIV from latency. These results identify SMYD2 as a new factor involved in mediating HIV latency in T cell lines.

SMYD2 Methylates Tat at K51

Figures 3A, 3B:
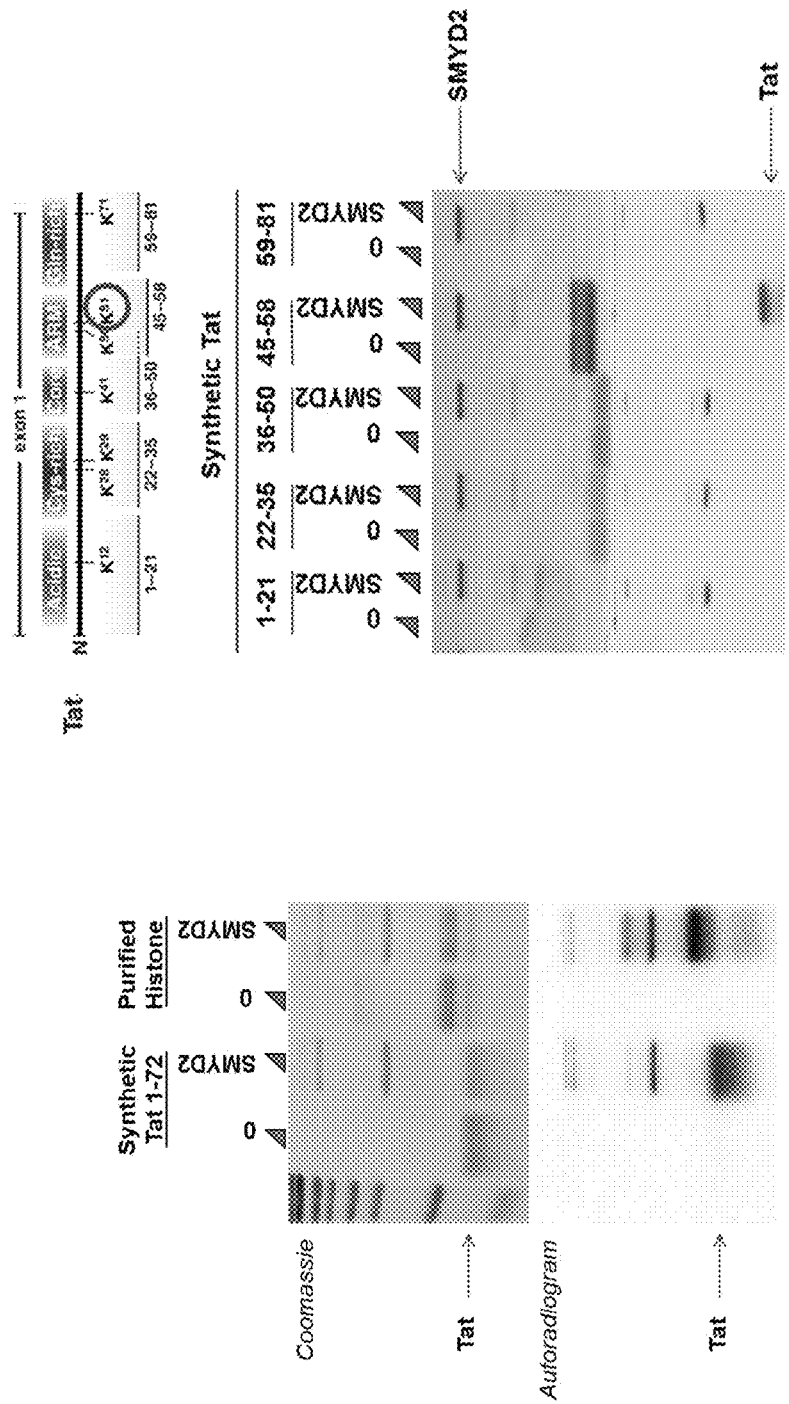
FIGS. 3A and 3B depict methylation of HIV Tat by SMYD2 in vitro.

As SMYD2 is known as a protein methyltransferase (p53, Rb), it was tested whether Tat is methylated by SMYD2. Full-length synthetic Tat protein (aa 1-72) was incubated with recombinant SMYD2 enzyme and radiolabeled S-adenosyl-L-methionine (SAM). Reactions were resolved by gel electrophoresis and developed by autoradiography. As shown in FIG. 3A, Tat was methylated in response to SMYD2. As expected, SMYD2 also methylated histone H3 and p53, known substrates of SMYD2, but not other putative substrates such as p65 and Sp1.

Figure 4:
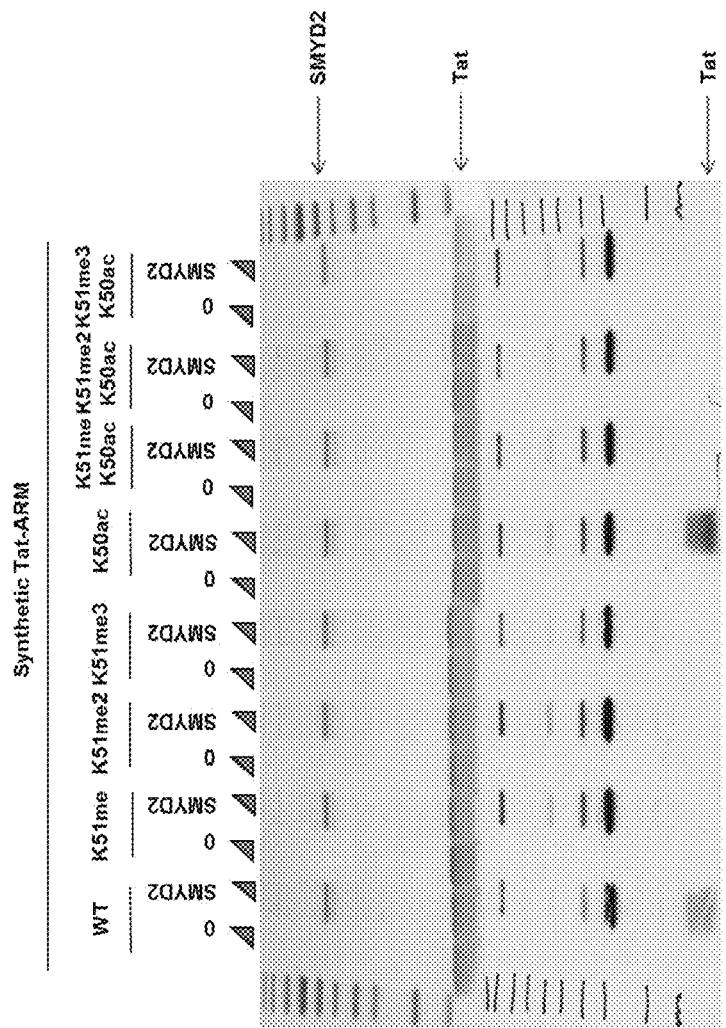
FIG. 4 depicts SMYD2-mediated methylation of Tat at K51 in vitro.

To map the site of methylation in Tat, short synthetic Tat peptides were subjected to in vitro methylation assays. As shown in FIG. 3B, methylation by SMYD2 was observed with one peptide (aa 45-58), corresponding to the Tat ARM. The Tat ARM contains two lysines, K50 and K51. Both residues are strictly conserved among HIV-1 isolates. To determine which lysine is methylated by SMYD2, in vitro methylation assays were performed with ARM peptides containing alanine substitutions at position K50, K51, or both. As shown in FIG. 4, methylation by SMYD2 was abrogated when K51 or both lysines were mutated, indicating that K51 is the target of SMYD2 in the Tat ARM. Acetylation of K50 slightly enhanced Tat methylation by SMYD2. Analysis of SMYD2-methylated Tat protein with K51me-specific antibodies showed reactivity with the K51me3-, but not K51me1-, specific antibody, indicating that SMYD2 might trimethylate Tat at K51. The Tat K51me3-specific antibody requires further purification as it also cross-reacts with unmodified Tat.

Example 2: Small-Molecule SMYD2 Inhibitors Activate Latent HIV

Materials and Methods

J-Lat (clones A2 and A72) cell lines were cultured as described in Jordan et al., *EMBO J.* 2003 Apr. 15:22(8):1868-77. Human αCD3/αCD28 beads (Life Technologies) were used at a concentration of 1 bead/cell ratio. JQ1 (Sigma-Aldrich) was used at a concentration of 0.1-10 μM. Ingenol 3,20-dibenzoate (Sigma-Aldrich) was used at concentrations of 5-200 nM, and SAHA (Sigma-Aldrich) was used at concentrations of 110 nM, 330 nM, or 1 μM.

Primary T-Cell Model of HIV Latency ("Greene Model")

Peripheral blood mononuclear cells (PBMC) were isolated by Ficoll-Hypaque density gradient centrifugation of buffy coats from HIV-seronegative donors (Blood Centers of the Pacific). PBMCs were immediately processed to isolate CD4$^+$ T cells. Total CD4$^+$ T cells were isolated by negative selection, according to manufacturer's protocol, with the EasySep CD4$^+$ T-cell Enrichment Kit (Stem Cell Technologies). Isolated CD4$^+$ T cells were cultured in RPMI as described above at a concentration of 1×10$^6$ cells/ml for 24 h before HIV infection.

CD4$^+$ T cells were counted, collected as pellets by centrifugation at 1500 rpm for 5 min at room temperature, and resuspended in the appropriate volume of concentrated viral NL4-3-Luc supernatant. Typically, 50-200 ng of p24Gag per 4×10$^5$ CD4$^+$ T cells were used. Spinoculations with NL4-3-Luc virus were performed in 96-well V-bottom plates with up to 5×10$^5$ HLAC or CD4 T cells per well. All spinoculations were performed in volumes of 200 µl or less. Cells and virus were centrifuged at 2000 rpm for 1.5-2 h at room temperature. After spinoculation, cells were pooled and cultured at a concentration of 1×10$^6$ cells/ml in RPMI 1640 containing 10% FBS and supplemented with 5 µM saquinavir for 3 days to prevent residual spreading infection. Saquinavir was purchased from Sigma.

For reactivation of latent HIV-1 provirus, cells were counted and collected as pellets by centrifugation at 1500 rpm for 10 min. Cells were then plated in 96-well U-bottom plates at concentrations of 1×10$^6$/200 µl in the presence of the indicated activator. Unless otherwise indicated, cells were cultured either in medium alone or stimulated with 5 µg/ml phytohemagglutinin (PHA) (Sigma), 10 ng/ml TNF-α, anti-CD3+anti-CD28 beads at a ratio of 1:1. SAHA, JQ1 and X2 were tested at the indicated concentrations. Cells were harvested 48 hr after stimulation, washed one time with PBS, and lysed in 60 µl of Cell Lysis Buffer (Promega). After 15 min of lysis, the luciferase activity in cell extracts was quantified with a BD Monolight Luminometer after mixing 20 µl of lysate with 100 µl of substrate (Luciferase Assay System-Promega). Relative light units were normalized to protein content determined by BCA assay (Pierce). Cell survival rates were measured by flow cytometry immediately before lysis.

Results

Small-Molecule SMYD2 Inhibitors Reactivate HIV in J-Lat Cell Lines

Figure 5A:
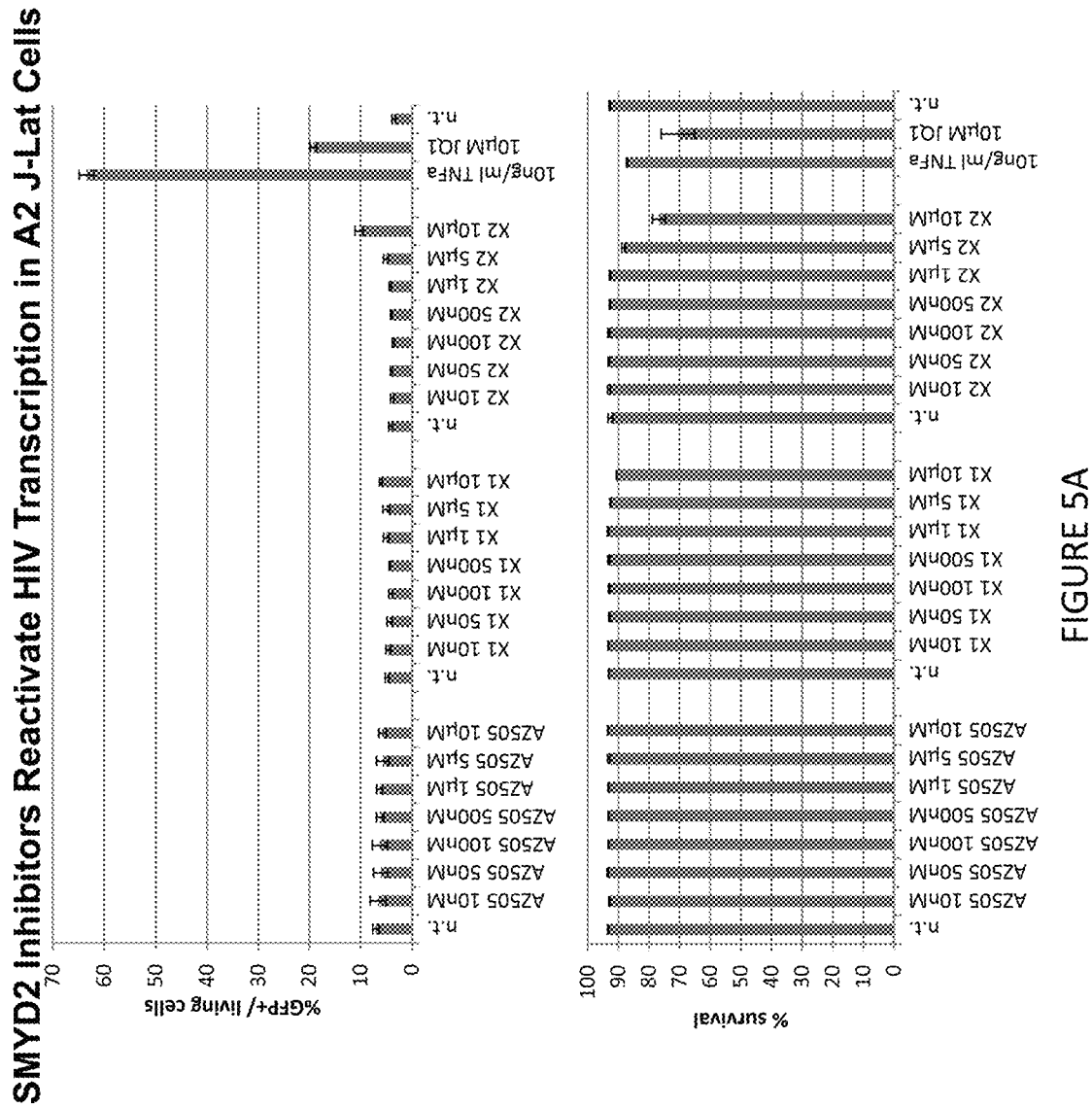
FIG. 5A provides a graph depicting the effect of AZ505, and two additional small-molecule SMYD2 inhibitors, referred to herein as "X1" and "X2", on HIV transcription in A2 J-Lat cells.
Figure 5B:
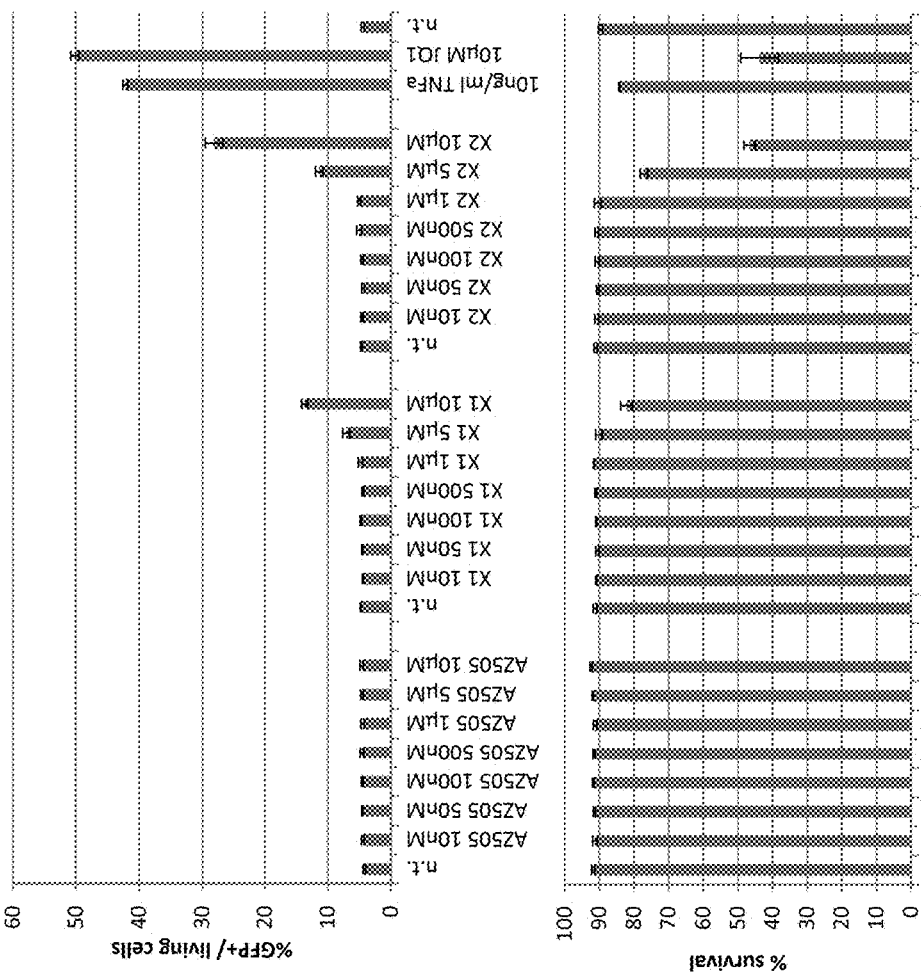
FIG. 5B provides a graph depicting the effect of AZ505, X1, and X2, on HIV transcription in A72 J-Lat cells.

As SMYD2 knockdown shows reactivation potential at the HIV LTR, it was speculated that treatment with SMYD2 inhibitors might activate Tat transcriptional activity and reactivate HIV from latency. To test this hypothesis, J-Lat cells (clone A2: LTR-Tat-IRES-GFP) were treated with SMYD2 inhibitors. As shown in FIGS. 5A and 5B, treatment with X2, a cell-permeable SMYD2 inhibitor, activated HIV transcription in a dose-dependent manner as measured by flow cytometry of GFP. Without intending to be bound by any specific theory, it is believed that the failure of AZ505 to effectively activate HIV transcription was due to its lack of cell permeability. Stimulation with X2 yielded up to threefold more GFP-expressing cells than control-treated cells. A slight increase in cell death was observed in the concentration that effectively activated HIV transcription. Again, this effect was not specific for Tat: the same effect was observed in A72 cells, containing a latent LTR-GFP construct lacking Tat. Both cell lines were co-treated with X2 and Ingenol 3,20-dibenzoate (a protein kinase C (PKC) activator), JQ1 (BET-bromodomain inhibitor), or the histone deacetylase (HDAC) inhibitor suberoylanilidehydroxamic acid (SAHA). The results are shown in FIGS. 6A-8. Adding JQ1 (FIG. 7) or SAHA (FIG. 8), but not Ingenol (FIG. 6A), to X2 enhanced the reactivation of HIV-LTR. Collectively, these results indicate the effectiveness of the SMYD2 inhibitor to reverse HIV latency in combination with other latency reversing agents.

Figure 9:
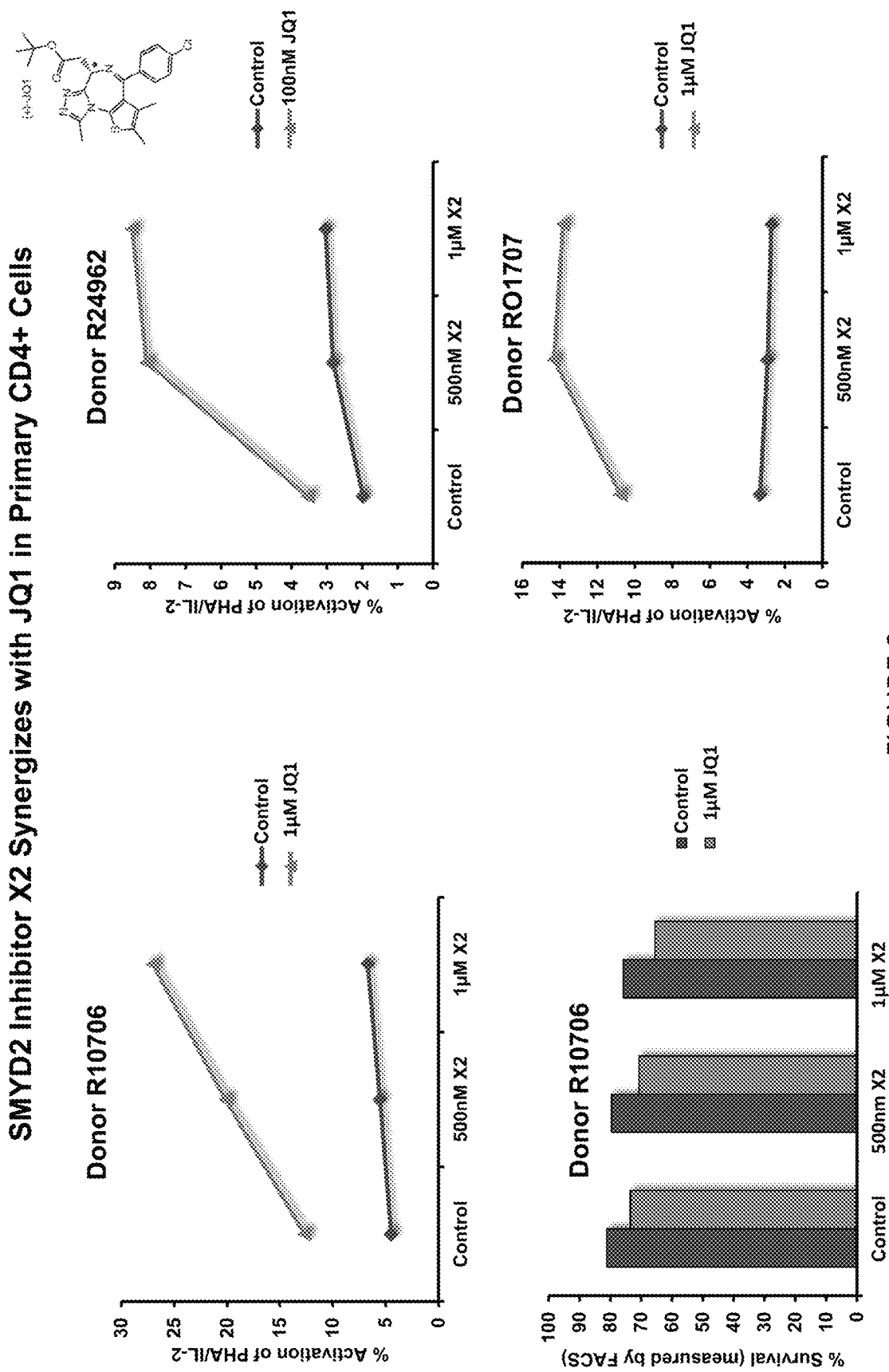
FIG. 9 depicts synergy between X2 and JQ1 in primary CD4⁺ T cells with respect to reactivation of latent HIV-1.
Figure 10:
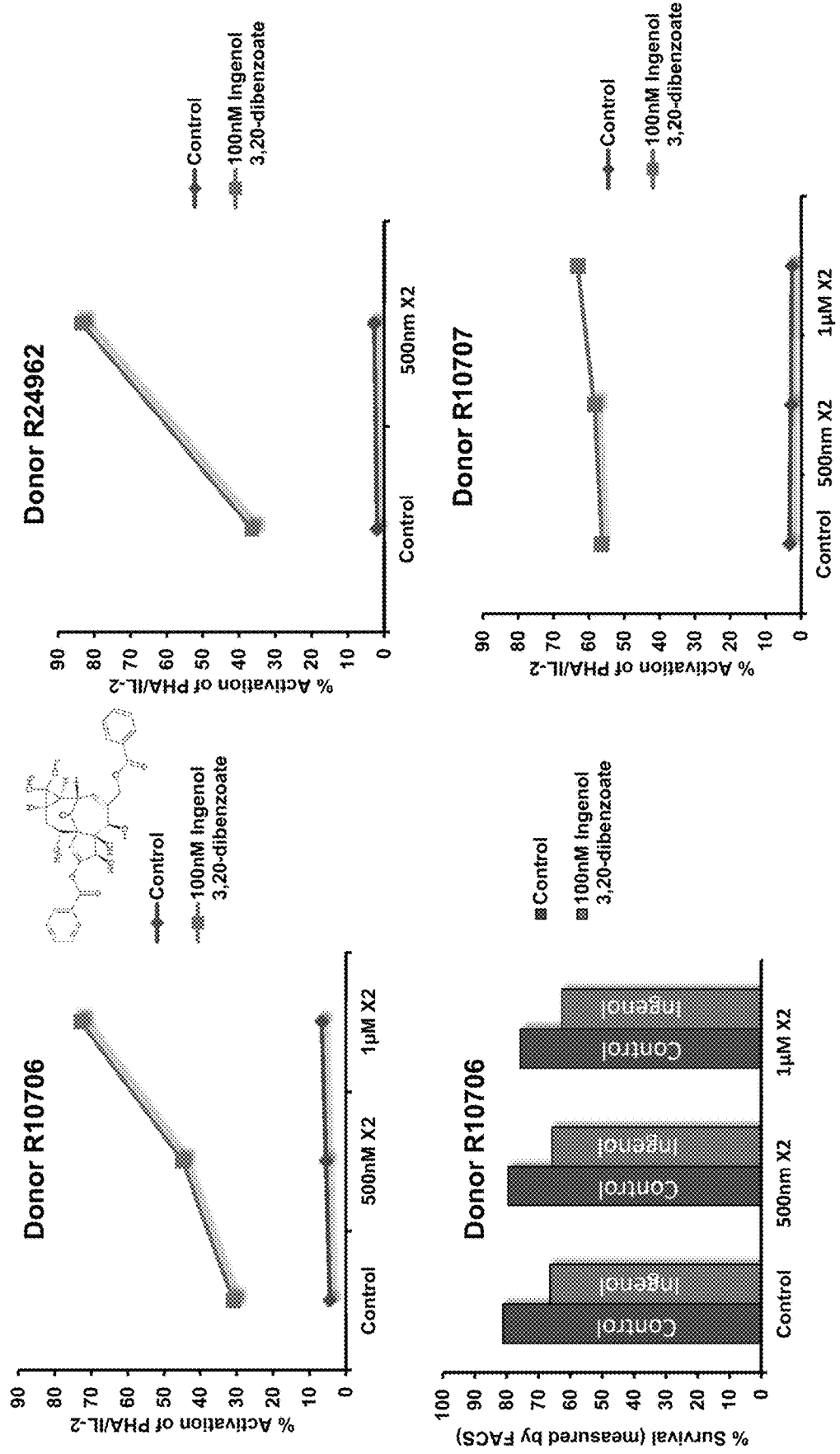
FIG. 10 depicts synergy between X2 and ingenol 3,20-dibenzoate in primary CD4⁺ T cells with respect to reactivation of latent HIV-1.
Figure 11:
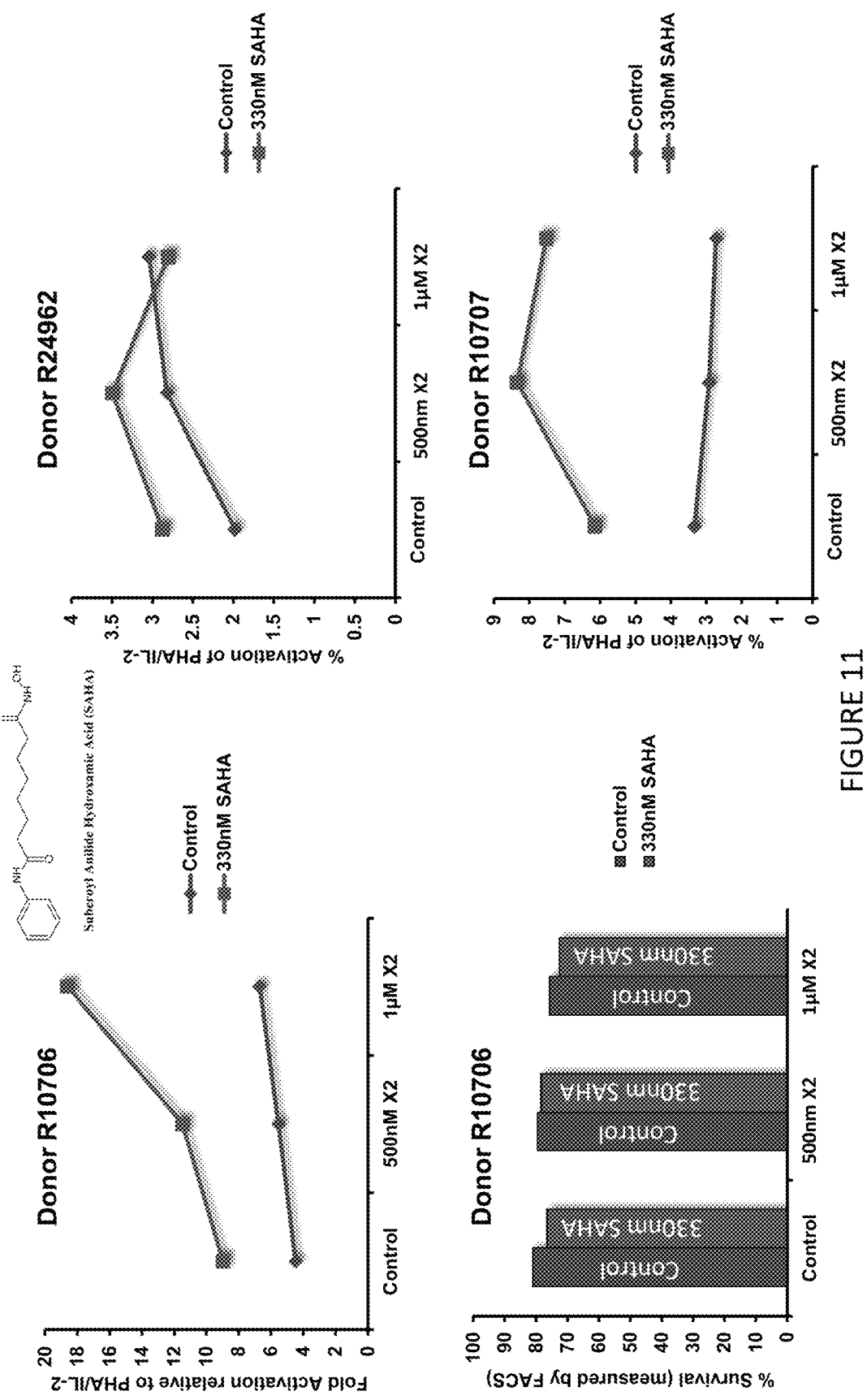
FIG. 11 depicts minimal synergy between X2 and the HDAC inhibitor SAHA in primary CD4⁺ T cells with respect to reactivation of latent HIV-1.

SMYD2 Inhibitor X2 Co-Treatment Reactivates HIV in a Primary CD4$^+$ T Cell Model Since X2 activated HIV from latency in A2 and A72 cell lines, this compound was tested in a primary T-cell model of latency (Lassen, Greene). In this model, CD4+ T cells were infected in a single-round infection with HIV clone NL4-3-Luc to generate a latent infection in vitro. To reactivate latent HIV-1, cells were treated with the indicated compounds or a combination of PHA/IL-2 as a control for maximal activation. X2 in combination with JQ1 reactivated latent HIV-1 at 8-25% of the rate achieved by costimulation with PHA/IL-2 (FIG. 9). X2 in combination with Ingenol 3,20-dibenzoate reactivated latent HIV-1 at 30-85% of the rate achieved by costimulation with PHA/IL-2 (FIG. 10). A modest activation was also observed in cells activated with X2 and SAHA (FIG. 11).

Example 3: Regulation of HIV-1 Latency Via SMYD2-Mediated Histone Methylation

Materials and Methods

HEK293T cells were obtained from the American Type Culture Collection. J-Lat (clones A2, A72, and 5A8) cell lines were described (Chan et al., 2013; Jordan et al., 2003). HEK293T cells were cultured in DMEM supplemented with 10% FBS, 1% L-glutamine and 1% penicillin-streptomycin (Life Technologies). J-Lat cells were cultured in RPMI supplemented with 10% FBS, 1% L-glutamine and 1% penicillin-streptomycin (Life Technologies). SMYD2 and RELA antibodies were purchased from Bethyl, Histone 4, H4K20me1, H4K20me2, and H4K20me3 antibodies were purchased from Active Motif, and rabbit IgG isotype control (10500C) was purchased from Thermo Fisher Scientific. TNFα (Sigma-Aldrich) was used at 0.5-10 ng/ml. Human αCD3/αCD28 Dynabeads (Invitrogen) were used at a 1 bead/cell ratio. JQ1 (Cayman Chemical) was used at 0.1-10 µM. Ingenol 3,20-dibenzoate (Santa Cruz Biotechnology) was used at 5-200 nM, and SAHA (Merck) was used at 110 nM, 330 nM, or 1 µM. Phorbol 12-myristate 13-acetate (PMA) (Sigma) was used at 10 nM and ionomycin (Sigma) was used at a concentration of 500 nM. UNC926 (Tocris Bioscience) was used at a concentration of 10 nM-100 µM. AZ505, AZ506, and AZ391 were used at a concentration of 10 nM-10 µM.

ShRNA-Mediated Knockdown Experiments and Flow Cytometry Analysis

ShRNA-expressing lentiviral vectors were purchased from Sigma-Aldrich. The plasmids used in the shRNA screen are listed in Table 1 below. The pLKO.1 vector containing a scrambled shRNA was used as control. Pseudo-typed viral stocks were produced in 2×10$^6$ HEK293T cells by the calcium phosphate method by co-transfecting 10 µg of shRNA-expressing lentiviral vectors, with 6.5 µg of the lentiviral packaging construct pCMVdelta R8.91 and 3.5 µg of VSV-G glycoprotein-expressing vector (Naldini et al., 1996), and titered for p24 content. J-Lat 5A8, A72 and A2 cells were spininfected with virus (1 ng of p24 per 10$^6$ cells) containing shRNAs against KMTs or nontargeting control shRNAs and were selected with puromycin (2 µg/ml; Sigma). After 7 days of selection, cells were treated with the indicated concentration of drugs. The percentage of GFP$^+$ cells was determined after 18 h using a MACSQuant VYB FACS analyzer (Miltenyi Biotech GmbH). Cell viability was monitored by forward-and-side scatter analysis. Analysis was conducted on 3×10,000 live cells per condition. Data were analyzed using FlowJo 9.5 (Tree Star).

TABLE 1

The RNAi Consortium (TRC) database numbers and target sequences of shRNAs used:

| Gene | TRC Number | Target Sequence | SEQ ID NOs |
|---|---|---|---|
| ASH1L | TRCN0000246167 | GAGTCGATTGATCCAATTAAA | 78 |
| ASH1L | TRCN0000246168 | CGTCTACGAAAGGCCTATTAC | 79 |
| DOT1L | TRCN0000236345 | TCGCCAACACGAGTGTTATAT | 80 |
| DOT1L | TRCN0000236343 | CACGTTGAACAAGTGCATTTA | 81 |
| DOT1L | TRCN0000236342 | CACATTGGAGAGAGGCGATTT | 82 |
| DOT1L | TRCN0000236344 | GCCCGCAAGAAGAAGCTAAAC | 83 |
| EHMT1 | TRCN0000036054 | CGAGTCAATAACGCCAGCTAT | 84 |
| EHMT1 | TRCN0000036057 | CCTCGGTTCTGAGTCGTATAA | 85 |
| EHMT2 | TRCN0000115667 | CACACATTCCTGACCAGAGAT | 86 |
| EHMT2 | TRCN0000115668 | CCTCTTCGACTTAGACAACAA | 87 |
| EZH1 | TRCN0000355734 | AGACGTGCAAGCAGGTCTTTC | 88 |
| EZH1 | TRCN0000355735 | CTATCTGGCAGTGCGAGAATG | 89 |
| EZH2 | TRCN0000040074 | GCTAGGTTAATTGGGACCAAA | 90 |
| EZH2 | TRCN0000040075 | CCAACACAAGTCATCCCATTA | 91 |
| MLL | TRCN0000005954 | GCACTGTTAAACATTCCACTT | 92 |
| MLL | TRCN0000005956 | CGCCTAAAGCAGCTCTCATTT | 93 |
| MLL2 | TRCN0000235742 | CATCTACATGTTCCGAATAAA | 94 |
| MLL2 | TRCN0000235743 | CGTAGAAGAGGACCTACTAAT | 95 |
| MLL2 | TRCN0000013138 | CCCACCTGAATCATCACCTTT | 96 |
| MLL2 | TRCN0000013140 | CCTCGCCTCAAGAAATGGAAA | 97 |
| MLL3 | TRCN0000008742 | GAGGCGATTCAACACACCATT | 98 |
| MLL3 | TRCN0000008743 | CCCTGTTAGAATGCCCAGTTT | 99 |
| MLL4 | TRCN0000005958 | ACCCTCATGTTCAGGGTGGAT | 100 |
| MLL4 | TRCN0000005959 | CCAGCACTATAAGTTCCGTTA | 101 |
| MLL5 | TRCN0000150550 | GCTGATTTGATGCTGTATGAT | 102 |
| MLL5 | TRCN0000154711 | GCTGTTCCCTTCCAGATTTAA | 103 |
| NSD1 | TRCN0000238373 | GTGCTAATTTCACGGTATAAA | 104 |
| NSD1 | TRCN0000238372 | CCGAGACGTCTCAGGTTAATC | 105 |
| NSD2 | TRCN0000019816 | CCTCTCTTTGAATCTTCCATT | 106 |
| NSD2 | TRCN0000019817 | CGGAAAGCCAAGTTCACCTTT | 107 |
| SETD1B | TRCN0000237962 | GGAGATTACCTATGACTATAA | 108 |
| SETD1B | TRCN0000237964 | ACATGCGGGAGAAGCGTTATG | 109 |
| SETD2 | TRCN0000003030 | CCTGAAGAATGATGAGATAAT | 110 |
| SETD2 | TRCN0000003032 | GCCCTATGACTCTCTTGGTTA | 111 |
| SETD5 | TRCN0000253861 | AGCGTGTATTCCACTCATAAT | 112 |
| SETD5 | TRCN0000253863 | AGACTTGTTGAGCCCATTAAA | 113 |
| SETD6 | TRCN0000419700 | GACCTATGCCACAGACTTAAA | 114 |
| SETD6 | TRCN0000417114 | GTGGACATACGGTAGTAATAA | 115 |
| SETD7/9 | TRCN0000078628 | GCCAGGGTATTATTATAGAAT | 116 |
| SETD7/9 | TRCN0000078631 | CTTATGAATCAGAAAGGGTTT | 117 |
| SETD8 | TRCN0000148268 | GTTTCCTGAAACTGGGTTAAT | 118 |
| SETD8 | TRCN0000130036 | GAATCGCAAACTTACGGATTT | 119 |
| SETDB1 | TRCN0000147130 | CAGTGACTAATTGTGAGTCTT | 120 |
| SETDB1 | TRCN0000179094 | CGTGACTTCATAGAGGAGTAT | 121 |
| SETDB2 | TRCN0000159172 | GCTGAAATTAAAGCCATGCAA | 122 |
| SETDB2 | TRCN0000160242 | CCTGTTTGTGAAATTAGCTTA | 123 |
| SETMAR | TRCN0000146300 | CAAGTGTTCAAGACGCATAAA | 124 |
| SETMAR | TRCN0000179441 | GAAAGGCTAGATCATGGGAAA | 125 |
| SMYD1 | TRCN0000130695 | CGCACATCTTCGGAGTGATTA | 126 |
| SMYD1 | TRCN0000130477 | GCAATCATGAGGCAGTGAAAT | 127 |
| SMYD2 | TRCN0000276083 | GCTGTGAAGGAGTTTGAATCA | 128 |
| SMYD2 | TRCN0000130403 | GCTGTGAAGGAGTTTGAATCA | 129 |
| SMYD2 | TRCN0000130774 | GCTCTGTGTTTGAGGACAGTA | 130 |
| SMYD3 | TRCN0000123292 | AGCCTGATTGAAGATTTGATT | 131 |
| SMYD3 | TRCN0000123293 | CAGCCTGATTGAAGATTTGAT | 132 |
| SMYD4 | TRCN0000134109 | CCAGAAGATGAAATCCTGTTT | 133 |
| SMYD4 | TRCN0000134652 | GCTTATGCGTAGATCCTTTAA | 134 |
| SMYD5 | TRCN0000155095 | GCTATGGGAATTACAACCCAT | 76 |
| SMYD5 | TRCN0000156306 | CTGTGACACTCTGGAGTTGAA | 77 |
| SUV39H1 | TRCN0000158337 | CGTTGGGATTCATGGCCTATT | 135 |
| SUV39H1 | TRCN0000157251 | GCAGGTGTACAACGTCTTCAT | 136 |
| SUV39H2 | TRCN0000006938 | GCACAGATTGCTTCTTTCAAA | 137 |
| SUV39H2 | TRCN0000011057 | GCCCACCTTCAGACTTCTATT | 138 |
| SUV420H1 | TRCN0000359162 | CATCTAAGCTAACTCATATAA | 139 |
| SUV420H1 | TRCN0000359230 | TTGGTTCTTGATCCCTATTTA | 140 |
| SUV420H2 | TRCN0000437411 | TGACCCTTGACTCCAGCATAG | 141 |
| SUV420H2 | TRCN0000446372 | GTGTCCACTCGTGCTTGGAAA | 142 |
| SUV420H2 | TRCN0000145137 | GAATGACTTCAGCATCATGTA | 143 |
| SUV420H2 | TRCN0000143270 | GTGTGACCTCATCTTTCTCAT | 144 |
| L3MBTL1 | TRCN0000353634 | ATCGGATAAAGATCCACTTTG | 145 |

In Vitro Methylation Assays

In vitro Methylation assays were performed as described (Nishioka et al., 2002). For reactions, 2 μg of histones (isolated from HEK293T cells), recombinant histone 4 (New England Biolabs), synthetic histone 4 aa 1-21 and aa 15-24 peptides (Cayman Chemical), or synthetic histone H4 aa 1-21 with a K20A mutation (GenScript) were incubated with recombinant WT SMYD2 (Sigma-Aldrich) or SMYD2 Y240F (Active Motif) in a buffer containing 50 mM Tris-HCl, pH 9, 0.01% Tween 20, 2 mM DTT and 1.1 μCi of H3-labeled SAM (Perkin Elmer) overnight at 30° C. Reaction mixtures were fractionated on 15% SDS-PAGE for proteins or on 10-20% Tris-Tricine gradient gels for peptides (BioRad). After Coomassie staining, gels were treated with Amplify (GE Healthcare) for 30 min, dried and exposed to hyperfilm (GE Healthcare) overnight.

Experiments with Primary CD4+ Cells from Latently HIV-1-Infected Individuals

Four aviremic HIV-1-infected individuals were recruited from the SCOPE cohorts at the University of California, San Francisco. Table 2 details the characteristics of the study participants.

Peripheral blood mononuclear cells (PBMCs) from whole blood or continuous flow centrifugation leukapheresis product were purified using density centrifugation on a Ficoll-Hypaque gradient. Resting CD4+ lymphocytes were enriched by negative depletion with an EasySepHuman CD4+ T Cell Isolation Kit (Stemcell). Cells were cultured in RPMI medium supplemented with 10% fetal bovine serum, penicillin/streptomycin and 5 μM saquinavir. Five million resting CD4+ lymphocytes were stimulated with latency-reversing agents (LRAs) at the indicated concentrations (20-500 nM AZ391, 100 nM JQ1, 25 μl/1×10$^6$ T cells αCD3/αCD28 Dynabeads (Life Technologies) for 48 hours. After LRA treatment, cells were collected, lysed and total RNA was isolated with an RNeasy kit (Quiagen). A Superscript III One-Step RT-PCR system (Life Technologies) was used to generate and pre-amplify cell-associated viral mRNA. Reaction mixes contained 15 μl of a PCR mix containing reaction mix, Superscript III, primers (900 nM final concentration) and 10 μl purified RNA. Pre-amplification was carried out using the following steps: reverse transcription at 50° C. for 30 min, denaturation at 95° C. for 2 min, 10 cycles of amplification (94° C. 15 s, 55° C. 30 s, 68° C. 5 min) on a GeneAmp PCR system 9700 (Thermo Fisher). Subsequently, droplet digital PCR (ddPCR) was applied to quantify pre-amplified cDNA. Each 25 μl ddPCR mix comprised the ddPCR Probe Supermix (no dUTP), 900 nM primers, 250 nM probe, and 4 μl cDNA. The following cycling conditions were used: 10 minutes at 95° C., 40 cycles each consisting of 30 second denaturation at 94° C. followed by 59.4° C. extension for 60 seconds, and a final 10 minutes at 98° C. Reaction mixes were loaded into the Bio-Rad QX-100 emulsification device and droplets were formed following the manufacturer's instructions. Then, samples were transferred to a 96-well reaction plate and sealed with a pre-heated Eppendorf 96-well heat sealer for 2 seconds, as recommended by Bio-Rad. Finally, samples were amplified on a BioRad C1000 Thermocycler and analyzed using a BioRad QX100 ddPCR Reader.

Nucleotide coordinates are indicated relative to HXB2 consensus sequence. Primers and probe used for HIV-1 mRNA measurement were as described (Laird et al., 2015):

```
forward (5'→3')
                                    (SEQ ID NO: 32)
CAGATGCTGCATATAAGCAGCTG (9501-9523), reverse (5'→3')
                                    (SEQ ID NO: 33)
TTTTTTTTTTTTTTTTTTTTTTTGAAGCAC (9629-poly A),
probe (5'→3')
                                    (SEQ ID NO: 34)
FAM-CCTGTACTGGGTCTCTCTGG-MGB (9531-9550).
```

TABLE 2

Characteristics of HIV-1-infected study participants.

| Patient ID | Age | Gender | Ethnicity | CD4 T cell count | Year of first HIV+ test | ART Regimen | Peak self-reported VL (copies ml−1) |
|---|---|---|---|---|---|---|---|
| #2013 | 68 | Male | White | 715 | 1986 | ABC/TCV/3TC | 110000 |
| #2511 | 48 | Male | White | 334 | 2001 | EFV/TDF/FTC, RGV | 489873 |
| #2158 | 60 | Male | African American | 434 | 1999 | TMQ | 128447 |
| #1036 | 48 | Male | African American | 410 | 1990 | EGV/TDF/FTC/COBI | 132724 |

ABC, abacavir; TCV, tivicay; 3TC, lamivudine; EFV, Efavirenz; TDF, tenofovir; FTC, emtricitabine; RGV, raltegravir; TMQ, Triumeq; EGV, Elvitegravir; COBI, Cobicistat.

RNA Isolation, Reverse Transcription, and Quantitative RT-PCR

RNA was isolated using RNeasy Plus Mini Kit (Qiagen) and reverse-transcribed using SuperScript III Reverse Transcriptase (Invitrogen) as per the manufacturer's instructions. Quantitative RT-PCR was carried out using Maxima SYBR Green qPCR Master Mix (Thermo Scientific) on SDS 2.4 software (Applied Biosystems) in a total volume of 12 μL. Primer efficiencies were around 100%. Dissociation curve analysis was performed after the end of the PCR to confirm the presence of a single and specific product.

Chromatin Immunoprecipitation

J-Lat A2 and A72 cells were treated with TNFα (10 ng/ml) for 18 h. Cells were fixed with 1% formaldehyde (v/v) in fixation buffer (1 mM EDTA, 0.5 mM EGTA, 50 mM Hepes, pH 8.0, 100 mM NaCl), and fixation was stopped after 10 min by addition of glycine to 125 mM. The cell membrane was lysed for 15 min on ice (5 mM Pipes, pH 8.0, 85 mM KCl, 0.5% NP40, protease inhibitors). After washing with nuclear swell buffer (25 mM HEPES, pH 7.5, 4 mM KCl, 1 mM DTT, 0.5% NP-40, 0.5 mM PMSF) and micrococcal nuclease (MNase) digestion buffer (20 mM Tris pH 7.5, 2.5 mM CaCl2, 5 mM NaCl, 1 mM DTT, 0.5% NP-40), the pellet was resuspended in MNase buffer (15 mM Tris-HCl, pH 7.5, 5 mM MgCl2, 1 mM CaCl2, and 25 mM NaCl). Subsequently, samples were incubated with MNase (New England Biolabs) for 10 min at RT. The reaction was quenched with 0.5 M EDTA and incubated on ice for 5 min. Cells were lysed (1% SDS, 10 mM EDTA, 50 mM Tris-HCl, pH 8.1, protease inhibitors), and chromatin DNA was sheared to 200-1000-bp average size through sonication (Ultrasonic Processor CP-130, Cole Parmer). Cellular debris was pelleted, and the supernatant was recovered. Protein A/G Sepharose beads were blocked with single-stranded salmon sperm DNA and BSA, washed and resuspended in immunoprecipitation buffer. Blocked protein A/G Sepharose beads were added to the digested chromatin fractions and rotated at 4° C. for 2 h to preclear chromatin. Lysates were incubated overnight at 4° C. with 5 µg of SMYD2, RELA, histone H4, H4K20me1, H4K20me2, H4K20me3 antibodies, or IgG control. After incubation with protein A/G agarose beads for 2 h and washing three times with low salt buffer (0.1% SDS, 1% Triton X-100, 2 mM EDTA, 20 mM Tris-HCl, pH 8.1, 150 mM NaCl), one time with high salt buffer (0.1% SDS, 1% Triton X-100, 2 mM EDTA, 20 mM Tris-HCl, pH 8.1, 500 mM NaCl) and twice with TE-buffer (1 mM EDTA, 10 mM Tris-HCl, pH 8.1), chromatin was eluted and recovered with Agencourt AMPure XP beads (Beckman Coulter). Bound chromatin and input DNA were treated with RNase H (New England Biolabs) and Proteinase K (Sigma-Aldrich) at 37° C. for 30 min. Immunoprecipitated chromatin was quantified by real-time PCR using the Maxima SYBR Green qPCR Master Mix (Thermo Scientific) and the ABI 7700 Sequence Detection System (Applied Biosystems). The SDS 2.4 software (Applied Biosystems) was used for analysis. The specificity of each PCR reaction was confirmed by melting curve analysis using the Dissociation Curve software (Applied Biosystems). All chromatin immunoprecipitations and qPCRs were repeated at least three times, and representative results were shown.

Primer sequences were:

```
HIV LTR Nuc1 forward:
                              (SEQ ID NO: 35)
5' AGTGTGTGCCCGTCTGTTGT 3', HIV LTR Nuc1 reverse:
                              (SEQ ID NO: 36)
5' TTCGCTTTCAGGTCCCTGTT 3', AXIN2 forward
                              (SEQ ID NO: 37)
5' GCCAGAGTCAAGCCAGTAGTC 3', AXIN2 reverse:
                              (SEQ ID NO: 38)
5' TAGCCTAATGTGGAGTGGATGTG 3'.
```

Mass Spectrometry Analysis

Samples were denatured and reduced in 2 M urea, 10 mM NH4HCO3, 2 mM DTT for 30 min at 60° C., then alkylated with 2 mM iodoacetamide for 45 min at room temperature. Samples were then digested with 0.5 µg of LysC (Roche) overnight at 37 C. Following digestion, samples were concentrated using C18 ZipTips (Millipore) according to the manufacturer's specifications. Desalted samples were evaporated to dryness and resuspended in 0.1% formic acid for mass spectrometry analysis.

Digested samples were analyzed in technical duplicate on a Thermo Fisher Orbitrap Fusion mass spectrometry system equipped with a Easy nLC 1200 ultra-high pressure liquid chromatography system interfaced via a Nanospray Flex nanoelectrospray source. Samples were injected on a C18 reverse phase column (25 cm×75 um packed with ReprosilPur C18 AQ 1.9 um particles). Peptides were separated by an organic gradient from 5-30% ACN in 0.1% formic acid over 112 minutes at a flow rate of 300 nl/min. The MS continuously acquired spectra in a data-dependent manner throughout the gradient, acquiring a full scan in the Orbitrap (at 120,000 resolution with an AGC target of 200,000 and a maximum injection time of 100 ms) followed by as many MS/MS scans as could be acquired on the most abundant ions in 3 s in the dual linear ion trap (rapid scan type with an intensity threshold of 5000, HCD collision energy of 29%, AGC target of 10,000, a maximum injection time of 35 ms, and an isolation width of 1.6 m/z). Singly and unassigned charge states were rejected. Dynamic exclusion was enabled with a repeat count of 1, an exclusion duration of 20 s, and an exclusion mass width of +/−10 ppm.

Raw mass spectrometry data were assigned to histone H4 sequences with the MaxQuant software package (version 1.5.5.1) (Cox and Mann, 2008). Variable modifications were allowed for N-terminal protein acetylation, methionine oxidation, and lysine methylation. A static modification was indicated for carbamidomethyl cysteine. All other settings were left as MaxQuant defaults. MaxQuant-identified peptides were quantified by MS1 filtering using the Skyline software suite (MacLean et al., 2010).

Ex Vivo Infection of Tonsil-Derived (HLAC) Cells

HLAC cells were isolated by Ficoll-Histopaque density gradient centrifugation of sheared tonsils from HIV-seronegative donors (Vanderbilt University Medical Center, Nashville, Tenn.). Isolated HLAC cells were counted, collected as pellets by centrifugation at 1500 rpm for 5 min at room temperature, and re-suspended in the appropriate volume of concentrated viral NL4.3-Luc supernatant. Typically, 50-100 ng of p24 Gag per 4×105 HLAC were used. Spinoculations were performed in 96-well V-bottom plates in volumes of 200 µl or less. Cells and virus were centrifuged at 2000 rpm for 1.5-2 h at room temperature. After spinoculation, cells were pooled and cultured at 1×106 cells/ml in RPMI 1640 containing 10% FBS and supplemented with 5 µM Saquinavir (Sigma-Aldrich) for 3 days to prevent any residual spreading infection.

For reactivation of latent HIV-1 provirus, cells were counted and collected as pellets by centrifugation at 1500 rpm for 10 min. Cells were then plated in 96-well U-bottom plates at 1×106 per 200 µl in the presence of 30 µM Raltegravir (Santa Cruz Biotechnology) and the indicated activator. Cells were harvested 48 h after stimulation, washed one time with PBS, and lysed in 60 µl of Passive Lysis Buffer (Promega). After 15 min of lysis, the luciferase activity in cell extracts was quantified with a Perkin Elmer EnSpire 2300 Multimode plate reader after mixing 20 µl of lysate with 100 µl of substrate (Luciferase Assay System-Promega). Relative light units (RLU) were normalized to protein content determined by Bradford assay (BioRad). Cell viability was measured with CellTiter-Blue Cell Viability Assay (Promega).

T-Cell Activation Analysis

Human CD4+ T cells isolated from blood (Blood Centers of the Pacific, San Francisco, Calif.) by negative selection using RosetteSep Human CD4+ T Cell Enrichment Cocktail (StemCell Technologies) were incubated for 24 h in 6-well plates with AZ391 (1 µM), JQ1 (500 nM), or IL-2 (20 U/ml), all dissolved in DMSO at a 1:10,000 dilution. CD69 and CD25 expression was measured by flow cytometry gating on CD3+CD4+ T cells using FITC-labeled antibodies for CD3 (11-0048-42, eBioscience), APC-conjugated CD25 antibodies (17-0259-42, eBioscience), PerCP-labeled antibodies for CD4 (300528, Biolegend), and CD69-V450 (560740, BD Horizon). Staining was performed for 30 min on ice in FACS buffer (PBS, 2% FBS), and samples were analyzed on a BD Biosciences LSRII flow cytometer.

Results

ShRNA Screen Identifies Novel KMTs Involved in HIV-1 Latency

Figure 14A:
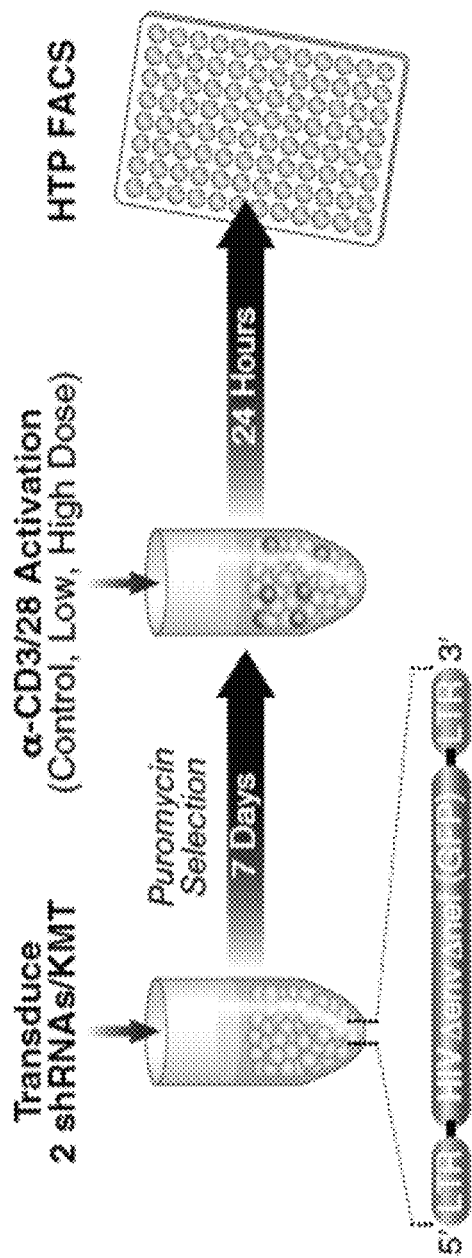
FIGS. 14A-C depict a schematic representation of an shRNA screen and data showing that SMYD2, ASH1L, SUV420H1, and SUV39H1 are repressors of HIV transcription. (A) Schematic representation of screen. (B) Heat map of shRNA hits identified. (C) Fold activation of SMYD2, ASH1L, SUV420H1, and SUV39H1 knocked down in Jurkat A2 (LTR-Tat-IRES-GFP) and A72 (LTR-GFP) J-Lat cells without co-stimulation.
Figure 14:
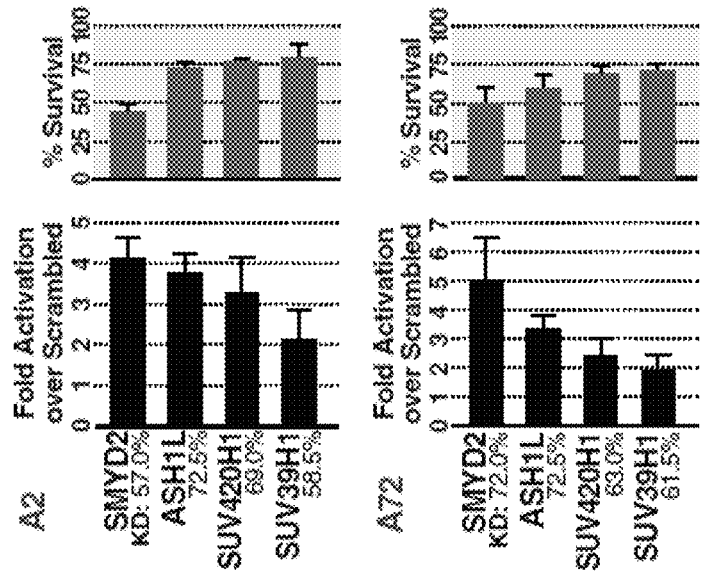
Figure 14:
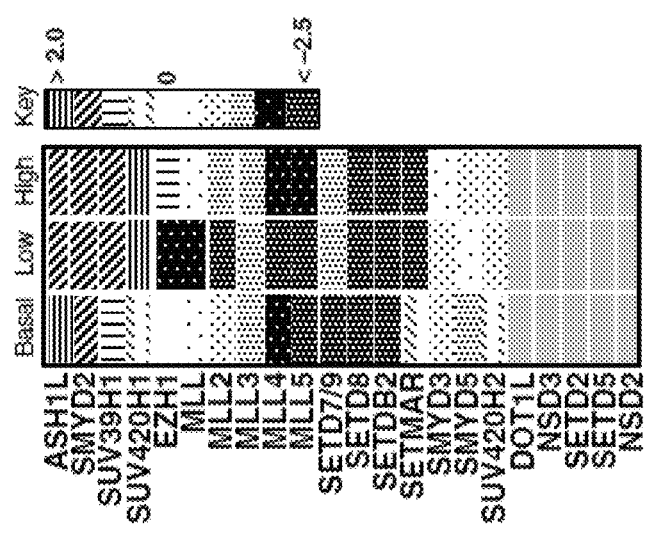

To identify novel epigenetic regulators of HIV latency, small hairpin RNAs (shRNAs) that target 31 cellular KMTs were screened in the CD4$^+$ J-Lat 5A8 cell line harboring a latent full-length HIV provirus with the fluorescent marker GFP inserted into the nef open-reading frame to allow monitoring of transcriptional activity by flow cytometry (FIG. 14A) (Chan et al., 2013). HIV transcription can be induced in this cell line with αCD3/28 antibodies mimicking T cell-receptor engagement. The line also closely clustered with patient-derived cells in a recent study comparing different latency reversing agents (LRAs) in distinct models of HIV latency (Spina et al., 2013). Cells were transduced with lentiviral vectors expressing two different shRNAs targeting each KMT or a scrambled control, followed by puromycin treatment to select successfully transduced cells. Cells were then stimulated with a suboptimal or saturating dose of αCD3/28 antibodies or were left unstimulated for 24 hours, followed by flow cytometry of GFP. A particular KMT was of interest if its knockdown resulted in a difference in GFP$^+$ cells that was at least −0.5- or +1.5-fold relative to the scrambled control. Phenotypes that emerged were transcriptional activation that occurred spontaneously or in synergy with αCD3/28 stimulation (hash line patterned) and transcriptional repression (dotted patterned) (FIG. 14B). For five KMTs, the screen was not conclusive, as one shRNA activated and one inhibited the response (grey) (FIG. 14B). For 9 KMTs, shRNA treatment induced no notable changes (Table 3).

TABLE 3 shRNA screen of cellular KMTs in the CD4$^+$ J-Lat 5A8 cell line

| Gene | Plate# | TRC# | Batch 1 No ab | Batch 1 0.125 µg | Batch 1 1 µg | Batch 2 No ab | Batch 2 0.125 µg | Batch 2 1 µg | Average 1/2 No Ab | Ave. 1/2 0.125 | Ave. 1/2 1 µg |
|---|---|---|---|---|---|---|---|---|---|---|---|
| NF-κB RelA | | TRCN0000353629 | −2.152 | −1.755 | | −2.567 | −1.981 | −2.133 | | | |
| EZH2 | 1D9 | TRCN0000040074 | −1.387 | −1.020 | | −1.045 | 1.239 | 1.168 | | | |
| EZH2 | 1D10 | TRCN0000040075 | 1.265 | 1.178 | | −1.012 | 1.051 | −1.066 | | | |
| SETD7 | 1E1 | TRCN0000078628 | −1.742 | −1.113 | | −1.610 | −1.059 | −1.203 | | | |
| SETD7 | 1E2 | TRCN0000078631 | −1.283 | −1.234 | | −1.752 | −1.476 | −1.615 | | | |
| EHMT2 | 1E4 | TRCN0000115667 | −2.502 | −1.073 | | −1.706 | 1.010 | −1.106 | | | |
| EHMT2 | 1E5 | TRCN0000115668 | −1.270 | 1.012 | | −1.786 | 1.051 | −1.090 | | | |
| DOT1L | 2B2 | TRCN0000236345 | 3.130 | 1.302 | | 5.704 | 2.057 | 1.736 | | | |
| DOT1L | 2B3 | TRCN0000236343 | −1.452 | −1.844 | | −4.066 | −1.754 | −1.950 | | | |
| SETD1B | 2B6 | TRCN0000237962 | −1.732 | −1.178 | | −3.609 | −1.139 | −1.252 | | | |
| SETD1B | 2B7 | TRCN0000237964 | 1.294 | −1.340 | | −1.764 | −1.241 | −1.444 | | | |
| NSD1 | 2C3 | TRCN0000238373 | −1.695 | −1.288 | | −2.058 | −1.086 | −1.231 | | | |
| NSD1 | 2C4 | TRCN0000238372 | 1.486 | 1.098 | | 1.029 | 1.220 | 1.102 | | | |
| NF-κB RelA | | TRCN0000353629 | −1.883 | −2.512 | −2.335 | −1.709 | −2.137 | −2.109 | −1.796 | −2.325 | −2.222 |
| ASH1 | 2C8 | TRCN0000246167 | −1.171 | −1.005 | 1.098 | −1.058 | −1.281 | −1.242 | −1.115 | −1.143 | −0.072 |
| ASH1 | 2C9 | TRCN0000246168 | 1.467 | 1.582 | 1.320 | 1.194 | 1.673 | 1.611 | 1.330 | 1.627 | 1.466 |
| MLL | 1A5 | TRCN0000005954 | −1.310 | −1.824 | 1.006 | −1.478 | −1.785 | −1.474 | −1.394 | −1.805 | −0.234 |
| MLL | 1A6 | TRCN0000005956 | −2.635 | −1.294 | 1.108 | −2.278 | 1.068 | 1.309 | −2.457 | −0.113 | 1.209 |
| SUV39H1 | 1F5 | TRCN0000158337 | −1.192 | 1.259 | 1.529 | −1.404 | 1.389 | 1.501 | −1.298 | 1.324 | 1.515 |
| SUV39H1 | 1F6 | TRCN0000157251 | −2.683 | 1.366 | 1.408 | −1.748 | −1.376 | −1.111 | −2.215 | −0.005 | 0.149 |
| SUV39H2 | 1B2 | TRCN0000006938 | −2.097 | −1.250 | −1.005 | −1.704 | −1.588 | −1.186 | −1.901 | −1.419 | −1.095 |
| SUV39H2 | 3C4 | TRCN0000011057 | −1.834 | −1.351 | −1.153 | −1.701 | −1.374 | −1.098 | −1.768 | −1.362 | −1.126 |
| SUV420H1 | 2F8 | TRCN0000359162 | −1.375 | −1.107 | −1.022 | 1.004 | −1.203 | −1.146 | −0.185 | −1.155 | −1.084 |
| SUV420H1 | 2F9 | TRCN0000359230 | 1.447 | 1.590 | 1.596 | 1.942 | 1.830 | 1.698 | 1.695 | 1.710 | 1.647 |
| SUV420H2 | 2F10 | TRCN0000145137 | 1.341 | −3.269 | −2.342 | −1.219 | −1.460 | −1.145 | 0.061 | −2.365 | −1.743 |
| SUV420H2 | 2F11 | TRCN0000143270 | −1.636 | −1.780 | −1.393 | 1.007 | −1.708 | −1.461 | −0.314 | −1.744 | −1.427 |
| MLL2 | 1B7 | TRCN0000013138 | −3.660 | −2.054 | −1.388 | −3.227 | −2.416 | −1.637 | −3.444 | −2.235 | −1.513 |
| MLL2 | 1B8 | TRCN0000013140 | −2.313 | −2.134 | −1.257 | −2.345 | −2.161 | −1.296 | −2.329 | −2.148 | −1.277 |
| MLL3 | 1B3 | TRCN0000008742 | −2.683 | −1.692 | −1.511 | −2.813 | −1.807 | −1.547 | −2.748 | −1.749 | −1.529 |
| MLL3 | 1B4 | TRCN0000008743 | −1.574 | −1.816 | −1.384 | −2.673 | −1.675 | −1.257 | −2.123 | −1.745 | −1.321 |
| MLL4 | 1A8 | TRCN0000005958 | −4.466 | −2.338 | −1.610 | −3.879 | −2.480 | −2.139 | −4.172 | −2.409 | −1.875 |
| MLL4 | 1A9 | TRCN0000005959 | −1.170 | −1.022 | 1.087 | −1.731 | −1.567 | −1.121 | −1.450 | −1.295 | −0.017 |
| NF-κB RelA | | TRCN0000353629 | −2.830 | −2.605 | −2.397 | −1.344 | −2.216 | −2.193 | −2.087 | −2.410 | −2.295 |
| NSD2 | A6 | TRCN0000019816 | −2.406 | −2.843 | −1.913 | −1.183 | −2.969 | −2.301 | −1.795 | −2.906 | −2.107 |
| NSD2 | H5 | TRCN0000019817 | 1.274 | 1.455 | 1.338 | 1.389 | 1.483 | 1.524 | 1.331 | 1.469 | 1.431 |
| MLL5 | 1F3 | TRCN0000150550 | −7.679 | −3.184 | −2.185 | −2.012 | −2.841 | −1.999 | −4.846 | −3.012 | −2.092 |
| MLL5 | 1F4 | TRCN0000154711 | −2.941 | −1.324 | −1.197 | −1.087 | −1.047 | 1.120 | −2.014 | −1.185 | −0.039 |
| EHMT1 | 1D7 | TRCN0000036054 | −3.261 | −1.162 | −1.148 | 1.098 | 1.252 | −2.204 | −0.032 | 0.103 | |
| EHMT1 | 1D8 | TRCN0000036057 | 1.406 | −1.121 | −1.104 | 1.052 | 1.008 | 1.024 | 1.229 | −0.056 | −0.040 |
| SETD8 | 1E9 | TRCN0000148268 | −4.731 | −3.410 | −2.615 | −2.169 | −2.830 | −1.883 | −3.450 | −3.120 | −2.249 |
| SETD8 | 1E10 | TRCN0000130036 | −2.942 | −2.284 | −1.768 | −1.771 | −1.810 | −1.414 | −2.356 | −2.047 | −1.591 |
| NF-κB RelA | | TRCN0000353629 | −1.374 | −2.530 | −2.339 | −1.234 | −1.594 | −1.727 | −1.304 | −2.062 | −2.033 |
| SETDB1 | 1G1 | TRCN0000147130 | −1.018 | 1.208 | 1.359 | 1.096 | 1.014 | 1.034 | 0.039 | 1.111 | 1.197 |
| SETDB1 | 1G2 | TRCN0000179094 | 3.306 | 1.370 | 1.380 | 2.630 | 1.233 | 1.131 | 2.968 | 1.301 | 1.256 |
| SETDB2 | 1F7 | TRCN0000159172 | −2.379 | −2.934 | −2.478 | −1.931 | −2.790 | −2.728 | −2.155 | −2.862 | −2.603 |
| SETDB2 | 1F8 | TRCN0000160242 | 1.078 | −2.433 | −2.625 | 1.352 | −2.295 | −2.018 | 1.215 | −2.364 | −2.321 |
| SETMAR | 1G7 | TRCN0000146300 | 1.672 | −2.471 | −2.703 | −1.234 | −1.876 | −2.274 | 0.219 | −2.174 | −2.488 |
| SETMAR | 1G8 | TRCN0000179441 | −1.328 | −1.259 | −1.014 | 1.144 | −1.206 | −1.385 | −0.092 | −1.233 | −1.199 |

TABLE 3-continued shRNA screen of cellular KMTs in the CD4+ J-Lat 5A8 cell line

| Gene | Plate# | TRC# | Batch 1 No ab | Batch 1 0.125 µg | Batch 1 1 µg | Batch 2 No ab | Batch 2 0.125 µg | Batch 2 1 µg | Average 1/2 No Ab | Ave. 1/2 0.125 | Ave. 1/2 1 µg |
|---|---|---|---|---|---|---|---|---|---|---|---|
| SETD5 | 2D11 | TRCN0000253861 | 1.685 | 1.420 | 1.414 | 1.300 | 1.455 | 1.253 | 1.493 | 1.437 | 1.333 |
| SETD5 | 1D12 | TRCN0000253863 | 1.064 | −1.876 | −1.476 | 1.053 | −1.822 | −1.503 | 1.059 | −1.849 | −1.489 |
| NF-κB RelA | | TRCN0000353629 | −1.652 | −2.757 | −2.277 | −1.374 | −2.203 | −2.333 | −1.513 | −2.480 | −2.305 |
| SETD2 | 1A3 | TRCN0000003030 | −1.987 | 1.978 | 1.968 | −2.134 | 1.560 | 1.502 | −2.060 | 1.769 | 1.735 |
| SETD2 | 1A4 | TRCN0000003032 | −1.303 | −2.912 | −1.911 | −1.347 | −2.284 | −1.823 | −1.325 | −2.598 | −1.867 |
| EZH1 | 3B1 | TRCN0000355734 | −1.678 | −2.254 | 1.013 | −1.654 | −1.629 | 1.059 | −1.666 | −1.941 | 1.036 |
| EZH1 | 3B2 | TRCN0000355735 | −1.415 | 1.014 | 1.328 | −1.221 | 1.202 | 1.151 | −1.318 | 1.108 | 1.239 |
| SETD6 | 3B4 | TRCN0000419700 | 1.096 | −1.506 | −1.258 | −1.179 | −1.112 | 1.216 | −0.041 | −1.309 | −0.021 |
| SETD6 | 3B5 | TRCN0000417114 | −1.340 | −1.152 | 1.060 | −1.852 | 1.043 | 1.030 | −1.596 | −0.054 | 1.045 |
| DOT1L | 2B2 | TRCN0000236345 | 4.712 | 1.837 | 1.517 | 6.883 | 2.316 | 1.749 | 5.797 | 2.076 | 1.633 |
| DOT1L | 2B3 | TRCN0000236343 | −3.947 | −2.420 | −1.918 | −3.456 | −2.173 | −1.798 | −3.702 | −2.297 | −1.858 |
| MLL2 | 1B7 | TRCN0000013138 | −3.022 | −2.572 | −1.617 | −3.432 | −2.397 | −1.457 | −3.227 | −2.485 | −1.537 |
| MLL2 | 1B8 | TRCN0000013140 | −1.459 | −2.360 | −1.812 | −2.005 | −2.381 | −1.679 | −1.732 | −2.371 | −1.746 |
| NF-κB RelA | | TRCN0000353629 | −2.567 | −2.693 | −2.284 | −1.091 | −2.386 | −2.638 | −1.829 | −2.540 | −2.461 |
| DOT1L | 2B4 | TRCN0000236342 | −1.573 | −1.453 | −1.429 | −1.314 | −2.021 | −1.455 | −1.444 | −1.737 | −1.442 |
| DOT1L | 2B5 | TRCN0000236344 | −3.878 | 1.246 | 1.487 | −3.795 | −1.234 | 1.171 | −3.837 | 0.006 | 1.329 |
| MLL2 | 2A10 | TRCN0000235742 | −2.811 | −1.012 | 1.440 | −1.599 | −1.260 | 1.068 | −2.205 | −1.136 | 1.254 |
| MLL2 | 2A11 | TRCN0000235743 | −2.403 | 1.024 | 1.371 | −2.046 | −1.207 | 1.017 | −2.224 | −0.092 | 1.194 |
| SUV420H2 | 1F10 | TRCN0000145137 | −3.046 | 1.317 | 1.184 | −1.295 | −1.273 | −1.299 | −2.171 | 0.022 | −0.058 |
| SUV420H2 | 1F11 | TRCN0000143270 | 1.217 | −1.701 | −1.638 | −1.034 | −1.387 | −1.367 | 0.092 | −1.544 | −1.502 |
| SUV420H2 | 3C1 | TRCN0000437411 | −2.171 | 1.300 | 1.329 | −1.719 | −1.035 | 1.048 | −1.945 | 0.132 | 1.188 |
| SUV420H2 | 3C2 | TRCN0000446372 | 1.586 | 1.328 | 1.133 | 1.402 | 1.226 | 1.072 | 1.494 | 1.277 | 1.103 |

Four KMTs were identified as repressors of HIV latency, as their knockdown with both shRNAs induced transcriptional activation (ASH1L, SMYD2, SUV39H1, and SUV420H1). EZH1, a component of the PRC2 complex linked to HIV latency (Friedman et al., 2011), showed hyperactivation only after high-dose αCD3/28 treatment. Twelve KMTs were identified as coactivators of the reactivation response, including SET7/9, which was previously identified as a transcriptional activator of HIV that methylates the viral transactivator Tat (Pagans et al., 2010). To independently confirm repressive activities of ASH1L, SMYD2, SUV39H1, and SUV420H1, the screen was repeated in two other J-Lat clones, A72 and A2. These clones contain HIV minigenomes composed of just the HIV promoter in the 5'LTR that drives GFP expression (LTR-GFP; A72) or an LTR-Tat-IRES-GFP cassette where transcriptional activity is driven by the viral transactivator Tat (A2) (Jordan et al., 2003; Jordan et al., 2001). In both cells lines, spontaneous latency reversal (≥2× increase in GFP+ cells) was observed in cells lacking SMYD2, ASH1L, SUV420H1, and SUV39H1, with SMYD2 representing the top hit in both cell lines (FIG. 14C). Reactivation was also observed in the absence of Tat in A72 cells.

Inhibition of SMYD2 Reactivates HIV-1 from Latency

Figure 6A:
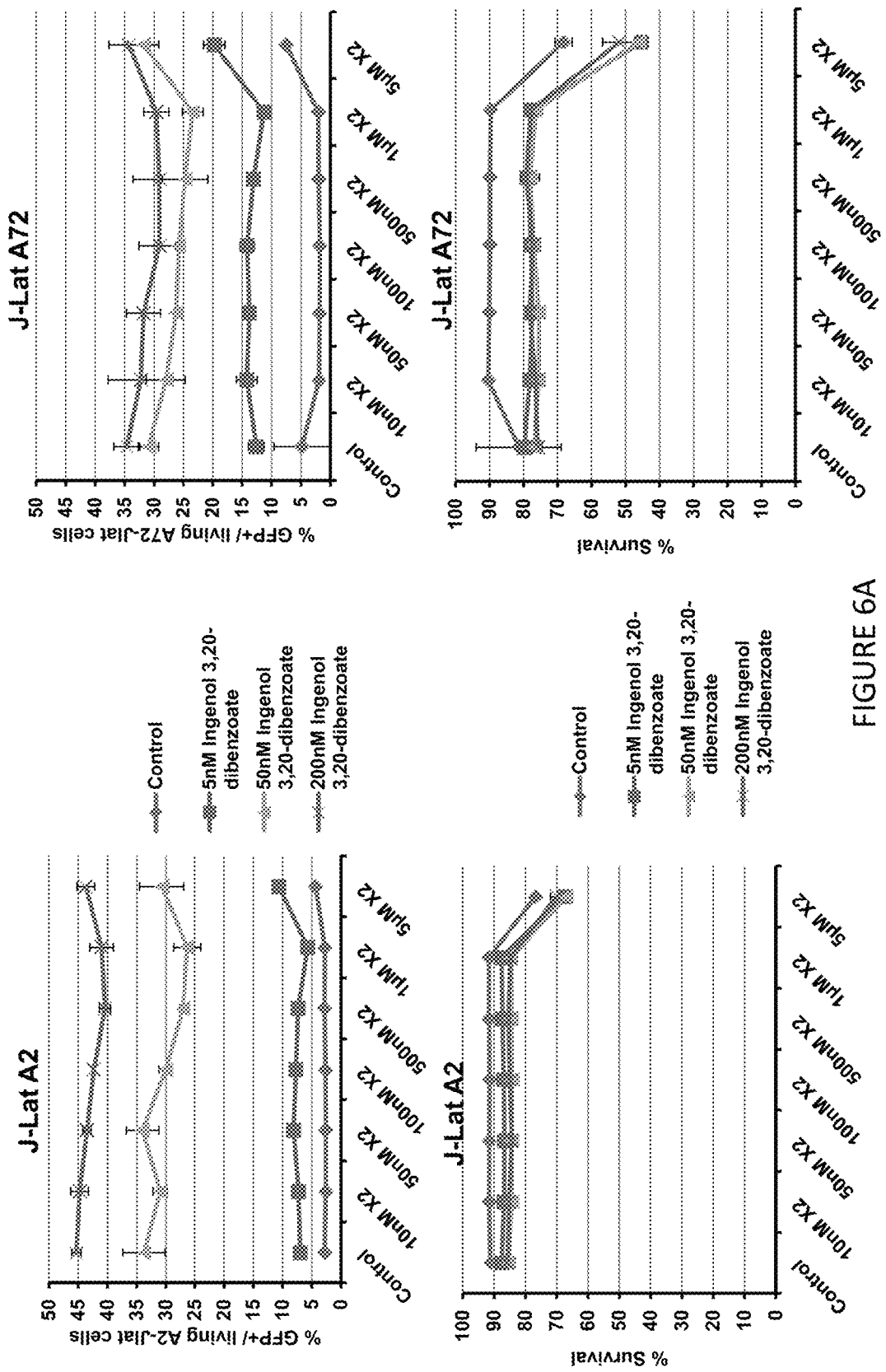
FIG. 6A provides graphs depicting results of an experiment demonstrating a lack of synergy between X2 and Ingenol in A2 J-Lat and A72 J-Lat cells.
Figure 6B:
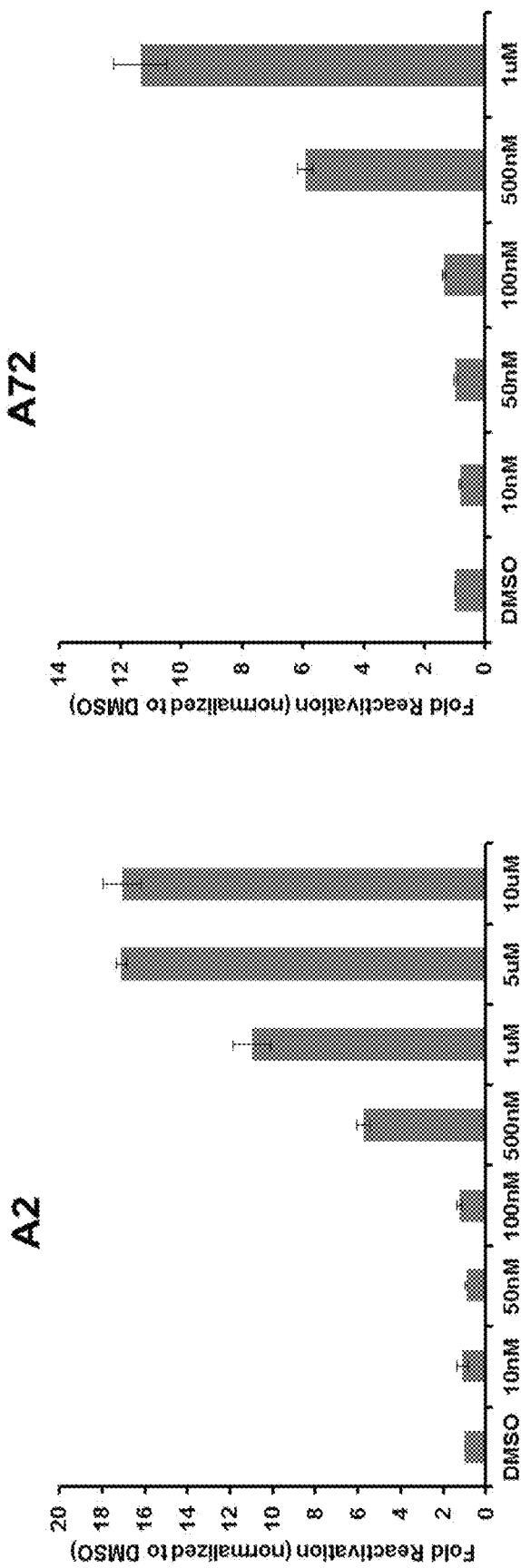
FIG. 6B provides graphs depicting results of an experiment demonstrating reactivation of the HIV-LTR by Ingenol in A2 J-Lat and A72 J-Lat cells.
Figure 7:
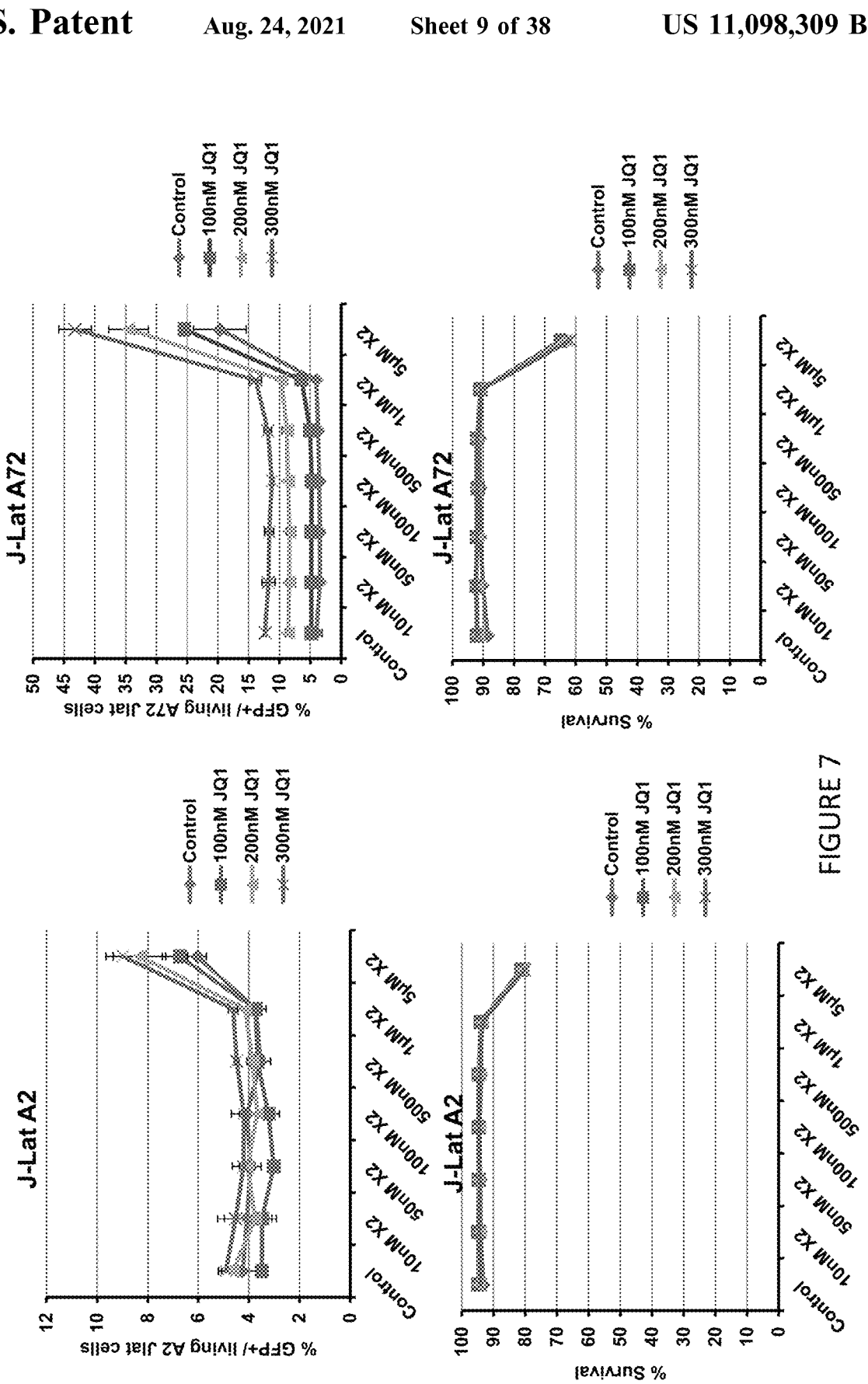
FIG. 7 depicts synergy between X2 and JQ1 in A2 J-Lat and A72 J-Lat cells with respect to reactivation of the HIV-LTR.
Figure 8:
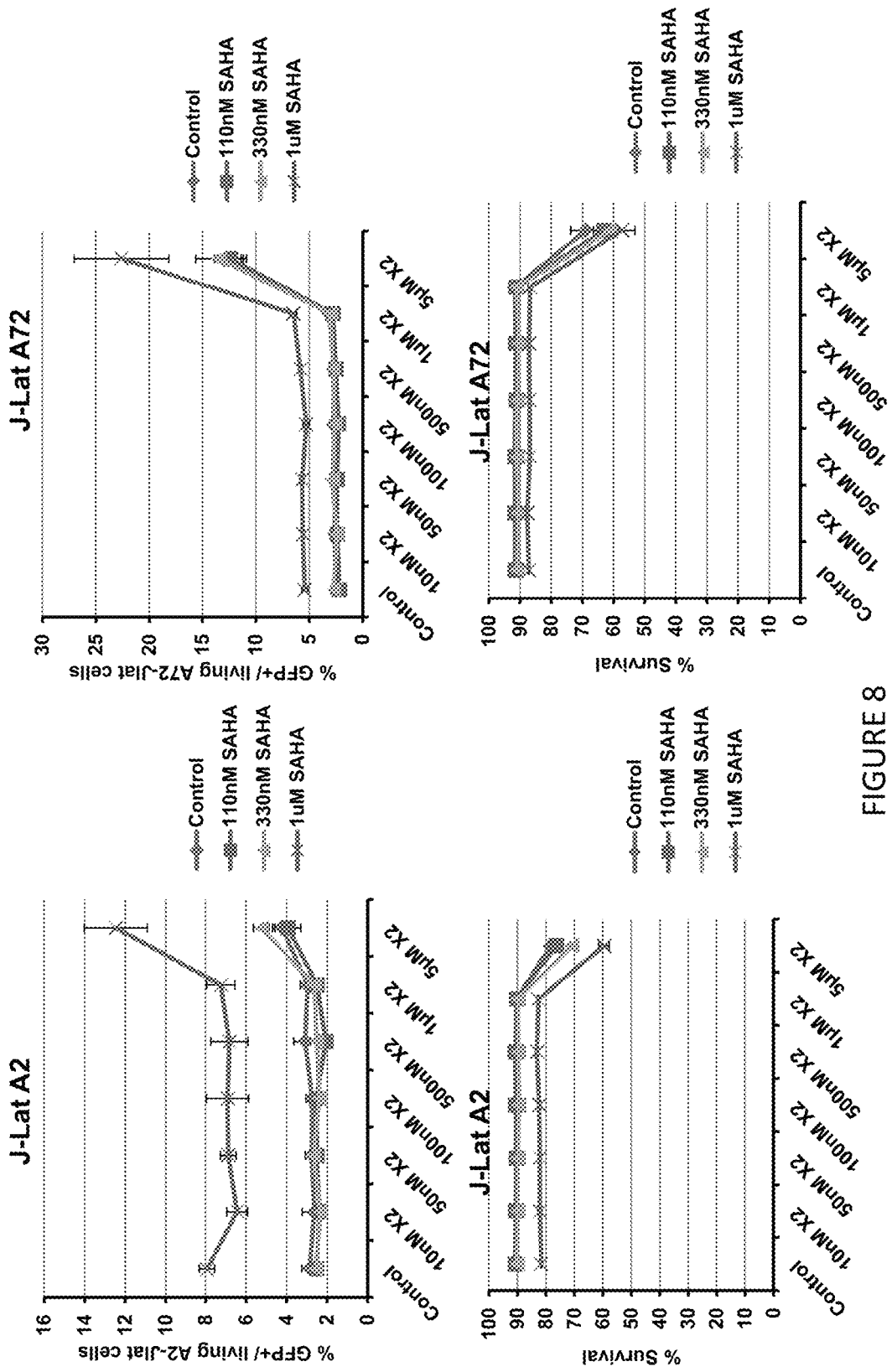
FIG. 8 depicts synergy between X2 and SAHA in A2 J-Lat and A72 J-Lat cells with respect to reactivation of the HIV-LTR.

Because of SMYD2's role in p53 and RB tumor suppressor inactivation and cancer development (Hamamoto et al., 2015; Huang et al., 2006), a specific SMYD2 inhibitor (AZ505) was developed (Ferguson et al., 2011). AZ505 is a substrate-competitive inhibitor that binds the peptide-binding groove of the enzyme with a calculated $K_d$ of 0.5 µM, approximately sevenfold lower than the p53 peptide. AZ505 is not cell-penetrable, but subsequent efforts identified a novel series of potent, cell-permeable SMYD2 inhibitors, including analogs AZ506 ($IC_{50}$=0.017 µM) and AZ391 ($IC_{50}$=0.027 µM) (Cowen, 2013; Throner, 2015). The ability of these compounds to reverse HIV latency was tested in the J-Lat A72 cell line. Indeed, both compounds, but not AZ505, activated GFP expression at high concentrations (5 and 10 µM), with AZ391 inducing up to 30% GFP+ cells similar to the activity of TNFα or the BET inhibitor JQ1 (FIG. 5B). AZ391 reduced cell viability and increased cytotoxicity and caspase-3/7 activity at concentrations above 5 µM (FIGS. 22A-D). When AZ391 was combined with increasing amounts of LRAs (JQ1; SAHA-an HDAC inhibitor; ingenol 3,20-dibenzoate-a protein kinase C agonist), more than additive effects with JQ1 were observed, less with SAHA and practically no combination effect were observed with ingenol 3,20-dibenzoate (FIGS. 6A, 7 and 8). Positive effects of AZ391 in combination with JQ1 were also observed in ex vivo infected human lymphocyte aggregate cultures (HLAC) from tonsils spin-infected with high concentrations of an HIV-luciferase reporter virus as described (Kutsch et al., 2002) (FIG. 21A-E).

Figure 15A:
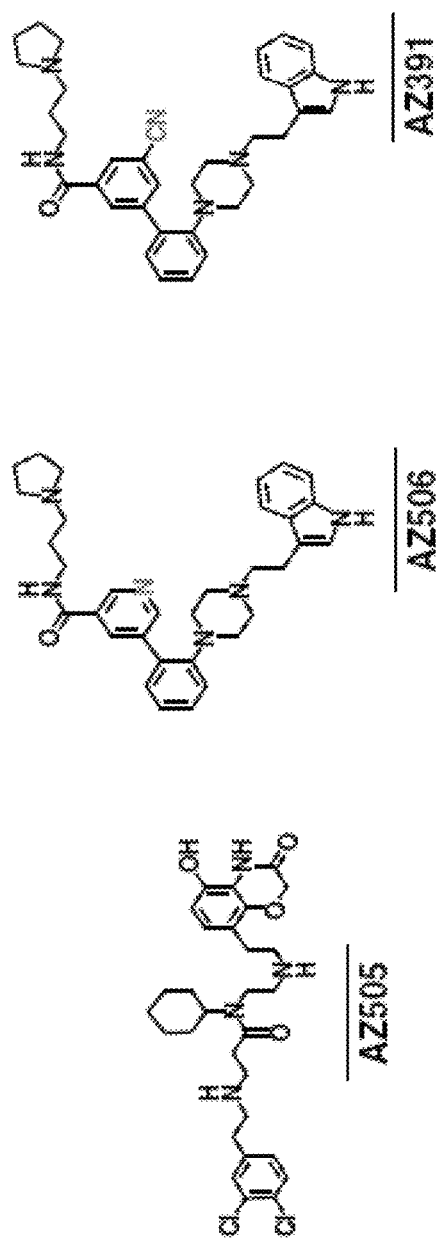
Figure 15B:
Figure 15D:
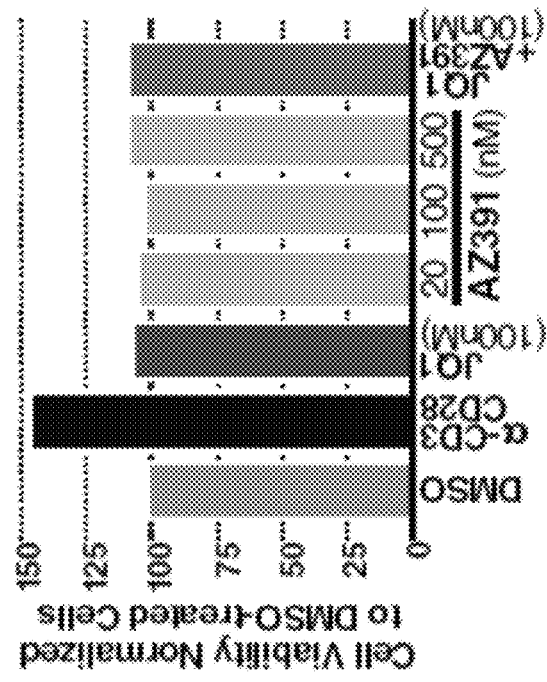
Figure 15C:
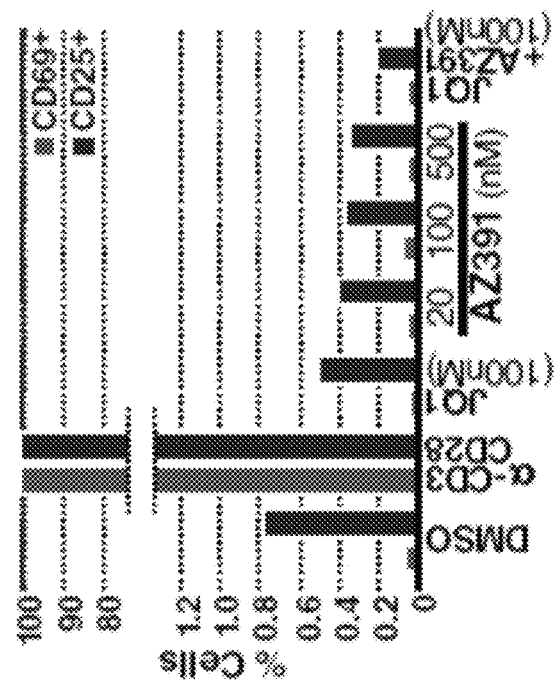

Next, AZ391 was tested in CD4+ T cells from HIV-1-infected individuals on suppressive ART. Four HIV-1-infected individuals, who met the criteria of suppressive ART, which is undetectable plasma HIV-1 RNA levels (<50 copies/ml) for a minimum of six months, and a CD4+ T cell count of at least 350 cells/mm³, were enrolled (Table 2). In a pilot experiment, five million purified CD4+ T cells from one individual were treated ex vivo with increasing, non-toxic concentrations of AZ391 (maximal 500 nM), JQ1 or a combination of both, or vehicle alone. After 48 hours, levels of intracellular HIV-1 mRNA were measured by droplet digital RT-PCR using a previously published primer/probe set (Laird et al., 2015). AZ391 treatment increased intracellular HIV-1 mRNA levels in a dose-dependent manner to a similar extent as JQ1; however, no additive or synergistic effects between both drugs were observed (FIG. 15B). This was confirmed in the three additional donors, whose CD4+ T cells all responded to AZ391 (500 nM) with increased intracellular HIV-1 mRNA levels to similar levels as JQ1 (mean increases of 1.5-10-fold) (FIG. 15E). No synergy with JQ1 was observed (not shown). Without intending to be bound by any particular theory, it may be that the difference in synergistic effect seen for AZ391 and JQ1 in tonsil resident T-cells as described in Example 2 compared with peripheral blood T-cells as described in Example 3 is due to the activation status the two T-cell populations. In all experiments, activation with αCD3/αCD28 antibodies was included as a positive control, which elevated levels of intracellular HIV-1 mRNA between 2.7 and 40-fold (FIG. 15B/E). No increase in global T-cell activation (FIG. 15C/F) and no impact on cell viability were observed in response to AZ391 treatment at the indicated concentrations (FIG. 15D/G).

SMYD2 Associates with the HIV Promoter in Cells

Figure 16A:
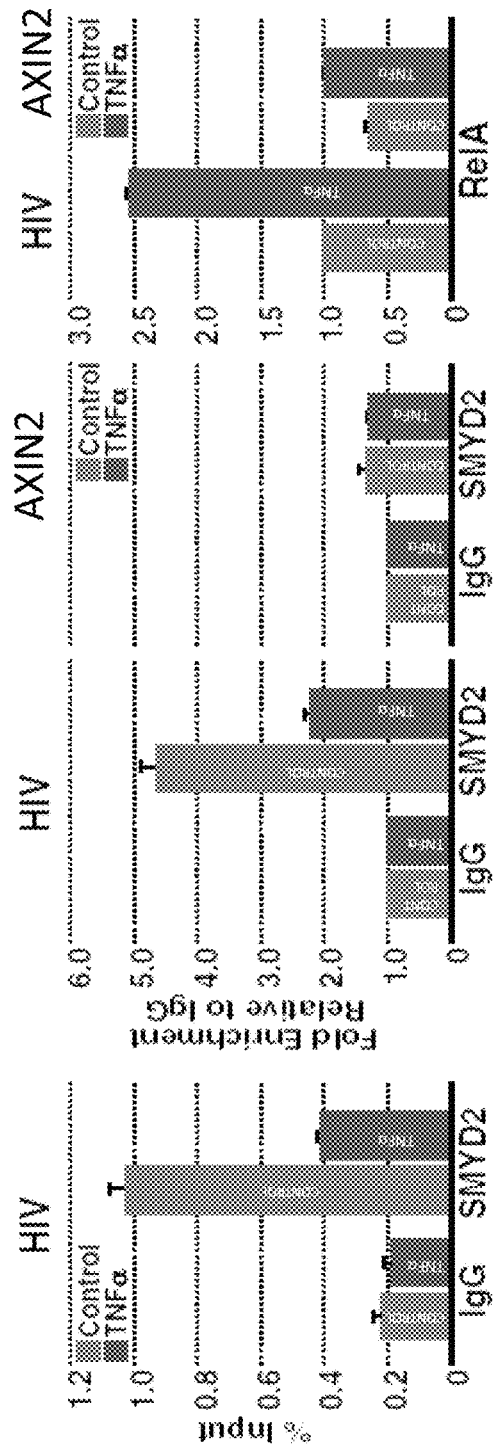
FIGS. 16A and 16B depict data showing that SMYD2 associates with the HIV promoter in cells under non-stimulated conditions and the absence of SMYD2 after efficient knockdown of SMYD2 by shRNA. (A) SMYD2 is present at the HIV-LTR under non-stimulated conditions (control—left), and was displaced in response to TNFα stimulation (right). RELA is recruited to the HIV promoter after treatment with TNFα (right). No association of SMYD2 or RELA with AXIN2 was observed. All chromatin immunoprecipitations and qPCRs were repeated at least three times and representative results of three technical replicates are shown. In the left panel, results are expressed as percent enrichment over input DNA values. In the right and all following ChIP panels, results are expressed as fold increase over IgG control (IgG=1). (B) Confirmation of SMYD2 knockdown by qPCR in A72 J-Lat cells (left). SMYD2 is present at the HIV-LTR in scramble control cells (left) and absent in SMYD2 knockdown cells (right). All ChIPs and qPCRs were repeated at least three times, and representative results of three technical replicates are shown.
Figure 16B:
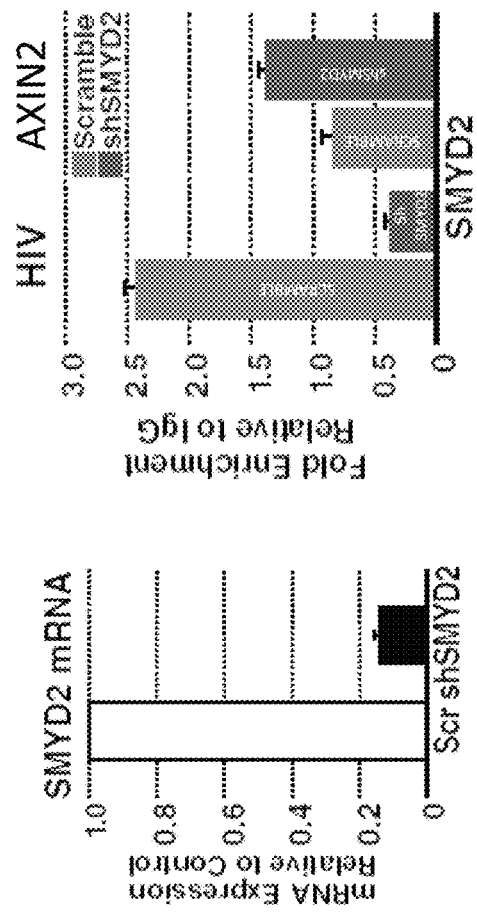

To examine SMYD2's association with the latent HIV promoter, ChIP experiments were used. Chromatin was prepared from J-Lat A72 cells, either unstimulated or stimulated with TNFα, incubated with a ChIP-grade SMYD2 or IgG control antibodies, and immunoprecipitated as described (Schroder et al., 2013). DNA extracted from the immunoprecipitated material or the input control, and quantitative PCR analysis was performed with primers specific for the region within the HIV promoter occupied by nuc-1 or for the irrelevant AXIN2 gene (Kaehlcke et al., 2003). Significant enrichment over the input and the IgG control was observed for SMYD2 at the HIV LTR, but not at the AXIN2 gene, demonstrating specific association of SMYD2 with the latent promoter (FIG. 16A, light grey bars). After TNFα activation, recruitment was reversed, consistent with a model that the repressive activity of SMYD2 was displaced when latency was reversed (FIG. 16A, dark grey bars). The opposite was observed when experiments were performed with antibodies specific for the NF-κB RELA subunit, a factor recruited to the HIV promoter in response to TNFα treatment (FIG. 16A) (Williams et al., 2006). Similar results were obtained in the A2 cell line (FIG. 23A). Upon knockdown of SMYD2, the ChIP signal for SMYD2 was lost at the HIV promoter, but no change was observed at the AXIN2 gene, confirming the specificity of the results (FIG. 16B).

SMYD2 Monomethylates Lysine 20 in Histone 4

Figures 17A, 17B, 17C:
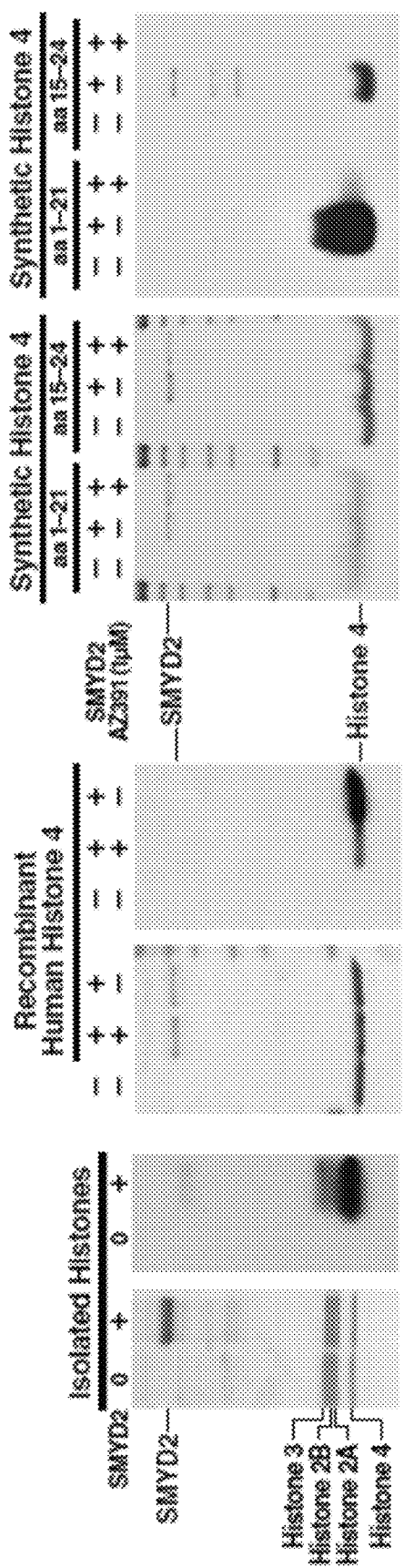
FIGS. 17A-H depict data showing that SMYD2 methylates histone 4, specifically at lysine 20. (A) In vitro methylation assays of histones isolated from HEK293T cells. (B) In vitro SMYD2 methylation assay of recombinant full-length histone H4, with or without AZ391. (C) In vitro SMYD2 methylation assays of synthetic histone H4 peptides (aa 1-21, left, and aa 15-24, right) in the presence or absence of AZ391. (D) In vitro SMYD2 methylation assay of synthetic histone H4 peptide (aa 1-21) with or without a K20A mutation. (E) In vitro methylation assays of human recombinant histone H4 using wildtype or catalytically inactive (Y240F) SMYD2. All in vitro methylation assays of recombinant histone H4 or H4 peptides were repeated at least three times, and representative Coomassie stain (left) and autoradiography (right) are shown. (F-H) In vitro SMYD2 methylation assay of recombinant full-length histone H4 was subjected to mass spectrometry. (F) Annotated HCD MS/MS spectrum of the histone H4 LysC peptide RHRKVLRDIQGITK (SEQ ID NO:29) containing K20 methylation. b ions and y ions are indicated, with specific ions labeled atop each peak. (G-H) Integrated MS1 intensity for the RHRKmeVLRDIQGITK (SEQ ID NO:30) peptide (G) and an unmodified histone H4 peptide (H) TVTAMDVVYALK (SEQ ID NO:31) across different samples. Error bars indicate standard deviation between technical replicate MS analyses.

To identify the target for SMYD2 at the latent HIV promoter, in vitro methylation assays were performed with recombinant SMYD2 and radio-labeled S-adenosyl methionine (SAM) on purified human histones. Histone H4 was prominently methylated by SMYD2 (FIG. 17A). Histone H3 (H3K4 and H3K36) has been identified as the main SMYD2 target (Abu-Farha et al., 2008; Brown et al., 2006). However, Wu et al. showed in a radiometric assay that histone H4 is a more efficient substrate for SMYD2 with a specific activity 3-5-fold higher than histone H3 (Wu et al., 2011). This prior finding was confirmed with recombinant human histone H4, which was avidly methylated by SMYD2, a process inhibited by AZ391 (FIG. 17B). To map the site of methylation in histone H4, two short, synthetic histone H4 peptides (amino acids (aa) 1-21 and aa 15-24) (SEQ ID NOs:40-41) were used and subjected them to in vitro methylation assays. Both peptides were efficiently methylated by SMYD2, a process suppressed by the addition of AZ391 (FIG. 17C). Both peptides contain lysines K16 and $K_{20}$. The mono-, di- and trimethylated states of K20 are well known (van Nuland and Gozani, 2016), while K16 is known to be acetylated, and was only recently found to be also methylated in a comprehensive mass spectrometry study (Tan et al., 2011). K20 methylation states are catalyzed by different enzymes with SETD8 known to be a monomethyltransferase for H4K20 and SUV420H1/2 acting as K20 di- and trimethyltransferases (Beck et al., 2012). SMYD2 is known mainly as a monomethyltransferase although dimethylation of H3K36 by SMYD2 has been reported (Brown et al., 2006).

Figures 17D, 17E:
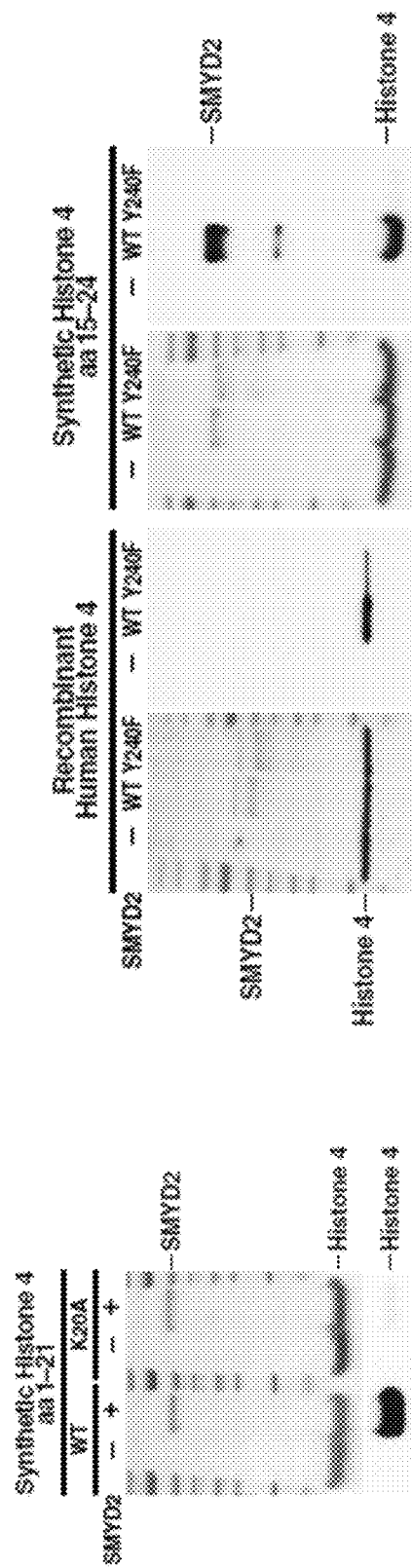
Figure 17F:
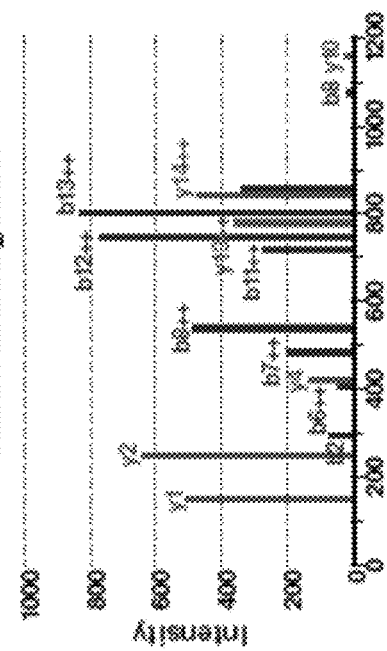
Figure 17H:
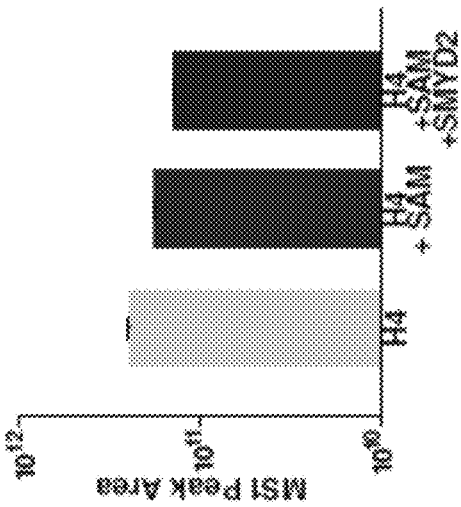
Figure 17G:
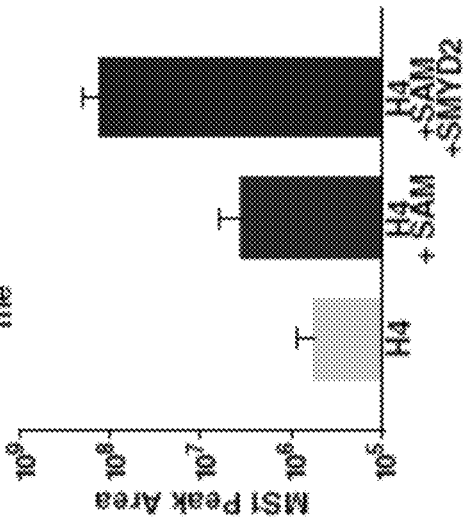

To determine if K20 is the site of methylation in H4, in vitro methylation assays were performed with a K20A-mutated histone H4 peptide. K20 was efficiently methylated by SMYD2 in the wildtype peptide, a process abolished by the H4K20A mutation (FIG. 17D). Similarly, in vitro methylation assays were performed with a catalytically dead SMYD2 methyltransferase (Y240F) (Saddic et al., 2010), which methylated histone H4 with substantially decreased efficiency and failed to methylate the histone H4 peptide (FIG. 17E). To further validate H4K20 methylation by SMYD2 in the context of full-length H4 protein, in vitro methylation reactions with histone H4 were performed using non-radiolabeled SAM and the products were subjected to a LS/MS analysis. This analysis confirmed monomethylation of K20 (FIG. 17F/G/H). No methylation of K16 was detected.

As antibodies against the different methylated states of H4K20 are readily available, ChIP analysis was next performed in A72 cells followed by qPCR specific for the HIV promoter. It was found that, like SMYD2, H4K20me1, but not H4K20me2/3, was markedly enriched at the latent HIV promoter (FIG. 18A, left panel). Upon treatment with TNFα, the H4K20me1 mark decreased, and H4K20me2/3 marks increased, consistent with a model in which H4K20me1 is associated with suppressed and H4K20me2/3 with activated HIV transcription. Importantly, the known suppressive mark associated with SMYD2 activity, H3K36me2, was unchanged after TNFα treatment at the HIV-1 LTR while H3K4me1 was enhanced in accordance with its reported function in transcriptional activation (Abu-Farha et al., 2008) (FIG. 24A). Levels of histone H4 changed only minimally upon activation, and comparable results were obtained when values were normalized to total H4 levels (FIG. 18A, right panel).

Next, ChIP analysis was performed in SMYD2 knockdown A72 cells. SMYD2 knockdown and confirmed by western blotting (FIG. 24B). Importantly, H4K20me1 was sevenfold lower after treatment with SMYD2 shRNAs than with control shRNA-treated cells. (FIG. 18B). Consistent with SMYD2 methylating H4K20 directly rather than acting indirectly via the known monomethyltransferase for H4K20, SETD8, SMYD2 knockdown did not change the expression levels of SETD8 (FIG. 24C). Collectively, these data identify H4K20me1 as a new histone mark associated with HIV-1 latency and implicate SMYD2 as a new H4K20 monomethyltransferase at the latent HIV LTR.

Recruitment of Reader Protein L3MBTL1 to the Latent HIV-1 Promoter

Figure 19C:
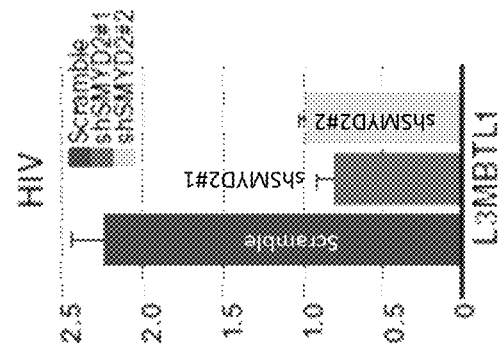
FIGS. 19A-C depict ChIP data showing that L3MBTL1 associates with the HIV promoter in cells. (A) ChIP experiments of L3MBTL1 in A72 J-Lat cells, either non-stimulated (control) or in response to TNFα stimulation at the HIV LTR nuc-1 region (left) or at the AXIN2 gene (right). All ChIPs and qPCRs were repeated at least three times, and representative results of three technical replicates are shown. (B) ChIP experiments of L3MBTL1 in A2 J-Lat cells, either non-stimulated (control) or in response to TNFα stimulation at the HIV LTR nuc-1 region (left) or at the AXIN2 gene (right). All ChIPs and qPCRs were repeated at least three times, and representative results of three technical replicates are shown. (C) ChIP experiments of L3MBTL1 performed in two SMYD2 knockdown A2 cell lines or scramble control cells. All ChIPs and qPCRs were repeated at least three times, and representative results of three technical replicates are shown.
Figure 19A:
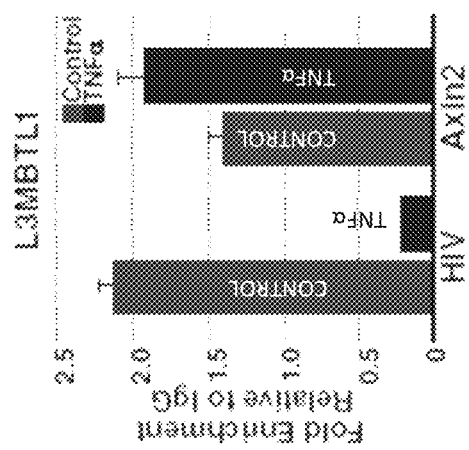
Figure 19B:
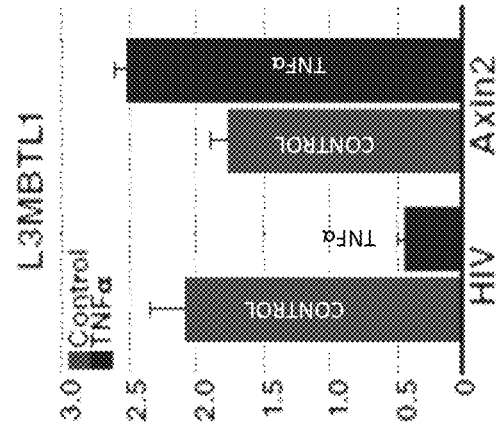
Figure 20:
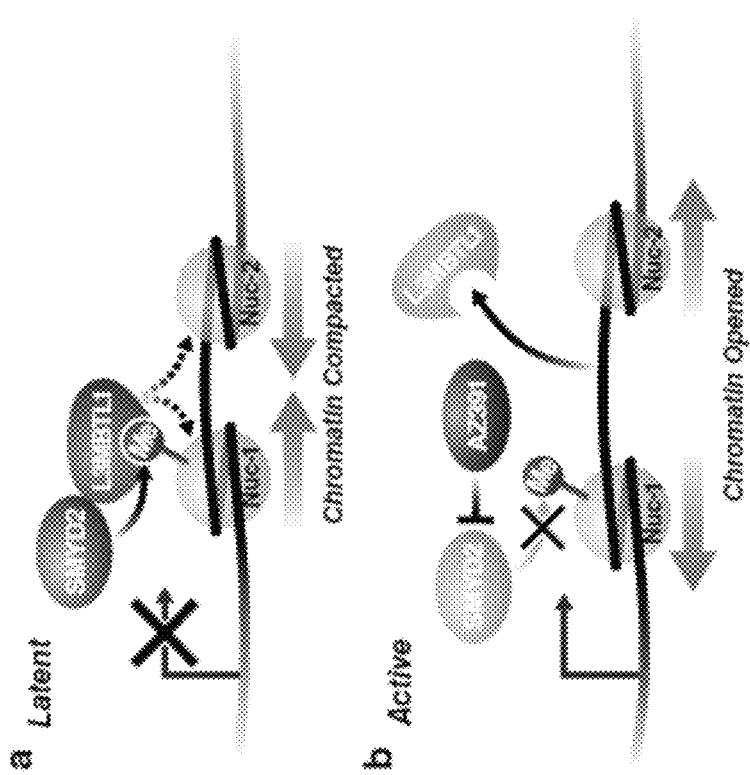
FIG. 20 provides a schematic of a model of the repressive function of SMYD2 at the latent HIV promoter located in the 5' long terminal repeat.
Figure 21E:
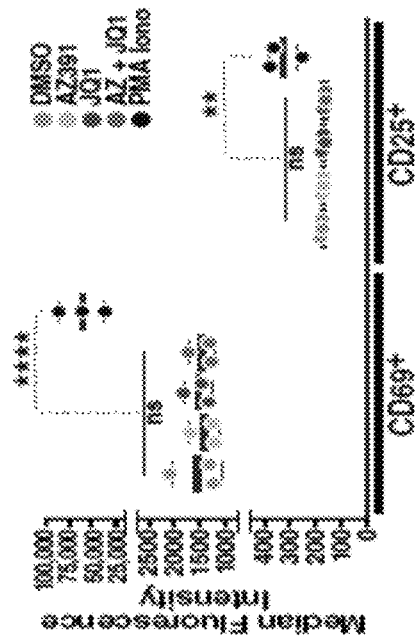
Figure 21D:
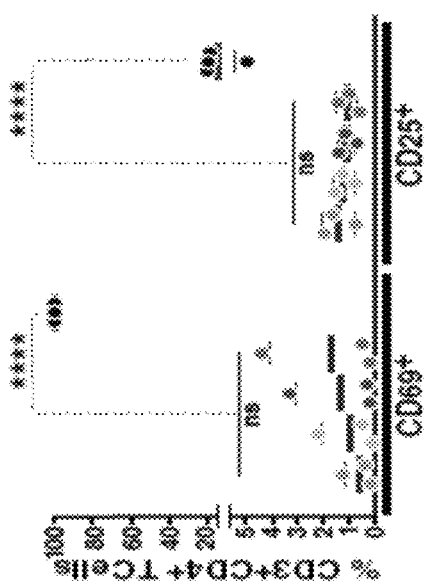
Figure 22A:
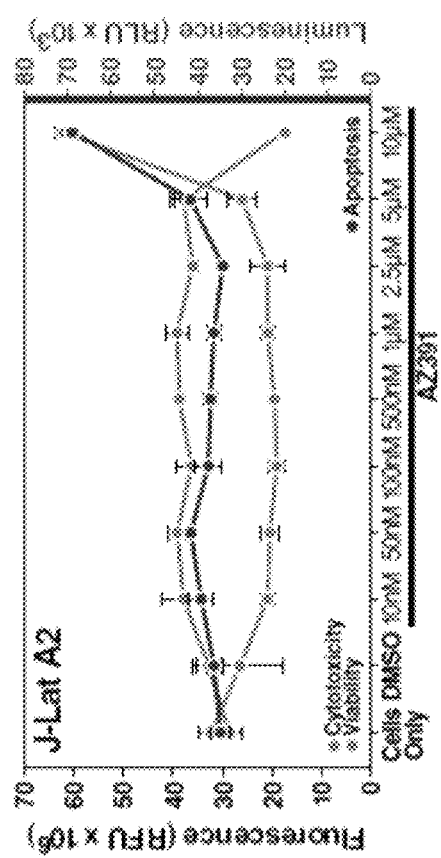
Figure 22B:
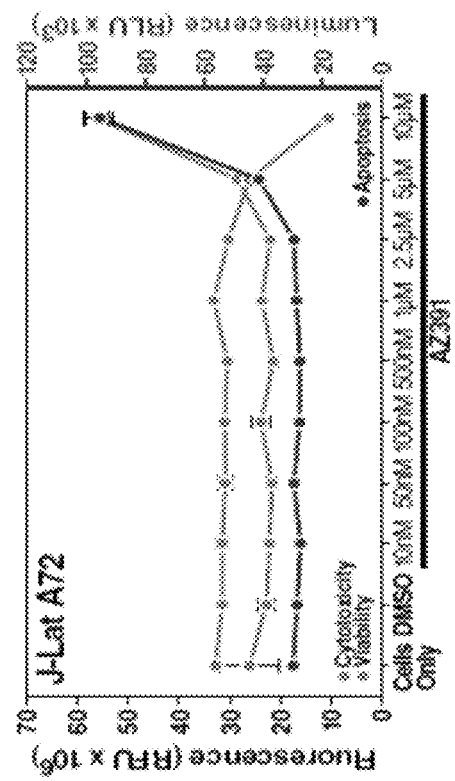
Figure 22C:
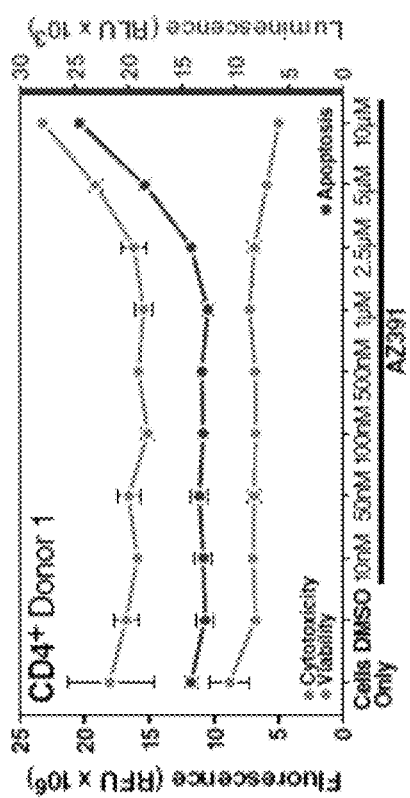
Figure 22D:
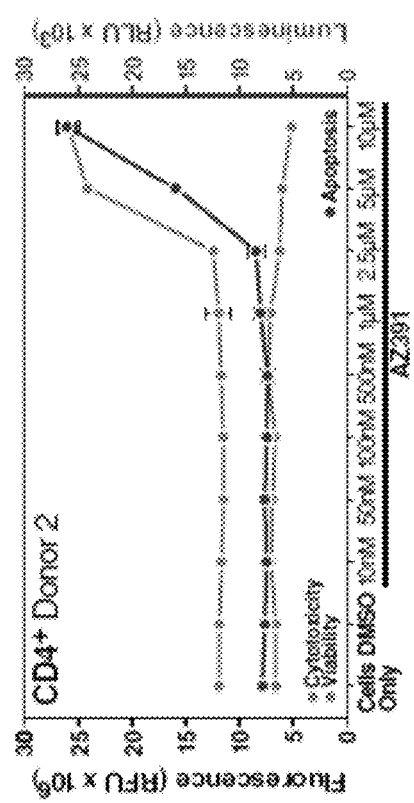
Figure 25A:
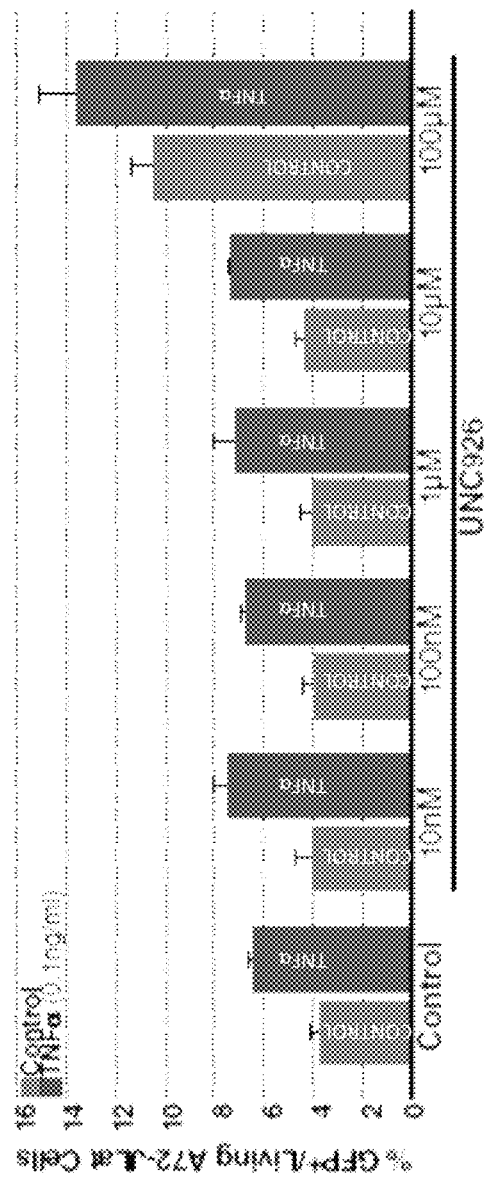
Figure 25B:
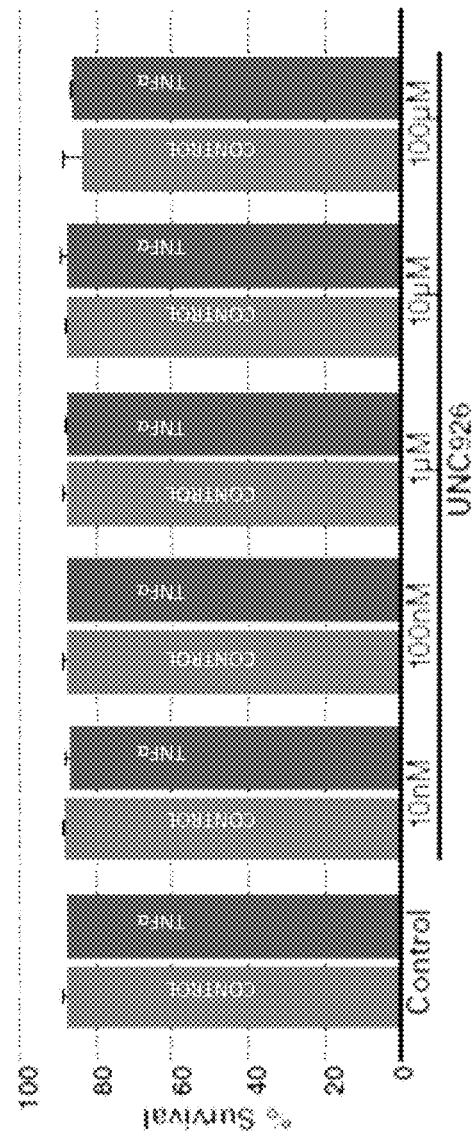
Figures 25C, 25D, 25E:
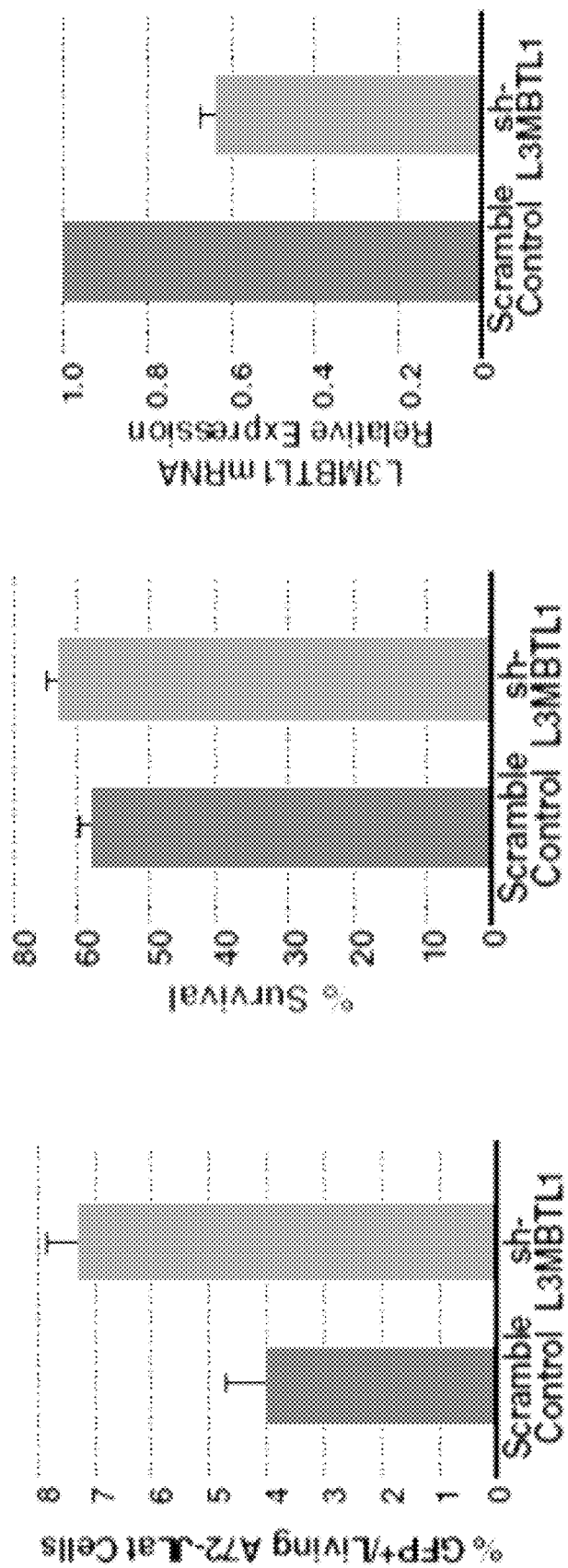

L3MBTL1 is an MBT (malignant brain tumor) family member, a highly conserved group of 11 proteins characterized by multiple MBT domains that together bind mono- and dimethylated histones (Bonasio et al., 2010). H4K20me1/2 was identified as a docking site for L3MBTL1 in chromatin by the Reinberg laboratory, who also documented chromatin-compacting properties for purified L3MBTL1 on reconstituted nucleosomal arrays (Trojer et al., 2007). To determine if the chromatin-compacting activity of L3MBTL1 is recruited to the latent HIV promoter, ChIP experiments were performed with L3MBTL1 antibodies and found L3MBTL1 enriched at latent and disenriched at the TNFα-activated HIV promoter in A72 (FIG. 19A) and A2 cells (FIG. 19B). Importantly, upon knockdown of SMYD2, L3MBTL1 was dissociated from the latent HIV promoter (FIG. 19C). In support of the model that L3MBTL1 is involved in HIV-1 latency, a doubling in basal transcriptional activity was observed in A72 J-Lat cells treated with the L3MBTL1 inhibitor UNC926 (Herold et al., 2012) (FIG. 25A,B). Similarly, L3MBTL1 knockdown in A72 J-Lat reproducibly activated HIV-1 transcription (FIG. 25C-E).

Example 4: SMYD5 Supports HIV-1 Reactivation from Latency

Materials and Methods

HEK293T cells were obtained from the American Type Culture Collection. J-Lat (clones A2, A72, and 5A8) have been previously described. HEK293T cells were cultured in DMEM supplemented with 10% FBS, 1% L-glutamine and 1% penicillin-streptomycin (Life Technologies). J-Lat cells were cultured in RPMI supplemented with 10% FBS, 1% L-glutamine and 1% penicillin-streptomycin (Life Technologies). Histones were isolated from HEK293T cells. The recombinant Tat peptides were synthesized by PSL Peptide Specialty Laboratories GmbH (German Cancer Research Center). Recombinant p65, SP1, CyclinT1/CDK9 and SMYD5 were purchased from Active Motif. Human αCD3/αCD28 Dynabeads (Invitrogen) were used at a 1 bead/cell ratio.

ShRNA-Mediated Knockdown Experiments, Flow Cytometry Analysis

ShRNA-expressing lentiviral vectors were purchased from Sigma-Aldrich. The plasmids TRCN0000155095 (Target sequence: GCTATGGGAATTACAACCCAT) (SEQ ID NO:76) and TRCN0000156306 (Target sequence: CTGTGACACTCTGGAGTTGAA) (SEQ ID NO:77) were used to deplete SMYD5. The pLKO.1 vector containing a scrambled shRNA was used as control. Pseudotyped viral stocks were produced in $2 \times 10^6$ HEK293T cells by the calcium phosphate method by co-transfecting 10 μg of shRNA-expressing lentiviral vectors, with 6.5 μg of the lentiviral packaging construct pCMVdelta R8.91 and 3.5 of VSV-G glycoprotein-expressing vector (Naldini et al. Science 1996; 272:263-7), and titered for p24 content. J-Lat 5A8, A72 and A2 cells were spininfected with virus (1 ng of p24 per $10^6$ cells) containing shRNAs against KMTs or nontargeting control shRNAs for 2 hr. Infected cells were selected with puromycin (2 μg/ml; Sigma-Aldrich) and after 4 days of selection, cells were treated with the indicated concentration of drugs. The percentage of GFP$^+$ cells was determined after 18 h using a MACSQuant VYB FACS analyzer (Miltenyi Biotech GmbH). Cell viability was monitored by forward-and-side scatter analysis. Analysis was conducted on 3×10,000 live cells per condition. Data were analyzed using FlowJo 9.5 (Tree Star).

RNA Isolation, Reverse Transcription, and Quantitative RT-PCR

RNA was isolated using RNeasy Plus Mini Kit (Qiagen) and reverse-transcribed using SuperScript III Reverse Transcriptase (Invitrogen) as per the manufacturer's instructions. Quantitative RT-PCR was carried out using Maxima SYBR Green qPCR Master Mix (Thermo Scientific) on SDS 2.4 software (Applied Biosystems) in a total volume of 12 μL. Primer efficiencies were around 100%. Dissociation curve analysis was performed after the end of the PCR to confirm the presence of a single and specific product.

In Vitro Methylation Assays

Methylation assays were performed as described (Nishioka et al. *Mol Cell* 2002; 9:1201-13). For reactions, 2 μg of histones (isolated from HEK293T cells), or synthetic Tat peptides (German Cancer Research Center) were incubated with recombinant full-length SMYD5 (Active Motif, #31409, purified from Sf9 cells) in a buffer containing 50 mM Tris-HCl, pH 9, 0.01% Tween 20, 2 mM DTT and 1.1 μCi of H$^3$-labeled SAM (Perkin Elmer) overnight at 30° C. Reaction mixtures were fractionated on 15% SDS-PAGE for proteins or on 10-20% Tris-Tricine gradient gels for peptides (BioRad). After Coomassie staining, gels were treated with Amplify (GE Healthcare) for 30 min, dried and exposed to hyperfilm (GE Healthcare) overnight.

Luciferase Assays $1 \times 10^5$ HeLa cells were transfected with 25 ng LTR-Luciferase construct and 50, 100 or 500 ng ng of DNA containing SMYD5 expressing plasmids or empty vector using X-tremegene 9 following manufacturer instructions (Roche Diagnostics, Indianapolis, Ind.). Cells were harvested 48 hr after stimulation, washed one time with PBS, and lysed in 60 μl of Passive Lysis Buffer (Dual-Luciferase Assay System-Promega). After 15 min of lysis, the luciferase activity in cell extracts was quantified with a Monolight 2010 Luminometer (Analytical Luminescence Laboratory) after mixing 20 μl of lysate with 100 μl of substrate. Relative light units (RLU) were normalized to protein content determined by Bradford assay (BioRad). Co-transfection of 10 ng eF1α-Renilla was used to control for transfection efficiency.

Results

Figure 26A:
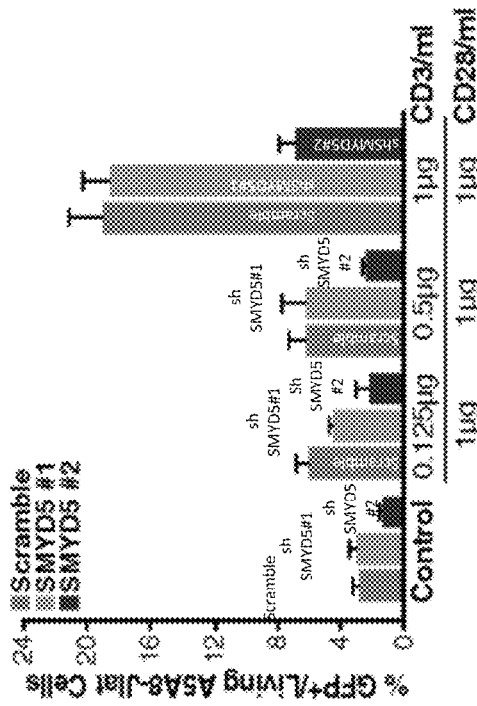
Figure 26B:
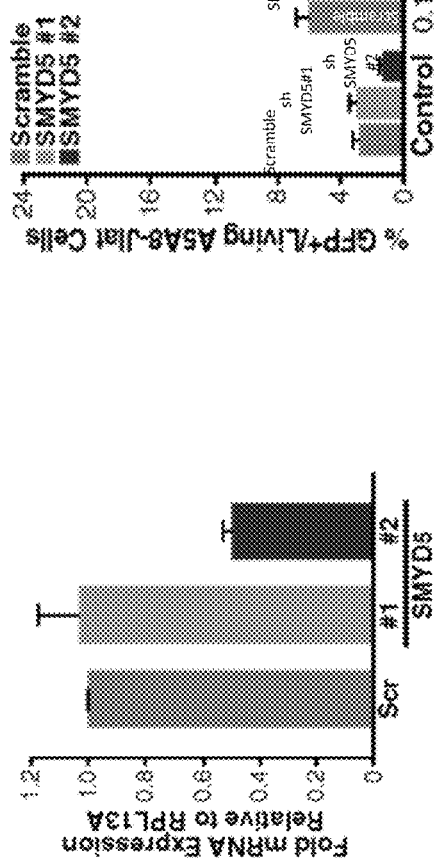
Figure 26D:
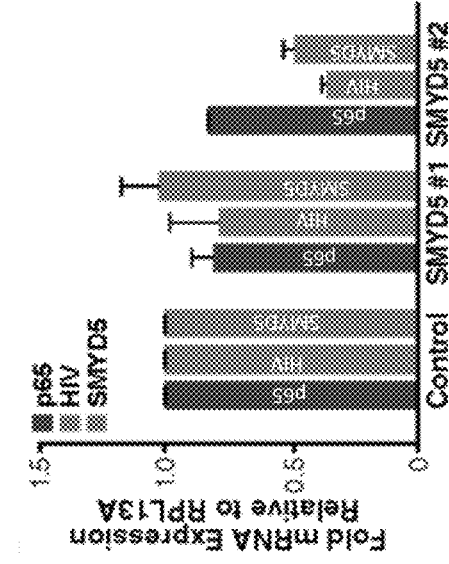
Figure 26C:
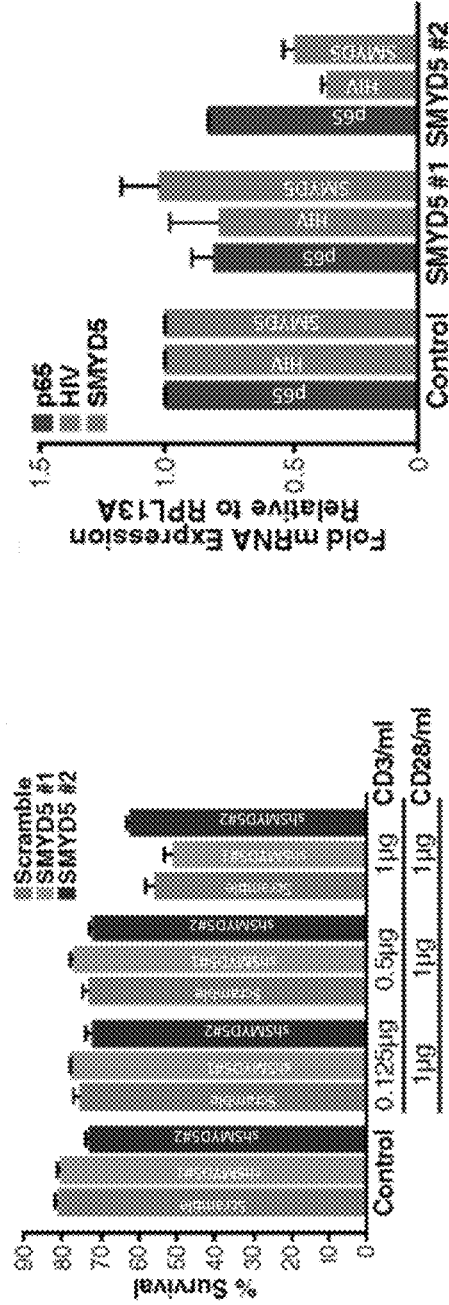

To confirm results from the shRNA screen, SMYD5 was individually knocked down in J-Lat 5A8 cells. Cells were transduced with lentiviral vectors expressing two different shRNAs targeting SMYD5 or a scrambled control shRNA, followed by puromycin treatment to select successfully transduced cells. The shRNA knockdown was confirmed using qPCR and failed for #1 and was ~50% effective for #2 (FIG. 26A). Cells were then stimulated with suboptimal, medium, or saturating doses of CD3/28 antibodies or were left unstimulated for 24 hours, followed by flow cytometry of GFP. Successful knockdown of SMYD5 with shRNA#2 suppressed reactivation of viral latency even at high CD3/CD38 concentrations, while shRNA#1 had no effect (FIG. 26B). Cell viability was monitored and showed no difference between control and SMYD5 knockdown cells (FIG. 26C). To test effects of SMYD5 on basal HIV-1 transcription we analyzed RNAs from nonactivated control and SMYD5 knockdown cells with primers specific for the viral LTR; mRNAs for SMYD5 and the NF-κB factor p65 were used as controls (FIG. 26D). SMYD5 knockdown reduced basal HIV-1 transcription by ~50% mirroring the knockdown efficiency of shRNA#2 (FIG. 26D). In independent experiments to investigate the biological role of SMYD5 during HIV transcription, HeLa cells were transfected with an HIV LTR luciferase construct and expression vectors for Tat and SMYD5. Overexpression of SMYD5 marked activation of a co-transfected viral LTR-luciferase reporter construct was observed (FIGS. 28A and 28B). To identify the target for SMYD5 in HIV-1 infection, we performed in vitro methylation assays with recombinant SMYD5 on purified human histones, Tat (aa 1-72) [SEQ ID NO:39], NF-κB, RelA, Sp1, and P-TEFb components cyclin T1 and CDK9. Reactions included 3H-SAM and were performed with or without recombinant SMYD5 enzyme. After gel electrophoresis, coomassie staining and autoradiography no methylation was detected for RelA, Sp1, cyclin T1 and CDK9 (FIG. 27). However, histones H3 and H1 were weakly and Tat strongly methylated by SMYD5 (FIG. 27). To map the site of methylation in Tat, we performed in vitro methylation reactions using non-radiolabeled SAM and subjected them to reversed-phase liquid chromatography electrospray tandem mass spectrometry (LC-MS/MS). This analysis identified a single site, trimethylation of K41, identified in two distinct peptides (not shown). No mono or dimethylation at Tat K41 was observed.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a human immunodeficiency virus (HIV) infection in an individual, the method comprising:
   administering to an individual an effective amount of a first active agent, wherein the first active agent is a SET domain-containing methyltransferase inhibitor that reactivates latent HIV integrated into the genome of a cell in the individual, wherein the SET domain-containing methyltransferase inhibitor is selected from the group consisting of a SMYD2 inhibitor, an ASH1L inhibitor, and a SUV420H1 inhibitor; and
   administering to the individual an effective amount of a second active agent, wherein the second active agent inhibits an immunodeficiency virus function selected from viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

2. The method of claim 1, wherein one or both of said administering steps is by a vaginal route of administration, a rectal route of administration, an oral route of administration, or an intravenous route of administration.

3. The method of claim 1, comprising administering an additional agent that reactivates latent HIV, wherein the additional agent is a histone deacetylase (HDAC) inhibitor, a protein kinase C (PKC) activator, or a bromodomain inhibitor.

4. The method of claim 3, the second agent is a HDAC inhibitor, and wherein the HDAC inhibitor is suberoylanilidehydroxamic (SAHA), romidepsin, or sodium butyrate.

5. The method of claim 3, wherein the second agent is a PKC activator, and wherein the PKC activator is prostratin, bryostatin, a chemical analog of prostratin, or a chemical analog of bryostatin.

6. The method of claim 3, the second agent is a bromodomain inhibitor, and wherein the bromodomain inhibitor is JQ1.

7. The method of claim 1, wherein the SET domain-containing methyltransferase inhibitor is a small molecule SET domain-containing methyltransferase inhibitor.

8. The method of claim 7, wherein the small molecule SET domain-containing methyltransferase inhibitor is selected from the group consisting of: AZ506, AZ391, LLY-507, A-196, BIX-01294, UNC0638, or a pharmaceutically acceptable derivative thereof.

9. The method of claim 1, wherein the SET domain-containing methyltransferase inhibitor is an siNA, or a nucleic acid encoding an siNA.

* * * * *